United States Patent
Schaffer et al.

(10) Patent No.: US 9,005,928 B2
(45) Date of Patent: Apr. 14, 2015

(54) CELLS AND METHODS FOR PRODUCING RHAMNOLIPIDS

(75) Inventors: Steffen Schaffer, Herten (DE); Mirja Wessel, Bochum (DE); Anja Thiessenhusen, Muenster (DE); Nadine Stein, Recklinghausen (DE)

(73) Assignee: Evonik DeGussa GmbH, Essen (DE)

( * ) Notice: Subject to any disclaimer, the term of this patent is extended or adjusted under 35 U.S.C. 154(b) by 0 days.

(21) Appl. No.: 13/812,625

(22) PCT Filed: Jul. 20, 2011

(86) PCT No.: PCT/EP2011/062441
§ 371 (c)(1),
(2), (4) Date: Jan. 28, 2013

(87) PCT Pub. No.: WO2012/013554
PCT Pub. Date: Feb. 2, 2012

(65) Prior Publication Data
US 2013/0130319 A1 May 23, 2013

(30) Foreign Application Priority Data
Jul. 28, 2010 (DE) .................. 10 2010 032 484

(51) Int. Cl.
C12N 1/20 (2006.01)
C12P 19/44 (2006.01)
A01N 43/16 (2006.01)
C12N 9/10 (2006.01)

(52) U.S. Cl.
CPC ............. *C12P 19/44* (2013.01); *A01N 43/16* (2013.01); *C12N 9/1051* (2013.01)

(58) Field of Classification Search
None
See application file for complete search history.

(56) References Cited

U.S. PATENT DOCUMENTS

| | | | |
|---|---|---|---|
| 4,601,893 A | 7/1986 | Cardinal | |
| 5,175,108 A | 12/1992 | Bachmann et al. | |
| 6,136,576 A | 10/2000 | Diaz-Torres et al. | |
| 7,118,904 B2 | 10/2006 | Mockel et al. | |
| 2007/0020624 A1 | 1/2007 | Rubenfield et al. | |

FOREIGN PATENT DOCUMENTS

| | | |
|---|---|---|
| DE | 100 31 999 A1 | 4/2001 |
| EP | 0 472 869 A2 | 3/1992 |
| EP | 1 083 225 A1 | 3/2001 |
| GB | 1009370 | 11/1965 |
| WO | 96/15246 A1 | 5/1996 |
| WO | WO 2004/050882 A1 | 6/2004 |
| WO | WO 2004/083385 A2 | 9/2004 |

OTHER PUBLICATIONS

Rahim et al. Mol. Microbiol. (2001) 40(3), 708-718.*
Ochsner et al. J. Biol. Chem. (1994) 269 (31) 19787-1995.*
Lohaus, C., et al., "Proteomforschung" Biospektrum, 1998, vol. 5, pp. 32-39.
Rodriguez, R. L., et al., "Vectors: a survey of molecular cloning vectors and their uses", 1987, pp. 179-204, Butterworths Publishers, Stoneham, Massachusetts.
http://web.archive.org/web/20071210070444/http://www3.dsmz.de/species/bacteria.htm, printed on Dec. 3, 2013.
http://web.archive.org/web/20071026085918/http://www3.dsmz.de/species/yeasts.htm, printed on Dec. 3, 2013.
http://web.archive.org/web/20071210070449/http://www3.dsmz.de/species/fungi.htm, printed on Dec. 3, 2013.
Huisman, G. W., et al., "Metabolism of Poly(3-hydroxyalkanoates) (PHAs) by *Pseudomonas oleovorans*", The Journal of Biological Chemistry, Feb. 5, 1991, vol. 266, No. 4, pp. 2191-2198.
Liebl, W. et al., High efficiency electroporation of intact *Corynebacterium glutamicum* cells, FEMS Microbiology, (1989), Letters 65, pp. 299-304.
Altschul, S.F. et al., "Basic Local Alignment Search Tool", J. Mol. Biol., Oct. 1990, vol. 215, No. 3, pp. 403-410.
Cha, M. et al., "Heterologous production of *Pseudomonas aeruginosa* EMS1 biosurfactant *Pseudomonas putida*", May 2008, Biosource Technology, vol. 99, No. 7, pp. 2192-2199.
Rehm, B.H.A. et al., "Role of Fatty Acid De Novo Biosynthesis in Polyhydroxyalkanoic Acid (PHA) and Rhamnolipid Synthesis by Pseudomonads: Establishment of the Transacylase (Pha-G)-Mediated Pathway for PHA Biosynthesis in *Escherichia coli*", Applied and Environmental Microbiology, Jul. 2001, vol. 67, No. 7, pp. 3102-3109.
Devereux, J. et al., "A Comprehensive set of Sequence Analysis Programs for the VAX", Nucleic Acids Research, Jan. 1984, vol. 12, No. 1, pp. 387-395.
Kovach, M.E. et al., "Four new derivatives of the broad-host-range cloning vector pBBR1MCS, carrying different antibiotic-resistance cassettes", Gene, Dec. 1, 1995, vol. 166, No. 1, pp. 175-176.
Iwasaki, K. et al., "Transformation of *Pseudomonas putida* by Electroporation", Biosci. Biotechnol. Biochem., May 1994, vol. 58, No. 5, pp. 851-854.
Ben-Bassat, A., et al., Processing of the Initiation Methionine from Proteins: Properties of the *Escherichia coli* Methionine Aminopeptidase and its Gene Structure, Journal of Bacteriology, Feb. 1987, vol. 169, No. 2, pp. 751-757.
Sahin-Toth, M., et al. "Cysteine scanning mutagenesis of the N-terminal 32 amino acid residues in the lactose permease of *Escherichia coli*", Protein Science, Feb. 1994, vol. 3, No. 2, pp. 240-247.
Ouyang, S., et al., "Construction of pha-Operon-Defined Knockout Mutants of *Pseudomonas putida* KT2442 and their Applications in Poly(hydroxyalkanoate) Production", Macromol. Biosci, Feb. 12, 2007, vol. 7, No. 2, pp. 227-233.
Singh, B., et al., "Characterization of a *Pseudomonas putida* transporter (AatJMQP) required for acidic amino acid uptake: biochemical properties and regulation by the Aau two-component system", Microbiology, Mar. 2008, vol. 154 (Pt. 3), pp. 797-809.
Dubeau, D., et al., "*Burkhoideria thailandensis* harbors two identical rhl gene clusters responsible for the biosynthesis of rhamnolipds", BMC Microbiology, Dec. 17, 2009, vol. 9, No. 263, pp. 1-12.
Jensen, P.R., et al., "Artificial Promoters for Metabolic Optimization", Biotechnology and Bioengineering, Apr. 20/May 5, 1998, Issue 2-3, pp. 191-195.

(Continued)

*Primary Examiner* — Nashaat Nashed
(74) *Attorney, Agent, or Firm* — Scully, Scott, Murphy & Presser, P.C.

(57) ABSTRACT

The invention relates to cells and nucleic acids and also use thereof for producing rhamnolipids, and also methods for producing rhamnolipids.

14 Claims, 3 Drawing Sheets

(56) References Cited

OTHER PUBLICATIONS

Reinscheid, D.J., et al., "Stable Expression of hom-1-thrB in *Corynebacterium glutamicum* and Its Effect on the Carbon Flux to Threonine and Related Amino Acids", Applied and Environmental Microbiology, Jan. 1994, vol. 60, No. 1, pp. 126-132.

Labarre, J., et al., Gene Replacement, Integration, and Amplification at the gdhA Locus of *Corynebacterium glutamicum*, Journal of Bacteriology, Feb. 1993, vol. 175, No. 4, pp. 1001-1007.

Schafer, A., et al., "Increased Fertility of *Corynebacterium glutamicum* Recipients Intergeneric Matings with *Escherichia coli* after Stress Exposure", Applied and Environmental Microbiology, Feb. 1994, vol. 60, No. 2, pp. 756-759.

Freedberg, W.B., et al., "Three Kinds of Controls Affecting the Expression of the glp Regulon in *Escherichia coli*", Journal of Bacteriology, Sep. 1973, vol. 115, No. 3, pp. 816-823.

Ray, W.K., et al., "Characterization of a 12-Kilodalton Rhodanese Encoded by glpE of *Escherichia coli* and Its Interaction with Thioredoxin", Journal of Bacteriology, Apr. 2000, vol. 182, No. 8, pp. 2277-2284.

Malumbres, M., et al., "Codon preference in Corynebacteria", Gene, Nov. 30, 1993, vol. 134, No. 1, pp. 15-24.

O'Regan, M., et al., "Cloning and nucleotide sequence of the phosphoenolpyruvate carboxylase-coding gene of *Corynebacterium glutamicum* ATCC13032", Gene, Apr. 30, 1989, vol. 77, No. 2, pp. 237-251.

Eikmanns, B.J., et al., "A family of *Corynebacterium glutamicum/Escherichia coli* shuttle vectors for cloning, controlled gene expression, and promoter probing", Gene, Jun. 15, 1991, vol. 102, No. 1, pp. 93-98.

Guerrero, C., et al., "Directed mutagenesis of a regulatory palindromic sequence upstream from the *Brevibacterium* lactofermentum tryotophan operon", Gene, Jan. 28, 1994, vol. 138, No. 1-2, pp. 35-41.

Donahue, J.L., et al., "Purification and Characterization of glpX-Encoded Fructose 1,6-Bisphosphatase, a New Enzyme of the Glycerol 3-Phosphate Regulon of *Escherichia coli*", Journal of Bacteriology, Oct. 2000, vol. 182, No. 19, pp. 5624-5627.

Wilson, M.J., et al., "Analysis of Promoters Recognized by PvdS, an Extracytoplasmic-Function Sigma Factor Protein from *Pseudomonas aeruginosa*", Journal of Bacteriology, Mar. 2001, vol. 183, No. 6, pp. 2151-2155.

Lottspeich, F., "Proteomanalyse—ein Weg zur Funktionsanalyse von Proteinen", Angew. Chem., Sep. 3, 1999, vol. 111, No. 17, pp. 2630-2647.

Tsuchiya, M., et al., Genetic Control Systems of *Escherichia coli* Can Confer Inducible Expression of Cloned Genes in Coryneform Bacteria, Bio/technology, Apr. 1988, vol. 6, pp. 428-430.

Lee, Y., et al., "Inactivation of the *Pseudomonas putida* KT2440 dsbA gene promotes extracellular matrix production and biofilm formation", FEMS Microbiol. Lett., Aug. 2009, vol. 297, pp. 38-48.

Tauch, A., et al., "*Corynebacterium glutamicum* DNA is subjected to methylation-restriction in *Escherichia coli*", FEMS Microbiol. Lett., Nov. 1, 1994, vol. 123, No. 3, pp. 343-348.

Dunican, L.K., et al., "High Frequency Transformation of Whole Cells of Amino Acid Producing Coryneform Bacteria Using High Voltage Electroporation", Bio/technology, Oct. 1989, vol. 7, pp. 1067-1070.

Thierbach, G., et al., "Transformation of spheroplasts and protoplasts of *Corynebacterium glutamicum*", Appl. Microbiol. Biotechnol., Oct. 1988, vol. 29, pp. 356-362.

Schwarzer, A., et al., "Manipulation of *Corynebacterium glutamicum* by Gene Disruption and Replacement", Bio/technology, Jan. 1991, vol. 9, pp. 84-87.

Martin, J.F., et al., "Cloning Systems in Amino Acid-Producing Corynebacteria", Bio/technology, Feb. 1987, vol. 5, pp. 137-146.

Ren, Q., et al., "Mutants of *Pseudomonas putida* affected in poly-3-hydroxyalkanoate synthesis", Appl. Microbiol. Biotechnol., Jun. 1998, vol. 49, pp. 743-750.

Hochuli, E., et al., "Genetic Approach to Facilitate Purification of Recombinant Proteins with a Novel Metal Chelate Adsorbent", Bio/Technology, Nov. 1988, pp. 1321-1325.

Hermann, T., et al., "Proteome analysis of *Corynebacterium glutamicum*", Electrophoresis, May 2001, vol. 22, No. 9, pp. 1712-1723.

De Eugenio, L.I., et al., The turnover of medium-chain-length polyhydroxyalkanoates in *Pseudomonas putida* KT2442 and the fundamental role of PhaZ depolymerase for the metabolic balance:, Environmental Microbiology, Jan. 2010, vol. 12, No. 1, pp. 207-221.

Leitermann, F., et al., "Rhamnolipids", Handbook of Hydrocarbon and Lipid Microbiology, Jan. 1, 2010, vol. 4, pp. 3037-3051.

Goeddel, D.V., "Systems for Heterologous Gene Expression", Methods in Enzymology, Jun. 11, 1990, vol. 185, pp. 3-7.

Ochsner, Urs A. et al., "Production of *Pseudomonas aeruginosa* Rhamnolipid Biosurfactants in Heterologous Hosts", Applied and Environmental Microbiology (Sep. 1995), vol. 61, No. 9, pp. 3503-3506.

Fang, Xiangdong et al., "Final Report: Bio-Engineering High Performance Microbial Strains for MEOR by Directed Protein Evolution Technology", Oil & Natural Gas Technology (Jul. 2, 2008), prepared for U.S. Dept. of Energy, National Energy Technology Laboratory, pp. II-V, 1-90.

"*Pseudomonas aeruginosa* rhamnosyl transferase genes and regulatory protein gene, complete cds.", XP002657937, retrieved from EBI accession No. EM_PRO: L28170, (May 6, 1994).

International Search Report dated Oct. 7, 2011 issued in PCT/EP2011/062441.

\* cited by examiner

CELLS AND METHODS FOR PRODUCING RHAMNOLIPIDS

FIELD OF THE INVENTION

The invention relates to cells and nucleic acids and also use thereof for producing rhamnolipids, and also methods for producing rhamnolipids.

PRIOR ART

Surfactants are nowadays produced essentially based on the basis of petrochemical raw materials. The use of surfactants based on renewable raw materials is a suitable alternative on account of the foreseeable shortage of petrochemical raw materials and increasing demand for products that are based on renewable raw materials or are biodegradable.

Rhamnolipids consist of one (monorhamnosyl lipids) or two rhamnose radicals (dirhamnosyl lipids) and one or two 3-hydroxy fatty acid residues (see *Handbook of Hydrocarbon and Lipid Microbiology,* 2010, pages 3037-51). They have surface-active properties, which are needed in all sorts of applications for use as a surfactant (see Leitermann et al., 2009).

These lipids are nowadays produced using wild-type isolates of different human- and animal-pathogenic bacteria, in particular representatives of the genera *Pseudomonas* and *Burkholderia* (see *Handbook of Hydrocarbon and Lipid Microbiology,* 2010, pages 3037-51). The fact that these production organisms are able to cause diseases reduces the customer acceptance for the conventionally produced rhamnolipids very considerably. Moreover, higher safety requirements also have an effect on the production costs owing to increased capital expenditure and possibly additional working-up steps.

Although to some extent high product titers, and also space-time and/or carbon yields can be achieved with the aid of these production organisms, this requires the use of vegetable oils as the sole or co-substrate (see *Handbook of Hydrocarbon and Lipid Microbiology,* 2010, pages 3037-51). Vegetable oils, however, are comparatively expensive raw materials in comparison to other carbon sources, such as, for example, glucose, sucrose or polysaccharides such as, for example, starch, cellulose and hemicellulose, glycerol, CO, $CO_2$ or $CH_4$. Moreover, rhamnolipids distinguish themselves on account of their surfactant character in that they are susceptible to heavy foaming in fermentation processes. This is in particular the case if lipophilic substrates are employed. This problem is markedly reduced on use of water-soluble substrates such as, for example, glucose, sucrose, polysaccharides (starch, cellulose, hemicellulose) or glycerol. Finally, the properties of the rhamnolipids produced by the wild-type isolates can only be influenced to a restricted extent. Up to now, this takes place exclusively via the optimization of the process management (pH, oxygen supply, media composition, feeding strategies, nitrogen supply, temperature, choice of substrate, etc.). However, a very specific influence of certain product properties, such as, for example, the ratio of the various rhamnolipid species (number of rhamnose and 3-hydroxy fatty acid radicals) or chain length and degree of saturation of the 3-hydroxy fatty acid radicals would be desirable to be able to modulate the product properties relevant for the application.

Rhamnolipids, if they are to be employed in a large extent as surfactants in household, cleaning, cosmetic, food processing, pharmaceutical, plant protection and other applications, must appear to be in competition with the surfactants employed nowadays. These are high volume chemicals, which can be produced at very low costs, without obvious health risks for the customer and with clearly defined and modulatable product specifications. Therefore rhamnolipids must also be able to be produced at costs as low as possible, without health risks for the customer and with defined properties as far as possible.

Although rhamnolipids have already been produced in GRAS organisms (generally regarded as save) based on convenient carbon sources, such as, for example, glucose or glycerol, these are in this case exclusively monorhamnosyl lipids (Ochsner et al. Appl. Environ. Microbiol. 1995. 61(9): 3503-3506).

Cha et al. in Bioresour Technol. 2008. 99(7):2192-9, on the other hand, describe the production of monorhamnosyl lipids from soybean oil in *P. putida* by introduction of the genes rh/A and rh/B from *Pseudomonas aeruginosa*.

There is therefore an increasing need for the inexpensive and, from the health point of view, safe production of mono- and dirhamnosyl lipids having defined and modulatable properties. This modulation can be carried out, for example, by means of a balanced supply of the individual enzyme activities, which reduces the enrichment of monorhamnosyl lipids. This modulation, however, can also be carried out, for example, by the use of enzymes having certain properties, e.g. with respect to substrate specificity and thus, for example, the chain length of the hydroxy fatty acids incorporated in rhamnolipids.

The present invention therefore has the object of providing a possibility of producing rhamnolipids from readily accessible carbon sources using safe production hosts.

DESCRIPTION OF THE INVENTION

Surprisingly, it has been found that the cells and methods described below, in which these cells are employed, make a contribution to solving the stated object of the invention.

The present invention therefore relates to cells, which are able to form rhamnolipids and compared to their wild-type have at least one increased activity of a gene product of homologs of the gene products rh/A, rh/B and rh/C.

The invention further relates to a method for producing rhamnolipids using the aforementioned cells as a biocatalyst and simple carbon sources:

It is an advantage of the present invention that organisms can be employed that are, non-pathogenic and simple to culture.

It is a further advantage that use of oils as the sole or co-substrate is not necessary.

Another advantage is that with the aid of the invention rhamnolipids having defined and modulatable properties can be produced.

It is another advantage of the present invention that dirhamnosyl lipids can be produced.

A further advantage is that rhamnolipids can be produced with higher space-time and carbon yields than with cells without enhancement of these activities.

A contribution to achieving the object mentioned at the outset is made by a cell, preferably an isolated cell, which is able to form at least one rhamnolipid of the general formula (I) or its salt,

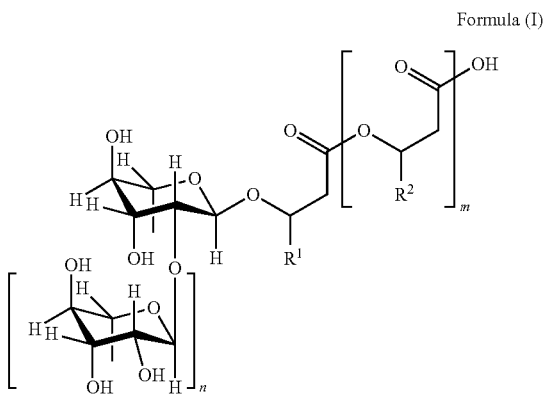

Formula (I)

wherein
m=2, 1 or 0, in particular 1 or 0,
n=1 or 0, in particular 1,
$R^1$ and $R^2$=independently of one another identical or different organic radical having 2 to 24, preferably 5 to 13 carbon atoms, in particular optionally branched, optionally substituted, in, particular hydroxy-substituted, optionally unsaturated, in particular optionally mono-, di- or tri-unsaturated, alkyl radical, preferably that selected from the group consisting of pentenyl, heptenyl, nonenyl, undecenyl and tridecenyl and $(CH_2)_o$—$CH_3$ with o=1 to 23, preferably 4 to 12, characterized in that it has been genetically modified such that, compared to its wild-type, it has an increased activity of at least one of the enzymes $E_1$, $E_2$ and $E_3$, wherein the enzyme $E_1$ is able to catalyze the conversion of 3-hydroxyalkanoyl-ACP via 3-hydroxyalkanoyl-3-hydroxyalkanoic acid-ACP to hydroxyalkanoyl-3-hydroxyalkanoic acid, the enzyme $E_2$ is a rhamnosyltransferase I and is able to catalyze the conversion of dTDP-rhamnose and 3-hydroxyalkanoyl-3-hydroxyalkanoate to α-L-rhamnopyranosyl-3-hydroxyalkanoyl-3-hydroxyalkanoate and the enzyme $E_3$ is a rhamnosyltransferase II and is able to catalyze the conversion of dTDP-rhamnose and α-L-rhamnopyranosyl-3-hydroxyalkanoyl-3-hydroxyalkanoate to α-L-rhamnopyranosyl-(1-2)-α-L-rhamnopyranosyl-3-hydroxyalkanoyl-3-hydroxyalkanoate, wherein these enzymes $E_1$, $E_2$ and $E_3$ preferably are selected from the group consisting of
at least one enzyme $E_1$ selected from
an enzyme $E_{1a}$ having polypeptide sequence Seq ID No. 2 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 2 by deletion, insertion, substitution or a combination thereof and that still has at least 10%, preferably 50%, particularly preferably 80%, in particular more than 90% of the enzymatic activity of the enzyme having the reference sequence Seq ID No. 2, wherein enzymatic activity for an enzyme $E_{1a}$ is understood as meaning the ability preferably to convert 3-hydroxydecanoyl-ACP via 3-hydroxydecanoyl-3-hydroxydecanoic acid-ACP to hydroxydecanoyl-3-hydroxydecanoic acid,
an enzyme $E_{1b}$ having polypeptide sequence Seq ID No. 18 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 18 by deletion, insertion, substitution or a combination thereof and that still has at least 10%, preferably 50%, particularly preferably 80%, in particular more than 90% of the enzymatic activity of the enzyme having the reference sequence Seq ID No. 18, wherein enzymatic activity for an enzyme $E_{1b}$ is understood as meaning the ability preferably to convert 3-hydroxytetradecanoyl-ACP via 3-hydroxytetradecanoyl-3-hydroxytetradecanoic acid-ACP to hydroxytetradecanoyl-3-hydroxytetradecanoic acid,
an enzyme $E_{1c}$ having polypeptide sequence Seq ID No. 78 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 78 by deletion, insertion, substitution or a combination thereof and that still has at least 10%, preferably 50%, particularly preferably 80%, in particular more than 90% of the enzymatic activity of the enzyme having the reference sequence Seq ID No. 78, wherein enzymatic activity for an enzyme $E_{1c}$ is understood as meaning the ability preferably to convert 3-hydroxytetradecanoyl-ACP via 3-hydroxytetradecanoyl-3-hydroxytetradecanoic acid-ACP to hydroxytetradecanoyl-3-hydroxytetradecanoic acid,
an enzyme $E_{1d}$ having polypeptide sequence Seq ID No. 80 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 80 by deletion, insertion, substitution or a combination thereof and that still has at least 10%, preferably 50%, particularly preferably 80%, in particular more than 90% of the enzymatic activity of the enzyme having the reference sequence Seq ID No. 80, wherein enzymatic activity for an enzyme $E_{1d}$ is understood as meaning the ability preferably to convert 3-hydroxytetradecanoyl-ACP via 3-hydroxytetradecanoyl-3-hydroxytetradecanoic acid-ACP to hydroxytetradecanoyl-3-hydroxytetradecanoic acid, and
an enzyme $E_{1e}$ having polypeptide sequence Seq ID No. 82 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 82 by deletion, insertion, substitution or a combination thereof and that still has at least 10%, preferably 50%, particularly preferably 80%, in particular more than 90% of the enzymatic activity of the enzyme having the reference sequence Seq ID No. 82, wherein enzymatic activity for an enzyme $E_{1e}$ is understood as meaning the ability preferably to convert 3-hydroxytetradecanoyl-ACP via 3-hydroxytetradecanoyl-3-hydroxytetradecanoic acid-ACP to hydroxytetradecanoyl-3-hydroxytetradecanoic acid,
at least one enzyme $E_2$ having polypeptide sequence selected from
an enzyme $E_{2a}$ having polypeptide sequence Seq ID No. 4 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 4 by deletion, insertion, substitution or a combination thereof and that still has at least 10%, preferably 50%, particularly preferably 80%, in particular more than 90% of the enzymatic activity of the enzyme having the reference sequence Seq ID No. 4, wherein enzymatic activity for an enzyme $E_{2a}$ is understood as meaning the ability preferably to convert dTDP-rhamnose and 3-hydroxydecanoyl-3-hydroxydecanoic acid to α-L-rhamnopyranosyl-3-hydroxydecanoyl-3-hydroxydecanoic acid,
an enzyme $E_{2b}$ having polypeptide sequence Seq ID No. 20 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 20 by deletion, insertion, substitution or a combination thereof and that still has at least 10%, preferably 50%, particularly preferably 80%, in particular more than 90% of the enzymatic activity of the enzyme having the reference sequence Seq ID No. 20, wherein enzymatic activity for an enzyme $E_{2b}$ is understood as meaning the ability preferably to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, an enzyme $E_{2c}$ having polypeptide sequence Seq ID No. 84 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 84 by deletion, insertion, substitution or a combination thereof and that still has at least 10%, preferably 50%, particularly preferably 80%, in particular more than 90% of the enzymatic activity of the enzyme having the reference sequence Seq ID No. 84, wherein enzymatic activity for an enzyme $E_{2o}$ is understood as meaning the ability preferably to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, an enzyme $E_{2d}$ having polypeptide sequence Seq ID No. 86 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 86 by deletion, insertion, substitution or a combination thereof and that still has at least 10%, preferably 50%, particularly preferably 80%, in particular more than 90% of the enzymatic activity of the enzyme having the reference sequence Seq ID No. 86, wherein enzymatic activity for an enzyme $E_{2d}$ is understood as meaning the ability preferably to convert dTDP-rhamnose and 3-hydroxytetradecanoyl-3-hydroxytetradecanoic acid to xa-L-rhamnopyranosyl-3-hydroxytetradecanoyl-3-hydroxytetradecanoic acid, and an enzyme $E_{2e}$ having polypeptide sequence Seq ID No. 88 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 88 by deletion, insertion, substitution or a combination thereof and that still has at least 10%, preferably 50%, particularly preferably 80%, in particular more than 90% of the enzymatic activity of the enzyme having the reference sequence Seq ID No. 88, wherein enzymatic activity for an enzyme $E_{2e}$ is understood as meaning the ability preferably to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and at least one enzyme $E_3$ selected from an enzyme $E_{3a}$ having polypeptide sequence Seq ID No. 6 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 6 by deletion, insertion, substitution or a combination thereof and that still has at least 10%, preferably 50%, particularly preferably 80%, in particular more than 90% of the enzymatic activity of the enzyme having the reference sequence Seq ID No. 6, wherein enzymatic activity for an enzyme $E_{3a}$ is understood as meaning the ability preferably to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, an enzyme $E_{3b}$ having polypeptide sequence Seq ID No. 22 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 22 by deletion, insertion, substitution or a combination thereof and that still has at least 10%, preferably 50%, particularly preferably 80%, in particular more than 90% of the enzymatic activity of the enzyme having the reference sequence Seq ID No. 22, wherein enzymatic activity for an enzyme $E_{3b}$ is understood as meaning the ability preferably to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, an enzyme $E_{3c}$ having polypeptide sequence Seq ID No. 90 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq. ID No. 90 by deletion, insertion, substitution or a combination thereof and that still has at least 10%, preferably*50%, particularly preferably 80%, in particular more than 90% of the enzymatic activity of the enzyme having the reference sequence Seq ID No. 90, wherein enzymatic activity for an enzyme $E_{3c}$ is understood as meaning the ability preferably to convert dTDP-rhamnose and α-L-rhamnopyranosyl-3-hydroxytetradecanoyl-3-hydroxytetradecanoic acid to ca-L-rhamnopyranosyl-(1-2)-α-L-rhamnopyranosyl-3-hydroxytetradecanoyl-3-hydroxytetradecanoic acid, and an enzyme $E_{3d}$ having polypeptide sequence Seq ID No. 92 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 92 by deletion, insertion, substitution or a combination thereof and that still has at least 10%, preferably 50%, particularly preferably 80%, in particular more than 92% of the enzymatic activity of the enzyme having the reference sequence Seq ID No. 92, wherein enzymatic activity for an enzyme $E_{3d}$ is understood as meaning the ability preferably to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid.

For general survey compare FIG. 1.

"Wild-type" of a cell herein designates a cell, the genome of which is present in a state as is formed naturally by evolution. The term is used both for the entire cell as well as for individual genes. The term "wild-type" therefore in particular does not include those cells or those genes, the gene sequences of which have been modified at least partially by man by means of recombinant methods.

The term "rhamnolipid" is understood in connection with the present invention as meaning a compound of the general formula (I) or its salt.

It is obvious that the activities actually indicated above for the enzymes $E_{1a}$ to $E_{3b}$ is only a special exemplary choice of a broader activity spectrum of the aforementioned enzymes; the respective activity mentioned is that for which a reliable measuring method is available in the case of a given enzyme. Thus it is obvious that an enzyme which a substrate having an unbranched, saturated $CO_{10}$-alkyl radical likewise—even though optionally with decreased activity—will convert those substrates that contain a $C_6$- or $C_{16}$-alkyl radical, which can optionally also be branched or unsaturated.

The term "increased activity of an enzyme" is preferably to be understood as meaning increased intracellular activity.

The embodiments now following for increasing the enzyme activity in cells apply both for the increase in the activity of the enzyme $E_1$ to $E_3$ as well as for all subsequently mentioned enzymes, the activity of which can optionally be increased.

In principle, an increase in the enzymatic activity can be achieved by increasing the copy number of the gene sequence or the gene sequences which code for the enzyme, using a strong promotor or an improved ribosome binding site, attenuating a negative regulation of gene expression, for example by transcription regulators, or amplifying a positive regulation of gene expression, modifying the codon usage of the gene, in various ways increasing the half-life of the mRNA or of the enzyme, modifying the regulation of the expression of the gene or utilizing a gene or allele that codes for an appropriate enzyme having an increased activity and optionally combining these measures. According to the invention, genetically modified cells are produced, for example, by transformation, transduction, conjugation or a combination of these methods using a vector that contains the desired gene, an allele of this gene or parts thereof and optionally contains a promoter making possible the expression of the gene. Heterologous expression is in particular achieved by integration of the gene or the alleles in the chromosome of the cell or an extrachromosomally replicating vector.

DE-A-100 31 999 gives a general survey of the possibilities for increasing the enzyme activity in cells as exemplified by pyruvate carboxylase, which is inserted hereby as a reference and whose disclosure content with respect to the possibilities for increasing the enzyme activity in cells forms a part of the disclosure of the present invention.

The expression of the above and all subsequently mentioned enzymes or genes is detectable with the aid of 1- and 2-dimensional protein gel separation and subsequent optical identification of the protein concentration in the gel using appropriate analytical software. If the increase in an enzyme activity is based exclusively on an increase in the expression of the corresponding gene, the quantification of the increase in the enzyme activity can be determined in a simple manner by a comparison of the 1- or 2-dimensional protein separations between wild-type and genetically modified cell. A customary method for the preparation of the protein gels in the case of cryneforme bacteria and for the identification of the proteins is the procedure described by Hermann et al. (Electrophoresis, 22: 1712.23 (2001)). The protein concentration can likewise be analyzed by Western Blot hybridization using an antibody specific for the protein to be detected (Sambrook et al., Molecular Cloning: a laboratory manual, 2nd Ed. Cold Spring Harbor Laboratory Press, Cold Spring Harbor, N.Y. USA, 1989) and subsequent optical analysis using appropriate software for the concentration determination (Lohaus and Meyer (1989) Biospektrum, 5: 32-39; Lottspeich (1999) Angewandte Chemie 111: 2630-2647). The activity of DNA-binding proteins can be measured by means of DNA band shift assays (also called gel retardation) (Wilson et al. (2001) Journal of Bacteriology, 183: 2151-2155). The action of DNA-binding proteins on the expression of other genes can be detected by various well-described methods of the reporter gene assay (Sambrook et al., Molecular Cloning: a laboratory manual, 2nd Ed. Cold Spring Harbor Laboratory Press, Cold Spring Harbor, N.Y. USA, 1989). The intracellular enzymatic activities can be determined according to various described methods (Donahue et al. (2000) Journal of Bacteriology 182 (19): 5624-5627; Ray et al. (2000) Journal of Bacteriology 182 (8): 2277-2284; Freedberg et al. (1973) Journal of Bacteriology 115 (3): 816-823). If in the following embodiments no practical methods are indicated for the determination of the activity of a certain enzyme, the determination of the increase in the enzyme activity and also the determination of the decrease of an enzyme activity preferably take place by means of the methods described in Hermann et al., Electophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

If the increase in the enzyme activity is accomplished by mutation of the endogenous gene, such mutations can be randomly produced either by conventional methods, such as, for example, by UV irradiation or by mutagenic chemicals, or selectively by means of genetic engineering methods such as deletion(s), insertion(s) and/or nucleotide exchange(s). Modified cells are obtained by these mutations. Particularly preferred mutants of enzymes are in particular also those enzymes that are no longer feedback-, product- or substrate-inhibitable or are so to a reduced degree at least in comparison to the wild-type enzyme.

If the increase in the enzyme activity is accomplished by increase in the synthesis of an enzyme, the copy number of the corresponding genes is increased or the promoter and regulation region or the ribosome binding site, which is situated upstream of the structural gene, is mutated. Expression cassettes, which are incorporated upstream of the structural gene, act in the same manner. It is additionally possible, by means of inducible promoters, to increase the expression at any desired point in time. In addition, however, also "enhancers" can be assigned to the enzyme gene as regulatory sequences, which likewise bring about increased gene expression by means of an improved interaction between RNA polymerase and DNA. As a result of measures for the prolongation of the lifetime of the mRNA, the expression is likewise improved. Furthermore, by prevention of the degradation of the enzyme protein the enzyme activity is likewise increased. The genes or gene constructs are present here either in plasmids having a different copy number or are integrated and amplified in the chromosome.

Alternatively, an overexpression of the genes concerned can furthermore be achieved by modification of the media composition and culture management. The person skilled in the art finds directions for this, inter alia, in Martin et al. (Bio/Technology 5, 137-146 (1987)), in Guerrero et al. (Genes 138, 35-41 (1994)), Tsuchiya and Morinaga (Bio/Technology 6, 428-430 (1988)), in Eikmanns et al. (Genes 102, 93-98 (1991)), in EP-A-0 472 869, in U.S. Pat. No. 4,601,893, in Schwarzer and POhler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Genes 134, 15-24 (1993)), in JP-A-10-229891, in Jensen and Hammer (Biotechnology and Bioengineering 58, 191-195 (1998)) and in known textbooks of genetics and molecular biology. The measures described above likewise lead, like the mutations, to genetically modified cells.

Episomal plasmids, for example, are employed for increasing the expression of the respective genes. Suitable plasmids or vectors are in principle all embodiments available for this purpose to the person skilled in the art. Such plasmids and vectors can be taken, for example, from the brochures of the companies Novagen, Promega, New England Biolabs, Clontech or Gibco BRL. Further preferred plasmids and vectors can be found in: Glover, D. M. (1985) DNA cloning: a practical approach, Vol. I-III, IRL Press Ltd., Oxford; Rodriguez, R. L. and Denhardt, D. T (eds) (1988) Vectors: a survey of molecular cloning vectors and their uses, 179-204, Butterworth, Stoneham; Goeddel, D. V. (1990) Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York.

The plasmid vector, which contains the gene to be amplified, is then converted to the desired strain by conjugation or transformation. The method of conjugation is described, for example, in Schäfer et al., Applied and Environmental Microbiology 60: 756-759 (1994). Methods for transformation are described, for example, in Thierbach et al., Applied Microbiology and Biotechnology 29: 356-362 (1988), Dunican and Shivnan, Bio/Technology 7: 1067-1070 (1989) and Tauch et al., FEMS Microbiology Let-ters 123: 343-347 (1994). After homologous recombination by means of a "cross-over" event, the resulting strain contains at least two copies of the gene concerned.

Under the formulation used above and in the following embodiments "an activity of an enzyme $E_x$ increased in comparison to its wild-type" is preferably always to be understood as meaning an activity of the respective enzyme $E_x$ increased by a factor of at least 2, particularly preferably of at least 10, moreover preferably of at least 100, moreover still more preferably of at least 1,000 and most preferably of at least 10,000. Furthermore the cell according to the invention, which has "an increased activity of an enzyme $E_x$ compared to its wild-type", in particular also comprises a cell, whose wild-type contains no or at least no detectable activity of this enzyme $E_x$ and which shows a detectable activity of this enzyme $E_x$ only after increasing the enzyme activity, for example by overexpression. In this connection, the term "overexpression" or the formulation used in the following embodiments "increasing the expression" also comprises the case where a starting cell, for example a wild-type cell, has no or at least no detectable expression and a detectable synthesis of the enzyme $E_x$ is induced only by recombinant methods.

Changes of amino acid radicals of a given polypeptide sequence, which lead to no significant changes in the properties and function of the given polypeptide, are known to the person skilled in the art. Thus, for example, "conserved amino acids" can be mutually exchanged; examples of such suitable amino acid substitutions are: Ala for Ser; Arg for Lys; Asn for Gln or His; Asp for Glu; Cys for Ser; Gln for Asn; Glu for Asp; Gly for Pro; H is for Asn or Gln; Ile for Leu or Val; Leu for Met or Val; Lys for Arg or Gln or Glu; Met for Leu or Ile; Phe for Met or Leu or Tyr; Ser for Thr; Thr for Ser; Trp for Tyr; Tyr for Trp or Phe; Val for Ile or Leu. It is likewise known that changes, particularly at the N- or C-terminus of a polypeptide, in the form of, for example, amino acid insertions or deletions often exert no significant influence on the function of the polypeptide.

The activity of an enzyme can be determined by disrupting cells which contain this activity in a manner known to the person skilled in the art, for example with the aid of a ball mill, a French press or of an ultrasonic disintegrator and subsequently separating off cells, cell debris and disruption aids, such as, for example, glass beads, by centrifugation for 10 minutes at 13,000 rpm and 4° C. Using the resulting cell-free crude extract, enzyme assays with subsequent LC-ESI-MS detection of the products can then be carried out. Alternatively, the enzyme can be enriched in the manner known to the person skilled in the art by chromatographic methods (such as nickel-nitrilotriacetic acid affinity chromatography, streptavidin affinity chromatography, gel filtration chromatography or ion-exchange chromatography) or else purified to homogeneity.

The activity of the enzyme $E_1$ is then determined using the samples obtained as described above in the following manner: A standard assay contains 100 µM E. coli ACP, 1 mM β-mercaptoethanol, 200 µM malonyl-coenzyme A, 40 µM octandyl-coenzyme A (for $E_{1a}$) or dodecanoyl-coenzyme A (for $E_{1b}$), 100 µM NADPH, 2 µg of E. coli FabD, 2 µg of Mycobacterium tuberculosis FabH, 1 µg of E. coli FabG, 0.1 M sodium phosphate buffer, pH 7.0, and 5 µg of enzyme $E_1$ in a final volume of 120 µL. ACP, β-mercaptoethanol and sodium phosphate buffer are preincubated for 30 min at 37° C. to reduce the ACP completely. The reaction is started by addition of enzyme $E_1$. The reactions are stopped using 2 ml of water, which has been acidified with HCl to pH 2.0, and subsequently extracted twice with 2 ml of chloroform/methanol (2:1 (v:v)). Phase separation takes place by centrifugation (16,100 g, 5 min, RT). The lower organic phase is removed, evaporated completely in the vacuum centrifuge and the sediment is taken up in 50 µl of methanol. Undissolved constituents are sedimented by centrifugation (16,100 g, 5 min, RT) and the sample is analyzed by means of LC-ESI-MS. The identification of the products takes place by analysis of the corresponding mass traces and the $MS^2$ spectra.

The activity of the enzyme $E_2$ is then determined as follows using the samples obtained as described above: a standard assay can consist of 185 µl of 10 mM tris-HCl (pH 7.5), 10 µl of 125 mM dTDP-rhamnose and 50 µl of protein crude extract (about 1 mg of total protein) or purified protein in solution (5 µg of purified protein). The reaction is started by the addition of 10 µl of 10 mM ethanolic solution of 3-hydroxydecanoyl-3-hydroxydecanoic acid (for $E_{2a}$) or 3-hydroxy-tetradecanoyl-3-hydroxytetradecanoic acid (for $E_{2b}$) and incubated for 1 h at 30° C. with shaking (600 rpm). Subsequently, the reaction is treated with 1 ml of acetone. Undissolved constituents are sedimented by centrifugation (16,100 g, 5 min, RT) and the sample is analyzed by means of LC-ESI-MS. The identification of the products takes place by analysis of the corresponding mass traces and the $MS^2$ spectra.

The activity of the enzyme $E_3$ is then determined as follows using the samples obtained as described above: a standard assay can consist of 185 µl of 10 mM tris-HCl (pH 7.5), 10 µl of 125 mM of dTDP-rhamnose and 50 µl of protein crude extract (about 1 mg of total protein) or purified protein in solution (5 µg of purified protein). The reaction is started by the addition of 10 µl of 10 mM ethanolic solution of α-L-rhamnopyranosyl-3-hydroxydecanoyl-3-hydroxydecanoic acid (for $E_{3a}$) or α-L-rhamnopyranosyl-3-hydroxytetradecanoyl-3-hydroxytetradecanoic acid (for $E_{3b}$) and incubated for 1 h at 30° C. with shaking (600 rpm). Subsequently, the reaction is treated with 1 ml of acetone. Undissolved constituents are sedimented by centrifugation (16,100 g, 5 min, RT) and the sample is analyzed by means of LC-ESI-MS. The identification of the products takes place by analysis of the corresponding mass traces and the $MS^2$ spectra.

Cells according to the invention are preferred that have increased activities of the following enzyme combinations: $E_1$, $E_2$, $E_3$, $E_1E_2$, $E_1E_3$, $E_2E_3$ and $E_1E_2E_3$, of which the combination $E_2$, $E_2E_3$ and $E_1E_2E_3$, in particular $E_1E_2E_3$ is particularly preferred.

In a preferred embodiment of the cell according to the invention that has an increased activity of the enzyme combination $E_1E_2E_3$, n is preferably =1.

The cells according to the invention can be prokaryotes or eukaryotes. These can be mammalian cells (such as, for example, cells from man), plant cells or microorganisms such as yeasts, fungi or bacteria, wherein microorganisms are particularly preferred and bacteria and yeasts are most preferred.

Suitable bacteria, yeasts or fungi are in particular those bacteria, yeasts or fungi that are deposited in the Deutsche Sammlung von Mikroorganismen and Zellkulturen (German Collection of Microorganisms and Cell Cultures) GmbH (DSMZ), Brunswick, Germany, as listed on the DSMZ website.

Preferred cells according to the invention are those of the genera *Aspergillus, Corynebacterium, Brevibacterium, Bacillus, Acinetobacter, Alcaligenes, Lactobacillus, Paracoccus, Lactococcus, Candida, Pichia; Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium* and *Cupriavidus*, wherein *Aspergillus nidulans, Aspergillus niger, Alcaligenes latus, Bacillus megaterium, Bacillus subtilis, Brevibacterium flavum, Brevibacterium lactofermentum, Burkholderia andropogonis, B. brasilensis, B. calcdonica, B. caribensis, B. caryophylli, B. fungorum, B. gladioli, B. glathei, B. glumae, B. graminis, B. hospita, B. kururiensis, B. phenazinium, B. phymatum, B. phytofirmans, B. plantarii, B. sacchari, B. singaporensis, B. sordidicola, B. terricola, B. tropica, B. tuberum, B. ubonensis, B. unamae, B. xenovorans, B. anthina, B. pyrrocinia, B. thailandensis, Candida blankii, Candida rugosa, Corynebacterium glutamicum, Corynebacterium efficiens, Escherichia coli, Hansenula polymorpha, Kluveromyces lactis, Methylobacterium extorquens, Paracoccus versutus, Pseudomonas argentinensis, P. borbori, P. citronelolis, P. flavescens, P. mendocina, P. nitroreducens, P. oleovorans, P. pseudoalcaligenes, P. resinovorans, P. straminea, P. aurantiaca, P. aureofaciens, P. chlororaphis, P. fragi, P. lundensis, P. taetrolens, P. antarctica, P. azotoformans, P. blatchfordae, P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. proteolytica, P. rhodesiae, P. synxantha, P. thivervalensis, P. tolaasii, P. veronii, P. denitrificans, P. pertucinogena, P. cremoricolorata, P. fulva, P. monteilii, P. mosselii, P. parafulva, P. putida, P. balearica, P. stutzeri, P. amygdali, P. avellanae, P. caricapapayae, P. cichorii, P. coronafaciens, P. ficuserectae, P. helianthi, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. psychrophila, P. psychrotolerans, P. rathonis, P. reptilivora, P. resiniphila, P. rhizosphaerae, P. rubescens, P. salomonii, P. segitis, P. septica, P. simiae, P. suis, P. thermotolerans, P. aeruginosa, P. tremae, P. trivialis, P. turbinellae, P. tuticorinensis, P. umsongensis, P. vancouverensis, P. vranovensis, P. xanthomarina, Ralstonia eutropha, Rhodospirillum rubrum, Rhodobacter sphaeroides Saccharomyces cerevisiae, Yarrowia lipolytica* and *Zymomonas mobilis*, in particular *Pseudomonas putida, Escherichia coli* and *Burkholderia thailandensis* are particularly preferred.

Preferred cells according to the invention are able as the wild-type to form no or no detectable amounts of rhamnolipids and as the wild-type moreover have preferably no or no detectable activity of the enzymes $E_1$, $E_2$ and $E_3$.

It is advantageous according to the invention if the cell according to the invention is a cell which is able as the wild-type to form polyhydroxyalkanoates having chain lengths of the mono-alkanoate of $C_6$ to $C_{16}$. Such cells are, for example, *Burkholderia sp., Burkholderia thailandensis, Pseudomonas sp., Pseudomonas putida, Pseudomonas aeruginosa, Pseudomonas oleovorans, Pseudomonas stutzeri, Pseudomonas fluorescens, Pseudomonas citronellolis, Pseudomonas resinovorans, Comamonas testosteroni, Aeromonas hydrophila, Cupriavidus necator, Alcaligenes latus* and *Ralstonia eutropha*. In this connection, preferred cells according to the invention are genetically modified such that, compared to their wild-type, they are able to form fewer polyhydroxyalkanoates.

Such cells are described, for example, in De Eugenio et al., Environ Microbiol. 2010. 12(1):207-21 and Rehm et al., Appl Environ Microbiol. 2001. 67(7):3102-9.

Such a cell, able to form fewer polyhydroxyalkanoates compared to its wild-type, is in particular characterized in that, compared to its wild-type, it has a decreased activity of at least one enzyme $E_9$ or $E_{10}$, wherein $E_9$ represents a polyhydroxyalkanoate synthase, EC:2.3.1.-, in particular having polypeptide sequence Seq ID No. 30 or Seq ID No. 32 or having a polypeptide sequence in which up to 25%, preferably up to 20%, particularly preferably up to 15% in particular up to 10, 9, 8, 7, 6, 5, 4, 3, 2, 1% of the amino acid radicals compared to the respective reference sequence Seq ID No. 30 or Seq ID No. 32 are modified by deletion, insertion, substitution or a combination thereof and that still has at least 10%, preferably 50%, particularly preferably 80%, in particular more than 90% of the enzymatic activity of the enzyme having the respective reference sequence Seq ID No. 30 or Seq ID No. 32, wherein enzymatic activity for an enzyme $E_9$ is understood as meaning the ability to convert 3-hydroxyalkanoyl-coenzyme A to poly-3-hydroxyalkanoic acid, in particular 3-hydroxytetradecanoyl-coenzyme A to poly-3-hydroxytetradecanoic acid, and $E_{10}$ represents a 3-hydroxyalkanoyl-ACP:coenzyme A transferase, in particular having polypeptide sequence Seq ID No. 34 or Seq ID No. 36 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the respective reference sequence Seq ID No. 0.34 or Seq ID No. 36 by deletion, insertion, substitution or a combination thereof and that still has at least 10%, preferably 50%, particularly preferably 80%, in particular more than 90% of the enzymatic activity of the enzyme having the respective reference sequence Seq ID No. 34 or Seq ID No. 36, wherein enzymatic activity for an enzyme $E_{10}$ is understood as meaning the ability to convert 3-hydroxyalkanoyl-ACP to 3-hydroxy-alkananoyl-coenzyme A, in particular 3-hydroxyalkananoyl-ACP to 3-hydroxytetradecanoyl-coenzyme A.

For a general survey compare FIG. 1.

The activity of the enzyme $E_9$ is then determined using the samples obtained as described above for the enzymes Etto $E_3$, by first mixing 560 µl of 100 mM tris/HCl, pH 7.5, 20 µl of 35 mM DTNB in DMSO and 20 µl of 41 mM 3-hydroxydecanoyl-coenzyme A. Subsequently, 5 µg of purified enzyme $E_9$ in 100 µl of tris/HCl, pH 7.5 are added, and subsequently the increase in the extinction at 412 nm (caused by addition of 5,5'-dithiobis(2-nitrobenzoate) (DTNB) to free SH groups) over time (ΔE/min) is recorded continuously for 1 min in a spectrophotometer.

The activity of the enzyme $E_{10}$ is then determined using the samples obtained as described above for the enzymes $E_1$ to $E_3$. The standard assay contains 3 mM $MgCl_2$, 40 µM hydroxydecanoyl-coenzyme A and 20 μM E. coli ACP in 50 mM tris-HCl, pH 7.5, in a total volume of 200 μl. The reaction is started by addition of 5 μg of purified enzyme $E_{10}$ in 50 μl of tris/HCl, pH 7.5 and incubated for 1 h at 30° C. The reaction is stopped by addition of 50% (w/v) trichloroacetic acid and 10 mg/ml of BSA (30 μl). Released coenzyme A is determined spectrophotometrically by recording the increase in the extinction at 412 nm, caused by addition of 5,5'-dithio-bis(2-nitrobenzoate) (DTNB) to free SH groups, over time.

The formulation "decreased activity of an enzyme $E_x$" used is accordingly preferably understood as meaning an activity decreased by a factor of at least 0.5, particularly preferably of at least 0.1, moreover preferably of at least 0.01, moreover even more preferably of at least 0.001 and most preferably of at least 0.0001. The formulation "decreased activity" also comprises no detectable activity ("activity of zero"). The decrease in the activity of a certain enzyme can be effected, for example, by selective mutation or by other measures known to the person skilled in the art for decreasing the activity of a certain enzyme.

Methods for decreasing enzymatic activities in microorganisms are known to the person skilled in the art.

In particular, molecular biological techniques offer themselves here. The person skilled in the art finds instructions for the modification and decrease of protein expression and concomitant lowering of enzyme activity especially for *Pseudomonas* and *Burkholderia*, in particular for interrupting specific genes, for example, in Dubeau et al. 2009. BMC Microbiology 9:263; Singh & Röhm. Microbiology. 2008. 154:797-809 or Lee et al. FEMS Microbiol Lett. 2009. 297 (1):38-48.

Cells preferred according to the invention are characterized in that the decrease in the enzymatic activity is achieved by modification of a gene comprising one of the said nucleic acid sequences, wherein the modification is selected from the group comprising, preferably consisting of, insertion of foreign DNA in the gene, deletion of at least parts of the gene, point mutations in the gene sequence, RNA interference (siRNA), antisense RNA or modification (insertion, deletion or point mutations) of regulatory sequences, such as, for example, promoters and terminators or of ribosome binding sites, which flank the gene.

Foreign DNA is to be understood in this connection as meaning any DNA sequence which is "foreign" to the gene (and not to the organism), i.e. endogenous DNA sequences can also function in this connection as "foreign DNA".

In this connection it is particularly preferred that the gene is interrupted by insertion of a selection marker gene, thus the foreign DNA is a selection marker gene, wherein preferably the insertion was effected by homologous recombination in the gene locus.

In a preferred embodiment of the cell according to the invention, the cells concerned are *Pseudomonas putida* cells, which have a decreased polyhydroxyalkanoate synthesis compared to their wild-type. Such cells are described, for example, in Ren et al., Journal Applied Microbiology and Biotechnology 1998 June, 49(6):743-50 as GPp121, GPp122, GPp123 and GPp124, in Huisman et al., J Biol. Chem. 1991 Feb. 5; 266(4):2191-8 as GPp104 as well as in De Eugenio et al., Environ Microbiol. 2010. 12(1):207-21 as KT42C1 and in Ouyang et al. Macromol Biosci. 2007. 7(2): 227-33 as KTOY01 and KTOY02 and are preferred cells according to the invention.

For the case where the cell according to the invention is able to form a rhamnolipid having m=1, it is preferred that the radical

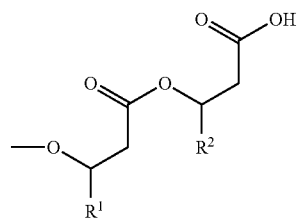

defined by means of $R^1$ and $R^2$ is derived from 3-hydroxyoctanoyl-3-hydroxyoctanoic acid, 3-hydroxyoctanoyl-3-hydroxydecanoic acid, 3-hydroxydecanoyl-3-hydroxyoctanoic acid, 3-hydroxyoctanoyl-3-hydroxydecenoic acid, 3-hydroxydecenoyl-3-hydroxyoctanoic acid, 3-hydroxyoctanoyl-3-hydroxydodecanoic acid, 3-hydroxydodecanoyl-3-hydroxyoctanoic acid, 3-hydroxyoctanoyl-3-hydroxydodecenoic acid, 3-hydroxydodecenoyl-3-hydroxyoctanoic acid, 3-hydroxydecanoyl-3-hydroxydecanoic acid, 3-hydroxydecanoyl-3-hydroxydecenoic acid, 3-hydroxydecenoyl-3-hydroxydecanoic acid, 3-hydroxydecanoyl-3-hydroxydecenoic acid, 3-hydroxydecenoyl-3-hydroxydecenoic acid, 3-hydroxydodecanoyl-3-hydroxydodecanoic acid, 3-hydroxydecanoyl-3-hydroxydecanoic acid, 3-hydroxydecanoyl-3-hydroxydodecenoic acid, 3-hydroxydodecenoyl-3-hydroxytetradecenoic acid, 3-hydroxytetradecanoyl-3-hydroxydecenoic acid, 3-hydroxydodecenoyl-3-hydroxydecanoic acid, 3-hydroxydecanoyl-3-hydroxytetradecanoic acid, 3-hydroxytetradecanoyl-3-hydroxydecanoic acid, 3-hydroxydecanoyl-3-hydroxytetradecenoic acid, 3-hydroxytetradecenoyl-3-hydroxydecanoic acid, 3-hydroxydodecanoyl-3-hydroxydodecenoic acid, 3-hydroxydodecanoyl-3-hydroxydecanoic acid, 3-hydroxydodecenoyl-3-hydroxydecanoic acid, 3-hydroxytetradecanoyl-3-hydroxytetradecanoic acid, 3-hydroxydodecanoyl-3-hydroxytetradecanoic acid, 3-hydroxytetradecanoyl-3-hydroxyhexadecanoyl-3-hydroxytetradecanoic acid, 3-hydroxytetradecanoyl-3-hydroxyhexadecanoic acid or 3-hydroxyhexadecanoyl-3-hydroxyhexadecanoic acid.

It is obvious to the person skilled in the art that a cell according to the invention is also able to form mixtures of different rhamnolipids of the general formula (I).

In this connection, it is preferred that the cells according to the invention are able to form mixtures of rhamnolipids of the general formula (I), which are characterized in that in more than 80% by weight, preferably more than 90% by weight, particularly preferably more than 95% by weight of the rhamnolipids formed n is =1 and the radical defined by means of $R^1$ and $R^2$ is derived in less than 10% by weight, preferably less than 5% by weight, particularly preferably less than 2% by weight of the rhamnolipids formed, from 3-hydroxydecanoyl-3-hydroxyoctanoic acid or 3-hydroxyoctanoyl-3-hydroxydecanoic acid, wherein the % by weight indicated refers to the sum of all rhamnolipids of the general formula (I) formed.

It is advantageous if the cell according to the invention has additionally been genetically modified with respect to $E_1$ to $E_3$ such that, compared to its wild-type, it has an increased activity as in each case specified below of at least one of the enzymes selected from the group consisting of at least one enzyme $E_4$, a dTTP:α-D-glucose-1-phosphate thymidylyl transferase, EC 2.7.7.24, in particular one having polypeptide sequence Seq ID No. 10 or having a polypeptide sequence in which up to 25%, preferably up to 20%, particularly preferably up to 15% in particular up to 10, 9, 8, 7, 6, 5, 4, 3, 2, 1% of the amino acid radicals compared to the reference sequence Seq ID No. 10 are modified by deletion, insertion, substitution or a combination thereof and that still has at least 10%, preferably 50%, particularly preferably 80%, in particular more than 90% of the enzymatic activity of the enzyme having the reference sequence Seq ID No. 10, wherein enzymatic activity for an enzyme $E_4$ is understood as meaning the ability to convert α-D-glucose-1-phosphate and dTTP to dTDP-glucose, at least one enzyme $E_5$, a dTTP-glucose-4,6-hydrolyase, EC 4.2.1.46, in particular one having polypeptide sequence Seq ID No. 12 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 12 by deletion, insertion, substitution or a combination thereof and that still has at least 10%, preferably 50%, particularly preferably 80%, in particular more than 90% of the enzymatic activity of the enzyme having the reference sequence Seq ID No. 12, wherein enzymatic activity for an enzyme $E_5$ is understood as meaning the ability to convert dTDP glucose to dTDP-4-dehydro-6-deoxy-D-glucose, at least one enzyme $E_6$, a dTDP-4-dehydrorhamnose-3,5-epimerase, EC 5.1.3.13, in particular one having polypeptide sequence Seq ID No. 14 or having a polypeptide sequence in which up to 25%, preferably up to 20%, particularly preferably up to 15% in particular up to 10, 9, 8, 7, 6, 5, 4, 3, 2, 1% of the amino acid radicals compared to the reference sequence Seq ID No. 14 are modified by deletion, insertion, substitution or a combination thereof and that still has at least 10%, preferably 50%, particularly preferably 80%, in particular more than 90% of the enzymatic activity of the enzyme having the reference sequence Seq ID No. 14, wherein enzymatic activity for an enzyme $E_6$ is understood as meaning the ability to convert dTDP-4-dehydro-6-deoxy-D-glucose to dTDP-4-dehydro-6-deoxy-L-mannose and at least one enzyme $E_7$, a dTDP-4-dehydrorhamnose reductase, EC 1.1.1.133, in particular one having polypeptide sequence Seq ID No. 16 or having a polypeptide sequence in which up to 25%, preferably up to 20%, particularly preferably up to 15% in particular up to 10, 9, 8, 7, 6, 5, 4, 3, 2, 1% of the amino acid radicals compared to the reference sequence Seq ID No. 16 are modified by deletion, insertion, substitution or a combination thereof and that still has at least 10%, preferably 50%, particularly preferably 80%, in particular more than 90% of the enzymatic activity of the enzyme having the reference sequence Seq ID No. 16, wherein enzymatic activity for an enzyme $E_7$ is understood as meaning the ability to convert dTDP-4-dehydro-6-deoxy-L-mannose to dTDP-6-deoxy-L-mannose.

The activity of the enzyme $E_4$ is determined using the samples obtained as above for the enzymes $E_1$ to $E_3$, by incubating α-D-glucose-1-phosphate (1.3 mM) with dTTP (5 mM) and 5 μg of purified enzyme $E_4$ in 50 μl of sodium phosphate buffer, pH 8.5 and stopping the reaction after 5, 10 and 20 min incubation at 30° C. by addition of 20 μl of chloroform. The mixture is then vortexed and centrifuged for 5 min at 16,000 g and room temperature. The aqueous phase is transferred to a new reaction vessel and the organic phase is extracted again with 80 μl of water. Both aqueous phases are combined and analyzed by means of HPLC. A Phenosphere ODS2 column (250×4.6 mm; Phenomenex, Torrance, USA) or a Spheresorb ODS2 column (250×4.6 mm; Waters, Milford, USA) is used here. The elution of the analytes takes place at a flow rate of 1 ml min$^{-1}$ using 0.5 M KH$_2$PO$_4$ (eluent A) for 15 min, followed by a linear gradient up to 80% eluent A and 20% methanol over a period of 14 min at a flow rate of 0.7 ml min$^{-1}$. Analytes which elute from the ODS2 columns are then injected into a Phenosphere SAX ion exchanger column (250×4.6 mm; Phenomenex, Torrance, USA) and the analytes are eluted using a flow rate of 1 ml min$^-$ and a linear ammonium formate gradient (2 to 600 mM over 25 min). The quantification of dTDP-glucose then takes place by means of its UV absorption using a photodiode array detector (DAD): The absorption maximum of thymidine is at 267 nm. The calibration takes place by means of authentic nucleotide sugar (Sigma-Aldrich, Munich, USA).

The activity of the enzyme $E_5$ is then determined using the samples obtained as described above for the enzymes $E_1$ to $E_3$ by incubating dTDP-α-D-glucose (1.3 mM) with 5 μg of purified enzyme $E_5$ in 50 μl of sodium phosphate buffer, pH 8.5, and stopping the reaction after 5, 10 and 20 min incubation at 30° C. by addition of 20 μl of chloroform. The mixture is then vortexed and centrifuged for 5 min at 16,000 g and room temperature. The aqueous phase is transferred to a new reaction vessel and the organic phase is again extracted with 80 μl of water. Both aqueous phases are combined and analyzed by means of HPLC. A Phenosphere ODS2 column (250×4.6 mm; Phenomenex, Torrance, USA) or a Spheresorb ODS2 column (250×4.6 mm; Waters, Milford, USA) is used here. The elution of the analytes takes place at a flow rate of 1 ml min$^-$ using 0.5 M KH$_2$PO$_4$ (eluent A) for 15 min, followed by a linear gradient of up to 80% eluent A and 20% methanol over a period of 14 min at a flow rate of 0.7 ml min$^{-1}$. Analytes which elute from the ODS2 columns are then injected into a Phenosphere SAX ion exchanger column (250×4.6 mm; Phenomenex, Torrance, USA) and the analytes are eluted using a flow rate of 1 ml min$^-$ and a linear ammonium formate gradient (2 to 600 mM over 25 min). The quantification of dTDP-glucose and dTDP-4-dehydro-6-deoxy-D-glucose then takes place by means of their UV absorption using a photodiode array detector (DAD). The absorption maximum of thymidine is at 267 nm. The calibration takes place by means of authentic nucleotide sugar (Sigma-Aldrich, Munich, USA).

The activity of the enzyme $E_6$ is then determined using the samples obtained as described above for the enzymes $E_1$ to $E_3$, by first incubating dTDP-α-D-glucose (1.3 mM) with 5 μg of purified enzyme $E_5$ in 50 μl of sodium phosphate buffer, pH 8.5, for 10 min at 30° C. Subsequently, 0.5 μg of purified enzyme $E_6$ are added, and after 5, 10 and 20 min incubation at 30° C. the reaction is stopped by addition of 20 μl of chloroform. The mixture is then vortexed and centrifuged for 5 min at 16,000 g and room temperature. The aqueous phase is transferred to a new reaction vessel and the organic phase is again extracted with 80 μl of water. Both aqueous phases are combined and analyzed by means of HPLC. A Phenosphere ODS2 column (250×46 mm; Phenomenex, Torrance, USA) or a Spheresorb ODS2 column (250×4.6 mm; Waters, Milford, USA) is used here. The elution of the analytes takes place at a flow rate of 1 ml min$^{-1}$ using 0.5 M KH$_2$PO$_4$ (eluent A) for 15 min, followed by a linear gradient of up to 80% eluent A and 20% methanol over a period of 14 min at a flow rate of 0.7 ml min$^{-1}$. Analytes which elute from the ODS2 columns are then injected into a Phenosphere SAX ion exchanger column (250×4.6 mm; Phenomenex, Torrance, USA) and the analytes are eluted using a flow rate of 1 ml min$^{-1}$ and a linear ammonium formate gradient (2 to 600 mM over 25 min). The quantification of dTDP-glucose, dTDP-4-dehydro-6-deoxy-D-glucose and dTDP-6-deoxy-L-mannose then takes place by means of their UV absorption using a photodiode array detector (DAD). The absorption maximum of thymidine is at 267 nm. The calibration takes place by means of authentic nucleotide sugar (Sigma-Aldrich, Munich, USA).

The activity of the enzyme $E_7$ is then determined using the samples obtained as described above for the enzymes $E_1$ to $E_3$, by first incubating dTDP-α-D-glucose (1.3 mM) with 5 µg of purified enzyme $E_5$ in 50 µl of sodium phosphate buffer, pH 8.5, for 10 min at 30° C. Subsequently, 5 µg of purified enzyme $E_6$ and 0.5 µg of purified enzyme $E_7$ as well as NADPH (10 mM) are added, and after incubation at 30° C. for 5, 10 and 20 min the reaction is stopped by addition of 20 µl chloroform. The mixture is then vortexed and centrifuged for 5 min at 16,000 g and room temperature. The aqueous phase is transferred to a new reaction vessel and the organic phase is again extracted with 80 µl of water. Both aqueous phases are combined and analyzed by means of HPLC. A Phenosphere ODS2 column (250×4.6 mm; Phenomenex, Torrance, USA) or a Spheresorb ODS2 column (250×4.6 mm; Waters, Milford, USA) is used here. The elution of the analytes takes place at a flow rate of 1 ml min$^{-1}$ using 0.5 M KH$_2$PO$_4$ (eluent A) for 15 min, followed by a linear gradient of up to 80% eluent A and 20% methanol over a period of 14 min at a flow rate of 0.7 ml min$^-$. Analytes which elute from the ODS2 columns are then injected into a Phenosphere SAX ion exchanger column (250×4.6 mm; Phenomenex, Torrance, USA) and the analytes are eluted using a flow rate of 1 ml min$^-$ and a linear ammonium formate gradient (2 to 600 mM over 25 min). The quantification of dTDP-glucose, dTDP-4-dehydro-6-deoxy-D-glucose, dTDP-6-deoxy-L-mannose and dTDP-4-dehydro-6-deoxy-L-mannose then takes place by means of their UV absorption using a photodiode array detector (DAD). The absorption maximum of thymidine is 267 nm. The calibration takes place by means of authentic nucleotide sugar (Sigma-Aldrich, Munich, USA).

Cells according to the invention are preferred, which have increased activities of the following enzyme combinations: $E_4E_5$, $E_4E_6$, $E_4E_7$, $E_5E_6$, $E_5E_7$, $E_6E_7$, $E_4E_5E_6$, $E_4E_5E_7$, $E_5E_6E_7$, $E_4E_6E_7$, $E_4E_5E_6E_7$,
of which the combination
$E_4E_5E_6E_7$
is particularly preferred.

It can be advantageous according to the invention if the cell according to the invention has been genetically modified in the fatty acid biosynthesis such that the enzymatic reactions, which lead to the conversion of acyl-ACP and malonyl-coenzyme A to 3-ketoacyl-ACP and/or to the conversion of 3-ketoacyl-ACP to (R)-3-hydroxyalkanoyl-ACP, are increased. Additionally or alternatively it can be advantageous according to the invention if the cell according to the invention has been genetically modified in the fatty acid biosynthesis such that the enzymatic reactions, which lead to the conversion of (R)-3-hydroxyalkanoyl-ACP to trans-2-enoyl-ACP and/or to the conversion of trans-2-enoyl-ACP to acyl-ACP, are attenuated.

It can be just as advantageous if the cell according to the invention has been genetically modified in the β-oxidation of fatty acids such that the enzymatic reactions, which lead to the conversion of acyl-coenzyme A to trans-2-enoyl-coenzyme A and/or to the conversion of trans-2-enoyl-coenzyme A to (S)-3-hydroxyalkanoyl-coenzyme A, are increased. Additionally or alternatively, it can be advantageous according to the invention if the cell according to the invention in the β-oxidation of fatty acids has been genetically modified such that the enzymatic reactions, which lead to the conversion of (S)-3-hydroxyalkanoyl-coenzyme A to 3-ketoacyl-coenzyme A and/or to the conversion of 3-ketoacyl-coenzyme A to acyl-coenzyme A and acetyl-coenzyme A, are diminished.

For a general survey compare FIG. 1.

Since the cells according to the invention can be used advantageously for the production of rhamnolipids and since these lipids are subsequently optionally purified, it is advantageous if the cells according to the invention have an increased activity compared to their wild-type of at least an enzyme $E_8$, which catalyzes the export of a rhamnolipid of the general formula (I) from the cell into the surrounding medium.

Preferably, in this connection proteins $E_8$ are selected from the group consisting of an enzyme $E_8$ having polypeptide sequence Seq ID No. 8, Seq ID No. 24, Seq ID No. 26 or Seq ID No. 28 or having a polypeptide sequence in which up to 25%, preferably up to 20%, particularly preferably up to 15% in particular up to 10, 9, 8, 7, 6, 5, 4, 3, 2, 1% of the amino acid radicals are modified by deletion, insertion, substitution or a combination thereof compared to the respective reference sequence Seq ID No. 8, Seq ID No. 24, Seq ID No. 26 or Seq ID No. 28 and that still has at least 50%, preferably 65%, particularly preferably 80%, in particular more than 90% of the enzymatic activity of the enzyme having the respective reference sequence Seq ID No. 8, Seq ID No. 24, Seq ID No. 26 or Seq ID No. 28, wherein enzymatic activity for an enzyme $E_8$ is understood as meaning the ability to export a rhamnolipid of the general formula (I) from the cell into the surrounding medium.

A further, preferred embodiment of cells according to the invention is characterized in that it contains at least one of the nucleic acids or vectors according to the invention mentioned below.

Cells according to the invention can advantageously be used for the production of rhamnolipids. Thus a further subject of the invention is the use of cells according to the invention for the production of compounds of the general formula (I).

A further subject of the present invention is a method for producing rhamnolipids of the general formula (I), wherein
m=2, 1 or 0, in particular 1 or 0,
n=1 or 0, in particular 1,
$R^1$ and $R^2$=independently of one another identical or different organic radical having 2 to 24, preferably 5 to 13 carbon atoms, in particular optionally branched, optionally substituted, in particular hydroxy-substituted, optionally unsaturated, in particular optionally mono-, di- or tri-unsaturated, alkyl radical, preferably that selected from the group consisting of pentenyl, heptenyl, nonenyl, undecenyl and tridecenyl and $(CH_2)_o$—$CH_3$ having o=1 to 23, preferably 4 to 12, comprising the process steps
I) bringing into contact the cell according to the invention with a medium containing a carbon source
II) culturing the cell under conditions that make it possible for the cell to form rhamnolipid from the carbon source and
III) optionally isolating the rhamnolipids formed.

The genetically modified cells according to the invention can be brought into contact with the nutrient medium continuously or discontinupusly in the batch process (batch culture) or in the fed-batch process (feed process) or repeated fed-batch process (repetitive feed process) for the purpose of the production of the abovementioned products and thus cultured. A semi-continuous process is also conceivable, as is described in GB-A-1009370. A summary of known culturing methods are described in the textbook of Chmiel ("Bioprozesstechnik 1. Einführung in die Bioverfahrenstechnik" [Bioprocess Technology 1. Introduction to the Bioprocess Technique](Gustav Fischer Verlag, Stuttgart, 1991)) or in the textbook of Storhas ("Bioreaktoren und periphere Einrichtungen" [Bioreactors and Peripheral Devices], Vieweg Verlag, Brunswick/Wiesbaden, 1994).

The culture medium to be used must satisfy in a suitable manner the demands of the respective strains. Descriptions of culture media of different yeast strains are contained, for example, in "Nonconventional yeast in biotechnology" (Ed. Klaus Wolf, Springer-Verlag Berlin, 1996). The carbon source used can be carbohydrates such as, for example, glucose, sucrose, arabinose, xylose, lactose, fructose, maltose, molasses, starch, cellulose and hemicellulose, vegetable and animal oils and fats such as, for example, soybean oil, safflower oil, peanut oil, hempseed oil, jatropha oil, coconut fat, calabash oil, linseed oil, corn oil, poppyseed oil, evening primrose oil, olive oil, palm kernel oil, palm oil, rapeseed oil, sesame oil, sunflower oil, grapeseed oil, walnut oil, wheat germ oil and coconut oil, fatty acids, such as, for example, caprylic acid, capric acid, lauric acid, myristic acid, palmitic acid, palmitoleic acid, stearic acid, arachidonic acid, behenic acid, oleic acid, linoleic acid, linolenic acid, gamma-linolenic acid and its methyl or ethyl ester as well as fatty acid mixtures, mono-, di- and triglycerides containing the fatty acids just mentioned, alcohols such as, for example, glycerol, ethanol and methanol, hydrocarbons such as methane, carbon-containing gases and gas mixtures, such as CO, $CO_2$, synthesis or flue gas, amino acids such as L-glutamate or L-valine or organic acids such as, for example, acetic acid. These substances can be used individually or as a mixture. The use of carbohydrates, in particular of monosaccharides, oligosaccharides or polysaccharides, as the carbon source as is described in U.S. Pat. No. 6,01,494 and U.S. Pat. No. 6,136,576 as well as of hydrocarbons, in particular of alkanes, alkenes and alkynes as well as the monocarboxylic acids derived therefrom and the mono-, di and triglycerides derived from these monocarboxylic acids, as well as of glycerol and acetate, is particularly preferred. Mono-, di- and triglycerides containing the esterification products of glycerol with caprylic acid, capric acid, lauric acid, myristic acid, palmitic acid, palmitoleic acid, stearic acid, arachidonic acid, behenic acid, oleic acid, linoleic acid, linolenic acid and/or gamma-linolenic acid are very particularly preferred.

It is a great advantage of the present invention that the cells according to the invention are able to form rhamnolipids from the simplest carbon sources such as, for example, glucose, sucrose or glycerol, such that a provision of longer-chain C sources in the medium during the method according to the invention is not necessary. Thus it is advantageous in the case of lack of availability that the medium in step I) of the method according to the invention contains no or no detectable amounts of carboxylic acids having a chain length of greater than six carbon atoms or esters or glycerides derivable from these.

The nitrogen source used can be organic nitrogen-containing compounds such as peptones, yeast extract, meat extract, malt extract, cornsteep water, soybean meal and urea or inorganic compounds such as ammonium sulfate, ammonium chloride, ammonium phosphate, ammonium carbonate and ammonium nitrate, ammonia, ammonium hydroxide or ammonia water. The nitrogen sources can be used individually or as a mixture.

The phosphorus source used can be phosphoric acid, potassium dihydrogenphosphate or dipotassium hydrogenphosphate or the corresponding sodium-containing salts. The culture medium must furthermore contain salts of metals such as, for example, magnesium sulfate or iron sulfate, which are necessary for growth. Finally, essential growth promoters such as amino acids and vitamins can be employed additionally to the abovementioned substances. Suitable precursors can moreover be added to the culture medium. The said feedstocks can be added to the culture in the form of a single batch or fed in a suitable manner during culturing.

Basic compounds such as sodium hydroxide, potassium hydroxide, ammonia or ammonia water or acidic compounds such as phosphoric acid or sulfuric acid are suitably employed for pH control of the culture. Antifoam agents such as, for example, fatty acid polyglycol esters can be employed for the control of the foam development. Suitable selectively acting substances such as, for example, antibiotics can be added to the medium for maintaining the stability of plasmids. To maintain aerobic conditions, oxygen or oxygen-containing gas mixtures such as, for example, air are incorporated into the culture.

The temperature of the culture is normally more than 20° C., preferably more than 25° C., it can also be more than 40° C., wherein advantageously a culturing temperature of 95° C., particularly preferably 90° C. and most preferably 80° C. is not exceeded.

In step III) of the method according to the invention, the rhamnolipids formed by the cells can optionally be isolated from the cells and/or the nutrient medium, wherein for the isolation all methods known to the person skilled in the art for the isolation of low molecular weight substances from complex compositions are possible, such as, for example, filtration, extraction, adsorption (chromatography) or cry stallization.

Moreover, the product phase contains residues of biomass and various impurities, such as oils, fatty acids and other nutrient media constituents. The separation of the impurities preferably takes place in a solvent-free process. Thus, for example, the product phase can be diluted with water to facilitate the adjustment of the pH. The product and aqueous phases can then be homogenized by converting the rhamnolipids into a water-soluble form by lowering or raising the pH by acids or alkalis. Potentially, the solubilization of the rhamnolipids in the aqueous phase can be assisted by incubation at higher temperatures, e.g. at 60 to 90° C., and constant mixing. By subsequent raising or lowering of the pH by alkalis or acids the rhamnolipids can then again be converted into a water-insoluble form, such that they can easily be separated from the aqueous phase. The product phase can then be washed once or several times with water to remove the water-soluble impurities.

Oil residues can be separated off, for example by extraction by means of suitable solvents advantageously by means of organic solvents. An alkane such as, for example, n-hexane is preferred as a solvent.

The separation of the product from the aqueous phase can be effected alternatively to the solvent-free process described above using a suitable solvent, e.g. an ester such as, for example, ethyl acetate or butyl acetate. The said extraction steps can be carried out in any desired sequence.

In this connection, solvents are preferably employed, in particular organic solvents. n-Pentanol is preferred as a solvent. A distillation, for example, takes place for the removal of the solvent. Subsequently, the lyophilized product can be further purified, for example by means of chromatographic methods. By way of example, at this point precipitation by means of suitable solvents, extraction by means of suitable solvents, complexation, for example by means of cyclodextrins or cyclodextrin derivatives, crystallization, purification or isolation by means of chromatographic methods or conversion of the rhamnolipids into easily separable derivatives may be mentioned.

The rhamnolipids that can be produced using the method according to the invention are likewise a subject of the present invention, in particular also the rhamnolipid mixtures described above, that can be produced using the method according to the invention.

The rhamnolipids and mixtures that can be produced using the method according to the invention can advantageously be employed in cleaning agents, in cosmetic or pharmaceutical formulations as well as in plant protection formulations.

Thus a further subject of the present invention is the use of the rhamnolipids obtained using the method according to the invention for the production of cosmetic, dermatological or pharmaceutical formulations, of plant protection formulations and of care and cleaning agents and surfactant concentrates.

The term "care agents" is understood here as meaning a formulation that fulfills the purpose of maintaining an article in its original form, reducing or avoiding the effects of external influences (e.g. time, light, temperature, pressure, pollution, chemical reaction with other reactive compounds coming into contact with the article) such as, for example, aging, pollution, material fatigue, or even improving desired positive properties of the article. For the last point, for example, an improved hair gloss or a greater elasticity of the article considered may be mentioned.

"Plant protection formulations" are to be understood as meaning those formulations that by the nature of their preparation are obviously used for plant protection; this is in particular the case if at least one compound from the classes consisting of the herbicides, fungicides, insecticides, acaricides, nematicides, protective substances against bird damage, plant nutrients and soil structure-improving agents is contained in the formulation.

According to the invention, rhamnolipids produced using the method according to the invention are preferably used in care and cleaning agents for housekeeping, industry, in particular for hard surfaces, leather or textiles.

A contribution to achieving the object is provided by an isolated nucleic acid, which contains at least in each case a sequence selected from the three groups [A1 to G1], [A2 to G2] and [A3 to G3],
wherein
the group [A1 to G1] consists of the following sequences:
A1a) a sequence according to Seq ID No. 1, wherein this sequence codes for a protein, which is able
to convert 3-hydroxydecanoyl-ACP via 3-hydroxydecanoyl-3-hydroxydecanoyl-ACP to 3-hydroxydecanoyl-3-hydroxydecanoic acid,
B1a) an intron-free sequence that is derived from a sequence according to A1a) and that encodes the same protein or peptide as the sequence according to Seq ID No. 1,
C1a) a sequence that encodes a protein or peptide that comprises the amino acid sequence according to Seq ID No. 2; and that is preferably able
to convert 3-hydroxydecanoyl-ACP via 3-hydroxydecanoyl-3-hydroxydecanoyl-ACP to 3-hydroxydecanoyl-3-hydroxydecanoic acid,
D1a) a sequence that is identical with a sequence according to one of the groups A1a) to C1a), particularly preferably according to group A1a), to at least 70%, particularly preferably to at least 90%, moreover preferably to at least 95% and most preferably to at least 99%, wherein this sequence preferably codes for a protein or peptide, which is able
to convert 3-hydroxydecanoyl-ACP via 3-hydroxydecanoyl-3-hydroxydecanoyl-ACP to 3-hydroxydecanoyl-3-hydroxydecanoic acid,
E1a) a sequence that hybridizes or, taking into consideration the degeneracy of the genetic code, would hybridize with the complementary strand of a sequence according to one of the groups A1a) to D1a), particularly preferably according to group A1a), wherein this sequence preferably codes for a protein or peptide, which is able
to convert 3-hydroxydecanoyl-ACP via 3-hydroxydecanoyl-3-hydroxydecanoyl-ACP to 3-hydroxydecanoyl-3-hydroxydecanoic acid,
F1a) a derivative of a sequence according to one of the groups A1a) to E1a), particularly preferably according to group A1a), obtained by substitution, addition, inversion and/or deletion of at least one base, preferably of at least 2 bases, moreover preferably of at least 5 bases and most preferably of at least 10 bases, but preferably of not more than 100 bases, particularly preferably of not more than 50 bases and most preferably of not more than 25 bases, wherein this derivative preferably codes for a protein or peptide, which is able
to convert 3-hydroxydecanoyl-ACP via 3-hydroxydecanoyl-3-hydroxydecanoyl-ACP to 3-hydroxydecanoyl-3-hydroxydecanoic acid,
G1a) a complementary sequence to a sequence according to one of the groups A1a) to F1a), particularly preferably according to group A1a),
A1b) a sequence according to Seq ID No. 17, wherein this sequence codes for a protein, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid,
B1b) an intron-free sequence that is derived from a sequence according to A1b) and that encodes the same protein or peptide as the sequence according to Seq ID No. 17,
C1b) a sequence that encodes a protein or peptide that comprises the amino acid sequence according to Seq ID No. 18, and that preferably is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid,
D1b) a sequence that is identical with a sequence according to one of the groups A1b) to C1b), particularly preferably according to group A1b), to at least 70%, particularly preferably to at least 90%, moreover preferably to at least 95% and most preferably to at least 99%, wherein this sequence preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid,
E1b) a sequence that hybridizes or, taking into consideration the degeneracy of the genetic code, would hybridize with the complementary strand of a sequence according to one of the groups A1b) to D1b), particularly preferably according to group A1b), wherein this sequence preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid,
F1b) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A1b) to E1b), particularly preferably according to group A1b), wherein this derivative preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, and G1b) a complementary sequence to a sequence according to one of the groups A1b) to F1b), particularly preferably according to group A1b), and A1c) a sequence according to Seq ID No. 77, wherein this sequence codes for a protein, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, B1c) an intron-free sequence that is derived from a sequence according to A1c) and that encodes the same protein or peptide as the sequence according to Seq ID No. 77, C1c) a sequence that encodes a protein or peptide that comprises the amino acid sequence according to Seq ID No. 78, and that preferably is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, D1c) a sequence that is identical with a sequence according to one of the groups A1c) to C1c), particularly preferably according to group A1c), to at least 70%, particularly preferably to at least 90%, moreover preferably to at least 95% and most preferably to at least 99%, wherein this sequence preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, E1c) a sequence that hybridizes or, taking into consideration the degeneracy of the genetic code, would hybridize with the complementary strand of a sequence according to one of the groups A1c) to D1c), particularly preferably according to group A1c), wherein this sequence preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, F1c) a derivative obtained by substitution, addition, inversion and/or deletion of at least one base, preferably of at least 2 bases, moreover preferably of at least 5 bases and most preferably of at least 10 bases, but preferably of not more than 100 bases, particularly preferably of not more than 50 bases and most preferably of not more than 25 bases of a sequence according to one of the groups A1c) to E1c), particularly preferably according to group A1c), wherein this derivative preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, and G1c) a complementary sequence to a sequence according to one of the groups A1c) to F1c), particularly preferably according to group A1c), and A1d) a sequence according to Seq ID No. 79, wherein this sequence codes for a protein, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, B1d) an intron-free sequence that is derived from a sequence according to A1d) and that encodes the same protein or peptide as the sequence according to Seq ID No. 79, C1d) a sequence that encodes a protein or peptide that comprises the amino acid sequence according to Seq ID No. 80, and that preferably is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, D1d) a sequence that is identical with a sequence according to one of the groups A1d) to C1d), particularly preferably according to group A1d), to at least 70%, particularly preferably to at least 90%, moreover preferably to at least 95% and most preferably to at least 99%, wherein this sequence preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, E1d) a sequence that hybridizes or, taking into consideration the degeneracy of the genetic code, would hybridize with the complementary strand of a sequence according to one of the groups A1d) to D1d), particularly preferably according to group A1d), wherein this sequence preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, F1d) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A1d) to E1d), particularly preferably according to group A1d), wherein this derivative preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, and G1d) a complementary sequence to a sequence according to one of the groups A1d) to F1d), particularly preferably according to group A1d), and A1e) a sequence according to Seq ID No. 81, wherein this sequence codes for a protein, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, B1e) an intron-free sequence that is derived from a sequence according to A1e) and that encodes the same protein or peptide as the sequence according to Seq ID No. 81, C1e) a sequence that encodes a protein or peptide that comprises the amino acid sequence according to Seq ID No. 82, and that preferably is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, D1e) a sequence that is identical with a sequence according to one of the groups A1e) to C1e), particularly preferably according to group A1e), to at least 70%, particularly preferably to at least 90%, moreover preferably to at least 95% and most preferably to at least 99%, wherein this sequence preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, E1e) a sequence that hybridizes or, taking into consideration the degeneracy of the genetic code, would hybridize with the complementary strand of a sequence according to one of the groups A1e) to D1e), particularly preferably according to group A1e), wherein this sequence preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, F1e) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A1e) to E1e), particularly preferably according to group A1e), wherein this derivative preferably codes for a protein or peptide, which is able
to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, and
G1e) a complementary sequence to a sequence according to one of the groups A1e) to F1e), particularly preferably according to group A1e), and
the group [A2 to G2] consists of the following sequences:
A2a) a sequence according to Seq ID No. 3, wherein this sequence codes for a protein, which is able
to convert dTDP-rhamnose and 3-hydroxydecanoyl-3-hydroxydecanoic acid to α-L-rhamnopyranosyl-3-hydroxydecanoyl-3-hydroxydecanoic acid,
B2a) an intron-free sequence that is derived from a sequence according to A2a) and that encodes the same protein or peptide as the sequence according to Seq ID No. 3,
C2a) a sequence that encodes a protein or peptide that comprises the amino acid sequence according to Seq ID No. 4, and which preferably is able
to convert dTDP-rhamnose and 3-hydroxydecanoyl-3-hydroxydecanoic acid to α-L-rhamnopyranosyl-3-hydroxydecanoyl-3-hydroxydecanoic acid,
D2a) a sequence that is identical with a sequence according to one of the groups A2a) to C2a), particularly preferably according to group A2a), to at least 80%, particularly preferably to at least 90%, moreover preferably to at least 95% and most preferably to at least 99%, wherein this sequence preferably codes for a protein or peptide, which is able
to convert dTDP-rhamnose and 3-hydroxydecanoyl-3-hydroxydecanoic acid to α-L-rhamnopyranosyl-3-hydroxydecanoyl-3-hydroxydecanoic acid,
E2a) a sequence that hybridizes or, taking into consideration the degeneracy of the genetic code, would hybridize with the complementary strand of a sequence according to one of the groups A2a) to D2a), particularly preferably according to group A2a), wherein this sequence preferably codes for a protein or peptide, which is able
to convert dTDP-rhamnose and 3-hydroxydecanoyl-3-hydroxydecanoic acid to α-L-rhamnopyranosyl-3-hydroxydecanoyl-3-hydroxydecanoic acid,
F2a) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A2a) to E2a), particularly preferably according to group A2a), wherein this derivative preferably codes for a protein or peptide, which is able
to convert dTDP-rhamnose and 3-hydroxydecanoyl-3-hydroxydecanoic acid to α-L-rhamnopyranosyl-3-hydroxydecanoyl-3-hydroxydecanoic acid,
G2a) a complementary sequence to a sequence according to one of the groups A2a) to F2a), particularly preferably according to group A2a),
A2b) a sequence according to Seq ID No. 19, wherein this sequence codes for a protein, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
B2b) an intron-free sequence that is derived from a sequence according to A2b) and that encodes the same protein or peptide as the sequence according to Seq ID No. 19,
C2b) a sequence that encodes a protein or peptide that comprises the amino acid sequence according to Seq ID No. 20, and which preferably is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
D2b) a sequence that is identical with a sequence according to one of the groups A2b) to C2b), particularly preferably according to group A2b), to at least 70%, particularly preferably to at least 90%, moreover preferably to at least 95% and most preferably to at least 99%, wherein this sequence preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
E2b) a sequence that hybridizes or, taking into consideration the degeneracy of the genetic code, would hybridize with the complementary strand of a sequence according to one of the groups A2b) to D2b), particularly preferably according to group A2b), wherein this sequence preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
F2b) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A2b) to E2b), particularly preferably according to group A2b), wherein this derivative preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and
G2b) a complementary sequence to a sequence according to one of the groups A2b) to F2b), particularly preferably according to group A2b),
A2c) a sequence according to Seq ID No. 83, wherein this sequence codes for a protein, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
B2c) an intron-free sequence that is derived from a sequence according to A2c) and that encodes the same protein or peptide as the sequence according to Seq ID No. 83,
C2c) a sequence that encodes a protein or peptide that comprises the amino acid sequence according to Seq ID No. 84, and which preferably is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
D2c) a sequence that is identical with a sequence according to one of the groups A2c) to C2c), particularly preferably according to group A2c), to at least 70%, particularly preferably to at least 90%, moreover preferably to at least 95% and most preferably to at least 99%, wherein this sequence preferably codes for a protein or peptide, which is able
to convert dTDP=rhamnose and 3-hydroxytetradecanoyl-3-hydroxytetradecanoicacid to α-L-rhamnopyranosyl-3-hydroxytetradecanoyl-3-hydroxytetradecanoic acid,
E2c) a sequence that hybridizes or, taking into consideration the degeneracy of the genetic code, would hybridize with the complementary strand of a sequence according to one of the groups A2c) to D2c), particularly preferably according to group A2c), wherein this sequence preferably codes for a protein or peptide, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, F2c) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A2c) to E2c), particularly preferably according to group A2c), wherein this derivative preferably codes for a protein or peptide, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and G2c) a complementary sequence to a sequence according to one of the groups A2c) to F2c), particularly preferably according to group A2c), A2d) a sequence according to Seq ID No. 85, wherein this sequence codes for a protein, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, B2d) an intron-free sequence that is derived from a sequence according to A2d) and that encodes the same protein or peptide as the sequence according to Seq ID No. 85, C2d) a sequence that encodes a protein or peptide that comprises the amino acid sequence according to Seq ID No. 86, and which preferably is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, D2d) a sequence that is identical with a sequence according to one of the groups A2d) to C2d), particularly preferably according to group A2d), to at least 70%, particularly preferably to at least 90%, moreover preferably to at least 95% and most preferably to at least 99%, wherein this sequence preferably codes for a protein or peptide, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, E2d) a sequence that hybridizes or taking into consideration the degeneracy of the genetic code, would hybridize with the complementary strand of a sequence according to one of the groups A2d) to D2d), particularly preferably according to group A2d), wherein this sequence preferably codes for a protein or peptide, which is able to convert dTDP-rharinose and 3-hydroxytetradecanoyl-3-hydroxytetradecanoic acid to α-L-rhamnopyranosyl-3-hydroxytetradecanocanoyl-3-hydroxytetradecanoic acid, F2d) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A2d) to E2d), particularly preferably according to group A2d), wherein this derivative preferably codes for a protein or peptide, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and G2d) a complementary sequence to a sequence according to one of the groups A2d) to F2d), particularly preferably according to group A2d), and A2e) a sequence according to Seq ID No. 87, wherein this sequence codes for a protein, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, B2e) an intron-free sequence that is derived from a sequence according to A2e) and that encodes the same protein or peptide as the sequence according to Seq ID No. 87, C2e) a sequence that encodes a protein or peptide that comprises the amino acid sequence according to Seq ID No. 88, and which preferably is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, D2e) a sequence that is identical with a sequence according to one of the groups A2e) to C2e), particularly preferably according to group A2e), to at least 70%, particularly preferably to at least 90%, moreover preferably to at least 95% and most preferably to at least 99%, wherein this sequence preferably codes for a protein or peptide, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, E2e) a sequence that hybridizes or, taking into consideration the degeneracy of the genetic code, would hybridize with the complementary strand of a sequence according to one of the groups A2e) to D2e), particularly preferably according to group A2e), wherein this sequence preferably codes for a protein or peptide, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, F2e) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence, according to one of the groups A2e) to E2e), particularly preferably according to group A2e), wherein this derivative preferably codes for a protein or peptide, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and G2e) a complementary sequence to a sequence according to one of the groups A2e) to F2e), particularly preferably according to group A2e), and the group [A3 to G3] consists of the following sequences:

A3a) a sequence according to Seq ID No. 5, wherein this sequence codes for a protein, which is able to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, B3a) an intron-free sequence that is derived from a sequence according to A3a) and that encodes the same protein or peptide as the sequence according to Seq ID No. 5, C3a) a sequence that encodes a protein or peptide that comprises the amino acid sequence according to Seq ID No. 6, and which preferably is able to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, D3a) a sequence that is identical with a sequence according to one of the groups A3a) to C3a), particularly preferably according to group A3a), to at least 80%, particularly preferably to at least 90%, moreover preferably to at least 95% and most preferably to at least 99%, wherein this sequence preferably codes for a protein or peptide, which is able to convert dTDP-rhamnose and α-L-rhamnopyranosyl-3-hydroxydecanoyl-3-hydroxydecanoic acid to α-L-rhamnopyranosyl-(1-2)-α-L-rhamnopyransyl-3-hydroxydecanoyl-3-hydroxydecanoic acid, E3a) a sequence that hybridizes or, taking into consideration the degeneracy of the genetic code, would hybridize with the complementary strand of a sequence according to one of the groups A3a) to D3a), particularly preferably according to group A3a), wherein this sequence preferably codes for a protein or peptide, which is able to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, F3a) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A3a) to E3a), particularly preferably according to group A3a), wherein this derivative preferably codes for a protein or peptide, which is able to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, G3a) a complementary sequence to a sequence according to one of the groups A3a) to F3a), particularly preferably according to group A3a), A3b) a sequence according to Seq ID No. 21, wherein this sequence codes for a protein, which is able to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, B3b) an intron-free sequence that is derived from a sequence according to A3b) and that encodes the same protein or peptide as the sequence according to Seq ID No. 21, C3b) a sequence that encodes a protein or peptide that comprises the amino acid sequence according to Seq ID No. 22, and which preferably is able to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, D3b) a sequence that is identical with a sequence according to one of the groups A3b) to C3b); particularly preferably according to group A3b), to at least 60%, particularly preferably to at least 90%, moreover preferably to at least 95% and most preferably to at least 99%, wherein this sequence preferably codes for a protein or peptide, which is able to convert dTDP-rhamnose and α-L-rhamnopyranosyl-3-hydroxytetradecanoyl-3-hydroxy-tetradecanol acid to α-L-rhamnopyranosyl-(1-2)-α-L-rhamnopyranosyl-3-hydroxytetradecanoyl-3-hydroxytetradecanoic acid, E3b) a sequence that hybridizes or, taking into consideration the degeneracy of the genetic code, would hybridize with the complementary strand of a sequence according to one of the groups A3b) to D3b), particularly preferably according to group A3b), wherein this sequence preferably codes for a protein or peptide, which is able to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, F3b) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A3b) to E3b), particularly preferably according to group A3b), wherein this derivative preferably codes for a protein or peptide, which is able to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, and G3b) a complementary sequence to a sequence according to one of the groups A3b) to F3b), particularly preferably according to group A3b), A3c) a sequence according to Seq ID No. 89, wherein this sequence codes for a protein, which is able to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, B3c) an intron-free sequence that is derived from a sequence according to A3c) and that encodes the same protein or peptide as the sequence according to Seq ID No. 89, C3c) a sequence that encodes a protein or peptide that comprises the amino acid sequence according to Seq ID No. 90, and which preferably is able to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, D3c) a sequence that is identical with a sequence according to one of the groups A3c) to C3c); particularly preferably according to group A3c), to at least 60%, particularly preferably to at least 90%, moreover preferably to at least 95% and most preferably to at least 99%, wherein this sequence preferably codes for a protein or peptide, which is able to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, E3c) a sequence that hybridizes or, taking into consideration the degeneracy of the genetic code, would hybridize with the complementary strand of a sequence according to one of the groups A3c) to D3c), particularly preferably according to group A3c), wherein this sequence preferably codes for a protein or peptide, which is able to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, F3c) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A3c) to E3c), particularly preferably according to group A3c), wherein this derivative preferably codes for a protein or peptide, which is able to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, and G3c) a complementary sequence to a sequence according to one of the groups A3c) to F3c), particularly preferably according to group A3c) and A3d) a sequence according to Seq ID No. 91, wherein this sequence codes for a protein, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoc acid, B3d) an intron-free sequence that is derived from a sequence according to A3d) and that encodes the same protein or peptide as the sequence according to Seq ID No. 91, C3d) a sequence that encodes a protein or peptide that comprises the amino acid sequence according to Seq ID No. 92, and which preferably is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, D3d) a sequence that is identical with a sequence according to one of the groups A3d) to C3d), particularly preferably according to group A3d), to at least 60%, particularly preferably to at least 90%, moreover preferably to at least 95% and most preferably to at least 99%, wherein this sequence preferably codes for a protein or peptide, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, E3d) a sequence that hybridizes or, taking into consideration the degeneracy of the genetic code, would hybridize with the complementary strand of a sequence according to one of the groups A3d) to D3d), particularly preferably according to group A3d), wherein this sequence preferably codes for a protein or peptide, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, F3d) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A3d) to E3d), particularly preferably according to group A3d), wherein this derivative preferably codes for a protein or peptide, which is able
to convert dTDP-rhamnose and α-L-rhamnopyranosyl-3-hydroxytetradecanoyl-3-hydroxytetradecanoicacid to α-L-rhamnopyranosyl-(1-2)-α-L-rhamnopyranosyl-3-hydroxytetradecanoyl-3-hydroxytetradecanoic acid, and G3d) a complementary sequence to a sequence according to one of the groups A3d) to F3d), particularly preferably according to group A3d).

The "nucleotide identity" or "amino acid identity" is determined here with the aid of known methods. Generally, specific computer programs having algorithms taking into consideration special requirements are used.

Preferred methods for the determination of the identity for the present produce the greatest agreement between the sequences to be compared. Computer programs for the determination of the identity comprise, but are not restricted to, the GCG program package, including. GAP (Deveroy, J. et al., Nucleic Acid Research 12 (1984), page 387, Genetics Computer Group University of Wisconsin, Medicine (Wi)), and BLASTP, BLASTN and FASTA (Altschul, S. et al., Journal of Molecular Biology 215 (1990), pages 403-410). The BLAST program can be obtained from the National Center for Biotechnology Information (NCBI) and from further sources (BLAST handbook, Altschul S. et al., NCBI NLM NIH Bethesda N. Dak. 22894; Altschul S. et al., above). The known Smith-Waterman algorithm can likewise be used for the determination of the nucleotide identity.

Preferred parameters for the determination of the "nucleotide identity" are, when using the BLASTN program (Altschul, S. et al., Journal of Molecular Biology 215 (1990), pages 403-410:

| | |
|---|---|
| Expect Threshold: | 10 |
| Word size: | 28 |
| Match Score: | 1 |
| Mismatch Score: | −2 |
| Gap costs: | Linear |

The above parameters are the default parameters in the nucleotide sequence comparison. The GAP program is likewise suitable for use with the above parameters.

Preferred parameters for the determination of the "amino acid identity" are, when using the BLASTP program (Altschul, S. et al., Journal of Molecular Biology 215 (1990), pages 403-410:

| | |
|---|---|
| Expect Threshold: | 10 |
| Word size: | 3 |
| Matrix: | BLOSUM62 |
| Gap costs: | Existence: 11; Extension: 1 |
| Compositional adjustments: | Conditional compositional score matrix adjustment |

The above parameters are the default parameters in the amino acid sequence comparison. The GAP program is likewise suitable for use with the above parameters.

An identity of 60% according to the above algorithm means 60% identity in connection with the present invention. The same applies for higher identities.

The feature "sequence that hybridizes or, taking into consideration the degeneracy of the genetic code," would hybridize with the complementary strand of a sequence indicates a sequence that under preferably stringent conditions hybridizes, or would hybridize taking into consideration the degeneracy of the genetic code, with the complementary strand of a reference sequence. For example, the hybridizations can be carried out at 68° C. in 2×SSC or according to the protocol of the digoxigenin labeling kits of the company Boehringer (Mannheim). Preferred hybridization conditions are, for example, incubation at 65° C. overnight in. 7% SDS, 1% BSA, 1 mM EDTA, 250 mM sodium phosphate buffer (pH 7.2) and subsequent washing at 65° C. with 2×SSC; 0.1% SDS.

The derivatives of the DNA isolated according to the invention, which according to alternatives F1), F2) or F3) can be obtained by substitution, addition, inversion and/or deletion of one or more bases of a sequence according to one of the groups A1) to E1), A2) to E2) and A3) to E3), include in particular those sequences which lead to conservative amino acid exchanges in the protein which they encode, such as, for example, to the exchange of glycine for alanine or of aspartic acid for glutamic acid. Such functionally neutral mutations are described as sense mutations and lead to no fundamental modification of the activity of the polypeptide. Furthermore, it is known that changes at the N- and/or C-terminus of a polypeptide do not significantly impair its function or can even stabilize this, so that also DNA sequences in which bases are attached at the 3'-end or at the 5-end of the sequence containing the nucleic acids according to the invention are accordingly comprised by the present invention. The person skilled in the art finds information on this, inter alia, in Ben-Bassat et al. (Journal of Bacteriology 169:751-757 (1987)), in O'Regan et al. (Gene 77:237-251 (1989)), in Sahin-Toth et al. (Protein Sciences 3:240-247 (1994)), in Hochuli et al. (Bio/Technology 6:1321-1325 (1988)) and in known textbooks of genetics and molecular biology.

The nucleic acid according to the invention is preferably a vector, in particular an expression vector or a gene overexpression cassette. Suitable vectors are all vectors known to the person skilled in the art that are customarily employed for the inclusion of DNA into a host cell. These vectors can both replicate autonomously, as they have replication origins, such as, for example, those of the 2μ plasmid or ARS (autonomously replicating sequences) or integrate into the chromosomes (non-replicative plasmids). Vectors are also understood as meaning linear DNA fragments that have no replication origins at all, such as, for example, gene insertion or gene overexpression cassettes. Gene overexpression cassettes customarily consist of a marker, the genes to be overexpressed as well as regulatory regions relevant for the expression of the genes, such as, for example, promoters and terminators. Preferred vectors are selected from the group comprising plasmids and cassettes, such as, for example, *E. coli* yeast shuttle plasmids; expression vectors, gene insertion, or gene overexpression cassettes are particularly preferred, in particular the vectors Seq ID No. 38, Seq ID No. 40, Seq ID No. 42, Seq ID No. 45 and Seq ID No. 47 described below.

According to a preferred embodiment of the vector according to the invention, the sequences of the groups [A1 to G1], [A2 to G2] and [A3 to G3] are under the control of at least one constitutive or regulatable promoter, which is suitable for the expression of the polypeptide encoded by these DNA sequences in the cell of a microorganism, preferably a bacteria, yeast or fungal cell, wherein *Aspergillus nidulans, Aspergillus niger, Alcaligenes latus, Bacillus megaterium, Bacillus subtilis, Brevibacterium flavum, Brevibacterium lactofermentum, Burkholderia andropogonis, B. brasilensis, B. calcdonica, B. caribensis, B. caryophylli, B. fungorum, B. gladioli, B. glathei, B. glumae, B. graminis, B. hospita, B. kururiensis, B. phenazinium, B. phymatum, B. phytofirmans, B. plantarii, B. sacchari, B. singaporensis, B. sordidicola, B. terricola, B. tropica, B. tuberum, B. ubonensis, B. unamae, B. xenovorans, B. anthina, B. pyrrocinia, B. thailandensis, Candida blankii, Candida rugosa, Corynebacterium glutamicum, Corynebacterium efficiens, Escherichia coli, Hansenula polymorpha, Kluveromyces lactis, Methylobacterium extorquens, Paracoccus versutus, Pseudomonas argentinensis, P. borbori, P. citronellols, P. flavescens, P. mendocina, P. nitroreducens, P. oleovorans, P. pseudoalcaligenes, P. resinovorans, P. straminea, P. aurantiaca, P. aureofaciens, P. chlororaphis, P. fragi, P. lundensis, P. taetrolens, P. antarctica, P. azotoformans, P. blatchfordae, P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. proteolytica, P. rhodesiae, P. synxantha, P. thivervalensis, P. tolaasii, P. veronii, P. denitrificans, P. pertucinogena, P. cremoricolorata, P. fulva, P. monteilii, P. mosselii, P. parafulva, P. putida, P. balearica, P. stutzeri, P. amygdali, P. avellanae, P. caricapapayae, P. cichorii, P. coronafaciens, P. Ficuserectae, P. helianthi, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis; P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. psychrophila, P. psychrotolerans, P. rathonis, P. reptilivora, P. resiniphila, P. rhiizosphaerae, P. rubescens, P. salomonii, P. segitis, P. septica, P. simiae, P. suis, P. thermotolerans, P. aeruginosa, P. tremae, P. trivialis, P. turbinellae, P. tuticorinensis, P. umsongensis, P. vancouverensis, P. vranovensis, P. xanthomarina, Ralstonia eutropha, Rhodospirillum rubrum, Rhodobacter sphaeroides, Saccharomyces cerevisiae, Yarrowia lipolytica, Zymomonas mobilis,* in particular *Pseudomonas putida, Escherichia coli* and *Burkholderia thailandensis,* are particularly preferred. Examples of constitutive promoters are lac, lacUV5, tac, trc (in each case in the absence of the LacI repressor in the cells according to the invention), Ltet-O1 (in the absence of the TetR repressor in the cells according to the invention), T5 and gap. Examples of inducible promoters are lac, lacUV5, tac, trc (in each case in the presence of the LacI repressor in the cells according to the invention), Ltet-O1 (in the presence of the TetR repressor in the cells according to the invention), T5 (in combination with a lac operator and the presence of the LacI repressor in the cells according to the invention), SP6 and T7 (in the presence of the gene encoding the cognate RNA polymerase, whose expression, for its part, is regulated). The vector according to the invention should in addition to a promoter preferably comprise a ribosome binding site as well as a terminator. It is particularly preferred here that the nucleic acid according to the invention is incorporated in an expression cassette of the vector comprising the promoter, the ribosome binding site and the terminator. In addition to the abovementioned structural elements, the vector can additionally comprise selection genes known to the person skilled in the art.

All percentages (%) indicated are percentages by mass if not indicated otherwise.

In the examples presented below, the present invention is described by way of example, without the invention, whose range of application results from the entire description and the claims, being intended to be restricted to the embodiments mentioned in the examples.

EXAMPLES

Figure 1:
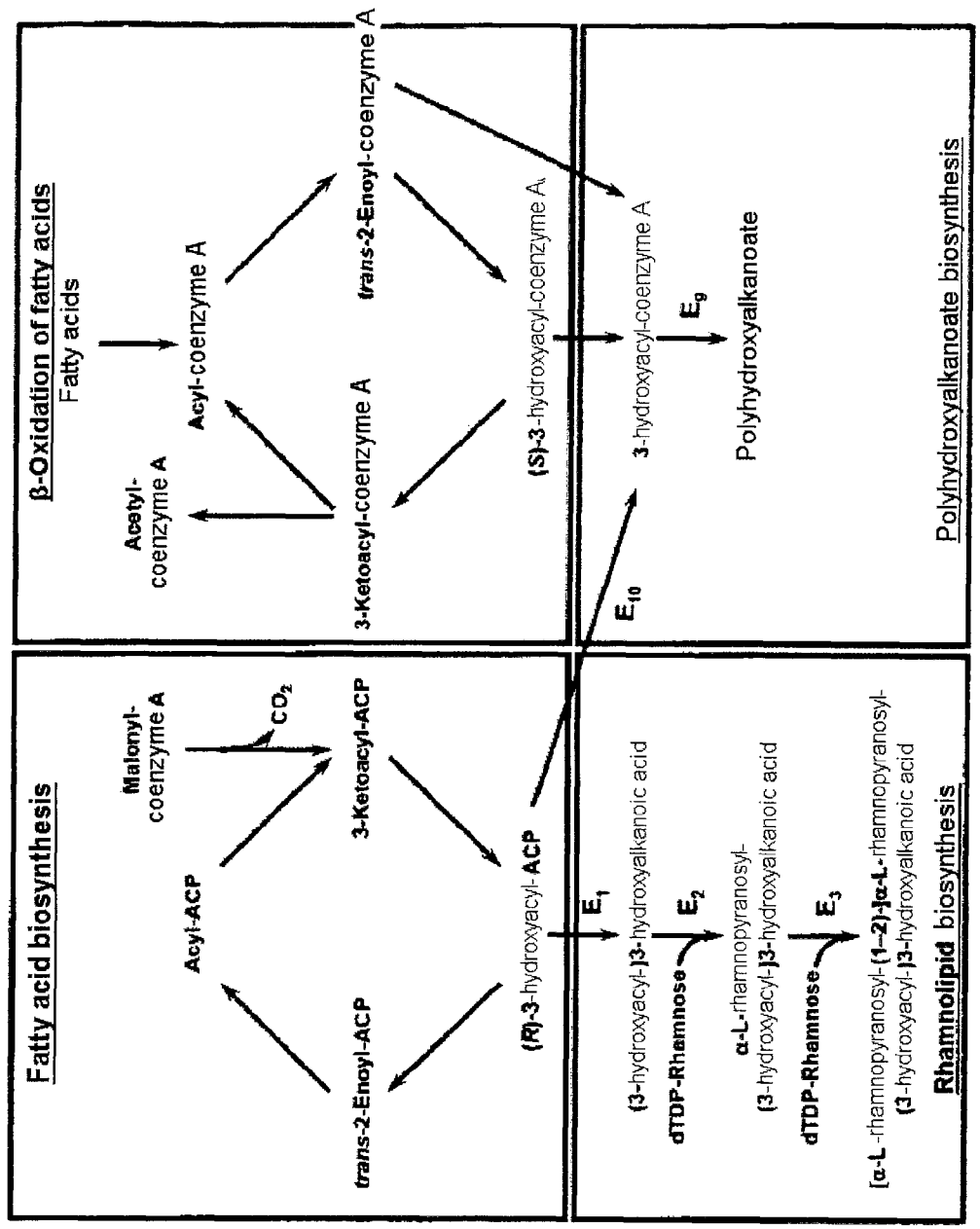
FIG. 1: Fatty acid biosynthesis, β-oxidation of fatty acids and linkage of these metabolic pathways with the biosynthesis of rhamnolipids (enzymes $E_1$, $E_2$ and $E_3$) and polyhydroxyalkanoates (enzymes $E_9$ and $E_{10}$). The carbon flows in fatty acid biosynthesis, β-oxidation of fatty acids, rhamnolipid biosynthesis and polyhydroxyalkanoate biosynthesis are shown. Consumption and formation of coenzymes, redox equivalents as well as nucleotides are not shown.

1. Construction of a Vector pBBR1MCS-2::AB for the Heterologous Expression of the *Pseudomonas aeruginosa* 1707 Genes rhlA and rhlB in *Pseudomonas putida*

For the heterologous expression of the *Pseudomonas aeruginosa* DSM1707 genes rhlA and rhlB, the plasmid pBBR1MCS-2::AB (Seq ID No. 38) was constructed. For this, the synthetic operon rhlAB (Seq ID No. 37) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::AB, the synthetic operon was cleaved from the vector by means of BglII and XbaI and subsequently ligated into the expression vector pBBR1MCS-2 (Seq ID No. 49) cleaved with BamHI and XbaI (described in Kovach et al., 1995: Four new derivatives of the broad host range cloning vector pBBR1MCS carrying different antibiotic-resistance cassettes. Gene, 166:175-176). The resulting plasmid pBBR1MCS-2::AB (Seq ID No. 38) is 7422 base pairs in size. The ligation and the transformation of chemically competent *E. coli* DH5α cells (Gibco-BRL, Karlsruhe) took place in the manner known to the person skilled in the art. The authenticity of the insert was checked by DNA sequence analysis.

The transformation of *Pseudomonas putida* KT2440 and GPp104 using the vectors pBBR1MCS-2 (Seq ID No. 49) and pBBR1MCS-2::AB took place as previously described (Iwasaki et al. Biosci. Biotech. Biochem. 1994. 58(5):851-854). The plasmid DNA of 10 clones was isolated and analyzed. The strains obtained carrying the plasmids were named *P. putida* KT2440 pBBR1MCS-2, *P. putida* GPp104 pBBR1MCS-2, *P. putida* KT2440 pBBR1MCS-2::AB and *P. putida* GPp104 pBBR1MCS-2::AB.

2. Construction of a Vector pBBR1MCS-2::ABC for the Heterologous Expression of the *Pseudomonas aeruginosa* DSM1707 genes rhlA, rhlB and rhlC in *Pseudomonas putida*

For the heterologous expression of the *Pseudomonas aeruginosa* DSM1707 genes rhlA, rhlB and rhlC, the plasmid pBBR1MCS-2::ABC (Seq ID No. 40) was constructed. For this, the synthetic operon rhlABC (Seq ID No. 39) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::ABC, the synthetic operon was cleaved from the vector by means of BglII and XbaI and subsequently ligated into the expression vector pBBR1MCS-2 (Seq ID No. 49) cleaved with BamHI and XbaI (Kovach et al., 1995: Four new derivatives of the broad host range cloning vector pBBR1MCS carrying different antibiotic-resistance cassettes. Gene, 166:175-176). The resulting plasmid pBBR1MCS-2::ABC (Seq ID No. 40) is 8409 base pairs in size. The ligation and the transformation of chemically competent *E. coli* DH5α cells (Gibco-BRL, Karlsruhe) took place in the manner known to the person skilled in the art. The authenticity of the insert was checked by DNA sequence analysis.

The transformation of *Pseudomonas putida* KT2440 and GPp104 using the vector pBBR1MCS-2::ABC took place as previously described (Iwasaki et al. Biosci. Biotech. Biochem. 1994. 58(5):851-854). The plasmid DNA of every 10 clones was isolated and analyzed. The strains obtained carrying the plasmids were named *P. putida* KT2440 pBBR1MCS-2::ABC and *P. putida* GPp104 pBBR1MCS-2::ABC.

3. Construction of a Vector pBBR1MCS-2::ABM for the Heterologous Expression of the *Pseudomonas aeruginosa* DSM1707 Genes rhlA, rhlB and pa1131 in *Pseudomonas putida*

For the heterologous expression of the *Pseudomonas aeruginosa* DSM1707 genes rhlA, rhlB and pa1131 the plasmid pBBRtMCS-2::ABM (Seq ID No. 42) was constructed. For this, the synthetic operon rhlAB-pa1131 (Seq ID No. 41) was synthesized by the company GeneArt AG (Regensburg) and intercloned in the commercial vector pMA (GeneArt AG). The basis for the synthesis was the already known genomic sequence of the *Pseudomonas aeruginosa* DSM 1707. Starting from the vector pMA::ABM the synthetic operon was cleaved from the vector by means of BglI and XbaI and subsequently ligated into the expression vector pBBR1MCS-2 (Seq ID No. 49) cleaved with BamHI and XbaI (Kovach et al., 1995: Four new derivatives of the broad host range cloning vector pBBR1MCS carrying different antibiotic-resistance cassettes. Gene, 166:175-176). The resulting plasmid pBBR1MCS-2::ABM (Seq ID No. 42) is 8702 base pairs in size. The ligation and the transformation of chemically competent *E. coli* DH5α cells (Gibco-BRL, Karlsruhe) took place in the manner known to the person skilled in the art. The authenticity of the insert was checked by DNA sequence analysis.

The transformation of *Pseudomonas putida* KT2440 and GPp104 using the vector pBBR1MCS-2::ABM took place as previously described (Iwasaki et al. Biosci. Biotech. Biochem. 1994. 58(5):851-854). The plasmid DNA of every 10 clones was isolated and analyzed. The strains obtained carrying the plasmids were named *P. putida* KT2440 pBBR1MCS-2::ABM and *P. putida* GPp104 pBBR1MCS-2::ABM.

4. Quantification of Rhamnolipid Production by Recombinant *P. Putida* Strains The recombinant strains *P. putida* KT2440 pBBR1MCS-2; *P. putida* KT2440 pBBR1MCS-2::AB; *P. putida* KT2440 pBBR1MCS-2::ABC; *P. putida* KT2440 pBBR1MCS-2::ABM; *P. putida* GPp104 pBBR1MCS-2; *P. putida* GPp104 pBBR1MCS-2::AB, *P. putida* GPp104 pBBR1MCS-2::ABC and *P. putida* GPp104 pBBR1MCS-2::ABM were cultured on LB agar kanamycin (50 μg/ml) plates.

For the production of the rhamnolipids, the medium designated below as CMP medium was used. This consists of 2% (w/v) glucose, 0.007% (w/v) $KH_2PO_4$, 0.11% $Na_2HPO_4 \times 2\, H_2O$, 0.2% (w/v) $NaNO_3$, 0.04% (w/v) $MgSO_4 \times H_2O$, 0.01% (w/v) $CaCl_2 \times 2\, H_2O$ and 0.2% (v/v) of a trace element solution. This consists of 0.2% (w/v) $FeSO_4 \times 7\, H_2O$, 0.15% (w/v) $MnSO_4 \times H_2O$ and 0.06% (w/v) $(NH_4)MO_7O_{24} \times 4\, H_2O$. The pH of the medium was adjusted to 6.7 with NaOH and the medium was subsequently sterilized by means of an autoclave (121° C., 20 min). An adjustment of the pH during the culturing was not necessary.

For the investigation of the rhamnolipid production in the shaker flask a preculture was first, prepared. For this, an inoculation loop of a strain freshly streaked on an LB agar plate was used and 10 ml of LB medium was inoculated into a 100 ml Erlenmeyer flask. All recombinant P. putida strains were in the LB medium, to which 50 µg/ml of kanamycin was added. The culturing of the strains took place overnight at 30° C. and 200 rpm.

The precultures were used to inoculate 50 ml of CMP medium in the 250 ml Erlenmeyer flask (start $OD_{600}$ 0.1). The cultures were cultured at 200 rpm and 30° C. for at most 120 h. At intervals of 24 h, a sample of 1 ml of broth was removed from the culture flask. The sample preparation for the following chromatographic analyses took place as follows:

Using a displacement pipette (Combitip), 1 ml of acetone was introduced into a 2 ml reaction vessel and the reaction vessel was immediately closed for the minimization of evaporation. The addition of 1 ml of broth followed. After vortexing of the broth/acetone mixture, this was centrifuged off for 3 min at 13,000 rpm, and 800 µl of the supernatant was transferred to an HPLC vessel.

For the detection and for the quantification of rhamnolipids, an evaporative light scattering detector (Sedex LT-ELSD Model 85LT) was used. The actual measurement was carried out by means of Agilent Technologies 1200 Series (Santa Clara, Calif.) and the Zorbax SB-C8 rapid resolution column (4.6×150 mm, 3.5 µm, Agilent). The injection volume was 5 µl and the runtime of the method was 20 min. As mobile phase, aqueous 0.1% TFA (trifluoroacetic acid, solution A) and methanol (solution B) was used. The column temperature was 40° C. The ELSD (detector temperature 60° C.) and the DAD (diode array, 210 nm) served as detectors. The gradient used in the method was:

| t [min] | Solution B vol. % | Flow [ml/min] |
| --- | --- | --- |
| 0.00 | 70% | 1.00 |
| 15.00 | 100% | 1.00 |
| 15.01 | 70% | 1.00 |
| 20.00 | 70% | 1.00 |

Figure 2:
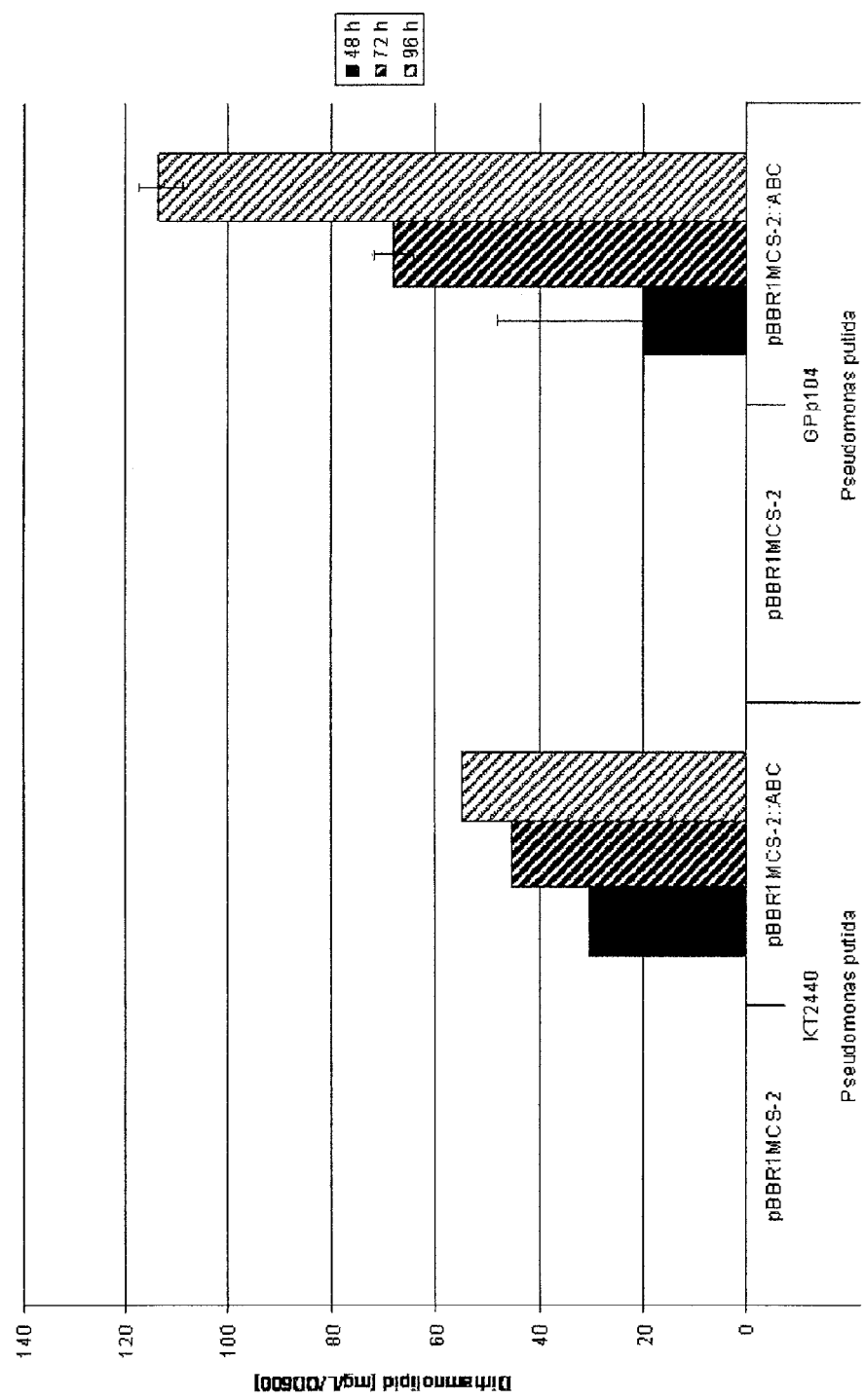
FIG. 2: Dirhamnosyl lipid formation (mg/l/OD 600 nm) of the recombinant strains P. putida KT2440 pBBR1MCS-2 and pBBR1MCS-2::ABC as well as GPp104 pBBR1MCS-2 and pBBR1MCS-2::ABC after 48 h, 72 h and 96 h culturing in CMP medium. The analysis of the rhamnolipid concentration took place by means of HPLC.
Figure 3:
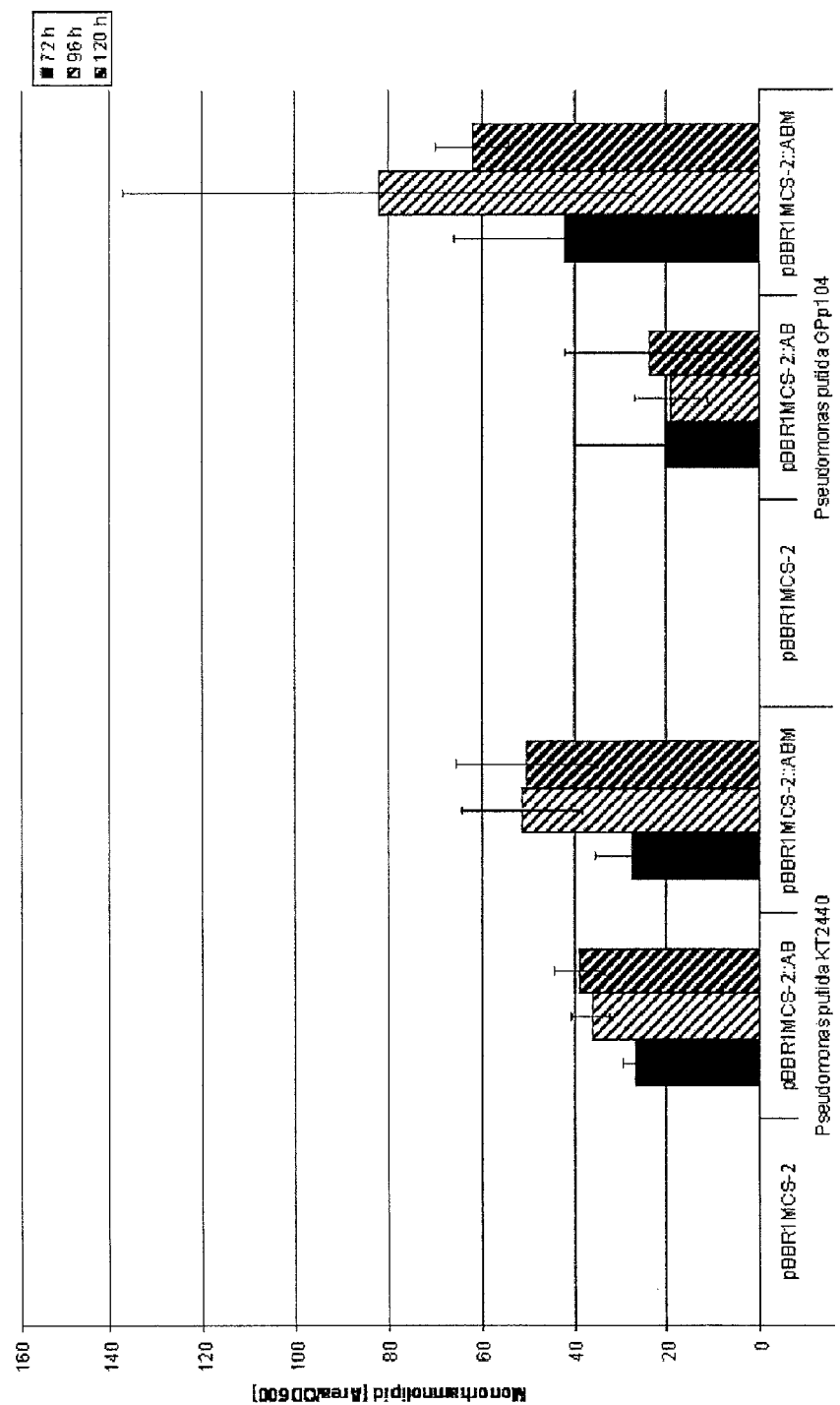
FIG. 3: Monorhamnosyl lipid formation (peakl area/OD 600 nm) of the recombinant strains P. putida KT2440 pBBR1MCS-2, pBBR1MCS-2::AB and pBBR1MCS-2::ABM as well as GPp104 pBBR1MCS-2, pBBR1MCS-2::AB and pBBR1MCS-2::ABM after 48 h, 72 h and 96 h culturing in CMP medium. The analysis of the rhamnolipid concentration took place by means of HPLC.

While P. putida KT2440 pBBR1MCS-2 and GPp104 pBBR1MCS-2 produced no rhamnolipids, in the recombinant strains P. putida KT2440 pBBR1MCS-2::AB, P. putida KT2440 pBBR1MCS-2::ABC, P. putida KT2440 pBBR1MCS-2::ABM, P. putida GPp104 pBBR1MCS-2::AB, P. putida GPp104 pBBR1MCS-2::ABC and P. putida GPp104 pBBR1MCS-2::ABM the formation of different rhamnolipid species was detectable (FIGS. 2 and 3).

By the incorporation of pBBR1MCS-2::AB and pBBR1MCS-2::ABM into P. putida, it was possible to generate monorhamnosyl lipids (FIG. 3). Since no reference material for monorhamnosyl lipids was present, the identification of the products took place by analysis of the corresponding mass traces and the $MS^2$ spectra in LC-MS.

If rhlC (pBBR1MCS-2::ABC) was additionally incorporated into the strains, mono- and dirhamnosyl lipids were produced (FIG. 2).

The direct comparison of the rhamnolipid formation by P. putida pBBR1MCS-2::AB and P. putida pBBR1MCS-2::ABM shows that the coexpression of P. aeruginosa p3111 with P. aeruginosa rhlAB leads to an improvement in the rhamnolipid biosynthesis (FIG. 3). While the strains P. putida KT2440 pBBR1MCS-2::AB and P. putida GPp104 pBBR1MCS-2::AB had produced about 39 (P. putida KT2440 pBBR1MCS-2::AB) and 23 peak areas rhamnolipids/OD 600 nm (P. putida GPp104 pBBR1MCS-2::AB) after 120 h, the strains P. putida KT2440 pBBR1MCS-2::ABM and P. putida GPp104 pBBR1MCS-2::ABM formed about 50 (P. putida KT2440 pBBR1MCS-2::ABM) and 62 peak areas rhamnolipids/OD 600 nm (P. putida GPp104 pBBR1MCS-2::ABM) after 120 h.

If the monorhamnosyl lipid synthesis of the strains P. putida KT2440 pBBR1MCS-2::ABM and P. putida GPp104 pBBR1MCS-2::ABM was compared, it was possible in the PHA-negative mutant P. putida GPp104 pBBR1MCS-2::ABM to detect 62 peak areas/OD 600 nm (120 h culturing) and with P. putida-KT2440-pBBR1MCS-2::ABM 50 area/OD 600 nm-monorhamnosyl lipids (FIG. 3).

A comparative analysis of the dirhamnosyl lipid formation (mg/l/OD 600 nm) in the strains P. putida KT2440 and GPp104 likewise showed a greater formation of the dirhamnosyl lipids in the PHA-negative strain background of the P. putida GPp104. P. putida GPp104 pBBR1MCS-2::ABC formed on average 113 mg/l/OD 600 nm of dirhamnosyl lipids (96 h), whereas with P. putida KT2440 pBBR1MCS-2::ABC only 55 mg/l/OD 600 nm of dirhamnosyl lipids could be detected after 96 h (FIG. 2).

Thus it was possible to show that the use of a strain background attenuated with respect to PHA synthesis leads to an improvement in the rhamnolipid biosynthesis.

5. Construction of a vector pBBR1MCS-2::ABMC for the heterologous expression of the Pseudomonas aeruginosa DSM1707 genes rhlA, rhlB, pa1131 and rhlC in Pseudomonas putida For the heterologous expression of the Pseudomonas aeruginosa DSM1707 genes rhlA, rhlB, pa1131 and rhlC, the plasmid pBBR1MCS-2::ABMC (Seq ID No. 51) was constructed. For this, the synthetic operon rhlAB-pa1131-rhlC (Seq ID No. 50) was synthesized by the company GeneArt AG (Regensburg) and intercloned in the commercial vector pMA (GeneArt AG). The basis for the synthesis was the already known genomic sequence of the Pseudomonas aeruginosa DSM1707. Starting from the vector pMA::ABMC the synthetic operon was cleaved by means of BglII and XbaI from the vector and subsequently ligated into the expression vector pBBR1MCS-2 (Seq ID No. 49) cleaved with BamHI and XbaI (Kovach et al., 1995: Four new derivatives of the broad-host-range cloning vector pBBR1MCS carrying different antibiotic-resistance cassettes. Gene, 166: 175-176). The resulting plasmid pBBR1MCS-2::ABMC (Seq ID No. 51) is 9663 base pairs in size. The ligation and the transformation of chemically competent E. coli DH5α cells (Gibco-BRL, Karlsruhe) took place in a manner known to the person skilled in the art. The authenticity of the insert was checked by DNA sequence analysis.

The transformation of Pseudomonas putida KT2440 and GPp104 using the vector pBBR1MCS-2::ABMC took place as previously described (Iwasaki et al. Biosci. Biotech. Biochem. 1994. 58(5):851-854). The plasmid DNA of every 10 clones was isolated and analyzed. The strains obtained carrying the plasmids were named P. putida KT2440 pBBR1MCS-2::ABMC and P. putida GPp104 pBBR1MCS-2::ABMC.

6. Qualitative Comparison of the Rhamnolipid Production by Recombinant P. Putida Strains and P. aeruginosa Strains The recombinant strains P: putida GPp104 pBBR1MCS-2 and P; putida GPp104 pBBR1MCS-2::ABMC and P. aeruginosa DSM 19880 were cultured on LB agar kanamycin (50 µg/ml; *P. putida*) and LB agar plates (*P. aeruginosa*).

For the production of the rhamnolipids the medium below designated as CMP medium was used. This consists of 2% (w/v) glucose, 0.007% (w/v) $KH_2PO_4$, 0.11% $Na_2HPO_4 \times 2$ $H_2O$, 0.2% (w/v) $NaNO_3$, 0.04% (w/v) $MgSO_4 \times H_2O$, 0.01% (w/v) $CaCl_2 \times 2$ $H_2O$ and 0.2% (v/v) of a trace element solution. This consists of 0.2% (w/v) $FeSO_4 \times 7$ $H_2O$, 0.15% (w/v) $MnSO_4 \times H_2O$ and 0.06% (w/v) $(NH_4)MO_7O_{24} \times 4$ $H_2O$. The pH of the medium was adjusted to 6.7 using NaOH and the medium was subsequently sterilized by means of an autoclave (121° C., 20 min). An adjustment of the pH during the culturing was not necessary.

For the investigation of the rhamnolipid production in the shaker flask, a preculture was first prepared. For this, an inoculation loop of a strain freshly streaked on LB agar plate was used and 10 ml of LB medium was inoculated into a 100 ml Erlenmeyer flask. The recombinant *P. putida* strains were cultured in the LB medium, to which 50 µg/ml of kanamycin was added. *P. aeruginosa* was cultured in the LB medium. The culturing of the strains took place at 30° C. and 200 rpm overnight.

The precultures were used to inoculate 50 ml of CMP medium in the 250 ml Erlenmeyer flask (start $OD_{600}$ 0.1). The cultures were cultured at 200 rpm and 30° C. for at most 120 h. At intervals of 24 h, a sample of 1 ml of broth was removed from the culture flask. The sample preparation for the following chromatographic analyses took place as follows:

Using a displacement pipette (Combitip), 1 ml of acetone was introduced into a 2 ml reaction vessel and the reaction vessel was immediately closed for the minimization of evaporation. The addition of 1 ml of broth followed. After vortexing of the broth/acetone mixture, this was centrifuged off for 3 min at 13,000 rpm, and 800 µl of the supernatant were transferred to an HPLC vessel.

For the identification of the products formed, 5 µl were injected into an Accela UPLC unit (Thermo Scientific, Dreieich). The substances to be investigated were analyzed using a semi UPLC column "Pursuit XRs ULTRA (C8, 2.8 µm, 2.1× 100 mm) (Varian, Darmstadt). The separation took place within 25 min by means of a gradient consisting of the mobile phase A1 ($H_2O$, 0.1% (v/v) TFA) and the mobile phase B1 (methanol, 0.1% (v/v) TFA) using a flow rate of 0.3 ml/min at 40° C. The time course of the gradient was the following:

| Time [min] | Mobile phase A1 [%] | Mobile phase B1 [%] |
| --- | --- | --- |
| 0 | 30 | 70 |
| 15 | 0 | 100 |
| 25 | 0 | 100 |
| 25.01 | 30 | 70 |
| 32 | 30 | 70 |

Detection took place by means of DAD detector in the wavelength range from 200-600 nm and mass-selectively using a high-resolution FT-ICR LTQ-FT mass spectrometer (Thermo Scientific, Dreieich) in the scanning range m/e 100-1000. Ionization took place by means of ESI (electrospray ionization). Exact masses and empirical chemical formulae were determined with the aid of the FT-ICR mass analyzer, using a resolution of R=100000 and a mass accuracy of <2 ppm. The identification of the products takes place by analysis of the corresponding mass traces and the $MS^2$ spectra. To be able to compare the strains, the peak areas of the corresponding substances were contrasted.

As shown in FIG. 4, the strain *P. putida* GPp104 pBBR1MCS-2 formed no rhamnolipids at all. *P. putida* GPp104 pBBR1MCS-2::ABMC and *P. aeruginosa* DSM 19880 formed rhamnolipids, wherein the ratio between di- and monorhamnosyl lipids formed with *P. putida* GPp104 pBBR1MCS-2::ABMC was, for example, 4:1, with *P. aeruginosa* DSM 19880, for example, 2:1. Moreover, the strain *P. putida* GPp104 pBBR1MCS-2::ABMC in contrast to *P. aeruginosa* DSM 19880 formed no or only very few rhamnolipids having a radical determined by means of $R^1$ and $R^2$ derived from 3-hydroxyoctanoyl-3-hydroxydecanoic acid or 3-hydroxydecanoyl-3-hydroxyoctanoic acid.

7. Construction of a Vector pBBR1MCS-2::rfbBDAC and pBBR1MCS-2::ABC_rfbBDAC for Heterologous Expression in *Pseudomonas putida*

At the company Trenzyme GmbH (Konstanz), the rhamnose biosynthesis operon rfbBDAC was amplified starting from chromosomal DNA of *Pseudomonas putida* KT244. For this, the following primers were used:

```
RL1:                                    (Seq ID No. 48)
5'-TATATATAGAATTCGCGTCATCTGTCTACGACAACAC-3'

RL2:                                    (Seq ID No. 43)
5'-TATATATAGAATTCGGCTGCGCTACCGCAGCCCTTC-3'
```

The PCR product obtained was intercloned in Trenzyme's alligator cloning system and transformed in *E. coli* DH5α (New England Biolabs; Frankfurt). Vectors of different candidates were analyzed and sequenced. After successful and error-free DNA sequencing, the vector was cleaved by means of EcoRI and the target fragment rfbBDAC was isolated. For a further inter-cloning, the vector pBBR1MCS-2 (Kovach et al., 1995: Four new derivatives of the broad-host-range cloning vector pBBR1MCS carrying different antibiotic-resistance cassettes. Gene, 166:175-176) was cleaved in the same manner. The cleaved target fragment (rfbBDAC) and the cleaved vector (pBBR1MCS-2) were merged by conventional ligation. The resulting vector pBBR1MCS-2::rfbBDAC (Seq ID No. 45) was likewise transformed in *E. coli* DH5α (New England Biolabs; Frankfurt). Some candidates of the transformants were investigated with respect to the successful uptake of the plasmid.

The vector pBBR1MCS-2::rfbBDAC served as a matrix for a PCR. The following oligonucleotides were used:

```
RL_XbaI-fw:                             (Seq ID No. 44)
5'-TATATATATCTAGAATTAATGCAGCTGGCACGAC-3'

RL_Xba_rev:                             (Seq ID No. 46)
5'-GGCCGCTCTAGAACTAGTGGA-3'
```

The PCR was carried out using the Phusion™ High-Fidelity Master Mix of New England Biolabs (Frankfurt) polymerase. It was carried out in the manner known to the person skilled in the art. The target sequence (lac promoter and rfbBDAC) was intercloned in the Trenzyme alligator cloning system. *E. coli* DH5α (New England Biolabs; Frankfurt) transformants were selected and the plasmid DNA of different candidates was isolated and sequenced. After the sequence had been checked and investigated for correctness, the vector was cleaved using XbaI. The target fragment was ligated into the pBBR1MCS-2::ABC likewise cleaved using XbaI (see above) by means of conventional ligation methods.

The target vector pBBR1MCS-2::ABC_rfbBDAC obtained (Seq ID No. 47) has a size of 12249 base pairs. The insert of the vector was sequenced. The carrying-out of the PCR, the checking of the successful amplification of the PCR by means of agarose gel electrophoresis, ethidium bromide staining of the DNA, determination of the PCR fragment size, purification of the PGR products and DNA concentration determination took place in the manner known to the person skilled in the art.

The transformation of *Pseudomonas putida* KT2440 and GPp104 using the vector pBBR1MCS-2::ABC_rfbBDAC took place as previously described (Iwasaki et al. Biosci. Biotech. Biochem. 1994. 58(5):851-854). The plasmid DNA of every 10 clones was isolated and analyzed. The strains obtained carrying the plasmids are named *P. putida* KT2440 pBBR1MCS-2::ABC_rfbBDAC and *P. putida* GPp104 pBBR1MCS-2::ABC_rfbBDAC.

8. Quantification of the Rhamnolipid Production by Recombinant *P. putida* Strains with and without Overexpression of the rfbBDAC Operon The recombinant strains *P. putida* KT2440 pBBR1MCS-2; *P. putida* KT2440 pBBR1MCS-2::ABC, *P. putida* KT2440 pBBR1MCS-2::ABC_rfbBDAC, *P. putida* GPp104 pBBR1MCS-2, *P. putida* GPp104 pBBR1MCS-2::ABC and *P. putida* GPp104 pBBR1MCS-2::ABC_rfbBDAC are cultured on LB agar kanamycin (50 µg/ml) plates.

For the production of the rhamnolipids, the medium designated below as CMP medium is used. This consists of 2% (w/v) glucose, 0.007% (w/v) $KH_2PO_4$, 0.11% $Na_2HPO_4 \times 2\, H_2O$, 0.2% (w/v) $NaNO_3$, 0.04% (w/v) $MgSO_4 \times H_2O$, 0.01% (w/v) $CaCl_2 \times 2\, H_2O$ and 0.2% (v/v) of a trace element solution. This consists of 0.2% (w/v) $FeSO_4 \times 7\, H_2O$, 0.15% (w/v) $MnSO_4 \times H_2O$ and 0.06% (w/v) $(NH_4)MO_7O_{24} \times 4\, H_2O$. The pH of the medium is adjusted to 6.7 using NaOH and the medium is subsequently sterilized by means of an autoclave (121° C., 20 min). An adjustment of the pH during the culturing is not necessary.

For the investigation of the rhamnolipid production in the shaker flask, a preculture is first prepared. For this, an inoculation loop of a strain freshly streaked on LB agar plate is used and 10 ml of LB medium are inoculated into a 100 ml Erlenmeyer flask. All recombinant *P. putida* strains are cultured in the LB medium, to which 50 µg/ml of kanamycin is added. The culturing of the *P. putida* strains was carried out at 30° C. and 200 rpm overnight.

The precultures are used to inoculate 50 ml of CMP medium in the 250 ml Erlenmeyer flask (start $OD_{600}$ 0.1). The cultures are cultured at 200 rpm and 30° C. for at most 120 h. At intervals of 24 h, a sample of 1 ml broth is removed from the culture flask. The sample preparation for the following chromatographic analyses takes place as follows:

Using a displacement pipette (Combitip), 1 ml of acetone is introduced into a 2 mL reaction vessel and the reaction vessel is closed immediately for the minimization of evaporation. The addition of 1 ml of broth follows. After vortexing of the broth/acetone mixture, this is centrifuged off for 3 min at 13,000 rpm, and 800 µl of the supernatant are transferred to an HPLC vessel. For the detection and for the quantification of rhamnolipids, an evaporative light scattering detector (Sedex LT-ELSD Model 85LT) is used. The actual measurement is carried out by means of Agilerit Technologies 1200 Series (Santa Clara, Calif.) and the Zorbax SB-C8 rapid resolution column (4.6×150 mm, 3.5 µm, Agilent). The injection volume is 5 µl and the runtime of the method is 20 min. As a mobile phase, aqueous 0.1% TFA (trifluoroacetic acid, solution A) and methanol (solution B) is used. The column temperature is 40° C. The ELSD (detector temperature 60° C.) and the DAD (diode array, 210 nm) serve as detectors. The gradient used in the method is:

| t [min] | Solution B vol. % | Flow [ml/min] |
|---------|-------------------|---------------|
| 0.00    | 70%               | 1.00          |
| 15.00   | 100%              | 1.00          |
| 15.01   | 70%               | 1.00          |
| 20.00   | 70%               | 1.00          |

While *P. putida* KT2440 pBBR1MCS-2 and GPp104 pBBR1MCS-2 produce no rhamnolipids, in the recombinant strains *P. putida* KT2440 pBBR1MCS-2::ABC, *P. putida* KT2440 pBBR1MCS-2::ABC_rfbBDAC; *P. putida* GPp104 pBBR1MCS-2::ABC and *P. putida* GPp104 pBBR1MCS-2::ABC_rfbBDAC the formation of rhamnolipids is detectable.

*P. putida* KT2440 pBBR1MCS-2::ABC_rfbBDAC shows in comparison to *P. putida* KT2440 pBBR1MCS-2::ABC and *P. putida* GPp104 pBBR1MCS-2::ABC_rfbBDAC shows in comparison to *P. putida* GPp104 pBBR1MCS-2::ABC an increased formation of the di- and monorhamnosyl lipids. This clearly shows the positive influence of the amplification of the expression of rfbBDAC on the formation of mono- and dirhamnosyl lipids.

If the mono- and dirhamnosyl lipid biosynthesis of the strains *P. putida* KT2440 pBBR1MCS-2::ABC_rfbBDAC and *P. putida* GPp104 pBBR1MCS-2::ABC_rfbBDAC is compared, an increased mono- and dirhamnosyl lipid synthesis is detected in the PHA-negative mutant *P. putida* GPp104 pBBR1MCS-2::ABC_rfbBDAC.

As already described above, the rhamnolipid biosynthesis is increased with the use of a strain background inactivated in the PHA synthesis.

9. Generation of Recombinant *E. Coli* W3110 pBBR1MCS-2::ABC and *E. Coli* W3110 pBBR1MCS-2::ABC_rfbBDAC The transformation of *E. coli* W3110 took place as previously described (Miller JH. A Short Course in Bacterial Genetics: A Laboratory Manual and Handbook for *Escherichia coil* and Related Bacteria. Plainview, N.Y.: Cold Spring Harbor Lab. Press; 1992) by means of electroporation. The plasmid DNA of every 10 clones was isolated and analyzed. The strains obtained carrying the plasmids were named *E. coli* W3110 pBBR1MCS-2::ABC_rfbBDAC and *E. coli* W3110 pBBR1MCS-2::ABC_rfbBDAC.

10. Quantification of the Rhamnolipid Production by Recombinant *E. Coli* Strains with and without Overexpression of the rfbBDAC Operon The recombinant strains *E. coli* W3110 pBBR1MCS-2; *E. coli* W3110 pBBR1MCS-2::ABC and *E. coli* W3110 pBBR1MCS-2::ABC_rfbBDAC are cultured on LB agar kanamycin (50 µg/ml) plates.

For the production of the rhamnolipids, the medium designated in the following as CMP medium is used. This consists of 2% (w/v) glucose, 0.007% (w/v) $KH_2PO_4$, 0.11% $Na_2HPO_4 \times 2\, H_2O$, 0.2% (w/v) $NaNO_3$, 0.04% (w/v) $MgSO_4 \times H_2O$, 0.01% (w/v) $CaCl_2 \times 2\, H_2O$ and 0.2% (v/v) of a trace element solution. This consists of 0.2% (w/v) $FeSO_4 \times 7\, H_2O$, 0.15% (w/v) $MnSO_4 \times H_2O$ and 0.06% (w/v) $(NH_4)MO_7O_{24} \times 4\, H_2O$. The pH of the medium is adjusted to 6.7 using NaOH and the medium is subsequently sterilized by means of an autoclave (121° C., 20 min). An adjustment of the pH during the culturing is not necessary.

For the investigation of the rhamnolipid production in the shaker flask, a preculture is first prepared. For this, an inoculation loop of a strain freshly streaked on LB agar plate is used and ml of LB medium is inoculated into a 100 ml Erlenmeyer flask. All recombinant *E. coli* strains are cultured in the LB medium, to which 50 µg/ml of kanamycin is added. The culturing of the *E. coli* strains took place at 37° C. and 200 rpm overnight.

The precultures are used to inoculate 50 ml of CMP medium in the 250 ml Erlenmeyer flask (start $OD_{600}$ 0.1). The cultures are cultured at 200 rpm and 30° C. for at most 120 h. At intervals of 24 h a sample of 1 ml of broth is removed from the culture flask. The sample preparation for the following chromatographic analyses takes place as follows:

Using a displacement pipette (Combitip), 1 ml of acetone is introduced into a 2 ml reaction vessel and the reaction vessel is closed immediately for the minimization of evaporation. The addition of 1 ml of broth follows. After vortexing of the broth/acetone mixture, this is centrifuged off for 3 min at 13,000 rpm, and 800 µl of the supernatant are transferred to an HPLC vessel. For detection and for the quantification of rhamnolipids, an evaporative light scattering detector (Sedex LT-ELSD Model 85LT) is used. The actual measurement is carried out by means of Agilent Technologies 1200 Series (Santa Clara, Calif.) and the Zorbax SB-C8 rapid resolution column (4.6×150 mm, 3.5 µm, Agilent). The injection volume is 5 µl and the runtime of the method is 20 min. Aqueous 0.1% TFA (trifluoroacetic acid, solution A) and methanol (solution B) is used as the mobile phase. The column temperature is 40° C. The ELSD (detector temperature 60° C.) and the DAD (diode array, 210 nm) serve as detectors. The gradient used in the method is:

| t [min] | Solution B vol. % | Flow [ml/min] |
|---|---|---|
| 0.00 | 70% | 1.00 |
| 15.00 | 100% | 1.00 |
| 15.01 | 70% | 1.00 |
| 20.00 | 70% | 1.00 |

While *E. coli* W3110 pBBR1MCS-2 produces no rhamnolipids, the formation of mono- and dirhamnosyl lipids is detectable in the recombinant strains *E. coli* W3110 pBBR1MCS-2::ABC and *E. coli* W3110 pBBR1MCS-2::ABC_rfbBDAC, wherein *E. coli* W3110 pBBR1MCS-2::ABC_rfbBDAC forms significantly more mono- and dirhamnosyl lipids than *E. coli* W3110 pBBR1MCS-2::ABC. This shows that the heterologous expression of rhlABC of *Pseudomonas aeruginosa* DSM1707 leads to the formation of mono- and dirhamnosyl lipids in *E. coli*. This furthermore shows the positive influence of the reinforcement of the expression of rfbBDAC on the formation of mono- and dirhamnosyl lipids.

11. Construction of a Vector pBBR1MCS-2::ABC-BTH_II1077-II1080-II1081 for the Heterologous Expression of the *Pseudomonas aeruginosa* DSM1707 Genes rhlA, rhlB and rhlC and the *Burkholderia thailandensis* E264 Genes BTH_II1077, BT_II1080 and BT_II1081 in *Pseudomonas putida*

For the heterologous expression of the *Pseudomonas aeruginosa* DSM1707 genes rhlA, rhlB and rhlC and the *B. thailandensis* E264 genes BTH II1077, BT_II1080 and BT_II1081 in *Pseudomonas putida*, the plasmid pBBR1MCS-2::ABC-BTH_II1077-II1080-II1081 (Seq ID No. 69) is constructed. For this, the synthetic operon BTH_II1077, BT_II1080 and BT_II1081 (Seq ID No. 70) is synthesized by the company DNA 2.0 (Menlo Park, Calif., USA) and intercloned in the commercial vector pJ294 (DNA 2.0; Menlo Park, Calif., USA). The basis for the synthesis is the genomic sequence of the strain *B. thailandensis* E264. Starting from the vector pJ294-BTH_II1077-II1080-II1081, the synthetic operon is cleaved from this vector by means of XbaI and subsequently ligated into the vector pBBR1MCS-2::ABC (Seq ID No. 40) likewise cleaved using XbaI. The target vector pBBR1MCS-2::ABC-BTH_II1077-II1080-II1081 (Seq ID No. 69) obtained has a size of 13768 base pairs. The insert of the vector is sequenced. The carrying-out of the PCR, the checking of the successful amplification of the PCR by means of agarose gel electrophoresis, ethidium bromide staining of the DNA, determination of the PCR fragment size, purification of the PCR products and DNA concentration determination takes place in the manner known to the person skilled in the art.

The transformation of *Pseudomonas putida* KT2440 and GPp104 using the vector pBBR1MCS-2::ABC-BTH_II1077-II1080-II1081 (Seq ID No. 69) takes place as previously described (Iwasaki et al. Biosci. Biotech. Biochem. 1994. 58(5):851-854). The plasmid DNA of every 10 clones is isolated and analyzed. The strains obtained carrying the plasmids are named *P. putida* KT2440 pBBR1MCS-2::ABC-BTH_II1077-II1080-II1081 and *P. putida* GPp104 pBBR1MCS-2::ABC-BTH_II1077-II1080-II1081.

12. Quantification of the Rhamnolipid Production by Recombinant *P. Putida* Strains with and without Overexpression of the *B. thailandensis* E264 Genes BTH_II1077, BT_II1080 and BT_II1081

The recombinant strains *P. putida* strains *P. putida* KT2440 pBBR1MCS-2::AB, *P. putida* KT2440 pBBR1MCS-2::AB-BTH_II1077-II1080-II1081, *P. putida* GPp104 pBBR1MCS-2::AB, *P. putida* GPp104 pBBR1MCS-2::AB-BTH_II1077-II1080-II1081, *P. putida* KT2440 pBBR1MCS-2::ABC, *P. putida* KT2440 pBBR1MCS-2::ABC-BTH_II1077-II1080-II1081 *P. putida* GPp104 pBBR1MCS-2::ABC and *P. putida* GPp104 pBBR1MCS-2::ABC-BTH_II1077-II1080-II1081 generated in the Examples 1, 2 and 11 are cultured on LB agar kanamycin (50 µg/ml) plates.

For the production of the rhamnolipids, the medium designated in the following as M9 medium is used. This medium consists of 2% (w/v) glucose, 0.3% (w/v) $KH_2PO_4$, 0.679% $Na_2HPO_4$, 0.05% (w/v) NaCl, 0.2% (w/v) $NH_4Cl$, 0.049% (w/v) $MgSO_4×7$ $H_2O$ and 0.1% (v/v) of a trace element solution. This consists of 1.78% (w/v) $FeSO_4×7$ $H_2O$, 0.191% (w/v) $MnCl_2×7$ $H_2O$, 3.65% (w/v) HCl, 0.187% (w/v) $ZnSO_4×7$ $H_2O$, 0.084% (v/v) Na EDTA×2 $H_2O$, 0.03% (v/v) $H_3BO_3$, 0.025% (w/v) $Na_2MoO_4×2$ $H_2O$ and 0.47% (w/v) $CaCl_2×2$ $H_2O$. The pH of the medium is adjusted to 7.4 using $NH_4OH$ and the medium is subsequently sterilized by means of an autoclave (121° C., 20 min). An adjustment of the pH during the culturing is not necessary. For the investigation of the rhamnolipid production in the shaker flask, a preculture is first prepared. For this, an inoculation loop of a strain freshly streaked on LB agar plate is used and ml of LB medium are inoculated into a 100 ml Erlenmeyer flask. All recombinant *P. putida* strains are cultured in LB medium, to which 50 μg/ml of kanamycin was added. The culturing of the P. putida strains takes place at 37° C. and 200 rpm overnight.

The precultures are used to inoculate 50 ml of M9 medium (+50 μg/ml of kanamycin) in the 250 ml Erlenmeyer flask (start $OD_{600}$ 0.1). The cultures are cultured at 200 rpm and 30° C. At intervals of 24 h, a sample of 1 ml of broth is removed from the culture flask. The sample preparation for the following chromatographic analyses and the chromatographic analyses themselves are carried out as described in Example 4.

It is shown that the recombinant strains P. putida KT2440 pBBR1MCS-2::AB-BTH_II1077-II1080-II1081 and P. putida GPp104 pBBR1MCS-2::AB-BTH_II1077-II1080-II1081 form significantly more monorhamnosyl lipids than the strains P. putida KT2440 pBBR1MCS-2::AB and P. putida GPp104 pBBR1MCS-2::AB. This demonstrates that the amplification of BTH_II1077-II1080-II1081 from B. thailandensis E264 increases the formation of monorhamnosyl lipids in P. putida strains containing the Pseudomonas aeruginosa DSM1707 genes rhlAB.

It is furthermore shown that the recombinant strains P. putida KT2440 pBBR1MCS-2::ABC-BTH_II1077-II1080-II1081 and P. putida GPp104 pBBR1MCS-2::ABC-BTH_II1077-II1080-II1081 form significantly more mono- and dirhamnosyl lipids than the strains P. putida KT2440 pBBR1MCS-2::ABC and P. putida GPp104 pBBR1MCS-2::ABC. This proves that the amplification of BTH_II1007-II1080-II1081 from B. thaiandensis E264 increases the formation of mono- and dirhamnosyl lipids in P. putida strains containing the Pseudomonas aeruginosa DSM1707 genes rhlABC.

It is finally shown that the reduction of the polyhydroxybutyrate formation in the strain background P. putida GPp104 compared to the strain P. putida KT2440 leads to an increased rhamnolipid formation; as the strains P. putida KT2440 pBBR1MCS-2::AB, P. putida KT2440 pBBR1MCS-2::ABC, P. putida KT2440 pBBR1MCS-2::AB-BTH_II077-II1080-II1081 and P. putida KT2440 pBBR1MCS-2::ABC-BTH_II1077-II1080-II1081 are able to form significantly fewer mono-( ) and mono- and dirhamnosyl lipids ( ) than the corresponding control strains P. putida GPp104 pBBR1MCS-2::AB, P. putida GPp104 pBBR1MCS-2::ABC, P. putida GPp104 pBBR1MCS-2::AB-BTH_II1077-II1080-II1081 and P. putida GPp104 pBBR1MCS-2::ABC-BTH_II1077-II1080-II1081.

13. Construction of a Vector pBBR1MCS-2::ABCM for the Heterologous Expression of the Pseudomonas aeruginosa DSM1707 genes rhlA, rhlB, pa1131 and rhlC in Pseudomonas putida For the heterologous expression of the Pseudomonas aeruginosa DSM1707 genes rhlA, rhlB, pa1131 and rhlC, the plasmid pBBR1MCS-2::ABCM (Seq ID No. 58) was constructed. For this, the gene pa1131 (Seq ID No. 59) was amplified starting from genomic DNA of the strain Pseudomonas aeruginosa PAO1 (DSM 1707) containing the oligonucleotides

```
MFS2.0_xbal_fw:                    (Seq ID No. 60)
5'-AGGAAATCTAGATGAGAGGCCGGCAAGGATAC-3'

MFS2.0_Xbal_rev:                   (Seq ID No. 61)
5'-CCAGGTTCTAGACGCCAGGATTGAACAGTACC-3'.
```

The amplification of the PCR product (1483 base pairs) was carried out using the Phusion™ High-Fidelity Master Mix from New England Biolabs (Frankfurt) polymerase. The PCR product was cleaved using XbaI and ligated in the vector pBBR1MCS-2::ABC (Seq ID No. 40) likewise cleaved using XbaI by means of Fast Link Ligation Kit (Epicentre Technologies; Madison, Wis., USA). The target vector pBBR1MCS-2::ABCM (Seq ID No. 58) obtained has a size of 9892 base pairs. The insert of the vector was sequenced. The chromosomal DNA was isolated by means of DNeasy Blood and Tissue Kit (Qiagen; Hilden) according to manufacturer's instructions. The carrying-out of the PCR, the checking of the successful amplification of the PCR by means of agarose gel electrophoresis, ethidium bromide staining of the DNA, determination of the PCR fragment size, purification of the PCR products and DNA concentration determination took place in a manner known to the person skilled in the art. The transformation of Pseudomonas putida KT2440 and GPp104 using the vector pBBR1MCS-2::ABCM took place as previously described (Iwasaki et al. Biosci. Biotech. Biochem. 1994. 58(5):851-854). The plasmid DNA of every 10 clones was isolated and analyzed. The strains obtained carrying the plasmids were named P. putida KT2440 pBBR1MCS-2::ABCM and P. putida GPp104 pBBR1MCS-2::ABCM.

14. Quantification of the Rhamnolipid Production by Recombinant P. putida Strains with and without Overexpression of the Pseudomonas aeruginosa DSMI 707 pa1131 gene The recombinant strains P. putida strains P. putida KT2440 pBBR1MCS-2::ABC, P. putida KT2440 pBBR1MCS-2::ABCM, P. putida KT2440 pBBR1MCS-2::ABC and P. putida GPp104 pBBR1MCS-2::ABCM generated in the Examples 2 and 13 were cultured on LB agar kanamycin (50 μg/ml) plates. The subsequent culturing for the production of the rhamnolipids took place as described in Example 12.

The sample preparation for the following chromatographic analyses and the chromatographic analyses themselves took place as described in Example 4.

The results are shown in the following table.

Formation of di- and monorhamnosyl lipids by P. putida strains with and without overexpression of the P. aeruginosa gene pa1131 after 48 h incubation

| P. putida strains | Dirhamnosyl lipids [mg/l] | Monorhamnosyl lipids [peak area] |
|---|---|---|
| KT2440 pBBR1MCS-2::ABC | 310 | 19 |
| KT2440 pBBR1MCS-2::ABCM | 1053 | 314 |
| GPp104 pBBR1MCS-2::ABC | 689 | 127 |
| GPp104 pBBR1MCS-2::ABCM | 960 | 1090 |

The results show that the overexpression of the P. aeruginosa gene pa1131 in both strain backgrounds (KT2440: wild-type and GPp104 having inactivated polyhydroxybutyrate formation) leads to an increased formation of di- and monorhamnosyl lipids. The results furthermore show that the reduction of the polyhydroxybutyrate formation in GPp104 generally leads to an increased formation of rhamnosyl lipids.

15. Construction of a Vector pEC-XT99A::AB for the Heterologous Expression of the Genes rhlA and rhlB from Pseudomonas aeruginosa DSM1707 in Corynebacterium glutamicum For the heterologous expression of the genes rhlA and rhlB from Pseudomonas aeruginosa DSM1707 in Corynebacte-

*rium glutamicum*, the plasmid pEC-XT99A::AB (Seq ID No. 52) is constructed. For this, the synthetic operon rhlAB (Seq ID No. 37) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::AB, the synthetic operon is cleaved from the vector by means of BglII and XbaI and subsequently ligated into the expression vector pEC-XT99A (U.S. Pat. No. 7,118,904) cleaved using BamHI and XbaI. The resulting plasmid pEC-XT99A::AB (Seq ID No. 52) is 9793 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *C. glutamicum* ATCC13032 using the vector pEC-XT99A::AB takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented with 5 mg/l of tetracycline). The plates were incubated at 33° C. for two days. The strain obtained carrying the plasmid is named *C. glutamicum* pEC-XT99A::AB.

16. Construction of a Vector pEC-XT99A::ABC for the Heterologous Expression of the Genes rhlA, rhlB and rhlC from *Pseudomonas aeruginosa* DSM1707 in *Corynebacterium glutamicum*

For the heterologous expression of the genes rhlA, rhlB and rhlC from *Pseudomonas aeruginosa* DSM1707 in *Corynebacterium glutamicum*, the plasmid pEC-XT99A::ABC (Seq ID No. 53) is constructed. For this, the synthetic operon rhlABC (Seq ID No. 39) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::ABC, the synthetic operon is cleaved from the vector by means of BglII and XbaI and subsequently ligated into the expression vector pEC-XT99A (U.S. Pat. No. 7,118,904) cleaved using BamHI and XbaI. The resulting plasmid pEC-XT99A::ABC (Seq ID No. 53) is 10780 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *C. glutamicum* ATCC13032 using the vector pEC-XT99A::ABC takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented using 5 mg/l of tetracycline). The plates were incubated at 33° C. for two days. The strain obtained carrying the plasmid is named *C. glutamicum* pEC-XT99A::ABC.

17. Construction of a Vector pEC-XT99A::ABM for the Heterologous Expression of the Genes rhlA, rhlB and pa1131 from *Pseudomonas aeruginosa* DSM1707 in *Corynebacterium glutamicum*

For the heterologous expression of the genes rhlA, rhlB and pa1131 from *Pseudomonas aeruginosa* DSM1707 in *Corynebacterium glutamicum*, the plasmid pEC-XT99A::ABM (Seq ID No. 54) is constructed. For this, the synthetic operon rhlABM (Seq ID No. 41) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::ABM, the synthetic operon is cleaved from the vector by means of BglII and XbaI and subsequently ligated into the expression vector pEC-XT99A (U.S. Pat. No. 7,118, 904) cleaved using BamHI and XbaI. The resulting plasmid pEC-XT99A::ABM (Seq ID No. 54) is 11073 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *C. glutamicum* ATCC13032 using the vector pEC-XT99A::ABM takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented with 5 mg/l of tetracycline). The plates were incubated at 33° C. for two days. The strain obtained carrying the plasmid is named *C. glutamicum* pEC-XT99A::ABM.

18. Construction of a Vector pEC-XT99A::ABCM for the Heterologous Expression of the Genes rhlA, rhlB, pa1131 and rhlC from *Pseudomonas aeruginosa* DSM1707 in *Corynebacterium glutamicum*

For the heterologous expression of the genes rhlA, rhlB, pa1131 and rhlC from *Pseudomonas aeruginosa* DSM1707 in *Corynebacterium glutamicum*, the plasmid pEC-XT99A::ABCM (Seq ID No. 55) is constructed. For this, the gene pa131 (Seq ID No. 59) was amplified starting from genomic DNA of the strain *Pseudomonas aeruginosa* PAO1 (DSM 1707) using the oligonucleotides

```
MFS2.0_xbal_fw:                  (Seq ID No. 60)
5'-AGGAAATCTAGATGAGAGGCCGGCAAGGATAC-3'

MES2.0_Xbal_rev:                 (Seq ID No. 61)
5-CCAGGTTCTAGACGCCAGGATTGAACAGTACC-3'.
```

The amplification of the PCR product (1483 base pairs) was carried out using the Phusion™ High-Fidelity Master Mix from New England Biolabs (Frankfurt) polymerase. The PCR product was cleaved using XbaI and ligated into the vector pBBR1MCS-2::ABC (Seq ID No. 40) likewise cleaved using XbaI by means of Fast Link Ligation Kit (Epicentre Technologies; Madison, Wis., USA). The target vector pEC-XT99A::ABCM (Seq ID No 55) obtained has a size of 12263 base pairs. The insert of the vector was sequenced. The chromosomal DNA was isolated by means of DNeasy Blood and Tissue Kit (Qiagen; Hilden) according to manufacturer's instructions. The carrying-out of the PCR, the checking of the successful amplification of the PCR by means of agarose gel electrophoresis, ethidium bromide staining of the DNA, determination of the PCR fragment size, purification of the PCR products and DNA concentration determination took place in the manner known to the person skilled in the art.

The transformation of *C. glutamicum* ATCC13032 using the vector pEC-XT99A::ABCM takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented with 5 mg/l of tetracycline). The plates were incubated for two days at 33° C. The strain obtained carrying the plasmid is named *C. glutamicum* pEC-XT99A::ABCM.

19. Construction of a Vector pVWEX1::rfbBDAC for Heterologous Expression in *C. glutamicum*

For the heterologous expression of the genes rfbBDAC from *P. putida* under the control of the lac promoter in *C. glutamicum*, the vector pVWEX1::rfbBDAC (Seq ID No. 57) is constructed.

For this, the vector pBBR1MCS-2::rfbBDAC (Seq ID No. 45) is digested using XbaI and the fragment (3840 bp) containing the genes rfbBDAC from *P. putida* KT2440 and the lac promoter is ligated into the vector pVWEX1 (Seq ID No. 56) digested with XbaI. The resulting plasmid pVWEX1::rfbBDAC (Seq ID No. 57) is 12311 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *C. glutamicum* ATCC13032 pEC-XT99A, ATCC13032 pEC-XT99A::AB, ATCC13032 pEC-XT99A::ABM, ATCC13032 pEC-XT99A::ABC and ATCC13032 pEC-XT99A::ABCM using the vector pVWEX1::rfbBDAC takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented with 5 mg/l of tetracycline and 25 mg/l of kanamycin). The plates were incubated at 33° C. for two days. The strains obtained carrying the plasmids are named *C. glutamicum* pEC-XT99A pVWEX1::rfbBDAC, *C. glutamicum* pEC-XT99A::AB pVWEX1::rfbBDAC, *C. glutamicum* pEC-XT99A::ABM pVWEX1::rfbBDAC, *C. glutamicum* pEC-XT99A::ABC pVWEX1::rfbBDAC and *C. glutamicum* pEC-XT99A::ABCM pVWEX1::rfbBDAC.

20. Quantification of the Rhamnolipid Production by Recombinant *C. Glutamicum* Strains The recombinant strains *C. glutamicum* strains generated in the Examples 15 to 19 *C. glutamicum* pEC-XT99A, *C. glutamicum* pEC-XT99A::AB, *C. glutamicum* pEC-XT99A::ABC, *C. glutamicum* pEC-XT99A::ABM, *C. glutamicum* pEC-XT99A::ABCM, *C. glutamicum* pEC-XT99A pVWEX1::rfbBDAC, *C. glutamicum* pEC-XT99A:: AB pVWEX1::rfbBDAC, *C. glutamicum* pEC-XT99A:: ABM pVWEX1::rfbBDAC, *C. glutamicum* pEC-XT99A:: ABC pVWEX1::rfbBDAC and *C. glutamicum* pEC-XT99A::ABCM pVWEX1::rfbBDAC are cultured on LBHIS agar plates using 5 mg/l of tetracycline and 5 mg/l of tetracycline and 25 mg/l of kanamycin. For the investigation of the rhamnolipid production in the shaker flask, precultures are first prepared. For this, an inoculation loop of a strain freshly streaked on an LBHIS agar plate is used and 10 ml of LBHIS medium (18.5 g/l of brain heart infusion broth, 0.5 M sorbitol, 5 g/l of Bacto tryptone, 2.5 g/l of Bacto yeast extract and 5 g/l of NaCl, supplemented with 5 mg/l of tetracycline or 5 mg/l of tetracycline and 25 mg/l of kanamycin) is inoculated into a 100 ml Erlenmeyer flask. The culturing of the strains takes place at 33° C. and 200 rpm overnight. The next morning, 50 ml of CGXII medium (containing 5 mg/l of tetracycline or 5 mg/l of tetracycline and 25 mg/l of kanamycin) are inoculated into a 500 ml Erlenmeyer flask containing baffles with 1 ml of the preculture (start $OD_{600}$ 0.1).

CGXII Medium:
   20 g/l of $(NH_4)_2SO_4$ (Merck)
   5 g/l of urea (Merck)
   1 g/l of $KH_2PO_4$ (Merck)
   1 g/l of $K_2HPO_4$ (Merck)
   0.25 g/l of $MgSO_4 \cdot 7 H_2O$ (Merck)
   10 mg/l of $CaCl_2$ (Merck)
   42 g/l of MOPS (Roth)
   0.2 mg/l of biotin (Merck)
   1 ml/l of trace salt solution
   adjust to pH 7 using NaOH
   after autoclaving add 1 ml/l of protocatechuic acid (30 g/l dissolved in dil. NaOH, sterile-filtered) and 40 g/l of glucose (Merck)

Trace Salt Solution:
   10 g/l of $FeSO_4 \cdot 7 H_2O$ (Merck)
   10 g/l of $MnSO_4 \cdot H_2O$ (Merck)
   1 g/l of $ZnSO_4 \cdot 7 H_2O$ (Merck)
   0.2 g/l of $CuSO_4 \cdot 5 H_2O$ (Merck)
   20 mg/l of $NiCl_2 \cdot 6 H_2O$ (Merck)
   to dissolve acidify to pH 1 using HCl The cultures are cultured at 200 rpm and 33° C. up to an optical density (600 nm) of 0.4-0.6. At this optical density, the cultures are induced by the addition of IPTG (isopropyl-β-D-thiogalactopyranoside; 1 mM final concentration). The subsequent expression likewise takes place at 33° C. and 200 rpm for 72 h. At intervals of 24 h, a sample of 1 ml of broth is removed from the culture flask. The sample preparation for the following chromatographic analyses and the chromatographic analyses themselves are carried out as described in Example 4.

While *C. glutamicum* pEC-XT99A produces no rhamnolipids, in the recombinant strains *C. glutamicum* pEC-XT99A::AB, *C. glutamicum* pEC-XT99A::ABC, *C. glutamicum* pEC-XT99A::ABM and *C. glutamicum* pEC-XT99A::ABCM the formation of rhamnolipids is detectable. With the aid of reference materials, it is shown that *C. glutamicum* pEC-XT99A::AB and *C. glutamicum* pEC-XT99A::ABM only form monorhamnosyl lipids, while *C. glutamicum* pEC-XT99A::ABC, *C. glutamicum* pEC-XT99A::ABM and *C. glutamicum* pEC-XT99A::ABCM are able to form dirhamnosyl lipids and monorhamnosyl lipids. Furthermore, it is shown that *C. glutamicum* pEC-XT99A:: ABM and *C. glutamicum* pEC-XT99A::ABCM are able to form more monorhamnosyl lipids or dirhamnosyl lipids and monorhamnosyl lipids than the respective reference strains *C. glutamicum* pEC-XT99A::AB and *C. glutamicum* pEC-XT99A::ABC without amplification of the pa131 gene from *Pseudomonas aeruginosa*.

Moreover, it is shown that the strains *C. glutamicum* pEC-XT99A::AB pVWEX1::rfbBDAC, *C. glutamicum* pEC-XT99A::ABM pVWEX1::rfbBDAC, *C. glutamicum* pEC-XT99A::ABC pVWEX1::rfbBDAC and *C. glutamicum* pEC-XT99A::ABCM pVWEX1::rfbBDAC form significantly more mono-(*C. glutamicum* pEC-XT99A::AB pVWEX1::rfbBDAC and *C. glutamicum* pEC-XT99A:: ABM pVVVEX1::rfbBDAC) or mono- and dirhamnosyl lipids (*C. glutamicum* pEC-XT99A::ABC pVWEX1::rfbBDAC and *C. glutamicum* pEC-XT99A::ABCM pVWEX1::rfbBDAC) than the strains, *C. glutamicum* pEC-XT99A::

ABM, *C. glutamicum* pEC-XT99A::ABC and *C. glutamicum* pEC-XT99A::ABCM without amplification of the of the rfbBDA genes from *P. putida*.

21. Construction of *Pseudomonas* Strains that Carry the Plasmids pBBR1MCS-2, pBBR1MCS-2::AB, pBBR1MCS-2::ABC, pBBR1MCS-2::ABM and pBBR1MCS-2::ABCM The plasmids pBBR1MCS-2, pBBR1MCS-2::AB, pBBR1MCS-2::ABC, pBBR1MCS-2::ABM and pBBR1MCS-2::ABCM are incorporated in *Pseudomonas fluorescens* DSM 50090, *Pseudomonas fluorescens* DSM 9958, *Pseudomonas putida* DSM 6899, *Pseudomonas putida* DSM 50204, *Pseudomonas putida* 50194, *P. brassicacearum* DSM 13227, *P. stutzeri* DSM 10701, *Pseudomonas stutzeri* DSM 4166 and *Pseudomonas fulva* DSM 17717 by electroporation. The transformation of *Pseudomonas* strains takes place as described previously (Iwasaki et al. Biosci. Biotech. Biochem. 1994. 58(5):851-854). The selection of the transformants takes place on nutrient agar plates (5 g/l of peptone; 3 g/l of meat extract; 15 g/l of agar; pH 7; supplemented with 50 mg/l of kanamycin). The plates are incubated at 30° C. or rather 28° C. for two days. The strains obtained, carrying the plasmids, are named *Pseudomonas fluorescens* DSM 50090 pBBR1MCS-2, *Pseudomonas fluorescens* DSM 9958 pBBR1MCS-2, *Pseudomonas putida* DSM 6899 pBBR1MCS-2, *Pseudomonas putida* DSM 50204 pBBR1MCS-2, *Pseudomonas putida* 50194 pBBR1MCS-2, *P. brassicacearum* DSM 13227 pBBR1MCS-2, *P. stutzeri* DSM 10701 pBBR1MCS-2, *Pseudomonas stutzeri* DSM 4166 pBBR1MCS-2, *Pseudomonas fulva* DSM 17717 pBBR1MCS-2, *Pseudomonas fluorescens* DSM 50090 pBBR1MCS-2::AB, *Pseudomonas fluorescens* DSM 9958 pBBR1MCS-2::AB, *Pseudomonas putida* DSM-6899 pBBR1MCS-2::AB, *Pseudomonas putida* DSM 50204 pBBR1MCS-2::AB, *Pseudomonas putida* 50194 pBBR1MCS-2::AB, *P. brassicacearum* DSM 13227 pBBR1MCS-2::AB, *P. stutzeri* DSM 10701 pBBR1MCS-2::AB, *Pseudomonas stutzeri* DSM 4166 pBBR1MCS-2::AB, *Pseudomonas fulva* DSM 17717 pBBR1MCS-2::AB, *Pseudomonas fluorescens* DSM 50090 pBBR1MCS-2::ABC, *Pseudomonas fluorescens* DSM 9958 pBBR1MCS-2::ABC, *Pseudomonas putida* DSM 6899 pBBR1MCS-2::ABC, *Pseudomonas putida* DSM 50204 pBBR1MCS-2::ABC, *Pseudomonas putida* 50194 pBBR1MCS-2::ABC, *P. brassicacearum* DSM 13227 pBBR1MCS-2::ABC, *P. stutzeri* DSM 10701 pBBR1MCS-2::ABC, *Pseudomonas stutzeri* DSM 4166 pBBR1MCS-2::ABC, *Pseudomonas fulva* DSM 17717 pBBR1MCS-2::ABC, *Pseudomonas fluorescens* DSM 50090 pBBR1MCS-2::ABCM, *Pseudomonas fluorescens* DSM 9958 pBBR1MCS-2::ABCM, *Pseudomonas putida* DSM 6899 pBBR1MCS-2::ABCM, *Pseudomonas putida* DSM 50204 pBBR1MCS-2::ABCM, *Pseudomonas putida* 50194 pBBR1MCS-2::ABCM, *P. brassicacearum* DSM 13227 pBBR1MCS-2::ABCM, *P. stutzeri* DSM 10701 pBBR1MCS-2::ABCM, *Pseudomonas stutzeri* DSM 4166 pBBR1MCS-2::ABCM, *Pseudomonas fulva* DSM 17717 pBBR1MCS-2::ABCM, *Pseudomonas fluorescens* DSM 50090 pBBR1MCS-2::ABM, *Pseudomonas fluorescens* DSM 9958 pBBR1MCS-2::ABM, *Pseudomonas putida* DSM 6899 pBBR1MCS-2::ABM, *Pseudomonas putida* DSM 50204 pBBR1MCS-2::ABM, *Pseudomonas putida* 50194 pBBR1MCS-2::ABM, *P. brassicacearum* DSM 13227 pBBR1MCS-2::ABM, *P. stutzeri* DSM 10701 pBBR1MCS-2::ABM, *Pseudomonas stutzeri* DSM 4166 pBBR1MCS-2::ABM and *Pseudomonas fulva* DSM 17717 pBBR1MCS-2::ABM.

22. Quantification of the Rhamnolipid Production by Recombinant *Pseudomonas* Strains The recombinant strains *Pseudomonas* strains *Pseudomonas fluorescens* DSM 50090, *Pseudomonas fluorescens* DSM 9958 pBBR1MCS-2, *Pseudomonas putida* DSM 6899 pBBR1MCS-2, *Pseudomonas putida* DSM 50204 pBBR1MCS-2, *Pseudomonas putida* 50194 pBBR1MCS-2, *P. brassicacearum* DSM 13227 pBBR1MCS-2, *P. stutzeri* DSM 10701 pBBR1MCS-2, *Pseudomonas stutzeri* DSM 4166 pBBR1MCS-2, *Pseudomonas fulva* DSM 17717 pBBR1MCS-2, *Pseudomonas fluorescens* DSM 50090 pBBR1MCS-2::AB, *Pseudomonas fluorescens* DSM 9958 pBBR1MCS-2::AB, *Pseudomonas putida* DSM 6899 pBBR1MCS-2::AB, *Pseudomonas putida* DSM 50204 pBBR1MCS-2::AB, *Pseudomonas putida* 50194 pBBR1MCS-2::AB, *P. brassicacearum* DSM 13227 pBBR1MCS-2::AB, *P. stutzeri* DSM 10701 pBBR1MCS-2::AB, *Pseudomonas stutzeri* DSM 4166 pBBR1MCS-2::AB, *Pseudomonas fulva* DSM 17717 pBBR1MCS-2::AB, *Pseudomonas fluorescens* DSM 50090 pBBR1MCS-2::ABC, *Pseudomonas fluorescens* DSM 9958 pBBR1MCS-2::ABC, *Pseudomonas putida* DSM 6899 pBBR1MCS-2::ABC, *Pseudomonas putida* DSM 50204 pBBR1MCS-2::ABC, *Pseudomonas putida* 50194 pBBR1MCS-2::ABC, *P. brassicacearum* DSM 13227 pBBR1MCS-2::ABC, *P. stuitzeri*. DSM 10701 pBBR1MCS-2::ABC; *Pseudomonas stutzeri* DSM 4166 pBBR1MCS-2::ABC, *Pseudomonas fulva* DSM 17717 pBBR1MCS-2::ABC, *Pseudomonas fluorescens* DSM 50090 pBBR1MCS-2::ABCM, *Pseudomonas fluorescens* DSM 9958 pBBR1MCS-2::ABCM, *Pseudomonas putida* DSM 6899 pBBR1MCS-2::ABCM, *Pseudomonas putida* DSM 50204 pBBR1MCS-2::ABCM, *Pseudomonas putida* 50194 pBBR1MCS-2::ABCM, *P. brassicacearum* DSM 13227 pBBR1MCS-2::ABCM, *P. stutzeri* DSM 10701 pBBR1MCS-2::ABCM, *Pseudomonas stutzeri* DSM 4166 pBBR1MCS-2::ABCM, *Pseudomonas fulva* DSM 17717 pBBR1MCS-2::ABCM, *Pseudomonas fluorescens* DSM 50090 pBBR1MCS-2::ABM, *Pseudomonas fluorescens* DSM 9958 pBBR1MCS-2::ABM, *Pseudomonas putida* DSM 6899 pBBR1MCS-2::ABM, *Pseudomonas putida* DSM 50204 pBBR1MCS-2::ABM, *Pseudomonas putida* 50194 pBBR1MCS-2::ABM, *P. brassicacearum* DSM 13227 pBBR1MCS-2::ABM, *P. stutzeri* DSM 10701 pBBR1MCS-2::ABM, *Pseudomonas stutzeri* DSM 4166 pBBR1MCS-2::ABM and *Pseudomonas fulva* DSM 17717 pBBR1MCS-2::ABM generated in Example 21 are cultured on LB agar kanamycin (50 µg/ml) plates. The subsequent culturing for the production of the rhamnolipids takes place as described in Example 12. The sample preparation for the following chromatographic analyses and the chromatographic analyses themselves are carried out as described in Example 4.

While the *Pseudomonas* strains *Pseudomonas fluorescens* DSM 50090, *Pseudomonas fluorescens* DSM 9958 pBBR1MCS-2, *Pseudomonas putida* DSM 6899 pBBR1MCS-2, *Pseudomonas putida* DSM 50204 pBBR1MCS-2, *Pseudomonas putida* 50194 pBBR1MCS-2, *P. brassicacearum* DSM 13227 pBBR1MCS-2, *P. stutzeri* DSM 10701 pBBR1MCS-2, *Pseudomonas stutzeri* DSM 4166 pBBR1MCS-2, *Pseudomonas fulva* DSM 17717 pBBR1MCS-2 produce no rhamnolipids, in the recombinant strains *Pseudomonas fluorescens* DSM 50090 pBBR1MCS- 2::AB, *Pseudomonas fluorescens* DSM 9958 pBBR1MCS-2::AB, *Pseudomonas putida* DSM 6899 pBBR1MCS-2::AB, *Pseudomonas putida* DSM 50204 pBBR1MCS-2::AB, *Pseudomonas putida* 50194 pBBR1MCS-2::AB, *P. brassicacearum* DSM 13227 pBBR1MCS-2::AB, *P. stutzeri* DSM 10701 pBBR1MCS-2::AB, *Pseudomonas stutzeri* DSM 4166 pBBR1MCS-2::AB, *Pseudomonas* fulva DSM 17717 pBBR1MCS-2::AB, *Pseudomonas fluorescens* DSM 5.0090 pBBR1MCS-2::ABM, Pseudomonasfluorescens DSM 9958 pBBR1MCS-2::ABM, *Pseudomonas putida* DSM 6899 pBBR1MCS-2::ABM, *Pseudomonas putida* DSM 50204 pBBR1MCS-2::ABM, *Pseudomonas putida* 50194 pBBR1MCS-2::ABM, *P. brassicacearum* DSM 13227 pBBR1MCS-2::ABM, *P. stutzeri* DSM 10701 pBBR1MCS-2::ABM, *Pseudomonas stutzeri* DSM 4166 pBBR1MCS-2::ABM and *Pseudomonas* fulva DSM 17717 pBBR1MCS-2::ABM the formation of monorhamnosyl lipids and in the strains *Pseudomonas fluorescens* DSM 50090 pBBR1MCS-2::ABC, *Pseudomonas fluorescens* DSM 9958 pBBR1MCS-2::ABC, *Pseudomonas putida* DSM 6899 pBBR1MCS-2::ABC, *Pseudomonas putida* DSM 50204 pBBR1MCS-2::ABC, *Pseudomonas putida* 50194 pBBR1MCS-2::ABC, *P. brassicacearum* DSM 13227 pBBR1MCS-2::ABC, *P. stutzeri* DSM 10701 pBBR1MCS-2::ABC, *Pseudomonas stutzeri* DSM 4166 pBBR1MCS-2::ABC, *Pseudomonas* fulva DSM 17717 pBBR1MCS-2::ABC, *Pseudomonas fluorescens* DSM 50090 pBBR1MCS-2::ABCM, *Pseudomonas fluorescens* DSM 9958 pBBR1MCS-2::ABCM, *Pseudomonas putida* DSM 6899 pBBR1MCS-2::ABCM, *Pseudomonas putida* DSM 50204 pBBR1MCS-2::ABCM, *Pseudomonas putida* 50194 pBBR1MCS-2::ABCM, *P. Brassicacearum* DSM 13227 pBBR1MCS-2::ABCM, *P. stutzeri* DSM 10701 pBBR1MCS-2::ABCM, *Pseudomonas stutzeri* DSM 4166 pBBR1MCS-2::ABCM and *Pseudomonas* fulva DSM 17717 pBBR1MCS-2::ABCM the formation of mono- and dirhamnosyl lipids is detectable.

Moreover, fewer monorhamnosyl lipids are formed by the recombinant *Pseudomonas* strains *Pseudomonas fluorescens* DSM 50090 pBBR1MCS-2::ABM, *Pseudomonas fluorescens* DSM 9958 pBBR1MCS-2::ABM, *Pseudomonas putida* DSM 6899 pBBR1MCS-2::ABM, *Pseudomonas putida* DSM 50204 pBBR1MCS-2::ABM, *Pseudomonas putida* 50194 pBBR1MCS-2::ABM, *P. brassicacearum* DSM 13227 pBBR1MCS-2::ABM, *P. stutzeri* DSM 10701 pBBR1MCS-2::ABM, *Pseudomonas stutzeri* DSM 4166 pBBR1MCS-2::ABM *Pseudomonas* fulva DSM 17717 pBBR1MCS-2::ABM and by the recombinant *Pseudomonas* strains *Pseudomonas fluorescens* DSM 50090 pBBR1MCS-2::ABCM, *Pseudomonas fluorescens* DSM 9958 pBBR1MCS-2::ABCM, *Pseudomonas putida* DSM 6899 pBBR1MCS-2::ABCM, *Pseudomonas putida* DSM 50204 pBBR1MCS-2::ABCM, *Pseudomonas putida* 50194 pBBR1MCS-2::ABCM, *P. brassicacearum* DSM 13227 pBBR1MCS-2::ABCM, *P. stutzeri* DSM 10701 pBBR1MCS-2::ABCM, *Pseudomonas stutzeri* DSM 4166 pBBR1MCS-2::ABCM and *Pseudomonas* fulva DSM 17717 pBBR1MCS-2::ABCM fewer mono- and dirhamnosyl lipids are formed than by the respective reference strains without the *P. aeruginosa* gene pa1131 *Pseudomonas fluorescens* DSM 50090 pBBR1MCS-2::AB, *Pseudomonas fluorescens* DSM 9958 pBBR1MCS-2::AB, *Pseudomonas putida* DSM 6899pBBR1MCS-2::AB, *Pseudomonas putida* DSM 50204 pBBR1MCS-2::AB, *Pseudomonas putida* 50194 pBBR1MCS-2::AB, *P. brassicacearum* DSM 13227 pBBR1MCS-2:AB, *P. stutzeri* DSM 10701 pBBR1MCS-2::AB, *Pseudomonas stutzeri* DSM 4166 pBBR1MCS-2::AB and *Pseudomonas* fulva DSM 17717 pBBR1MCS-2::AB and *Pseudomonas fluorescens* DSM 50090 pBBR1MCS-2::ABC, *Pseudomonas fluorescens* DSM 9958 pBBR1MCS-2::ABC, *Pseudomonas putida* DSM 6899 pBBR1MCS-2::ABC, *Pseudomonas putida* DSM 50204 pBBR1MCS-2::ABC, *Pseudomonas putida* 50194 pBBR1MCS-2::ABC, *P. brassicacearum* DSM 13227 pBBR1MCS-2::ABC, *P. stutzeri* DSM 10701 pBBR1MCS-2::ABC, *Pseudomonas stutzeri* DSM 4166 pBBR1MCS-2::ABC and *Pseudomonas* fulva DSM 17717 pBBR1MCS-2::ABC without amplification of the pa1131 gene from *Pseudomonas aeruginosa*.

23. Construction of the Vectors pBBR1MCS-2::ABPAO1-C1 and pBBR1MCS-2::ABPA 7-CE264 for the heterologous expression of alternative rhlA, rhlB and rhlC genes from *Pseudomonas aeruginosa* PAO1, *Pseudomonas aeruginosa* PA7, *Pseudomonas aeruginosa* 1 and *Burkholderia thailandensis* E264 in *P. putida*

For the heterologous expression of the genes rhlA, rhlB and rhlC from *Pseudomonas aeruginosa* PAO1 and *Pseudomonas aeruginosa* PA7, the plasmids pBBR1MCS-2::ABPAO1 (Seq ID No. 62) and pBBR1MCS-2::ABPA7 (Seq ID No. 63) are first constructed. For this, the synthetic operons rhlABPAO1 (Seq ID No. 64) and rhlABPA7 (Seq ID No. 65) are synthesized by the company DNA 2.0 (Menlo Park, Calif., U.S.A) and intercloned in the commercial vector pJ294 (DNA 2.0). The basis for the synthesis is the already known genomic sequence of the strains *Pseudomonas aeruginosa* PAO1 and *Pseudomonas aeruginosa* PA7. Starting from the vectors pJ294::ABPAO1 and pJ294::ABPA7, the synthetic operons are cleaved from the vectors by means of KpnI and XbaI and subsequently ligated into the expression vector pBBR1MCS-2 (Seq ID No. 49) (Kovach et al., 1995: Four new derivatives of the broad-host-range cloning vector pBBR1MCS carrying different antibiotic-resistance cassettes. Gene, 166:175-176) cleaved using KpnI and XbaI. The resulting plasmids pBBR1MCS-2::ABPAO1 (Seq ID No. 62) and pBBR1MCS-2::ABPA7 (Seq ID No. 63) are 7332 and 7354 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

In the second step, the plasmids pBBR1MCS-2::ABPAO1-C1 (Seq ID No. 66) and pBBR1MCS-2::ABPA7-CE264 (Seq ID No. 67) are produced. For this, the rhlC genes from *Pseudomonas aeruginosa* 1 (Seq ID No. 68) and *Burkholderia thailandensis* E264 (Seq ID No. 76) are synthesized by the company DNA 2.0 (Menlo Park; CA, U.S.A) and intercloned in the commercial vector pJ294 (DNA 2.0). The basis for the synthesis is the already known genomic sequence of the strains *Pseudomonas aeruginosa* 1 and *Burkholderia thailandensis* E264. Starting from the vectors pJ294::C1 and pJ294::CE264, the rhlC genes are cleaved from the vectors by means of Xba and SacI and subsequently ligated into the vectors pBBR1MCS-2::ABPAO1 (Seq ID No. 62) and pBBR1MCS-2::ABPA7 (Seq ID No. 63) likewise cleaved using Xba and SacI. The resulting plasmids pBBR1MCS-2:: ABPAO1-C1 (Seq ID No. 66) and pBBR1MCS-2::ABPA7-CE264 (Seq ID No. 67) are 8325 and 8335 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *Pseudomonas putida* KT2440 and GPp104 using the vectors pBBR1MCS-2, pBBR1MCS-2::

ABPAO1-C1 and pBBR1MCS-2::ABPA7-CE264 takes place as previously described (Iwasaki et al. Biosci. Biotech. Biochem. 1994. 58(5):851-854). The plasmid DNA of every 10 clones was isolated and analyzed. The strains obtained carrying the plasmids are named P. putida KT2440 pBBR1MCS-2, P. putida KT2440 pBBR1MCS-2::ABPAO1-C1, P. putida KT2440 pBBR1MCS-2::ABPA7-CE264, P. putida GPp104 pBBR1MCS-2, P. putida GPp104 pBBR1MCS-2::ABPAO1-C1 and P. putida GPp104 pBBR1MCS-2::ABPA7-CE264.

24. Quantification of the Rhamnolipid Production by Recombinant P. Putida Strains Having Alternative rhlA, rhlB and rhlC genes from Pseudomonas aeruginosa PAO1, Pseudomonas aeruginosa PA7, Pseudomonas aeruginosa 1 and Burkholderia thailandensis E264

The recombinant strains P. putida strains generated in Example 23 are cultured on LB agar kanamycin (50 µg/ml) plates. The subsequent culturing for the production of the rhamnolipids takes place as described in Example 12. The sample preparation for the following chromatographic analyses and the chromatographic analyses themselves are carried out as described in Example 4.

While the strains P. putida KT2440 pBBR1MCS-2 and P. putida GPp104 pBBR1MCS-2 are not able to produce mono- and dirhamnosyl lipids, the strains P. putida KT2440 pBBR1MCS-2::ABPAO1-C1, P. putida KT2440 pBBR1MCS-2::ABPA7-CE264, P. putida GPp104 pBBR1MCS-2::ABPAO1-C1 and P. putida GPp104 pBBR1MCS-2::ABPA7-CE264 form both mono- as well as dirhamnosyl lipids. It is shown that the strains are able to produce more mono- and dirhamnosyl lipids with an attenuation of the polyhydroxybutyrate formation (P. putida GPp104 pBBR1MCS-2::ABPAO1-C1 and P. putida GPp104 pBBR1MCS-2::ABPA7-CE264) than the strains without attenuation of the polyhydroxybutyrate formation (P. putida KT2440 pBBR1MCS-2::ABPAO1-C1 and P. putida KT2440 pBBR1MCS-2::ABPA7-CE264).

25. Construction of the Vectors pBBR1MCS-2::AB_rfbBDAC, pBBR1MCS-2::ABM_rfbBDAC and pBBR1MCS-2::ABMC_rfbBDAC for the overexpression of the P. putida rfbBDAC operon in P. putida and E. coli For the construction of the vectors pBBR1MCS-2::AB_rfbBDAC, pBBR1MCS-2::ABM_rfbBDAC and pBBR1MCS-2::ABMC_rfbBDAC for the overexpression of the P. putida rfbBDAC operon in P. putida and E. coli, the P. putida rfbBDAC operon was first amplified by PCR. The vector pBBR1MCS-2::rfbBDAC (Seq ID No. 45) served as matrix for a PCR. The following oligonucleotides were used:

```
RL_AgeI-fw:                        (Seq ID No. 71)
5'-TATATATAACCGGTATTAATGCAGCTGGCACGAC-3'

RL_AgeI_rev:                       (Seq ID No. 72)
5'-GGCCGACCGGTACTAGTGGA-3'
```

The PCR was carried out using the Phusion™ High-Fidelity Master Mix of New England Biolabs (Frankfurt) polymerase. It took place in the manner known to the person skilled in the art. The target sequence (lac promoter and rfbBDAC) was intercloned in the Trenzyme alligator cloning system. E. coli DH5α (New England Biolabs; Frankfurt) transformants were selected and the plasmid DNA of different candidates was isolated and sequenced. After the sequence had been checked and examined for correctness, the vector was cleaved using AgeI. The target fragment was ligated into the vectors pBBR1MCS-2::AB (Seq ID No. 38), pBBR1MCS-2::ABM (Seq ID No. 42) and pBBR1MCS-2::ABMC (Seq ID No. 51) likewise cleaved using AgeI by means of conventional ligation methods. The resulting vectors pBBR1MCS-2::AB_rfbBDAC (Seq ID No. 73), pBBR1MCS-2::ABM_rfbBDAC (Seq ID No. 74) and pBBR1MCS-2::ABMC_rfbBDAC (Seq ID No. 75) have sizes of 11960, 13289 and 14250 base pairs. The inserts of the vectors were sequenced. The carrying-out of the PCR, the checking of the successful amplification of the PCR by means of agarose gel electrophoresis, ethidium bromide staining of the DNA, determination of the PCR fragment size, purification of the PCR products and DNA concentration determination took place in the manner known to the person skilled in the art. The transformation of Pseudomonas putida KT2440 using the vectors pBBR1MCS-2::AB_rfbBDAC, pBBR1MCS-2::ABM_rfbBDAC and pBBR1MCS-2::ABM-C_rfbBDAC took place as previously described (Iwasaki et al. Biosci. Biotech. Biochem. 1994. 58(5):851-854). The plasmid DNA of every 10 clones was isolated and analyzed. The strains obtained carrying the plasmids are named P. putida KT2440 pBBR1MCS-2::AB_rfbBDAC, P. putida KT2440 pBBR1MCS-2::ABM_rfbBDAC and P. putida KT2440 pBBR1MCS-2::ABMC_rfbBDAC.

26. Quantification of the Rhamnolipid Production by Recombinant P. putida KT2440 pBBR1MCS-2::AB_rfbBDAC, P. putida KT2440 pBBR1MCS-2::ABM_rfbBDAC, P. putida KT2440 pBBR1MCS-2::ABC_rfbBDAC, P. putida KT2440 pBBR1MCS-2::ABMC_rfbBDAC, P. putida KT2440 pBBR1MCS-2::AB, P. putida KT2440 pBBR1MCS-2::ABM, P. putida KT2440 pBBR1MCS-2::ABC and P. putida KT2440 pBBR1MCS-2::ABMC The recombinant strains P. putida strains generated in the Examples 2, 7 and 25 are cultured on LB agar-kanamycin (50 µg/ml) plates. The subsequent culturing for the production of the rhamnolipids takes place as described in Example 12. The sample preparation for the following chromatographic analyses and the chromatographic analyses themselves take place as described in Example 4.

It is shown that P. putida KT2440 pBBR1MCS-2::AB_rfbBDAC, P. putida KT2440 pBBR1MCS-2::ABM_rfbBDAC, P. putida KT2440 pBBR1MCS-2::AB and P. putida KT2440 pBBR1MCS-2::ABM are able to form monorhamnosyl lipids, while P. putida KT2440 pBBR1MCS-2::ABM-C_rfbBDAC, P. putida KT2440 pBBR1MCS-2::ABC_rfbBDAC, P. putida KT2440 pBBR1MCS-2::ABC and P. putida KT2440 pBBR1MCS-2::ABMC are able to form mono- and dirhamnosyl lipids.

Furthermore, it is shown that P. putida KT2440 pBBR1MCS-2::ABM_rfbBDAC, P. putida KT2440 pBBR1MCS-2::ABM, KT2440 pBBR1MCS-2::ABMC_rfbBDAC and KT2440 pBBR1MCS-2::ABMC are able to form more mono- and dirhamnosyl lipids than the corresponding control strains P. putida KT2440 pBBR1MCS-2::AB_rfbBDAC, P. putida KT2440 pBBR1MCS-2::AB, KT2440 pBBR1MCS-2::ABC_rfbBDAC and KT2440 pBBR1MCS-2::ABC without amplification of the Pseudomonas aeruginosa gene pa1131.

Finally, it is showh that P. putida KT2440 pBBR1MCS-2::AB_rfbBDAC, P. putida KT2440 pBBR1MCS-2::ABM_rfbBDAC, P. putida KT2440 pBBR1MCS-2::ABC_rfbBDAC, P. putida KT2440 pBBR1MCS-2::ABMC_rfbBDAC are able to form more mono-(*P. putida* KT2440 pBBR1MCS-2::AB_rfbBDAC and *P. putida* KT2440 pBBR1MCS-2::ABM_rfbBDAC) and mono- and dirhamnosyl lipids (*P. putida* KT2440 pBBR1MCS-2::ABC_rfbBDAC and *P. putida* KT2440 pBBR1MCS-2::ABMC_rfbBDAC) than the respective control strains *P. putida* KT2440 pBBR1MCS-2::AB, *P. putida* KT2440 pBBR1MCS-2::ABM, *P. putida* KT2440 pBBR1MCS-2::ABC, *P. putida* KT2440 pBBR1MCS-2::ABMC without amplification of the *P. putida* genes rfbBDAC.

27. Generation of recombinant *E. coli* W3110 pBBR1MCS-2::AB, *E. coli* W3110 pBBR1MCS-2::ABM, *E. coli* W3110 pBBR1MCS-2::ABC, *E. coli* W3110 pBBR1MCS-2::ABCM, *E. coli* W3110 pBBR1MCS-2::AB_rfbBDAC, *E. coli* W3110 pBBRMCS-2::ABM_rfbBDAC, *E. coli* W3110 pBBR1MCS-2::ABC_rfbBDAC and *E. coli* W3110 pBBR1MCS-2::ABCM_rfbBDAC The transformation of *E. coli* W3110 took place as described previously (Miller J H. A Short Course in Bacterial Genetics: A Laboratory Manual and Handbook for *Escherichia coli* and Related Bacteria. Plainview, N.Y.: Cold Spring Harbor Lab. Press; 1992) by means of electroporation. The plasmid DNA of every 10 clones was isolated and analyzed. The obtained strains carrying the plasmids were named *E. coli* W3110 pBBR1MCS-2::AB, *E. coli* W3110 pBBR1MCS-2::ABM, *E. coli* W3110 pBBR1MCS-2::ABC, *E. coli* W3110 pBBR1MCS-2::ABCM, *E. coli* W3110 pBBR1MCS-2::AB_rfbBDAC, *E. coli* W3110 pBBR1MCS-2::ABM_rfbBDAC, *E. coli* W3110 pBBR1MCS-2::ABC_rfbBDAC and *E. coli* W3110 pBBR1MCS-2::ABCM_rfbBDAC.

28. Quantification of the Rhamnolipid Production by Recombinant *E. Coli* W3110 pBBR1MCS-2::AB, *E. coli* W3110 pBBR1MCS-2::ABM, *E. coli* W3110 pBBR1MCS-2::ABC, *E. coli* W3110 pBBR1MCS-2::ABCM, *E. coli* W3110 pBBR1MCS-2::AB_rfbBDAC, *E. coli* W3110 pBBR1MCS-2::ABM_rfbBDAC, *E. coli* W3110 pBBR1MCS-2::ABC_rfbBDAC and *E. coli* W3110 pBBR1MCS-2::ABCM_rfhbBDAC The recombinant-*E. coli* strains generated in Example 27 are cultured on LB agar kanamycin (50 µg/ml) plates. The subsequent culturing for the production of the rhamnolipids takes place as described in Example 10. The sample preparation for the following chromatographic analyses and the chromatographic analyses themselves take place as described in Example 4.

It is shown that *E. coli* W3110 pBBR1MCS-2::AB, *E. coli* W3110 pBBR1MCS-2::ABM, *E. coli* W3110 pBBR1MCS-2::AB_rfbBDAC and *E. coli* W3110 pBBR1MCS-2::ABM_rfbBDAC are able to form monorhamnosyl lipids, while *E. coli* W3110 pBBR1MCS-2::ABC, *E. coli* W3110 pBBR1MCS-2::ABCM, *E. coli* W3110 pBBR1MCS-2::ABC_rfbBDAC and *E. coli* W3110 pBBR1MCS-2::ABCM_rfbBDAC are able to form mono- and dirhamnosyl lipids. Furthermore, it is shown that *E. coli* W3110 pBBR1MCS-2::ABM and *E. coli* W3110 pBBR1MCS-2::ABM_rfbBDAC form more monorhamnosyl lipids than *E. coli* W3110 pBBR1MCS-2::AB and *E. coli* W3110 pBBR1MCS-2::AB_rfbBDAC without amplification of the *Pseudomonas aeruginosa* gene pa1131.

Furthermore, it is shown that *E. coli* W3110 pBBR1MCS-2::ABCM and *E. coli* W3110 pBBR1MCS-2::ABCM_rfbBDAC form more mono- and dirhamnosyl lipids than *E. coli* W3110 pBBR1MCS-2::ABC and *E. coli* W3110 pBBR1MCS-2::ABC_rfbBDAC without amplification of the *Pseudomonas aeruginosa* gene pa1131. Furthermore, it is shown that *E. coli* W3110 pBBR1MCS-2::ABM and *E. coli* W3110 pBBR1MCS-2::ABM_rfbBDAC form more monorhamnosyl lipids than *E. coli* W3110 pBBR1MCS-2::AB and *E. coli* W3110 pBBR1MCS-2::AB_rfbBDAC without amplification of the *Pseudomonas aeruginosa* gene pa1131. Finally, it is shown that *E. coli* W3110 pBBR1MCS-2::AB_rfbBDAC, *E. coli* W3110 pBBR1MCS-2::ABM_rfbBDAC, *E. coli* W3110 pBBR1MCS-2::ABC_rfbBDAC and *E. coli* W3110 pBBR1MCS-2::ABCM_rfbBDAC are able to form more mono-(*E. coli* W3110 pBBR1MCS-2::AB_rfbBDAC, *E. coli* W3110 pBBR1MCS-2::ABM_rfbBDAC) and mono- and dirhamnosyl lipids (*E. coli* W3110 pBBR1MCS-2::ABC_rfbBDAC and *E. coli* W3110 pBBR1MCS-2::ABCM_rfbBDAC) than the respective control strains *E. coli* W3110 pBBR1MCS-2::AB, *E. coli* W3110 pBBR1MCS-2::ABM, *E. coli* W3110 pBBR1MCS-2::ABC and *E. coli* W3110 pBBR1MCS-2::ABCM without amplification of the *P. putida* genes rfbBDAC.

The invention claimed is:

1. A genetically modified *Pseudomonas putida* cell, which is able to form at least one rhamnolipid of general formula (I),

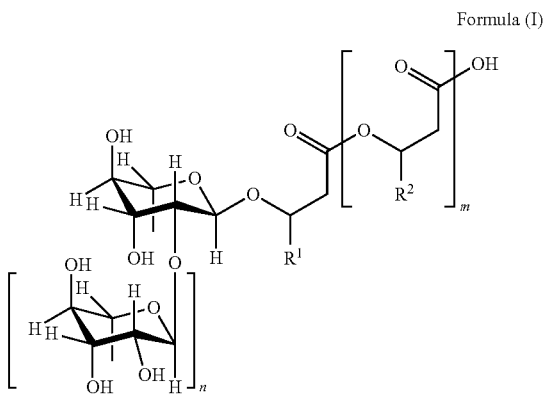

Formula (I)

wherein m=2, 1 or 0, n=1 or 0, $R^1$ and $R^2$ are organic residues having 2 to 24 carbon atoms, wherein said cell has been genetically modified such that, compared to its wild-type, the cell has an increased activity of at least one of the enzymes $E_1$, $E_2$ and $E_3$, wherein the enzyme $E_1$ has at least 95% amino acid identity to SEQ ID NO: 2, the enzyme $E_2$ has at least 95% amino acid identity to SEQ ID NO: 4, and the enzyme $E_3$ has at least 95% amino acid identity to SEQ ID NO: 6;

and wherein said cell is also genetically modified such that, compared to its wild-type, the cell has increased activity of at least one enzyme selected from the group consisting of: $E_4$, which has at least 95% amino acid identity to SEQ ID NO: 10, $E_5$, which has at least 95% amino acid identity to SEQ ID NO: 12, $E_6$, which has at least 95% amino acid identity to SEQ ID NO: 16, and $E_7$, which has at least 95% amino acid identity to SEQ ID NO: 14.

2. The genetically modified cell of claim 1, wherein said cell has increased activities of an enzyme combination selected from $E_1E_2$, $E_2E_3$ and $E_1E_2E_3$.

3. The genetically modified cell of claim 1, wherein said cell has an increased activity of the enzyme combination $E_1E_2E_3$ and n is =1.

4. The genetically modified cell of claim 1, wherein the wild-type of said cell forms polyhydroxyalkanoates having chain lengths of $C_6$ to $C_{16}$.

5. The genetically modified cell of claim 4, wherein said cell, compared to its wild-type, has a decreased activity of at least one enzyme $E_9$ or $E_{10}$, wherein $E_9$ has an amino acid sequence with at least 95% identity to the amino acid sequence of SEQ ID NO: 30 or SEQ ID NO: 32, and $E_{10}$ has an amino acid sequence with at least 95% identity to the amino acid sequence of SEQ ID NO: 34 or SEQ ID NO: 36.

6. The genetically modified cell of claim 1, wherein said cell is selected from the group consisting of *P. putida* GPp121, *P. putida* GPp122, *P. putida* GPp123, *P. putida* GPp124 and *P. putida* GPp104, *P. putida* KT42C1, *P. putida* KTOY01 and *P. putida* KTOY02.

7. The genetically modified cell of claim 1, wherein said cell, compared to its wild-type, has increased activity of each of the enzymes $E_4$, $E_5$, $E_6$, and $E_7$.

8. The genetically modified cell of claim 1, wherein said cell, compared to its wild-type, further has an increased activity of an enzyme $E_8$, which catalyzes rhamnolipid export from the cell into the surrounding medium.

9. The genetically modified cell of claim 1, wherein said genetic modification comprises introduction into said cell of at least one vector comprising a sequence selected from:

a sequence with at least 95% identity to SEQ ID NO: 1, a sequence with at least 95% identity to SEQ ID NO: 3, and a sequence with at least 95% identity to SEQ ID NO: 5.

10. The genetically modified cell of claim 9, wherein the vector comprises the sequence of SEQ ID NO: 40, SEQ ID NO: 42, SEQ ID NO: 45, or SEQ ID NO: 47.

11. The genetically modified cell of claim 9, wherein said at least one vector comprises:

a sequence with at least 95% identity to SEQ ID NO: 1, a sequence with at least 95% identity to SEQ ID NO: 3, and a sequence with at least 95% identity to SEQ ID NO: 5.

12. The genetically modified cell of claim 9, wherein said at least one vector further comprises a sequence selected from:

a sequence with at least 95% identity to SEQ ID NO: 9, a sequence with at least 95% identity to SEQ ID NO: 11, a sequence with at least 95% identity to SEQ ID NO: 13, and a sequence with at least 95% identity to SEQ ID NO: 15.

13. A method for producing rhamnolipids of general formula (I)

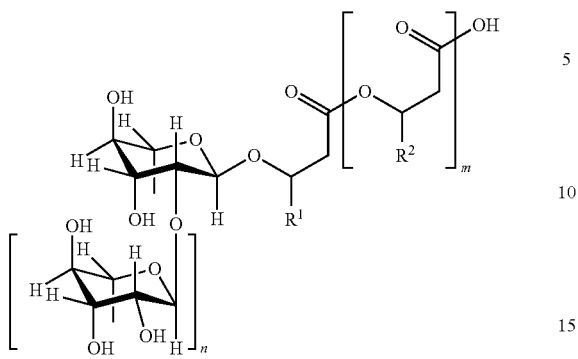

Formula (I)

wherein
m=2, 1 or 0,
n=1 or 0
$R^1$ and $R^2$ are organic residues having 2 to 24 carbon atoms,
wherein said method comprises
   I) contacting a genetically modified *Pseudomonas putida* cell according to claim 1 with a medium containing a carbon source; and
   II) culturing the cell under conditions in which the cell forms rhamnolipids from the carbon source.

14. A vector comprising at least one nucleic acid sequence selected from the group consisting of SEQ ID NO: 41, and SEQ ID NO: 50.

* * * * *

SEQUENCE LISTING

```
<160> NUMBER OF SEQ ID NOS: 92

<210> SEQ ID NO 1
<211> LENGTH: 888
<212> TYPE: DNA
<213> ORGANISM: Pseudomonas aeruginosa
<220> FEATURE:
<221> NAME/KEY: CDS
<222> LOCATION: (1)..(888)

<400> SEQUENCE: 1 atg cgg cgc gaa agt ctg ttg gta tcg gtt tgc aag ggc ctg cgg gta      48
Met Arg Arg Glu Ser Leu Leu Val Ser Val Cys Lys Gly Leu Arg Val
1               5                   10                  15 cat gtc gag cgc gtt ggg cag gat ccc ggg cgc agc acg gtg atg ctg      96
His Val Glu Arg Val Gly Gln Asp Pro Gly Arg Ser Thr Val Met Leu
            20                  25                  30 gtc aac ggc gcg atg gcg acc acc gcc tcg ttc gcc cgg acc tgc aag     144
Val Asn Gly Ala Met Ala Thr Thr Ala Ser Phe Ala Arg Thr Cys Lys
```

```
                 35                  40                  45
tgc ctg gcc gaa cat ttc aac gtg gtg ctg ttc gac ctg ccc ttc gcc    192
Cys Leu Ala Glu His Phe Asn Val Val Leu Phe Asp Leu Pro Phe Ala
     50                  55                  60 ggg cag tcg cgt cag cac aac ccg cag cgg ggg ttg atc acc aag gac    240
Gly Gln Ser Arg Gln His Asn Pro Gln Arg Gly Leu Ile Thr Lys Asp
 65                  70                  75                  80 gac gag gtg gaa atc ctc ctg gcg ctg atc gag cgc ttc gag gtc aat    288
Asp Glu Val Glu Ile Leu Leu Ala Leu Ile Glu Arg Phe Glu Val Asn
                 85                  90                  95 cac ctg gtc tcc gcg tcc tgg ggc ggt atc tcc acg ctg ctg gcg ctg    336
His Leu Val Ser Ala Ser Trp Gly Gly Ile Ser Thr Leu Leu Ala Leu
            100                 105                 110 tcg cgc aat ccg cgc ggc atc cgc agc tcg gtg gtg atg gca ttc gcc    384
Ser Arg Asn Pro Arg Gly Ile Arg Ser Ser Val Val Met Ala Phe Ala
        115                 120                 125 cct gga ctg aac cag gcg atg ctc gac tac gtc ggg cgg gcg cag gcg    432
Pro Gly Leu Asn Gln Ala Met Leu Asp Tyr Val Gly Arg Ala Gln Ala
    130                 135                 140 ctg atc gag ctg gac gac aag tcg gcg atc ggc cat ctg ctc aac gag    480
Leu Ile Glu Leu Asp Asp Lys Ser Ala Ile Gly His Leu Leu Asn Glu
145                 150                 155                 160 acc gtc ggc aaa tac ctg ccg ccg cgc ctg aaa gcc agc aac cat cag    528
Thr Val Gly Lys Tyr Leu Pro Pro Arg Leu Lys Ala Ser Asn His Gln
                165                 170                 175 cac atg gct tcg ctg gcc acc ggc gaa tac gag cag gcg cgc ttt cac    576
His Met Ala Ser Leu Ala Thr Gly Glu Tyr Glu Gln Ala Arg Phe His
            180                 185                 190 atc gac cag gtg ctg gcg ctc aac gat cgg ggc tac ctg gct tgc ctg    624
Ile Asp Gln Val Leu Ala Leu Asn Asp Arg Gly Tyr Leu Ala Cys Leu
        195                 200                 205 gag cgg atc cag agc cac gtg cat ttc atc aac ggc agc tgg gac gaa    672
Glu Arg Ile Gln Ser His Val His Phe Ile Asn Gly Ser Trp Asp Glu
    210                 215                 220 tac acc acc gcc gag gac gcc cgc cag ttc cgc gac tac ctg ccg cac    720
Tyr Thr Thr Ala Glu Asp Ala Arg Gln Phe Arg Asp Tyr Leu Pro His
225                 230                 235                 240 tgc agt ttc tcg cgg gtg gag ggc acc ggg cat ttc ctc gac ctg gag    768
Cys Ser Phe Ser Arg Val Glu Gly Thr Gly His Phe Leu Asp Leu Glu
                245                 250                 255 tcc aag ctg gcc gcg gta cgc gtg cac cgc gcc ctg ctc gag cac ctg    816
Ser Lys Leu Ala Ala Val Arg Val His Arg Ala Leu Leu Glu His Leu
            260                 265                 270 ctg aag caa ccg gag ccg cag cgg gcg gaa cgc gcg gcg gga ttc cac    864
Leu Lys Gln Pro Glu Pro Gln Arg Ala Glu Arg Ala Ala Gly Phe His
        275                 280                 285 gag atg gcc atc ggc tac gcc tga                                    888
Glu Met Ala Ile Gly Tyr Ala
    290                 295

<210> SEQ ID NO 2
<211> LENGTH: 295
<212> TYPE: PRT
<213> ORGANISM: Pseudomonas aeruginosa

<400> SEQUENCE: 2

Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30
```

```
Val Asn Gly Ala Met Ala Thr Thr Ala Ser Phe Ala Arg Thr Cys Lys
         35                  40                  45

Cys Leu Ala Glu His Phe Asn Val Val Leu Phe Asp Leu Pro Phe Ala
 50                  55                  60

Gly Gln Ser Arg Gln His Asn Pro Gln Arg Gly Leu Ile Thr Lys Asp
 65                  70                  75                  80

Asp Glu Val Glu Ile Leu Leu Ala Leu Ile Glu Arg Phe Glu Val Asn
                 85                  90                  95

His Leu Val Ser Ala Ser Trp Gly Gly Ile Ser Thr Leu Leu Ala Leu
             100                 105                 110

Ser Arg Asn Pro Arg Gly Ile Arg Ser Ser Val Val Met Ala Phe Ala
         115                 120                 125

Pro Gly Leu Asn Gln Ala Met Leu Asp Tyr Val Gly Arg Ala Gln Ala
     130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295

<210> SEQ ID NO 3
<211> LENGTH: 1281
<212> TYPE: DNA
<213> ORGANISM: Pseudomonas aeruginosa
<220> FEATURE:
<221> NAME/KEY: CDS
<222> LOCATION: (1)..(1281)

<400> SEQUENCE: 3 atg cac gcc atc ctc atc gcc atc ggc tcg gcc ggc gac gta ttt ccc      48
Met His Ala Ile Leu Ile Ala Ile Gly Ser Ala Gly Asp Val Phe Pro
 1               5                  10                  15 ttc atc ggc ctg gcc cgg acc ctg aaa ttg cgc ggg cac cgc gtg agc      96
Phe Ile Gly Leu Ala Arg Thr Leu Lys Leu Arg Gly His Arg Val Ser
             20                  25                  30 ctc tgc acc atc ccg gtg ttt cgc gac gcg gtg gag cag cac ggc atc     144
Leu Cys Thr Ile Pro Val Phe Arg Asp Ala Val Glu Gln His Gly Ile
         35                  40                  45 gcg ttc gtc ccg ctg agc gac gaa ctg acc tac cgc cgg acc atg ggc     192
Ala Phe Val Pro Leu Ser Asp Glu Leu Thr Tyr Arg Arg Thr Met Gly
     50                  55                  60
```

```
gat ccg cgc ctg tgg gac ccc aag acg tcc ttc ggc gtg ctc tgg caa        240
Asp Pro Arg Leu Trp Asp Pro Lys Thr Ser Phe Gly Val Leu Trp Gln
 65                  70                  75                  80 acc atc gcc ggg atg atc gag ccg gtc tac gag tac gtc tcg gcg cag        288
Thr Ile Ala Gly Met Ile Glu Pro Val Tyr Glu Tyr Val Ser Ala Gln
                 85                  90                  95 cgc cat gac gac atc gtg gtg gtc ggc tcg ctc tgg gcg ctg ggc gca        336
Arg His Asp Asp Ile Val Val Val Gly Ser Leu Trp Ala Leu Gly Ala
            100                 105                 110 cgc atc gct cac gag aag tac ggg att ccc tac ctg tcc gcg cag gtc        384
Arg Ile Ala His Glu Lys Tyr Gly Ile Pro Tyr Leu Ser Ala Gln Val
        115                 120                 125 tcg cca tcg acc ttg ttg tcg gcg cac ctg ccg ccg gta cac ccc aag        432
Ser Pro Ser Thr Leu Leu Ser Ala His Leu Pro Pro Val His Pro Lys
    130                 135                 140 ttc aac gtg ccc gag cag atg ccg ctg gcg atg cgc aag ctg ctc tgg        480
Phe Asn Val Pro Glu Gln Met Pro Leu Ala Met Arg Lys Leu Leu Trp
145                 150                 155                 160 cgc tgc atc gag cgc ttc aag ctg gat cgc acc tgc gcg ccg gat atc        528
Arg Cys Ile Glu Arg Phe Lys Leu Asp Arg Thr Cys Ala Pro Asp Ile
                165                 170                 175 aac gcg gtg cgg cgc aag gtc ggc ctg gag acg ccg gtg aag cgc atc        576
Asn Ala Val Arg Arg Lys Val Gly Leu Glu Thr Pro Val Lys Arg Ile
            180                 185                 190 ttc acc caa tgg atg cat tcg ccg cag ggc gtg gtc tgc ctg ttc ccg        624
Phe Thr Gln Trp Met His Ser Pro Gln Gly Val Val Cys Leu Phe Pro
        195                 200                 205 gcc tgg ttc gcg ccg ccc cag cag gat tgg ccg caa ccc ctg cac atg        672
Ala Trp Phe Ala Pro Pro Gln Gln Asp Trp Pro Gln Pro Leu His Met
    210                 215                 220 acc ggc ttc ccg ctg ttc gac ggc agt atc ccg ggg acc ccg ctc gac        720
Thr Gly Phe Pro Leu Phe Asp Gly Ser Ile Pro Gly Thr Pro Leu Asp
225                 230                 235                 240 gac gaa ctg caa cgc ttt ctc gat cag ggc agc cgg ccg ctg gtg ttc        768
Asp Glu Leu Gln Arg Phe Leu Asp Gln Gly Ser Arg Pro Leu Val Phe
                245                 250                 255 acc cag ggc tcg acc gaa cac ctg cag ggc gac ttc tac gcc atg gcc        816
Thr Gln Gly Ser Thr Glu His Leu Gln Gly Asp Phe Tyr Ala Met Ala
            260                 265                 270 ctg cgc gcg ctg gaa cgc ctc ggc gcg cgt ggg atc ttc ctc acc ggc        864
Leu Arg Ala Leu Glu Arg Leu Gly Ala Arg Gly Ile Phe Leu Thr Gly
        275                 280                 285 gcc ggc cag gaa ccg ctg cgc ggc ttg ccg aac cac gtg ctg cag cgc        912
Ala Gly Gln Glu Pro Leu Arg Gly Leu Pro Asn His Val Leu Gln Arg
    290                 295                 300 gcc tac gcg cca ctg gga gcc ttg ctg cca tcg tgc gcc ggg ctg gtc        960
Ala Tyr Ala Pro Leu Gly Ala Leu Leu Pro Ser Cys Ala Gly Leu Val
305                 310                 315                 320 cat ccg ggc ggt atc ggc gcc atg agc ctg gcc ttg gcg gcg ggg gtg       1008
His Pro Gly Gly Ile Gly Ala Met Ser Leu Ala Leu Ala Ala Gly Val
                325                 330                 335 ccg cag gtg ctg ctg ccc tgc gcc cac gac cag ttc gac aat gcc gaa       1056
Pro Gln Val Leu Leu Pro Cys Ala His Asp Gln Phe Asp Asn Ala Glu
            340                 345                 350 cgg ctg gtc cgg ctc ggc tgc ggg atg cgc ctg ggc gtg cca ttg cgc       1104
Arg Leu Val Arg Leu Gly Cys Gly Met Arg Leu Gly Val Pro Leu Arg
        355                 360                 365 gag cag gag ttg cgc ggg gcg ctg tgg cgc ttg ctc gag gac ccg gcc       1152
Glu Gln Glu Leu Arg Gly Ala Leu Trp Arg Leu Leu Glu Asp Pro Ala
    370                 375                 380
```

```
atg gcg gcg gcc tgt cgg cgt ttc atg gaa ttg tca caa ccg cac agt      1200
Met Ala Ala Ala Cys Arg Arg Phe Met Glu Leu Ser Gln Pro His Ser
385                 390                 395                 400 atc gct tgc ggt aaa gcg gcc cag gtg gtc gaa cgt tgt cat agg gag      1248
Ile Ala Cys Gly Lys Ala Ala Gln Val Val Glu Arg Cys His Arg Glu
                405                 410                 415 ggg gat gcg cga tgg ctg aag gct gcg tcc tga                          1281
Gly Asp Ala Arg Trp Leu Lys Ala Ala Ser
420                 425
```

<210> SEQ ID NO 4
<211> LENGTH: 426
<212> TYPE: PRT
<213> ORGANISM: Pseudomonas aeruginosa

<400> SEQUENCE: 4

```
Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
                20                  25                  30

Leu Cys Thr Ile Pro Val Phe Arg Asp Ala Val Glu Gln His Gly Ile
            35                  40                  45

Ala Phe Val Pro Leu Ser Asp Glu Leu Thr Tyr Arg Arg Thr Met Gly
        50                  55                  60

Asp Pro Arg Leu Trp Asp Pro Lys Thr Ser Phe Gly Val Leu Trp Gln
65                  70                  75                  80

Thr Ile Ala Gly Met Ile Glu Pro Val Tyr Glu Tyr Val Ser Ala Gln
                85                  90                  95

Arg His Asp Asp Ile Val Val Gly Ser Leu Trp Ala Leu Gly Ala
            100                 105                 110

Arg Ile Ala His Glu Lys Tyr Gly Ile Pro Tyr Leu Ser Ala Gln Val
        115                 120                 125

Ser Pro Ser Thr Leu Leu Ser Ala His Leu Pro Val His Pro Lys
130                 135                 140

Phe Asn Val Pro Glu Gln Met Pro Leu Ala Met Arg Lys Leu Leu Trp
145                 150                 155                 160

Arg Cys Ile Glu Arg Phe Lys Leu Asp Arg Thr Cys Ala Pro Asp Ile
                165                 170                 175

Asn Ala Val Arg Arg Lys Val Gly Leu Glu Thr Pro Val Lys Arg Ile
            180                 185                 190

Phe Thr Gln Trp Met His Ser Pro Gln Gly Val Val Cys Leu Phe Pro
        195                 200                 205

Ala Trp Phe Ala Pro Pro Gln Gln Asp Trp Pro Gln Pro Leu His Met
    210                 215                 220

Thr Gly Phe Pro Leu Phe Asp Gly Ser Ile Pro Gly Thr Pro Leu Asp
225                 230                 235                 240

Asp Glu Leu Gln Arg Phe Leu Asp Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Gly Ala Arg Gly Ile Phe Leu Thr Gly
        275                 280                 285

Ala Gly Gln Glu Pro Leu Arg Gly Leu Pro Asn His Val Leu Gln Arg
    290                 295                 300

Ala Tyr Ala Pro Leu Gly Ala Leu Leu Pro Ser Cys Ala Gly Leu Val
```

```
                 305                 310                 315                 320
His Pro Gly Gly Ile Gly Ala Met Ser Leu Ala Leu Ala Ala Gly Val
                    325                 330                 335

Pro Gln Val Leu Leu Pro Cys Ala His Asp Gln Phe Asp Asn Ala Glu
                340                 345                 350

Arg Leu Val Arg Leu Gly Cys Gly Met Arg Leu Gly Val Pro Leu Arg
            355                 360                 365

Glu Gln Glu Leu Arg Gly Ala Leu Trp Arg Leu Leu Glu Asp Pro Ala
        370                 375                 380

Met Ala Ala Ala Cys Arg Arg Phe Met Glu Leu Ser Gln Pro His Ser
385                 390                 395                 400

Ile Ala Cys Gly Lys Ala Ala Gln Val Val Glu Arg Cys His Arg Glu
                    405                 410                 415

Gly Asp Ala Arg Trp Leu Lys Ala Ala Ser
                420                 425

<210> SEQ ID NO 5
<211> LENGTH: 978
<212> TYPE: DNA
<213> ORGANISM: Pseudomonas aeruginosa
<220> FEATURE:
<221> NAME/KEY: CDS
<222> LOCATION: (1)..(978)

<400> SEQUENCE: 5
```

| | | | | | | | | | | | | | | | | |
|---|---|---|---|---|---|---|---|---|---|---|---|---|---|---|---|---|
| atg | gac | cgg | ata | gac | atg | ggc | gtg | ctg | gtg | gta | ctg | ttc | aat | cct | ggc | 48 |
| Met | Asp | Arg | Ile | Asp | Met | Gly | Val | Leu | Val | Val | Leu | Phe | Asn | Pro | Gly | |
| 1 | | | | 5 | | | | | 10 | | | | | 15 | | |
| gac | gac | gac | ctg | gaa | cac | ctt | ggc | gaa | ctg | gcg | gcg | gcg | ttt | ccg | caa | 96 |
| Asp | Asp | Asp | Leu | Glu | His | Leu | Gly | Glu | Leu | Ala | Ala | Ala | Phe | Pro | Gln | |
| | | 20 | | | | | 25 | | | | | 30 | | | | |
| ctg | cgc | ttc | ctt | gcc | gtc | gac | aac | tca | ccg | cac | agc | gat | ccg | cag | cgc | 144 |
| Leu | Arg | Phe | Leu | Ala | Val | Asp | Asn | Ser | Pro | His | Ser | Asp | Pro | Gln | Arg | |
| | | | 35 | | | | | 40 | | | | | 45 | | | |
| aat | gcc | cgg | ctg | cgc | ggg | caa | ggc | atc | gcc | gtg | ctg | cac | cac | ggc | aac | 192 |
| Asn | Ala | Arg | Leu | Arg | Gly | Gln | Gly | Ile | Ala | Val | Leu | His | His | Gly | Asn | |
| | 50 | | | | | 55 | | | | | 60 | | | | | |
| cgg | cag | ggc | atc | gcc | ggc | gcc | ttc | aac | cag | gga | ctc | gac | gcg | cta | ttc | 240 |
| Arg | Gln | Gly | Ile | Ala | Gly | Ala | Phe | Asn | Gln | Gly | Leu | Asp | Ala | Leu | Phe | |
| 65 | | | | | 70 | | | | | 75 | | | | | 80 | |
| cgg | cgt | ggc | gtg | cag | ggt | gtg | ctg | ctg | ctc | gac | cag | gac | tcc | cgt | ccc | 288 |
| Arg | Arg | Gly | Val | Gln | Gly | Val | Leu | Leu | Leu | Asp | Gln | Asp | Ser | Arg | Pro | |
| | | | | 85 | | | | | 90 | | | | | 95 | | |
| ggc | ggc | gcc | ttc | ctc | gcc | gcc | cag | tgg | cgc | aac | ctg | cag | gcg | cgc | aac | 336 |
| Gly | Gly | Ala | Phe | Leu | Ala | Ala | Gln | Trp | Arg | Asn | Leu | Gln | Ala | Arg | Asn | |
| | | | 100 | | | | | 105 | | | | | 110 | | | |
| ggt | cag | gcc | tgc | ctg | ctc | ggc | cca | cgg | atc | ttc | gac | cgg | ggt | gac | cgg | 384 |
| Gly | Gln | Ala | Cys | Leu | Leu | Gly | Pro | Arg | Ile | Phe | Asp | Arg | Gly | Asp | Arg | |
| | | 115 | | | | | 120 | | | | | 125 | | | | |
| cgc | ttc | ctg | ccg | gcc | atc | cat | ctc | gac | gga | ctg | acg | ctc | agg | caa | ttg | 432 |
| Arg | Phe | Leu | Pro | Ala | Ile | His | Leu | Asp | Gly | Leu | Thr | Leu | Arg | Gln | Leu | |
| | 130 | | | | | 135 | | | | | 140 | | | | | |
| tct | ctg | gac | ggc | ctg | acg | acc | ccg | cag | cgc | acc | tcg | ttc | ctg | atc | tcc | 480 |
| Ser | Leu | Asp | Gly | Leu | Thr | Thr | Pro | Gln | Arg | Thr | Ser | Phe | Leu | Ile | Ser | |
| 145 | | | | | 150 | | | | | 155 | | | | | 160 | |
| tcc | ggc | tgc | ctg | ctg | acc | cgc | gag | gcc | tac | cag | cgc | ctc | ggc | cac | ttc | 528 |
| Ser | Gly | Cys | Leu | Leu | Thr | Arg | Glu | Ala | Tyr | Gln | Arg | Leu | Gly | His | Phe | |
| | | | | 165 | | | | | 170 | | | | | 175 | | |
| gac | gag | gaa | ctg | ttc | atc | gac | cac | gtg | gac | acc | gaa | tac | agc | ctg | cgc | 576 |

```
                        Asp Glu Glu Leu Phe Ile Asp His Val Asp Thr Glu Tyr Ser Leu Arg
                                        180                 185                 190 gcc cag gcg ctg gac gtg ccc ctg tac gtc gac ccg cgg ctg gtc ctc                      624
Ala Gln Ala Leu Asp Val Pro Leu Tyr Val Asp Pro Arg Leu Val Leu
            195                 200                 205 gag cac cgc atc ggc acg cgc aag acc cgc cgc ctc ggc ggt ctc agc                      672
Glu His Arg Ile Gly Thr Arg Lys Thr Arg Arg Leu Gly Gly Leu Ser
210                 215                 220 ctc agc gcg atg aac cac gcc ccg ctg cgc cgc tac tac ctg gcg cgc                      720
Leu Ser Ala Met Asn His Ala Pro Leu Arg Arg Tyr Tyr Leu Ala Arg
225                 230                 235                 240 aac ggc ctg ctg gtc ctg cgc cgc tac gcc cgg tcc tcg ccg ctg gcc                      768
Asn Gly Leu Leu Val Leu Arg Arg Tyr Ala Arg Ser Ser Pro Leu Ala
                245                 250                 255 ctg ctg gcg aac ctg ccg acc ctg acc cag ggc ctc gcg gtg ctc ctg                      816
Leu Leu Ala Asn Leu Pro Thr Leu Thr Gln Gly Leu Ala Val Leu Leu
            260                 265                 270 ctc gaa cgc gac aag ctg ctc aag ctg cgc tgc ctg ggc tgg ggc ctg                      864
Leu Glu Arg Asp Lys Leu Leu Lys Leu Arg Cys Leu Gly Trp Gly Leu
        275                 280                 285 tgg gac ggc ctg cgg gga cgc ggc ggc gcg ctg gag acc aac cgc ccg                      912
Trp Asp Gly Leu Arg Gly Arg Gly Gly Ala Leu Glu Thr Asn Arg Pro
290                 295                 300 cgc ctg ctg aag cgc ctc gcc ggc ccg gcc gtg gcg tcc gta gct tcc                      960
Arg Leu Leu Lys Arg Leu Ala Gly Pro Ala Val Ala Ser Val Ala Ser
305                 310                 315                 320 ggc aag gcc aag gcc tag                                                              978
Gly Lys Ala Lys Ala
                325

<210> SEQ ID NO 6
<211> LENGTH: 325
<212> TYPE: PRT
<213> ORGANISM: Pseudomonas aeruginosa

<400> SEQUENCE: 6

Met Asp Arg Ile Asp Met Gly Val Leu Val Val Leu Phe Asn Pro Gly
1               5                   10                  15

Asp Asp Asp Leu Glu His Leu Gly Glu Leu Ala Ala Ala Phe Pro Gln
            20                  25                  30

Leu Arg Phe Leu Ala Val Asp Asn Ser Pro His Ser Asp Pro Gln Arg
        35                  40                  45

Asn Ala Arg Leu Arg Gly Gln Gly Ile Ala Val Leu His His Gly Asn
    50                  55                  60

Arg Gln Gly Ile Ala Gly Ala Phe Asn Gln Gly Leu Asp Ala Leu Phe
65                  70                  75                  80

Arg Arg Gly Val Gln Gly Val Leu Leu Leu Asp Gln Asp Ser Arg Pro
                85                  90                  95

Gly Gly Ala Phe Leu Ala Ala Gln Trp Arg Asn Leu Gln Ala Arg Asn
            100                 105                 110

Gly Gln Ala Cys Leu Leu Gly Pro Arg Ile Phe Asp Arg Gly Asp Arg
        115                 120                 125

Arg Phe Leu Pro Ala Ile His Leu Asp Gly Leu Thr Leu Arg Gln Leu
    130                 135                 140

Ser Leu Asp Gly Leu Thr Thr Pro Gln Arg Thr Ser Phe Leu Ile Ser
145                 150                 155                 160

Ser Gly Cys Leu Leu Thr Arg Glu Ala Tyr Gln Arg Leu Gly His Phe
                165                 170                 175
```

```
Asp Glu Glu Leu Phe Ile Asp His Val Asp Thr Glu Tyr Ser Leu Arg
            180                 185                 190

Ala Gln Ala Leu Asp Val Pro Leu Tyr Val Asp Pro Arg Leu Val Leu
            195                 200                 205

Glu His Arg Ile Gly Thr Arg Lys Thr Arg Arg Leu Gly Gly Leu Ser
210                 215                 220

Leu Ser Ala Met Asn His Ala Pro Leu Arg Arg Tyr Tyr Leu Ala Arg
225                 230                 235                 240

Asn Gly Leu Leu Val Leu Arg Arg Tyr Ala Arg Ser Ser Pro Leu Ala
                245                 250                 255

Leu Leu Ala Asn Leu Pro Thr Leu Thr Gln Gly Leu Ala Val Leu Leu
                260                 265                 270

Leu Glu Arg Asp Lys Leu Leu Lys Leu Arg Cys Leu Gly Trp Gly Leu
            275                 280                 285

Trp Asp Gly Leu Arg Gly Arg Gly Gly Ala Leu Glu Thr Asn Arg Pro
            290                 295                 300

Arg Leu Leu Lys Arg Leu Ala Gly Pro Ala Val Ala Ser Val Ala Ser
305                 310                 315                 320

Gly Lys Ala Lys Ala
            325

<210> SEQ ID NO 7
<211> LENGTH: 1269
<212> TYPE: DNA
<213> ORGANISM: Pseudomonas aeruginosa
<220> FEATURE:
<221> NAME/KEY: CDS
<222> LOCATION: (1)..(1269)

<400> SEQUENCE: 7 gtg tcc acg acc agc ctc tgc ccc tcc gcc acg cgg gaa cac ggt ccc      48
Val Ser Thr Thr Ser Leu Cys Pro Ser Ala Thr Arg Glu His Gly Pro
1               5                   10                  15 ggc gcg aaa cgc gtc ctg cct ctg ctg ttc ctc acc tgc ctg ctg gat      96
Gly Ala Lys Arg Val Leu Pro Leu Leu Phe Leu Thr Cys Leu Leu Asp
            20                  25                  30 gcc gct ggc gtc ggc ctg atc gtg ccc ctg ctg ccg acg ctg atc ggc     144
Ala Ala Gly Val Gly Leu Ile Val Pro Leu Leu Pro Thr Leu Ile Gly
        35                  40                  45 agc gtg gcg ccg ctg gcg gtc cgc gac gcg gcc acc tgg ggc gcc gcc     192
Ser Val Ala Pro Leu Ala Val Arg Asp Ala Ala Thr Trp Gly Ala Ala
    50                  55                  60 ctg gtg atg acc ttc gcg ctg ctg caa ttg ttc ttt tcg ccg gtc ctc     240
Leu Val Met Thr Phe Ala Leu Leu Gln Leu Phe Phe Ser Pro Val Leu
65                  70                  75                  80 ggc agc ctc agc gac cgc ttc gga cgc cgc ccc gtc ctg gtc ctg gcg     288
Gly Ser Leu Ser Asp Arg Phe Gly Arg Arg Pro Val Leu Val Leu Ala
                85                  90                  95 atg ctc ggc ttc gcc ctc agc tat ctg ctg ctg gcg ctg gcc gac agc     336
Met Leu Gly Phe Ala Leu Ser Tyr Leu Leu Leu Ala Leu Ala Asp Ser
            100                 105                 110 ctc tgg atg ctg ttc ctc ggt cgc gcg ctg gcc ggg ctc acc ggc gcc     384
Leu Trp Met Leu Phe Leu Gly Arg Ala Leu Ala Gly Leu Thr Gly Ala
        115                 120                 125 agc gtg gcc acc gcg atg gcc tgc gcg gct gac ctc ggc acg cac ggg     432
Ser Val Ala Thr Ala Met Ala Cys Ala Ala Asp Leu Gly Thr His Gly
    130                 135                 140 cag cgc acc cgg cac ttc ggc tgg ctg tac gcc ggc ctc gcc ctg ggc     480
```

```
                Gln Arg Thr Arg His Phe Gly Trp Leu Tyr Ala Gly Leu Ala Leu Gly
                145                 150                 155                 160 atg atc ctc ggc ccc gcc ctc ggt ggg ctg ctg gcg gtg cac ggc acg        528
Met Ile Leu Gly Pro Ala Leu Gly Gly Leu Leu Ala Val His Gly Thr
                165                 170                 175 acg ctg ccg ctg ttg ctg gcc gcc ggc ctg tgc ctg ctc aac gcc ctg        576
Thr Leu Pro Leu Leu Leu Ala Ala Gly Leu Cys Leu Leu Asn Ala Leu
                180                 185                 190 ctc gcc ggc ctg ttc ctc gag gaa acc ctg ccc ccg acg cga cgc cgc        624
Leu Ala Gly Leu Phe Leu Glu Glu Thr Leu Pro Pro Thr Arg Arg Arg
            195                 200                 205 cgc ctg gac ccg agg cgg atg aat gcc ttg cgc tcg atc agc ggc ctg        672
Arg Leu Asp Pro Arg Arg Met Asn Ala Leu Arg Ser Ile Ser Gly Leu
        210                 215                 220 gct cgg caa ccg ggg gtc gga cgc ctg ctg gcg gtg ctt gcc ctg gta        720
Ala Arg Gln Pro Gly Val Gly Arg Leu Leu Ala Val Leu Ala Leu Val
225                 230                 235                 240 ttc ctc ggc ttg cag gcg gtg atg gtg gtc tgg ccg ttc ttc gtg atc        768
Phe Leu Gly Leu Gln Ala Val Met Val Val Trp Pro Phe Phe Val Ile
                245                 250                 255 gag aag ttt cac tgg agc agc gcc tgg atc ggc tac tcg ctg gcc ctc        816
Glu Lys Phe His Trp Ser Ser Ala Trp Ile Gly Tyr Ser Leu Ala Leu
                260                 265                 270 tac ggc gtg ctc gcg gtg ctc gcc cag acc ctc ggc gtg aac ctc tgc        864
Tyr Gly Val Leu Ala Val Leu Ala Gln Thr Leu Gly Val Asn Leu Cys
            275                 280                 285 aag cgg cgc ctg gac gac gcc cgc ctg ctg cgc ctg ggc ctc gcc ctg        912
Lys Arg Arg Leu Asp Asp Ala Arg Leu Leu Arg Leu Gly Leu Ala Leu
        290                 295                 300 caa ggc tgc ggc ctg ctg ctg ttc gcc ctg gtc gac tcg tca ttc tgg        960
Gln Gly Cys Gly Leu Leu Leu Phe Ala Leu Val Asp Ser Ser Phe Trp
305                 310                 315                 320 ctg gtc tgc gcg ctg ctg ccc ttc gcg ctc ggc agc ctc gcc acc ccg       1008
Leu Val Cys Ala Leu Leu Pro Phe Ala Leu Gly Ser Leu Ala Thr Pro
                325                 330                 335 gcc atg cag ggg ctg ctc tcg gcc cgc gtg ccg gtc gac cgc cag ggc       1056
Ala Met Gln Gly Leu Leu Ser Ala Arg Val Pro Val Asp Arg Gln Gly
                340                 345                 350 gag ttg cag ggc gtg ctg agc agc ctg atg agc ctc gcc gcg atc gtc       1104
Glu Leu Gln Gly Val Leu Ser Ser Leu Met Ser Leu Ala Ala Ile Val
            355                 360                 365 ggt ccg ccg ctg atg agc ggc ctg ttc cac tgg ggc agc ggt ccg ctc       1152
Gly Pro Pro Leu Met Ser Gly Leu Phe His Trp Gly Ser Gly Pro Leu
        370                 375                 380 gcg ccg ctg ccc ctg gcc ggc gcg cca ttc ctc gcc ggc gcc ctt ctc       1200
Ala Pro Leu Pro Leu Ala Gly Ala Pro Phe Leu Ala Gly Ala Leu Leu
385                 390                 395                 400 gtt ctg gcc ggg ctg gtc ctg gcc tgg caa ctt cga cct acg gga gaa       1248
Val Leu Ala Gly Leu Val Leu Ala Trp Gln Leu Arg Pro Thr Gly Glu
                405                 410                 415 gaa cga tca tgg acc gga tag                                           1269
Glu Arg Ser Trp Thr Gly
            420

<210> SEQ ID NO 8
<211> LENGTH: 422
<212> TYPE: PRT
<213> ORGANISM: Pseudomonas aeruginosa

<400> SEQUENCE: 8
```

```
Val Ser Thr Thr Ser Leu Cys Pro Ser Ala Thr Arg Glu His Gly Pro
1               5                   10                  15

Gly Ala Lys Arg Val Leu Pro Leu Leu Phe Leu Thr Cys Leu Leu Asp
            20                  25                  30

Ala Ala Gly Val Gly Leu Ile Val Pro Leu Leu Pro Thr Leu Ile Gly
            35                  40                  45

Ser Val Ala Pro Leu Ala Val Arg Asp Ala Ala Thr Trp Gly Ala Ala
50                  55                  60

Leu Val Met Thr Phe Ala Leu Leu Gln Leu Phe Phe Ser Pro Val Leu
65                  70                  75                  80

Gly Ser Leu Ser Asp Arg Phe Gly Arg Arg Pro Val Leu Val Leu Ala
                85                  90                  95

Met Leu Gly Phe Ala Leu Ser Tyr Leu Leu Ala Leu Ala Asp Ser
                100                 105                 110

Leu Trp Met Leu Phe Leu Gly Arg Ala Leu Ala Gly Leu Thr Gly Ala
                115                 120                 125

Ser Val Ala Thr Ala Met Ala Cys Ala Ala Asp Leu Gly Thr His Gly
                130                 135                 140

Gln Arg Thr Arg His Phe Gly Trp Leu Tyr Ala Gly Leu Ala Leu Gly
145                 150                 155                 160

Met Ile Leu Gly Pro Ala Leu Gly Gly Leu Leu Ala Val His Gly Thr
                165                 170                 175

Thr Leu Pro Leu Leu Leu Ala Ala Gly Leu Cys Leu Leu Asn Ala Leu
                180                 185                 190

Leu Ala Gly Leu Phe Leu Glu Glu Thr Leu Pro Pro Thr Arg Arg Arg
                195                 200                 205

Arg Leu Asp Pro Arg Arg Met Asn Ala Leu Arg Ser Ile Ser Gly Leu
                210                 215                 220

Ala Arg Gln Pro Gly Val Gly Arg Leu Leu Ala Val Leu Ala Leu Val
225                 230                 235                 240

Phe Leu Gly Leu Gln Ala Val Met Val Val Trp Pro Phe Phe Val Ile
                245                 250                 255

Glu Lys Phe His Trp Ser Ser Ala Trp Ile Gly Tyr Ser Leu Ala Leu
                260                 265                 270

Tyr Gly Val Leu Ala Val Leu Ala Gln Thr Leu Gly Val Asn Leu Cys
                275                 280                 285

Lys Arg Arg Leu Asp Asp Ala Arg Leu Leu Arg Leu Gly Leu Ala Leu
                290                 295                 300

Gln Gly Cys Gly Leu Leu Leu Phe Ala Leu Val Asp Ser Ser Phe Trp
305                 310                 315                 320

Leu Val Cys Ala Leu Leu Pro Phe Ala Leu Gly Ser Leu Ala Thr Pro
                325                 330                 335

Ala Met Gln Gly Leu Leu Ser Ala Arg Val Pro Val Asp Arg Gln Gly
                340                 345                 350

Glu Leu Gln Gly Val Leu Ser Ser Leu Met Ser Leu Ala Ala Ile Val
                355                 360                 365

Gly Pro Pro Leu Met Ser Gly Leu Phe His Trp Gly Ser Gly Pro Leu
                370                 375                 380

Ala Pro Leu Pro Leu Ala Gly Ala Pro Phe Leu Ala Gly Ala Leu Leu
385                 390                 395                 400

Val Leu Ala Gly Leu Val Leu Ala Trp Gln Leu Arg Pro Thr Gly Glu
                405                 410                 415

Glu Arg Ser Trp Thr Gly
```

<210> SEQ ID NO 9
<211> LENGTH: 882
<212> TYPE: DNA
<213> ORGANISM: Pseudomonas putida
<220> FEATURE:
<221> NAME/KEY: CDS
<222> LOCATION: (1)..(882)

<400> SEQUENCE: 9

| | | | | | | | | | | | | | | | | |
|---|---|---|---|---|---|---|---|---|---|---|---|---|---|---|---|---|
| atg | gct | cgt | aaa | gga | att | att | ctg | gcc | ggc | ggt | tcg | ggt | aca | cgc | ctg | 48 |
| Met | Ala | Arg | Lys | Gly | Ile | Ile | Leu | Ala | Gly | Gly | Ser | Gly | Thr | Arg | Leu | |
| 1 | | | 5 | | | | 10 | | | | 15 | | | | | |
| cat | ccg | gcc | aca | ctt | tcg | gtt | tcg | aag | cag | ctg | ctg | ccg | gtg | tat | gac | 96 |
| His | Pro | Ala | Thr | Leu | Ser | Val | Ser | Lys | Gln | Leu | Leu | Pro | Val | Tyr | Asp | |
| | | 20 | | | | 25 | | | | 30 | | | | | | |
| aaa | ccg | atg | atc | tac | tac | ccg | ctg | agc | acc | ctg | ctc | gct | ggt | atc | | 144 |
| Lys | Pro | Met | Ile | Tyr | Tyr | Pro | Leu | Ser | Thr | Leu | Leu | Ala | Gly | Ile | | |
| | 35 | | | | 40 | | | | 45 | | | | | | | |
| cgg | gac | atc | ctg | atc | att | tcc | acc | ccg | cag | gac | acc | ccg | cgc | ttc | gaa | 192 |
| Arg | Asp | Ile | Leu | Ile | Ile | Ser | Thr | Pro | Gln | Asp | Thr | Pro | Arg | Phe | Glu | |
| 50 | | | | 55 | | | | 60 | | | | | | | | |
| cag | ctg | ctg | ggc | gat | ggc | agc | cag | tgg | ggc | ctg | aac | ctg | tca | tac | gca | 240 |
| Gln | Leu | Leu | Gly | Asp | Gly | Ser | Gln | Trp | Gly | Leu | Asn | Leu | Ser | Tyr | Ala | |
| 65 | | | | 70 | | | | 75 | | | | 80 | | | | |
| ata | caa | cca | agc | ccg | gat | ggc | ttg | gcg | caa | gcg | ttc | acc | atc | ggc | gct | 288 |
| Ile | Gln | Pro | Ser | Pro | Asp | Gly | Leu | Ala | Gln | Ala | Phe | Thr | Ile | Gly | Ala | |
| | | | 85 | | | | 90 | | | | 95 | | | | | |
| gac | ttc | atc | ggt | aac | gac | cct | tct | gcg | ttg | gtt | ctc | ggt | gac | aat | att | 336 |
| Asp | Phe | Ile | Gly | Asn | Asp | Pro | Ser | Ala | Leu | Val | Leu | Gly | Asp | Asn | Ile | |
| | | | 100 | | | | 105 | | | | 110 | | | | | |
| ttc | tac | ggc | cat | gac | ttc | cag | gca | ctg | cta | ttg | aac | gca | gat | aaa | cgt | 384 |
| Phe | Tyr | Gly | His | Asp | Phe | Gln | Ala | Leu | Leu | Leu | Asn | Ala | Asp | Lys | Arg | |
| | | 115 | | | | 120 | | | | 125 | | | | | | |
| gaa | tcc | ggt | gct | tca | gta | ttc | gct | tat | cat | gtt | cat | gac | cca | gaa | cgc | 432 |
| Glu | Ser | Gly | Ala | Ser | Val | Phe | Ala | Tyr | His | Val | His | Asp | Pro | Glu | Arg | |
| 130 | | | | 135 | | | | 140 | | | | | | | | |
| tat | ggc | gta | gcg | gag | ttt | gac | gat | agc | ggt | cgc | gta | ttg | tcg | ctg | gaa | 480 |
| Tyr | Gly | Val | Ala | Glu | Phe | Asp | Asp | Ser | Gly | Arg | Val | Leu | Ser | Leu | Glu | |
| 145 | | | | 150 | | | | 155 | | | | 160 | | | | |
| gaa | aaa | ccg | gca | gtt | cca | aag | tct | agc | tat | gcg | gtc | acc | ggc | ctg | tat | 528 |
| Glu | Lys | Pro | Ala | Val | Pro | Lys | Ser | Ser | Tyr | Ala | Val | Thr | Gly | Leu | Tyr | |
| | | | 165 | | | | 170 | | | | 175 | | | | | |
| ttc | tat | gac | aat | cag | gta | gtc | aat | ctg | gct | cgc | gag | ctg | aag | cct | tcc | 576 |
| Phe | Tyr | Asp | Asn | Gln | Val | Val | Asn | Leu | Ala | Arg | Glu | Leu | Lys | Pro | Ser | |
| | | | 180 | | | | 185 | | | | 190 | | | | | |
| cca | cgt | ggc | gag | ctg | gaa | atc | acc | gac | ctc | aac | aac | ctt | tac | ttg | cag | 624 |
| Pro | Arg | Gly | Glu | Leu | Glu | Ile | Thr | Asp | Leu | Asn | Asn | Leu | Tyr | Leu | Gln | |
| | | 195 | | | | 200 | | | | 205 | | | | | | |
| cag | cag | cag | ttg | cag | gtc | gaa | atc | atg | ggc | cgt | ggc | tat | gcg | tgg | ctc | 672 |
| Gln | Gln | Gln | Leu | Gln | Val | Glu | Ile | Met | Gly | Arg | Gly | Tyr | Ala | Trp | Leu | |
| | | 210 | | | | 215 | | | | 220 | | | | | | |
| gac | acc | ggc | acg | cac | gac | agt | ctg | ctg | gag | gct | agc | cag | tac | atc | gca | 720 |
| Asp | Thr | Gly | Thr | His | Asp | Ser | Leu | Leu | Glu | Ala | Ser | Gln | Tyr | Ile | Ala | |
| 225 | | | | 230 | | | | 235 | | | | 240 | | | | |
| acc | atg | gag | cgc | cgt | cag | ggc | ttg | aaa | gtc | gcc | tgc | cct | gag | gaa | att | 768 |
| Thr | Met | Glu | Arg | Arg | Gln | Gly | Leu | Lys | Val | Ala | Cys | Pro | Glu | Glu | Ile | |
| | | | 245 | | | | 250 | | | | 255 | | | | | |
| tgc | tac | cgc | gct | ggc | tgg | atc | aac | gct | gag | caa | ctc | gag | tgc | ctg | gct | 816 |
| Cys | Tyr | Arg | Ala | Gly | Trp | Ile | Asn | Ala | Glu | Gln | Leu | Glu | Cys | Leu | Ala | |

```
                        260                 265                 270
caa cca ctg ctg aaa aac ggt tat ggc aag tat ctg cag aac ttg ctg        864
Gln Pro Leu Leu Lys Asn Gly Tyr Gly Lys Tyr Leu Gln Asn Leu Leu
    275                 280                 285 aaa gag aag gtg ttc tga                                                 882
Lys Glu Lys Val Phe
    290
```

<210> SEQ ID NO 10
<211> LENGTH: 293
<212> TYPE: PRT
<213> ORGANISM: Pseudomonas putida

<400> SEQUENCE: 10

```
Met Ala Arg Lys Gly Ile Ile Leu Ala Gly Gly Ser Gly Thr Arg Leu
1               5                   10                  15

His Pro Ala Thr Leu Ser Val Ser Lys Gln Leu Leu Pro Val Tyr Asp
            20                  25                  30

Lys Pro Met Ile Tyr Tyr Pro Leu Ser Thr Leu Leu Ala Gly Ile
        35                  40                  45

Arg Asp Ile Leu Ile Ile Ser Thr Pro Gln Asp Thr Pro Arg Phe Glu
50                  55                  60

Gln Leu Leu Gly Asp Gly Ser Gln Trp Gly Leu Asn Leu Ser Tyr Ala
65                  70                  75                  80

Ile Gln Pro Ser Pro Asp Gly Leu Ala Gln Ala Phe Thr Ile Gly Ala
                85                  90                  95

Asp Phe Ile Gly Asn Asp Pro Ser Ala Leu Val Leu Gly Asp Asn Ile
            100                 105                 110

Phe Tyr Gly His Asp Phe Gln Ala Leu Leu Leu Asn Ala Asp Lys Arg
        115                 120                 125

Glu Ser Gly Ala Ser Val Phe Ala Tyr His Val His Asp Pro Glu Arg
130                 135                 140

Tyr Gly Val Ala Glu Phe Asp Asp Ser Gly Arg Val Leu Ser Leu Glu
145                 150                 155                 160

Glu Lys Pro Ala Val Pro Lys Ser Ser Tyr Ala Val Thr Gly Leu Tyr
                165                 170                 175

Phe Tyr Asp Asn Gln Val Val Asn Leu Ala Arg Glu Leu Lys Pro Ser
            180                 185                 190

Pro Arg Gly Glu Leu Glu Ile Thr Asp Leu Asn Asn Leu Tyr Leu Gln
        195                 200                 205

Gln Gln Gln Leu Gln Val Glu Ile Met Gly Arg Gly Tyr Ala Trp Leu
210                 215                 220

Asp Thr Gly Thr His Asp Ser Leu Leu Glu Ala Ser Gln Tyr Ile Ala
225                 230                 235                 240

Thr Met Glu Arg Arg Gln Gly Leu Lys Val Ala Cys Pro Glu Glu Ile
                245                 250                 255

Cys Tyr Arg Ala Gly Trp Ile Asn Ala Glu Gln Leu Glu Cys Leu Ala
            260                 265                 270

Gln Pro Leu Leu Lys Asn Gly Tyr Gly Lys Tyr Leu Gln Asn Leu Leu
        275                 280                 285

Lys Glu Lys Val Phe
    290
```

<210> SEQ ID NO 11
<211> LENGTH: 1101
<212> TYPE: DNA

<213> ORGANISM: Pseudomonas putida
<220> FEATURE:
<221> NAME/KEY: CDS
<222> LOCATION: (1)..(1101)

<400> SEQUENCE: 11

```
atg att cta gta aca ggc gga gcc ggc ttc atc ggc tca aat ttc gta        48
Met Ile Leu Val Thr Gly Gly Ala Gly Phe Ile Gly Ser Asn Phe Val
1               5                   10                  15 ctg caa tgg tgt gcg cac aat gag gaa ccc gtc ctc aac ctc gac gcc        96
Leu Gln Trp Cys Ala His Asn Glu Glu Pro Val Leu Asn Leu Asp Ala
            20                  25                  30 ctg acc tac gca ggc aac ctg gcc aac ctg cag ccg ctg gaa ggc aac       144
Leu Thr Tyr Ala Gly Asn Leu Ala Asn Leu Gln Pro Leu Glu Gly Asn
        35                  40                  45 cct cag cat cgc ttt gtg caa ggc aat att tgc gat gct gcg ctt ctg       192
Pro Gln His Arg Phe Val Gln Gly Asn Ile Cys Asp Ala Ala Leu Leu
    50                  55                  60 acc aag ctg ttc gca gag cac cgc ccg cgc gcc gtg gtt cac ttc gcg       240
Thr Lys Leu Phe Ala Glu His Arg Pro Arg Ala Val Val His Phe Ala
65                  70                  75                  80 gcg gaa tcc cat gta gac cgc tca atc acc ggc ccc gaa gcg ttt gtc       288
Ala Glu Ser His Val Asp Arg Ser Ile Thr Gly Pro Glu Ala Phe Val
                85                  90                  95 gaa acc aac gtg atg ggc acg ttt cgc ttg ctt gaa gcc gcc cgg gcg       336
Glu Thr Asn Val Met Gly Thr Phe Arg Leu Leu Glu Ala Ala Arg Ala
            100                 105                 110 cat tgg aat agt ttg gaa ggt gca gag aag gag gcc ttc cgt ttc ctc       384
His Trp Asn Ser Leu Glu Gly Ala Glu Lys Glu Ala Phe Arg Phe Leu
        115                 120                 125 cat gtc tct acc gac gaa gtc tac ggc aca cta ggg cca aac gac ccg       432
His Val Ser Thr Asp Glu Val Tyr Gly Thr Leu Gly Pro Asn Asp Pro
    130                 135                 140 gcg ttc acc gaa acc acg ccg tac gcg ccg aac agc cca tac tcc gcc       480
Ala Phe Thr Glu Thr Thr Pro Tyr Ala Pro Asn Ser Pro Tyr Ser Ala
145                 150                 155                 160 agc aag gca gcc agc gac cat ctg gta cgc tcg tat ttc cat acc tac       528
Ser Lys Ala Ala Ser Asp His Leu Val Arg Ser Tyr Phe His Thr Tyr
                165                 170                 175 ggc atg ccg gta ctc act acc aac tgc tcc aac aat tac ggg ccg ctc       576
Gly Met Pro Val Leu Thr Thr Asn Cys Ser Asn Asn Tyr Gly Pro Leu
            180                 185                 190 cac ttc ccg gaa aaa ctg atc ccg ctg atg atc gtc aac gca ctc gcc       624
His Phe Pro Glu Lys Leu Ile Pro Leu Met Ile Val Asn Ala Leu Ala
        195                 200                 205 ggt aag gcg ctg cct gtc tat ggc gac ggc cag caa atc cgc gac tgg       672
Gly Lys Ala Leu Pro Val Tyr Gly Asp Gly Gln Gln Ile Arg Asp Trp
    210                 215                 220 ctg tat gtc gaa gat cac tgc tcg ggc atc cgt cgc gta ctg gaa gcc       720
Leu Tyr Val Glu Asp His Cys Ser Gly Ile Arg Arg Val Leu Glu Ala
225                 230                 235                 240 ggt gcg ttc ggc gag acg tac aat att ggc ggc tgg aat gaa aaa gcc       768
Gly Ala Phe Gly Glu Thr Tyr Asn Ile Gly Gly Trp Asn Glu Lys Ala
                245                 250                 255 aac att gac att gtg cgt aca ctc tgc agc ctt ctc gac gag atg gca       816
Asn Ile Asp Ile Val Arg Thr Leu Cys Ser Leu Leu Asp Glu Met Ala
            260                 265                 270 cct gcg gca tcg cgc cag gta atc aat cag aag acc ggc gag cct gtc       864
Pro Ala Ala Ser Arg Gln Val Ile Asn Gln Lys Thr Gly Glu Pro Val
        275                 280                 285
```

| gaa Glu 290 | cag Gln | tat Tyr | gca Ala | gaa Glu | ctc Leu 295 | atc Ile | gcc Ala | tac Tyr | gta Val | acc Thr 300 | gac Asp | cgc Arg | cca Pro | ggc Gly | cat His | 912 |

| gac Asp 305 | cgc Arg | cgt Arg | tat Tyr | gcc Ala 310 | atc Ile | gat Asp | gca Ala | cgc Arg | aag Lys 315 | atc Ile | gag Glu | cgg Arg | gag Glu | ctc Leu | ggc Gly 320 | 960 |

| tgg Trp | aaa Lys | cct Pro | gcc Ala | gaa Glu 325 | acc Thr | ttc Phe | gag Glu | acg Thr | ggc Gly 330 | att Ile | cga Arg | aag Lys | aca Thr | gtc Val 335 | gct Ala | 1008 |

| tgg Trp | tac Tyr | ttg Leu | gcc Ala | aac Asn 340 | cag Gln | aaa Lys | tgg Trp | gta Val | aaa Lys 345 | ggt Gly | gtc Val | atg Met | gac Asp | ggc Gly 350 | agc Ser | 1056 |

| tac Tyr | cgt Arg | gac Asp | tgg Trp 355 | gtg Val | gca Ala | caa Gln | caa Gln | tac Tyr 360 | ggg Gly | gca Ala | aat Asn | aaa Lys | gcg Ala 365 | tga | | 1101 |

<210> SEQ ID NO 12
<211> LENGTH: 366
<212> TYPE: PRT
<213> ORGANISM: Pseudomonas putida

<400> SEQUENCE: 12

Met Ile Leu Val Thr Gly Gly Ala Gly Phe Ile Gly Ser Asn Phe Val
1               5                   10                  15

Leu Gln Trp Cys Ala His Asn Glu Glu Pro Val Leu Asn Leu Asp Ala
                20                  25                  30

Leu Thr Tyr Ala Gly Asn Leu Ala Asn Leu Gln Pro Leu Glu Gly Asn
            35                  40                  45

Pro Gln His Arg Phe Val Gln Gly Asn Ile Cys Asp Ala Ala Leu Leu
    50                  55                  60

Thr Lys Leu Phe Ala Glu His Arg Pro Arg Ala Val Val His Phe Ala
65                  70                  75                  80

Ala Glu Ser His Val Asp Arg Ser Ile Thr Gly Pro Glu Ala Phe Val
                85                  90                  95

Glu Thr Asn Val Met Gly Thr Phe Arg Leu Leu Glu Ala Ala Arg Ala
            100                 105                 110

His Trp Asn Ser Leu Glu Gly Ala Glu Lys Glu Ala Phe Arg Phe Leu
        115                 120                 125

His Val Ser Thr Asp Glu Val Tyr Gly Thr Leu Gly Pro Asn Asp Pro
    130                 135                 140

Ala Phe Thr Glu Thr Thr Pro Tyr Ala Pro Asn Ser Pro Tyr Ser Ala
145                 150                 155                 160

Ser Lys Ala Ala Ser Asp His Leu Val Arg Ser Tyr Phe His Thr Tyr
                165                 170                 175

Gly Met Pro Val Leu Thr Thr Asn Cys Ser Asn Asn Tyr Gly Pro Leu
            180                 185                 190

His Phe Pro Glu Lys Leu Ile Pro Leu Met Ile Val Asn Ala Leu Ala
        195                 200                 205

Gly Lys Ala Leu Pro Val Tyr Gly Asp Gly Gln Gln Ile Arg Asp Trp
    210                 215                 220

Leu Tyr Val Glu Asp His Cys Ser Gly Ile Arg Arg Val Leu Glu Ala
225                 230                 235                 240

Gly Ala Phe Gly Glu Thr Tyr Asn Ile Gly Gly Trp Asn Glu Lys Ala
                245                 250                 255

Asn Ile Asp Ile Val Arg Thr Leu Cys Ser Leu Leu Asp Glu Met Ala
            260                 265                 270

```
                Pro Ala Ala Ser Arg Gln Val Ile Asn Gln Lys Thr Gly Glu Pro Val
                                275                 280                 285

Glu Gln Tyr Ala Glu Leu Ile Ala Tyr Val Thr Asp Arg Pro Gly His
                        290                 295                 300

Asp Arg Arg Tyr Ala Ile Asp Ala Arg Lys Ile Glu Arg Glu Leu Gly
                305                 310                 315                 320

Trp Lys Pro Ala Glu Thr Phe Glu Thr Gly Ile Arg Lys Thr Val Ala
                                325                 330                 335

Trp Tyr Leu Ala Asn Gln Lys Trp Val Lys Gly Val Met Asp Gly Ser
                        340                 345                 350

Tyr Arg Asp Trp Val Ala Gln Gln Tyr Gly Ala Asn Lys Ala
                        355                 360                 365

<210> SEQ ID NO 13
<211> LENGTH: 549
<212> TYPE: DNA
<213> ORGANISM: Pseudomonas putida
<220> FEATURE:
<221> NAME/KEY: CDS
<222> LOCATION: (1)..(549)

<400> SEQUENCE: 13 atg caa gcc att ccg ctg gat atc ccc gaa gtc gtg ctg ttt acc ccc       48
Met Gln Ala Ile Pro Leu Asp Ile Pro Glu Val Val Leu Phe Thr Pro
1               5                   10                  15 aag gtt ttt ggc gac gaa cgt ggt ttc ttc tac gag agc ttc aac gcc       96
Lys Val Phe Gly Asp Glu Arg Gly Phe Phe Tyr Glu Ser Phe Asn Ala
                20                  25                  30 cgt gtt ttc agc gaa gtg acc ggc ctg cag ccc gac ttc gta caa gac      144
Arg Val Phe Ser Glu Val Thr Gly Leu Gln Pro Asp Phe Val Gln Asp
            35                  40                  45 aac cac tcg cgc tcg gta aaa ggc gtg ctc cgt ggc ctg cac tat cag      192
Asn His Ser Arg Ser Val Lys Gly Val Leu Arg Gly Leu His Tyr Gln
        50                  55                  60 ctg gca cct cac gcc cag ggc aag ctg gtg cgt gtg gtg caa ggc gaa      240
Leu Ala Pro His Ala Gln Gly Lys Leu Val Arg Val Val Gln Gly Glu
65                  70                  75                  80 gtc ttc gat gtt gcg gtg gat atc cgt cgc tcg tcc aca acc ttc ggt      288
Val Phe Asp Val Ala Val Asp Ile Arg Arg Ser Ser Thr Thr Phe Gly
                85                  90                  95 aaa tgg gta ggt gcg gtg ttg tcg gcc gag aac aag aac cag ctg tgg      336
Lys Trp Val Gly Ala Val Leu Ser Ala Glu Asn Lys Asn Gln Leu Trp
                100                 105                 110 atc ccg cca ggg ttc gca cac ggg ttc gtc acg ttg agt gaa acc gca      384
Ile Pro Pro Gly Phe Ala His Gly Phe Val Thr Leu Ser Glu Thr Ala
            115                 120                 125 gag ttc ctc tac aag acc acc gac ttc tac tcg ccg cag tgc gag cgc      432
Glu Phe Leu Tyr Lys Thr Thr Asp Phe Tyr Ser Pro Gln Cys Glu Arg
        130                 135                 140 tgc att gcc tgg aat gat ccg gca gtg ggt atc gaa tgg ccc atc gac      480
Cys Ile Ala Trp Asn Asp Pro Ala Val Gly Ile Glu Trp Pro Ile Asp
145                 150                 155                 160 tcc gta cca agc ttg tct ggc aag gac cag ctt ggg gtc gca ttg gct      528
Ser Val Pro Ser Leu Ser Gly Lys Asp Gln Leu Gly Val Ala Leu Ala
                165                 170                 175 gac gcc gaa ctg ttc gac taa                                          549
Asp Ala Glu Leu Phe Asp
            180

<210> SEQ ID NO 14
```

<211> LENGTH: 182
<212> TYPE: PRT
<213> ORGANISM: Pseudomonas putida

<400> SEQUENCE: 14

```
Met Gln Ala Ile Pro Leu Asp Ile Pro Glu Val Val Leu Phe Thr Pro
1               5                   10                  15

Lys Val Phe Gly Asp Glu Arg Gly Phe Phe Tyr Glu Ser Phe Asn Ala
                20                  25                  30

Arg Val Phe Ser Glu Val Thr Gly Leu Gln Pro Asp Phe Val Gln Asp
                35                  40                  45

Asn His Ser Arg Ser Val Lys Gly Val Leu Arg Gly Leu His Tyr Gln
            50                  55                  60

Leu Ala Pro His Ala Gln Gly Lys Leu Val Arg Val Val Gln Gly Glu
65                  70                  75                  80

Val Phe Asp Val Ala Val Asp Ile Arg Arg Ser Ser Thr Thr Phe Gly
                85                  90                  95

Lys Trp Val Gly Ala Val Leu Ser Ala Glu Asn Lys Asn Gln Leu Trp
                100                 105                 110

Ile Pro Pro Gly Phe Ala His Gly Phe Val Thr Leu Ser Glu Thr Ala
                115                 120                 125

Glu Phe Leu Tyr Lys Thr Thr Asp Phe Tyr Ser Pro Gln Cys Glu Arg
            130                 135                 140

Cys Ile Ala Trp Asn Asp Pro Ala Val Gly Ile Glu Trp Pro Ile Asp
145                 150                 155                 160

Ser Val Pro Ser Leu Ser Gly Lys Asp Gln Leu Gly Val Ala Leu Ala
                165                 170                 175

Asp Ala Glu Leu Phe Asp
            180
```

<210> SEQ ID NO 15
<211> LENGTH: 903
<212> TYPE: DNA
<213> ORGANISM: Pseudomonas putida
<220> FEATURE:
<221> NAME/KEY: CDS
<222> LOCATION: (1)..(903)

<400> SEQUENCE: 15

```
gtg aaa atc ctg ctg ttg ggg aaa aac ggg caa gta ggc tgg gag cta      48
Val Lys Ile Leu Leu Leu Gly Lys Asn Gly Gln Val Gly Trp Glu Leu
1               5                   10                  15 cag cgc gcc ttg gcg ccg ctg ggt gag gtc att gcg ctg gat cgt cag      96
Gln Arg Ala Leu Ala Pro Leu Gly Glu Val Ile Ala Leu Asp Arg Gln
                20                  25                  30 ggg gcc gag ggc tta tgt ggc gac ttg tcc aac ctg gac ggc ttg gcc     144
Gly Ala Glu Gly Leu Cys Gly Asp Leu Ser Asn Leu Asp Gly Leu Ala
            35                  40                  45 gct acg att cgt cag ctg gcg ccg gac gtg atc gtc aac gct gct gcc     192
Ala Thr Ile Arg Gln Leu Ala Pro Asp Val Ile Val Asn Ala Ala Ala
        50                  55                  60 tac act gca gtg gat aaa gct gag agc gat cag gca ctg gct gca atg     240
Tyr Thr Ala Val Asp Lys Ala Glu Ser Asp Gln Ala Leu Ala Ala Met
65                  70                  75                  80 atc aat gcc gcg gct cct gct gta tta gca cgt gaa aca gca gct ttg     288
Ile Asn Ala Ala Ala Pro Ala Val Leu Ala Arg Glu Thr Ala Ala Leu
                85                  90                  95 ggc gcc tgg ttg att cac tat tcc acc gat tat gta ttt gac ggc agc     336
Gly Ala Trp Leu Ile His Tyr Ser Thr Asp Tyr Val Phe Asp Gly Ser
```

|  |  |  |  |  |  |  |  |  |  |  |  |  |  |  |  |
|---|---|---|---|---|---|---|---|---|---|---|---|---|---|---|---|
|  |  | 100 |  |  |  | 105 |  |  |  | 110 |  |  |  |  |  |
| ggc | agt | cag | cgc | tgg | gag | gaa | act | gcg | cct | acc | ggc | ccc | ctt | tcg | gtc | 384 |
| Gly | Ser | Gln | Arg | Trp | Glu | Glu | Thr | Ala | Pro | Thr | Gly | Pro | Leu | Ser | Val |
|  |  | 115 |  |  |  | 120 |  |  |  | 125 |  |  |  |  |  |
| tac | ggc | cgg | acc | aag | ctg | gaa | ggc | gag | cat | gcc | att | ctc | gcc | agc | ggc | 432 |
| Tyr | Gly | Arg | Thr | Lys | Leu | Glu | Gly | Glu | His | Ala | Ile | Leu | Ala | Ser | Gly |
|  |  | 130 |  |  |  | 135 |  |  |  | 140 |  |  |  |  |  |
| gcc | aag | gcc | gtg | gta | ctg | cgc | acc | agc | tgg | gtg | tat | gct | gcg | cgc | ggg | 480 |
| Ala | Lys | Ala | Val | Val | Leu | Arg | Thr | Ser | Trp | Val | Tyr | Ala | Ala | Arg | Gly |
| 145 |  |  |  |  | 150 |  |  |  |  | 155 |  |  |  |  | 160 |
| cac | aat | ttt | gcc | aag | acc | atg | ctg | cgc | ctg | gcg | gcg | gag | cgt | gag | acg | 528 |
| His | Asn | Phe | Ala | Lys | Thr | Met | Leu | Arg | Leu | Ala | Ala | Glu | Arg | Glu | Thr |
|  |  |  |  | 165 |  |  |  |  | 170 |  |  |  |  | 175 |  |
| ttg | agc | gtg | gta | gca | gac | caa | ttt | ggc | gca | ccc | acg | ggc | gct | gac | ctg | 576 |
| Leu | Ser | Val | Val | Ala | Asp | Gln | Phe | Gly | Ala | Pro | Thr | Gly | Ala | Asp | Leu |
|  |  |  | 180 |  |  |  |  | 185 |  |  |  |  | 190 |  |  |
| atc | gcc | gac | gtt | act | gca | cac | atc | ctg | cgg | caa | atc | ttc | aat | ggg | caa | 624 |
| Ile | Ala | Asp | Val | Thr | Ala | His | Ile | Leu | Arg | Gln | Ile | Phe | Asn | Gly | Gln |
|  |  |  | 195 |  |  |  |  | 200 |  |  |  |  | 205 |  |  |
| gac | aac | cgt | cac | ctg | gca | ggg | att | tac | cac | ttg | gct | gcg | tcc | ggt | gaa | 672 |
| Asp | Asn | Arg | His | Leu | Ala | Gly | Ile | Tyr | His | Leu | Ala | Ala | Ser | Gly | Glu |
|  | 210 |  |  |  |  | 215 |  |  |  |  | 220 |  |  |  |  |
| acc | tct | tgg | cat | ggt | ttt | gct | cag | ttc | gtg | ctg | gcg | cat | gct | caa | cgc | 720 |
| Thr | Ser | Trp | His | Gly | Phe | Ala | Gln | Phe | Val | Leu | Ala | His | Ala | Gln | Arg |
| 225 |  |  |  |  | 230 |  |  |  |  | 235 |  |  |  |  | 240 |
| act | ggc | gta | gcg | ctg | aaa | gtg | aca | gct | gat | aag | gtt | gcc | gca | atc | agc | 768 |
| Thr | Gly | Val | Ala | Leu | Lys | Val | Thr | Ala | Asp | Lys | Val | Ala | Ala | Ile | Ser |
|  |  |  |  | 245 |  |  |  |  | 250 |  |  |  |  | 255 |  |
| acc | gaa | gct | tat | cca | gta | cct | gca | cca | cgt | ccg | cgc | aac | tcg | cgc | ctg | 816 |
| Thr | Glu | Ala | Tyr | Pro | Val | Pro | Ala | Pro | Arg | Pro | Arg | Asn | Ser | Arg | Leu |
|  |  |  | 260 |  |  |  |  | 265 |  |  |  |  | 270 |  |  |
| gca | ctg | ggc | aaa | ctg | gaa | aac | acg | ttc | aat | ttc | aaa | atg | ccg | ctt | tgg | 864 |
| Ala | Leu | Gly | Lys | Leu | Glu | Asn | Thr | Phe | Asn | Phe | Lys | Met | Pro | Leu | Trp |
|  |  | 275 |  |  |  |  | 280 |  |  |  |  | 285 |  |  |  |
| gag | caa | ggc | gtg | caa | cgt | atg | ctg | gac | gaa | atc | cag | taa |  |  |  | 903 |
| Glu | Gln | Gly | Val | Gln | Arg | Met | Leu | Asp | Glu | Ile | Gln |  |  |  |  |
|  | 290 |  |  |  |  | 295 |  |  |  |  | 300 |  |  |  |  |

<210> SEQ ID NO 16
<211> LENGTH: 300
<212> TYPE: PRT
<213> ORGANISM: Pseudomonas putida

<400> SEQUENCE: 16

| Val | Lys | Ile | Leu | Leu | Gly | Lys | Asn | Gly | Gln | Val | Gly | Trp | Glu | Leu |
|---|---|---|---|---|---|---|---|---|---|---|---|---|---|---|
| 1 |  |  |  | 5 |  |  |  |  | 10 |  |  |  |  | 15 |

| Gln | Arg | Ala | Leu | Ala | Pro | Leu | Gly | Glu | Val | Ile | Ala | Leu | Asp | Arg | Gln |
|---|---|---|---|---|---|---|---|---|---|---|---|---|---|---|---|
|  |  |  | 20 |  |  |  |  | 25 |  |  |  |  | 30 |  |  |

| Gly | Ala | Glu | Gly | Leu | Cys | Gly | Asp | Leu | Ser | Asn | Leu | Asp | Gly | Leu | Ala |
|---|---|---|---|---|---|---|---|---|---|---|---|---|---|---|---|
|  |  |  | 35 |  |  |  |  | 40 |  |  |  |  | 45 |  |  |

| Ala | Thr | Ile | Arg | Gln | Leu | Ala | Pro | Asp | Val | Ile | Val | Asn | Ala | Ala | Ala |
|---|---|---|---|---|---|---|---|---|---|---|---|---|---|---|---|
|  |  |  | 50 |  |  |  |  | 55 |  |  |  |  | 60 |  |  |

| Tyr | Thr | Ala | Val | Asp | Lys | Ala | Glu | Ser | Asp | Gln | Ala | Leu | Ala | Ala | Met |
|---|---|---|---|---|---|---|---|---|---|---|---|---|---|---|---|
| 65 |  |  |  |  | 70 |  |  |  |  | 75 |  |  |  |  | 80 |

| Ile | Asn | Ala | Ala | Ala | Pro | Ala | Val | Leu | Ala | Arg | Glu | Thr | Ala | Ala | Leu |
|---|---|---|---|---|---|---|---|---|---|---|---|---|---|---|---|
|  |  |  |  | 85 |  |  |  |  | 90 |  |  |  |  | 95 |  |

| Gly | Ala | Trp | Leu | Ile | His | Tyr | Ser | Thr | Asp | Tyr | Val | Phe | Asp | Gly | Ser |
|---|---|---|---|---|---|---|---|---|---|---|---|---|---|---|---|
|  |  |  | 100 |  |  |  |  | 105 |  |  |  |  | 110 |  |  |

-continued

```
Gly Ser Gln Arg Trp Glu Glu Thr Ala Pro Thr Gly Pro Leu Ser Val
            115                 120                 125

Tyr Gly Arg Thr Lys Leu Glu Gly Glu His Ala Ile Leu Ala Ser Gly
        130                 135                 140

Ala Lys Ala Val Val Leu Arg Thr Ser Trp Val Tyr Ala Ala Arg Gly
145                 150                 155                 160

His Asn Phe Ala Lys Thr Met Leu Arg Leu Ala Ala Glu Arg Glu Thr
                165                 170                 175

Leu Ser Val Val Ala Asp Gln Phe Gly Ala Pro Thr Gly Ala Asp Leu
            180                 185                 190

Ile Ala Asp Val Thr Ala His Ile Leu Arg Gln Ile Phe Asn Gly Gln
        195                 200                 205

Asp Asn Arg His Leu Ala Gly Ile Tyr His Leu Ala Ala Ser Gly Glu
    210                 215                 220

Thr Ser Trp His Gly Phe Ala Gln Phe Val Leu Ala His Ala Gln Arg
225                 230                 235                 240

Thr Gly Val Ala Leu Lys Val Thr Ala Asp Lys Val Ala Ala Ile Ser
                245                 250                 255

Thr Glu Ala Tyr Pro Val Pro Ala Pro Arg Pro Arg Asn Ser Arg Leu
            260                 265                 270

Ala Leu Gly Lys Leu Glu Asn Thr Phe Asn Phe Lys Met Pro Leu Trp
        275                 280                 285

Glu Gln Gly Val Gln Arg Met Leu Asp Glu Ile Gln
    290                 295                 300

<210> SEQ ID NO 17
<211> LENGTH: 1041
<212> TYPE: DNA
<213> ORGANISM: Burkholderia thailandensis
<220> FEATURE:
<221> NAME/KEY: CDS
<222> LOCATION: (1)..(1041)

<400> SEQUENCE: 17 atg cgc ggt tcc ggc gag tgg gta gcc gct gcg gcg cgc gtg agg cag       48
Met Arg Gly Ser Gly Glu Trp Val Ala Ala Ala Ala Arg Val Arg Gln
1               5                   10                  15 ggc

```
gag gtg gag att ctg ctg cac ctg gcc gag cgg ttc gag ccg agt ttc    432
Glu Val Glu Ile Leu Leu His Leu Ala Glu Arg Phe Glu Pro Ser Phe
    130                 135                 140 ctg ctg tcg gtg tcg tgg ggc ggg gtg gcg tcg ctg ttc gcg ctg gcg    480
Leu Leu Ser Val Ser Trp Gly Gly Val Ala Ser Leu Phe Ala Leu Ala
145                 150                 155                 160 cgg ggg tgc gcg agc gtg cgg cgg gcg gtg atc gcg tcg ttc tcg ccg    528
Arg Gly Cys Ala Ser Val Arg Arg Ala Val Ile Ala Ser Phe Ser Pro
                165                 170                 175 ttc ctg aac gac gcg atg acg gat tac gtg acg cgc gcg cgc gat cac    576
Phe Leu Asn Asp Ala Met Thr Asp Tyr Val Thr Arg Ala Arg Asp His
            180                 185                 190 atc gcg gcg ggg gag aac ctg aag gcg gcg cag ttg ctc aac gac acg    624
Ile Ala Ala Gly Glu Asn Leu Lys Ala Ala Gln Leu Leu Asn Asp Thr
        195                 200                 205 gtg ggg cgc tac ctg ccg cgg atc atg aag ctg tac aac tac cgg tat    672
Val Gly Arg Tyr Leu Pro Arg Ile Met Lys Leu Tyr Asn Tyr Arg Tyr
    210                 215                 220 ctg acg aag ctg ccg cgc acc gag cag gac cag gtg gcg ttc cac gtc    720
Leu Thr Lys Leu Pro Arg Thr Glu Gln Asp Gln Val Ala Phe His Val
225                 230                 235                 240 gac cag atc ctg tcg atg cgg ccg gag cag tac ctg ccg gaa ttc cgc    768
Asp Gln Ile Leu Ser Met Arg Pro Glu Gln Tyr Leu Pro Glu Phe Arg
                245                 250                 255 cag atc ggc tgc gcg gtg aag ttc atc aac ggc gag ctg gac gag tac    816
Gln Ile Gly Cys Ala Val Lys Phe Ile Asn Gly Glu Leu Asp Glu Tyr
            260                 265                 270 acg acg gcg tcg gac gtg cgg cgg ctg gcg gcc tac gtg cgg cgc gcg    864
Thr Thr Ala Ser Asp Val Arg Arg Leu Ala Ala Tyr Val Arg Arg Ala
        275                 280                 285 gag ttc gcg acg atc cgg cag gcg ggg cac ttc ctg gac ctc gag ggg    912
Glu Phe Ala Thr Ile Arg Gln Ala Gly His Phe Leu Asp Leu Glu Gly
    290                 295                 300 cgt cag cag cag gag cag ctt cgc gcg gcg atc ctg ggc ttc ttc ggc    960
Arg Gln Gln Gln Glu Gln Leu Arg Ala Ala Ile Leu Gly Phe Phe Gly
305                 310                 315                 320 gac gag cgg gcg agc gcg gcg cgc gac gac gcg cag gac gag acg ctc   1008
Asp Glu Arg Ala Ser Ala Ala Arg Asp Asp Ala Gln Asp Glu Thr Leu
                325                 330                 335 gcg ccg ctc ggt cag ttg ccg gcg ctg tcg tag                       1041
Ala Pro Leu Gly Gln Leu Pro Ala Leu Ser
            340                 345

<210> SEQ ID NO 18
<211> LENGTH: 346
<212> TYPE: PRT
<213> ORGANISM: Burkholderia thailandensis

<400> SEQUENCE

```
Asn Gly Ala Leu Ala Thr Thr Ala Ser Phe Gly Gln Thr Ile Arg Tyr
                 85                  90                  95

Leu Gly Glu Arg Val Asn Ala Val Cys Phe Asp Leu Pro Tyr Ala Gly
            100                 105                 110

Gln Ser Arg Gln His Asn Pro Gly Glu Tyr Ile Leu Thr Lys Asp Asp
            115                 120                 125

Glu Val Glu Ile Leu Leu His Leu Ala Glu Arg Phe Glu Pro Ser Phe
130                 135                 140

Leu Leu Ser Val Ser Trp Gly Gly Val Ala Ser Leu Phe Ala Leu Ala
145                 150                 155                 160

Arg Gly Cys Ala Ser Val Arg Arg Ala Val Ile Ala Ser Phe Ser Pro
                165                 170                 175

Phe Leu Asn Asp Ala Met Thr Asp Tyr Val Thr Arg Ala Arg Asp His
            180                 185                 190

Ile Ala Ala Gly Glu Asn Leu Lys Ala Ala Gln Leu Leu Asn Asp Thr
            195                 200                 205

Val Gly Arg Tyr Leu Pro Arg Ile Met Lys Leu Tyr Asn Tyr Arg Tyr
210                 215                 220

Leu Thr Lys Leu Pro Arg Thr Glu Gln Asp Gln Val Ala Phe His Val
225                 230                 235                 240

Asp Gln Ile Leu Ser Met Arg Pro Glu Gln Tyr Leu Pro Glu Phe Arg
                245                 250                 255

Gln Ile Gly Cys Ala Val Lys Phe Ile Asn Gly Glu Leu Asp Glu Tyr
            260                 265                 270

Thr Thr Ala Ser Asp Val Arg Arg Leu Ala Ala Tyr Val Arg Arg Ala
            275                 280                 285

Glu Phe Ala Thr Ile Arg Gln Ala Gly His Phe Leu Asp Leu Glu Gly
290                 295                 300

Arg Gln Gln Gln Glu Gln Leu Arg Ala Ala Ile Leu Gly Phe Phe Gly
305                 310                 315                 320

Asp Glu Arg Ala Ser Ala Ala Arg Asp Asp Ala Gln Asp Glu Thr Leu
                325                 330                 335

Ala Pro Leu Gly Gln Leu Pro Ala Leu Ser
            340                 345
```

<210> SEQ ID NO 19
<211> LENGTH: 1482
<212> TYPE: DNA
<213> ORGANISM: Burkholderia thailandensis
<220> FEATURE:
<221> NAME/KEY: CDS
<222> LOCATION: (1

```
            Asn Asp Glu Ala Met Ala Lys Val Ile Val Thr Ala Ile Gly Ser Ala
            65                  70                  75                  80 ggc gac gtg cac ccg ttg ctg ggg gtg agc cgg gcg ctg tcg gcg cgg              288
Gly Asp Val His Pro Leu Leu Gly Val Ser Arg Ala Leu Ser Ala Arg
                85                  90                  95 ggc cac gag gtg gtg ttc tgc acg cat gcg ccg ttc gag gcg gcg gtg              336
Gly His Glu Val Val Phe Cys Thr His Ala Pro Phe Glu Ala Ala Val
            100                 105                 110 cgc gcg agc ggc ttc gcg ttc gtg ccg gtg ggc acg gcc gag gac tac              384
Arg Ala Ser Gly Phe Ala Phe Val Pro Val Gly Thr Ala Glu Asp Tyr
                115                 120                 125 gtg cgg gcg atg gcg gac ccg gcg ctg tgg gat ccg cgc acg tcg ttc              432
Val Arg Ala Met Ala Asp Pro Ala Leu Trp Asp Pro Arg Thr Ser Phe
        130                 135                 140 aag acg ctg tgg cgg gtg atc gcg ccg gtg gtg agg ccg cac ttc gag              480
Lys Thr Leu Trp Arg Val Ile Ala Pro Val Val Arg Pro His Phe Glu
145                 150                 155                 160 gtg ctg cgc gcg ctg agc gac gcg gac acg gtg ctg gtg ggc acg ctg              528
Val Leu Arg Ala Leu Ser Asp Ala Asp Thr Val Leu Val Gly Thr Leu
                165                 170                 175 tgg gcg ttc tcg gcg cgg ctg atg cag gag cgc ttc ggc acg cgg tac              576
Trp Ala Phe Ser Ala Arg Leu Met Gln Glu Arg Phe Gly Thr Arg Tyr
            180                 185                 190 gtg tcg gtg cag gtg tcg ccg tcg acg ctg ctg tcg gcg cat gcg ccg              624
Val Ser Val Gln Val Ser Pro Ser Thr Leu Leu Ser Ala His Ala Pro
                195                 200                 205 ccg acg cac aag cgg ctg acg atc ccg aag ggc ctg ccg ctg gcg gtg              672
Pro Thr His Lys Arg Leu Thr Ile Pro Lys Gly Leu Pro Leu Ala Val
        210                 215                 220 aag gcg ggg ctg atg acg ctg atc gag cgg cag gtg ctg gac cgg gtg              720
Lys Ala Gly Leu Met Thr Leu Ile Glu Arg Gln Val Leu Asp Arg Val
225                 230                 235                 240 tgc ggc ccg gag ctg aac gcg gcg cgg cag gcg ctg ggc ctg gcg ccg              768
Cys Gly Pro Glu Leu Asn Ala Ala Arg Gln Ala Leu Gly Leu Ala Pro
                245                 250                 255 gcg aag cgg atc ctg ggc cgg tgg ctg cat tcg acg gac ggg gtg ctg              816
Ala Lys Arg Ile Leu Gly Arg Trp Leu His Ser Thr Asp Gly Val Leu
            260                 265                 270 tgc ctg ttt ccg tcg tgg ttc gcg ccg gcg cag ccg gac tgg ccg gcg              864
Cys Leu Phe Pro Ser Trp Phe Ala Pro Ala Gln Pro Asp Trp Pro Ala
                275                 280                 285 aac cac ctg caa agc ggg ttt ccg ctg ttc aac gac gcg ggt ccg gcg              912
Asn His Leu Gln Ser Gly Phe Pro Leu Phe Asn Asp Ala Gly Pro Ala
        290                 295                 300 cag gcg gat gcg gag ctg gag gcg ttc gtc gcg tcg ggc gag gcg ccg              960
Gln Ala Asp Ala Glu Leu Glu Ala Phe Val Ala Ser Gly Glu Ala Pro
305                 310                 315                 320 gtg gtg ttc acg gcg ggc tcg acg ctg gtg gac ggc cgc acg tat gag             1008
Val Val Phe Thr Ala Gly Ser Thr Leu Val Asp Gly Arg Thr Tyr Glu
                325                 330                 335 cac gcg gtg acg cag gtg ctg cag gcc acg ggg gtg cgg ggg att ctg             1056
His Ala Val Thr Gln Val Leu Gln Ala Thr Gly Val Arg Gly Ile Leu
            340                 345                 350 ctc gcg ccg gat gcg ccg gat gcg ccg gca tcg gac ggg gcg gcg             1104
Leu Ala Pro Asp Ala Pro Asp Ala Pro Ala Ser Asp Gly Ala Ala
                355                 360                 365 ctg ctc aag cgc cgc tac gtg ccg ctc gcg gcg ttg ctg ccg cgc tgc             1152
Leu Leu Lys Arg Arg Tyr Val Pro Leu Ala Ala Leu Leu Pro Arg Cys
        370                 375                 380
```

```
cgg gcg ctg gtg cac cac ggg ggg atc ggg acg gcg tcg ctc gcg tac    1200
Arg Ala Leu Val His His Gly Gly Ile Gly Thr Ala Ser Leu Ala Tyr
385                 390                 395                 400 gcg gcg ggg gtg ccg cag gtg gtg acg ccg ttc gcg cac gac cag ttc    1248
Ala Ala Gly Val Pro Gln Val Val Thr Pro Phe Ala His Asp Gln Phe
                405                 410                 415 gac aac gcg cag cgg gtg gcg gcg agc ggc tgc ggg gtg cgg ctg gac    1296
Asp Asn Ala Gln Arg Val Ala Ala Ser Gly Cys Gly Val Arg Leu Asp
            420                 425                 430 gcg ccg gtg cgc ggc gag ccg ctc gcg cgg gcg ctg gcg cag gtg ctg    1344
Ala Pro Val Arg Gly Glu Pro Leu Ala Arg Ala Leu Ala Gln Val Leu
        435                 440                 445 ggc gac gcg gcg atg gcg gcg cgc tgc gcg cag gtg cgc gcg cgg atg    1392
Gly Asp Ala Ala Met Ala Ala Arg Cys Ala Gln Val Arg Ala Arg Met
    450                 455                 460 gcg gcg gag ccg aac ggc tgc gac gcg gcg gcg cgc ttc atc gag cgc    1440
Ala Ala Glu Pro Asn Gly Cys Asp Ala Ala Ala Arg Phe Ile Glu Arg
465                 470                 475                 480 ttc gcg ccg ggc gtc gcg gcg cgg cgg gcg cag ccg gca tga            1482
Phe Ala Pro Gly Val Ala Ala Arg Arg Ala Gln Pro Ala
                485                 490
```

<210> SEQ ID NO 20
<211> LENGTH: 493
<212> TYPE: PRT
<213> ORGANISM: Burkholderia thailandensis

<400> SEQUENCE: 20

```
Met Asp Ala Gly Arg Ile Gly Leu His Asp Ala Ala Ala Gly Arg
1               5                   10                  15

Ile Gly Met Thr Glu Ala Phe Ala Ser Arg Ala Arg Cys Ser Ala Ala
                20                  25                  30

Ala Leu Ala Ala Gly G

```
                    225                 230                 235                 240
Cys Gly Pro Glu Leu Asn Ala Ala Arg Gln Ala Leu Gly Leu Ala Pro
                245                 250                 255

Ala Lys Arg Ile Leu Gly Arg Trp Leu His Ser Thr Asp Gly Val Leu
            260                 265                 270

Cys Leu Phe Pro Ser Trp Phe Ala Pro Ala Gln Pro Asp Trp Pro Ala
        275                 280                 285

Asn His Leu Gln Ser Gly Phe Pro Leu Phe Asn Asp Ala Gly Pro Ala
    290                 295                 300

Gln Ala Asp Ala Glu Leu Glu Ala Phe Val Ala Ser Gly Glu Ala Pro
305                 310                 315                 320

Val Val Phe Thr Ala Gly Ser Thr Leu Val Asp Gly Arg Thr Tyr Glu
                325                 330                 335

His Ala Val Thr Gln Val Leu Gln Ala Thr Gly Val Arg Gly Ile Leu
            340                 345                 350

Leu Ala Pro Asp Ala Pro Asp Ala Pro Ala Ala Ser Asp Gly Ala Ala
        355                 360                 365

Leu Leu Lys Arg Arg Tyr Val Pro Leu Ala Ala Leu Leu Pro Arg Cys
    370                 375                 380

Arg Ala Leu Val His His Gly Gly Ile Gly Thr Ala Ser Leu Ala Tyr
385                 390                 395                 400

Ala Ala Gly Val Pro Gln Val Val Thr Pro Phe Ala His Asp Gln Phe
                405                 410                 415

Asp Asn Ala Gln Arg Val Ala Ala Ser Gly Cys Gly Val Arg Leu Asp
            420                 425                 430

Ala Pro Val Arg Gly Glu Pro Leu Ala Arg Ala Leu Ala Gln Val Leu
        435                 440                 445

Gly Asp Ala Ala Met Ala Ala Arg Cys Ala Gln Val Arg Ala Arg Met
    450                 455                 460

Ala Ala Glu Pro Asn Gly Cys Asp Ala Ala Ala Arg Phe Ile Glu Arg
465                 470                 475                 480

Phe Ala Pro Gly Val Ala Ala Arg Arg Ala Gln Pro Ala
                485                 490

<210> SEQ ID NO 21
<211> LENGTH: 966
<212> TYPE: DNA
<213> ORGANISM: Burkholderia thailandensis
<220> FEATURE:
<221> NAME/KEY: CDS
<222> LOCATION: (1)..(966)

<400> SEQUENCE: 21 atg acg atc ctg

|  |  |
|---|---|
| gcg cag ggc gtc gag gcg gtc gcg ctg ttc gac cag gac tcg acg gtg<br>Ala Gln Gly Val Glu Ala Val Ala Leu Phe Asp Gln Asp Ser Thr Val<br>                         85                      90                   95 | 288 |
| ccg gcc ggg tac ttc gag cgg atg cgc gag gcg tgc gcg caa ctg ggt<br>Pro Ala Gly Tyr Phe Glu Arg Met Arg Glu Ala Cys Ala Gln Leu Gly<br>             100                    105                    110 | 336 |
| gag caa ccg ggc gcg cac gcg ggc gcg ttc atc gcg ggc ccg cgg atc<br>Glu Gln Pro Gly Ala His Ala Gly Ala Phe Ile Ala Gly Pro Arg Ile<br>        115                    120                    125 | 384 |
| tac gac gcg aac gag cag cgc ttc ctg ccg gag ctg atg acg agc ggg<br>Tyr Asp Ala Asn Glu Gln Arg Phe Leu Pro Glu Leu Met Thr Ser Gly<br>130                      135                    140 | 432 |
| gtg acg gtg cgc cgc gtg cgg gtg gag ggc gag acg gcg ccg cag cgc<br>Val Thr Val Arg Arg Val Arg Val Glu Gly Glu Thr Ala Pro Gln Arg<br>145                      150                    155                    160 | 480 |
| tgc gcg ttc ctg atc tcg tcg ggc agc gtg att tcg cgg gcc gcg tac<br>Cys Ala Phe Leu Ile Ser Ser Gly Ser Val Ile Ser Arg Ala Ala Tyr<br>                  165                    170                    175 | 528 |
| gcg cgg ctc ggt cga ttc gac gag gcg ctg ttc atc gat cac gtc gac<br>Ala Arg Leu Gly Arg Phe Asp Glu Ala Leu Phe Ile Asp His Val Asp<br>            180                    185                    190 | 576 |
| acc gag tat tgc ctg cgc gcg ctc gcg cac aac gtg ccg ctg tac gtg<br>Thr Glu Tyr Cys Leu Arg Ala Leu Ala His Asn Val Pro Leu Tyr Val<br>        195                    200                    205 | 624 |
| gtg ccg ccg ctc gtg ctg acg cac cgg atc ggc gcg cgg cgc cgg cac<br>Val Pro Pro Leu Val Leu Thr His Arg Ile Gly Ala Arg Arg Arg His<br>        210                    215                    220 | 672 |
| aag gtg ggg ccg ttc gag ctg acg gcg atg cat cac ggg tgg ttg cgc<br>Lys Val Gly Pro Phe Glu Leu Thr Ala Met His His Gly Trp Leu Arg<br>225                      230                    235                    240 | 720 |
| cga tac tac ggc gcg cgc aac gcg atg caa ctg ggg ctg cag tac ggc<br>Arg Tyr Tyr Gly Ala Arg Asn Ala Met Gln Leu Gly Leu Gln Tyr Gly<br>                  245                    250                    255 | 768 |
| ttg cgg ttt ccg gtg gcg ctg gtg ccg aat ctg ctg acg ata tgg cag<br>Leu Arg Phe Pro Val Ala Leu Val Pro Asn Leu Leu Thr Ile Trp Gln<br>            260                    265                    270 | 816 |
| gtg atc cag gtg gtg ctg tgc gag cgg gag aag ggc gcg aag ctg cgc<br>Val Ile Gln Val Val Leu Cys Glu Arg Glu Lys Gly Ala Lys Leu Arg<br>        275                    280                    285 | 864 |
| ggg atc gcg ctg ggc gtg ctc gac ggc ctg ttc ggg cgg ctg gga tcg<br>Gly Ile Ala Leu Gly Val Leu Asp Gly Leu Phe Gly Arg Leu Gly Ser<br>        290                    295                    300 | 912 |
| ttc gac gat gcg cgc gcg ggc gcg gcg gcg cgc gag ccg gtg cgg cag<br>Phe Asp Asp Ala Arg Ala Gly Ala Ala Ala Arg Glu Pro Val Arg Gln<br>305                      310                    315                    320 | 960 |
| gaa tga<br>Glu | 966 |

<210> SEQ ID NO 22
<211> LENGTH: 321
<212> TYPE: PRT
<213> ORGANISM: Burkholderia thailandensis

<400> SEQUENCE: 22

Met Thr Ile Leu Gly Ala Leu Val Ile Leu Tyr Asp Pro Thr Asp Glu
1               5                   10                  15

Gln Leu Ser Gly Leu Glu Ala Leu Ala Arg Asp Ser Asp Ala Leu Val
            20                  25                  30

```
Val Val Asp Asn Thr Pro His Glu His Ala Ala Ala Arg Glu Arg Val
         35                  40                  45

Arg Ala Leu Ser Ala Arg Thr Asn Thr Val Trp Arg His His Gly Asn
 50                  55                  60

Arg Gly Gly Val Ala Gly Gly Tyr Asn Ala Gly Leu Ser Val Leu Phe
 65                  70                  75                  80

Ala Gln Gly Val Glu Ala Val Ala Leu Phe Asp Gln Asp Ser Thr Val
                 85                  90                  95

Pro Ala Gly Tyr Phe Glu Arg Met Arg Glu Ala Cys Ala Gln Leu Gly
            100                 105                 110

Glu Gln Pro Gly Ala His Ala Gly Ala Phe Ile Ala Gly Pro Arg Ile
        115                 120                 125

Tyr Asp Ala Asn Glu Gln Arg Phe Leu Pro Glu Leu Met Thr Ser Gly
130                 135                 140

Val Thr Val Arg Arg Val Arg Val Glu Gly Glu Thr Ala Pro Gln Arg
145                 150                 155                 160

Cys Ala Phe Leu Ile Ser Ser Gly Ser Val Ile Ser Arg Ala Ala Tyr
                165                 170                 175

Ala Arg Leu Gly Arg Phe Asp Glu Ala Leu Phe Ile Asp His Val Asp
            180                 185                 190

Thr Glu Tyr Cys Leu Arg Ala Leu Ala His Asn Val Pro Leu Tyr Val
        195                 200                 205

Val Pro Pro Leu Val Leu Thr His Arg Ile Gly Ala Arg Arg His
210                 215                 220

Lys Val Gly Pro Phe Glu Leu Thr Ala Met His His Gly Trp Leu Arg
225                 230                 235                 240

Arg Tyr Tyr Gly Ala Arg Asn Ala Met Gln Leu Gly Leu Gln Tyr Gly
                245                 250                 255

Leu Arg Phe Pro Val Ala Leu Val Pro Asn Leu Leu Thr Ile Trp Gln
            260                 265                 270

Val Ile Gln Val Val Leu Cys Glu Arg Glu Lys Gly Ala Lys Leu Arg
        275                 280                 285

Gly Ile Ala Leu Gly Val Leu Asp Gly Leu Phe Gly Arg Leu Gly Ser
290                 295                 300

Phe Asp Asp Ala Arg Ala Gly Ala Ala Arg Glu Pro Val Arg Gln
305                 310                 315                 320

Glu

<210> SEQ ID NO 23
<211> LENGTH: 1557
<212> TYPE: DNA
<213> ORGANISM: Burkholderia thailandensis
<220> FEATURE:
<221> NAME/KEY: CDS
<222> LOCATION: (1)..(1557)

<400> SEQUENCE: 23 atg tcg gcg gat cag gcg

| | | |
|---|---|---|
| atc tcg ggc agc ctc ggg gtg tcg aac agc cag ggc acg tgg gtg atc<br>Ile Ser Gly Ser Leu Gly Val Ser Asn Ser Gln Gly Thr Trp Val Ile<br>50                    55                      60 | | 192 |
| agc tcg tac tcg gtg gcc gcg gcg atc gcg gtg ccg ctg acg ggg tgg<br>Ser Ser Tyr Ser Val Ala Ala Ala Ile Ala Val Pro Leu Thr Gly Trp<br>65                    70                    75                    80 | | 240 |
| ctt gcg cgg cgc gtg ggc gag ctg agg ctg ttc gtg gcg tcg gtg atc<br>Leu Ala Arg Arg Val Gly Glu Leu Arg Leu Phe Val Ala Ser Val Ile<br>                85                    90                    95 | | 288 |
| ctg ttc acg ctg acg tcg ctg ctg tgc ggg ctc gcg cgg gac ctg gag<br>Leu Phe Thr Leu Thr Ser Leu Leu Cys Gly Leu Ala Arg Asp Leu Glu<br>              100                       105                    110 | | 336 |
| gtg ctg gtt gcg tgc cgg gcg ctg cag ggg ctg ttc tcg ggg ccg atg<br>Val Leu Val Ala Cys Arg Ala Leu Gln Gly Leu Phe Ser Gly Pro Met<br>              115                       120                    125 | | 384 |
| gtg ccg ctg tcg cag acg atc ctg atg cgc gcg ttc ccg ccg gcg cgg<br>Val Pro Leu Ser Gln Thr Ile Leu Met Arg Ala Phe Pro Pro Ala Arg<br>130                      135                       140 | | 432 |
| cgc acg ctg gcg ctg gcg ctg tgg ggg atg acg gtg ctc ctc gcg ccg<br>Arg Thr Leu Ala Leu Ala Leu Trp Gly Met Thr Val Leu Leu Ala Pro<br>145                      150                       155                    160 | | 480 |
| atc ttc ggg ccg gtg gtg ggc ggc tgg ctg atc gac aac ttc tcg tgg<br>Ile Phe Gly Pro Val Val Gly Gly Trp Leu Ile Asp Asn Phe Ser Trp<br>                  165                       170                    175 | | 528 |
| ccg tgg atc ttc ctg atc aac ctg ccg atc ggg ctg ttc tcg ttc gcg<br>Pro Trp Ile Phe Leu Ile Asn Leu Pro Ile Gly Leu Phe Ser Phe Ala<br>              180                       185                    190 | | 576 |
| gtg tgc acg ctg atg ctg cgc ccg cag gcg cag cgc ggc gag gcg agc<br>Val Cys Thr Leu Met Leu Arg Pro Gln Ala Gln Arg Gly Glu Ala Ser<br>              195                     200                    205 | | 624 |
| ccg atc gac gcg ccg ggg atc gtg ctg ctg gtg atc ggg gtg ggc tcg<br>Pro Ile Asp Ala Pro Gly Ile Val Leu Leu Val Ile Gly Val Gly Ser<br>210                      215                       220 | | 672 |
| ctg cag gcg atg ctg gac ctg ggg cac gac cgg ggc tgg ttc gat tcg<br>Leu Gln Ala Met Leu Asp Leu Gly His Asp Arg Gly Trp Phe Asp Ser<br>225                      230                       235                    240 | | 720 |
| ccg ctg atc acg gcg ctg gcg atc gcg gcg ggg gtg tcg ctc gtg tcg<br>Pro Leu Ile Thr Ala Leu Ala Ile Ala Ala Gly Val Ser Leu Val Ser<br>              245                     250                    255 | | 768 |
| ctg ctg atc tgg gag ctg ggc gag gcg cat ccg gtg gtg gat ctg agc<br>Leu Leu Ile Trp Glu Leu Gly Glu Ala His Pro Val Val Asp Leu Ser<br>              260                     265                    270 | | 816 |
| ctg ttc cgg gag cgg acc ttc acg ttc tgc gtg gtg atc atc tcg ctg<br>Leu Phe Arg Glu Arg Thr Phe Thr Phe Cys Val Val Ile Ile Ser Leu<br>              275                     280                    285 | | 864 |
| ggg atg atg agc ttc tcg gtg gtg ggg gtg gtg ttt ccg ctg tgg ctg<br>Gly Met Met Ser Phe Ser Val Val Gly Val Val Phe Pro Leu Trp Leu<br>290                      295                       300 | | 912 |
| cag gcg gtg atg gga tac acg gcg tac cag gcg ggg ctg gcg acg gcg<br>Gln Ala Val Met Gly Tyr Thr Ala Tyr Gln Ala Gly Leu Ala Thr Ala<br>305                      310                     315                    320 | | 960 |
| tcg atg ggg gtg ctg gcg ctg gtg ttc tcg atc ctg gtg ggg ctg tac<br>Ser Met Gly Val Leu Ala Leu Val Phe Ser Ile Leu Val Gly Leu Tyr<br>              325                     330                    335 | | 1008 |
| gcg agc cgg gtg gac gcg cgg gtg ctg gtg acg ttc ggg ttc ggg gtg<br>Ala Ser Arg Val Asp Ala Arg Val Leu Val Thr Phe Gly Phe Gly Val<br>                  340                     345                    350 | | 1056 |
| ttt gcg gcg gtg atg tgg tgg agc acg cac ttc acg ctg tcg atg acg<br>Phe Ala Ala Val Met Trp Trp Ser Thr His Phe Thr Leu Ser Met Thr<br>355                      360                     365 | | 1104 |

-continued

| | | |
|---|---|---|
| ttc gcg cag gtg gtg acg ccg cgg ctg att cag ggg atg ggg ctg ccg<br>Phe Ala Gln Val Val Thr Pro Arg Leu Ile Gln Gly Met Gly Leu Pro<br>370                              375                            380 | 1152 |
| tgc ttc ttc ata ccg ctg acg gcg gcg acg ctg tcg cgg gtg ccg gac<br>Cys Phe Phe Ile Pro Leu Thr Ala Ala Thr Leu Ser Arg Val Pro Asp<br>385                           390                           395                        400 | 1200 |
| gag aag ctg gcg gcg gcg tcg agc ctg tcg aac ttc ctg cgg acg ctg<br>Glu Lys Leu Ala Ala Ala Ser Ser Leu Ser Asn Phe Leu Arg Thr Leu<br>                              405                           410                           415 | 1248 |
| tcg gcg gcg ttc ggc acg gcg ctg agc gtg acg tgg tgg gac aac cgg<br>Ser Ala Ala Phe Gly Thr Ala Leu Ser Val Thr Trp Trp Asp Asn Arg<br>                   420                           425                           430 | 1296 |
| gcg acg tac cac tac gcg gtg gtg tcg caa tcg gtg acg cgc gcc tcg<br>Ala Thr Tyr His Tyr Ala Val Val Ser Gln Ser Val Thr Arg Ala Ser<br>                              435                           440                           445 | 1344 |
| gag aac acg cag cgg tac gtg gac gcg ctg cac gcg atg ggg ctg cac<br>Glu Asn Thr Gln Arg Tyr Val Asp Ala Leu His Ala Met Gly Leu His<br>450                              455                           460 | 1392 |
| ggc gcg cgg gag ctg agc tcg ctg cac cag gtg gtg cgg cag cag gcg<br>Gly Ala Arg Glu Leu Ser Ser Leu His Gln Val Val Arg Gln Gln Ala<br>465                              470                           475                        480 | 1440 |
| tac atg atg gcg acg aac gac atg ttc tac atg gcg agc gcg acg tgc<br>Tyr Met Met Ala Thr Asn Asp Met Phe Tyr Met Ala Ser Ala Thr Cys<br>                              485                           490                           495 | 1488 |
| ctg ctg ctg gcg ggg ctg atg tgg ctg acg cgg ccg aag cgg ggc gcg<br>Leu Leu Leu Ala Gly Leu Met Trp Leu Thr Arg Pro Lys Arg Gly Ala<br>                   500                           505                           510 | 1536 |
| gcg gcg gcg ctc ggg cac tga<br>Ala Ala Ala Leu Gly His<br>                   515 | 1557 |

```
<210> SEQ ID NO 24
<211> LENGTH: 518
<212> TYPE: PRT
<213> ORGANISM: Burkholderia thailandensis

<400> SEQUENCE: 24
```

Met Ser Ala Asp Gln Ala Gly Val Ala Pro Ala Ala Pro Leu
1                  5                    10                  15

Arg Gly Ala Lys Leu Ala Leu Leu Thr Phe Ala Leu Ser Leu Ala Thr
               20                    25                    30

Phe Ile Glu Val Leu Asp Ser Thr Val Ala Asn Val Ala Val Pro Ala
               35                    40                    45

Ile Ser Gly Ser Leu Gly Val Ser Asn Ser Gln Gly Thr Trp Val Ile
50                         55                    60

Ser Ser Tyr Ser Val Ala Ala Ile Ala Val Pro Leu Thr Gly Trp
65                        70                    75                    80

Leu Ala Arg Arg Val Gly Glu Leu Arg Leu Phe Val Ala Ser Val Ile
               85                    90                    95

Leu Phe Thr Leu Thr Ser Leu Leu Cys Gly Leu Ala Arg Asp Leu Glu
                   100                  105                  110

Val Leu Val Ala Cys Arg Ala Leu Gln Gly Leu Phe Ser Gly Pro Met
               115                  120                  125

Val Pro Leu Ser Gln Thr Ile Leu Met Arg Ala Phe Pro Pro Ala Arg
          130                  135                  140

Arg Thr Leu Ala Leu Ala Leu Trp Gly Met Thr Val Leu Leu Ala Pro
145                        150                    155                    160

```
Ile Phe Gly Pro Val Gly Gly Trp Leu Ile Asp Asn Phe Ser Trp
            165                 170                 175
Pro Trp Ile Phe Leu Ile Asn Leu Pro Ile Gly Leu Phe Ser Phe Ala
        180                 185                 190
Val Cys Thr Leu Met Leu Arg Pro Gln Ala Gln Arg Gly Glu Ala Ser
            195                 200                 205
Pro Ile Asp Ala Pro Gly Ile Val Leu Val Ile Gly Val Gly Ser
210                 215                 220
Leu Gln Ala Met Leu Asp Leu Gly His Asp Arg Gly Trp Phe Asp Ser
225                 230                 235                 240
Pro Leu Ile Thr Ala Leu Ala Ile Ala Ala Gly Val Ser Leu Val Ser
            245                 250                 255
Leu Leu Ile Trp Glu Leu Gly Glu Ala His Pro Val Val Asp Leu Ser
            260                 265                 270
Leu Phe Arg Glu Arg Thr Phe Thr Phe Cys Val Val Ile Ile Ser Leu
        275                 280                 285
Gly Met Met Ser Phe Ser Val Gly Val Val Phe Pro Leu Trp Leu
        290                 295                 300
Gln Ala Val Met Gly Tyr Thr Ala Tyr Gln Ala Gly Leu Ala Thr Ala
305                 310                 315                 320
Ser Met Gly Val Leu Ala Leu Val Phe Ser Ile Leu Val Gly Leu Tyr
            325                 330                 335
Ala Ser Arg Val Asp Ala Arg Val Leu Val Thr Phe Gly Phe Gly Val
            340                 345                 350
Phe Ala Ala Val Met Trp Trp Ser Thr His Phe Thr Leu Ser Met Thr
        355                 360                 365
Phe Ala Gln Val Thr Pro Arg Leu Ile Gln Gly Met Gly Leu Pro
        370                 375                 380
Cys Phe Phe Ile Pro Leu Thr Ala Ala Thr Leu Ser Arg Val Pro Asp
385                 390                 395                 400
Glu Lys Leu Ala Ala Ser Ser Leu Ser Asn Phe Leu Arg Thr Leu
            405                 410                 415
Ser Ala Ala Phe Gly Thr Ala Leu Ser Val Thr Trp Trp Asp Asn Arg
            420                 425                 430
Ala Thr Tyr His Tyr Ala Val Val Ser Gln Ser Val Thr Arg Ala Ser
        435                 440                 445
Glu Asn Thr Gln Arg Tyr Val Asp Ala Leu His Ala Met Gly Leu His
        450                 455                 460
Gly Ala Arg Glu Leu Ser Ser Leu His Gln Val Val Arg Gln Gln Ala
465                 470                 475                 480
Tyr Met Met Ala Thr Asn Asp Met Phe Tyr Met Ala Ser Ala Thr Cys
            485                 490                 495
Leu Leu Leu Ala Gly Leu Met Trp Leu Thr Arg Pro Lys Arg Gly Ala
            500                 505                 510
Ala Ala Ala Leu Gly His
            515
```

<210> SEQ ID NO 25
<211> LENGTH: 1662
<212> TYPE: DNA
<213> ORGANISM: Burkholderia thailandensis
<220> FEATURE:
<221> NAME/KEY: CDS
<222> LOCATION: (1)..(1662)

<400> SEQUENCE: 25

-continued

| | |
|---|---|
| atg cgc gcg cgg gcg cgg cgg cgc gcg agc cgg tgc ggc agg aat gaa<br>Met Arg Ala Arg Ala Arg Arg Ala Ser Arg Cys Gly Arg Asn Glu<br>1                        5                        10                        15 | 48 |
| cgg aac ggg ccg cag cgg gat acc gga aag caa gaa gga cgc atc ata<br>Arg Asn Gly Pro Gln Arg Asp Thr Gly Lys Gln Glu Gly Arg Ile Ile<br>                    20                        25                        30 | 96 |
| cga atg acg cag aca gca acg caa gca gcc act cgc gcg atg atc gcg<br>Arg Met Thr Gln Thr Ala Thr Gln Ala Ala Thr Arg Ala Met Ile Ala<br>            35                        40                        45 | 144 |
| aca gga agc cgc gcg gcg cgc cgg ctc gcg gca gcc gcg ctc gcg tgg<br>Thr Gly Ser Arg Ala Ala Arg Arg Leu Ala Ala Ala Ala Leu Ala Trp<br>        50                        55                        60 | 192 |
| gcg ctc gcc ggc tgc gtg ccg tcg ggc ttc gag ccg gcg ctc gcg ccg<br>Ala Leu Ala Gly Cys Val Pro Ser Gly Phe Glu Pro Ala Leu Ala Pro<br>65                        70                        75                        80 | 240 |
| cgc acg ccg ggc gac gac gcg ctc gcg cac acg gcg ggg ggc gcc gcg<br>Arg Thr Pro Gly Asp Asp Ala Leu Ala His Thr Ala Gly Gly Ala Ala<br>                    85                        90                        95 | 288 |
| cac ggc gca tgg ccg agc ccc gac tgg gtc cgg cag ctc ggc gat ccg<br>His Gly Ala Trp Pro Ser Pro Asp Trp Val Arg Gln Leu Gly Asp Pro<br>              100                        105                       110 | 336 |
| caa ctc gac gcg ctc gtc gac gag gcg ctg cgg cag aac ccg acg ctg<br>Gln Leu Asp Ala Leu Val Asp Glu Ala Leu Arg Gln Asn Pro Thr Leu<br>            115                        120                       125 | 384 |
| cag gcc gcg cag gcg cgc atc ggc gtc gcg cag tcg cag ctg cag cag<br>Gln Ala Ala Gln Ala Arg Ile Gly Val Ala Gln Ser Gln Leu Gln Gln<br>130                        135                        140 | 432 |
| ttc gaa tcg ctg acg ggg ctc acc gcg acg gcg ggc gcg tcg ctc tcc<br>Phe Glu Ser Leu Thr Gly Leu Thr Ala Thr Ala Gly Ala Ser Leu Ser<br>145                        150                        155                        160 | 480 |
| aag gcg cac gtg ccg cgc tcg ggc ggc acc atc aat acg acg ttc aac<br>Lys Ala His Val Pro Arg Ser Gly Gly Thr Ile Asn Thr Thr Phe Asn<br>                    165                        170                       175 | 528 |
| ggc ttg ccg gtg tcg gtg ccg ctc gtc ggc gaa tcg gtg gtg tcg tcg<br>Gly Leu Pro Val Ser Val Pro Leu Val Gly Glu Ser Val Val Ser Ser<br>                  180                        185                       190 | 576 |
| tcg tcg ctg ttc gtc ggg ctg aac tat cag ctg gac ctg tgg ggc aag<br>Ser Ser Leu Phe Val Gly Leu Asn Tyr Gln Leu Asp Leu Trp Gly Lys<br>              195                        200                       205 | 624 |
| aac gcg gcg gcc acg cgc ggg ctg ctg tcg atg cgc gat gcg gcg cgc<br>Asn Ala Ala Ala Thr Arg Gly Leu Leu Ser Met Arg Asp Ala Ala Arg<br>210                        215                        220 | 672 |
| gtg gag gcc gag cag gcg cgg ctc gcg ctg tcg gtg gcg atc gtg acg<br>Val Glu Ala Glu Gln Ala Arg Leu Ala Leu Ser Val Ala Ile Val Thr<br>225                        230                        235                        240 | 720 |
| ctg tac ggc gag ctg gac cgc gcg tat gcg ctg cgc gag ctg ctg cag<br>Leu Tyr Gly Glu Leu Asp Arg Ala Tyr Ala Leu Arg Glu Leu Leu Gln<br>                    245                        250                       255 | 768 |
| cag aag cgc cgc gcg agc gag cag gtg gag acg gtg ctg cgc gag cgc<br>Gln Lys Arg Arg Ala Ser Glu Gln Val Glu Thr Val Leu Arg Glu Arg<br>            260                        265                       270 | 816 |
| gcg gcg cgc ggg atc gac aac ggc tac gat gcg gac gac gcg gcg ctc<br>Ala Ala Arg Gly Ile Asp Asn Gly Tyr Asp Ala Asp Asp Ala Ala Leu<br>            275                        280                       285 | 864 |
| aag cgg ggc aag ctg ctc gag cag ctc gcg ctg acc gac gag cag atc<br>Lys Arg Gly Lys Leu Leu Glu Gln Leu Ala Leu Thr Asp Glu Gln Ile<br>290                        295                        300 | 912 |
| cag ttg cag aag ctg caa ctg ggg gtg ctg agc ggg cgg ggg ccg gag<br>Gln Leu Gln Lys Leu Gln Leu Gly Val Leu Ser Gly Arg Gly Pro Glu | 960 |

| | | |
|---|---|---|
| cgc ggg ctg tcg ctc gcg cgg ccg aag ctc gcg ccg ctc gcg gac gcg<br>Arg Gly Leu Ser Leu Ala Arg Pro Lys Leu Ala Pro Leu Ala Asp Ala<br>325 330 335 | 1008 | |
| ccg ctg ccg gcg cgg ctg ccg gcc ggg ctg ctg ggg cgg cgg ccg gac<br>Pro Leu Pro Ala Arg Leu Pro Ala Gly Leu Leu Gly Arg Arg Pro Asp<br>340 345 350 | 1056 | |
| atc gtc gcg gcg cgg ctg cgg gtg gag gcg gcg tac gcg gcg atc gac<br>Ile Val Ala Ala Arg Leu Arg Val Glu Ala Ala Tyr Ala Ala Ile Asp<br>355 360 365 | 1104 | |
| ggc acg cgc gcg tcg ttc tac ccg gac gtg aac ctg gcg gcg ctg ggc<br>Gly Thr Arg Ala Ser Phe Tyr Pro Asp Val Asn Leu Ala Ala Leu Gly<br>370 375 380 | 1152 | |
| ggg ctg ttc gcg ctc acg ccg gcg tcg ctg ttc aag cac gat gcg ctg<br>Gly Leu Phe Ala Leu Thr Pro Ala Ser Leu Phe Lys His Asp Ala Leu<br>385 390 395 400 | 1200 | |
| ggc ggc tcg atc ggt ccg gcg ctg tcg ctg ccg atc ttc gat cgc ggc<br>Gly Gly Ser Ile Gly Pro Ala Leu Ser Leu Pro Ile Phe Asp Arg Gly<br>405 410 415 | 1248 | |
| cgg ctg aag gcg aag ctg ggg ggc gac gtg gcg aac gcg gac gtg gcg<br>Arg Leu Lys Ala Lys Leu Gly Gly Asp Val Ala Asn Ala Asp Val Ala<br>420 425 430 | 1296 | |
| ctg gcg ctg tac aac cag acg gtg gat gcg gcg ctg ggc gag gtg gcg<br>Leu Ala Leu Tyr Asn Gln Thr Val Asp Ala Ala Leu Gly Glu Val Ala<br>435 440 445 | 1344 | |
| cgg cag ttg acg tcg ctg tcg acg gtg gat gcg ctg ctc gag gcg cag<br>Arg Gln Leu Thr Ser Leu Ser Thr Val Asp Ala Leu Leu Glu Ala Gln<br>450 455 460 | 1392 | |
| cag cag gcg gtg cgc tcg gcg cag cgg atg gtg gcg ctg gcg cag gac<br>Gln Gln Ala Val Arg Ser Ala Gln Arg Met Val Ala Leu Ala Gln Asp<br>465 470 475 480 | 1440 | |
| cgg cac cgg cgg ggg atg ggg atg cgc aag gac gtg aac gtg gcg aag<br>Arg His Arg Arg Gly Met Gly Met Arg Lys Asp Val Asn Val Ala Lys<br>485 490 495 | 1488 | |
| ctg acg ctg ctg gac gag cgt gcg cac gtg atc gag ctg cag gcg cgg<br>Leu Thr Leu Leu Asp Glu Arg Ala His Val Ile Glu Leu Gln Ala Arg<br>500 505 510 | 1536 | |
| cgg cgg acg ctg cgg gtg ggg ctg atc ggg gcg ctg ggc ggc ggc ttc<br>Arg Arg Thr Leu Arg Val Gly Leu Ile Gly Ala Leu Gly Gly Gly Phe<br>515 520 525 | 1584 | |
| gac gcg cgg ccg gcg ggc ggc gcg ccg ctc gcg cag ggc aag ccg ttc<br>Asp Ala Arg Pro Ala Gly Gly Ala Pro Leu Ala Gln Gly Lys Pro Phe<br>530 535 540 | 1632 | |
| gcg gcg gcg agc gac agg ccg ccc gat tga<br>Ala Ala Ala Ser Asp Arg Pro Pro Asp<br>545 550 | 1662 | |

<210> SEQ ID NO 26
<211> LENGTH: 553
<212> TYPE: PRT
<213> ORGANISM: Burkholderia thailandensis

<400> SEQUENCE: 26

Met Arg Ala Arg Ala Arg Arg Ala Ser Arg Cys Gly Arg Asn Glu
1

-continued

Thr Gly Ser Arg Ala Ala Arg Arg Leu Ala Ala Ala Leu Ala Trp
    50              55                  60
Ala Leu Ala Gly Cys Val Pro Ser Gly Phe Glu Pro Leu Ala Pro
65              70                  75                  80
Arg Thr Pro Gly Asp Asp Ala Leu Ala His Thr Ala Gly Gly Ala Ala
            85                  90                  95
His Gly Ala Trp Pro Ser Pro Asp Trp Val Arg Gln Leu Gly Asp Pro
                100                 105                 110
Gln Leu Asp Ala Leu Val Asp Glu Ala Leu Arg Gln Asn Pro Thr Leu
            115                 120                 125
Gln Ala Ala Gln Ala Arg Ile Gly Val Ala Gln Ser Gln Leu Gln Gln
130                 135                 140
Phe Glu Ser Leu Thr Gly Leu Thr Ala Thr Ala Gly Ala Ser Leu Ser
145                 150                 155                 160
Lys Ala His Val Pro Arg Ser Gly Gly Thr Ile Asn Thr Thr Phe Asn
                165                 170                 175
Gly Leu Pro Val Ser Val Pro Leu Val Gly Glu Ser Val Val Ser Ser
            180                 185                 190
Ser Ser Leu Phe Val Gly Leu Asn Tyr Gln Leu Asp Leu Trp Gly Lys
        195                 200                 205
Asn Ala Ala Ala Thr Arg Gly Leu Leu Ser Met Arg Asp Ala Ala Arg
210                 215                 220
Val Glu Ala Glu Gln Ala Arg Leu Ala Leu Ser Val Ala Ile Val Thr
225                 230                 235                 240
Leu Tyr Gly Glu Leu Asp Arg Ala Tyr Ala Leu Arg Glu Leu Leu Gln
            245                 250                 255
Gln Lys Arg Arg Ala Ser Glu Gln Val Glu Thr Val Leu Arg Glu Arg
        260                 265                 270
Ala Ala Arg Gly Ile Asp Asn Gly Tyr Asp Ala Asp Ala Ala Leu
        275                 280                 285
Lys Arg Gly Lys Leu Leu Glu Gln Leu Ala Leu Thr Asp Glu Gln Ile
290                 295                 300
Gln Leu Gln Lys Leu Gln Leu Gly Val Leu Ser Gly Arg Gly Pro Glu
305                 310                 315                 320
Arg Gly Leu Ser Leu Ala Arg Pro Lys Leu Ala Pro Leu Ala Asp Ala
            325                 330                 335
Pro Leu Pro Ala Arg Leu Pro Ala Gly Leu Leu Gly Arg Arg Pro Asp
                340                 345                 350
Ile Val Ala Ala Arg Leu Arg Val Glu Ala Ala Tyr Ala Ala Ile Asp
            355                 360                 365
Gly Thr Arg Ala Ser Phe Tyr Pro Asp Val Asn Leu Ala Ala Leu Gly
        370                 375                 380
Gly Leu Phe Ala Leu Thr Pro Ala Ser Leu Phe Lys His Asp Ala Leu
385                 390                 395                 400
Gly Gly Ser Ile Gly Pro Ala Leu Ser Leu Pro Ile Phe Asp Arg Gly
            405                 410                 415
Arg Leu Lys Ala Lys Leu Gly Gly Asp Val Ala Asn Ala Asp Val Ala
        420                 425                 430
Leu Ala Leu Tyr Asn Gln Thr Val Asp Ala Ala Leu Gly Glu Val Ala
            435                 440                 445
Arg Gln Leu Thr Ser Leu Ser Thr Val Asp Ala Leu Leu Glu Ala Gln
450                 455                 460
Gln Gln Ala Val Arg Ser Ala Gln Arg Met Val Ala Leu Ala Gln Asp

```
                    465                 470                 475                 480
Arg His Arg Arg Gly Met Gly Met Arg Lys Asp Val Asn Val Ala Lys
                        485                 490                 495

Leu Thr Leu Leu Asp Glu Arg Ala His Val Ile Glu Leu Gln Ala Arg
                500                 505                 510

Arg Arg Thr Leu Arg Val Gly Leu Ile Gly Ala Leu Gly Gly Phe
            515                 520                 525

Asp Ala Arg Pro Ala Gly Gly Ala Pro Leu Ala Gln Gly Lys Pro Phe
530                 535                 540

Ala Ala Ala Ser Asp Arg Pro Pro Asp
545                 550

<210> SEQ ID NO 27
<211> LENGTH: 1401
<212> TYPE: DNA
<213> ORGANISM: Burkholderia thailandensis
<220> F

```
gaa cac gcg gct ctc gat ggg gat gta cga gga gac ggt gaa ggc gcg      672
Glu His Ala Ala Leu Asp Gly Asp Val Arg Gly Asp Gly Glu Gly Ala
    210                 215                 220 cga ggc gga cct gaa gct tgc gca gca ggc gta tcc gga gga act ggc      720
Arg Gly Gly Pro Glu Ala Cys Ala Ala Gly Val Ser Gly Gly Thr Gly
225                 230                 235                 240 gcg gcg aaa gtc gtc gct ggc gaa cgc gca ggc ggc gct ggc ggg ggc      768
Ala Ala Lys Val Val Ala Gly Glu Arg Ala Gly Gly Ala Gly Gly Gly
                245                 250                 255 gca ggc gca gct gga ggc ggc gcg cgc gct ggg cag cga gcg gcc ggt      816
Ala Gly Ala Ala Gly Gly Gly Ala Arg Ala Gly Gln Arg Ala Ala Gly
            260                 265                 270 cga gca gaa ccc ggc ggt gca gca ggc ggc cgc gca gtt caa gct ggc      864
Arg Ala Glu Pro Gly Gly Ala Ala Gly Gly Arg Ala Val Gln Ala Gly
        275                 280                 285 gta ccg gaa cct gag gcg cac gac gat cgt gtc gcc ggt gga cgg cac      912
Val Pro Glu Pro Glu Ala His Asp Asp Arg Val Ala Gly Gly Arg His
    290                 295                 300 ggt cgg tca gcg gtc ggt gca gat cgg tca gca ggt ggg gcc ggg ggt      960
Gly Arg Ser Ala Val Gly Ala Asp Arg Ser Ala Gly Gly Ala Gly Gly
305                 310                 315                 320 gcc gct gat gtc ggt ggt gca gtt gcg gca ggt gtg ggt gga ggc gaa     1008
Ala Ala Asp Val Gly Gly Ala Val Ala Ala Gly Val Gly Gly Gly Glu
                325                 330                 335 ctt caa gga agg gca gat ccg gca cat gcg ggt ggg cca gcc ggt gcg     1056
Leu Gln Gly Arg Ala Asp Pro Ala His Ala Gly Gly Pro Ala Gly Ala
            340                 345                 350 gct cga atc gga cct gta cgg cgc gcg ggt gac gta cca cgg ccg ggt     1104
Ala Arg Ile Gly Pro Val Arg Arg Ala Gly Asp Val Pro Arg Pro Gly
        355                 360                 365 gga ggg ggt ctc ggc ggg cac ggg cag cgc gtt ctc gat gct gcc gtc     1152
Gly Gly Gly Leu Gly Gly His Gly Gln Arg Val Leu Asp Ala Ala Val
    370                 375                 380 gca gaa cgc ggc ggg gaa ctg gat caa ggt ggt gca gcg cct gcc ggt     1200
Ala Glu Arg Gly Gly Glu Leu Asp Gln Gly Gly Ala Ala Pro Ala Gly
385                 390                 395                 400 ggt gat ctc gct gga gcc gtc gga gct ggc ggc gca ccc gct gcg ggt     1248
Gly Asp Leu Ala Gly Ala Val Gly Ala Gly Gly Ala Pro Ala Ala Gly
                405                 410                 415 ggg gct gtc gat gcg cgc gac ggt gga gac gaa ggt gcg tgg cgg ccg     1296
Gly Ala Val Asp Ala Arg Asp Gly Gly Asp Glu Gly Ala Trp Arg Pro
            420                 425                 430 cct gct cga cgg cga cgc gcc gct gcc ggg gct gcg cac gcg ggt gca     1344
Pro Ala Arg Arg Arg Ala Ala Gly Ala Ala His Ala Gly Ala
        435                 440                 445 cga agc gca ggc ggg cga ggc cga ggc cgc ggc ttc ggc agt gat tcg     1392
Arg Ser Ala Gly Gly Arg Gly Arg Gly Arg Gly Phe Gly Ser Asp Ser
    450                 455                 460 gga gaa tga                                                         1401
Gly Glu
465

<210> SEQ ID NO 28
<211> LENGTH: 466
<212> TYPE: PRT
<213> ORGANISM: Burkholderia thailandensis

<400> SEQUENCE: 28

Met Arg Pro Glu Ala Thr Asp Thr Arg Arg His Arg His Gln Arg His
1

```
Leu His Arg Val His Glu Arg Phe Asn Arg His Arg Pro Arg Ala Ser
             20                  25                  30

Lys Pro Val Gly Pro Ile Arg Asp Gly Leu Arg Ala Gly Pro Ala Val
             35                  40                  45

Ala Gly Arg Arg His Arg His His Ala Arg Glu Asp Leu Glu Arg Tyr
 50                  55                  60

Arg His Arg Tyr Pro Ala Arg Glu Gly Ala His Arg Ser Gly Arg Pro
 65                  70                  75                  80

Arg Arg Arg Ala Arg Ala Ala Arg Ala Gly Ala Arg Ala Ile Ala
                 85                  90                  95

Ser Ala Ala Gly Ser Arg Gly Asp Ala Arg Arg Ala Pro Arg Asp Ala
                100                 105                 110

Pro Pro Ala Leu Arg Ala Val Leu Arg Ala Ala Gly Ala Gly Arg Ala
                115                 120                 125

Asp Arg Gly Ala Leu Leu Val Arg Arg Ala Leu Gln Arg Gly Asp
130                 135                 140

Gly Arg Arg Val Arg Gly Arg Gln Arg Gly Ala Asp Arg Arg Ala Asp
145                 150                 155                 160

Pro Gly Asp Gly Asp Arg Arg Ala Gly Gly His Ala Ala Gly Glu
                165                 170                 175

Gly Gly Ala Gly Ala Gly Glu Ala Arg Arg Gly Arg Val Gly Gly
                180                 185                 190

Val Arg Ala Gly Ala Gly Ala Ala Arg Ala Gly Gly Ala Ala Gly Gly
                195                 200                 205

Glu His Ala Ala Leu Asp Gly Asp Val Arg Gly Asp Gly Glu Gly Ala
                210                 215                 220

Arg Gly Gly Pro Glu Ala Cys Ala Ala Gly Val Ser Gly Gly Thr Gly
225                 230                 235                 240

Ala Ala Lys Val Val Ala Gly Glu Arg Ala Gly Gly Ala Gly Gly Gly
                245                 250                 255

Ala Gly Ala Ala Gly Gly Gly Ala Arg Ala Gly Gln Arg Ala Ala Gly
                260                 265                 270

Arg Ala Glu Pro Gly Gly Ala Gly Gly Arg Ala Val Gln Ala Gly
275                 280                 285

Val Pro Glu Pro Glu Ala His Asp Asp Arg Val Ala Gly Gly Arg His
                290                 295                 300

Gly Arg Ser Ala Val Gly Ala Asp Arg Ser Ala Gly Gly Ala Gly Gly
305                 310                 315                 320

Ala Ala Asp Val Gly Gly Ala Val Ala Ala Gly Val Gly Gly Gly Glu
                325                 330                 335

Leu Gln Gly Arg Ala Asp Pro Ala His Ala Gly Gly Pro Ala Gly Ala
                340                 345                 350

Ala Arg Ile Gly Pro Val Arg Arg Ala Gly Asp Val Pro Arg Pro Gly
                355                 360                 365

Gly Gly Gly Leu Gly Gly His Gly Gln Arg Val Leu Asp Ala Ala Val
                370                 375                 380

Ala Glu Arg Gly Gly Glu Leu Asp Gln Gly Ala Ala Pro Ala Gly
385                 390                 395                 400

Gly Asp Leu Ala Gly Ala Val Gly Ala Gly Gly Ala Pro Ala Ala Gly
                405                 410                 415

Gly Ala Val Asp Ala Arg Asp Gly Gly Asp Glu Gly Ala Trp Arg Pro
                420                 425                 430
```

```
Pro Ala Arg Arg Arg Ala Ala Gly Ala Ala His Ala Gly Ala
        435                 440                 445

Arg Ser Ala Gly Gly Arg Gly Arg Gly Phe Gly Ser Asp Ser
450                 455                 460

Gly Glu
465

<210> SEQ ID NO 29
<211> LENGTH: 1680
<212> TYPE: DNA
<213> ORGANISM: Pseudomonas putida
<220> FEATURE:
<221> NAME/KEY: CDS
<222> LOCATION: (1)..(1680)

<400> SEQUENCE: 29 atg agt aac aag aac aac gat gag cta cag cgg cag gcc tcg gaa aac    48
Met Ser Asn Lys Asn Asn Asp Glu Leu Gln Arg Gln Ala Ser Glu Asn
1               5                   10                  15 acc atg ggg ctg aac ccg gtc atc ggc atc cgc cgc aag gac ctg ttg    96
Thr Met Gly Leu Asn Pro Val Ile Gly Ile Arg Arg Lys Asp Leu Leu
            20                  25                  30 agc tcg gca cgc acc gtg ctg cgc cag gcc gtg cgc caa ccg ctg cac   144
Ser Ser Ala Arg Thr Val Leu Arg Gln Ala Val Arg Gln Pro Leu His
        35                  40                  45 agc gcc aag cat gtg gct cac ttt ggc ctg gag ctg aag aac gtg ttg   192
Ser Ala Lys His Val Ala His Phe Gly Leu Glu Leu Lys Asn Val Leu
    50                  55                  60 ctg ggc aaa tcc agc ctg gcc ccg gac agc gac gac cgt cgc ttc aat   240
Leu Gly Lys Ser Ser Leu Ala Pro Asp Ser Asp Asp Arg Arg Phe Asn
65                  70                  75                  80 gac ccg gcc tgg agc aac aac ccg ctg tac cgc cgc tac ctg caa acc   288
Asp Pro Ala Trp Ser Asn Asn Pro Leu Tyr Arg Arg Tyr Leu Gln Thr
                85                  90                  95 tac ctg gcc tgg cgc aag gag ctg cag gac tgg gtg agc agc agc gac   336
Tyr Leu Ala Trp Arg Lys Glu Leu Gln Asp Trp Val Ser Ser Ser Asp
            100                 105                 110 ctg tcc ccc cag gac atc agc cgc ggc cag ttc gtc atc aac ctg atg   384
Leu Ser Pro Gln Asp Ile Ser Arg Gly Gln Phe Val Ile Asn Leu Met
        115                 120                 125 acc gag gcc atg gcg ccg acc aat acc ctg tcc aac ccg gct gcg gtc   432
Thr Glu Ala Met Ala Pro Thr Asn Thr Leu Ser Asn Pro Ala Ala Val
    130                 135                 140 aaa cgc ttc ttc gaa acc ggc ggc aag agc ctg ctc gat ggc ctg tcc   480
Lys Arg Phe Phe Glu Thr Gly Gly Lys Ser Leu Leu Asp Gly Leu Ser
145                 150                 155                 160 aac ctg gcc aag gac atg gtc aac aac ggc ggc atg ccc agc cag gtg   528
Asn Leu Ala Lys Asp Met Val Asn Asn Gly Gly Met Pro Ser Gln Val
                165                 170                 175 aac atg gat gcc ttc gaa gtg ggc aag aac ctg ggc acc agc gaa ggc   576
Asn Met Asp Ala Phe Glu Val Gly Lys Asn Leu Gly Thr Ser Glu Gly
            180                 185                 190 gcg gtg gtg tac cgc aac gat gtg ctg gaa ctg atc cag tac agc ccc   624
Ala Val Val Tyr Arg Asn Asp Val Leu Glu Leu Ile Gln Tyr Ser Pro
        195                 200                 205 atc acc gag cag gtg cat gcc cgt ccg ctg ctg gtg gtg cca ccg cag   672
Ile Thr Glu Gln Val His Ala Arg Pro Leu Leu Val Val Pro Pro Gln
    210                 215                 220 atc aac aag ttc tac gtg ttc gac ctc agc ccg gaa aag agc ctg gcg   720
Ile Asn Lys Phe Tyr Val Phe Asp Leu Ser Pro Glu Lys Ser Leu Ala
225                 230                 235                 240
```

```
cgc ttc tgc ctg cgc tcg cag cag cag acc ttc atc atc agc tgg cgc      768
Arg Phe Cys Leu Arg Ser Gln Gln Gln Thr Phe Ile Ile Ser Trp Arg
            245                 250                 255 aac ccg acc aag gcc cag cgt gaa tgg ggc ctg tcc acc tac atc gat      816
Asn Pro Thr Lys Ala Gln Arg Glu Trp Gly Leu Ser Thr Tyr Ile Asp
            260                 265                 270 gcg ctg aaa gaa gcc gtc gac gcg gtg ctg tcg att acc ggc agc aag      864
Ala Leu Lys Glu Ala Val Asp Ala Val Leu Ser Ile Thr Gly Ser Lys
            275                 280                 285 gac ctg aac atg ctc ggc gcc tgc tcc ggt ggc atc act tgt acc gca      912
Asp Leu Asn Met Leu Gly Ala Cys Ser Gly Gly Ile Thr Cys Thr Ala
            290                 295                 300 ctg gtc ggg cac tat gcc gca ttg ggc gag aac aag gtc aac gcc ctg      960
Leu Val Gly His Tyr Ala Ala Leu Gly Glu Asn Lys Val Asn Ala Leu
305                 310                 315                 320 acc gtg ctg gtc agc gtg ctg gac acc acc atg gac aac cag gtt gct     1008
Thr Val Leu Val Ser Val Leu Asp Thr Thr Met Asp Asn Gln Val Ala
                325                 330                 335 ttg ttt gtc gac gag cag acc ttg gag gcc gcc aag cgc cac tcc tat     1056
Leu Phe Val Asp Glu Gln Thr Leu Glu Ala Ala Lys Arg His Ser Tyr
                340                 345                 350 cag gcg ggc gtg ctg gaa ggc agc gaa atg gcc aag gtg ttc gcc tgg     1104
Gln Ala Gly Val Leu Glu Gly Ser Glu Met Ala Lys Val Phe Ala Trp
            355                 360                 365 atg cgc ccc aac gac ctg atc tgg aac tac tgg gta aac aac tac ctg     1152
Met Arg Pro Asn Asp Leu Ile Trp Asn Tyr Trp Val Asn Asn Tyr Leu
370                 375                 380 ctc ggc aat gag ccc ccc gtg ttc gac atc ctg ttc tgg aac aac gac     1200
Leu Gly Asn Glu Pro Pro Val Phe Asp Ile Leu Phe Trp Asn Asn Asp
385                 390                 395                 400 acc acg cgc ctg ccg gcc gcc ttc cac ggc gac ctg atc gaa atg ttc     1248
Thr Thr Arg Leu Pro Ala Ala Phe His Gly Asp Leu Ile Glu Met Phe
                405                 410                 415 aag agc aac ccg ctg acc cgc ccc gac gcc ctg aaa gtg tgc ggc acc     1296
Lys Ser Asn Pro Leu Thr Arg Pro Asp Ala Leu Lys Val Cys Gly Thr
                420                 425                 430 gcg atc gac ctg aaa cag gtc aaa tgc gac atc tac agc ctc gcc ggc     1344
Ala Ile Asp Leu Lys Gln Val Lys Cys Asp Ile Tyr Ser Leu Ala Gly
            435                 440                 445 acc aac gac cac atc acc ccc tgg ccg tca tgc tac cgc tcg gca cat     1392
Thr Asn Asp His Ile Thr Pro Trp Pro Ser Cys Tyr Arg Ser Ala His
450                 455                 460 ctg ttc ggc ggc aag atc gaa ttc gta ctg tcc aac agc ggg cat atc     1440
Leu Phe Gly Gly Lys Ile Glu Phe Val Leu Ser Asn Ser Gly His Ile
465                 470                 475                 480 cag agc atc ctc aac ccg ccg ggc aac ccg aag gca cgt ttc atg acc     1488
Gln Ser Ile Leu Asn Pro Pro Gly Asn Pro Lys Ala Arg Phe Met Thr
                485                 490                 495 ggt gcc gat cgc ccg ggt gac ccg gtg gcc tgg cag gaa aat gcc atc     1536
Gly Ala Asp Arg Pro Gly Asp Pro Val Ala Trp Gln Glu Asn Ala Ile
                500                 505                 510 aag cat gca gac tcc tgg tgg ctg cac tgg cag agt tgg ctg ggc gag     1584
Lys His Ala Asp Ser Trp Trp Leu His Trp Gln Ser Trp Leu Gly Glu
            515                 520                 525 cgt gcc ggc gcg ctg aaa aag gca ccg acc cgc ctg ggc aac cgt acc     1632
Arg Ala Gly Ala Leu Lys Lys Ala Pro Thr Arg Leu Gly Asn Arg Thr
530                 535                 540 tat gcc gcc ggc gaa gcc tcc cca ggc acc tac gtt cac gag cgt tga    1680
Tyr Ala Ala Gly Glu Ala Ser Pro Gly Thr Tyr Val His Glu Arg
```

<210> SEQ ID NO 30
<211> LENGTH: 559
<212> TYPE: PRT
<213> ORGANISM: Pseudomonas putida

<400> SEQUENCE: 30

```
Met Ser Asn Lys Asn Asp Glu Leu Gln Arg Gln Ala Ser Glu Asn
1               5                   10                  15

Thr Met Gly Leu Asn Pro Val Ile Gly Ile Arg Arg Lys Asp Leu Leu
                20                  25                  30

Ser Ser Ala Arg Thr Val Leu Arg Gln Ala Val Arg Gln Pro Leu His
                35                  40                  45

Ser Ala Lys His Val Ala His Phe Gly Leu Glu Leu Lys Asn Val Leu
            50                  55                  60

Leu Gly Lys Ser Ser Leu Ala Pro Asp Ser Asp Arg Arg Phe Asn
65                  70                  75                  80

Asp Pro Ala Trp Ser Asn Asn Pro Leu Tyr Arg Arg Tyr Leu Gln Thr
                    85                  90                  95

Tyr Leu Ala Trp Arg Lys Glu Leu Gln Asp Trp Val Ser Ser Asp
                100                 105                 110

Leu Ser Pro Gln Asp Ile Ser Arg Gly Gln Phe Val Ile Asn Leu Met
            115                 120                 125

Thr Glu Ala Met Ala Pro Thr Asn Thr Leu Ser Asn Pro Ala Ala Val
130                 135                 140

Lys Arg Phe Phe Glu Thr Gly Gly Lys Ser Leu Leu Asp Gly Leu Ser
145                 150                 155                 160

Asn Leu Ala Lys Asp Met Val Asn Asn Gly Gly Met Pro Ser Gln Val
                165                 170                 175

Asn Met Asp Ala Phe Glu Val Gly Lys Asn Leu Gly Thr Ser Glu Gly
                180                 185                 190

Ala Val Val Tyr Arg Asn Asp Val Leu Glu Leu Ile Gln Tyr Ser Pro
            195                 200                 205

Ile Thr Glu Gln Val His Ala Arg Pro Leu Leu Val Val Pro Pro Gln
210                 215                 220

Ile Asn Lys Phe Tyr Val Phe Asp Leu Ser Pro Glu Lys Ser Leu Ala
225                 230                 235                 240

Arg Phe Cys Leu Arg Ser Gln Gln Thr Phe Ile Ile Ser Trp Arg
                245                 250                 255

Asn Pro Thr Lys Ala Gln Arg Glu Trp Gly Leu Ser Thr Tyr Ile Asp
                260                 265                 270

Ala Leu Lys Glu Ala Val Asp Ala Val Leu Ser Ile Thr Gly Ser Lys
            275                 280                 285

Asp Leu Asn Met Leu Gly Ala Cys Ser Gly Gly Ile Thr Cys Thr Ala
290                 295                 300

Leu Val Gly His Tyr Ala Ala Leu Gly Glu Asn Lys Val Asn Ala Leu
305                 310                 315                 320

Thr Val Leu Val Ser Val Leu Asp Thr Thr Met Asp Asn Gln Val Ala
                325                 330                 335

Leu Phe Val Asp Glu Gln Thr Leu Glu Ala Ala Lys Arg His Ser Tyr
                340                 345                 350

Gln Ala Gly Val Leu Glu Gly Ser Glu Met Ala Lys Val Phe Ala Trp
            355                 360                 365
```

```
Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Ser Asn Pro Leu Thr Arg Pro Asp Ala Leu Lys Val Cys Gly Thr
                420                 425                 430

Ala Ile Asp Leu Lys Gln Val Lys Cys Asp Ile Tyr Ser Leu Ala Gly
            435                 440                 445

Thr Asn Asp His Ile Thr Pro Trp Pro Ser Cys Tyr Arg Ser Ala His
    450                 455                 460

Leu Phe Gly Gly Lys Ile Glu Phe Val Leu Ser Asn Ser Gly His Ile
465                 470                 475                 480

Gln Ser Ile Leu Asn Pro Pro Gly Asn Pro Lys Ala Arg Phe Met Thr
                485                 490                 495

Gly Ala Asp Arg Pro Gly Asp Pro Val Ala Trp Gln Glu Asn Ala Ile
                500                 505                 510

Lys His Ala Asp Ser Trp Trp Leu His Trp Gln Ser Trp Leu Gly Glu
            515                 520                 525

Arg Ala Gly Ala Leu Lys Lys Ala Pro Thr Arg Leu Gly Asn Arg Thr
    530                 535                 540

Tyr Ala Ala Gly Glu Ala Ser Pro Gly Thr Tyr Val His Glu Arg
545                 550                 555
```

```
<210> SEQ ID NO 31
<211> LENGTH: 1683
<212> TYPE: DNA
<213> ORGANISM: Pseudomonas putida
<220> FEATURE:
<221> NAME/KEY: CDS
<222> LOCATION: (1)..(1683)

<400> SEQUENCE: 31
```

```
atg aca gac aaa ccg gcc aaa gga tcg aca acg ctc ccc gcc acc cgc        48
Met Thr Asp Lys Pro Ala Lys Gly Ser Thr Thr Leu Pro Ala Thr Arg
1               5                   10                  15 atg aac gtg cag aac gcc atc ctc ggc ctg cgc ggc cgc gac ctg ctt        96
Met Asn Val Gln Asn Ala Ile Leu Gly Leu Arg Gly Arg Asp Leu Leu
            20                  25                  30 tcc acg ctg cgc aac gtc ggc cgc cac ggc ctg cgc cac ccg ctg cat       144
Ser Thr Leu Arg Asn Val Gly Arg His Gly Leu Arg His Pro Leu His
        35                  40                  45 acc gcg cat cat ctg ctg gcg ctt ggc ggg cag ttg ggc cgg gtg atg       192
Thr Ala His His Leu Leu Ala Leu Gly Gly Gln Leu Gly Arg Val Met
    50                  55                  60 ctg ggg gac acg ccc tac cag ccg aac ccg cgt gac gca cgc ttc agt       240
Leu Gly Asp Thr Pro Tyr Gln Pro Asn Pro Arg Asp Ala Arg Phe Ser
65                  70                  75                  80 gac ccg acc tgg agc cag aac ccg ttc tac cgc cgc ggc ctg caa gcc       288
Asp Pro Thr Trp Ser Gln Asn Pro Phe Tyr Arg Arg Gly Leu Gln Ala
                85                  90                  95 tat ctg gcc tgg cag aag cag aca cgc cag tgg atc gat gaa agc cat       336
Tyr Leu Ala Trp Gln Lys Gln Thr Arg Gln Trp Ile Asp Glu Ser His
            100                 105                 110 ttg aac gac gat gat cga gcc cgc gcc cac ttc ctg ttc aac ctg atc       384
Leu Asn Asp Asp Asp Arg Ala Arg Ala His Phe Leu Phe Asn Leu Ile
        115                 120                 125
```

```
aac gat gcg ctg gcg ccc agc aac tca ctg ctc aat ccg cag gcg gtc     432
Asn Asp Ala Leu Ala Pro Ser Asn Ser Leu Leu Asn Pro Gln Ala Val
    130                 135                 140 aag ggg ctg ttc aac acc ggc ggc cag agc ctg gtg cgc ggc gtg gct     480
Lys Gly Leu Phe Asn Thr Gly Gly Gln Ser Leu Val Arg Gly Val Ala
145                 150                 155                 160 cac ctg ctc gac gac ctg cgt cac aac gat ggg ctg cct cgt cag gtg     528
His Leu Leu Asp Asp Leu Arg His Asn Asp Gly Leu Pro Arg Gln Val
                165                 170                 175 gac gag cgc gcc ttc gaa gtg ggc gtt aac ctg gcc gca acc cct ggc     576
Asp Glu Arg Ala Phe Glu Val Gly Val Asn Leu Ala Ala Thr Pro Gly
            180                 185                 190 gca gtg gta ttt cgc aac gag ctg ctg gag ctg atc cag tac tcg ccg     624
Ala Val Val Phe Arg Asn Glu Leu Leu Glu Leu Ile Gln Tyr Ser Pro
        195                 200                 205 atg agc gaa aag cag cac gca cgc cca ctg ctg gtc gtg ccg cct cag     672
Met Ser Glu Lys Gln His Ala Arg Pro Leu Leu Val Val Pro Pro Gln
    210                 215                 220 atc aac agg ttc tac atc ttc gac ctc agc gcg acc aac agc ttc gtc     720
Ile Asn Arg Phe Tyr Ile Phe Asp Leu Ser Ala Thr Asn Ser Phe Val
225                 230                 235                 240 cag tac atg ctc aaa agc ggc ttg cag gtg ttc atg gtc agc tgg agc     768
Gln Tyr Met Leu Lys Ser Gly Leu Gln Val Phe Met Val Ser Trp Ser
                245                 250                 255 aac ccc gac cca cgc cac cgt gaa tgg ggc ctt tcc agc tat gtg caa     816
Asn Pro Asp Pro Arg His Arg Glu Trp Gly Leu Ser Ser Tyr Val Gln
                260                 265                 270 gcc ctg gag gaa gcg ctc aat gcc tgc cgc agt atc agc ggc aac cgc     864
Ala Leu Glu Glu Ala Leu Asn Ala Cys Arg Ser Ile Ser Gly Asn Arg
            275                 280                 285 gac ccc aac ctg atg ggt gcc tgt gcc ggc ggc ctg acc atg gcc gca     912
Asp Pro Asn Leu Met Gly Ala Cys Ala Gly Gly Leu Thr Met Ala Ala
        290                 295                 300 ctg caa ggc cat ctg caa gcc aag aag caa ttg cgc cgg gtg cgc agt     960
Leu Gln Gly His Leu Gln Ala Lys Lys Gln Leu Arg Arg Val Arg Ser
305                 310                 315                 320 gcc acg tat ctg gtc agc ttg ctg gac agc aag ttc gaa agc ccg gcc    1008
Ala Thr Tyr Leu Val Ser Leu Leu Asp Ser Lys Phe Glu Ser Pro Ala
                325                 330                 335 agc ctg ttc gcc gat gag cag acc atc gaa gcg gcc aag cga cgc tcc    1056
Ser Leu Phe Ala Asp Glu Gln Thr Ile Glu Ala Ala Lys Arg Arg Ser
                340                 345                 350 tat cag cgt ggc gtg ctg gac ggt ggt gaa gtg gcg cgg atc ttc gcc    1104
Tyr Gln Arg Gly Val Leu Asp Gly Gly Glu Val Ala Arg Ile Phe Ala
            355                 360                 365 tgg atg cgg ccc aac gac ctg atc tgg aac tac tgg gta aac aac tac    1152
Trp Met Arg Pro Asn Asp Leu Ile Trp Asn Tyr Trp Val Asn Asn Tyr
        370                 375                 380 ctg ctc ggc aag aca ccg cct gcg ttc gac atc ctg tac tgg aat gcc    1200
Leu Leu Gly Lys Thr Pro Pro Ala Phe Asp Ile Leu Tyr Trp Asn Ala
385                 390                 395                 400 gac agc acg cgc ctg ccc gcc gcg ctg cat ggc gac ctg ctg gag ttt    1248
Asp Ser Thr Arg Leu Pro Ala Ala Leu His Gly Asp Leu Leu Glu Phe
                405                 410                 415 ttc aag ctc aac ccc ttg acc tac gcg tcc ggg ctg gag gtg tgc ggt    1296
Phe Lys Leu Asn Pro Leu Thr Tyr Ala Ser Gly Leu Glu Val Cys Gly
                420                 425                 430 acg ccg atc gac ctg cag cag gtc aat atc gac agc ttt acc gtg gcc    1344
Thr Pro Ile Asp Leu Gln Gln Val Asn Ile Asp Ser Phe Thr Val Ala
            435                 440                 445
```

```
ggc agc aac gac cac atc aca cca tgg gat gcg gtg tac cgc tcg gcc    1392
Gly Ser Asn Asp His Ile Thr Pro Trp Asp Ala Val Tyr Arg Ser Ala
    450                 455                 460 ttg ctg ctg ggt ggc gag cgg cgc ttc gtg ctg gcc aac agc ggg cat    1440
Leu Leu Leu Gly Gly Glu Arg Arg Phe Val Leu Ala Asn Ser Gly His
465                 470                 475                 480 atc cag agc atc atc aac ccg cca ggc aac ccc aag gcc tac tac ctg    1488
Ile Gln Ser Ile Ile Asn Pro Pro Gly Asn Pro Lys Ala Tyr Tyr Leu
                485                 490                 495 gcc aac ccc aag ctg agc agc gac cca cgc gcc tgg ttc cac gac gcc    1536
Ala Asn Pro Lys Leu Ser Ser Asp Pro Arg Ala Trp Phe His Asp Ala
            500                 505                 510 aag cgc agt gaa ggc agc tgg tgg ccg ttg tgg ctg gag tgg atc acc    1584
Lys Arg Ser Glu Gly Ser Trp Trp Pro Leu Trp Leu Glu Trp Ile Thr
        515                 520                 525 gca cgc tcc ggc ctg ctc aag gca ccg cgt act gaa ctg ggc aac gcc    1632
Ala Arg Ser Gly Leu Leu Lys Ala Pro Arg Thr Glu Leu Gly Asn Ala
    530                 535                 540 act tac cca ctg cta ggc ccc gcg cca ggc acc tac gtg ctg acc cga    1680
Thr Tyr Pro Leu Leu Gly Pro Ala Pro Gly Thr Tyr Val Leu Thr Arg
545                 550                 555                 560 tga                                                                1683
```

```
<210> SEQ ID NO 32
<211> LENGTH: 560
<212> TYPE: PRT
<213> ORGANISM: Pseudomonas putida

<400> SEQUENCE: 32

Met Thr Asp Lys Pro Ala Lys Gly Ser Thr Thr Leu Pro Ala Thr Arg
1               5                   10                  15

Met Asn Val Gln Asn Ala Ile Leu Gly Leu Arg Gly Arg Asp Leu Leu
            20                  25                  30

Ser Thr Leu Arg Asn Val Gly Arg His Gly Leu Arg His Pro Leu His
        35                  40                  45

Thr Ala His His Leu Leu Ala Leu Gly Gly Gln Leu Gly Arg Val Met
    50                  55                  60

Leu Gly Asp Thr Pro Tyr Gln Pro Asn Pro Arg Asp Ala Arg Phe Ser
65                  70                  75                  80

Asp Pro Thr Trp Ser Gln Asn Pro Phe Tyr Arg Arg Gly Leu Gln Ala
                85                  90                  95

Tyr Leu Ala Trp Gln Lys Gln Thr Arg Gln Trp Ile Asp Glu Ser His
            100                 105                 110

Leu Asn Asp Asp Arg Ala Arg Ala His Phe Leu Phe Asn Leu Ile
        115                 120                 125

Asn Asp Ala Leu Ala Pro Ser Asn Ser Leu Leu Asn Pro Gln Ala Val
    130                 135                 140

Lys Gly Leu Phe Asn Thr Gly Gly Gln Ser Leu Val Arg Gly Val Ala
145                 150                 155                 160

His Leu Leu Asp Asp Leu Arg His Asn Asp Gly Leu Pro Arg Gln Val
                165                 170                 175

Asp Glu Arg Ala Phe Glu Val Gly Val Asn Leu Ala Ala Thr Pro Gly
            180                 185                 190

Ala Val Val Phe Arg Asn Glu Leu Leu Glu Leu Ile Gln Tyr Ser Pro
        195                 200                 205

Met Ser Glu Lys Gln His Ala Arg Pro Leu Leu Val Val Pro Pro Gln
```

```
                210             215             220
Ile Asn Arg Phe Tyr Ile Phe Asp Leu Ser Ala Thr Asn Ser Phe Val
225                 230                 235                 240

Gln Tyr Met Leu Lys Ser Gly Leu Gln Val Phe Met Val Ser Trp Ser
                245                 250                 255

Asn Pro Asp Pro Arg His Arg Glu Trp Gly Leu Ser Ser Tyr Val Gln
                260                 265                 270

Ala Leu Glu Glu Ala Leu Asn Ala Cys Arg Ser Ile Ser Gly Asn Arg
            275                 280                 285

Asp Pro Asn Leu Met Gly Ala Cys Ala Gly Gly Leu Thr Met Ala Ala
        290                 295                 300

Leu Gly His Leu Gln Ala Lys Lys Gln Leu Arg Arg Val Arg Ser
305                 310                 315                 320

Ala Thr Tyr Leu Val Ser Leu Leu Asp Ser Lys Phe Glu Ser Pro Ala
                325                 330                 335

Ser Leu Phe Ala Asp Glu Gln Thr Ile Glu Ala Ala Lys Arg Arg Ser
                340                 345                 350

Tyr Gln Arg Gly Val Leu Asp Gly Gly Glu Val Ala Arg Ile Phe Ala
            355                 360                 365

Trp Met Arg Pro Asn Asp Leu Ile Trp Asn Tyr Trp Val Asn Asn Tyr
370                 375                 380

Leu Leu Gly Lys Thr Pro Pro Ala Phe Asp Ile Leu Tyr Trp Asn Ala
385                 390                 395                 400

Asp Ser Thr Arg Leu Pro Ala Ala Leu His Gly Asp Leu Leu Glu Phe
                405                 410                 415

Phe Lys Leu Asn Pro Leu Thr Tyr Ala Ser Gly Leu Glu Val Cys Gly
                420                 425                 430

Thr Pro Ile Asp Leu Gln Gln Val Asn Ile Asp Ser Phe Thr Val Ala
                435                 440                 445

Gly Ser Asn Asp His Ile Thr Pro Trp Asp Ala Val Tyr Arg Ser Ala
            450                 455                 460

Leu Leu Leu Gly Gly Glu Arg Arg Phe Val Leu Ala Asn Ser Gly His
465                 470                 475                 480

Ile Gln Ser Ile Ile Asn Pro Pro Gly Asn Pro Lys Ala Tyr Tyr Leu
                485                 490                 495

Ala Asn Pro Lys Leu Ser Ser Asp Pro Arg Ala Trp Phe His Asp Ala
            500                 505                 510

Lys Arg Ser Glu Gly Ser Trp Trp Pro Leu Trp Leu Glu Trp Ile Thr
        515                 520                 525

Ala Arg Ser Gly Leu Leu Lys Ala Pro Arg Thr Glu Leu Gly Asn Ala
        530                 535                 540

Thr Tyr Pro Leu Leu Gly Pro Ala Pro Gly Thr Tyr Val Leu Thr Arg
545                 550                 555                 560
```

<210> SEQ ID NO 33
<211> LENGTH: 888
<212> TYPE: DNA
<213> ORGANISM: Pseudomonas putida
<220> FEATURE:
<221> NAME/KEY: CDS
<222> LOCATION: (1)..(888)

<400> SEQUENCE: 33

```
atg agg cca gaa atc gct gta ctt gat atc caa ggt cag tat cgg gtt    48
Met Arg Pro Glu Ile Ala Val Leu Asp Ile Gln Gly Gln Tyr Arg Val
1               5                   10                  15
```

| | | | | | | | | | | | | | | | |
|---|---|---|---|---|---|---|---|---|---|---|---|---|---|---|---|
| tac | acg | gag | ttc | tat | cgc | gcg | gat | gcg | gcc | gaa | aac | acg | atc | atc | ctg | 96 |
| Tyr | Thr | Glu | Phe | Tyr | Arg | Ala | Asp | Ala | Ala | Glu | Asn | Thr | Ile | Ile | Leu | |
| | | | 20 | | | | | 25 | | | | | 30 | | | |

```
tac acg gag ttc tat cgc gcg gat gcg gcc gaa aac acg atc atc ctg      96
Tyr Thr Glu Phe Tyr Arg Ala Asp Ala Ala Glu Asn Thr Ile Ile Leu
             20                  25                  30 atc aac ggc tcg ctg gcc acc acg gcc tcg ttc gcc cag acg gta cgt     144
Ile Asn Gly Ser Leu Ala Thr Thr Ala Ser Phe Ala Gln Thr Val Arg
 35                  40                  45 aac ctg cac cca cag ttc aac gtg gtt ctg ttc gac cag ccg tat tca     192
Asn Leu His Pro Gln Phe Asn Val Val Leu Phe Asp Gln Pro Tyr Ser
 50                  55                  60 ggc aag tcc aag ccg cac aac cgt cag gaa cgg ctg atc agc aag gag     240
Gly Lys Ser Lys Pro His Asn Arg Gln Glu Arg Leu Ile Ser Lys Glu
 65                  70                  75                  80 acc gag gcg cat atc ctc ctt gag ctg atc gag cac ttc cag gca gac     288
Thr Glu Ala His Ile Leu Leu Glu Leu Ile Glu His Phe Gln Ala Asp
                     85                  90                  95 cac gtg atg tct ttt tcg tgg ggt ggc gca agc acg ctg ctg gcg ctg     336
His Val Met Ser Phe Ser Trp Gly Gly Ala Ser Thr Leu Leu Ala Leu
                    100                 105                 110 gcg cac cag ccg cgg tac gtg aag aag gca gtg gtg agt tcg ttc tcg     384
Ala His Gln Pro Arg Tyr Val Lys Lys Ala Val Val Ser Ser Phe Ser
                115                 120                 125 cca gtg atc aac gag cca atg cgc gac tat ctg gac cgt ggc tgc cag     432
Pro Val Ile Asn Glu Pro Met Arg Asp Tyr Leu Asp Arg Gly Cys Gln
130                 135                 140 tac ctg gcc gcc tgc gac cgt tat cag gtc ggc aac ctg gtc aat gac     480
Tyr Leu Ala Ala Cys Asp Arg Tyr Gln Val Gly Asn Leu Val Asn Asp
145                 150                 155                 160 acc atc ggc aag cac ttg ccg tcg ctg ctc aaa cgc ttc aac tac cgc     528
Thr Ile Gly Lys His Leu Pro Ser Leu Leu Lys Arg Phe Asn Tyr Arg
                    165                 170                 175 cat gtg agc agc ctg gac agc cac gag tac gca cag atg cac ttc cac     576
His Val Ser Ser Leu Asp Ser His Glu Tyr Ala Gln Met His Phe His
                    180                 185                 190 atc aac caa gtg ctg gag cac gac ctg gaa cgt gcg ctg caa ggc gcg     624
Ile Asn Gln Val Leu Glu His Asp Leu Glu Arg Ala Leu Gln Gly Ala
                195                 200                 205 cgc aat atc aac atc ccg gtg ttg ttc atc aac ggc gaa cgc gac gag     672
Arg Asn Ile Asn Ile Pro Val Leu Phe Ile Asn Gly Glu Arg Asp Glu
210                 215                 220 tac acc acg gtc gaa gat gcg cgg cag ttc agc aag cat gtg ggc aga     720
Tyr Thr Thr Val Glu Asp Ala Arg Gln Phe Ser Lys His Val Gly Arg
225                 230                 235                 240 agc cag ttc agc gtg atc cgc gat gcg ggc cac ttc ctg gac atg gag     768
Ser Gln Phe Ser Val Ile Arg Asp Ala Gly His Phe Leu Asp Met Glu
                    245                 250                 255 aac aag acc gcc tgc gag aac acc cgc agt gtc atg ctg ggg ttc ctc     816
Asn Lys Thr Ala Cys Glu Asn Thr Arg Ser Val Met Leu Gly Phe Leu
                260                 265                 270 aag cca acc gtg cgt gaa ccc cgc caa cgt tac caa ccc gtg caa cag     864
Lys Pro Thr Val Arg Glu Pro Arg Gln Arg Tyr Gln Pro Val Gln Gln
                275                 280                 285 ggg cag cat gca ttg gcc atc tga                                     888
Gly Gln His Ala Leu Ala Ile
            290                 295

<210> SEQ ID NO 34
<211> LENGTH: 295
<212> TYPE: PRT
<213> ORGANISM: Pseudomonas putida
```

<400> SEQUENCE: 34

```
Met Arg Pro Glu Ile Ala Val Leu Asp Ile Gln Gly Gln Tyr Arg Val
1               5                   10                  15

Tyr Thr Glu Phe Tyr Arg Ala Asp Ala Ala Glu Asn Thr Ile Ile Leu
            20                  25                  30

Ile Asn Gly Ser Leu Ala Thr Thr Ala Ser Phe Ala Gln Thr Val Arg
        35                  40                  45

Asn Leu His Pro Gln Phe Asn Val Val Leu Phe Asp Gln Pro Tyr Ser
    50                  55                  60

Gly Lys Ser Lys Pro His Asn Arg Gln Glu Arg Leu Ile Ser Lys Glu
65                  70                  75                  80

Thr Glu Ala His Ile Leu Leu Glu Leu Ile Glu His Phe Gln Ala Asp
                85                  90                  95

His Val Met Ser Phe Ser Trp Gly Gly Ala Ser Thr Leu Leu Ala Leu
            100                 105                 110

Ala His Gln Pro Arg Tyr Val Lys Lys Ala Val Val Ser Ser Phe Ser
        115                 120                 125

Pro Val Ile Asn Glu Pro Met Arg Asp Tyr Leu Asp Arg Gly Cys Gln
    130                 135                 140

Tyr Leu Ala Ala Cys Asp Arg Tyr Gln Val Gly Asn Leu Val Asn Asp
145                 150                 155                 160

Thr Ile Gly Lys His Leu Pro Ser Leu Leu Lys Arg Phe Asn Tyr Arg
                165                 170                 175

His Val Ser Ser Leu Asp Ser His Glu Tyr Ala Gln Met His Phe His
            180                 185                 190

Ile Asn Gln Val Leu Glu His Asp Leu Glu Arg Ala Leu Gln Gly Ala
        195                 200                 205

Arg Asn Ile Asn Ile Pro Val Leu Phe Ile Asn Gly Glu Arg Asp Glu
    210                 215                 220

Tyr Thr Thr Val Glu Asp Ala Arg Gln Phe Ser Lys His Val Gly Arg
225                 230                 235                 240

Ser Gln Phe Ser Val Ile Arg Asp Ala Gly His Phe Leu Asp Met Glu
                245                 250                 255

Asn Lys Thr Ala Cys Glu Asn Thr Arg Ser Val Met Leu Gly Phe Leu
            260                 265                 270

Lys Pro Thr Val Arg Glu Pro Arg Gln Arg Tyr Gln Pro Val Gln Gln
        275                 280                 285

Gly Gln His Ala Leu Ala Ile
    290                 295
```

<210> SEQ ID NO 35
<211> LENGTH: 903
<212> TYPE: DNA
<213> ORGANISM: Pseudomonas aeruginosa
<220> FEATURE:
<221> NAME/KEY: CDS
<222> LOCATION: (1)..(903)

<400> SEQUENCE: 35

```
atg agg ccg gaa aca gcc atc atc gag atc cac ggg caa tac agg att      48
Met Arg Pro Glu Thr Ala Ile Ile Glu Ile His Gly Gln Tyr Arg Ile
1               5                   10                  15 cac acc gag ttc tac ggc aac ccc gcg gcg cag caa acc atc atc ctg      96
His Thr Glu Phe Tyr Gly Asn Pro Ala Ala Gln Gln Thr Ile Ile Leu
            20                  25                  30 gtc aac ggc tcg ctg tcg acc aca gcg tcc ttc gcc cag acc gtg aag     144
Val Asn Gly Ser Leu Ser Thr Thr Ala Ser Phe Ala Gln Thr Val Lys
```

| | | | | | | | | | | | | | | |
|---|---|---|---|---|---|---|---|---|---|---|---|---|---|---|
|Val|Asn|Gly|Ser|Leu|Ser|Thr|Thr|Ala|Ser|Phe|Ala|Gln|Thr|Val|Lys|
| | |35| | | |40| | | |45| | | | |

```
tac ctg cag ccg cat tac aac gtg gtc ctc tac gac cag ccg tat gcc        192
Tyr Leu Gln Pro His Tyr Asn Val Val Leu Tyr Asp Gln Pro Tyr Ala
 50                  55                  60 ggc cag tcc aaa ccc cat aac gaa aac cac acg ccg atc agc aag gaa        240
Gly Gln Ser Lys Pro His Asn Glu Asn His Thr Pro Ile Ser Lys Glu
 65                  70                  75                  80 tgc gag gcc agg atc ctg ctg gaa ctg atc gaa cgc ttc cgt gcc gag        288
Cys Glu Ala Arg Ile Leu Leu Glu Leu Ile Glu Arg Phe Arg Ala Glu
                 85                  90                  95 gta gtg atg tcg ttc tcg tgg ggc ggc gtc gcc acc ctg ctg gcc ctg        336
Val Val Met Ser Phe Ser Trp Gly Gly Val Ala Thr Leu Leu Ala Leu
            100                 105                 110 gcg caa cgt ccc gga cgg atc cgc agg gcg gtg gtc aac tca ttc tcg        384
Ala Gln Arg Pro Gly Arg Ile Arg Arg Ala Val Val Asn Ser Phe Ser
        115                 120                 125 cct cag ctc aac ccg gcc atg ctc gac tac ctg cat cgc ggc ctc gac        432
Pro Gln Leu Asn Pro Ala Met Leu Asp Tyr Leu His Arg Gly Leu Asp
    130                 135                 140 tac ctc gcc gcc tgc gat cgc acc cag atc ggc aac ctg gtc aac gaa        480
Tyr Leu Ala Ala Cys Asp Arg Thr Gln Ile Gly Asn Leu Val Asn Glu
145                 150                 155                 160 acc atc ggc cgc tac ctg cca cag ttg ttc aag cgc tac aac ttc cgc        528
Thr Ile Gly Arg Tyr Leu Pro Gln Leu Phe Lys Arg Tyr Asn Phe Arg
                165                 170                 175 cac gtc agc agc ctg gac gag cac gaa tac cac cag atg cac ttc cat        576
His Val Ser Ser Leu Asp Glu His Glu Tyr His Gln Met His Phe His
            180                 185                 190 atc cgc gaa gtg ctg cgc ctg aac gcc gat agc tat acc gag agc ttc        624
Ile Arg Glu Val Leu Arg Leu Asn Ala Asp Ser Tyr Thr Glu Ser Phe
        195                 200                 205 gcc ggc atc gag atc ccg atg ctg ttc atg aac ggc gag ctg gac atc        672
Ala Gly Ile Glu Ile Pro Met Leu Phe Met Asn Gly Glu Leu Asp Ile
    210                 215                 220 tac acc acg ccc cac gaa gcc cgc cag ttc ggc caa ctg atc cgc ggc        720
Tyr Thr Thr Pro His Glu Ala Arg Gln Phe Gly Gln Leu Ile Arg Gly
225                 230                 235                 240 gcg gaa ttc cac acc atc cgc aat gcc ggc cac ttc atc gac gtc gag        768
Ala Glu Phe His Thr Ile Arg Asn Ala Gly His Phe Ile Asp Val Glu
                245                 250                 255 cac aag gcc gcc tgg cag cag acc cag gac gcc ctg ctg gcc ttc ctc        816
His Lys Ala Ala Trp Gln Gln Thr Gln Asp Ala Leu Leu Ala Phe Leu
            260                 265                 270 cgc ccg cag cgc acg cag ccg ctc aac ccg atc tac cgc ccc cag ccc        864
Arg Pro Gln Arg Thr Gln Pro Leu Asn Pro Ile Tyr Arg Pro Gln Pro
        275                 280                 285 aac ggc gcc agc gtc ccc ctc gcc gcc ctc gcc agc taa                    903
Asn Gly Ala Ser Val Pro Leu Ala Ala Leu Ala Ser
    290                 295                 300

<210> SEQ ID NO 36
<211> LENGTH: 300
<212> TYPE: PRT
<213> ORGANISM: Pseudomonas aeruginosa

<400> SEQUENCE: 36

Met Arg Pro Glu Thr Ala Ile Ile Glu Ile His Gly Gln Tyr Arg Ile
 1               5                  10                  15

His Thr Glu Phe Tyr Gly Asn Pro Ala Ala Gln Gln Thr Ile Ile Leu
```

```
            20                  25                  30
Val Asn Gly Ser Leu Ser Thr Thr Ala Ser Phe Ala Gln Thr Val Lys
            35                  40                  45

Tyr Leu Gln Pro His Tyr Asn Val Val Leu Tyr Asp Gln Pro Tyr Ala
    50                  55                  60

Gly Gln Ser Lys Pro His Asn Glu Asn His Thr Pro Ile Ser Lys Glu
65                  70                  75                  80

Cys Glu Ala Arg Ile Leu Leu Glu Leu Ile Glu Arg Phe Arg Ala Glu
                85                  90                  95

Val Val Met Ser Phe Ser Trp Gly Gly Val Ala Thr Leu Leu Ala Leu
            100                 105                 110

Ala Gln Arg Pro Gly Arg Ile Arg Arg Ala Val Val Asn Ser Phe Ser
        115                 120                 125

Pro Gln Leu Asn Pro Ala Met Leu Asp Tyr Leu His Arg Gly Leu Asp
130                 135                 140

Tyr Leu Ala Ala Cys Asp Arg Thr Gln Ile Gly Asn Leu Val Asn Glu
145                 150                 155                 160

Thr Ile Gly Arg Tyr Leu Pro Gln Leu Phe Lys Arg Tyr Asn Phe Arg
                165                 170                 175

His Val Ser Ser Leu Asp Glu His Glu Tyr His Gln Met His Phe His
            180                 185                 190

Ile Arg Glu Val Leu Arg Leu Asn Ala Asp Ser Tyr Thr Glu Ser Phe
        195                 200                 205

Ala Gly Ile Glu Ile Pro Met Leu Phe Met Asn Gly Glu Leu Asp Ile
210                 215                 220

Tyr Thr Thr Pro His Glu Ala Arg Gln Phe Gly Gln Leu Ile Arg Gly
225                 230                 235                 240

Ala Glu Phe His Thr Ile Arg Asn Ala Gly His Phe Ile Asp Val Glu
                245                 250                 255

His Lys Ala Ala Trp Gln Gln Thr Gln Asp Ala Leu Leu Ala Phe Leu
            260                 265                 270

Arg Pro Gln Arg Thr Gln Pro Leu Asn Pro Ile Tyr Arg Pro Gln Pro
        275                 280                 285

Asn Gly Ala Ser Val Pro Leu Ala Ala Leu Ala Ser
            290                 295                 300

<210> SEQ ID NO 37
<211> LENGTH: 2310
<212> TYPE: DNA
<213> ORGANISM: Pseudomonas aeruginosa

<400> SEQUENCE: 37
aggtaccaga tctggcattt ttgggaggtg tgaaatgcgg cgcgaaagtc tgttggtatc      60
ggtttgcaag ggcctgcggg tacatgtcga gcgcgttggg caggatcccg ggcgcagcac     120
ggtgatgctg gtcaacggcg cgatggcgac caccgcctcg ttcgcccgga cctgcaagtg     180
cctggccgaa catttcaacg tggtgctgtt cgacctgccc ttcgccgggc agtcgcgtca     240
gcacaacccg cagcggggt tgatcaccaa ggacgacgag gtggaaatcc tcctggcgct     300
gatcgagcgc ttcgaggtca atcacctggt ctccgcgtcc tggggcggta tctccacgct     360
gctggcgctg tcgcgcaatc cgcgcggcat ccgcagctcg gtggtgatgg cattcgcccc     420
tggactgaac caggcgatgc tcgactacgt cgggcgggcg caggcgctga tcgagctgga     480
cgacaagtcg gcgatcggcc atctgctcaa cgagaccgtc ggcaaatacc tgccgccgcg     540
```

```
cctgaaagcc agcaaccatc agcacatggc ttcgctggcc accggcgaat acgagcaggc    600
gcgcttccac atcgaccagg tgctggcgct caacgatcgg ggctacctgg cttgcctgga    660
gcggatccag agccacgtgc atttcatcaa cggcagctgg gacgaataca ccaccgccga    720
ggacgcccgc cagttccgcg actacctgcc gcactgcagt ttctcgcggg tggagggcac    780
cgggcatttc ctcgacctgg agtccaagct ggccgcggta cgcgtgcacc gcgccctgct    840
cgagcacctg ctgaagcaac cggagccgca gcggcggaa cgcgcggcgg gattccacga    900
gatggccatc ggctacgcct gaacccttga cctgcgaaga cccggcctgg ccgggctttg    960
cggttgcata acgcacggag tagcaccatg cacgccatcc tcatcgccat cggctcggcc   1020
ggcgacgtat ttcccttcat cggcctggcc cggaccctga aattgcgcgg gcaccgcgtg   1080
agcctctgca ccatcccggt gtttcgcgac gcggtggagc agcacggcat cgcgttcgtc   1140
ccgctgagcg acgaactgac ctaccgccgg accatgggcg atccgcgcct gtgggacccc   1200
aagacgtcct tcggcgtgct ctggcaaaac atcgccggga tgatcgagcc ggtctacgag   1260
tacgtctcgg cgcagcgcca tgacgacatc gtggtggtcg gctcgctctg ggcgctgggc   1320
gcacgcatcg ctcacgagaa gtacgggatt ccctacctgt ccgcgcaggt ctcgccatcg   1380
accttgttgt cggcgcacct gccgccggta cacccccaagt caacgtgcc cgagcagatg   1440 ccgctggcga tgcgcaagct gctctggcgc tgcatcgagc gcttcaagct ggatcgcacc   1500
tgcgcgccgg atatcaacgc ggtgcggcgc aaggtcggcc tggagacgcc ggtgaagcgc   1560
atcttcaccc aatggatgca ttcgccgcag ggcgtggtct gcctgttccc ggcctggttc   1620
gcgccgcccc agcaggattg gccgcaaccc ctgcacatga ccggcttccc gctgttcgac   1680
ggcagtatcc cggggacccc gctcgacgac gaactgcaac gctttctcga tcagggcagc   1740
cggccgctgt tgttcaccca gggctcgacc gaacacctgc agggcgactt ctacgccatg   1800
gccctgcgcg cgctggaacg cctcggcgcg cgtgggatct tcctcaccgg cgccggccag   1860
gaaccgctgc gcggcttgcc gaaccacgtg ctgcagcgcg cctacgcgcc actgggagcc   1920
ttgctgccat cgtgcgccgg gctggtccat ccggcggta tcggcgccat gagcctggcc   1980
ttggcggcgg gggtgccgca ggtgctgctg ccctgcgccc acgaccagtt cgacaatgcc   2040
gaacggctgg tccggctcgg ctgcgggatg cgcctgggcg tgccattgcg cgagcaggag   2100
ttgcgcgggg cgctgtggcg cttgctcgag gacccggcca tggcggcggc ctgtcggcgt   2160
ttcatggaat tgtcacaacc gcacagtatc gcttgcggta aagcggccca ggtggtcgaa   2220
cgttgtcata gggagggga tgcgcgatgg ctgaaggctg cgtcctgaac ggtgctggca   2280
taacagatag ggttgcctct agagagctca                                    2310
```

<210> SEQ ID NO 38
<211> LENGTH: 7422
<212> TYPE: DNA
<213> ORGANISM: Artificial
<220> FEATURE:
<223> OTHER INFORMATION: Vector

<400> SEQUENCE: 38

```
ctcgggccgt ctcttgggct tgatcggcct tcttgcgcat tcacgcgct cctgcggcgg      60 cctgtagggc aggctcatac ccctgccgaa ccgcttttgt cagccggtcg ccacggctt     120 ccggcgtctc aacgcgcttt gagattccca gcttttcggc caatccctgc ggtgcatagg    180
cgcgtggctc gaccgcttgc gggctgatgg tgacgtggcc cactggtggc cgctccaggg    240
cctcgtagaa cgcctgaatg cgcgtgtgac gtgccttgct gccctcgatg cccgttgca    300
```

```
gccctagatc ggccacagcg gccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgccccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt ctctggcagc aactcgcgca gtcggcccat cgcttcatcg gtgctgctgg    660
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcggcgccc tacgggcttg ctctccgggc    960
ttcgccctgc gcggtcgctg cgctcccttg ccagcccgtg gatatgtgga cgatggccgc   1020
gagcggccac cggctggctc gcttcgctcg gccgtggac aaccctgctg gacaagctga   1080
tggacaggct gcgcctgccc acgagcttga ccacagggat tgcccaccgg ctacccagcc   1140
ttcgaccaca tacccaccgg ctccaactgc gcggcctgcg gccttgcccc atcaattttt   1200
ttaattttct ctggggaaaa gcctccggcc tgcggcctgc gcgcttcgct tgccggttgg   1260
acaccaagtg gaaggcgggt caaggctcgc gcagcgaccg cgcagcggct tggccttgac   1320
gcgcctggaa cgacccaagc ctatgcgagt gggggcagtc gaaggcgaag cccgcccgcc   1380
tgcccccga gcctcacggc ggcgagtgcg ggggttccaa gggggcagcg ccaccttggg   1440
caaggccgaa ggccgcgcag tcgatcaaca agccccggag gggccacttt ttgccggagg   1500
gggagccgcg ccgaaggcgt gggggaaccc cgcagggg gtg cccttctttg gcaccaaag   1560
aactagatat agggcgaaat gcgaaagact taaaaatcaa caacttaaaa aaggggggta   1620
cgcaacagct cattgcggca ccccccgcaa tagctcattg cgtaggttaa agaaaatctg   1680
taattgactg ccacttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaaccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttgggc atggcgacct   2220
gcgccgcatc ccgaccctgt atccgggcga gcagcaacta ccgaccggcc ccggcgagga   2280
gccgccagc cagcccggca ttccgggcat ggaaccagac ctgccagcct tgaccgaaac   2340
ggaggaatgg gaacgcgcg ggcagcagcg cctgccgatg cccgatgagc cgtgttttct   2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520
ccctatacct tgtctgcctc cccgcgttgc gtcgcggtgc atggagccgg ccacctcga   2580
cctgaatgga agccggcggc acctcgctaa cggattcacc gtttttatca ggctctggga   2640
```

```
ggcagaataa atgatcatat cgtcaattat tacctccacg gggagagcct gagcaaactg    2700
gcctcaggca tttgagaagc acacggtcac actgcttccg gtagtcaata aaccggtaaa    2760
ccagcaatag acataagcgg ctatttaacg accctgccct gaaccgacga ccgggtcgaa    2820
tttgctttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagaggcaac cctatctgtt atgccagcac cgttcaggac gcagccttca gccatcgcgc    3300 atcccctcc ctatgacaac gttcgaccac ctgggccgct ttaccgcaag cgatactgtg    3360
cggttgtgac aattccatga aacgccgaca ggccgccgcc atggcgggt cctcgagcaa    3420 gcgccacagc gccccgcgca actcctgctc gcgcaatggc acgcccaggc gcatcccgca    3480
gccgagccgg accagccgtt cggcattgtc gaactggtcg tgggcgcagg gcagcagcac    3540
ctgcggcacc cccgccgcca aggccaggct catggcgccg ataccgcccg gatggaccag    3600
cccggcgcac gatggcagca aggctcccag tggcgcgtag gcgcgctgca gcacgtggtt    3660
cggcaagccg cgcagcggtt cctggccggc gccggtgagg aagatcccac gcgcgccgag    3720
gcgttccagc gcgcgcaggg ccatggcgta gaagtcgccc tgcaggtgtt cggtcgagcc    3780
ctgggtgaac accagcggcc ggctgccctg atcgagaaag cgttgcagtt cgtcgtcgag    3840
cggggtcccc gggatactgc cgtcgaacag cgggaagccg gtcatgtgca ggggttgcgg    3900
ccaatcctgc tgggcggcg cgaaccaggc cgggaacagg cagaccacgc cctgcggcga    3960
atgcatccat tgggtgaaga tgcgcttcac cggcgtctcc aggccgacct tgcgccgcac    4020
cgcgttgata tccggcgcgc aggtgcgatc cagcttgaag cgctcgatgc agcgccagag    4080
cagcttgcgc atcgccagcg gcatctgctc gggcacgttg aacttgggg gtaccggcgg    4140 caggtgcgcc gacaacaagg tcgatggcga gacctgcgcg gacaggtagg gaatcccgta    4200
cttctcgtga gcgatgcgtg cgcccagcgc ccagagcgag ccgaccacca cgatgtcgtc    4260
atggcgctgc gccgagacgt actcgtagac cggctcgatc atcccggcga tggtttgcca    4320
gagcacgccg aaggacgtct tggggtccca caggcgcgga tcgcccatgg tccgcggta    4380 ggtcagttcg tcgctcagcg ggacgaacgc gatgccgtgc tgctccaccg cgtcgcgaaa    4440
caccgggatg gtgcagaggc tcacgcggtg cccgcgcaat ttcagggtcc gggcaggcc    4500 gatgaaggga aatacgtcgc cggccgagcc gatggcgatg aggatggcgt gcatggtgct    4560
actccgtgcg ttatgcaacc gcaaagcccg gccaggccgg gtcttcgcag gtcaagggtt    4620
caggcgtagc cgatggccat ctcgtggaat cccgccgcg gttccgcccg ctgcggctcc    4680
ggttgcttca gcaggtgctc gagcagggcg cggtgcacgc gtaccgcggc cagcttggac    4740
tccaggtcga ggaaatgccc ggtgccctcc acccgcgaga aactgcagtg cggcaggtag    4800
tcgcggaact ggcgggcgtc ctcggcggtg gtgtattcgt cccagctgcc gttgatgaaa    4860
tgcacgtggc tctggatccg ctccaggcaa gccaggtagc cccgatcgtt gagcgccagc    4920
acctggtcga tgtgaaagcg cgcctgctcg tattcgccgg tggccagcga agccatgtgc    4980
tgatggttgc tggctttcag gcgcggcggc aggtatttgc cgacggtctc gttgagcaga    5040
```

```
tggccgatcg ccgacttgtc gtccagctcg atcagcgcct gcgcccgccc gacgtagtcg    5100
agcatcgcct ggttcagtcc aggggcgaat gccatcacca ccgagctgcg gatgccgcgc    5160
ggattgcgcg acagcgccag cagcgtggag ataccgcccc aggacgcgga gaccaggtga    5220
ttgacctcga agcgctcgat cagcgccagg aggatttcca cctcgtcgtc cttggtgatc    5280 aaccccgct gcgggttgtg ctgacgcgac tgcccggcga agggcaggtc gaacagcacc     5340
acgttgaaat gttcggccag gcacttgcag gtccgggcga acgaggcggt ggtcgccatc    5400
gcgccgttga ccagcatcac cgtgctgcgc ccgggatcct gcccaacgcg ctcgacatgt    5460
acccgcaggc ccttgcaaac cgataccaac agactttcgc gccgcatttc acacctccca    5520
aaaatgccag atcccccggg ctgcaggaat cgatatcaa gcttatcgat accgtcgacc     5580 tcgaggggg gcccggtacc cagcttttgt tcccttttagt gagggttaat tgcgcgcttg    5640
gcgtaatcat ggtcatagct gtttcctgtg tgaaattgtt atccgctcac aattccacac    5700
aacatacgag ccggaagcat aaagtgtaaa gcctggggtg cctaatgagt gagctaactc    5760
acattaattg cgttgcgctc actgcccgct ttccagtcgg gaaacctgtc gtgccagctg    5820
cattaatgaa tcggccaacg cgcggggaga ggcggtttgc gtattgggcg catgcataaa    5880
aactgttgta attcattaag cattctgccg acatggaagc catcacaaac ggcatgatga    5940
acctgaatcg ccagcggcat cagcaccttg tcgccttgcg tataatattt gcccatgggg    6000
gtgggcgaag aactccagca tgagatcccc gcgctggagg atcatccagc cggcgtcccg    6060
gaaaacgatt ccgaagccca acctttcata aaggcggcg gtggaatcga aatctcgtga    6120
tggcaggttg ggcgtcgctt ggtcggtcat ttcgaacccc agagtcccgc tcagaagaac    6180
tcgtcaagaa ggcgatagaa ggcgatgcgc tgcgaatcgg gagcggcgat accgtaaagc    6240
acgaggaagc ggtcagccca ttcgccgcca agctcttcag caatatcacg ggtagccaac    6300
gctatgtcct gatagcggtc cgccacaccc agccggccac agtcgatgaa tccagaaaag    6360
cggccatttt ccaccatgat attcggcaag caggcatcgc catgggtcac gacgagatcc    6420
tcgccgtcgg gcatgcgcgc cttgagcctg gcgaacagtt cggctggcgc gagcccctga    6480
tgctcttcgt ccagatcatc ctgatcgaca agaccggctt ccatccgagt acgtgctcgc    6540
tcgatgcgat gttttcgctt gtggtcgaat gggcaggtag ccggatcaag cgtatgcagc    6600
cgccgcattg catcagccat gatggatact ttctcggcag gagcaaggtg agatgacagg    6660
agatcctgcc ccggcacttc gcccaatagc agccagtccc ttcccgcttc agtgacaacg    6720
tcgagcacag ctgcgcaagg aacgcccgtc gtggccagcc acgatagccg cgctgcctcg    6780
tcctgcagtt cattcagggc accggacagg tcggtcttga caaaaagaac cgggcgcccc    6840
tgcgctgaca gccggaacac ggcggcatca gagcagccga ttgtctgttg tgcccagtca    6900
tagccgaata gcctctccac ccaagcggcc ggagaacctg cgtgcaatcc atcttgttca    6960
atcatgcgaa acgatcctca tcctgtctct tgatcagatc ttgatcccct gcgccatcag    7020
atccttggcg gcaagaaagc catccagttt actttgcagg gcttcccaac cttaccagag    7080
ggcgccccag ctggcaattc cggttcgctt gctgtccata aaaccgccca gtctagctat    7140
cgccatgtaa gcccactgca agctacctgc tttctctttg cgcttgcgtt ttcccttgtc    7200
cagatagccc agtagctgac attcatccca ggtggcactt tcggggaaa tgtgcgcgcc    7260 cgcgttcctg ctgcgctgg gcctgttcct ggcgctggac ttcccgctgt tccgtcagca    7320
gcttttcgcc cacggccttg atgatcgcgg cggccttggc ctgcatatcc cgattcaacg    7380
```

```
gccccagggc gtccagaacg ggcttcaggc gctcccgaag gt            7422

<210> SEQ ID NO 39
<211> LENGTH: 3294
<212> TYPE: DNA
<213> ORGANISM: Pseudomonas aeruginosa

<400> SEQUENCE: 39
aggtaccaga tctggcattt ttgggaggtg tgaaatgcgg cgcgaaagtc tgttggtatc     60
ggtttgcaag ggcctgcggg tacatgtcga gcgcgttggg caggatcccg ggcgcagcac    120
ggtgatgctg gtcaacggcg cgatggcgac caccgcctcg ttcgcccgga cctgcaagtg    180
cctggccgaa catttcaacg tggtgctgtt cgacctgccc ttcgccgggc agtcgcgtca    240
gcacaacccg cagcgggggt tgatcaccaa ggacgacgag gtggaaatcc tcctggcgct    300
gatcgagcgc ttcgaggtca atcacctggt ctccgcgtcc tggggcggta tctccacgct    360
gctggcgctg tcgcgcaatc cgcgcggcat ccgcagctcg gtggtgatgg cattcgcccc    420
tggactgaac caggcgatgc tcgactacgt cgggcggggcg caggcgctga tcgagctgga    480
cgacaagtcg gcgatcggcc atctgctcaa cgagaccgtc ggcaaatacc tgccgccgcg    540
cctgaaagcc agcaaccatc agcacatggc ttcgctggcc accggcgaat acgagcaggc    600
gcgctttcac atcgaccagg tgctggcgct caacgatcgg ggctacctgg cttgcctgga    660
gcggatccag agccacgtgc atttcatcaa cggcagctgg gacgaataca ccaccgccga    720
ggacgcccgc cagttccgcg actacctgcc gcactgcagt ttctcgcggg tggagggcac    780
cgggcatttc ctcgacctgg agtccaagct ggccgcggta cgcgtgcacc gcgccctgct    840
cgagcacctg ctgaagcaac cggagccgca gcgggcggaa cgcgcggcgg gattccacga    900
gatggccatc ggctacgcct gaacccttga cctgcgaaga cccggcctgg ccgggctttg    960
cggttgcata acgcacggag tagcaccatg cacgccatcc tcatcgccat cggctcggcc   1020
ggcgacgtat ttcccttcat cggcctggcc cggaccctga aattgcgcgg caccgcgtg    1080
agcctctgca ccatcccggt gtttcgcgac gcggtggagc agcacggcat cgcgttcgtc   1140
ccgctgagcg acgaactgac ctaccgccgg accatgggcg atccgcgcct gtgggacccc   1200
aagacgtcct tcggcgtgct ctggcaaacc atcgccggga tgatcgagcc ggtctacgag   1260
tacgtctcgg cgcagcgcca tgacgacatc gtggtggtcg gctcgctctg ggcgctgggc   1320
gcacgcatcg ctcacgagaa gtacgggatt ccctacctgt ccgcgcaggt ctcgccatcg   1380
accttgttgt cggcgcacct gccgccggta caccccaagt caacgtgcc cgagcagatg   1440
ccgctggcga tgcgcaagct gctctggcgc tgcatcgagc gcttcaagct ggatcgcacc   1500
tgcgcgccgg atatcaacgc ggtgcggcgc aaggtcggcc tggagacgcc ggtgaagcgc   1560
atcttcaccc aatggatgca ttcgccgcag ggcgtggtct gcctgttccc ggcctggttc   1620
gcgccgcccc agcaggattg gccgcaaccc ctgcacatga ccggcttccc gctgttcgac   1680
ggcagtatcc cggggacccc gctcgacgac gaactgcaac gctttctcga tcagggcagc   1740
cggccgctgg tgttcacccc gggctcgacc gaacacctgc agggcgactt ctacgccatg   1800
gccctgcgcg cgctggaacg cctcggcgcg cgtgggatct tcctcaccgg cgccggccag   1860
gaaccgctgc gcggcttgcc gaaccacgtg ctgcagcgcg cctacgcgcc actgggagcc   1920
ttgctgccat cgtgcgccgg gctggtccat ccgggcggta tcggcgccat gagcctggcc   1980
ttggcggcg ggtgccgca ggtgctgctg ccctgcgccc acgaccagtt cgacaatgcc   2040
gaacggctgg tccggctcgg ctgcgggatg cgcctgggcg tgccattgcg cgagcaggag   2100
```

```
ttgcgcgggg cgctgtggcg cttgctcgag gacccggcca tggcggcggc ctgtcggcgt    2160
ttcatggaat tgtcacaacc gcacagtatc gcttgcggta aagcgcccca ggtggtcgaa    2220
cgttgtcata gggaggggga tgcgcgatgg ctgaaggctg cgtcctgacc tacgggagaa    2280
gaacgatcat ggaccggata gacatgggcg tgctggtggt actgttcaat cctggcgacg    2340
acgacctgga acaccttggc gaactggcgg cggcgtttcc gcaactgcgc ttccttgccg    2400
tcgacaactc accgcacagc gatccgcagc gcaatgcccg gctgcgcggg caaggcatcg    2460
ccgtgctgca ccacggcaac cggcagggca tcgccggcgc cttcaaccag ggactcgacg    2520
cgctattccg gcgtggcgtg cagggtgtgc tgctgctcga ccaggactcc cgtcccggcg    2580
gcgccttcct cgccgcccag tggcgcaacc tgcaggcgcg caacggtcag gcctgcctgc    2640
tcggcccacg gatcttcgac cggggtgacc ggcgcttcct gccggccatc catctcgacg    2700
gactgacgct caggcaattg tctctggacg gcctgacgac cccgcagcgc acctcgttcc    2760
tgatctcctc cggctgcctg ctgacccgcg aggcctacca cgcctcggc cacttcgacg    2820 aggaactgtt catcgaccac gtggacaccg aatacagcct gcgcgcccag gcgctggacg    2880 tgccctgta cgtcgacccg cggctggtcc tcgagcaccg catcggcacg cgcaagaccc    2940
gccgcctcgg cggtctcagc ctcagcgcga tgaaccacgc cccgctgcgc cgctactacc    3000
tggcgcgcaa cggcctgctg gtcctgcgcc gctacgcccg gtcctcgccg ctggccctgc    3060
tggcgaacct gccgaccctg acccagggcc tcgcggtgct cctgctcgaa cgcgacaagc    3120
tgctcaagct cgcgctgcctg gctggggcc tgtgggacgg cctgcgggga cgcggcggcg    3180
cgctggagac caaccgcccg cgcctgctga gcgcctcgc cggcccggcc gtggcgtccg    3240
tagcttccgg caaggccaag gcctagtcgg cgaaacgcat tccctctaga gagc          3294
```

```
<210> SEQ ID NO 40
<211> LENGTH: 8409
<212> TYPE: DNA
<213> ORGANISM: Artificial
<220> FEATURE:
<223> OTHER INFORMATION: Vector

<400> SEQUENCE: 40
accttcggga gcgcctgaag cccgttctgg acgccctggg gccgttgaat cgggatatgc      60
aggccaaggc cgccgcgatc atcaaggccg tgggcgaaaa gctgctgacg gaacagcggg     120
aagtccagcg ccagaaacag gcccagcgcc agcaggaacg cgggcgcgca catttccccg     180
aaaagtgcca cctgggatga atgtcagcta ctgggctatc tggacaaggg aaaacgcaag     240
cgcaaagaga aagcaggtag cttgcagtgg gcttacatgg cgatagctag actgggcggt     300
tttatggaca gcaagcgaac cggaattgcc agctggggcg ccctctggta aggttgggaa     360
gccctgcaaa gtaaactgga tggctttctt gccgccaagg atctgatggc gcaggggatc     420
aagatctgat caagagacag gatgaggatc gtttcgcatg attgaacaag atggattgca     480
cgcaggttct ccggccgctt gggtggagag gctattcggc tatgactggg cacaacagac     540
aatcggctgc tctgatgccg ccgtgttccg gctgtcagcg caggggcgcc cggttctttt     600
tgtcaagacc gacctgtccg gtgccctgaa tgaactgcag gacgaggcag cgcggctatc     660
gtggctggcc acgacgggcg ttccttgcgc agctgtgctc gacgttgtca ctgaagcggg     720
aagggactgg ctgctattgg gcgaagtgcc ggggcaggat ctcctgtcat ctcaccttgc     780
tcctgccgag aaagtatcca tcatggctga tgcaatgcgg cggctgcata cgcttgatcc     840
```

```
ggctacctgc ccattcgacc accaagcgaa acatcgcatc gagcgagcac gtactcggat    900
ggaagccggt cttgtcgatc aggatgatct ggacgaagag catcagggcc tcgcgccagc    960
cgaactgttc gccaggctca aggcgcgcat gcccgacggc gaggatctcg tcgtgaccca   1020
tggcgatgcc tgcttgccga atatcatggt ggaaaatggc cgcttttctg gattcatcga   1080
ctgtggccgg ctgggtgtgg cggaccgcta tcaggacata gcgttggcta cccgtgatat   1140
tgctgaagag cttggcggcg aatgggctga ccgcttcctc gtgctttacg gtatcgccgc   1200
tcccgattcg cagcgcatcg ccttctatcg ccttcttgac gagttcttct gagcgggact   1260
ctggggttcg aaatgaccga ccaagcgacg cccaacctgc catcacgaga tttcgattcc   1320
accgccgcct tctatgaaag gttgggcttc ggaatcgttt tccgggacgc cggctggatg   1380
atcctccagc gcgggatct catgctggag ttcttcgccc accccatgg gcaaatatta    1440
tacgcaaggc gacaaggtgc tgatgccgct ggcgattcag gttcatcatg ccgtttgtga   1500
tggcttccat gtcggcagaa tgcttaatga attacaacag ttttatgca tgcgcccaat    1560
acgcaaaccg cctctccccg cgcgttggcc gattcattaa tgcagctggc acgacaggtt   1620
tcccgactgg aaagcgggca gtgagcgcaa cgcaattaat gtgagttagc tcactcatta   1680
ggcaccccag gctttacact ttatgcttcc ggctcgtatg ttgtgtggaa ttgtgagcgg   1740
ataacaattt cacacaggaa acagctatga ccatgattac gccaagcgcg caattaaccc   1800
tcactaaagg gaacaaaagc tgggtaccgg cccccccctc gaggtcgacg gtatcgataa   1860
gcttgatatc gaattcctgc agcccggggg atctggcatt tttgggaggt gtgaaatgcg   1920
gcgcgaaagt ctgttggtat cggtttgcaa gggcctgcgg gtacatgtcg agcgcgttgg   1980
gcaggatccc gggcgcagca cggtgatgct ggtcaacggc gcgatggcga ccaccgcctc   2040
gttcgcccgg acctgcaagt gcctggccga acatttcaac gtggtgctgt cgacctgcc    2100
cttcgccggg cagtcgcgtc agcacaaccc gcagcggggg ttgatcacca aggacgacga   2160
ggtgaaaatc ctcctggcgc tgatcgagcg cttcgaggtc aatcacctgg tctccgcgtc   2220
ctggggcggt atctccacgc tgctggcgct gtcgcgcaat ccgcgcggca tccgcagctc   2280
ggtggtgatg gcattcgccc ctggactgaa ccaggcgatg ctcgactacg tcgggcgggc   2340
gcaggcgctg atcgagctgg acgacaagtc ggcgatcggc catctgctca acgagaccgt   2400
cggcaaatac ctgccgccgc gcctgaaagc cagcaaccat cagcacatgg cttcgctggc   2460
caccggcgaa tacgagcagg cgcgctttca catcgaccag gtgctggcgc tcaacgatcg   2520
gggctacctg gcttgcctgg agcggatcca gagccacgtg catttcatca cggcagctg    2580
ggacgaatac accaccgccg aggacgcccg ccagttccgc gactacctgc cgcactgcag   2640
tttctcgcgg gtggagggca ccgggcattt cctcgacctg gagtccaagc tggccgcggt   2700
acgcgtgcac cgcgccctgc tcgagcacct gctgaagcaa ccggagccgc agcgggcgga   2760
acgcgcggcg ggattccacg agatggccat cggctacgcc tgaacccttg acctgcgaag   2820
acccggcctg gccgggcttt gcggttgcat aacgcacgga gtagcaccat gcacgccatc   2880
ctcatcgcca tcggctcggc cggcgacgta tttcccttca tcggcctggc ccggaccctg   2940
aaattgcgcg gcaccgcgt gagcctctgc accatcccgg tgtttcgcga cgcggtggag    3000
cagcacggca tcgcgttcgt cccgctgagc gacgaactga cctaccgccg gaccatgggc   3060
gatccgcgcc tgtgggaccc caagacgtcc ttcggcgtgc tctggcaaac catcgccggg   3120
atgatcgagc cggtctacga gtacgtctcg gcgcagcgcc atgacgacat cgtggtggtc   3180
ggctcgctct gggcgctggg cgcacgcatc gctcacgaga agtacgggat tccctacctg   3240
```

```
tccgcgcagg tctcgccatc gaccttgttg tcggcgcacc tgccgccggt acaccccaag   3300
ttcaacgtgc ccgagcagat gccgctggcg atgcgcaagc tgctctggcg ctgcatcgag   3360
cgcttcaagc tggatcgcac ctgcgcgccg gatatcaacg cggtgcggcg caaggtcggc   3420
ctggagacgc cggtgaagcg catcttcacc aatggatgc attcgccgca gggcgtggtc    3480
tgcctgttcc cggcctggtt cgcgccgccc cagcaggatt ggccgcaacc cctgcacatg   3540
accggcttcc cgctgttcga cggcagtatc ccggggaccc cgctcgacga cgaactgcaa   3600
cgctttctcg atcagggcag ccggccgctg tgttcaccc agggctcgac cgaacacctg    3660
cagggcgact tctacgccat ggccctgcgc gcgctgaac gcctcggcgc gcgtgggatc    3720
ttcctcaccg gcgccggcca ggaaccgctg cgcggcttgc cgaaccacgt gctgcagcgc   3780
gcctacgcgc cactgggagc cttgctgcca tcgtgcgccg gctggtcca tccgggcggt    3840
atcggcgcca tgagcctggc cttggcggcg ggggtgccgc aggtgctgct gccctgcgcc   3900
cacgaccagt tcgacaatgc cgaacggctg gtccggctcg gctgcgggat gcgcctgggc   3960
gtgccattgc gcgagcagga gttgcgcggg gcgctgtggc gcttgctcga ggacccggcc   4020
atggcggcg cctgtcggcg tttcatggaa ttgtcacaac cgcacagtat cgcttgcggt    4080
aaagcggccc aggtggtcga acgttgtcat agggagggg atgcgcgatg gctgaaggct    4140
gcgtcctgac ctacgggaga agaacgatca tggaccggat agacatgggc gtgctggtgg   4200
tactgttcaa tcctggcgac gacgacctgg aacaccttgg cgaactggcg gcggcgtttc   4260
cgcaactgcg cttccttgcc gtcgacaact caccgcacag cgatccgcag cgcaatgccc   4320
ggctgcgcgg gcaaggcatc gccgtgctgc accacggcaa ccgcagggc atcgccggcg    4380
ccttcaacca gggactcgac gcgctattcc ggcgtggcgt gcagggtgtg ctgctgctcg    4440
accaggactc ccgtcccggc ggcgccttcc tcgccgccca gtggcgcaac ctgcaggcgc   4500
gcaacggtca ggcctgcctg ctcggcccac ggatcttcga ccggggtgac cggcgcttcc   4560
tgccggccat ccatctcgac ggactgacgc tcaggcaatt gtctctggac ggcctgacga   4620
ccccgcagcg cacctcgttc ctgatctcct ccggctgcct gctgacccgc gaggcctacc   4680
agcgcctcgg ccacttcgac gaggaactgt tcatcgacca cgtggacacc gaatacagcc   4740
tgcgcgccca ggcgctggac gtgccctgt acgtcgaccc gcggctggtc ctcgagcacc    4800
gcatcggcac gcgcaagacc cgccgcctcg gcggtctcag cctcagcgcg atgaaccacg   4860
ccccgctgcg ccgctactac ctggcgcgca acggcctgct ggtcctgcgc cgctacgccc   4920
ggtcctcgcc gctggccctg ctggcgaacc tgccgaccct gacccagggc ctcgcggtgc   4980
tcctgctcga acgcgacaag ctgctcaagc tgcgctgcct gggctggggc ctgtgggacg   5040
gcctgcgggg acgcggcggc gcgctggaga ccaaccgccc gcgcctgctg aagcgcctcg   5100
ccggcccggc cgtggcgtcc gtagcttccg gcaaggccaa ggcctagtcg gcgaaacgca   5160
ttccctctag agcggccgcc accgcggtgg agctccaatt cgccctatag tgagtcgtat   5220
tacgcgcgct cactggccgt cgttttacaa cgtcgtgact gggaaaaccc tggcgttacc   5280
caacttaatc gccttgcagc acatccccct ttcgccagct ggcgtaatag cgaagaggcc   5340
cgcaccgatc gcccttccca acagttgcgc agcctgaatg gcgaatggaa attgtaagcg   5400
ttaatatttt gttaaaattc gcgttaaatt tttgttaaat cagctcattt tttaaccaat   5460
aggccgactg cgatgagtgg cagggcgggg cgtaattttt ttaaggcagt tattggtgcc   5520
cttaaacgcc tggtgctacg cctgaataag tgataataag cggatgaatg gcagaaattc   5580
```

```
gaaagcaaat tcgacccggt cgtcggttca gggcagggtc gttaaatagc cgcttatgtc    5640
tattgctggt ttaccggttt attgactacc ggaagcagtg tgaccgtgtg cttctcaaat    5700
gcctgaggcc agtttgctca ggctctcccc gtggaggtaa taattgacga tatgatcatt    5760
tattctgcct cccagagcct gataaaaacg gtgaatccgt tagcgaggtg ccgccggctt    5820
ccattcaggt cgaggtggcc cggctccatg caccgcgacg caacgcgggg aggcagacaa    5880
ggtatagggc ggcgaggcgg ctacagccga tagtctggaa cagcgcactt acgggttgct    5940
gcgcaaccca agtgctaccg gcgcggcagc gtgacccgtg tcggcggctc caacggctcg    6000
ccatcgtcca gaaaacacgg ctcatcgggc atcggcaggc gctgctgccc gcgccgttcc    6060
cattcctccg tttcggtcaa ggctggcagg tctggttcca tgcccggaat gccgggctgg    6120
ctgggcggct cctcgccggg gccggtcggt agttgctgct cgcccggata cagggtcggg    6180
atgcggcgca ggtcgccatg ccccaacagc gattcgtcct ggtcgtcgtg atcaaccacc    6240
acggcggcac tgaacaccga caggcgcaac tggtcgcggg gctggccccca cgccacgcgg    6300 tcattgacca cgtaggccga cacggtgccg gggccgttga gcttcacgac ggagatccag    6360
cgctcggcca ccaagtcctt gactgcgtat tggaccgtcc gcaaagaacg tccgatgagc    6420
ttggaaagtg tcttctggct gaccaccacg gcgttctggt ggcccatctg cgccacgagg    6480
tgatgcagca gcattccgc cgtgggtttc ctcgcaataa gcccggccca cgcctcatgc    6540
gctttgcgtt ccgtttgcac ccagtgaccg ggcttgttct tggcttgaat gccgatttct    6600
ctggactgcg tggccatgct tatctccatg cggtagggtg ccgcacggtt gcggcaccat    6660
gcgcaatcag ctgcaacttt tcggcagcgc gacaacaatt atgcgttgcg taaaagtggc    6720
agtcaattac agattttctt taacctacgc aatgagctat tgcgggggt gccgcaatga    6780 gctgttgcgt acccccgttt tttaagttgt tgattttttaa gtctttcgca tttcgccta    6840 tatctagttc tttggtgccc aaagaagggc acccctgcgg ggttcccccca cgccttcggc    6900 gcggctcccc ctccggcaaa aagtggcccc tccgggggctt gttgatcgac tgcgcggcct    6960
tcggccttgc ccaaggtggc gctgccccct tggaaccccc gcactcgccg ccgtgaggct    7020
cggggggcag gcgggcgggc ttcgccttcg actgccccca ctcgcatagg cttgggtcgt    7080
tccaggcgcg tcaaggccaa gccgctgcgc ggtcgctgcg cgagccttga cccgccttcc    7140
acttggtgtc caaccggcaa gcgaagcgcg caggccgcag gccggaggct tttccccaga    7200
gaaaattaaa aaaattgatg gggcaaggcc gcaggccgcg cagttggagc cggtgggtat    7260
gtggtcgaag gctgggtagc cggtgggcaa tccctgtggt caagctcgtg ggcaggcgca    7320
gcctgtccat cagcttgtcc agcagggttg tccacgggcc gagcgaagcg agccagccgg    7380
tggccgctcg cggccatcgt ccacatatcc acgggctggc aagggagcgc agcgaccgcg    7440
cagggcgaag cccggagagc aagcccgtag gcgccgcag ccgccgtagg cggtcacgac    7500
tttgcgaagc aaagtctagt gagtatactc aagcattgag tggcccgccg gaggcaccgc    7560
cttgcgctgc ccccgtcgag ccggttggac accaaaaggg aggggcaggc atggcggcat    7620
acgcgatcat gcgatgcaag aagctggcga aaatgggcaa cgtggcggcc agtctcaagc    7680
acgcctaccg cgagcgcgag acgcccaacg ctgacgccag caggacgcca gagaacgagc    7740
actgggcggc cagcagcacc gatgaagcga tgggccgact gcgcgagttg ctgccagaga    7800
agcggcgcaa ggacgctgtg ttggcggtcg agtacgtcat gacggccagc ccggaatggt    7860
ggaagtcggc cagccaagaa cagcaggcgg cgttcttcga gaaggcgcac aagtggctgg    7920
cggacaagta cggggcggat cgcatcgtga cggccagcat ccaccgtgac gaaaccagcc    7980
```

| | |
|---|---|
| cgcacatgac cgcgttcgtg gtgccgctga cgcaggacgg caggctgtcg gccaaggagt | 8040 |
| tcatcggcaa caaagcgcag atgacccgcg accagaccac gtttgcggcc gctgtggccg | 8100 |
| atctagggct gcaacggggc atcgagggca gcaaggcacg tcacacgcgc attcaggcgt | 8160 |
| tctacgaggc cctggagcgg ccaccagtgg gccacgtcac catcagcccg caagcggtcg | 8220 |
| agccacgcgc ctatgcaccg cagggattgg ccgaaaagct gggaatctca aagcgcgttg | 8280 |
| agacgccgga agccgtggcc gaccggctga caaaagcggt tcggcagggg tatgagcctg | 8340 |
| ccctacaggc cgccgcagga gcgcgtgaga tgcgcaagaa ggccgatcaa gcccaagaga | 8400 |
| cggcccgag | 8409 |

<210> SEQ ID NO 41
<211> LENGTH: 3590
<212> TYPE: DNA
<213> ORGANISM: Pseudomonas aeruginosa

<400> SEQUENCE: 41

| | |
|---|---|
| aggtaccaga tctggcattt ttgggaggtg tgaaatgcgg cgcgaaagtc tgttggtatc | 60 |
| ggtttgcaag ggcctgcggg tacatgtcga gcgcgttggg caggatcccg ggcgcagcac | 120 |
| ggtgatgctg gtcaacggcg cgatggcgac caccgcctcg ttcgcccgga cctgcaagtg | 180 |
| cctggccgaa catttcaacg tggtgctgtt cgacctgccc ttcgccgggc agtcgcgtca | 240 |
| gcacaacccg cagcgggggt tgatcaccaa ggacgacgag gtggaaatcc tcctggcgct | 300 |
| gatcgagcgc ttcgaggtca atcacctggt ctccgcgtcc tggggcggta tctccacgct | 360 |
| gctggcgctg tcgcgcaatc cgcgcggcat ccgcagctcg gtggtgatgg cattcgcccc | 420 |
| tggactgaac caggcgatgc tcgactacgt cgggcgggcg caggcgctga tcgagctgga | 480 |
| cgacaagtcg gcgatcggcc atctgctcaa cgagaccgtc ggcaaatacc tgccgccgcg | 540 |
| cctgaaagcc agcaaccatc agcacatggc ttcgctggcc accggcgaat acgagcaggc | 600 |
| gcgctttcac atcgaccagg tgctggcgct caacgatcgg ggctacctgg cttgcctgga | 660 |
| gcggatccag agccacgtgc atttcatcaa cggcagctgg gacgaataca ccaccgccga | 720 |
| ggacgcccgc cagttccgcg actacctgcc gcactgcagt ttctcgcggg tggagggcac | 780 |
| cgggcatttc ctcgacctgg agtccaagct ggccgcggta cgcgtgcacc gcgccctgct | 840 |
| cgagcacctg ctgaagcaac cggagccgca gcgggcggaa cgcgcggcgg gattccacga | 900 |
| gatggccatc ggctacgcct gaacccttga cctgcgaaga cccggcctgg ccgggctttg | 960 |
| cggttgcata acgcacggag tagcaccatg cacgccatcc tcatcgccat cggctcggcc | 1020 |
| ggcgacgtat ttcccttcat cggcctggcc cggaccctga aattgcgcgg gcaccgcgtg | 1080 |
| agcctctgca ccatcccggt gtttcgcgac gcggtggagc agcacggcat cgcgttcgtc | 1140 |
| ccgctgagcg acgaactgac ctaccgccgg accatgggcg atccgcgcct gtgggacccc | 1200 |
| aagacgtcct tcggcgtgct ctggcaaacc atcgccggga tgatcgagcc ggtctacgag | 1260 |
| tacgtctcgg cgcagcgcca tgacgacatc gtggtggtcg gctcgctctg ggcgctgggc | 1320 |
| gcacgcatcg ctcacgagaa gtacgggatt ccctacctgt ccgcgcaggt ctcgccatcg | 1380 |
| accttgttgt cggcgcacct gccgccggta cacccccaagt tcaacgtgcc cgagcagatg | 1440 |
| ccgctggcga tgcgcaagct gctctggcgc tgcatcgagc gcttcaagct ggatcgcacc | 1500 |
| tgcgcgccgg atatcaacgc ggtgcggcgc aaggtcggcc tggagacgcc ggtgaagcgc | 1560 |
| atcttcaccc aatggatgca ttcgccgcag ggcgtggtct gcctgttccc ggcctggttc | 1620 |

```
gcgccgcccc agcaggattg ccgcaaccc ctgcacatga ccggcttccc gctgttcgac    1680
ggcagtatcc cggggacccc gctcgacgac gaactgcaac gctttctcga tcagggcagc    1740
cggccgctgg tgttcaccca gggctcgacc gaacacctgc agggcgactt ctacgccatg    1800
gccctgcgcg cgctggaacg cctcggcgcg cgtgggatct tcctcaccgg cgccggccag    1860
gaaccgctgc gcggcttgcc gaaccacgtg ctgcagcgcg cctacgcgcc actgggagcc    1920
ttgctgccat cgtgcgccgg gctggtccat ccgggcggta tcggcgccat gagcctggcc    1980
ttggcggcgg gggtgccgca ggtgctgctg ccctgcgccc acgaccagtt cgacaatgcc    2040
gaacggctgg tccggctcgg ctgcgggatg cgcctgggcg tgccattgcg cgagcaggag    2100
ttgcgcgggg cgctgtggcg cttgctcgag gacccggcca tggcggcggc ctgtcggcgt    2160
ttcatggaat tgtcacaacc gcacagtatc gcttgcggta aagcggccca ggtggtcgaa    2220
cgttgtcata gggaggggga tgcgcgatgg ctgaaggctg cgtcctgacg ccgggaggat    2280
cctggcgtgt ccacgaccag cctctgcccc tccgccacgc gggaacacgg tcccggcgcg    2340
aaacgcgtcc tgcctctgct gttcctcacc tgcctgctgg atgccgctgg cgtcggcctg    2400
atcgtgcccc tgctgccgac gctgatcggc agcgtggcgc cgctggcggt ccgcgacgcg    2460
gccacctggg gcgccgccct ggtgatgacc ttcgcgctgc tgcaattgtt cttttcgccg    2520
gtcctcggca gcctcagcga ccgcttcgga cgccgccccg tcctggtcct ggcgatgctc    2580
ggcttcgccc tcagctatct gctgctgcg ctggccgaca gcctctggat gctgttcctc    2640
ggtcgcgcgc tggccgggct caccggcgcc agcgtggcca ccgcgatggc ctgcgcggct    2700
gacctcggca cgcacgggca gcgcacccgg cacttcggct ggctgtacgc cggcctcgcc    2760
ctgggcatga tcctcggccc cgccctcggt gggctgctgg cggtgcacgg cacgacgctg    2820
ccgctgttgc tggccgccgg cctgtgcctg ctcaacgccc tgctcgccgg cctgttcctc    2880
gaggaaaccc tgccccccgac gcgacgccgc cgcctggacc cgaggcggat gaatgccttg    2940
cgctcgatca gcgccctggc tcggcaaccg gggtcggac gcctgctggc ggtgcttgcc    3000
ctggtattcc tcggcttgca ggcggtgatg gtggtctggc cgttcttcgt gatcgagaag    3060
tttcactgga gcagcgcctg gatcggctac tcgctgcccc tctacggcgt gctcgcggtg    3120
ctcgcccaga ccctcggcgt gaacctctgc aagcggcgcc tggacgacgc ccgcctgctg    3180
cgcctgggcc tcgccctgca aggctgcggc ctgctgctgt tcgccctggt cgactcgtca    3240
ttctggctgg tctgcgcgct gctgcccttc gcgctcggca gcctcgccac cccggccatg    3300
caggggctgc tctcggcccg cgtgccggtc gaccgcagg gcgagttgca gggcgtgctg    3360
agcagcctga tgagcctcgc cgcgatcgtc ggtccgccgc tgatgagcgg cctgttccac    3420
tggggcagcg gtccgctcgc gccgctgccc ctggccggcg cgccattcct cgccggcgcc    3480
cttctcgttc tggccgggct ggtcctggcc tgcaacttc gacctacggg agaagaacga    3540
tcatggaccg gatagacatg ggcgtgctgg tggtacttct agagagctca              3590

<210> SEQ ID NO 42
<211> LENGTH: 8702
<212> TYPE: DNA
<213> ORGANISM: Artificial
<220> FEATURE:
<223> OTHER INFORMATION: Vector

<400> SEQUENCE: 42
accttcggga gcgcctgaag cccgttctgg acgccctggg gccgttgaat cgggatatgc      60
aggccaaggc cgccgcgatc atcaaggccg tgggcgaaaa gctgctgacg gaacagcggg     120
```

```
aagtccagcg ccagaaacag gcccagcgcc agcaggaacg cgggcgcgca catttccccg    180
aaaagtgcca cctgggatga atgtcagcta ctgggctatc tggacaaggg aaaacgcaag    240
cgcaaagaga aagcaggtag cttgcagtgg gcttacatgg cgatagctag actgggcggt    300
tttatggaca gcaagcgaac cggaattgcc agctggggcg ccctctggta aggttgggaa    360
gccctgcaaa gtaaactgga tggctttctt gccgccaagg atctgatggc cagggatc     420
aagatctgat caagagacag gatgaggatc gtttcgcatg attgaacaag atggattgca    480
cgcaggttct ccggccgctt gggtggagag ctattcggc tatgactggg cacaacagac     540
aatcggctgc tctgatgccg ccgtgttccg gctgtcagcg caggggcgcc cggttctttt    600
tgtcaagacc gacctgtccg gtgccctgaa tgaactgcag gacgaggcag cgcggctatc    660
gtggctggcc acgacgggcg ttccttgcgc agctgtgctc gacgttgtca ctgaagcggg    720
aagggactgg ctgctattgg gcgaagtgcc ggggcaggat ctcctgtcat ctcaccttgc    780
tcctgccgag aaagtatcca tcatggctga tgcaatgcgg cggctgcata cgcttgatcc    840
ggctacctgc ccattcgacc accaagcgaa acatcgcatc gagcgagcac gtactcggat    900
ggaagccggt cttgtcgatc aggatgatct ggacgaagag catcaggggc tcgcgccagc    960
cgaactgttc gccaggctca aggcgcgcat gcccgacggc gaggatctcg tcgtgaccca   1020
tggcgatgcc tgcttgccga atatcatggt ggaaaatggc cgcttttctg gattcatcga   1080
ctgtggccgg ctgggtgtgg cggaccgcta tcaggacata gcgttggcta cccgtgatat   1140
tgctgaagag cttggcggcg aatgggctga ccgcttcctc gtgctttacg gtatcgccgc   1200
tcccgattcg cagcgcatcg ccttctatcg ccttcttgac gagttcttct gagcgggact   1260
ctggggttcg aaatgaccga ccaagcgacg cccaacctgc catcacgaga tttcgattcc   1320
accgccgcct tctatgaaag gttgggcttc ggaatcgttt tccgggacgc cggctggatg   1380
atcctccagc gcggggatct catgctggag ttcttcgccc accccatgg gcaaatatta   1440
tacgcaaggc gacaaggtgc tgatgccgct ggcgattcag gttcatcatg ccgtttgtga   1500
tggcttccat gtcggcagaa tgcttaatga attacaacag ttttatgca tgcgcccaat    1560
acgcaaaccg cctctccccg cgcgttggcc gattcattaa tgcagctggc acgacaggtt   1620
tcccgactgg aaagcgggca gtgagcgcaa cgcaattaat gtgagttagc tcactcatta   1680
ggcaccccag gctttacact ttatgcttcc ggctcgtatg ttgtgtggaa ttgtgagcgg   1740
ataacaattt cacacaggaa acagctatga ccatgattac gccaagcgcg caattaaccc   1800
tcactaaagg gaacaaaagc tgggtaccgg gccccccctc gaggtcgacg gtatcgataa   1860
gcttgatatc gaattcctgc agcccggggg atctggcatt tttgggaggt gtgaaatgcg   1920
gcgcgaaagt ctgttggtat cggtttgcaa gggcctgcgg gtacatgtcg agcgcgttgg   1980
gcaggatccc gggcgcagca cggtgatgct ggtcaacggc gcgatggcga ccaccgcctc   2040
gttcgcccgg acctgcaagt gcctggccga acatttcaac gtggtgctgt cgacctgcc   2100
cttcgccggg cagtcgcgtc agcacaaccc gcagcggggg ttgatcacca aggacgacga   2160
ggtggaaatc ctcctggcgc tgatcgagcg cttcgaggtc aatcacctgg tctccgcgtc   2220
ctggggcggt atctccacgc tgctggcgct gtcgcgcaat ccgcgcggca tccgcagctc   2280
ggtggtgatg gcattcgccc tggactgaa ccaggcgatg ctcgactacg tcgggcgggc    2340
gcaggcgctg atcgagctgg acgacaagtc ggcgatcggc catctgctca acgagaccgt   2400
cggcaaatac ctgccgccgc gcctgaaagc cagcaaccat cagcacatgg cttcgctggc   2460
```

```
caccggcgaa tacgagcagg cgcgctttca catcgaccag gtgctggcgc tcaacgatcg    2520
gggctacctg gcttgcctgg agcggatcca gagccacgtg catttcatca acggcagctg    2580
ggacgaatac accaccgccg aggacgcccg ccagttccgc gactacctgc cgcactgcag    2640
tttctcgcgg gtggagggca ccgggcattt cctcgacctg gagtccaagc tggccgcggt    2700
acgcgtgcac cgcgccctgc tcgagcacct gctgaagcaa ccggagccgc agcgggcgga    2760
acgcgcggcg ggattccacg agatggccat cggctacgcc tgaacccttg acctgcgaag    2820
acccggcctg gccgggcttt gcggttgcat aacgcacgga gtagcaccat gcacgccatc    2880
ctcatcgcca tcggctcggc cggcgacgta tttcccttca tcggcctggc ccggaccctg    2940
aaattgcgcg ggcaccgcgt gagcctctgc accatcccgg tgtttcgcga cgcggtggag    3000
cagcacggca tcgcgttcgt cccgctgagc gacgaactga cctaccgccg gaccatgggc    3060
gatccgcgcc tgtgggaccc caagacgtcc ttcggcgtgc tctggcaaac catcgccggg    3120
atgatcgagc cggtctacga gtacgtctcg gcgcagcgcc atgacgacat cgtggtggtc    3180
ggctcgctct gggcgctggg cgcacgcatc gctcacgaga agtacgggat tccctacctg    3240
tccgcgcagg tctcgccatc gaccttgttg tcggcgcacc tgccgccggt acaccccaag    3300
ttcaacgtgc ccgagcagat gccgctggcg atgcgcaagc tgctctggcg ctgcatcgag    3360
cgcttcaagc tggatcgcac ctgcgcgccg gatatcaacg cggtgcggcg caaggtcggc    3420
ctggagacgc cggtgaagcg catcttcacc caatggatgc attcgccgca gggcgtggtc    3480
tgcctgttcc cggcctggtt cgcgccgccc cagcaggatt ggccgcaacc cctgcacatg    3540
accggcttcc cgctgttcga cggcagtatc ccggggaccc cgctcgacga cgaactgcaa    3600
cgctttctcg atcagggcag ccggccgctg gtgttcaccc agggctcgac cgaacacctg    3660
cagggcgact tctacgccat ggccctgcgc gcgctggaac gcctcggcgc gcgtgggatc    3720
ttcctcaccg cgccggcca ggaaccgctg cgcggcttgc cgaaccacgt gctgcagcgc    3780
gcctacgcgc cactgggagc cttgctgcca tcgtgcgccg ggctggtcca tccgggcggt    3840
atcggcgcca tgagcctggc cttggcggcg ggggtgccgc aggtgctgct gccctgcgcc    3900
cacgaccagt tcgacaatgc cgaacggctg gtccggctcg gctgcgggat gcgcctgggc    3960
gtgccattgc gcgagcagga gttgcgcggg gcgctgtggc gcttgctcga ggacccggcc    4020
atggcggcg cctgtcggcg tttcatggaa ttgtcacaac cgcacagtat cgcttgcggt    4080
aaagcggccc aggtggtcga acgttgtcat agggaggggg atgcgcgatg gctgaaggct    4140
gcgtcctgac gccgggagga tcctggcgtg tccacgacca gcctctgccc ctccgccacg    4200
cgggaacacg gtcccggcgc gaaacgcgtc ctgcctctgc tgttcctcac ctgcctgctg    4260
gatgccgctg gcgtcggcct gatcgtgccc ctgctgccga cgctgatcgg cagcgtggcg    4320
ccgctggcgg tccgcgacgc ggccacctgg ggcgccgccc tggtgatgac cttcgcgctg    4380
ctgcaattgt tcttttcgcc ggtcctcggc agcctcagcg accgcttcgg acgccgcccc    4440
gtcctggtcc tggcgatgct cggcttcgcc ctcagctatc tgctgctggc gctggccgac    4500
agcctctgga tgctgttcct cggtcgcgcg ctggccgggc tcaccggcgc cagcgtggcc    4560
accgcgatgg cctgcgcggc tgacctcggc acgcacgggc agcgcacccg gcacttcggc    4620
tggctgtacg ccggcctcgc cctgggcatg atcctcggcc ccgccctcgg tgggctgctg    4680
gcggtgcacg gcacgacgct gccgcgtgttg ctggccgccg gctgtgcct gctcaacgcc    4740
ctgctcgccg gcctgttcct cgaggaaacc ctgccccga cgcgacgccg ccgcctggac    4800
ccgaggcgga tgaatgcctt gcgctcgatc agcggcctgg ctcggcaacc ggggtcgga    4860
```

```
cgcctgctgg cggtgcttgc cctggtattc ctcggcttgc aggcggtgat ggtggtctgg   4920
ccgttcttcg tgatcgagaa gtttcactgg agcagcgcct ggatcggcta ctcgctggcc   4980
ctctacggcg tgctcgcggt gctcgcccag accctcggcg tgaacctctg caagcggcgc   5040
ctggacgacg cccgcctgct gcgcctgggc ctcgccctgc aaggctgcgg cctgctgctg   5100
ttcgccctgg tcgactcgtc attctggctg gtctgcgcgc tgctgcccct cgcgctcggc   5160
agcctcgcca ccccggccat gcaggggctg ctctcggccc gcgtgccggt cgaccgccag   5220
ggcgagttgc agggcgtgct gagcagcctg atgagcctcg ccgcgatcgt cggtccgccg   5280
ctgatgagcg gcctgttcca ctggggcagc ggtccgctcg cgccgctgcc cctggccggc   5340
gcgccattcc tcgccggcgc ccttctcgtt ctggccgggc tggtcctggc ctggcaactt   5400
cgacctacgg gagaagaacg atcatggacc ggatagacat gggcgtgctg gtggtacttc   5460
tagagcggcc gccaccgcgg tggagctcca attcgcccta gtgagtcg tattacgcgc    5520 gctcactggc cgtcgtttta caacgtcgtg actgggaaaa ccctggcgtt acccaactta   5580
atcgccttgc agcacatccc cctttcgcca gctggcgtaa tagcgaagag gcccgcaccg   5640
atcgcccttc ccaacagttg cgcagcctga atggcgaatg gaaattgtaa gcgttaatat   5700
tttgttaaaa ttcgcgttaa attttttgtta aatcagctca tttttttaacc aataggccga   5760 ctgcgatgag tggcagggcg gggcgtaatt ttttttaaggc agttattggt gcccttaaac   5820
gcctggtgct acgcctgaat aagtgataat aagcggatga atggcagaaa ttcgaaagca   5880
aattcgaccc ggtcgtcggt tcagggcagg tcgttaaaat agccgcttat gtctattgct   5940
ggtttaccgg tttattgact accggaagca gtgtgaccgt gtgcttctca aatgcctgag   6000
gccagtttgc tcaggctctc cccgtggagg taataattga cgatatgatc atttattctg   6060
cctcccagag cctgataaaa acggtgaatc cgttagcgag gtgccgccgg cttccattca   6120
ggtcgaggtg gcccggctcc atgcaccgcg acgcaacgcg gggaggcaga caaggtatag   6180
ggcggcgagg cggctacagc cgatagtctg gaacagcgca cttacgggtt gctgcgcaac   6240
ccaagtgcta ccggcgcggc agcgtgaccc gtgtcggcgg ctccaacggc tcgccatcgt   6300
ccagaaaaca cggctcatcg ggcatcggca ggcgctgctg cccgcgccgt tcccattcct   6360
ccgtttcggt caaggctggc aggtctggtt ccatgcccgg aatgccgggc tggctgggcg   6420
gctcctcgcc ggggccggtc ggtagttgct gctcgcccgg atacagggtc gggatgcggc   6480
gcaggtcgcc atgccccaac agcgattcgt cctggtcgtc gtgatcaacc accacggcgg   6540
cactgaacac cgacaggcgc aactggtcgc ggggctggcc ccacgccacg cggtcattga   6600
ccacgtaggc cgacacggtg ccggggccgt tgagcttcac gacggagatc cagcgctcgg   6660
ccaccaagtc cttgactgcg tattggaccg tccgcaaaga acgtccgatg agcttggaaa   6720
gtgtcttctg gctgaccacc acggcgttct ggtggcccat ctgcgccacg aggtgatgca   6780
gcagcattgc cgccgtgggt ttcctcgcaa taagcccggc ccacgcctca tgcgctttgc   6840
gttccgtttg cacccagtga ccgggcttgt tcttggcttg aatgccgatt tctctggact   6900
gcgtggccat gcttatctcc atgcggtagg gtgccgcacg gttgcggcac catgcgcaat   6960
cagctgcaac ttttcggcag cgcgacaaca attatgcgtt gcgtaaaagt ggcagtcaat   7020
tacagatttt ctttaaccta cgcaatgagc tattgcgggg ggtgccgcaa tgagctgttg   7080
cgtacccccc ttttttaagt tgttgatttt taagtctttc gcatttcgcc ctatatctag   7140
ttctttggtg cccaaagaag ggcacccctg cggggttccc ccacgccttc ggcgcggctc   7200
```

-continued

```
cccctccggc aaaaagtggc ccctccgggg cttgttgatc gactgcgcgg ccttcggcct      7260
tgcccaaggt ggcgctgccc ccttggaacc cccgcactcg ccgccgtgag gctcgggggg      7320
caggcgggcg ggcttcgcct tcgactgccc ccactcgcat aggcttgggt cgttccaggc      7380
gcgtcaaggc caagccgctg cgcggtcgct gcgcgagcct tgacccgcct tccacttggt      7440
gtccaaccgg caagcgaagc gcgcaggccg caggccggag gcttttcccc agagaaaatt      7500
aaaaaaattg atggggcaag gccgcaggcc gcgcagttgg agccggtggg tatgtggtcg      7560
aaggctgggt agccggtggg caatccctgt ggtcaagctc gtgggcaggc gcagcctgtc      7620
catcagcttg tccagcaggg ttgtccacgg gccgagcgaa gcgagccagc cggtggccgc      7680
tcgcggccat cgtccacata tccacgggct ggcaagggag cgcagcgacc gcgcagggcg      7740
aagcccggag agcaagcccg tagggcgccg cagccgccgt aggcggtcac gactttgcga      7800
agcaaagtct agtgagtata ctcaagcatt gagtggcccg ccggaggcac cgccttgcgc      7860 tgccccgtc gagccggttg gacaccaaaa gggaggggca ggcatggcgg catacgcgat      7920
catgcgatgc aagaagctgg cgaaaatggg caacgtggcg gccagtctca agcacgccta      7980
ccgcgagcgc gagacgccca acgctgacgc cagcaggacg ccagagaacg agcactgggc      8040
ggccagcagc accgatgaag cgatgggccg actgcgcgag ttgctgccag agaagcggcg      8100
caaggacgct gtgttggcgg tcgagtacgt catgacggcc agcccggaat ggtggaagtc      8160
ggccagccaa gaacagcagg cggcgttctt cgagaaggcg cacaagtggc tggcggacaa      8220
gtacggggcg gatcgcatcg tgacggccag catccaccgt gacgaaacca gcccgcacat      8280
gaccgcgttc gtggtgccgc tgacgcagga cggcaggctg tcggccaagg agttcatcgg      8340
caacaaagcg cagatgaccc gcgaccagac cacgtttgcg gccgctgtgg ccgatctagg      8400
gctgcaacgg ggcatcgagg gcagcaaggc acgtcacacg cgcattcagg cgttctacga      8460
ggccctggag cggccaccag tgggccacgt caccatcagc ccgcaagcgg tcgagccacg      8520
cgcctatgca ccgcagggat tggccgaaaa gctgggaatc tcaaagcgcg ttgagacgcc      8580
ggaagccgtg gccgaccggc tgacaaaagc ggttcggcag gggtatgagc ctgccctaca      8640
ggccgccgca ggagcgcgtg agatgcgcaa gaaggccgat caagcccaag agacggcccg      8700
ag                                                                    8702
```

<210> SEQ ID NO 43
<211> LENGTH: 36
<212> TYPE: DNA
<213> ORGANISM: Artificial
<220> FEATURE:
<223> OTHER INFORMATION: Primer

<400> SEQUENCE: 43
tatatataga attcggctgc gctaccgcag cccttc      36

<210> SEQ ID NO 44
<211> LENGTH: 34
<212> TYPE: DNA
<213> ORGANISM: Artificial
<220> FEATURE:
<223> OTHER INFORMATION: Primer

<400> SEQUENCE: 44
tatatatatc tagaattaat gcagctggca cgac      34

<210> SEQ ID NO 45
<211> LENGTH: 8672

-continued

<212> TYPE: DNA
<213> ORGANISM: Artificial
<220> FEATURE:
<223> OTHER INFORMATION: Vector

<400> SEQUENCE: 45

```
ctcgggccgt ctcttgggct tgatcggcct tcttgcgcat ctcacgcgct cctgcggcgg     60
cctgtagggc aggctcatac ccctgccgaa ccgcttttgt cagccggtcg gccacggctt    120
ccggcgtctc aacgcgcttt gagattccca gcttttcggc caatccctgc ggtgcatagg    180
cgcgtggctc gaccgcttgc gggctgatgg tgacgtggcc cactggtggc cgctccaggg    240
cctcgtagaa cgcctgaatg cgcgtgtgac gtgccttgct gccctcgatg ccccgttgca    300
gccctagatc ggccacagcg gccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgccccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt tctgcggcagc aactcgcgca gtcggcccat cgcttcatcg gtgctgctgg    660
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacgcggc tgcggcgccc tacgggcttg ctctccgggc    960
ttcgccctgc gcggtcgctg cgctcccttg ccagcccgtg gatatgtgga cgatggccgc   1020
gagcggccac cggctggctc gcttcgctcg gcccgtggac aaccctgctg acaagctga   1080
tggacaggct gcgcctgccc acgagcttga ccacagggat tgcccaccgg ctacccagcc   1140
ttcgaccaca tacccaccgg ctccaactgc gcggcctgcg gccttgcccc atcaatttt   1200
ttaattttct ctggggaaaa gcctccggcc tgcggcctgc gcgcttcgct tgccggttgg   1260
acaccaagtg gaaggcgggt caaggctcgc gcagcgaccg cgcagcggct tggccttgac   1320
gcgcctggaa cgacccaagc ctatgcgagt gggggcagtc gaaggcgaag cccgcccgcc   1380
tgcccccga gcctcacggc ggcgagtgcg ggggttccaa gggggcagcg ccaccttggg   1440
caaggccgaa ggccgcgcag tcgatcaaca agccccggag gggccacttt ttgccggagg   1500
gggagccgcg ccgaaggcgt gggggaaccc cgcaggggtg cccttctttg ggcaccaaag   1560
aactagatat agggcgaaat gcgaaagact taaaatcaa caacttaaaa aagggggta     1620
cgcaacagct cattgcggca cccccgcaa tagctcattg cgtaggttaa agaaaatctg    1680
taattgactg ccactttac gcaacgcata attgttgtcg cgctgccgaa aagttgcagc    1740
tgattgcgca tggtgccgca accgtgcggc accctaccgc atggagataa gcatggccac    1800
gcagtccaga gaaatcggca ttcaagccaa gaacaagccc ggtcactggg tgcaaacgga   1860
acgcaaagcg catgaggcgt gggccgggct tattgcgagg aaaccacgg cggcaatgct    1920
gctgcatcac ctcgtggcgc agatgggcca ccagaacgcc gtggtggtca gccagaagac   1980
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
```

```
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacgcgcg ggcagcagcg cctgccgatg cccgatgagc cgtgttttct   2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520
ccctatacct tgtctgcctc cccgcgttgc gtcgcggtgc atggagccgg gccacctcga   2580
cctgaatgga agccggcggc acctcgctaa cggattcacc gttttatca ggctctggga    2640
ggcagaataa atgatcatat cgtcaattat tacctccacg gggagagcct gagcaaactg   2700
gcctcaggca tttgagaagc acacggtcac actgcttccg gtagtcaata aaccggtaaa   2760
ccagcaatag acataagcgg ctatttaacg accctgccct gaaccgacga ccgggtcgaa   2820
tttgctttcg aatttctgcc attcatccgc ttattatcac ttattcaggc gtagcaccag   2880
gcgtttaagg gcaccaataa ctgccttaaa aaaattacgc cccgccctgc cactcatcgc   2940
agtcggccta ttggttaaaa aatgagctga tttaacaaaa atttaacgcg aattttaaca   3000
aaatattaac gcttacaatt tccattcgcc attcaggctg cgcaactgtt gggaagggcg   3060
atcggtgcgg gcctcttcgc tattacgcca gctggcgaaa gggggatgtg ctgcaaggcg   3120
attaagttgg gtaacgccag ggttttccca gtcacgacgt tgtaaaacga cggccagtga   3180
gcgcgcgtaa tacgactcac tatagggcga attggagctc caccgcggtg gcggccgctc   3240
tagaactagt ggatccccg ggctgcagga attcggctgc gctaccgcag cccttctccg    3300
ctaaaaccgt tagtcgaaca gttcggcgtc agccaatgcg accccaagct ggtccttgcc   3360
agacaagctt ggtacggagt cgatgggcca ttcgataccc actgccggat cattccaggc   3420
aatgcagcgc tcgcactgcg gcgagtagaa gtcggtggtc ttgtagagga actctgcggt   3480
ttcactcaac gtgacgaacc cgtgtgcgaa ccctggcggg atccacagct ggttcttgtt   3540
ctcggccgac aacaccgcac ctacccattt accgaaggtt gtggacgagc acggatatc    3600
caccgcaaca tcgaagactt cgccttgcac cacacgcacc agcttgccct gggcgtgagg   3660
tgccagctga tagtgcaggc cacggagcac gccttttacc gagcgcgagt ggttgtcttg   3720
tacgaagtcg ggctgcaggc cggtcacttc gctgaaaaca cgggcgttga agctctcgta   3780
gaagaaacca cgttcgtcgc caaaaacctt gggggtaaac agcacgactt cggggatatc   3840
cagcggaatg gcttgcatca gaacaccttc tctttcagca agttctgcag atacttgcca   3900
taaccgtttt tcagcagtgg ttgagccagg cactcgagtt gctcagcgtt gatccagcca   3960
gcgcggtagc aaatttcctc agggcaggcg actttcaagc cctgacgcg ctccatggtt    4020
gcgatgtact ggctagcctc cagcagactg tcgtgcgtgc cggtgtcgag ccacgcatag   4080
ccacggccca tgatttcgac ctgcaactgc tgctgctgca agtaaaggtt gttgaggtcg   4140
gtgatttcca gctcgccacg tggggaaggc ttcagctcgc gagccagatt gactacctga   4200
ttgtcataga aatacaggcc ggtgaccgca tagctagact ttggaactgc cggttttcct   4260
tccagcgaca atacgcgacc gctatcgtca aactccgcta cgccatagcg ttctgggtca   4320
tgaacatgat aagcgaatac tgaagcaccg gattcacgtt tatctgcgtt caatagcagt   4380
gcctggaagt catggccgta gaaaatattg tcaccgagaa ccaacgcaga agggtcgtta   4440
ccgatgaagt cagcgccgat ggtgaacgct tgcgccaagc catccgggct tggttgtatt   4500
gcgtatgaca ggttcaggcc ccactggctg ccatcgccca gcagctgttc gaagcgcggg   4560
```

```
gtgtcctgcg gggtggaaat gatcaggatg tcccggatac cagcgagcag cagggtgctc   4620
agcgggtagt agatcatcgg tttgtcatac accggcagca gctgcttcga aaccgaaagt   4680
gtggccggat gcaggcgtgt acccgaaccg ccggccagaa taattccttt acgagccatg   4740
agagtcccta ttactggatt tcgtccagca tacgttgcac gccttgctcc caaagcggca   4800
ttttgaaatt gaacgtgttt tccagtttgc ccagtgccag gcgcgagttg cgcggacgtg   4860
gtgcaggtac tggataagct tcggtgctga ttgcggcaac cttatcagct gtcactttca   4920
gcgctacgcc agtgcgttga gcatgcgcca gcacgaactg agcaaaacca tgccaagagg   4980
tttcaccgga cgcagccaag tggtaaatcc ctgccaggtg acggttgtct tgcccattga   5040
agatttgccg caggatgtgt gcagtaacgt cggcgatcag gtcagcgccc gtgggtgcgc   5100
caaattggtc tgctaccacg ctcaacgtct cacgctccgc cgccaggcgc agcatggtct   5160
tggcaaaatt gtgcccgcgc gcagcataca cccagctggt gcgcagtacc acggccttgg   5220
cgccgctggc gagaatggca tgctcgcctt ccagcttggt ccggccgtag accgaaaggg   5280
ggccggtagg cgcagtttcc tcccagcgct gactgccgct gccgtcaaat acataatcgg   5340
tggaatagtg aatcaaccag gcgcccaaag ctgctgtttc acgtgctaat acagcaggag   5400
ccgcggcatt gatcattgca gccagtgcct gatcgctctc agctttatcc actgcagtgt   5460
aggcagcagc gttgacgatc acgtccggcg ccagctgacg aatcgtagcg gccaagccgt   5520
ccaggttgga caagtcgcca cataagccct cggcccctg acgatccagc gcaatgacct   5580
cacccagcgg cgccaaggcg cgctgtagct cccagcctac ttgcccgttt ttccccaaca   5640
gcaggatttt cacgctttat tgccccgta ttgttgtgcc acccagtcac ggtagctgcc   5700
gtccatgaca ccttttaccc atttctggtt ggccaagtac caagcgactg tctttcgaat   5760
gcccgtctcg aaggtttcgg cagtttccag ccgagctccc gctcgatctt gcgtgcatcg   5820
atggcataac ggcggtcatg gcctgggcgg tcggttacgt aggcgatgag ttctgcatac   5880
tgttcgacag gctcgccggt cttctgattg attacctggc gcgatgccgc aggtgccatc   5940
tcgtcgagaa ggctgcagag tgtacgcaca atgtcaatgt tggcttttc attccagccg   6000 ccaatattgt acgtctcgcc gaacgcaccg gcttccagta cgccgacggat gcccgagcag   6060 tgatcttcga catacagcca gtcgcggatt tgctggccgt cgccatagac aggcagcgcc   6120
ttaccggcga gtgcgttgac gatcatcagc gggatcagtt tttccgggaa gtggagcggc   6180
ccgtaattgt tggagcagtt ggtagtgagt accggcatgc cgtaggtatg gaaatacgag   6240
cgtaccagat ggtcgctggc tgccttgctg gcggagtatg gctgttcgg cgcgtacggc   6300 gtggtttcgg tgaacgccgg gtcgtttggc cctagtgtgc cgtagacttc gtcggtagag   6360
acatggagga aacggaaggc ctccttctct gcaccttcca aactattcca atgcgcccgg   6420
gcggcttcaa gcaagcgaaa cgtgcccatc acgttggttt cgacaaacgc ttcggggccg   6480
gtgattgagc ggtctacatg ggattccgcc gcgaagtgaa ccacggcgcg cgggcggtgc   6540
tctgcgaaca gcttggtcag aagcgcagca tcgcaaatat tgccttgcac aaagcgatgc   6600
tgagggttgc cttccagcgg ctgcaggttg gccaggttgc ctgcgtaggt cagggcgtcg   6660
aggttgagga cgggttcctc attgtgcgca caccattgca gtacgaaatt tgagccgatg   6720
aagccggctc cgcctgttac tagaatcata atttggctct aattggacaa aggtgttgt   6780 cgtagacaga tgacgcgaat tcgatatcaa gcttatcgat accgtcgacc tcgaggggg   6840 gcccggtacc cagcttttgt tccctttagt gagggttaat tgcgcgcttg gcgtaatcat   6900
```

```
ggtcatagct gtttcctgtg tgaaattgtt atccgctcac aattccacac aacatacgag      6960
ccggaagcat aaagtgtaaa gcctggggtg cctaatgagt gagctaactc acattaattg      7020
cgttgcgctc actgcccgct ttccagtcgg gaaacctgtc gtgccagctg cattaatgaa      7080
tcggccaacg cgcggggaga ggcggtttgc gtattgggcg catgcataaa aactgttgta      7140
attcattaag cattctgccg acatggaagc catcacaaac ggcatgatga acctgaatcg      7200
ccagcggcat cagcaccttg tcgccttgcg tataatattt gcccatgggg gtgggcgaag      7260
aactccagca tgagatcccc gcgctggagg atcatccagc cggcgtcccg gaaaacgatt      7320
ccgaagccca acctttcata aaggcggcg gtggaatcga atctcgtga tggcaggttg        7380 ggcgtcgctt ggtcggtcat ttcgaacccc agagtcccgc tcagaagaac tcgtcaagaa      7440
ggcgatagaa ggcgatgcgc tgcgaatcgg agcggcgat accgtaaagc acgaggaagc       7500
ggtcagccca ttcgccgcca agctcttcag caatatcacg ggtagccaac gctatgtcct      7560
gatagcggtc cgccacaccc agccggccac agtcgatgaa tccagaaaag cggccatttt      7620
ccaccatgat attcggcaag caggcatcgc catgggtcac gacgagatcc tcgccgtcgg      7680
gcatgcgcgc cttgagcctg gcgaacagtt cggctggcgc gagcccctga tgctcttcgt      7740
ccagatcatc ctgatcgaca gaccggctt ccatccgagt acgtgctcgc tcgatgcgat       7800
gtttcgcttg gtggtcgaat gggcaggtag ccggatcaag cgtatgcagc cgccgcattg      7860
catcagccat gatggatact ttctcggcag gagcaaggtg agatgacagg agatcctgcc      7920
ccggcacttc gcccaatagc agccagtccc ttcccgcttc agtgacaacg tcgagcacag      7980
ctgcgcaagg aacgcccgtc gtggccagcc acgatagccg cgctgcctcg tcctgcagtt      8040
cattcagggc accggacagg tcggtcttga caaaagaac cgggcgcccc tgcgctgaca       8100 gccgaacac ggcggcatca gagcagccga ttgtctgttg tgcccagtca tagccgaata       8160
gcctctccac ccaagcggcc ggagaacctg cgtgcaatcc atcttgttca atcatgcgaa      8220
acgatcctca tcctgtctct tgatcagatc ttgatcccct cgccatcag atccttggcg       8280 gcaagaaagc catccagttt actttgcagg gcttcccaac cttaccagag ggcgccccag      8340
ctggcaattc cggttcgctt gctgtccata aaaccgccca gtctagctat cgccatgtaa      8400
gcccactgca agctacctgc tttctctttg cgcttgcgtt ttcccttgtc cagatagccc      8460
agtagctgac attcatccca ggtggcactt tcggggaaa tgtgcgcgcc cgcgttcctg       8520
ctggcgctgg gcctgtttct ggcgctggac ttcccgctgt tccgtcagca gcttttcgcc      8580
cacggccttg atgatcgcgg cggccttggc ctgcatatcc cgattcaacg gccccagggc      8640
gtccagaacg ggcttcaggc gctcccgaag gt                                    8672

<210> SEQ ID NO 46
<211> LENGTH: 21
<212> TYPE: DNA
<213> ORGANISM: Artificial
<220> FEATURE:
<223> OTHER INFORMATION: Primer

<400> SEQUENCE: 46
ggccgctcta gaactagtgg a                                                21

<210> SEQ ID NO 47
<211> LENGTH: 12249
<212> TYPE: DNA
<213> ORGANISM: Artificial
<220> FEATURE:
<223> OTHER INFORMATION: Vector
```

<400> SEQUENCE: 47

```
ctcgggccgt ctcttgggct tgatcggcct tcttgcgcat ctcacgcgct cctgcggcgg      60
cctgtagggc aggctcatac ccctgccgaa ccgcttttgt cagccggtcg gccacggctt     120
ccggcgtctc aacgcgcttt gagattccca gcttttcggc caatccctgc ggtgcatagg     180
cgcgtggctc gaccgcttgc gggctgatgg tgacgtggcc cactggtggc cgctccaggg     240
cctcgtagaa cgcctgaatg cgcgtgtgac gtgccttgct gccctcgatg ccccgttgca     300
gccctagatc ggccacagcg gccgcaaacg tggtctggtc gcgggtcatc tgcgctttgt     360
tgccgatgaa ctccttggcc gacagcctgc cgtcctgcgt cagcggcacc acgaacgcgg     420
tcatgtgcgg gctggtttcg tcacggtgga tgctggccgt cacgatgcga tccgccccgt     480
acttgtccgc cagccacttg tgcgccttct cgaagaacgc cgcctgctgt tcttggctgg     540
ccgacttcca ccattccggg ctggccgtca tgacgtactc gaccgccaac acagcgtcct     600
tgcgccgctt ctctggcagc aactcgcgca gtcggcccat cgcttcatcg gtgctgctgg     660
ccgcccagtg ctcgttctct ggcgtcctgc tggcgtcagc gttgggcgtc tcgcgctcgc     720
ggtaggcgtg cttgagactg gccgccacgt tgcccatttt cgccagcttc ttgcatcgca     780
tgatcgcgta tgccgccatg cctgcccctc ccttttggtg tccaaccggc tcgacggggg     840
cagcgcaagg cggtgcctcc ggcgggccac tcaatgcttg agtatactca ctagactttg     900
cttcgcaaag tcgtgaccgc ctacgcggcg tgcggcgccc tacgggcttg ctctccgggc     960
ttcgccctgc gcggtcgctg cgctcccttg ccagcccgtg gatatgtgga cgatggccgc    1020
gagcggccac cggctggctc gcttcgctcg gcccgtggac aaccctgctg acaagctga    1080
tggacaggct gcgcctgccc acgagcttga ccacagggat tgcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt gggggcagtc gaaggcgaag cccgcccgcc    1380
tgcccccga gcctcacggc ggcgagtgcg ggggttccaa gggggcagcg ccaccttggg    1440
caaggccgaa ggccgcgcag tcgatcaaca agccccggag gggccacttt ttgccggagg    1500
gggagccgcg ccgaaggcgt gggggaaccc cgcaggggtg cccttctttg ggcaccaaag    1560
aactagatat agggcgaaat gcgaaagact taaaaatcaa caacttaaaa aagggggta    1620
cgcaacagct cattgcggca cccccgcaa tagctcattg cgtaggttaa agaaaatctg    1680
taattgactg ccacttttac gcaacgcata attgttgtcg cgctgccgaa aagttgcagc    1740
tgattgcgca tggtgccgca accgtgcggc accctaccgc atggagataa gcatggccac    1800
gcagtccaga gaaatcggca ttcaagccaa gaacaagccc ggtcactggg tgcaaacgga    1860
acgcaaagcg catgaggcgt gggccgggct tattgcgagg aaacccacgg cggcaatgct    1920
gctgcatcac ctcgtggcgc agatgggcca ccagaacgcc gtggtggtca gccagaagac    1980
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
tgccgccgtg gtggttgatc acgacgacca ggacgaatcg ctgttggggc atggcgacct    2220
gcgccgcatc ccgaccctgt atccgggcga gcagcaacta ccgaccggcc ccggcgagga    2280
```

```
gccgcccagc cagcccggca ttccgggcat ggaaccagac ctgccagcct tgaccgaaac    2340
ggaggaatgg gaacggcgcg ggcagcagcg cctgccgatg cccgatgagc cgtgttttct    2400
ggacgatggc gagccgttgg agccgccgac acgggtcacg ctgccgcgcc ggtagcactt    2460
gggttgcgca gcaacccgta agtgcgctgt tccagactat cggctgtagc cgcctcgccg    2520
ccctatacct tgtctgcctc cccgcgttgc gtcgcggtgc atggagccgg gccacctcga    2580
cctgaatgga agccggcggc acctcgctaa cggattcacc gttttatca ggctctggga    2640 ggcagaataa atgatcatat cgtcaattat tacctccacg gggagagcct gagcaaactg    2700
gcctcaggca tttgagaagc acacggtcac actgcttccg gtagtcaata aaccggtaaa    2760
ccagcaatag acataagcgg ctatttaacg accctgccct gaaccgacga ccgggtcgaa    2820 tttgcttttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagaactagt ggatccccccg ggctgcagga attcggctgc gctaccgcag cccttctccg    3300
ctaaaaccgt tagtcgaaca gttcggcgtc agccaatgcg accccaagct ggtccttgcc    3360
agacaagctt ggtacggagt cgatgggcca ttcgataccc actgccggat cattccaggc    3420
aatgcagcgc tcgcactgcg gcgagtagaa gtcggtggtc ttgtagagga actctgcggt    3480
ttcactcaac gtgacgaacc cgtgtgcgaa ccctggcggg atccacagct ggttcttgtt    3540
ctcggccgac aacaccgcac ctacccattt accgaaggtt gtggacgagc gacggatatc    3600
caccgcaaca tcgaagactt cgccttgcac cacacgcacc agcttgccct gggcgtgagg    3660
tgccagctga tagtgcaggc cacggagcac gccttttacc gagcgcgagt ggttgtcttg    3720
tacgaagtcg ggctgcaggc cggtcacttc gctgaaaaca cgggcgttga agctctcgta    3780
gaagaaacca cgttcgtcgc caaaaacctt gggggtaaac agcacgactt cggggatatc    3840
cagcggaatg gcttgcatca gaacaccttc tctttcagca agttctgcag atacttgcca    3900
taaccgtttt tcagcagtgg ttgagccagg cactcgagtt gctcagcgtt gatccagcca    3960
gcgcggtagc aaatttcctc agggcaggcg actttcaagc cctgacgcg ctccatggtt    4020 gcgatgtact ggctagcctc cagcagactg tcgtgcgtgc cggtgtcgag ccacgcatag    4080
ccacggccca tgatttcgac ctgcaactgc tgctgctgca agtaaaggtt gttgaggtcg    4140
gtgatttcca gctcgccacg tggggaaggc ttcagctcgc gagccagatt gactacctga    4200
ttgtcataga aatacaggcc ggtgaccgca tagctagact ttggaactgc cggttttttct    4260 tccagcgaca atacgcgacc gctatcgtca aactccgcta cgccatagcg ttctgggtca    4320
tgaacatgat aagcgaatac tgaagcaccg gattcacgtt tatctgcgtt caatagcagt    4380
gcctggaagt catggccgta gaaaatattg tcaccgagaa ccaacgcaga agggtcgtta    4440
ccgatgaagt cagcgccgat ggtgaacgct tgcgccaagc catccgggct tggttgtatt    4500
gcgtatgaca ggttcaggcc ccactggctg ccatcgccca gcagctgttc gaagcgcggg    4560
gtgtcctgcg gggtggaaat gatcaggatg tcccggatac cagcgagcag cagggtgctc    4620
agcgggtagt agatcatcgg tttgtcatac accggcagca gctgcttcga aaccgaaagt    4680
```

```
gtggccggat gcaggcgtgt acccgaaccg ccggccagaa taattccttt acgagccatg   4740
agagtcccta ttactggatt tcgtccagca tacgttgcac gccttgctcc caaagcggca   4800
ttttgaaatt gaacgtgttt tccagtttgc ccagtgccag gcgcgagttg cgcggacgtg   4860
gtgcaggtac tggataagct tcggtgctga ttgcggcaac cttatcagct gtcactttca   4920
gcgctacgcc agtgcgttga gcatgcgcca gcacgaactg agcaaaacca tgccaagagg   4980
tttcaccgga cgcagccaag tggtaaatcc ctgccaggtg acggttgtct tgcccattga   5040
agatttgccg caggatgtgt gcagtaacgt cggcgatcag gtcagcgccc gtgggtgcgc   5100
caaattggtc tgctaccacg ctcaacgtct cacgctccgc cgccaggcgc agcatggtct   5160
tggcaaaatt gtgcccgcgc gcagcataca cccagctggt gcgcagtacc acggccttgg   5220
cgccgctggc gagaatggca tgctcgcctt ccagcttggt ccggccgtag accgaaaggg   5280
ggccggtagg cgcagtttcc tcccagcgct gactgccgct gccgtcaaat acataatcgg   5340
tggaatagtg aatcaaccag gcgcccaaag ctgctgtttc acgtgctaat acagcaggag   5400
ccgcggcatt gatcattgca gccagtgcct gatcgctctc agctttatcc actgcagtgt   5460
aggcagcagc gttgacgatc acgtccggcg ccagctgacg aatcgtagcg gccaagccgt   5520
ccaggttgga caagtcgcca cataagccct cggcccctg acgatccagc gcaatgacct   5580
cacccagcgg cgccaaggcg cgctgtagct cccagcctac ttgcccgttt ttccccaaca   5640
gcaggatttt cacgctttat ttgccccgta ttgttgtgcc acccagtcac ggtagctgcc   5700
gtccatgaca cctttaccc atttctggtt ggccaagtac caagcgactg tctttcgaat   5760
gcccgtctcg aaggtttcgg caggtttcca gccgagctcc cgctcgatct tgcgtgcatc   5820
gatggcataa cggcggtcat ggcctgggcg gtcggttacg taggcgatga gttctgcata   5880
ctgttcgaca ggctcgccgg tcttctgatt gattacctgg cgcgatgccg caggtgccat   5940
ctcgtcgaga aggctgcaga gtgtacgcac aatgtcaatg ttggctttttt cattccagcc   6000 gccaatattg tacgtctcgc cgaacgcacc ggcttccagt acgcgacgga tgcccgagca   6060
gtgatcttcg acatacagcc agtcgcggat ttgctggccg tcgccataga caggcagcgc   6120
cttaccggcg agtgcgttga cgatcatcag cgggatcagt ttttccggga agtggagcgg   6180
cccgtaattg ttggagcagt tggtagtgag taccggcatg ccgtaggtat ggaaatacga   6240
gcgtaccaga tggtcgctgg ctgccttgct ggcggagtat gggctgttcg gcgcgtacgg   6300
cgtggtttcg gtgaacgccg ggtcgtttgg ccctagtgtg ccgtagactt cgtcggtaga   6360
gacatggagg aaacggaagg cctccttctc tgcaccttcc aaactattcc aatgcgcccg   6420
ggcggcttca gcaagcgaa acgtgcccat cacgttggtt tcgacaaacg cttcggggcc   6480
ggtgattgag cggtctacat gggattccgc cgcgaagtga accacggcgc gcgggcggtg   6540
ctctgcgaac agcttggtca gaagcgcagc atcgcaaata ttgccttgca caaagcgatg   6600
ctgagggttg ccttccagcg gctgcaggtt ggccaggttg cctgcgtagg tcagggcgtc   6660
gaggttgagg acgggttcct cattgtgcgc acaccattgc agtacgaaat ttgagccgat   6720
gaagccggct ccgcctgtta ctagaatcat aatttggctc taattggaca aaaggtgttg   6780
tcgtagacag atgacgcgaa ttcgatatca agcttatcga taccgtcgac ctcgaggggg   6840
ggcccggtac ccagcttttg ttccctttag tgagggttaa ttgcgcgctt ggcgtaatca   6900
tggtcatagc tgtttcctgt gtgaaattgt tatccgctca caattccaca caacatacga   6960
gccggaagca taaagtgtaa agcctggggt gcctaatgag tgagctaact cacattaatt   7020
```

```
gcgttgcgct cactgcccgc tttccagtcg ggaaacctgt cgtgccagct gcattaattc    7080
tagagggaat gcgtttcgcc gactaggcct tggccttgcc ggaagctacg gacgccacgg    7140
ccgggccggc gaggcgcttc agcaggcgcg ggcggttggt ctccagcgcg ccgccgcgtc    7200
cccgcaggcc gtcccacagg ccccagccca ggcagcgcag cttgagcagc ttgtcgcgtt    7260
cgagcaggag caccgcgagg ccctgggtca gggtcggcag gttcgccagc agggccagcg    7320
gcgaggaccg ggcgtagcgg cgcaggacca gcaggccgtt gcgcgccagg tagtagcggc    7380
gcagcggggc gtggttcatc gcgctgaggc tgagaccgcc gaggcggcgg gtcttgcgcg    7440
tgccgatgcg gtgctcgagg accagccgcg ggtcgacgta caggggcacg tccagcgcct    7500
gggcgcgcag gctgtattcg gtgtccacgt ggtcgatgaa cagttcctcg tcgaagtggc    7560
cgaggcgctg gtaggcctcg cgggtcagca ggcagccgga ggagatcagg aacgaggtgc    7620 gctgcgggt cgtcaggccg tccagagaca attgcctgag cgtcagtccg tcgagatgga    7680
tggccggcag gaagcgccgg tcaccccggt cgaagatccg tgggccgagc aggcaggcct    7740
gaccgttgcg cgcctgcagg ttgcgccact gggcggcgag gaaggcgccg ccgggacggg    7800
agtcctggtc gagcagcagc acaccctgca cgccacgccg gaatagcgcg tcgagtccct    7860
ggttgaaggc gccggcgatg ccctgccggt tgccgtggtg cagcacggcg atgccttgcc    7920
cgcgcagccg ggcattgcgc tgcggatcgc tgtgcggtga gttgtcgacg gcaaggaagc    7980
gcagttgcgg aaacgccgcc gccagttcgc caaggtgttc caggtcgtcg tcgccaggat    8040
tgaacagtac caccagcacg cccatgtcta tccggtccat gatcgttctt ctcccgtagg    8100
tcaggacgca gccttcagcc atcgcgcatc cccctcccta tgacaacgtt cgaccacctg    8160
ggccgcttta ccgcaagcga tactgtgcgg ttgtgacaat tccatgaaac gccgacaggc    8220
cgccgccatg gccgggtcct cgagcaagcg ccacagcgcc ccgcgcaact cctgctcgcg    8280
caatggcacg cccaggcgca tcccgcagcc gagccggacc agccgttcgg cattgtcgaa    8340
ctggtcgtgg gcgcagggca gcagcacctg cggcaccccc gccgcaagg ccaggctcat    8400 ggcgccgata ccgcccggat ggaccagccc ggcgcacgat ggcagcaagg ctcccagtgg    8460
cgcgtaggcg cgctgcagca cgtggttcgg caagccgcgc agcggttcct ggccggcgcc    8520
ggtgaggaag atcccacgcg cgccgaggcg ttccagcgcg cgcagggcca tggcgtagaa    8580
gtcgccctgc aggtgttcgg tcgagccctg ggtgaacacc agcggccggc tgccctgatc    8640
gagaaagcgt tgcagttcgt cgtcgagcgg ggtccccggg atactgccgt cgaacagcgg    8700
gaagccggtc atgtgcaggg gttgcggcca atcctgctgg ggcggcgcga accaggccgg    8760
gaacaggcag accacgccct gcggcgaatg catccattgg gtgaagatgc gcttcaccgg    8820
cgtctccagg ccgaccttgc gccgcaccgc gttgatatcc ggcgcgcagg tgcgatccag    8880
cttgaagcgc tcgatgcagc gccagagcag cttgcgcatc gccagcggca tctgctcggg    8940
cacgttgaac ttggggtgta ccggcggcag gtgcgccgac aacaaggtcg atggcgagac    9000
ctgcgcggac aggtagggaa tcccgtactt ctcgtgagcg atgcgtgcgc ccagcgccca    9060
gagcgagccg accaccacga tgtcgtcatg gcgctgcgcc gagacgtact cgtagaccgg    9120
ctcgatcatc ccggcgatgg tttgccagag cacgccgaag gacgtcttgg ggtcccacag    9180
gcgcggatcg cccatggtcc ggcggtaggt cagttcgtcg ctcagcggga cgaacgcgat    9240
gccgtgctgc tccaccgcgt cgcgaaacac cgggatggtg cagaggctca cgcggtgccc    9300
gcgcaatttc agggtccggg ccaggccgat gaagggaaat acgtcgccgg ccgagccgat    9360
ggcgatgagg atggcgtgca tggtgctact ccgtgcgtta tgcaaccgca aagcccggcc    9420
```

```
aggccgggtc ttcgcaggtc aagggttcag gcgtagccga tggccatctc gtggaatccc    9480
gccgcgcgtt ccgcccgctg cggctccggt tgcttcagca ggtgctcgag cagggcgcgg    9540
tgcacgcgta ccgcggccag cttggactcc aggtcgagga aatgcccggt gccctccacc    9600
cgcgagaaac tgcagtgcgg caggtagtcg cggaactggc gggcgtcctc ggcggtggtg    9660
tattcgtccc agctgccgtt gatgaaatgc acgtggctct ggatccgctc caggcaagcc    9720
aggtagcccc gatcgttgag cgccagcacc tggtcgatgt gaaagcgcgc ctgctcgtat    9780
tcgccggtgg ccagcgaagc catgtgctga tggttgctgg ctttcaggcg cggcggcagg    9840
tatttgccga cggtctcgtt gagcagatgg ccgatcgccg acttgtcgtc cagctcgatc    9900
agcgcctgcg cccgcccgac gtagtcgagc atcgcctggt tcagtccagg ggcgaatgcc    9960
atcaccaccg agctgcggat gccgcgcgga ttgcgcgaca gcgccagcag cgtggagata   10020
ccgccccagg acgcggagac caggtgattg acctcgaagc gctcgatcag cgccaggagg   10080
atttccacct cgtcgtcctt ggtgatcaac cccgctgcg gttgtgctg acgcgactgc   10140 ccggcgaagg gcaggtcgaa cagcaccacg ttgaaatgtt cggccaggca cttgcaggtc   10200
cgggcgaacg aggcggtggt cgccatcgcg ccgttgacca gcatcaccgt gctgcgcccg   10260
ggatcctgcc caacgcgctc gacatgtacc cgcaggccct tgcaaaccga taccaacaga   10320
ctttcgcgcc gcatttcaca cctcccaaaa atgccagatc ccccgggctg caggaattcg   10380
atatcaagct tatcgatacc gtcgacctcg agggggggcc cggtacccag cttttgttcc   10440
ctttagtgag ggttaattgc gcgcttggcg taatcatggt catagctgtt tcctgtgtga   10500
aattgttatc cgctcacaat tccacacaac atacgagccg gaagcataaa gtgtaaagcc   10560
tggggtgcct aatgagtgag ctaactcaca ttaattgcgt tgcgctcact gcccgctttc   10620
cagtcgggaa acctgtcgtg ccagctgcat taatgaatcg gccaacgcgc ggggagaggc   10680
ggtttgcgta ttgggcgcat gcataaaaac tgttgtaatt cattaagcat tctgccgaca   10740
tggaagccat cacaaacggc atgatgaacc tgaatcgcca gcggcatcag caccttgtcg   10800
ccttgcgtat aatatttgcc catggggtg ggcgaagaac tccagcatga tccccgcg   10860 ctggaggatc atccagccgg cgtcccggaa aacgattccg aagcccaacc tttcatagaa   10920
ggcggcggtg aatcgaaat ctcgtgatgg caggttgggc gtcgcttggt cggtcatttc   10980 gaacccccaga gtcccgctca aagaactcg tcaagaaggc gatagaaggc gatgcgctgc   11040
gaatcgggag cggcgatacc gtaaagcacg aggaagcggt cagcccattc gccgccaagc   11100
tcttcagcaa tatcacgggt agccaacgct atgtcctgat agcggtccgc cacacccagc   11160
cggccacagt cgatgaatcc agaaaagcgg ccattttcca ccatgatatt cggcaagcag   11220
gcatcgccat gggtcacgac gagatcctcg ccgtcgggca tgcgcgcctt gagcctggcg   11280
aacagttcgg ctggcgcgag cccctgatgc tcttcgtcca gatcatcctg atcgacaaga   11340
ccggcttcca tccgagtacg tgctcgctcg atgcgatgtt tcgcttggtg gtcgaatggg   11400
caggtagccg gatcaagcgt atgcagccgc cgcattgcat cagccatgat ggatactttc   11460
tcggcaggag caaggtgaga tgacaggaga tcctgccccg gcacttcgcc caatagcagc   11520
cagtcccttc ccgcttcagt gacaacgtcg agcacagctg cgcaaggaac gcccgtcgtg   11580
gccagccacg atagccgcgc tgcctcgtcc tgcagttcat tcagggcacc ggacaggtcg   11640
gtcttgacaa aaagaaccgg gcgcccctgc gctgacagcc ggaacacggc ggcatcagag   11700
cagccgattg tctgttgtgc ccagtcatag ccgaatagcc tctccaccca agcggccgga   11760
```

```
gaacctgcgt gcaatccatc ttgttcaatc atgcgaaacg atcctcatcc tgtctcttga    11820
tcagatcttg atccctgcg ccatcagatc cttggcggca agaaagccat ccagtttact    11880
ttgcagggct tcccaacctt accagagggc gccccagctg gcaattccgg ttcgcttgct    11940
gtccataaaa ccgcccagtc tagctatcgc catgtaagcc cactgcaagc tacctgcttt    12000
ctctttgcgc ttgcgttttc ccttgtccag atagcccagt agctgacatt catcccaggt    12060 ggcactttc ggggaaatgt gcgcgcccgc gttcctgctg cgctgggcc tgtttctggc    12120 gctggacttc ccgctgttcc gtcagcagct tttcgcccac ggccttgatg atcgcggcgg    12180
ccttggcctg catatcccga ttcaacggcc cagggcgtc cagaacgggc ttcaggcgct    12240
cccgaaggt                                                           12249
```

```
<210> SEQ ID NO 48
<211> LENGTH: 37
<212> TYPE: DNA
<213> ORGANISM: Artificial
<220> FEATURE:
<223> OTHER INFORMATION: Primer

<400> SEQUENCE: 48
tatatataga attcgcgtca tctgtctacg acaacac                                  37

<210> SEQ ID NO 49
<211> LENGTH: 5144
<212> TYPE: DNA
<213> ORGANISM: Artificial
<220> FEATURE:
<223> OTHER INFORMATION: Vector

<400> SEQUENCE: 49
```

```
ctcgggccgt ctcttgggct tgatcggcct tcttgcgcat ctcacgcgct cctgcggcgg      60
cctgtagggc aggctcatac ccctgccgaa ccgcttttgt cagccggtcg gccacggctt     120
ccggcgtctc aacgcgcttt gagattccca gcttttcggc caatccctgc ggtgcatagg     180
cgcgtggctc gaccgcttgc gggctgatgg tgacgtggcc cactggtggc cgctccaggg     240
cctcgtagaa cgcctgaatg cgcgtgtgac gtgccttgct gccctcgatg ccccgttgca     300
gccctagatc ggccacagcg gccgcaaacg tggtctggtc gcgggtcatc tgcgctttgt     360
tgccgatgaa ctccttggcc gacagcctgc cgtcctgcgt cagcggcacc acgaacgcgg     420
tcatgtgcgg gctggtttcg tcacggtgga tgctggccgt cacgatgcga tccgccccgt     480
acttgtccgc cagccacttg tgcgccttct cgaagaacgc cgcctgctgt tcttggctgg     540
ccgacttcca ccattccggg ctggccgtca tgacgtactc gaccgccaac acagcgtcct     600
tgcgccgctt ctctggcagc aactcgcgca gtcggcccat cgcttcatcg gtgctgctgg     660
ccgcccagtg ctcgttctct ggcgtcctgc tggcgtcagc gttgggcgtc tcgcgctcgc     720
ggtaggcgtg cttgagactg gccgccacgt tgcccatttt cgccagcttc ttgcatcgca     780
tgatcgcgta tgccgccatg cctgcccctc ccttttggtg tccaaccggc tcgacggggg     840
cagcgcaagg cggtgcctcc ggcgggccac tcaatgcttg agtatactca ctagactttg     900
cttcgcaaag tcgtgaccgc ctacggcgg tgcggcgccc tacggcttg ctctccgggc     960 ttcgccctgc gcggtcgctg cgctcccttg ccagcccgtg atatgtgga cgatggccgc    1020 gagcggccac cggctggctc gcttcgctcg gcccgtggac aaccctgctg gacaagctga    1080
tggacaggct gcgcctgccc acgagcttga ccacagggat tgcccaccgg ctacccagcc    1140
ttcgaccaca tacccaccgg ctccaactgc gcggcctgcg gccttgcccc atcaattttt    1200
```

```
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt gggggcagtc gaaggcgaag cccgcccgcc    1380 tgcccccga gcctcacggc ggcgagtgcg ggggttccaa gggggcagcg ccaccttggg     1440
caaggccgaa ggccgcgcag tcgatcaaca agccccggag gggccacttt tgccggagg     1500 gggagccgcg ccgaaggcgt gggggaaccc cgcaggggtg cccttctttg ggcaccaaag    1560
aactagatat agggcgaaat gcgaaagact taaaaatcaa caacttaaaa aaggggggta    1620
cgcaacagct cattgcggca ccccccgcaa tagctcattg cgtaggttaa agaaaatctg    1680
taattgactg ccacttttac gcaacgcata attgttgtcg cgctgccgaa aagttgcagc    1740
tgattgcgca tggtgccgca accgtgcggc accctaccgc atggagataa gcatggccac    1800
gcagtccaga gaaatcggca ttcaagccaa gaacaagccc ggtcactggg tgcaaacgga    1860
acgcaaagcg catgaggcgt gggccgggct tattgcgagg aaacccacgg cggcaatgct    1920
gctgcatcac ctcgtggcgc agatgggcca ccagaacgcc gtggtggtca gccagaagac    1980
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
tgccgccgtg gtggttgatc acgacgacca ggacgaatcg ctgttggggc atggcgacct    2220
gcgccgcatc ccgaccctgt atccgggcga gcagcaacta ccgaccggcc ccggcgagga    2280 gccgccagc cagcccggca ttccgggcat ggaaccagac ctgccagcct tgaccgaaac     2340
ggaggaatgg gaacgcgcg ggcagcagcg cctgccgatg cccgatgagc cgtgttttct     2400
ggacgatggc gagccgttgg agccgccgac acgggtcacg ctgccgcgcc ggtagcactt    2460
gggttgcgca gcaacccgta agtgcgctgt tccagactat cggctgtagc cgcctcgccg    2520
ccctatacct tgtctgcctc cccgcgttgc gtcgcggtgc atggagccgg gccacctcga    2580
cctgaatgga agccggcggc acctcgctaa cggattcacc gttttttatca ggctctggga    2640 ggcagaataa atgatcatat cgtcaattat tacctccacg gggagagcct gagcaaactg    2700
gcctcaggca tttgagaagc acacggtcac actgcttccg gtagtcaata aaccggtaaa    2760
ccagcaatag acataagcgg ctatttaacg accctgccct gaaccgacga ccgggtcgaa    2820 tttgcttcg aatttctgcc attcatccgt ttattatcac ttattcaggc gtagcaccag     2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tataggcga attggagctc caccgcggtg gcggccgctc    3240
tagaactagt ggatccccg ggctgcagga attcgatatc aagcttatcg ataccgtcga    3300
cctcgagggg gggcccggta cccagctttt gttccccttta gtgagggtta attgcgcgct    3360
tggcgtaatc atggtcatag ctgtttcctg tgtgaaattg ttatccgctc acaattccac    3420
acaacatacg agccgaagc ataaagtgta aagcctgggg tgcctaatga gtgagctaac    3480
tcacattaat tgcgttgcgc tcactgcccg ctttccagtc gggaaacctg tcgtgccagc    3540
```

```
tgcattaatg aatcggccaa cgcgcggga gaggcggttt gcgtattggg cgcatgcata    3600
aaaactgttg taattcatta agcattctgc cgacatggaa gccatcacaa acggcatgat    3660
gaacctgaat cgccagcggc atcagcacct tgtcgccttg cgtataatat ttgcccatgg    3720
gggtgggcga agaactccag catgagatcc ccgcgctgga ggatcatcca gccggcgtcc    3780
cggaaaacga ttccgaagcc caacctttca tagaaggcgg cggtggaatc gaaatctcgt    3840
gatggcaggt tgggcgtcgc ttggtcggtc atttcgaacc ccagagtccc gctcagaaga    3900
actcgtcaag aaggcgatag aaggcgatgc gctgcgaatc gggagcggcg ataccgtaaa    3960
gcacgaggaa gcggtcagcc cattcgccgc caagctcttc agcaatatca cgggtagcca    4020
acgctatgtc ctgatagcgg tccgccacac ccagccggcc acagtcgatg aatccagaaa    4080
agcggccatt ttccaccatg atattcggca agcaggcatc gccatgggtc acgacgagat    4140
cctcgccgtc gggcatgcgc gccttgagcc tggcgaacag ttcggctggc gcgagcccct    4200
gatgctcttc gtccagatca tcctgatcga caagaccggc ttccatccga gtacgtgctc    4260
gctcgatgcg atgtttcgct tggtggtcga atgggcaggt agccggatca agcgtatgca    4320
gccgccgcat tgcatcagcc atgatggata cttttctcggc aggagcaagg tgagatgaca    4380
ggagatcctg ccccggcact tcgcccaata gcagccagtc ccttcccgct tcagtgacaa    4440
cgtcgagcac agctgcgcaa ggaacgcccg tcgtggccag ccacgatagc cgcgctgcct    4500
cgtcctgcag ttcattcagg gcaccggaca ggtcggtctt gacaaaaaga accgggcgcc    4560
cctgcgctga cagccggaac acggcggcat cagagcagcc gattgtctgt tgtgcccagt    4620
catagccgaa tagcctctcc acccaagcgg ccggagaacc tgcgtgcaat ccatcttgtt    4680
caatcatgcg aaacgatcct catcctgtct cttgatcaga tcttgatccc ctgcgccatc    4740
agatccttgg cggcaagaaa gccatccagt ttactttgca gggcttccca accttaccag    4800
agggcgcccc agctggcaat tccggttcgc ttgctgtcca taaaaccgcc cagtctagct    4860
atcgccatgt aagcccactg caagctacct gctttctctt tgcgcttgcg ttttcccttg    4920
tccagatagc ccagtagctg acattcatcc caggtggcac ttttcgggga aatgtgcgcg    4980
cccgcgttcc tgctggcgct gggcctgttt ctggcgctgg acttcccgct gttccgtcag    5040
cagcttttcg cccacggcct tgatgatcgc ggcggccttg gcctgcatat cccgattcaa    5100
cggcccagg gcgtccagaa cgggcttcag gcgctcccga aggt              5144
```

<210> SEQ ID NO 50
<211> LENGTH: 4549
<212> TYPE: DNA
<213> ORGANISM: Pseudomonas aeruginosa

<400> SEQUENCE: 50

```
ggtaccagat ctggcatttt tgggaggtgt gaaatgcggc gcgaaagtct gttggtatcg      60
gtttgcaagg gcctgcgggt acatgtcgag cgcgttgggc aggatcccgg cgcagcacg     120
gtgatgctgg tcaacggcgc gatggcgacc accgcctcgt tcgcccggac ctgcaagtgc     180
ctggccgaac atttcaacgt ggtgctgttc gacctgccct tcgccgggca gtcgcgtcag     240
cacaacccgc agcggggggtt gatcaccaag gacgacgagg tggaaatcct cctggcgctg     300
atcgagcgct tcgaggtcaa tcacctggtc tccgcgtcct ggggcggtat ctccacgctg     360
ctggcgctgt cgcgcaatcc gcggcatc cgcagctcgg tggtgatggc attcgccct       420
ggactgaacc aggcgatgct cgactacgtc gggcgggcg aggcgctgat cgagctggac     480
gacaagtcgg cgatcggcca tctgctcaac gagaccgtcg gcaaatacct gccgccgcgc     540
```

```
ctgaaagcca gcaaccatca gcacatggct tcgctggcca ccggcgaata cgagcaggcg      600
cgctttcaca tcgaccaggt gctggcgctc aacgatcggg gctacctggc ttgcctggag      660
cggatccaga gccacgtgca tttcatcaac ggcagctggg acgaatacac caccgccgag      720
gacgcccgcc agttccgcga ctacctgccg cactgcagtt tctcgcgggt ggagggcacc      780
gggcatttcc tcgacctgga gtccaagctg gccgcggtac gcgtgcaccg cgccctgctc      840
gagcacctgc tgaagcaacc ggagccgcag cgggcggaac gcgcggcggg attccacgag      900
atggccatcg gctacgcctg aacccttgac ctgcgaagac ccggcctggc cgggctttgc      960
ggttgcataa cgcacggagt agcaccatgc acgccatcct catcgccatc ggctcggccg     1020
gcgacgtatt tcccttcatc ggcctggccc ggaccctgaa attgcgcggg caccgcgtga     1080
gcctctgcac catcccggtg tttcgcgacg cggtggagca gcacggcatc gcgttcgtcc     1140
cgctgagcga cgaactgacc taccgccgga ccatgggcga tccgcgcctg tgggacccca     1200
agacgtcctt cggcgtgctc tggcaaacca tcgccgggat gatcgagccg gtctacgagt     1260
acgtctcggc gcagcgccat gacgacatcg tggtggtcgg ctcgctctgg gcgctgggcg     1320
cacgcatcgc tcacgagaag tacgggattc cctacctgtc cgcgcaggtc tcgccatcga     1380
ccttgttgtc ggcgcacctg ccgccggtac accccaagtt caacgtgccc gagcagatgc     1440
cgctggcgat gcgcaagctg ctctggcgct gcatcgagcg cttcaagctg gatcgcacct     1500
gcgcgccgga tatcaacgcg gtgcggcgca aggtcggcct ggagacgccg gtgaagcgca     1560
tcttcaccca atggatgcat cgccgcagg gcgtggtctg cctgttcccg gcctggttcg     1620
cgccgcccca gcaggattgg ccgcaacccc tgcacatgac cggcttcccg ctgttcgacg     1680
gcagtatccc ggggacccc ctcgacgacg aactgcaacg ctttctcgat cagggcagcc     1740
ggccgctggt gttcacccag ggctcgaccg aacacctgca gggcgacttc tacgccatgg     1800
ccctgcgcgc gctggaacgc ctcggcgcgc gtgggatctt cctcaccggc gccgccagg     1860
aaccgctgcg cggcttgccg aaccacgtgc tgcagcgcgc ctacgcgcca ctgggagcct     1920
tgctgccatc gtgcgccggg ctggtccatc cgggcggtat cggcgccatg agcctggcct     1980
tggcggcggg ggtgccgcag gtgctgctgc cctgcgccca cgaccagttc gacaatgccg     2040
aacggctggt ccggctcggc tgcgggatgc gcctgggcgt gccattgcgc gagcaggagt     2100
tgcgcgggg gctgtggcgc ttgctcgagg acccggccat ggcggcggcc tgtcggcgtt     2160
tcatggaatt gtcacaaccg cacagtatcg cttgcggtaa agcggcccag gtggtcgaac     2220
gttgtcatag ggaggggat gcgcgatggc tgaaggctgc gtcctgacgc cgggaggatc     2280
ctggcgtgtc cacgaccagc ctctgccct ccgccacgcg ggaacacggt cccggcgcga     2340
aacgcgtcct gcctctgctg ttcctcacct gctgctgga tgccgctggc gtcggcctga     2400
tcgtgcccct gctgccgacg ctgatcggca gcgtggcgcc gctggcggtc cgcgacgcgg     2460
ccacctgggg cgccgccctg gtgatgacct tcgcgctgct gcaattgttc ttttcgccgg     2520
tcctcggcag cctcagcgac cgcttcggac gccgccccgt cctggtcctg gcgatgctcg     2580
gcttcgccct cagctatctg ctgctggcgc tggccgacag cctctggatg ctgttcctcg     2640
gtcgcgcgct ggccgggctc accggcgcca gcgtggccac cgcgatggcc tgcgcggctg     2700
acctcggcac gcacgggcag cgcacccggc acttcggctg gctgtacgcc ggcctcgccc     2760
tgggcatgat cctcggcccc gccctcggtg ggctgctggc ggtgcacggc acgacgctgc     2820
cgctgttgct ggccgccggc ctgtgcctgc tcaacgccct gctcgccggc ctgttcctcg     2880
```

| | |
|---|---|
| aggaaaccct gcccccgacg cgacgccgcc gcctggaccc gaggcggatg aatgccttgc | 2940 |
| gctcgatcag cggcctggct cggcaaccgg gggtcggacg cctgctggcg gtgcttgccc | 3000 |
| tggtattcct cggcttgcag gcggtgatgg tggtctggcc gttcttcgtg atcgagaagt | 3060 |
| ttcactggag cagcgcctgg atcggctact cgctggccct ctacgcgtg ctcgcggtgc | 3120 |
| tcgcccagac cctcggcgtg aacctctgca agcggcgcct ggacgacgcc cgcctgctgc | 3180 |
| gcctgggcct cgcccctgcaa ggctgcggcc tgctgctgtt cgcccctggtc gactcgtcat | 3240 |
| tctggctggt ctgcgcgctg ctgcccttcg cgctcggcag cctcgccacc ccggccatgc | 3300 |
| agggggctgct ctcggcccgc gtgccggtcg accgccaggg cgagttgcag ggcgtgctga | 3360 |
| gcagcctgat gagcctcgcc gcgatcgtcg gtccgccgct gatgagcggc ctgttccact | 3420 |
| ggggcagcgg tccgctcgcg ccgctgcccc tggccggcgc gccattcctc gccggcgccc | 3480 |
| ttctcgttct ggccgggctg gtcctggcct ggcaacttcg acctacggga gaagaacgat | 3540 |
| catggaccgg atagacatgg gcgtgctggt ggtactgttc aatcctggcg acgacgacct | 3600 |
| ggaacacctt ggcgaactgg cggcggcgtt tccgcaactg cgcttccttg ccgtcgacaa | 3660 |
| ctcaccgcac agcgatccgc agcgcaatgc ccggctgcgc gggcaaggca tcgccgtgct | 3720 |
| gcaccacggc aaccggcagg gcatcgccgg cgccttcaac cagggactcg acgcgctatt | 3780 |
| ccggcgtggc gtgcagggtg tgctgctgct cgaccaggac tcccgtcccg gcggcgcctt | 3840 |
| cctcgccgcc cagtggcgca acctgcaggc gcgcaacggt caggcctgcc tgctcggccc | 3900 |
| acggatcttc gaccggggtg accggcgctt cctgccggcc atccatctcg acggactgac | 3960 |
| gctcaggcaa ttgtctctgg acggcctgac gaccccgcag cgcacctcgt tcctgatctc | 4020 |
| ctccggctgc ctgctgaccc gcgaggccta ccagcgcctc ggccacttcg acgaggaact | 4080 |
| gttcatcgac cacgtggaca ccgaatacag cctgcgcgcc caggcgctgg acgtgccct | 4140 |
| gtacgtcgac ccgcgcgctgg tcctcgagca ccgcatcggc acgcgcaaga cccgccgcct | 4200 |
| cggcggtctc agcctcagcg cgatgaacca cgcccccgctg cgccgctact acctggcgcg | 4260 |
| caacggcctg ctggtcctgc ccgctacgc ccggtcctcg ccgctggccc tgctggcgaa | 4320 |
| cctgccgacc ctgacccagg gcctcgcggt gctcctgctc gaacgcgaca gctgctcaa | 4380 |
| gctgcgctgc ctgggctggg gcctgtggga cggcctgcgg ggacgcggcg gcgcgctgga | 4440 |
| gaccaaccgc ccgcgcctgc tgaagcgcct cgccggcccg gccgtggcgt ccgtagcttc | 4500 |
| cggcaaggcc aaggcctagt cggcgaaacg cattccctct agagagctc | 4549 |

<210> SEQ ID NO 51
<211> LENGTH: 9663
<212> TYPE: DNA
<213> ORGANISM: Artificial Sequence
<220> FEATURE:
<223> OTHER INFORMATION: vector

<400> SEQUENCE: 51

| | |
|---|---|
| ctcgggccgt ctcttgggct tgatcggcct tcttgcgcat ctcacgcgct cctgcggcgg | 60 |
| cctgtagggc aggctcatac ccctgccgaa ccgcttttgt cagccggtcg gccacggctt | 120 |
| ccggcgtctc aacgcgcttt gagattccca gcttttcggc caatccctgc ggtgcatagg | 180 |
| cgcgtggctc gaccgcttgc gggctgatgg tgacgtggcc cactggtggc cgctccaggg | 240 |
| cctcgtagaa cgcctgaatg cgcgtgtgac gtgccttgct gccctcgatg ccccgttgca | 300 |
| gccctagatc ggccacagcg gccgcaaacg tggtctggtc gcgggtcatc tgcgctttgt | 360 |
| tgccgatgaa ctccttggcc gacagcctgc cgtcctgcgt cagcggcacc acgaacgcgg | 420 |

```
tcatgtgcgg gctggtttcg tcacggtgga tgctggccgt cacgatgcga tccgccccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt ctctggcagc aactcgcgca gtcggcccat cgcttcatcg gtgctgctgg    660
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcggcgccc tacgggcttg ctctccgggc    960
ttcgccctgc gcggtcgctg cgctcccttg ccagcccgtg gatatgtgga cgatggccgc   1020
gagcggccac cggctggctc gcttcgctcg gcccgtggac aaccctgctg gacaagctga   1080
tggacaggct gcgcctgccc acgagcttga ccacagggat tgcccaccgg ctacccagcc   1140
ttcgaccaca tacccaccgg ctccaactgc gcggcctgcg gccttgcccc atcaatttt    1200
ttaattttct ctggggaaaa gcctccggcc tgcggcctgc gcgcttcgct tgccggttgg   1260
acaccaagtg gaaggcgggt caaggctcgc gcagcgaccg cgcagcggct tggccttgac   1320
gcgcctggaa cgacccaagc ctatgcgagt ggggcagtc gaaggcgaag cccgcccgcc    1380
tgccccccga gcctcacggc ggcgagtgcg ggggttccaa gggggcagcg ccaccttggg   1440
caaggccgaa ggccgcgcag tcgatcaaca agccccggag gggccacttt ttgccggagg   1500
gggagccgcg ccgaaggcgt gggggaaccc cgcaggggtg cccttctttg ggcaccaaag   1560
aactagatat agggcgaaat gcgaaagact taaaaatcaa caacttaaaa aaggggggta   1620
cgcaacagct cattgcggca cccccgcaa  tagctcattg cgtaggttaa agaaaatctg    1680
taattgactg ccacttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaaccacgg cggcaatgct    1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacgcgcg gcagcagcg cctgccgatg cccgatgagc cgtgttttct    2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520
ccctatacct tgtctgcctc cccgcgttgc gtcgcggtgc atggagccgg ccacctcga    2580
cctgaatgga agccggcggc acctcgctaa cggattcacc gttttttatca ggctctggga   2640
ggcagaataa atgatcatat cgtcaattat tacctccacg gggagagcct gagcaaactg   2700
gcctcaggca tttgagaagc acacggtcac actgcttccg gtagtcaata aaccggtaaa   2760
```

```
ccagcaatag acataagcgg ctatttaacg accctgccct gaaccgacga ccgggtcgaa    2820
tttgctttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagagggaat gcgtttcgcc gactaggcct tggccttgcc ggaagctacg gacgccacgg    3300
ccgggccggc gaggcgcttc agcaggcgcg ggcggttggt ctccagcgcg ccgccgcgtc    3360
cccgcaggcc gtcccacagg ccccagccca ggcagcgcag cttgagcagc ttgtcgcgtt    3420
cgagcaggag caccgcgagg ccctgggtca gggtcggcag gttcgccagc agggccagcg    3480
gcgaggaccg ggcgtagcgg cgcaggacca gcaggccgtt gcgcgccagg tagtagcggc    3540
gcagcggggc gtggttcatc gcgctgaggc tgagaccgcc gaggcggcgg gtcttgcgcg    3600
tgccgatgcg gtgctcgagg accagccgcg ggtcgacgta caggggcacg tccagcgcct    3660
gggcgcgcag gctgtattcg gtgtccacgt ggtcgatgaa cagttcctcg tcgaagtggc    3720
cgaggcgctg gtaggcctcg cgggtcagca ggcagccgga ggagatcagg aacgaggtgc    3780 gctgcgggt cgtcaggccg tccagagaca attgcctgag cgtcagtccg tcgagatgga    3840
tggccggcag gaagcgccgg tcaccccggt cgaagatccg tgggccgagc aggcaggcct    3900
gaccgttgcg cgcctgcagg ttgcgccact gggcggcgag gaaggcgccg ccgggacggg    3960
agtcctggtc gagcagcagc acaccctgca cgccacgccg gaatagcgcg tcgagtccct    4020
ggttgaaggc gccggcgatg ccctgccggt tgccgtggtg cagcacggcg atgccttgcc    4080
cgcgcagccg ggcattgcgc tgcggatcgc tgtgcggtga gttgtcgacg gcaaggaagc    4140
gcagttgcgg aaacgccgcc gccagttcgc caaggtgttc caggtcgtcg tcgccaggat    4200
tgaacagtac caccagcacg cccatgtcta tccggtccat gatcgttctt ctcccgtagg    4260
tcgaagttgc caggccagga ccagcccggc cagaacgaga agggcgccgg cgaggaatgg    4320
cgcgccggcc aggggcagcg gcgcgagcgg accgctgccc cagtggaaca ggccgctcat    4380
cagcggcgga ccgacgatcg cggcgaggct catcaggctg ctcagcacgc cctgcaactc    4440
gccctggcgg tcgaccggca cgcgggccga gagcagcccc tgcatggccg gggtggcgag    4500
gctgccgagc gcgaagggca gcagcgcgca gaccagccag aatgacgagt cgaccagggc    4560
gaacagcagc aggccgcagc cttgcaggc gaggcccagg cgcagcaggc gggcgtcgtc    4620
caggcgccgc ttgcagaggt tcacgccgag ggtctgggcg agcaccgcga gcacgccgta    4680
gagggccagc gagtagccga tccaggcgct gctccagtga aacttctcga tcacgaagaa    4740
cggccagacc accatcaccg cctgcaagcc gaggaatacc agggcaagca ccgccagcag    4800
gcgtccgacc cccggttgcc gagccaggcc gctgatcgag cgcaaggcat tcatccgcct    4860
cgggtccagg cggcggcgtc gcgtcggggg cagggtttcc tcgaggaaca ggccggcgag    4920
cagggcgttg agcaggcaca ggccggcggc cagcaacagc ggcagcgtcg tgccgtgcac    4980
cgccagcagc ccaccgaggg cggggccgag gatcatgccc agggcgaggc cggcgtacag    5040
ccagccgaag tgccgggtgc gctgcccgtg cgtgccgagg tcagccgcgc aggccatcgc    5100
ggtggccacg ctggcgccgg tgagcccggc cagcgcgcga ccgaggaaca gcatccagag    5160
```

```
gctgtcggcc agcgccagca gcagatagct gagggcgaag ccgagcatcg ccaggaccag    5220
gacggggcgg cgtccgaagc ggtcgctgag gctgccgagg accggcgaaa agaacaattg    5280
cagcagcgcg aaggtcatca ccagggcggc gccccaggtg gccgcgtcgc ggaccgccag    5340
cggcgccacg ctgccgatca gcgtcggcag caggggcacg atcaggccga cgccagcggc    5400
atccagcagg caggtgagga acagcagagg caggacgcgt ttcgcgccgg gaccgtgttc    5460
ccgcgtggcg gaggggcaga ggctggtcgt ggacacgcca ggatcctccc ggcgtcagga    5520
cgcagccttc agccatcgcg catccccctc cctatgacaa cgttcgacca cctgggccgc    5580
tttaccgcaa gcgatactgt gcggttgtga caattccatg aaacgccgac aggccgccgc    5640
catggccggg tcctcgagca agcgccacag cgccccgcgc aactcctgct cgcgcaatgg    5700
cacgcccagg cgcatcccgc agccgagccg gaccagccgt cggcattgt cgaactggtc     5760 gtgggcgcag ggcagcagca cctgcggcac ccccgccgcc aaggccaggc tcatggcgcc    5820
gataccgccc ggatggacca gcccggcgca cgatggcagc aaggctccca gtggcgcgta    5880
ggcgcgctgc agcacgtggt tcggcaagcc gcgcagcggt tcctggccgg cgccggtgag    5940
gaagatccca cgcgcgccga ggcgttccag cgcgcgcagg gccatggcgt agaagtcgcc    6000
ctgcaggtgt tcggtcgagc cctgggtgaa caccagcggc cggctgccct gatcgagaaa    6060
gcgttgcagt tcgtcgtcga gcggggtccc cgggatactg ccgtcgaaca gcgggaagcc    6120
ggtcatgtgc aggggttgcg gccaatcctg ctggggcggc gcgaaccagg ccgggaacag    6180
gcagaccacg ccctgcggcg aatgcatcca ttgggtgaag atgcgcttca ccggcgtctc    6240
caggccgacc ttgcgccgca ccgcgttgat atccggcgcg caggtgcgat ccagcttgaa    6300
gcgctcgatg cagcgccaga gcagcttgcg catcgccagc ggcatctgct cgggcacgtt    6360
gaacttgggg tgtaccggcg gcaggtgcgc cgacaacaag gtcgatggcg agacctgcgc    6420
ggacaggtag ggaatcccgt acttctcgtg agcgatgcgt gcgcccagcg cccagagcga    6480
gccgaccacc acgatgtcgt catggcgctg cgccgagacg tactcgtaga ccggctcgat    6540
catcccggcg atggtttgcc agagcacgcc gaaggacgtc ttggggtccc acaggcgcgg    6600
atcgcccatg gtccggcggt aggtcagttc gtcgctcagc gggacgaacg cgatgccgtg    6660
ctgctccacc gcgtcgcgaa acaccgggat ggtgcagagg ctcacgcggt gcccgcgcaa    6720
tttcagggtc cgggccaggc cgatgaaggg aaatacgtcg ccggccgagc cgatggcgat    6780
gaggatggcg tgcatggtgc tactccgtgc gttatgcaac cgcaaagccc ggccaggccg    6840
ggtcttcgca ggtcaagggt tcaggcgtag ccgatggcca tctcgtggaa tcccgccgcg    6900
cgttccgccc gctgcggctc cggttgcttc agcaggtgct cgagcagggc gcggtgcacg    6960
cgtaccgcgc ccagcttgga ctccaggtcg aggaaatgcc cggtgccctc cacccgcgag    7020
aaactgcagt gcggcaggta gtcgcgaac tggcgggcgt cctcggcggt ggtgtattcg     7080
tcccagctgc cgttgatgaa atgcacgtgg ctctggatcc gctccaggca agccaggtag    7140
ccccgatcgt tgagcgccag cacctggtcg atgtgaaagc gcgcctgctc gtattcgccg    7200
gtggccagcg aagccatgtg ctgatggttg ctggctttca ggcgcggcgg caggtatttg    7260
ccgacggtct cgttgagcag atggccgatc gccgacttgt cgtccagctc gatcagcgcc    7320
tgcgcccgcc cgacgtagtc gagcatcgcc tggttcagtc caggggcgaa tgccatcacc    7380
accgagctgc ggatgccgcg cggattgcgc gacagcgcca gcagcgtgga gataccgccc    7440
caggacgcgg agaccaggtg attgacctcg aagcgctcga tcagcgccag gaggatttcc    7500
```

```
acctcgtcgt ccttggtgat caaccccgc tgcgggttgt gctgacgcga ctgcccggcg      7560
aagggcaggt cgaacagcac cacgttgaaa tgttcggcca ggcacttgca ggtccgggcg      7620
aacgaggcgg tggtcgccat cgcgccgttg accagcatca ccgtgctgcg cccgggatcc      7680
tgcccaacgc gctcgacatg tacccgcagg cccttgcaaa ccgataccaa cagactttcg      7740
cgccgcattt cacacctccc aaaaatgcca gatccccgg gctgcaggaa ttcgatatca      7800
agcttatcga taccgtcgac ctcgaggggg ggcccggtac ccagcttttg ttccctttag      7860
tgagggttaa ttgcgcgctt ggcgtaatca tggtcatagc tgtttcctgt gtgaaattgt      7920
tatccgctca caattccaca acatacga gccggaagca taaagtgtaa agcctggggt       7980
gcctaatgag tgagctaact cacattaatt gcgttgcgct cactgcccgc tttccagtcg      8040
ggaaacctgt cgtgccagct gcattaatga atcggccaac gcgcggggag aggcggtttg      8100
cgtattgggc gcatgcataa aaactgttgt aattcattaa gcattctgcc gacatggaag      8160
ccatcacaaa cggcatgatg aacctgaatc gccagcggca tcagcacctt gtcgccttgc      8220
gtataatatt tgcccatggg ggtgggcgaa gaactccagc atgagatccc cgcgctggag      8280
gatcatccag ccggcgtccc ggaaaacgat tccgaagccc aacctttcat agaaggcggc      8340
ggtggaatcg aaatctcgtg atggcaggtt gggcgtcgct tggtcggtca tttcgaaccc      8400
cagagtcccg ctcagaagaa ctcgtcaaga aggcgataga aggcgatgcg ctgcgaatcg      8460
ggagcggcga taccgtaaag cacgaggaag cggtcagccc attcgccgcc aagctcttca      8520
gcaatatcac gggtagccaa cgctatgtcc tgatagcggt ccgccacacc cagccggcca      8580
cagtcgatga atccagaaaa gcggccattt tccaccatga tattcggcaa gcaggcatcg      8640
ccatgggtca cgacgagatc ctcgccgtcg gcatgcgcg ccttgagcct ggcgaacagt       8700
tcggctggcg cgagcccctg atgctcttcg tccagatcat cctgatcgac aagaccggct      8760
tccatccgag tacgtgctcg ctcgatgcga tgtttcgctt ggtggtcgaa tgggcaggta      8820
gccggatcaa gcgtatgcag ccgccgcatt gcatcagcca tgatggatac tttctcggca      8880
ggagcaaggt gagatgacag gagatcctgc cccggcactt cgcccaatag cagccagtcc      8940
cttcccgctt cagtgacaac gtcgagcaca gctgcgcaag gaacgcccgt cgtggccagc      9000
cacgatagcc gcgctgcctc gtcctgcagt tcattcaggg caccggacag gtcggtcttg      9060
acaaaaagaa ccgggcgccc ctgcgctgac agccggaaca cggcggcatc agagcagccg      9120
attgtctgtt gtgcccagtc atagccgaat agcctctcca cccaagcggc cggagaacct      9180
gcgtgcaatc catcttgttc aatcatgcga aacgatcctc atcctgtctc ttgatcagat      9240
cttgatcccc tgcgccatca gatccttggc ggcaagaaag ccatccagtt tactttgcag      9300
ggcttcccaa ccttaccaga gggcgcccca gctggcaatt ccggttcgct tgctgtccat      9360
aaaaccgccc agtctagcta tcgccatgta agcccactgc aagctacctg ctttctcttt      9420
gcgcttgcgt tttcccttgt ccagatagcc cagtagctga cattcatccc aggtggcact      9480
tttcggggaa atgtgcgcgc ccgcgttcct gctggcgctg ggcctgtttc tggcgctgga      9540
cttcccgctg ttccgtcagc agcttttcgc ccacggcctt gatgatcgcg gcggccttgg      9600
cctgcatatc ccgattcaac ggccccaggg cgtccagaac gggcttcagg cgctcccgaa      9660
ggt                                                                   9663
```

<210> SEQ ID NO 52
<211> LENGTH: 9793
<212> TYPE: DNA
<213> ORGANISM: Artificial Sequence
<220> FEATURE:
<223> OTHER INFORMATION: vector

<400> SEQUENCE: 52

| | |
|---|---|
| gatctggcat ttttgggagg tgtgaaatgc ggcgcgaaag tctgttggta tcggtttgca | 60 |
| agggcctgcg ggtacatgtc gagcgcgttg ggcaggatcc cgggcgcagc acggtgatgc | 120 |
| tggtcaacgg cgcgatggcg accaccgcct cgttcgcccg gacctgcaag tgcctggccg | 180 |
| aacatttcaa cgtggtgctg ttcgacctgc ccttcgccgg gcagtcgcgt cagcacaacc | 240 |
| cgcagcgggg gttgatcacc aaggacgacg aggtggaaat cctcctggcg ctgatcgagc | 300 |
| gcttcgaggt caatcacctg gtctccgcgt cctgggcgg tatctccacg ctgctggcgc | 360 |
| tgtcgcgcaa tccgcgcggc atccgcagct cggtggtgat ggcattcgcc cctggactga | 420 |
| accaggcgat gctcgactac gtcgggcggg cgcaggcgct gatcgagctg gacgacaagt | 480 |
| cggcgatcgg ccatctgctc aacgagaccg tcggcaaata cctgccgccg cgcctgaaag | 540 |
| ccagcaacca tcagcacatg gcttcgctgg ccaccggcga atacgagcag gcgcgctttc | 600 |
| acatcgacca ggtgctggcg ctcaacgatc ggggctacct ggcttgcctg gagcggatcc | 660 |
| agagccacgt gcatttcatc aacgcagct gggacgaata caccaccgcc gaggacgccc | 720 |
| gccagttccg cgactacctg ccgcactgca gtttctcgcg ggtggagggc accgggcatt | 780 |
| tcctcgacct ggagtccaag ctggccgcg tacgcgtgca ccgcgccctg ctcgagcacc | 840 |
| tgctgaagca accggagccg cagcgggcgg aacgcgcggc gggattccac gagatggcca | 900 |
| tcggctacgc ctgaaccctt gacctgcgaa gacccggcct ggccgggctt tgcggttgca | 960 |
| taacgcacgg agtagcacca tgcacgccat cctcatcgcc atcggctcgg ccggcgacgt | 1020 |
| atttcccttc atcggcctgg cccggaccct gaaattgcgc gggcaccgcg tgagcctctg | 1080 |
| caccatcccg gtgtttcgcg acgcggtgga gcagcacggc atcgcgttcg tcccgctgag | 1140 |
| cgacgaactg acctaccgcc ggaccatggg cgatccgcgc ctgtgggacc caagacgtc | 1200 |
| cttcggcgtg ctctggcaaa ccatcgccgg gatgatcgag ccggtctacg agtacgtctc | 1260 |
| ggcgcagcgc catgacgaca tcgtggtggt cggctcgctc tgggcgctgg gcgcacgcat | 1320 |
| cgctcacgag aagtacggga ttccctacct gtccgcgcag gtctcgccat cgaccttgtt | 1380 |
| gtcggcgcac ctgccgccgg tacacccccaa gttcaacgtg cccgagcaga tgccgctggc | 1440 |
| gatgcgcaag ctgctctggc gctgcatcga gcgcttcaag ctggatcgca cctgcgcgcc | 1500 |
| ggatatcaac gcggtgcggc gcaaggtcgg cctggagacg ccggtgaagc gcatcttcac | 1560 |
| ccaatggatg cattcgccgc agggcgtggt ctgcctgttc ccggcctggt tcgcgccgcc | 1620 |
| ccagcaggat tggccgcaac ccctgcacat gaccggcttc ccgctgttcg acggcagtat | 1680 |
| cccgggggacc ccgctcgacg acgaactgca acgctttctc gatcagggca gccggccgct | 1740 |
| ggtgttcacc cagggctcga ccgaacacct gcagggcgac ttctacgcca tggccctgcg | 1800 |
| cgcgctggaa cgcctcggcg cgcgtgggat cttcctcacc ggcgccgcc aggaaccgct | 1860 |
| gcgcggcttg ccgaaccacg tgctgcagcg cgcctacgcg ccactgggag ccttgctgcc | 1920 |
| atcgtgcgcc gggctggtcc atcgggcgg tatcggcgcc atgagcctgg ccttggcggc | 1980 |
| gggggtgccg caggtgctgc tgcccctgcgc ccacgaccag ttcgacaatg ccgaacggct | 2040 |
| ggtccggctc ggctgcggga tgcgcctggg cgtgccattg cgcgagcagg agttgcgcgg | 2100 |
| ggcgctgtgg cgcttgctcg aggacccggc catggcggcg cctgtcggc gtttcatgga | 2160 |
| attgtcacaa ccgcacagta tcgcttgcgg taaagcggcc caggtggtcg aacgttgtca | 2220 |

```
tagggaggggg gatgcgcgat ggctgaaggc tgcgtcctga acggtgctgg cataacagat    2280
agggttgcct ctagagtcga cctgcaggca tgcaagcttg gctgttttgg cggatgagag    2340
aagattttca gcctgataca gattaaatca gaacgcagaa gcggtctgat aaaacagaat    2400
ttgcctggcg gcagtagcgc ggtggtccca cctgacccca tgccgaactc agaagtgaaa    2460
cgccgtagcg ccgatggtag tgtggggtct ccccatgcga gagtagggaa ctgccaggca    2520
tcaaataaaa cgaaaggctc agtcgaaaga ctgggccttt cgttttatct gttgtttgtc    2580
ggtgaacgct ctcctgagta ggacaaatcc gccgggagcg gatttgaacg ttgcgaagca    2640
acggcccgga gggtggcggg caggacgccc gccataaact gccaggcatc aaattaagca    2700
gaaggccatc ctgacggatg ccttttttgc gtttctacaa actcttttg tttattttc     2760 taaatacatt caaatatgta tccgctcatg ctccttcgtc ggtgtcgtcg ccggatggtc    2820
tgcggtggtg ctcagcgtgg agacgcgcac cgtcacggac ccccatcaat cctgcctatt    2880
tgccacgttt aacaaggtag ttaagcgttc atttacgaag aaaacacgat aagctgcaca    2940
aatacctgaa aaagttgaac gccccgtgag cgggaactca cagggcgtcg ctaacccccc   3000
agtcatcagc tgggagaaag cactcaagac atgactctag ccgatccgca ggacacagtc    3060
acagctagcg cgtggaaatt gtccgccgat ctgttcgaca cccaccccga agctatgcgc    3120
tgcggctcac gcggctggac ggcagaagat cgccgcgaac tgctcgctca cctgggacgc    3180
gaaagcttcc agggcagcaa gacaagagat ttcgcgagcg cctggattaa aaacccggat    3240
accggcgaaa cccaaccaaa gctctaccgg gctggctcaa aagcgctgac gcggtgccag    3300
tacgttgcgc tgacgcacgc gcaacatgcc gcggtgatcg tgcttgacat cgatgtgccc    3360
agccaccagg ccggcgggaa gattgagcac gtaaacccgc aggtctacgc gattttagag    3420
aaatgggcac gcctagaaaa agcgccggct tggatcggcg tgaatccgct gagcgggaaa    3480
tgccagctca tctggctcat tgacccggtg tatgccgcag caggtaaaac cagcccaaat    3540
atgcgcctgc tggctgcaac gacggaagaa atgactcgtg ttttcggcgc tgaccaggct    3600
ttttcgcata ggctgagccg gtggccgctg cacgtctcag acgatccgac agcctataaa    3660
tggcactgcc agcatgatcg tgtggatcgg ctggccgacc taatgagat tgctcgaacg    3720 atgaccggat cacagaagcc gaaaaagtac attgagcagg acttttccag cggacgcgcc    3780
cgcattgaag cggcacaacg cgccaccgca gaagccaagg cgctagcgat tttgacgcg    3840 agcctgccga gcgccctgga cgcgtccggc gacctgatcg acggcgtgcg agtgctctgg    3900
acaaatccag agcgagcgcg cgacgagacc gcgtttcgcc acgcgttgac cgtgggatac    3960
cagctcaaag ctgctggtga gcgcctaaaa gatgccaaga tcatcgacgc gtatgaagtg    4020
gcgtacaacg ttgcccaggc ggtcggtgca gacggccggg agccggatct tcccgccatg    4080
cgtgatcgcc tgacgatggc gcgtcgtgtg cgcggctacg tggctaaagg ccagccagtc    4140
gtccctgctc gtcgggtgga aacgcagagc agccgagggc ggaaagctct agcgacgatg    4200
gggcgacggg gcgcagctac atcgaatgca cgcagatggg ctgacccaga aagtaagtat    4260
gcgcaggaga cgcgacagcg attagcggaa gcaaacaaac gccgagaaat gacaggcgag    4320
ttgctcgaac ttcgcgtcaa aactgcgatc ctggatgccc gttctcaatc ggttgctgat    4380
ccctcgactc gtgagcttgc aggcgaacta ggtgtcagtg aaaggcgcat ccaacaagtc    4440
agaaaggcac ttggaatgga agctaaacgc ggccgtccac gggctgaaaa ctaataaacg    4500
aaacaccgtc agcagaaaac ggttccccccc tttaggggtc ccgtccttgc tctggctctc    4560
acttgccctc accctccgct atccacgggc tgaaaactaa taaacgaaac accgtcagca    4620
```

```
gaaaacggtt ccccccttt agggtgtctc gctcctagct ctgatccctc cccggttcct   4680
ccccggcctg attttaagg ggggctcacg ctgtcggcag agaacggttc cccgccttct    4740
gctctggctc ttcctcgact ccctccccct caaaaatctc ctcgagatcc tggagacctt   4800
tttggagcta gcgcgttgct gcttcgcacc aacttgctca tgatgatttt cattttgct   4860 tgtgtgcttt tttgggttga accctccaaa gaggggaaac caggggcaca cctcatgcac   4920
taaagtgccg cttcgctggt cagggtgaaa tcacctggaa aaaagtgcg gtaaccgctg    4980 cgcttggcgt tttttctggg caagaagtct cgcaggtttt cgcaggagtg ccggaagaaa   5040
ttatcagaat tggggctaga attttaacg aacgttcgtt ataatggtgt catgaccttc    5100
acgacgaagt accaaaactg gcctgaagca tcagcggtgg atctctccga tgtcgcgctg   5160
gagtccgacg cactcgatgc cgccgtcgat ttaaaaacgg tgatcggatt tttccgcgcc   5220
ctcgatacga cagacgcgcc agcatcacgc gactgggcaa gtgccgcgag cgacctagaa   5280
acgcttgtgg ccgaccttga agagctggcc gacgagctgc gtgctcggca gcgccaggag   5340
gacgcgcagt agtggaggat cgcatcagct gcgcctactg cggtggcctg atcccacccc   5400
ggcctgaccc acgaggacgg cgcgcaaaat actgctcaga cgcgtgtcgt gccgcagcca   5460
gccgcgagcg cgccaacaag cgccacgccc aggaggtcga agccgcacgt cgaccgcgtg   5520
tagtgcgtgg cggaaacttc ttgcgtttcg caagagaaat cgtcccatt tctcgtcgga    5580 ctcggggaag gaagcgtgat gctctcggtc aagcacgtcg ctcgccagcg ctgcgaggag   5640
ttcggccttc gtgcggaagt gccagtagag gccgggctgc tgtacctgta agtgagccgc   5700
cagcgcgcga gtggtgaagc catcgagccc agtctcgtcg agcacctgcc gggccccgag   5760
caacacggac gtgcggtcga gacgcttccg gtggtgagtc atagttgcac tttatcatcg   5820
ataactttat cttagataaa gtgactgctc gctactctca tctgactgct cgctactctc   5880
atcgtggaat cctgacagcc gtgctcatca cggcgaccct cgatgctgca gggctgggcc   5940
tcgtgatgcc gatcttgcct acccttctcg accaggtcgg tgcccccgac gacatgatcc   6000
cactgcacgt cggactactg acagcgctct atgcgatcat gcagtttctt tgcgccccga   6060
tccttggccg actctctgac cgtttcggac gccgccgcgt gcttgtcgcc tccctcgcag   6120
gcgcgacgat cgactacctc gtgctcgcac tgacggacac gctgtgggtc ttttacctcg   6180
cccgcgcggt tgcaggcatt accggcgcca cgaacgccgt caccgcgacg gtgatcgccg   6240
acattactcc gccggatcag cgcgcaaaac gctacgggtg gctcggcgca tgctacggcg   6300
gtggcatgat cgcgggtccc gccattggcg gtcttttcgg cggggtctca ccgcatctgc   6360
cattcctcgt cgccgccgcg ctcgccggaa tcaccctcgt actcagcgcg agtcttctgc   6420
gtgagacgcg gccaccgggc agcaacggct cgcacgcaca gcaacccggt acggcgaagc   6480
gaaccgcagt gccggggatg cttatccttc tcgcagtctt cggcatcgtg cagttcatcg   6540
gccaagcacc aggctccacc tgggtgctct tcacgcagca gcgcctcgac tggaaccccg   6600
tcgaagtcgg cgtttcgcta tccatcttcg gaatggtgca agtattcgtg caggcggcac   6660
tgaccggacg catcgtgtcc cggatcggcg agacccgggc gatcctcgtc ggtatcgccg   6720
cagacgccat tgggctcatc ggccttgccc tcatcgccag cacatgggcg atgctaccga   6780
tcctcgcagc gctcggactc ggcagcatca cgttgcccgc actgcagacg ctgctctcga   6840
gacgcgcgcc cgagcagcag cagggacgcc tgcaggaac acttgcaagc ctgaacagcc    6900
tcacctcgat catcggcccg gtcaccttca ccggcatttt cgcactcacc cgaacgaatg   6960
```

```
cagacggcac cctctggatc tgcgccgcag cgctctacgt tctctgcgcc ctcctgatga   7020
tccgtgagac atgcgcctca cggcgatctc gataaccgcg ctaaggtgcc atcccgatgc   7080
gacgggatcg ctctgccacc agtcaagtct cccgtagccg gtatgagcat gaccaaaatc   7140
ccttaacgtg agttttcgtt ccactgagcg tcagaccccg tagaaaagat caaaggatct   7200
tcttgagatc ctttttttct gcgcgtaatc tgctgcttgc aaacaaaaaa accaccgcta   7260
ccagcggtgg tttgtttgcc ggatcaagag ctaccaactc tttttccgaa ggtaactggc   7320
ttcagcagag cgcagatacc aaatactgtc cttctagtgt agccgtagtt aggccaccac   7380
ttcaagaact ctgtagcacc gcctacatac ctcgctctgc taatcctgtt accagtggct   7440
gctgccagtg gcgataagtc gtgtcttacc gggttggact caagacgata gttaccggat   7500
aaggcgcagc ggtcgggctg aacggggggt tcgtgcacac agcccagctt ggagcgaacg   7560
acctacaccg aactgagata cctacagcgt gagctatgag aaagcgccac gcttcccgaa   7620
gggagaaagg cggacaggta tccggtaagc ggcagggtcg gaacaggaga gcgcacgagg   7680
gagcttccag ggggaaacgc ctggtatctt tatagtcctg tcgggtttcg ccacctctga   7740
cttgagcgtc gatttttgtg atgctcgtca gggggcgga gcctatggaa aaacgccagc   7800
aacgcggcct ttttacggtt cctggccttt tgctggcctt tgctcacat gttctttcct   7860
gcgttatccc ctgattctgt ggataaccgt attaccgcct ttgagtgagc tgataccgct   7920
cgccgcagcc gaacgaccga gcgcagcgag tcagtgagcg aggaagcgga agagcgcctg   7980
atgcggtatt ttctccttac gcatctgtgc ggtatttcac accgcatatg gtgcactctc   8040
agtacaatct gctctgatgc cgcatagtta agccagtata cactccgcta tcgctacgtg   8100
actgggtcat ggctgcgccc cgacacccgc caacacccgc tgacgcgccc tgacgggctt   8160
gtctgctccc ggcatccgct tacagacaag ctgtgaccgt ctccgggagc tgcatgtgtc   8220
agaggttttc accgtcatca ccgaaacgcg cgaggcagca gatcaattcg cgcgcgaagg   8280
cgaagcggca tgcatttacg ttgacaccat cgaatggtgc aaaaccttc gcggtatggc   8340
atgatagcgc ccggaagaga gtcaattcag ggtggtgaat gtgaaaccag taacgttata   8400
cgatgtcgca gagtatgccg gtgtctctta tcagaccgtt tcccgcgtgg tgaaccaggc   8460
cagccacgtt tctgcgaaaa cgcgggaaaa agtggaagcg gcgatggcgg agctgaatta   8520
cattcccaac cgcgtggcac aacaactggc gggcaaacag tcgttgctga ttggcgttgc   8580
cacctccagt ctggccctgc acgcgccgtc gcaaattgtc gcggcgatta atctcgcgc   8640
cgatcaactg ggtgccagcg tggtggtgtc gatggtagaa cgaagcggcg tcgaagcctg   8700
taaagcggcg gtgcacaatc ttctcgcgca acgcgtcagt gggctgatca ttaactatcc   8760
gctggatgac caggatgcca ttgctgtgga agctgcctgc actaatgttc cggcgttatt   8820
tcttgatgtc tctgaccaga cacccatcaa cagtattatt ttctcccatg aagacggtac   8880
gcgactgggc gtggagcatc tggtcgcatt gggtcaccag caaatcgcgc tgttagcggg   8940
cccattaagt tctgtctcgg cgcgtctgcg tctggctggc tggcataaat atctcactcg   9000
caatcaaatt cagccgatag cggaacggga aggcgactgg agtgccatgt ccggttttca   9060
acaaaccatg caaatgctga atgagggcat cgttcccact gcgatgctgg ttgccaacga   9120
tcagatggcg ctgggcgcaa tgcgcgccat taccgagtcc gggctgcgcg ttggtgcgga   9180
tatctcggta gtgggatacg acgataccga agacagctca tgttatatcc cgccgtcaac   9240
caccatcaaa caggattttc gcctgctggg gcaaaccagc gtggaccgct tgctgcaact   9300
ctctcagggc caggcggtga agggcaatca gctgttgccc gtctcactgg tgaaaagaaa   9360
```

| | |
|---|---|
| aaccaccctg gcgcccaata cgcaaaccgc ctctccccgc gcgttggccg attcattaat | 9420 |
| gcagctggca cgacaggttt cccgactgga aagcgggcag tgagcgcaac gcaattaatg | 9480 |
| tgagttagcg cgaattgatc tggttttgaca gcttatcatc gactgcacgg tgcaccaatg | 9540 |
| cttctggcgt caggcagcca tcggaagctg tggtatggct gtgcaggtcg taaatcactg | 9600 |
| cataattcgt gtcgctcaag gcgcactccc gttctggata atgttttttg cgccgacatc | 9660 |
| ataacggttc tggcaaatat tctgaaatga gctgttgaca attaatcatc cggctcgtat | 9720 |
| aatgtgtgga attgtgagcg gataacaatt tcacacagga aacagaccat ggaattcgag | 9780 |
| ctcggtaccc ggg | 9793 |

```
<210> SEQ ID NO 53
<211> LENGTH: 10780
<212> TYPE: DNA
<213> ORGANISM: Artificial Sequence
<220> FEATURE:
<223> OTHER INFORMATION: vector

<400> SEQUENCE: 53
```

| | |
|---|---|
| gatctggcat ttttgggagg tgtgaaatgc ggcgcgaaag tctgttggta tcggtttgca | 60 |
| agggcctgcg ggtacatgtc gagcgcgttg ggcaggatcc cgggcgcagc acggtgatgc | 120 |
| tggtcaacgg cgcgatggcg accaccgcct cgttcgcccg gacctgcaag tgcctggccg | 180 |
| aacatttcaa cgtggtgctg ttcgacctgc ccttcgccgg gcagtcgcgt cagcacaacc | 240 |
| cgcagcgggg gttgatcacc aaggacgacg aggtggaaat cctcctggcg ctgatcgagc | 300 |
| gcttcgaggt caatcacctg gtctccgcgt cctgggcgg tatctccacg ctgctggcgc | 360 |
| tgtcgcgcaa tccgcgcggc atccgcagct cggtggtgat ggcattcgcc cctggactga | 420 |
| accaggcgat gctcgactac gtcgggcggg cgcaggcgct gatcgagctg gacgacaagt | 480 |
| cggcgatcgg ccatctgctc aacgagaccg tcggcaaata cctgccgccg cgcctgaaag | 540 |
| ccagcaacca tcagcacatg gcttcgctgg ccaccggcga atacgagcag gcgcgcttc | 600 |
| acatcgacca ggtgctggcg ctcaacgatc ggggctacct ggcttgcctg agcggatcc | 660 |
| agagccacgt gcatttcatc aacggcagct gggacgaata caccaccgcc gaggacgccc | 720 |
| gccagttccg cgactacctg ccgcactgca gtttctcgcg ggtggagggc accgggcatt | 780 |
| tcctcgacct ggagtccaag ctggccgcgg tacgcgtgca ccgcgccctg ctcgagcacc | 840 |
| tgctgaagca accggagccg cagcgggcgg aacgcgcggc gggattccac gagatggcca | 900 |
| tcggctacgc ctgaaccctt gacctgcgaa gacccgcct ggccgggctt tgcggttgca | 960 |
| taacgcacgg agtagcacca tgcacgccat cctcatcgcc atcggctcgg ccggcgacgt | 1020 |
| atttcccttc atcggcctgg cccggaccct gaaattgcgc gggcaccgcg tgagcctctg | 1080 |
| caccatcccg gtgtttcgcg acgcggtgga gcagcacggc atcgcgttcg tcccgctgag | 1140 |
| cgacgaactg acctaccgcc ggaccatggg cgatccgcgc ctgtgggacc caagacgtc | 1200 |
| cttcggcgtg ctctggcaaa ccatcgccgg gatgatcgag ccggtctacg agtacgtctc | 1260 |
| ggcgcagcgc catgacgaca tcgtggtggt cggctcgctc tgggcgctgg gcgcacgcat | 1320 |
| cgctcacgag aagtacggga ttccctacct gtccgcgcag gtctcgcat cgaccttgtt | 1380 |
| gtcggcgcac ctgccgccgg tacccccaa gttcaacgtg cccgagcaga tgccgctggc | 1440 |
| gatgcgcaag ctgctctggc gctgcatcga gcgcttcaag ctggatcgca cctgcgcgcc | 1500 |
| ggatatcaac gcggtgcggc gcaaggtcgg cctggagacg ccggtgaagc gcatcttcac | 1560 |

| | |
|---|---|
| ccaatggatg cattcgccgc agggcgtggt ctgcctgttc ccggcctggt tcgcgccgcc | 1620 |
| ccagcaggat tggccgcaac ccctgcacat gaccggcttc ccgctgttcg acggcagtat | 1680 |
| cccggggacc ccgctcgacg acgaactgca acgctttctc gatcagggca gccggccgct | 1740 |
| ggtgttcacc cagggctcga ccgaacacct gcagggcgac ttctacgcca tggccctgcg | 1800 |
| cgcgctggaa cgcctcggcg cgcgtgggat cttcctcacc ggcgccggcc aggaaccgct | 1860 |
| gcgcggcttg ccgaaccacg tgctgcagcg cgcctacgcg ccactgggag ccttgctgcc | 1920 |
| atcgtgcgcc gggctggtcc atccgggcgg tatcggcgcc atgagcctgg ccttggcggc | 1980 |
| gggggtgccg caggtgctgc tgccctgcgc ccacgaccag ttcgacaatg ccgaacggct | 2040 |
| ggtccggctc ggctgcggga tgcgcctggg cgtgccattg cgcgagcagg agttgcgcgg | 2100 |
| ggcgctgtgg cgcttgctcg aggacccggc catggcggcg gcctgtcggc gtttcatgga | 2160 |
| attgtcacaa ccgcacagta tcgcttgcgg taaagcggcc caggtggtcg aacgttgtca | 2220 |
| tagggagggg gatgcgcgat ggctgaaggc tgcgtcctga cctacgggag aagaacgatc | 2280 |
| atggaccgga tagacatggg cgtgctggtg gtactgttca atcctggcga cgacgacctg | 2340 |
| gaacaccttg gcgaactggc ggcggcgttt ccgcaactgc gcttccttgc cgtcgacaac | 2400 |
| tcaccgcaca gcgatccgca gcgcaatgcc cggctgcgcg ggcaaggcat cgccgtgctg | 2460 |
| caccacggca accggcaggg catcgccggc gccttcaacc agggactcga cgcgctattc | 2520 |
| cggcgtggcg tgcagggtgt gctgctgctc gaccaggact cccgtcccgg cggcgccttc | 2580 |
| ctcgccgccc agtggcgcaa cctgcaggcg cgcaacggtc aggcctgcct gctcggccca | 2640 |
| cggatcttcg accggggtga ccggcgcttc ctgccggcca tccatctcga cggactgacg | 2700 |
| ctcaggcaat tgtctctgga cggcctgacg accccgcagc gcacctcgtt cctgatctcc | 2760 |
| tccggctgcc tgctgacccg cgaggcctac cagcgcctcg gccacttcga cgaggaactg | 2820 |
| ttcatcgacc acgtggacac cgaatacagc ctgcgcgccc aggcgctgga cgtgcccctg | 2880 |
| tacgtcgacc cgcggctggt cctcgagcac cgcatcggca cgcgcaagac ccgccgcctc | 2940 |
| ggcggtctca gcctcagcgc gatgaaccac gccccgctgc gccgctacta cctggcgcgc | 3000 |
| aacggcctgc tggtcctgcg ccgctacgcc cggtcctcgc cgctggccct gctggcgaac | 3060 |
| ctgccgaccc tgacccaggg cctcgcggtg ctcctgctcg aacgcgacaa gctgctcaag | 3120 |
| ctgcgctgcc tgggctgggg cctgtgggac ggcctgcggg gacgcggcgg cgcgctggag | 3180 |
| accaaccgcc cgcgcctgct gaagcgcctc gccggcccgg ccgtggcgtc cgtagcttcc | 3240 |
| ggcaaggcca aggcctagtc ggcgaaacgc attccctcta gagtcgacct gcaggcatgc | 3300 |
| aagcttggct gttttggcgg atgagagaag attttcagcc tgatacagat taaatcagaa | 3360 |
| cgcagaagcg gtctgataaa acagaatttg cctggcggca gtagcgcggt ggtcccacct | 3420 |
| gacccccatgc cgaactcaga agtgaaacgc cgtagcgccg atggtagtgt ggggtctccc | 3480 |
| catgcgagag tagggaactg ccaggcatca aataaaacga aaggctcagt cgaaagactg | 3540 |
| ggcctttcgt tttatctgtt gtttgtcggt gaacgctctc ctgagtagga caaatccgcc | 3600 |
| gggagcggat ttgaacgttg cgaagcaacg gcccggaggg tggcgggcag gacgcccgcc | 3660 |
| ataaactgcc aggcatcaaa ttaagcagaa ggccatcctg acggatggcc tttttgcgtt | 3720 |
| tctacaaaact cttttttgttt attttttctaa atacattcaa atatgtatcc gctcatgctc | 3780 |
| cttcgtcggt gtcgtcgccg gatggtctgc ggtggtgctc agcgtggaga cgcgcaccgt | 3840 |
| cacgaccccc catcaatcct gcctatttgc cacgtttaac aaggtagtta agcgttcatt | 3900 |
| tacgaagaaa acacgataag ctgcacaaat acctgaaaaa gttgaacgcc ccgtgagcgg | 3960 |

```
gaactcacag ggcgtcggct aaccccagt  catcagctgg gagaaagcac tcaagacatg   4020
actctagccg atccgcagga cacagtcaca gctagcgcgt ggaaattgtc cgccgatctg   4080
ttcgacaccc accccgaagc tatgcgctgc ggctcacgcg gctggacggc agaagatcgc   4140
cgcgaactgc tcgctcacct gggacgcgaa agcttccagg gcagcaagac aagagatttc   4200
gcgagcgcct ggattaaaaa cccggatacc ggcgaaaccc aaccaaagct ctaccgggct   4260
ggctcaaaag cgctgacgcg gtgccagtac gttgcgctga cgcacgcgca acatgccgcg   4320
gtgatcgtgc ttgacatcga tgtgcccagc caccaggccg gcgggaagat tgagcacgta   4380
aacccgcagg tctacgcgat tttagagaaa tgggcacgcc tagaaaaagc gccggcttgg   4440
atcggcgtga atccgctgag cgggaaatgc cagctcatct ggctcattga cccggtgtat   4500
gccgcagcag gtaaaaccag cccaaatatg cgcctgctgg ctgcaacgac ggaagaaatg   4560
actcgtgttt cggcgctga  ccaggctttt tcgcataggc tgagccggtg gccgctgcac   4620
gtctcagacg atccgacagc ctataaatgg cactgccagc atgatcgtgt ggatcggctg   4680
gccgacctaa tggagattgc tcgaacgatg accggatcac agaagccgaa aaagtacatt   4740
gagcaggact tttccagcgg acgcgcccgc attgaagcgg cacaacgcgc caccgcagaa   4800
gccaaggcgc tagcgatttt ggacgcgagc ctgccgagcg ccctggacgc gtccggcgac   4860
ctgatcgacg gcgtgcgagt gctctggaca aatccagagc gagcgcgcga cgagaccgcg   4920
tttcgccacg cgttgaccgt gggataccag ctcaaagctg ctggtgagcg cctaaaagat   4980
gccaagatca tcgacgcgta tgaagtggcg tacaacgttg cccaggcggt cggtgcagac   5040
ggccgggagc cggatcttcc cgccatgcgt gatcgcctga cgatggcgcg tcgtgtgcgc   5100
ggctacgtgg ctaaaggcca gccagtcgtc cctgctcgtc gggtggaaac gcagagcagc   5160
cgagggcgga aagctctagc gacgatgggg cgacggggcg cagctacatc gaatgcacgc   5220
agatgggctg acccagaaag taagtatgcg caggagacgc gacagcgatt agcggaagca   5280
aacaaacgcc gagaaatgac aggcgagttg ctcgaacttc gcgtcaaaac tgcgatcctg   5340
gatgcccgtt ctcaatcggt tgctgatccc tcgactcgtg agcttgcagg cgaactaggt   5400
gtcagtgaaa ggcgcatcca acaagtcaga aaggcacttg gaatggaagc taaacgcggc   5460
cgtccacggg ctgaaaacta ataaacgaaa caccgtcagc agaaaacggt tcccccttt    5520 aggggtcccg tccttgctct ggctctcact tgccctcacc ctccgctatc acgggctga   5580 aaactaataa acgaaacacc gtcagcagaa acggttccc  cccctttagg gtgtctcgct   5640
cctagctctg atccctcccc ggttcctccc cggcctgatt tttaaggggg gctcacgctg   5700
tcggcagaga acggttcccc gccttctgct ctggctcttc ctcgactccc tccccctcaa   5760
aaatctcctc gagatcctgg agaccttttt ggagctagcg cgttgctgct tcgcaccaac   5820
ttgctcatga tgattttcat ttttgcttgt gtgcttttt  gggttgaacc ctccaaagag   5880
gggaaaccag gggcacacct catgcactaa agtgccgctt cgctggtcag ggtgaaatca   5940
cctggaaaaa aagtgcggta accgctgcgc ttggcgtttt ttctgggcaa gaagtctcgc   6000
aggttttcgc aggagtgccg gaagaaatta tcagaattgg ggctagaatt tttaacgaac   6060
gttcgttata atggtgtcat gaccttcacg acgaagtacc aaaactggcc tgaagcatca   6120
gcggtggatc tctccgatgt cgcgctggag tccgacgcac tcgatgccgc cgtcgattta   6180
aaaacggtga tcggattttt ccgcgccctc gatacgacag acgcgccagc atcacgcgac   6240
tgggcaagtg ccgcgagcga cctagaaacg cttgtggccg accttgaaga gctggccgac   6300
```

```
gagctgcgtg ctcggcagcg ccaggaggac gcgcagtagt ggaggatcgc atcagctgcg    6360
cctactgcgg tggcctgatc ccaccccggc ctgacccacg aggacggcgc gcaaaatact    6420
gctcagacgc gtgtcgtgcc gcagccagcc gcgagcgcgc caacaagcgc cacgcccagg    6480
aggtcgaagc cgcacgtcga ccgcgtgtag tgcgtggcgg aaacttcttg cgtttcgcaa    6540
gagaaatgcg tcccatttct cgtcggactc ggggaaggaa gcgtgatgct ctcggtcaag    6600
cacgtcgctc gccagcgctg cgaggagttc ggccttcgtg cggaagtgcc agtagaggcc    6660
gggctgctgt acctgtaagt gagccgccag cgcgcgagtg gtgaagccat cgagcccagt    6720
ctcgtcgagc acctgccggg ccccgagcaa cacggacgtg cggtcgagac gcttccggtg    6780
gtgagtcata gttgcacttt atcatcgata actttatctt agataaagtg actgctcgct    6840
actctcatct gactgctcgc tactctcatc gtggaatcct gacagccgtg ctcatcacgg    6900
cgaccctcga tgctgcaggg ctgggcctcg tgatgccgat cttgcctacc cttctcgacc    6960
aggtcggtgc ccccgacgac atgatcccac tgcacgtcgg actactgaca gcgctctatg    7020
cgatcatgca gtttctttgc gccccgatcc ttggccgact ctctgaccgt ttcggacgcc    7080
gccgcgtgct tgtcgcctcc ctcgcaggcg cgacgatcga ctacctcgtg ctcgcactga    7140
cggacacgct gtgggtcttt tacctcgccc gcgcggttgc aggcattacc ggcgccacga    7200
acgccgtcac cgcgacggtg atcgccgaca ttactccgcc ggatcagcgc gcaaaacgct    7260
acgggtggct cggcgcatgc tacggcggtg gcatgatcgc gggtcccgcc attggcggtc    7320
ttttcggcgg ggtctcaccg catctgccat tcctcgtcgc cgccgcgctc gccggaatca    7380
ccctcgtact cagcgcgagt cttctgcgtg agacgcggcc accgggcagc aacggctcgc    7440
acgcacagca acccggtacg gcgaagcgaa ccgcagtgcc ggggatgctt atccttctcg    7500
cagtcttcgg catcgtgcag ttcatcggcc aagcaccagg ctccacctgg gtgctcttca    7560
cgcagcagcg cctcgactgg aaccccgtcg aagtcggcgt ttcgctatcc atcttcggaa    7620
tggtgcaagt attcgtgcag gcggcactga ccggacgcat cgtgtcccgg atcggcgaga    7680
cccgggcgat cctcgtcggt atcgccgcag acgccattgg gctcatcggc cttgccctca    7740
tcgccagcac atgggcgatg ctaccgatcc tcgcagcgct cggactcggc agcatcacgt    7800
tgcccgcact gcagacgctg ctctcgagac gcgcgcccga gcagcagcag ggacgcctgc    7860
agggaacact tgcaagcctg aacagcctca cctcgatcat cggcccggtc accttcaccg    7920
gcattttcgc actcacccga acgaatgcag acggcaccct ctggatctgc gccgcagcgc    7980
tctacgttct ctgcgccctc ctgatgatcc gtgagacatg cgcctcacgg cgatctcgat    8040
aaccgcgcta aggtgccatc ccgatgcgac gggatcgctc tgccaccagt caagtctccc    8100
gtagccggta tgagcatgac caaaatccct taacgtgagt tttcgttcca ctgagcgtca    8160
gaccccgtag aaaagatcaa aggatcttct tgagatcctt ttttttctgcg cgtaatctgc    8220
tgcttgcaaa caaaaaaacc accgctacca gcggtggttt gtttgccgga tcaagagcta    8280
ccaactcttt ttccgaaggt aactggcttc agcagagcgc agataccaaa tactgtcctt    8340
ctagtgtagc cgtagttagg ccaccacttc aagaactctg tagcaccgcc tacataccte    8400
gctctgctaa tcctgttacc agtggctgct gccagtggcg ataagtcgtg tcttaccggg    8460
ttggactcaa gacgatagtt accggataag gcgcagcggt cgggctgaac ggggggttcg    8520
tgcacacagc ccagcttgga gcgaacgacc tacaccgaac tgagatacct acagcgtgag    8580
ctatgagaaa gcgccacgct tcccgaaggg agaaaggcgg acaggtatcc ggtaagcggc    8640
agggtcggaa caggagagcg cacgagggag cttccagggg gaaacgcctg gtatctttat    8700
```

```
agtcctgtcg ggtttcgcca cctctgactt gagcgtcgat ttttgtgatg ctcgtcaggg    8760
gggcggagcc tatggaaaaa cgccagcaac gcggcctttt tacggttcct ggccttttgc    8820
tggccttttg ctcacatgtt ctttcctgcg ttatccctg attctgtgga taaccgtatt     8880
accgcctttg agtgagctga taccgctcgc cgcagccgaa cgaccgagcg cagcgagtca    8940
gtgagcgagg aagcggaaga gcgcctgatg cggtattttc tccttacgca tctgtgcggt    9000
atttcacacc gcatatggtg cactctcagt acaatctgct ctgatgccgc atagttaagc    9060
cagtatacac tccgctatcg ctacgtgact gggtcatggc tgcgccccga cacccgccaa    9120
cacccgctga cgcgccctga cgggcttgtc tgctcccggc atccgcttac agacaagctg    9180
tgaccgtctc cgggagctgc atgtgtcaga ggttttcacc gtcatcaccg aaacgcgcga    9240
ggcagcagat caattcgcgc gcgaaggcga agcggcatgc atttacgttg acaccatcga    9300
atggtgcaaa acctttcgcg gtatggcatg atagcgcccg gaagagagtc aattcagggt    9360
ggtgaatgtg aaaccagtaa cgttatacga tgtcgcagag tatgccggtg tctcttatca    9420
gaccgtttcc cgcgtggtga accaggccag ccacgtttct gcgaaaacgc gggaaaaagt    9480
ggaagcggcg atggcggagc tgaattacat tcccaaccgc gtggcacaac aactggcggg    9540
caaacagtcg ttgctgattg gcgttgccac ctccagtctg gccctgcacg cgccgtcgca    9600
aattgtcgcg gcgattaaat ctcgcgccga tcaactgggt gccagcgtgg tggtgtcgat    9660
ggtagaacga agcggcgtcg aagcctgtaa agcggcggtg cacaatcttc tcgcgcaacg    9720
cgtcagtggg ctgatcatta actatccgct ggatgaccag gatgccattg ctgtggaagc    9780
tgcctgcact aatgttccgg cgttatttct tgatgtctct gaccagacac ccatcaacag    9840
tattattttc tcccatgaag acggtacgcg actgggcgtg gagcatctgg tcgcattggg    9900
tcaccagcaa atcgcgctgt tagcgggccc attaagttct gtctcggcgc gtctgcgtct    9960
ggctggctgg cataaatatc tcactcgcaa tcaaattcag ccgatagcgg aacgggaagg   10020
cgactggagt gccatgtccg gttttcaaca aaccatgcaa atgctgaatg agggcatcgt   10080
tcccactgcg atgctggttg ccaacgatca gatggcgctg ggcgcaatgc gcgccattac   10140
cgagtccggg ctgcgcgttg gtgcggatat ctcggtagtg ggatacgacg ataccgaaga   10200
cagctcatgt tatatcccgc cgtcaaccac catcaaacag gattttcgcc tgctggggca   10260
aaccagcgtg gaccgcttgc tgcaactctc tcagggccag gcggtgaagg gcaatcagct   10320
gttgcccgtc tcactggtga aaagaaaaac cacccetggcg cccaatacgc aaaccgcctc   10380
tccccgcgcg ttggccgatt cattaatgca gctggcacga caggtttccc gactggaaag   10440
cgggcagtga gcgcaacgca attaatgtga gttagcgcga attgatctgg tttgacagct   10500
tatcatcgac tgcacggtgc accaatgctt ctggcgtcag gcagccatcg gaagctgtgg   10560
tatggctgtg caggtcgtaa atcactgcat aattcgtgtc gctcaaggcg cactcccgtt   10620
ctggataatg ttttttgcgc cgacatcata acggttctgg caaatattct gaaatgagct   10680
gttgacaatt aatcatccgg ctcgtataat gtgtggaatt gtgagcggat aacaatttca   10740
cacaggaaac agaccatgga attcgagctc ggtacccggg                         10780
```

<210> SEQ ID NO 54
<211> LENGTH: 11073
<212> TYPE: DNA
<213> ORGANISM: Artificial Sequence
<220> FEATURE:
<223> OTHER INFORMATION: vector

<400> SEQUENCE: 54

```
gatctggcat ttttgggagg tgtgaaatgc ggcgcgaaag tctgttggta tcggtttgca      60
agggcctgcg ggtacatgtc gagcgcgttg ggcaggatcc cgggcgcagc acggtgatgc     120
tggtcaacgg cgcgatggcg accaccgcct cgttcgcccg gacctgcaag tgcctggccg     180
aacatttcaa cgtggtgctg ttcgacctgc ccttcgccgg gcagtcgcgt cagcacaacc     240
cgcagcgggg gttgatcacc aaggacgacg aggtggaaat cctcctggcg ctgatcgagc     300
gcttcgaggt caatcacctg gtctccgcgt cctggggcgg tatctccacg ctgctggcgc     360
tgtcgcgcaa tccgcgcggc atccgcagct cggtggtgat ggcattcgcc cctggactga     420
accaggcgat gctcgactac gtcgggcggg cgcaggcgct gatcgagctg gacgacaagt     480
cggcgatcgg ccatctgctc aacgagaccg tcggcaaata cctgccgccg cgcctgaaag     540
ccagcaacca tcagcacatg gcttcgctgg ccaccggcga atacgagcag gcgcgcttttc    600
acatcgacca ggtgctggcg ctcaacgatc ggggctacct ggcttgcctg gagcggatcc     660
agagccacgt gcatttcatc aacggcagct gggacgaata caccaccgcc gaggacgccc     720
gccagttccg cgactacctg ccgcactgca gtttctcgcg ggtggagggc accgggcatt     780
tcctcgacct ggagtccaag ctggccgcgg tacgcgtgca ccgcgccctg ctcgagcacc     840
tgctgaagca accggagccg cagcgggcgg aacgcgcggc gggattccac gagatggcca     900
tcggctacgc ctgaacccttt gacctgcgaa gacccgcct ggccgggctt tgcggttgca     960
taacgcacgg agtagcacca tgcacgccat cctcatcgcc atcggctcgg ccggcgacgt    1020
atttcccttc atcggcctgg cccggaccct gaaattgcgc gggcaccgcg tgagcctctg    1080
caccatcccg gtgtttcgcg acgcggtgga gcagcacggc atcgcgttcg tcccgctgag    1140
cgacgaactg acctaccgcc ggaccatggg cgatccgcgc ctgtgggacc caagacgtc     1200
cttcggcgtg ctctggcaaa ccatcgccgg gatgatcgag ccggtctacg agtacgtctc    1260
ggcgcagcgc catgacgaca tcgtggtggt cggctcgctc tgggcgctgg gcgcacgcat    1320
cgctcacgag aagtacggga ttccctacct gtccgcgcag gtctcgccat cgaccttgtt    1380
gtcggcgcac ctgccgccgg tacaccccaa gttcaacgtg cccgagcaga tgccgctggc    1440
gatgcgcaag ctgctctggc gctgcatcga gcgcttcaag ctggatcgca cctgcgcgcc    1500
ggatatcaac gcggtgcggc gcaaggtcgg cctggagacg ccggtgaagc gcatcttcac    1560
ccaatggatg cattcgccgc agggcgtggt ctgcctgttc ccggcctggt tcgcgccgcc    1620
ccagcaggat tggccgcaac ccctgcacat gaccggcttc ccgctgttcg acggcagtat    1680
cccggggacc ccgctcgacg acgaactgca acgctttctc gatcagggca gccggccgct    1740
ggtgttcacc cagggctcga ccgaacacct gcagggcgac ttctacgcca tggccctgcg    1800
cgcgctggaa cgcctcggcg cgcgtgggat cttcctcacc ggcgccggcc aggaaccgct    1860
gcgcggcttg ccgaaccacg tgctgcagcg cgcctacgcg ccactgggag ccttgctgcc    1920
atcgtgcgcc gggctggtcc atccgggcgg tatcggcgcc atgagcctgg ccttggcggc    1980
gggggtgccg caggtgctgc tgccctgcgc ccacgaccag ttcgacaatg ccgaacggct    2040
ggtccggctc ggctgcggga tgcgcctggg cgtgccattg cgcgagcagg agttgcgcgg    2100
ggcgctgtgg cgcttgctcg aggacccggc catggcggcg gcctgtcggc gtttcatgga    2160
attgtcacaa ccgcacagta tcgcttgcgg taaagcggcc caggtggtcg aacgttgtca    2220
tagggagggg gatgcgcgat ggctgaaggc tgcgtcctga cgccgggagg atcctggcgt    2280
gtccacgacc agcctctgcc cctccgccac gcgggaacac ggtcccggcg cgaaacgcgt    2340
```

```
cctgcctctg ctgttcctca cctgcctgct ggatgccgct ggcgtcggcc tgatcgtgcc    2400
cctgctgccg acgctgatcg gcagcgtggc gccgctggcg gtccgcgacg cggccacctg    2460
gggcgccgcc ctggtgatga ccttcgcgct gctgcaattg ttcttttcgc cggtcctcgg    2520
cagcctcagc gaccgcttcg gacgccgccc cgtcctggtc ctggcgatgc tcggcttcgc    2580
cctcagctat ctgctgctgg cgctggccga cagcctctgg atgctgttcc tcggtcgcgc    2640
gctggccggg ctcaccggcg ccagcgtggc caccgcgatg gcctgcgcgg ctgacctcgg    2700
cacgcacggg cagcgcaccc ggcacttcgg ctggctgtac gccggcctcg ccctgggcat    2760
gatcctcggc cccgccctcg gtgggctgct ggcggtgcac ggcacgacgc tgccgctgtt    2820
gctggccgcc ggcctgtgcc tgctcaacgc cctgctcgcc ggcctgttcc tcgaggaaac    2880
cctgcccccg acgcgacgcc gccgcctgga cccgaggcgg atgaatgcct tgcgctcgat    2940
cagcggcctg gctcggcaac cggggggtcgg acgcctgctg gcggtgcttg ccctggtatt    3000
cctcggcttg caggcggtga tggtggtctg gccgttcttc gtgatcgaga agtttcactg    3060
gagcagcgcc tggatcggct actcgctggc cctctacggc gtgctcgcgg tgctcgccca    3120
gaccctcggc gtgaacctct gcaagcgcg cctggacgac gcccgcctgc tgcgcctggg    3180
cctcgccctg caaggctgcg gcctgctgct gttcgccctg gtcgactcgt cattctggct    3240
ggtctgcgcg ctgctgccct tcgcgctcgg cagcctcgcc accccggcca tgcaggggct    3300
gctctcggcc cgcgtgccgg tcgaccgcca gggcgagttg cagggcgtgc tgagcagcct    3360
gatgagcctc gccgcgatcg tcggtccgcc gctgatgagc ggcctgttcc actggggcag    3420
cggtccgctc gcgccgctgc ccctggccgg cgcgccattc ctcgccggcg cccttctcgt    3480
tctggccggg ctggtcctgg cctggcaact tcgacctacg ggagaagaac gatcatggac    3540
cggatagaca tgggcgtgct ggtggtactt ctagagtcga cctgcaggca tgcaagcttg    3600
gctgttttgg cggatgagag aagattttca gcctgataca gattaaatca gaacgcagaa    3660
gcggtctgat aaaacagaat ttgcctggcg gcagtagcgc ggtggtccca cctgacccca    3720
tgccgaactc agaagtgaaa cgccgtagcg ccgatggtag tgtggggtct ccccatgcga    3780
gagtagggaa ctgccaggca tcaaataaaa cgaaaggctc agtcgaaaga ctgggccttt    3840
cgttttatct gttgtttgtc ggtgaacgct ctcctgagta ggacaaatcc gccgggagcg    3900
gatttgaacg ttgcgaagca acggcccgga gggtggcggg caggacgccc gccataaact    3960
gccaggcatc aaattaagca gaaggccatc ctgacggatg ccttttttgc gtttctacaa    4020
actcttttgt tttatttttc taaatacatt caaatatgta tccgctcatg ctccttcgtc    4080
ggtgtcgtcg ccggatggtc tgcggtggtg ctcagcgtgg agacgcgcac cgtcacggac    4140
ccccatcaat cctgcctatt tgccacgttt aacaaggtag ttaagcgttc atttacgaag    4200
aaaacacgat aagctgcaca aatacctgaa aaagttgaac gccccgtgag cgggaactca    4260
cagggcgtcg gctaaccccc agtcatcagc tgggagaaag cactcaagac atgactctag    4320
ccgatccgca ggacacagtc acagctagcg cgtggaaatt gtccgccgat ctgttcgaca    4380 ccccaccccga agctatgcgc tgcggctcac gcggctggac ggcagaagat cgccgcgaac    4440
tgctcgctca cctgggacgc gaaagcttcc agggcagcaa gacaagagat ttcgcgagcg    4500
cctggattaa aaaccccggat accggcgaaa cccaaccaaa gctctaccgg gctggctcaa    4560
aagcgctgac gcggtgccag tacgttcgcg tgacgcacgc gcaacatgcc gcggtgatcg    4620
tgcttgacat cgatgtgccc agccaccagg ccggcgggaa gattgagcac gtaaacccgc    4680
```

```
aggtctacgc gattttagag aaatgggcac gcctagaaaa agcgccggct tggatcggcg    4740
tgaatccgct gagcgggaaa tgccagctca tctggctcat tgacccggtg tatgccgcag    4800
caggtaaaac cagcccaaat atgcgcctgc tggctgcaac gacggaagaa atgactcgtg    4860
ttttcggcgc tgaccaggct ttttcgcata ggctgagccg gtggccgctg cacgtctcag    4920
acgatccgac agcctataaa tggcactgcc agcatgatcg tgtggatcgg ctggccgacc    4980
taatggagat tgctcgaacg atgaccggat cacagaagcc gaaaaagtac attgagcagg    5040
acttttccag cggacgcgcc cgcattgaag cggcacaacg cgccaccgca gaagccaagg    5100
cgctagcgat tttggacgcg agcctgccga gcgccctgga cgcgtccggc gacctgatcg    5160
acggcgtgcg agtgctctgg acaaatccag agcgagcgcg cgacgagacc gcgtttcgcc    5220
acgcgttgac cgtgggatac cagctcaaag ctgctggtga gcgcctaaaa gatgccaaga    5280
tcatcgacgc gtatgaagtg gcgtacaacg ttgcccaggc ggtcggtgca gacggccggg    5340
agccggatct tcccgccatg cgtgatcgcc tgacgatggc gcgtcgtgtg cgcggctacg    5400
tggctaaagg ccagccagtc gtccctgctc gtcgggtgga aacgcagagc agccgagggc    5460
ggaaagctct agcgacgatg gggcgacggg gcgcagctac atcgaatgca cgcagatggg    5520
ctgacccaga aagtaagtat gcgcaggaga cgcgacagcg attagcggaa gcaaacaaac    5580
gccgagaaat gacaggcgag ttgctcgaac ttcgcgtcaa aactgcgatc ctggatgccc    5640
gttctcaatc ggttgctgat ccctcgactc gtgagcttgc aggcgaacta ggtgtcagtg    5700
aaaggcgcat ccaacaagtc agaaaggcac ttggaatgga agctaaacgc ggccgtccac    5760
gggctgaaaa ctaataaacg aaacaccgtc agcagaaaac ggttcccccc tttaggggtc    5820
ccgtccttgc tctggctctc acttgccctc accctccgct atccacgggc tgaaaactaa    5880
taaacgaaac accgtcagca gaaacggtt cccccctttt agggtgtctc gctcctagct    5940
ctgatccctc cccggttcct ccccggcctg attttaagg ggggctcacg ctgtcggcag    6000
agaacggttc cccgccttct gctctggctc ttcctcgact ccctccccct caaaaatctc    6060
ctcgagatcc tggagacctt tttggagcta gcgcgttgct gcttcgcacc aacttgctca    6120
tgatgatttt catttttgct tgtgtgcttt tttgggttga accctccaaa gaggggaaac    6180
caggggcaca cctcatgcac taaagtgccg cttcgctggt cagggtgaaa tcacctggaa    6240
aaaaagtgcg gtaaccgctg cgcttggcgt ttttctggg caagaagtct cgcaggtttt    6300
cgcaggagtg ccggaagaaa ttatcagaat tgggctaga atttttaacg aacgttcgtt    6360
ataatggtgt catgaccttc acgacgaagt accaaaactg gcctgaagca tcagcggtgg    6420
atctctccga tgtcgcgctg gagtccgacg cactcgatgc cgccgtcgat ttaaaaacgg    6480
tgatcggatt tttccgcgcc ctcgatacga cagacgcgcc agcatcacgc gactgggcaa    6540
gtgccgcgag cgacctagaa acgcttgtgg ccgaccttga agagctggcc gacgagctgc    6600
gtgctcggca gcgccaggag gacgcgcagt agtggaggat cgcatcagct gcgcctactg    6660
cggtggcctg atcccacccc ggcctgaccc acgaggacgg cgcgcaaaat actgctcaga    6720
cgcgtgtcgt gccgcagcca gccgcgagcg cgccaacaag cgccacgccc aggaggtcga    6780
agccgcacgt cgaccgcgtg tagtgcgtgg cggaaacttc ttgcgtttcg caagagaaat    6840
gcgtcccatt tctcgtcgga ctcggggaag gaagcgtgat gctctcggtc aagcacgtcg    6900
ctcgccagcg ctgcgaggag ttcggccttc gtgcggaagt gccagtagag ccgggctgc    6960 tgtacctgta agtgagccgc cagcgcgcga gtggtgaagc catcgagccc agtctcgtcg    7020
agcacctgcc gggccccgag caacacggac gtgcggtcga cacgcttccg gtggtgagtc    7080
```

```
atagttgcac tttatcatcg ataactttat cttagataaa gtgactgctc gctactctca    7140
tctgactgct cgctactctc atcgtggaat cctgacagcc gtgctcatca cggcgaccct    7200
cgatgctgca gggctgggcc tcgtgatgcc gatcttgcct acccttctcg accaggtcgg    7260
tgcccccgac gacatgatcc cactgcacgt cggactactg acagcgctct atgcgatcat    7320
gcagtttctt tgcgccccga tccttggccg actctctgac cgtttcggac gccgccgcgt    7380
gcttgtcgcc tccctcgcag gcgcgacgat cgactacctc gtgctcgcac tgacggacac    7440
gctgtgggtc ttttacctcg cccgcgcggt tgcaggcatt accggcgcca cgaacgccgt    7500
caccgcgacg gtgatcgccg acattactcc gccggatcag cgcgcaaaac gctacgggtg    7560
gctcggcgca tgctacggcg gtggcatgat cgcgggtccc gccattggcg gtcttttcgg    7620
cggggtctca ccgcatctgc cattcctcgt cgccgccgcg ctcgccggaa tcaccctcgt    7680
actcagcgcg agtcttctgc gtgagacgcg gccaccgggc agcaacggct cgcacgcaca    7740
gcaacccggt acggcgaagc gaaccgcagt gccggggatg cttatccttc tcgcagtctt    7800
cggcatcgtg cagttcatcg gccaagcacc aggctccacc tgggtgctct tcacgcagca    7860
gcgcctcgac tggaaccccg tcgaagtcgg cgtttcgcta tccatcttcg gaatggtgca    7920
agtattcgtg caggcggcac tgaccggacg catcgtgtcc cggatcggcg agacccgggc    7980
gatcctcgtc ggtatcgccg cagacgccat tgggctcatc ggccttgccc tcatcgccag    8040
cacatgggcg atgctaccga tcctcgcagc gctcggactc ggcagcatca cgttgcccgc    8100
actgcagacg ctgctctcga gacgcgcgcc cgagcagcag cagggacgcc tgcagggaac    8160
acttgcaagc ctgaacagcc tcacctcgat catcggcccg gtcaccttca ccggcatttt    8220
cgcactcacc cgaacgaatg cagacggcac cctctggatc tgcgccgcag cgctctacgt    8280
tctctgcgcc ctcctgatga tccgtgagac atgcgcctca cggcgatctc gataaccgcg    8340
ctaaggtgcc atcccgatgc gacgggatcg ctctgccacc agtcaagtct cccgtagccg    8400
gtatgagcat gaccaaaatc ccttaacgtg agttttcgtt ccactgagcg tcagaccccg    8460
tagaaaagat caaaggatct tcttgagatc cttttttttct gcgcgtaatc tgctgcttgc    8520
aaacaaaaaa accaccgcta ccagcggtgg tttgtttgcc ggatcaagag ctaccaactc    8580
tttttccgaa ggtaactggc ttcagcagag cgcagatacc aaatactgtc cttctagtgt    8640
agccgtagtt aggccaccac ttcaagaact ctgtagcacc gcctacatac ctcgctctgc    8700
taatcctgtt accagtggct gctgccagtg gcgataagtc gtgtcttacc gggttggact    8760
caagacgata gttaccggat aaggcgcagc ggtcgggctg aacggggggt tcgtgcacac    8820
agcccagctt ggagcgaacg acctacaccg aactgagata cctacagcgt gagctatgag    8880
aaagcgccac gcttcccgaa gggagaaagg cggacaggta tccggtaagc ggcagggtcg    8940
gaacaggaga gcgcacgagg gagcttccag ggggaaacgc ctggtatctt tatagtcctg    9000
tcgggtttcg ccacctctga cttgagcgtc gatttttgtg atgctcgtca gggggggcgga    9060 gcctatggaa aaacgccagc aacgcggcct ttttacggtt cctggccttt tgctggcctt    9120
ttgctcacat gttctttcct gcgttatccc ctgattctgt ggataaccgt attaccgcct    9180
ttgagtgagc tgataccgct cgccgcagcc gaacgaccga gcgcagcgag tcagtgagcg    9240
aggaagcgga agagcgcctg atgcggtatt ttctccttac gcatctgtgc ggtatttcac    9300
accgcatatg gtgcactctc agtacaatct gctctgatgc cgcatagtta agccagtata    9360
cactccgcta tcgctacgtg actgggtcat ggctgcgccc cgacacccgc caacacccgc    9420
```

```
tgacgcgccc tgacgggctt gtctgctccc ggcatccgct tacagacaag ctgtgaccgt    9480
ctccgggagc tgcatgtgtc agaggttttc accgtcatca ccgaaacgcg cgaggcagca    9540
gatcaattcg cgcgcgaagg cgaagcggca tgcatttacg ttgacaccat cgaatggtgc    9600 aaaaccttc gcggtatggc atgatagcgc ccggaagaga gtcaattcag ggtggtgaat     9660
gtgaaaccag taacgttata cgatgtcgca gagtatgccg gtgtctctta tcagaccgtt    9720
tcccgcgtgg tgaaccaggc cagccacgtt tctgcgaaaa cgcgggaaaa agtggaagcg    9780
gcgatggcgg agctgaatta cattcccaac cgcgtggcac aacaactggc gggcaaacag    9840
tcgttgctga ttggcgttgc cacctccagt ctggccctgc acgcgccgtc gcaaattgtc    9900
gcggcgatta aatctcgcgc cgatcaactg ggtgccagcg tggtggtgtc gatggtagaa    9960
cgaagcggcg tcgaagcctg taaagcggcg gtgcacaatc ttctcgcgca acgcgtcagt   10020
gggctgatca ttaactatcc gctggatgac caggatgcca ttgctgtgga agctgcctgc   10080
actaatgttc cggcgttatt tcttgatgtc tctgaccaga cacccatcaa cagtattatt   10140
ttctcccatg aagacggtac gcgactgggc gtggagcatc tggtcgcatt gggtcaccag   10200
caaatcgcgc tgttagcggg cccattaagt tctgtctcgg cgcgtctgcg tctggctggc   10260
tggcataaat atctcactcg caatcaaatt cagccgatag cggaacggga aggcgactgg   10320
agtgccatgt ccggttttca acaaaccatg caaatgctga atgagggcat cgttcccact   10380
gcgatgctgt tgccaacga tcagatgcgc ctgggcgcaa tgcgcgccat taccgagtcc    10440
gggctgcgcg ttggtgcgga tatctcggta gtgggatacg acgataccga agacagctca   10500
tgttatatcc cgccgtcaac caccatcaaa caggattttc gcctgctggg gcaaaccagc   10560
gtggaccgct tgctgcaact ctctcagggc caggcggtga agggcaatca gctgttgccc   10620
gtctcactgg tgaaaagaaa aaccaccctg gcgcccaata cgcaaaccgc ctctccccgc   10680
gcgttggccg attcattaat gcagctggca cgacaggttt cccgactgga aagcgggcag   10740
tgagcgcaac gcaattaatg tgagttagcg cgaattgatc tggtttgaca gcttatcatc   10800
gactgcacgg tgcaccaatg cttctggcgt caggcagcca tcggaagctg tggtatggct   10860
gtgcaggtcg taaatcactg cataattcgt gtcgctcaag cgcactccc gttctggata    10920 atgttttttg cgccgacatc ataacggttc tggcaaatat tctgaaatga gctgttgaca   10980
attaatcatc cggctcgtat aatgtgtgga attgtgagcg gataacaatt tcacacagga   11040
aacagaccat ggaattcgag ctcggtaccc ggg                                11073
```

```
<210> SEQ ID NO 55
<211> LENGTH: 12263
<212> TYPE: DNA
<213> ORGANISM: Artificial Sequence
<220> FEATURE:
<223> OTHER INFORMATION: vector

<400> SEQUENCE: 55
```

```
gatctggcat ttttgggagg tgtgaaatgc ggcgcgaaag tctgttggta tcggtttgca      60
agggcctgcg ggtacatgtc gagcgcgttg ggcaggatcc cgggcgcagc acggtgatgc     120
tggtcaacgg cgcgatggcg accaccgcct cgttcgcccg gacctgcaag tgcctggccg    180
aacatttcaa cgtggtgctg ttcgacctgc ccttcgccgg gcagtcgcgt cagcacaacc    240
cgcagcgggg gttgatcacc aaggacgacg aggtggaaat cctcctggcg ctgatcgagc    300
gcttcgaggt caatcacctg gtctccgcgt cctggggcgg tatctccacg ctgctggcgc    360
tgtcgcgcaa tccgcgcggc atccgcagct cggtggtgat ggcattcgcc cctggactga    420
```

-continued

| | | |
|---|---|---|
| accaggcgat gctcgactac gtcgggcggg cgcaggcgct gatcgagctg acgacaagt | 480 |
| cggcgatcgg ccatctgctc aacgagaccg tcggcaaata cctgccgccg cgcctgaaag | 540 |
| ccagcaacca tcagcacatg gcttcgctgg ccaccggcga atacgagcag gcgcgctttc | 600 |
| acatcgacca ggtgctggcg ctcaacgatc ggggctacct ggcttgcctg gagcggatcc | 660 |
| agagccacgt gcatttcatc aacggcagct gggacgaata caccaccgcc gaggacgccc | 720 |
| gccagttccg cgactacctg ccgcactgca gtttctcgcg ggtggagggc accgggcatt | 780 |
| tcctcgacct ggagtccaag ctggccgcgg tacgcgtgca ccgcgccctg ctcgagcacc | 840 |
| tgctgaagca accggagccg cagcgggcgg aacgcgcggc gggattccac agatggccat | 900 |
| cggctacgc ctgaaccctt gacctgcgaa gacccggcct ggccgggctt gcggttgca | 960 |
| taacgcacgg agtagcacca tgcacgccat cctcatcgcc atcggctcgg ccggcgacgt | 1020 |
| atttcccttc atcggcctgg cccggaccct gaaattgcgc gggcaccgcg tgagcctctg | 1080 |
| caccatcccg gtgtttcgcg acgcggtgga gcagcacggc atcgcgttcg tcccgctgag | 1140 |
| cgacgaactg acctaccgcc ggaccatggg cgatccgcgc ctgtgggacc caagacgtc | 1200 |
| cttcggcgtg ctctggcaaa ccatcgccgg gatgatcgag ccggtctacg agtacgtctc | 1260 |
| ggcgcagcgc catgacgaca tcgtggtggt cggctcgctc tgggcgctgg gcgcacgcat | 1320 |
| cgctcacgag aagtacggga ttccctacct gtccgcgcag gtctcgccat cgaccttgtt | 1380 |
| gtcggcgcac ctgccgccgg tacaccccaa gttcaacgtg cccgagcaga tgccgctggc | 1440 |
| gatgcgcaag ctgctctggc gctgcatcga gcgcttcaag ctggatcgca cctgcgcgcc | 1500 |
| ggatatcaac gcggtgcggc gcaaggtcgg cctggagacg ccggtgaagc gcatcttcac | 1560 |
| ccaatggatg cattcgccgc agggcgtggt ctgcctgttc ccggcctggt tcgcgccgcc | 1620 |
| ccagcaggat tggccgcaac ccctgcacat gaccggcttc ccgctgttcg acggcagtat | 1680 |
| cccgggacc ccgctcgacg acgaactgca acgctttctc gatcagggca gccggccgct | 1740 |
| ggtgttcacc cagggctcga ccgaacacct gcagggcgac ttctacgcca tggccctgcg | 1800 |
| cgcgctggaa cgcctcggcg cgcgtgggat cttcctcacc ggcgccggcc aggaaccgct | 1860 |
| gcgcggcttg ccgaaccacg tgctgcagcg cgcctacgcg ccactgggag ccttgctgcc | 1920 |
| atcgtgcgcc gggctggtcc atccgggcgg tatcggcgcc atgagcctgg ccttggcggc | 1980 |
| gggggtgccg caggtgctgc tgccctgcgc ccacgaccag ttcgacaatg ccgaacggct | 2040 |
| ggtccggctc ggctgcggga tgcgcctggg cgtgccattg cgcgagcagg agttgcgcgg | 2100 |
| ggcgctgtgg cgcttgctcg aggacccggc catggcggcg cctgtcggc gtttcatgga | 2160 |
| attgtcacaa ccgcacagta tcgcttgcgg taaagcggcc caggtggtcg aacgttgtca | 2220 |
| tagggagggg gatgcgcgat ggctgaaggc tgcgtcctga cctacgggag aagaacgatc | 2280 |
| atggaccgga tagacatggg cgtgctggtg gtactgttca atcctggcga cgacgacctg | 2340 |
| gaacaccttg gcgaactggc ggcggcgttt ccgcaactgc gcttccttgc cgtcgacaac | 2400 |
| tcaccgcaca gcgatccgca gcgcaatgcc cggctgcgcg ggcaaggcat cgccgtgctg | 2460 |
| caccacggca accggcaggg catcgccggc gccttcaacc agggactcga cgcgctattc | 2520 |
| cggcgtggcg tgcagggtgt gctgctgctc gaccaggact cccgtcccgg cggcgccttc | 2580 |
| ctcgccgccc agtggcgcaa cctgcaggcg cgcaacggtc aggcctgcct gctcggccca | 2640 |
| cggatcttcg accggggtga ccggcgcttc ctgccggcca tccatctcga cggactgacg | 2700 |
| ctcaggcaat tgtctctgga cggcctgacg accccgcagc gcacctcgtt cctgatctcc | 2760 |

```
tccggctgcc tgctgacccg cgaggcctac cagcgcctcg gccacttcga cgaggaactg   2820
ttcatcgacc acgtggacac cgaatacagc ctgcgcgccc aggcgctgga cgtgcccctg   2880
tacgtcgacc cgcggctggt cctcgagcac cgcatcggca cgcgcaagac ccgccgcctc   2940
ggcggtctca gcctcagcgc gatgaaccac gccccgctgc gccgctacta cctggcgcgc   3000
aacggcctgc tggtcctgcg ccgctacgcc cggtcctcgc cgctggccct gctggcgaac   3060
ctgccgaccc tgacccaggg cctgcgcgtg ctcctgctcg aacgcgacaa gctgctcaag   3120
ctgcgctgcc tgggctgggg cctgtgggac ggcctgcggg gacgcggcgg cgcgctggag   3180
accaaccgcc cgcgcctgct gaagcgcctc gccggcccgg ccgtggcgtc cgtagcttcc   3240
ggcaaggcca aggcctagtc ggcgaaacgc attccctcta gatgagaggc cggcaaggat   3300
acccgactgg cgcacgggtc gcatcattat gacatcacgc cgcccgcgg cgttgccgcg   3360 accgttcgtc gaacctgtga attccggtag ttccccttgc cctcgctggc gtcccaagat   3420
caggatttcc tgtgttcgcc gggaggatcc tggcgtgtcc acgaccagcc tctgcccctc   3480
cgccacgcgg gaacacggtc ccggcgcgaa acgcgtcctg cctctgctgt tcctcacctg   3540
cctgctggat gccgctggcg tcggcctgat cgtgcccctg ctgccgacgc tgatcggcag   3600
cgtggcgccc ctggcggtcc gcgacgcggc cacctggggc gccgcctgg tgatgacctt   3660 cgcgctgctg caattgttct tttcgccggt cctcggcagc ctcagcgacc gcttcggacg   3720
ccgccccgtc ctggtcctgg cgatgctcgg cttcgccctc agctatctgc tgctggcgct   3780
ggccgacagc ctctggatgc tgttcctcgg tcgcgcgctg gccgggctca ccggcgccag   3840
cgtgccaccg cgatggcct gcgcggctga cctcggcacg cacgggcagc gcacccggca   3900
cttcggctgg ctgtacgccg gcctcgccct gggcatgatc ctcggccccg ccctcggtgg   3960
gctgctggcg gtgcacggca cgacgctgcc gctgttgctg gccgccggcc tgtgcctgct   4020
caacgccctg ctcgccggcc tgttcctcga ggaaaccctg cccccgacgc gacgccgccg   4080 cctgacccg aggcggatga atgccttgcg ctcgatcagc ggcctggctc ggcaaccggg   4140
ggtcggacgc ctgctggcgg tgcttgccct ggtattcctc ggcttgcagg cggtgatggt   4200
ggtctggccg ttcttcgtga tcgagaagtt tcactggagc agcgcctgga tcggctactc   4260
gctggccctc tacggcgtgc tcgcggtgct cgcccagacc ctcggcgtga acctctgcaa   4320
gcggcgcctg gacgacgccc gcctgctgcg cctgggcctc gccctgcaag ctgcggcct   4380 gctgctgttc gccctggtcg actcgtcatt ctggctggtc tgcgcgctgc tgcccttcgc   4440
gctcggcagc ctcgccaccc cggccatgca ggggctgctc tcggcccgcg tgccggtcga   4500
ccgccagggc gagttgcagg gcgtgctgag cagcctgatg agcctcgccg cgatcgtcgg   4560
tccgccgctg atgagcggcc tgttccactg gggcagcggt ccgctcgcgc gctgccct   4620 ggccggcgcg ccattcctcg ccggcgccct tctcgttctg gccgggctgg tcctggcctg   4680
gcaacttcga cctacgggag aagaacgatc atggaccgga tagacatggg cgtgctggtg   4740
gtactgttca atcctggcgt ctagagtcga cctgcaggca tgcaagcttg ctgttttgg   4800 cggatgagag aagattttca gcctgataca gattaaatca gaacgcagaa gcggtctgat   4860
aaaacagaat ttgcctggcg gcagtagcgc ggtggtccca cctgacccca tgccgaactc   4920
agaagtgaaa cgccgtagcg ccgatggtag tgtgggtct cccatgcga gagtagggaa   4980 ctgccaggca tcaaataaaa cgaaaggctc agtcgaaaga ctgggccttt cgttttatct   5040
gttgtttgtc ggtgaacgct ctcctgagta ggacaaatcc gccgggagcg gatttgaacg   5100
ttgcgaagca acggcccgga gggtggcggg caggacgccc gccataaact gccaggcatc   5160
```

```
aaattaagca gaaggccatc ctgacggatg gccttttgc gtttctacaa actcttttg      5220 tttattttc taaatacatt caaatatgta tccgctcatg ctccttcgtc ggtgtcgtcg      5280
ccggatggtc tgcggtggtg ctcagcgtgg agacgcgcac cgtcacggac ccccatcaat      5340
cctgcctatt tgccacgttt aacaaggtag ttaagcgttc atttacgaag aaaacacgat      5400
aagctgcaca aatacctgaa aaagttgaac gccccgtgag cgggaactca cagggcgtcg      5460
gctaaccccc agtcatcagc tgggagaaag cactcaagac atgactctag ccgatccgca      5520
ggacacagtc acagctagcg cgtggaaatt gtccgccgat ctgttcgaca cccaccccga      5580
agctatgcgt tgcggctcac gcggctggac ggcagaagat cgccgcgaac tgctcgctca      5640
cctgggacgc gaaagcttcc agggcagcaa gacaagagat ttcgcgagcg cctggattaa      5700
aaacccggat accggcgaaa cccaaccaaa gctctaccgg gctggctcaa aagcgctgac      5760
gcggtgccag tacgttgcgc tgacgcacgc gcaacatgcc gcggtgatcg tgcttgacat      5820
cgatgtgccc agccaccagg ccggcggaa gattgagcac gtaaacccgc aggtctacgc      5880
gattttagag aaatgggcac gcctagaaaa agcgccggct tggatcggcg tgaatccgct      5940
gagcgggaaa tgccagctca tctggctcat tgacccggtg tatgccgcag caggtaaaac      6000
cagcccaaat atgcgcctgc tggctgcaac gacggaagaa atgactcgtg ttttcggcgc      6060
tgaccaggct ttttcgcata ggctgagccg gtggccgctg cacgtctcag acgatccgac      6120
agcctataaa tggcactgcc agcatgatcg tgtggatcgg ctggccgacc taatggagat      6180
tgctcgaacg atgaccggat cacagaagcc gaaaaagtac attgagcagg acttttccag      6240
cggacgcgcc cgcattgaag cggcacaacg cgccaccgca gaagccaagg cgctagcgat      6300
tttggacgcg agcctgccga gcgccctgga cgcgtccggc gacctgatcg acggcgtgcg      6360
agtgctctgg acaaatccag agcgagcgcg cgacgagacc gcgtttcgcc acgcgttgac      6420
cgtgggatac cagctcaaag ctgctggtga gcgcctaaaa gatgccaaga tcatcgacgc      6480
gtatgaagtg gcgtacaacg ttgcccaggc ggtcggtgca gacggccggg agccggatct      6540
tcccgccatg cgtgatcgcc tgacgatggc gcgtcgtgtg gcgggctacg tggctaaagg      6600
ccagccagtc gtccctgctc gtcgggtgga aacgcagagc agccgagggc ggaaagctct      6660
agcgacgatg gggcgacggg gcgcagctac atcgaatgca cgcagatggg ctgacccaga      6720
aagtaagtat gcgcaggaga gcgcgacacg attagcggaa gcaaacaaac gccgagaaat      6780
gacaggcgag ttgctcgaac ttcgcgtcaa aactgcgatc ctggatgccc gttctcaatc      6840
ggttgctgat ccctcgactc gtgagcttgc aggcgaacta ggtgtcagtg aaaggcgcat      6900
ccaacaagtc agaaaggcac ttggaatgga agctaaacgc ggccgtccac gggctgaaaa      6960
ctaataaacg aaacaccgtc agcagaaaac ggttcccccc tttaggggtc ccgtccttgc      7020
tctggctctc acttgccctc accctccgct atccacgggc tgaaaactaa taaacgaaac      7080
accgtcagca gaaaacggtt ccccccttt agggtgtctc gctcctagct ctgatccctc      7140
cccggttcct ccccggcctg attttaagg ggggctcacg ctgtcggcag agaacggttc      7200
cccgccttct gctctggctc ttcctcgact ccctcccct caaaaatctc ctcgagatcc      7260
tggagacctt tttggagcta gcgcgttgct gcttcgcacc aacttgctca tgatgatttt      7320
catttttgct tgtgtgcttt tttgggttga accctccaaa gaggggaaac caggggcaca      7380
cctcatgcac taaagtgccg cttcgctggt cagggtgaaa tcacctggaa aaaagtgcg      7440 gtaaccgctg cgcttggcgt ttttctggg caagaagtct cgcaggtttt cgcaggagtg      7500
```

```
ccggaagaaa ttatcagaat tggggctaga attttaacg aacgttcgtt ataatggtgt    7560
catgaccttc acgacgaagt accaaaactg gcctgaagca tcagcggtgg atctctccga    7620
tgtcgcgctg gagtccgacg cactcgatgc cgccgtcgat ttaaaaacgg tgatcggatt    7680
tttccgcgcc ctcgatacga cagacgcgcc agcatcacgc gactgggcaa gtgccgcgag    7740
cgacctagaa acgcttgtgg ccgaccttga agagctggcc gacgagctgc gtgctcggca    7800
gcgccaggag gacgcgcagt agtggaggat cgcatcagct gcgcctactg cggtggcctg    7860
atcccacccc ggcctgaccc acgaggacgg cgcgcaaaat actgctcaga cgcgtgtcgt    7920
gccgcagcca gccgcgagcg cgccaacaag cgccacgccc aggaggtcga agccgcacgt    7980
cgaccgcgtg tagtgcgtgg cggaaacttc ttgcgtttcg caagagaaat gcgtcccatt    8040
tctcgtcgga ctcggggaag gaagcgtgat gctctcggtc aagcacgtcg ctcgccagcg    8100
ctgcgaggag ttcggccttc gtgcggaagt gccagtagag gccgggctgc tgtacctgta    8160
agtgagccgc cagcgcgcga gtggtgaagc catcgagccc agtctcgtcg agcacctgcc    8220
gggccccgag caacacggac gtgcggtcga gacgcttccg gtggtgagtc atagttgcac    8280
tttatcatcg ataactttat cttagataaa gtgactgctc gctactctca tctgactgct    8340
cgctactctc atcgtggaat cctgacagcc gtgctcatca cggcgaccct cgatgctgca    8400
gggctgggcc tcgtgatgcc gatcttgcct acccttctcg accaggtcgg tgcccccgac    8460
gacatgatcc cactgcacgt cggactactg acagcgctct atgcgatcat gcagtttctt    8520
tgcgccccga tccttggccg actctctgac cgtttcggac gccgccgcgt gcttgtcgcc    8580
tccctcgcag gcgcgacgat cgactacctc gtgctcgcac tgacggacac gctgtgggtc    8640
ttttacctcg cccgcgcggt tgcaggcatt accggcgcca cgaacgccgt caccgcgacg    8700
gtgatcgccg acattactcc gccggatcag cgcgcaaaac gctacgggtg gctcggcgca    8760
tgctacggcg gtggcatgat cgcgggtccc gccattggcg gtcttttcgg cggggtctca    8820
ccgcatctgc cattcctcgt cgccgccgcg ctcgccggaa tcaccctcgt actcagcgcg    8880
agtcttctgc gtgagacgcg gccaccgggc agcaacggct cgcacgcaca gcaacccggt    8940
acggcgaagc gaaccgcagt gccggggatg cttatccttc tcgcagtctt cggcatcgtg    9000
cagttcatcg gccaagcacc aggctccacc tgggtgctct tcacgcagca gcgcctcgac    9060
tggaaccccg tcgaagtcgg cgtttcgcta tccatcttcg gaatggtgca agtattcgtg    9120
caggcggcac tgaccggacg catcgtgtcc cggatcggcg agacccgggc gatcctcgtc    9180
ggtatcgccg cagacgccat ggggctcatc ggccttgccc tcatcgccag cacatgggcg    9240
atgctaccga tcctcgcagc gctcggactc ggcagcatca cgttgcccgc actgcagacg    9300
ctgctctcga gacgcgcgcc cgagcagcag cagggacgcc tgcagggaac acttgcaagc    9360
ctgaacagcc tcacctcgat catcggcccg gtcaccttca ccggcatttt cgcactcacc    9420
cgaacgaatg cagacggcac cctctggatc tgcgccgcag cgctctacgt tctctgcgcc    9480
ctcctgatga tccgtgagac atgcgcctca cggcgatctc gataaccgcg ctaaggtgcc    9540
atcccgatgc gacgggatcg ctctgccacc agtcaagtct cccgtagccg gtatgagcat    9600
gaccaaaatc ccttaacgtg agttttcgtt ccactgagcg tcagaccccg tagaaaagat    9660
caaaggatct tcttgagatc cttttttttct gcgcgtaatc tgctgcttgc aaacaaaaaa    9720
accaccgcta ccagcggtgg tttgtttgcc ggatcaagag ctaccaactc ttttttccgaa    9780 ggtaactggc ttcagcagag cgcagatacc aaatactgtc cttctagtgt agccgtagtt    9840
aggccaccac ttcaagaact ctgtagcacc gcctacatac ctcgctctgc taatcctgtt    9900
```

-continued

```
accagtggct gctgccagtg gcgataagtc gtgtcttacc gggttggact caagacgata     9960
gttaccggat aaggcgcagc ggtcgggctg aacgggggt tcgtgcacac agcccagctt    10020
ggagcgaacg acctacaccg aactgagata cctacagcgt gagctatgag aaagcgccac    10080
gcttcccgaa gggagaaagg cggacaggta tccggtaagc ggcagggtcg aacaggaga    10140
gcgcacgagg gagcttccag ggggaaacgc ctggtatctt tatagtcctg tcgggtttcg    10200
ccacctctga cttgagcgtc gattttttgtg atgctcgtca gggggcgga gcctatggaa    10260
aaacgccagc aacgcggcct ttttacggtt cctggccttt tgctggcctt ttgctcacat    10320
gttctttcct gcgttatccc ctgattctgt ggataaccgt attaccgcct ttgagtgagc    10380
tgataccgct cgccgcagcc gaacgaccga gcgcagcgag tcagtgagcg aggaagcgga    10440
agagcgcctg atgcggtatt ttctccttac gcatctgtgc ggtatttcac accgcatatg    10500
gtgcactctc agtacaatct gctctgatgc cgcatagtta agccagtata cactccgcta    10560
tcgctacgtg actgggtcat ggctgcgccc cgacacccgc caacacccgc tgacgcgccc    10620
tgacgggctt gtctgctccc ggcatccgct tacagacaag ctgtgaccgt ctccgggagc    10680
tgcatgtgtc agaggttttc accgtcatca ccgaaacgcg cgaggcagca gatcaattcg    10740
cgcgcgaagg cgaagcggca tgcatttacg ttgacaccat cgaatggtgc aaaaccttc    10800
gcggtatggc atgatagcgc ccggaagaga gtcaattcag ggtggtgaat gtgaaaccag    10860
taacgttata cgatgtcgca gagtatgccg gtgtctctta tcagaccgtt tcccgcgtgg    10920
tgaaccaggc cagccacgtt tctgcgaaaa cgcgggaaaa agtggaagcg gcgatggcgg    10980
agctgaatta cattcccaac cgcgtggcac aacaactggc gggcaaacag tcgttgctga    11040
ttggcgttgc cacctccagt ctggccctgc acgcgccgtc gcaaattgtc gcggcgatta    11100
aatctcgcgc cgatcaactg ggtgccagcg tggtggtgtc gatggtagaa cgaagcggcg    11160
tcgaagcctg taaagcggcg gtgcacaatc ttctcgcgca acgcgtcagt gggctgatca    11220
ttaactatcc gctggatgac caggatgcca ttgctgtgga agctgcctgc actaatgttc    11280
cggcgttatt tcttgatgtc tctgaccaga cacccatcaa cagtattatt ttctcccatg    11340
aagacggtac gcgactgggc gtggagcatc tggtcgcatt gggtcaccag caaatcgcgc    11400
tgttagcggg cccattaagt tctgtctcgg cgcgtctgcg tctggctggc tggcataaat    11460
atctcactcg caatcaaatt cagccgatag cggaacggga aggcgactgg agtgccatgt    11520
ccggttttca acaaaccatg caaatgctga atgagggcat cgttcccact gcgatgctgg    11580
ttgccaacga tcagatggcg ctgggcgcaa tgcgcgccat taccgagtcc gggctgcgcg    11640
ttggtgcgga tatctcggta gtgggatacg acgataccga agacagctca tgttatatcc    11700
cgccgtcaac caccatcaaa caggattttc gcctgctggg gcaaaccagc gtggaccgct    11760
tgctgcaact ctctcagggc caggcggtga agggcaatca gctgttgccc gtctcactgg    11820
tgaaaagaaa aaccacccctg gcgcccaata cgcaaaccgc ctctccccgc gcgttggccg    11880
attcattaat gcagctggca cgacaggttt cccgactgga aagcgggcag tgagcgcaac    11940
gcaattaatg tgagttagcg cgaattgatc tggtttgaca gcttatcatc gactgcacgg    12000
tgcaccaatg cttctggcgt caggcagcca tcggaagctg tggtatggct gtgcaggtcg    12060
taaatcactg cataattcgt gtcgctcaag gcgcactccc gttctggata atgttttttg    12120
cgccgacatc ataacggttc tggcaaatat tctgaaatga gctgttgaca attaatcatc    12180
cggctcgtat aatgtgtgga attgtgagcg gataacaatt tcacacagga aacagaccat    12240
```

```
ggaattcgag ctcggtaccc ggg                                            12263
```

<210> SEQ ID NO 56
<211> LENGTH: 8471
<212> TYPE: DNA
<213> ORGANISM: Artificial Sequence
<220> FEATURE:
<223> OTHER INFORMATION: vector

<400> SEQUENCE: 56

```
aagcttgcat gcctgcaggt cgactctaga ggatccccgg gtaccgagct cgaattcact     60
ggccgtcgtt ttacagccaa gcttggctgt tttggcggat gagagaagat tttcagcctg    120
atacagatta atcagaacg cagaagcggt ctgataaaac agaatttgcc tggcggcagt    180
agcgcggtgg tcccacctga ccccatgccg aactcagaag tgaaacgccg tagcgccgat    240
ggtagtgtgg ggtctcccca tgcgagagta gggaactgcc aggcatcaaa taaaacgaaa    300
ggctcagtcg aaagactggg cctttcgttt tatctgttgt ttgtcggtga acgctctcct    360
gagtaggaca atccgccgg gagcggattt gaacgttgcg aagcaacggc ccggagggtg    420
gcgggcagga cgcccgccat aaactgccag gcatcaaatt aagcagaagg ccatcctgac    480
ggatggcctt tttgcgtttc tacaaactct tttgtttatt tttctaaata cattcaaata    540
tgtatccgct catgagacaa taaccctgat aaatgcttca ataatattga aaaggaaga    600
gtatgagtat tcaacatttc cgtgtcgccc ttattccctt ttttgcggca ttttgccttc    660
ctgttttgc tcacccagaa acgctggtga agtaaaaga tgctgaagat cagttgggtg    720
cacgagtggg ttacatcgaa ctggatctca acagcggtaa gatccttgag agttttcgcc    780
ccgaagaacg ttttccaatg atgagcactt tgatccccc tgcggcgtcg ctgatcgccc    840
tcgcgacgtt gtgcgggtgg cttgtccctg agggcgctgc gacagatagc taaaaatctg    900
cgtcaggatc gccgtagagc gcgcgtcgcg tcgattggag gcttcccctt tggttgacgg    960
tcttcaatcg ctctacggcg atcctgacgc tttttttgttg cgtaccgtcg atcgttttat   1020
ttctgtcgat cccgaaaaag ttttttgcctt ttgtaaaaaa cttctcggtc gccccgcaaa   1080
ttttcgattc cagatttttt aaaaaccaag ccagaaatac gacacaccgt ttgcagataa   1140
tctgtctttc ggaaaaatca agtgcgatac aaaattttta gcaccctga gctgcgcaaa   1200
gtcccgcttc gtgaaaattt tcgtgccgcg tgattttccg ccaaaaactt taacgaacgt   1260
tcgttataat ggtgtcatga ccttcacgac gaagtaccaa aattggcccg aatcatcagc   1320
tatggatctc tctgatgtcg cgctggagtc gacgcgctc gatgctgccg tcgatttaaa   1380
aacggtgatc ggatttttcc gagctctcga tacgacggac gcgccagcat cacgagactg   1440
ggccagtgcc gcgagcgacc tagaaactct cgtggcggat cttgaggagc tggctgacga   1500
gctgcgtgct cggcagcgcc aggaggacgc acagtagtgg aggatcgaat cagttgcgcc   1560
tactgcggtg gcctgattcc tccccggcct gacccgcgag gacggcgcgc aaaatattgc   1620
tcagatgcgt gtcgtgccgc agccagccgc gagcgcgcca acaaacgcca cgccgaggag   1680
ctggaggcgg ctaggtcgca aatggcgctg gaagtgcgtc cccgagcga atttttggcc   1740
atggtcgtca cagagctgga agcggcagcg agaattatcc gcgatcgtgg gcgcggtgccc   1800
gcaggcatga caaacatcgt aaatgccgcg tttcgtgtgg ccgtggccgc caggacgtg   1860
tcagcgccgc caccacctgc accgaatcgg cagcagcgtc gcgcgtcgaa aaagcgcaca   1920
ggcggcaaga agcgataagc tgcacgaata cctgaaaaat gttgaacgcc ccgtgagcgg   1980
taactcacag ggcgtcggct aaccccccagt ccaaacctgg gagaaagcgc tcaaaaatga   2040
```

```
ctctagcgga ttcacgagac attgacacac cggcctggaa attttccgct gatctgttcg    2100
acacccatcc cgagctcgcg ctgcgatcac gtggctggac gagcgaagac cgccgcgaat    2160
tcctcgctca cctgggcaga gaaaatttcc agggcagcaa gacccgcgac ttcgccagcg    2220
cttggatcaa agaccggac acgggagaaa cacagccgaa gttataccga gttggttcaa     2280
aatcgcttgc ccggtgccag tatgttgctc tgacgcacgc gcagcacgca gccgtgcttg    2340
tcctggacat tgatgtgccg agccaccagg ccggcgggaa aatcgagcac gtaaaccccg    2400
aggtctacgc gattttggag cgctgggcac gcctggaaaa agcgccagct tggatcggcg    2460
tgaatccact gagcgggaaa tgccagctca tctggctcat tgatccggtg tatgccgcag    2520
caggcatgag cagcccgaat atgcgcctgc tggctgcaac gaccgaggaa atgacccgcg    2580
ttttcggcgc tgaccaggct ttttcacata ggctgagccg gtggccactg cacgtctccg    2640
acgatcccac cgcgtaccgc tggcatgccc agcacaatcg cgtggatcgc ctagctgatc    2700
ttatggaggt tgctcgcatg atctcaggca cagaaaaacc taaaaaacgc tatgagcagg    2760
agttttctag cggacgggca cgtatcgaag cggcaagaaa agccactgcg gaagcaaaag    2820
cacttgccac gcttgaagca agcctgccga gcgccgctga agcgtctgga gagctgatcg    2880
acggcgtccg tgtcctctgg actgctccag ggcgtgccgc ccgtgatgag acggcttttc    2940
gccacgcttt gactgtggga taccagttaa aagcggctgg tgagcgccta aaagacacca    3000
agatcatcga cgcctacgag cgtgcctaca ccgtcgctca ggcggtcgga gcagacggcc    3060
gtgagcctga tctgccgccg atgcgtgacc gccagacgat ggcgcgacgt gtgcgcggct    3120
acgtcgctaa aggccagcca gtcgtccctg ctcgtcagac agagacgcag agcagccgag    3180
ggcgaaaagc tctggccact atgggaagac gtggcggtaa aaaggccgca gaacgctgga    3240
aagacccaaa cagtgagtac gcccgagcac agcgagaaaa actagctaag tccagtcaac    3300
gacaagctag gaaagctaaa ggaaatcgct tgaccattgc aggttggttt atgactgttg    3360
agggagagac tggctcgtgg ccgacaatca atgaagctat gtctgaattt agcgtgtcac    3420
gtcagaccgt gaatagagca cttaagtctg cgggcattga acttccacga ggacgccgta    3480
aagcttccca gtaaatgtgc catctcgtag gcagaaaacg gttcccccg tagggggtctc    3540 tctcttggcc tcctttctag gtcgggctga ttgctcttga agctctctag ggggctcac    3600 accataggca gataacggtt ccccaccggc tcacctcgta agcgcacaag gactgctccc    3660
aaagatcttc aaagccactg ccgcgactcc gcttcgcgaa gccttgcccc gcggaaattt    3720
cctccaccga gttcgtgcac accctatgc caagcttctt tcaccctaaa ttcgagagat    3780
tggattctta ccgtggaaat tcttcgcaaa aatcgtcccc tgatcgccct tgcgacgttg    3840 ctcgcggcg tgccgctggt tgcgcttggc ttgaccgact tgatcctccg gcgttcagcc    3900
tgtgccacag ccgacaggat ggtgaccacc atttgcccca tatcaccgtc ggtactgatc    3960
ccgtcgtcaa taaaccgaac cgctacaccc tgagcatcaa actctttat cagttggatc     4020 atgtcggcgg tgtcgcggcc aagacggtcg agcttcttca ccagaatgac atcaccttcc    4080
tccaccttca tcctcagcaa atccagcct tcccgatctg ttgaactgcc ggatgccttg     4140
tcggtaaaga tgcggttagc ttttacccct gcatctttga gcgctgaggt ctgcctcgtg    4200
aagaaggtgt tgctgactca taccaggcct gaatcgcccc atcatccagc cagaaagtga    4260
gggagccacg gttgatgaga gctttgttgt aggtggacca gttggtgatt ttgaactttt    4320
gctttgccac ggaacggtct gcgttgtcgg gaagatgcgt gatctgatcc ttcaactcag    4380
```

```
caaaagttcg atttattcaa caaagccgcc gtcccgtcaa gtcagcgtaa tgctctgcca      4440
gtgttacaac caattaacca attctgatta gaaaaactca tcgagcatca aatgaaactg      4500
caatttattc atatcaggat tatcaatacc atattttga aaaagccgtt tctgtaatga      4560
aggagaaaac tcaccgaggc agttccatag gatggcaaga tcctggtatc ggtctgcgat      4620
tccgactcgt ccaacatcaa tacaacctat taatttcccc tcgtcaaaaa taaggttatc      4680
aagtgagaaa tcaccatgag tgacgactga atccggtgag aatggcaaaa gcttatgcat      4740
ttctttccag acttgttcaa caggccagcc attacgctcg tcatcaaaat cactcgcatc      4800
aaccaaaccg ttattcattc gtgattgcgc ctgagcgaga cgaaatacgc gatcgctgtt      4860
aaaaggacaa ttacaaacag gaatcgaatg caaccggcgc aggaacactg ccagcgcatc      4920
aacaatattt tcacctgaat caggatattc ttctaatacc tggaatgctg ttttcccggg      4980
gatcgcagtg gtgagtaacc atgcatcatc aggagtacgg ataaaatgct tgatggtcgg      5040
aagaggcata aattccgtca gccagtttag tctgaccatc tcatctgtaa catcattggc      5100
aacgctacct ttgccatgtt tcagaaacaa ctctggcgca tcgggcttcc catacaatcg      5160
atagattgtc gcacctgatt gcccgacatt atcgcgagcc catttatacc catataaatc      5220
agcatccatg ttggaattta atcgcggcct cgagcaagac gtttcccgtt gaatatggct      5280
cataacaccc cttgtattac tgtttatgta agcagacagt tttattgttc atgatgatat      5340
atttttatct tgtgcaatgt aacatcagag attttgagac acaacgtggc tttgttgaat      5400
aaatcgaact tttgctgagt tgaaggatca gatcacgcat cttcccgaca acgcagaccg      5460
ttccgtggca aagcaaaagt tcaaaatcac caactggtcc acctacaaca aagctctcat      5520
caaccgtggc tccctcactt tctggctgga tgatggggcg attcaggcct ggtatgagtc      5580
agcaacacct tcttcacgag gcagacctca gcgctagcgg agtgtatact ggcttactat      5640
gttggcactg atgagggtgt cagtgaagtg cttcatgtgg caggagaaaa aaggctgcac      5700
cggtgcgtca gcagaatatg tgatacagga tatattccgc ttcctcgctc actgactcgc      5760
tacgctcggt cgttcgactg cggcgagcgg aaatggctta cgaacggggc ggagatttcc      5820
tggaagatgc caggaagata cttaacaggg aagtgagagg gccgcggcaa agccgttttt      5880
ccataggctc cgcccccctg acaagcatca cgaaatctga cgctcaaatc agtggtggcg      5940
aaacccgaca ggactataaa gataccaggc gtttccccct ggcggctccc tcgtgcgctc      6000
tcctgttcct gcctttcggt ttaccggtgt cattccgctg ttatggccgc gtttgtctca      6060
ttccacgcct gacactcagt tccgggtagg cagttcgctc caagctggac tgtatgcacg      6120
aaccccccgt tcagtccgac cgctgcgcct tatccggtaa ctatcgtctt gagtccaacc      6180
cggaaagaca tgcaaaagca ccactggcag cagccactgg taattgattt agaggagtta      6240
gtcttgaagt catgcgccgg ttaaggctaa actgaaagga caagttttgg tgactgcgct      6300
cctccaagcc agttacctcg gttcaaagag ttggtagctc agagaacctt cgaaaaaccg      6360
ccctgcaagg cggttttttc gttttcagag caagagatta cgcgcagacc aaaacgatct      6420
caagaagatc atcttattaa ggggtctgac gctcagtgga acgaaaactc acgttaaggg      6480
attttggtca tgagattatc aaaaaggatc ttcacctaga tccttttaaa ttaaaaatga      6540
agttttaaat caatctaaag tatatatgag taaacttggt ctgacagtta ccaatgctta      6600
atcagtgagg cacctatctc agcgatctgt ctatttcgtt catccatagt tgcctgactc      6660
cccgtcgtgt agataactac gatacgggag ggcttaccat ctggccccag tgctgcaatg      6720
ataccgcgag acccacgctc accggctcca gatttatcag caataaacca gccagccgga      6780
```

| | |
|---|---:|
| agggccgagc gcagaagtgg tcctgcaact ttatccgcct ccatccagtc tattaattgt | 6840 |
| tgccgggaag ctagagtaag tagttcgcca gttaatagtt gcgcaacgtt tgttgccatt | 6900 |
| gccgatgata agctgtcaaa catggcctgt cgcttgcggt attcggaatc ttgcacgccc | 6960 |
| tcgctcaagc cttcgtcact ggtcccgcca ccaaacgttt cggcgagaag caggccatta | 7020 |
| tcgccggcat ggcggccgac gcgcgggag aggcggtttg cgtattgggc gccagggtgg | 7080 |
| tttttctttt caccagtgag acgggcaaca gctgattgcc cttcaccgcc tggccctgag | 7140 |
| agagttgcag caagcggtcc acgctggttt gccccagcag gcgaaaatcc tgtttgatgg | 7200 |
| tggttaacgg cgggatataa catgagctgt cttcggtatc gtcgtatccc actaccgaga | 7260 |
| tatccgcacc aacgcgcagc ccggactcgg taatggcgcg cattgcgccc agcgccatct | 7320 |
| gatcgttggc aaccagcatc gcagtgggaa cgatgccctc attcagcatt tgcatggttt | 7380 |
| gttgaaaacc ggacatggca ctccagtcgc cttcccgttc cgctatcggc tgaatttgat | 7440 |
| tgcgagtgag atatttatgc cagccagcca gacgcagacg cgccgagaca gaacttaatg | 7500 |
| ggcccgctaa cagcgcgatt tgctggtgac ccaatgcgac cagatgctcc acgcccagtc | 7560 |
| gcgtaccgtc ttcatgggag aaaataatac tgttgatggg tgtctggtca gagacatcaa | 7620 |
| gaaataacgc cggaacatta gtgcaggcag cttccacagc aatggcatcc tggtcatcca | 7680 |
| gcggatagtt aatgatcagc ccactgacgc gttgcgcgag aagattgtgc accgccgctt | 7740 |
| tacaggcttc gacgccgctt cgttctacca tcgacaccac cacgctggca cccagttgat | 7800 |
| cggcgcgaga tttaatcgcc gcgacaattt cgcgacgcgc gtgcagggcc agactggagg | 7860 |
| tggcaacgcc aatcagcaac gactgtttgc ccgccagttg ttgtgccacg cggttgggaa | 7920 |
| tgtaattcag ctccgccatc gccgcttcca ctttttcccg cgtttcgca gaaacgtggc | 7980 |
| tggcctggtt caccacgcgg gaaacggtct gataagagac accggcatac tctgcgacat | 8040 |
| cgtataacgt tactggtttc acattcacca ccctgaattg actctcttcc gggcgctatc | 8100 |
| atgccatacc gcgaaaggtt ttgcaccatt cgatggtgtc aacgtaaatg catgccgctt | 8160 |
| cgccttcgcg cgcgaattgc aagctgatcc gggcttatcg actgcacggt gcaccaatgc | 8220 |
| ttctggcgtc aggcagccat cggaagctgt ggtatggctg tgcaggtcgt aaatcactgc | 8280 |
| ataattcgtg tcgctcaagg cgcactcccg ttctggataa tgttttttgc gccgacatca | 8340 |
| taacggttct ggcaaatatt ctgaaatgag ctgttgacaa ttaatcatcg gctcgtataa | 8400 |
| tgtgtggaat tgtgagcgga taacaatttc acacaggaaa cagaattaaa agatatgacc | 8460 |
| atgattacgc c | 8471 |

<210> SEQ ID NO 57
<211> LENGTH: 12311
<212> TYPE: DNA
<213> ORGANISM: Artificial Sequence
<220> FEATURE:
<223> OTHER INFORMATION: vector

<400> SEQUENCE: 57

| | |
|---|---:|
| aagcttgcat gcctgcaggt cgactctaga attaatgcag ctggcacgac aggtttcccg | 60 |
| actggaaagc gggcagtgag cgcaacgcaa ttaatgtgag ttagctcact cattaggcac | 120 |
| cccaggcttt acactttatg cttccggctc gtatgttgtg tggaattgtg agcggataac | 180 |
| aatttcacac aggaaacagc tatgaccatg attacgccaa gcgcgcaatt aaccctcact | 240 |
| aaagggaaca aaagctgggt accgggcccc cctcgaggt cgacggtatc gataagcttg | 300 |

```
atatcgaatt cgcgtcatct gtctacgaca acaccttttg tccaattaga gccaaattat    360
gattctagta acaggcggag ccggcttcat cggctcaaat ttcgtactgc aatggtgtgc    420
gcacaatgag gaacccgtcc tcaacctcga cgccctgacc tacgcaggca acctggccaa    480
cctgcagccg ctggaaggca accctcagca tcgctttgtg caaggcaata tttgcgatgc    540
tgcgcttctg accaagctgt tcgcagagca ccgcccgcgc gccgtggttc acttcgcggc    600
ggaatcccat gtagaccgct caatcaccgg ccccgaagcg tttgtcgaaa ccaacgtgat    660
gggcacgttt cgcttgcttg aagccgcccg ggcgcattgg aatagtttgg aaggtgcaga    720
gaaggaggcc ttccgtttcc tccatgtctc taccgacgaa gtctacgcca cactagggcc    780
aaacgacccg gcgttcaccg aaaccacgcc gtacgcgccg aacagcccat actccgccag    840
caaggcagcc agcgaccatc tggtacgctc gtatttccat acctacgca tgccggtact     900
cactaccaac tgctccaaca attacgggcc gctccacttc ccggaaaaac tgatcccgct    960
gatgatcgtc aacgcactcg ccggtaaggc gctgcctgtc tatggcgacg gccagcaaat   1020
ccgcgactgg ctgtatgtcg aagatcactg ctcgggcatc cgtcgcgtac tggaagccgg   1080
tgcgttcggc gagacgtaca atattggcgg ctggaatgaa aaagccaaca ttgacattgt   1140
gcgtacactc tgcagccttc tcgacgagat ggcacctgcg gcatcgcgcc aggtaatcaa   1200
tcagaagacc ggcgagcctg tcgaacagta tgcagaactc atcgcctacg taaccgaccg   1260
cccaggccat gaccgccgtt atgccatcga tgcacgcaag atcgagcggg agctcggctg   1320
gaaacctgcc gaaaccttcg agacgggcat tcgaaagaca gtcgcttggt acttggccaa   1380
ccagaaatgg gtaaaggtg tcatggacgg cagctaccgt gactgggtgg cacaacaata   1440
cggggcaaat aaagcgtgaa atcctgctg ttggggaaaa acgggcaagt aggctgggag   1500
ctacagcgcg ccttggcgcc gctgggtgag gtcattgcgc tggatcgtca gggggccgag   1560
ggcttatgtg gcgacttgtc caacctggac ggcttggccg ctacgattcg tcagctggcg   1620
ccggacgtga tcgtcaacgc tgctgcctac actgcagtgg ataaagctga gagcgatcag   1680
gcactggctg caatgatcaa tgccgcggct cctgctgtat tagcacgtga acagcagct   1740
ttgggcgcct ggttgattca ctattccacc gattatgtat ttgacggcag cggcagtcag   1800
cgctgggagg aaactgcgcc taccggcccc ctttcggtct acggccggac caagctggaa   1860
ggcgagcatg ccattctcgc cagcggcgcc aaggccgtgg tactgcgcac cagctgggtg   1920
tatgctgcgc gcgggcacaa ttttgccaag accatgctgc gcctggcggc ggagcgtgag   1980
acgttgagcg tggtagcaga ccaatttggc gcacccacgg gcgctgacct gatcgccgac   2040
gttactgcac acatcctgcg gcaaatcttc aatgggcaag acaaccgtca cctggcaggg   2100
atttaccact tggctgcgtc cggtgaaacc tcttggcatg gttttgctca gttcgtgctg   2160
gcgcatgctc aacgcactgg cgtagcgctg aaagtgacag ctgataaggt tgccgcaatc   2220
agcaccgaag cttatccagt acctgcacca cgtccgcgca actcgcgcct ggcactgggc   2280
aaactggaaa acacgttcaa tttcaaaatg ccgctttggg agcaaggcgt gcaacgtatg   2340
ctggacgaaa tccagtaata gggactctca tggctcgtaa aggaattatt ctggccggcg   2400
gttcgggtac acgcctgcat ccggccacac tttcggtttc gaagcagctg ctgccggtgt   2460
atgacaaacc gatgatctac taccgctga gcaccctgct gctcgctggt atccgggaca   2520
tcctgatcat ttccacccg caggacaccc cgcgcttcga acagctgctg ggcgatggca   2580
gccagtgggg cctgaacctg tcatacgcaa tacaaccaag cccggatggc ttggcgcaag   2640
cgttcaccat cggcgctgac ttcatcggta acgacccttc tgcgttggtt ctcggtgaca   2700
```

```
atattttcta cggccatgac ttccaggcac tgctattgaa cgcagataaa cgtgaatccg    2760
gtgcttcagt attcgcttat catgttcatg acccagaacg ctatggcgta gcggagtttg    2820
acgatagcgg tcgcgtattg tcgctggaag aaaaaccggc agttccaaag tctagctatg    2880
cggtcaccgg cctgtatttc tatgacaatc aggtagtcaa tctggctcgc gagctgaagc    2940
cttccccacg tggcgagctg gaaatcaccg acctcaacaa cctttacttg cagcagcagc    3000
agttgcaggt cgaaatcatg ggccgtggct atgcgtggct cgacaccggc acgcacgaca    3060
gtctgctgga ggctagccag tacatcgcaa ccatggagcg ccgtcagggc ttgaaagtcg    3120
cctgccctga ggaaatttgc taccgcgctg gctggatcaa cgctgagcaa ctcgagtgcc    3180
tggctcaacc actgctgaaa aacggttatg gcaagtatct gcagaacttg ctgaaagaga    3240
aggtgttctg atgcaagcca ttccgctgga tatccccgaa gtcgtgctgt ttaccccccaa    3300
ggttttttggc gacgaacgtg gtttcttcta cgagagcttc aacgcccgtg ttttcagcga    3360
agtgaccggc ctgcagcccg acttcgtaca agacaaccac tcgcgctcgg taaaaggcgt    3420
gctccgtggc ctgcactatc agctggcacc tcacgcccag ggcaagctgg tgcgtgtggt    3480
gcaaggcgaa gtcttcgatg ttgcggtgga tatccgtcgc tcgtccacaa ccttcggtaa    3540
atgggtaggt gcggtgttgt cggccgagaa caagaaccag ctgtggatcc cgccagggtt    3600
cgcacacggg ttcgtcacgt tgagtgaaac cgcagagttc ctctacaaga ccaccgactt    3660
ctactcgccg cagtgcgagc gctgcattgc ctggaatgat ccggcagtgg gtatcgaatg    3720
gcccatcgac tccgtaccaa gcttgtctgg caaggaccag cttggggtcg cattggctga    3780
cgccgaactg ttcgactaac ggttttagcg gagaagggct gcggtagcgc agccgaattc    3840
ctgcagcccg ggggatccac tagttctaga ggatccccgg gtaccgagct cgaattcact    3900
ggccgtcgtt ttacagccaa gcttggctgt tttggcggat gagagaagat tttcagcctg    3960
atacagatta aatcagaacg cagaagcggt ctgataaaac agaatttgcc tggcggcagt    4020
agcgcggtgg tcccacctga ccccatgccg aactcagaag tgaaacgccg tagcgccgat    4080
ggtagtgtgg ggtctcccca tgcgagagta gggaactgcc aggcatcaaa taaaacgaaa    4140
ggctcagtcg aaagactggg cctttcgttt tatctgttgt ttgtcggtga acgctctcct    4200
gagtaggaca atccgccggg agcggattt gaacgttgcg aagcaacggc ccggagggtg    4260
gcgggcagga cgcccgccat aaactgccag gcatcaaatt aagcagaagg ccatcctgac    4320
ggatggcctt tttgcgtttc tacaaactct tttgtttatt tttctaaata cattcaaata    4380
tgtatccgct catgagacaa taaccctgat aaatgcttca ataatattga aaaggaaga    4440
gtatgagtat tcaacatttc cgtgtcgccc ttattccctt ttttgcggca ttttgccttc    4500
ctgtttttgc tcacccagaa acgctggtga agtaaaaga tgctgaagat cagttgggtg    4560
cacgagtggg ttacatcgaa ctggatctca acagcggtaa gatccttgag agttttcgcc    4620
ccgaagaacg ttttccaatg atgagcactt ttgatccccc tgcggcgtcg ctgatcgccc    4680
tcgcgacgtt gtgcgggtgg cttgtccctg agggcgctgc gacagatagc taaaaatctg    4740
cgtcaggatc gccgtagagc gcgcgtcgcg tcgattggag gcttcccctt tggttgacgg    4800
tcttcaatcg ctctacggcg atcctgacgc ttttttgttg cgtaccgtcg atcgttttat    4860
ttctgtcgat cccgaaaaag ttttttgcctt ttgtaaaaaa cttctcggtc gccccgcaaa    4920
ttttcgattc cagatttttt aaaaaccaag ccagaaatac gacacaccgt ttgcagataa    4980
tctgtctttc ggaaaaatca agtgcgatac aaaattttta gcacccctga gctgcgcaaa    5040
```

```
gtcccgcttc gtgaaaattt tcgtgccgcg tgattttccg ccaaaaactt taacgaacgt    5100
tcgttataat ggtgtcatga ccttcacgac gaagtaccaa aattggcccg aatcatcagc    5160
tatggatctc tctgatgtcg cgctggagtc cgacgcgctc gatgctgccg tcgatttaaa    5220
aacggtgatc ggattttttcc gagctctcga tacgacggac gcgccagcat cacgagactg    5280
ggccagtgcc gcgagcgacc tagaaactct cgtggcggat cttgaggagc tggctgacga    5340
gctgcgtgct cggcagcgcc aggaggacgc acagtagtgg aggatcgaat cagttgcgcc    5400
tactgcggtg gcctgattcc tccccggcct gacccgcgag gacggcgcgc aaaatattgc    5460
tcagatgcgt gtcgtgccgc agccagccgc gagcgcgcca acaaacgcca cgccgaggag    5520
ctggaggcgg ctaggtcgca aatggcgctg gaagtgcgtc ccccgagcga aattttggcc    5580
atggtcgtca cagagctgga agcggcagcg agaattatcc gcgatcgtgg cgcggtgccc    5640
gcaggcatga caaacatcgt aaatgccgcg tttcgtgtgg ccgtggccgc ccaggacgtg    5700
tcagcgccgc caccacctgc accgaatcgg cagcagcgtc gcgcgtcgaa aaagcgcaca    5760
ggcggcaaga agcgataagc tgcacgaata cctgaaaaat gttgaacgcc ccgtgagcgg    5820
taactcacag ggcgtcggct aacccccagt ccaaacctgg gagaaagcgc tcaaaaatga    5880
ctctagcgga ttcacgagac attgacacac cggcctggaa attttccgct gatctgttcg    5940
acacccatcc cgagctcgcg ctgcgatcac gtggctggac gagcgaagac cgccgcgaat    6000
tcctcgctca cctgggcaga gaaaatttcc agggcagcaa gacccgcgac ttcgccagcg    6060
cttggatcaa agacccggac acgggagaaa cacagccgaa gttataccga gttggttcaa    6120
aatcgcttgc ccggtgccag tatgttgctc tgacgcacgc gcagcacgca gccgtgcttg    6180
tcctggacat tgatgtgccg agccaccagg ccggcgggaa aatcgagcac gtaaaccccg    6240
aggtctacgc gattttggag cgctgggcac gcctggaaaa agcgccagct tggatcggcg    6300
tgaatccact gagcgggaaa tgccagctca tctggctcat tgatccggtg tatgccgcag    6360
caggcatgag cagcccgaat atgcgcctgc tggctgcaac gaccgaggaa atgacccgcg    6420
ttttcggcgc tgaccaggct ttttcacata ggctgagccg gtggccactg cacgtctccg    6480
acgatcccac cgcgtaccgc tggcatgccc agcacaatcg cgtggatcgc ctagctgatc    6540
ttatggaggt tgctcgcatg atctcaggca cagaaaaacc taaaaaacgc tatgagcagg    6600
agttttctag cggacgggca cgtatcgaag cggcaagaaa agccactgcg gaagcaaaag    6660
cacttgccac gcttgaagca agcctgccga gcgccgctga agcgtctgga gagctgatcg    6720
acggcgtccg tgtcctctgg actgctccag ggcgtgccgc ccgtgatgag acggcttttc    6780
gccacgcttt gactgtggga taccagttaa aagcggctgg tgagcgccta aaagacacca    6840
agatcatcga cgcctacgag cgtgcctaca ccgtcgctca ggcggtcgga gcagacggcc    6900
gtgagcctga tctgccgccg atgcgtgacc gccagacgat ggcgcgacgt gtgcgcggct    6960
acgtcgctaa aggccagcca gtcgtccctg ctcgtcagac agagacgcag agcagccgag    7020
ggcgaaaagc tctggccact atgggaagac gtggcggtaa aaaggccgca gaacgctgga    7080
aagacccaaa cagtgagtac gcccgagcac agcgagaaaa actagctaag tccagtcaac    7140
gacaagctag gaaagctaaa ggaaatcgct tgaccattgc aggttggttt atgactgttg    7200
agggagagac tggctcgtgg ccgacaatca atgaagctat gtctgaattt agcgtgtcac    7260
gtcagaccgt gaatagagca cttaagtctg cgggcattga acttccacga ggacgccgta    7320
aagcttccca gtaaatgtgc catctcgtag gcagaaaacg gttccccccg tagggggtctc    7380 tctcttggcc tcctttctag gtcgggctga ttgctcttga agctctctag gggggctcac    7440
```

```
accataggca gataacggtt ccccaccggc tcacctcgta agcgcacaag gactgctccc   7500
aaagatcttc aaagccactg ccgcgactcc gcttcgcgaa gccttgcccc gcggaaattt   7560
cctccaccga gttcgtgcac acccctatgc caagcttctt tcaccctaaa ttcgagagat   7620
tggattctta ccgtggaaat tcttcgcaaa aatcgtcccc tgatcgccct tgcgacgttg   7680
ctcgcggcgg tgccgctggt tgcgcttggc ttgaccgact tgatcctccg gcgttcagcc   7740
tgtgccacag ccgacaggat ggtgaccacc atttgcccca tatcaccgtc ggtactgatc   7800
ccgtcgtcaa taaaccgaac cgctacaccc tgagcatcaa actcttttat cagttggatc   7860
atgtcggcgg tgtcgcggcc aagacggtcg agcttcttca ccagaatgac atcaccttcc   7920
tccaccttca tcctcagcaa atccagcccct tcccgatctg ttgaactgcc ggatgccttg   7980
tcggtaaaga tgcggttagc ttttaccccct gcatctttga gcgctgaggt ctgcctcgtg   8040
aagaaggtgt tgctgactca taccaggcct gaatcgcccc atcatccagc cagaaagtga   8100
gggagccacg gttgatgaga gctttgttgt aggtggacca gttggtgatt ttgaactttt   8160
gctttgccac ggaacggtct gcgttgtcgg gaagatgcgt gatctgatcc ttcaactcag   8220
caaaagttcg atttattcaa caaagccgcc gtcccgtcaa gtcagcgtaa tgctctgcca   8280
gtgttacaac caattaacca attctgatta gaaaaactca tcgagcatca aatgaaactg   8340
caatttattc atatcaggat tatcaatacc atattttga aaaagccgtt tctgtaatga   8400
aggagaaaac tcaccgaggc agttccatag gatggcaaga tcctggtatc ggtctgcgat   8460
tccgactcgt ccaacatcaa tacaacctat taatttcccc tcgtcaaaaa taaggttatc   8520
aagtgagaaa tcaccatgag tgacgactga atccggtgag aatggcaaaa gcttatgcat   8580
ttctttccag acttgttcaa caggccagcc attacgctcg tcatcaaaat cactcgcatc   8640
aaccaaaccg ttattcattc gtgattgcgc ctgagcgaga cgaaatacgc gatcgctgtt   8700
aaaaggacaa ttacaaacag gaatcgaatg caaccggcgc aggaacactg ccagcgcatc   8760
aacaatattt tcacctgaat caggatattc ttctaatacc tggaatgctg ttttcccggg   8820
gatcgcagtg gtgagtaacc atgcatcatc aggagtacgg ataaaatgct tgatggtcgg   8880
aagaggcata aattccgtca gccagtttag tctgaccatc tcatctgtaa catcattggc   8940
aacgctacct ttgccatgtt tcagaaacaa ctctggcgca tcgggcttcc catacaatcg   9000
atagattgtc gcacctgatt gcccgacatt atcgcgagcc catttatacc catataaatc   9060
agcatccatg ttggaattta atcgcggcct cgagcaagac gtttcccgtt gaatatggct   9120
cataacaccc cttgtattac tgtttatgta agcagacagt tttattgttc atgatgatat   9180
atttttatct tgtgcaatgt aacatcagag attttgagac acaacgtggc tttgttgaat   9240
aaatcgaact tttgctgagt tgaaggatca gatcacgcat cttcccgaca acgcagaccg   9300
ttccgtggca aagcaaaagt tcaaaatcac caactggtcc acctacaaca aagctctcat   9360
caaccgtggc tccctcactt tctggctgga tgatggggcg attcaggcct ggtatgagtc   9420
agcaacacct tcttcacgag gcagacctca gcgctagcgg agtgtatact ggcttactat   9480
gttggcactg atgagggtgt cagtgaagtg cttcatgtgg caggagaaaa aaggctgcac   9540
cggtgcgtca gcagaatatg tgatacagga tatattccgc ttcctcgctc actgactcgc   9600
tacgctcggt cgttcgactg cggcgagcgg aaatggctta cgaacggggc ggagatttcc   9660
tggaagatgc caggaagata cttaacaggg aagtgagagg gccgcggcaa agccgttttt   9720
ccataggctc cgcccccctg acaagcatca cgaaatctga cgctcaaatc agtggtggcg   9780
```

```
aaacccgaca ggactataaa gataccaggc gtttcccct ggcggctccc tcgtgcgctc    9840
tcctgttcct gcctttcggt ttaccggtgt cattccgctg ttatggccgc gtttgtctca    9900
ttccacgcct gacactcagt tccgggtagg cagttcgctc caagctggac tgtatgcacg    9960
aaccccccgt tcagtccgac cgctgcgcct tatccggtaa ctatcgtctt gagtccaacc   10020
cggaaagaca tgcaaaagca ccactggcag cagccactgg taattgattt agaggagtta   10080
gtcttgaagt catgcgccgg ttaaggctaa actgaaagga caagttttgg tgactgcgct   10140
cctccaagcc agttacctcg gttcaaagag ttggtagctc agagaacctt cgaaaaccg    10200
ccctgcaagg cggttttttc gttttcagag caagagatta cgcgcagacc aaaacgatct   10260
caagaagatc atcttattaa ggggtctgac gctcagtgga acgaaaactc acgttaaggg   10320
attttggtca tgagattatc aaaaaggatc ttcacctaga tccttttaaa ttaaaaatga   10380
agttttaaat caatctaaag tatatatgag taaacttggt ctgacagtta ccaatgctta   10440
atcagtgagg cacctatctc agcgatctgt ctatttcgtt catccatagt tgcctgactc   10500
cccgtcgtgt agataactac gatacgggag ggcttaccat ctggccccag tgctgcaatg   10560
ataccgcgag acccacgctc accggctcca gatttatcag caataaacca gccagccgga   10620
agggccgagc gcagaagtgg tcctgcaact ttatccgcct ccatccagtc tattaattgt   10680
tgccgggaag ctagagtaag tagttcgcca gttaatagtt tgcgcaacgt tgttgccatt   10740
gccgatgata agctgtcaaa catggcctgt cgcttgcggt attcggaatc ttgcacgccc   10800
tcgctcaagc cttcgtcact ggtcccgcca ccaaacgttt cggcgagaag caggccatta   10860
tcgccggcat ggcggccgac gcgcggggag aggcggtttg cgtattgggc gccagggtgg   10920
tttttctttt caccagtgag acgggcaaca gctgattgcc cttcaccgcc tggccctgag   10980
agagttgcag caagcggtcc acgctggttt gccccagcag gcgaaaatcc tgtttgatgg   11040
tggttaacgg cgggatataa catgagctgt cttcggtatc gtcgtatccc actaccgaga   11100
tatccgcacc aacgcgcagc ccggactcgg taatggcgcg cattgcgccc agcgccatct   11160
gatcgttggc aaccagcatc gcagtgggaa cgatgccctc attcagcatt tgcatggttt   11220
gttgaaaacc ggacatggca ctccagtcgc cttcccgttc cgctatcggc tgaatttgat   11280
tgcgagtgag atatttatgc cagccagcca gacgcagacg cgccgagaca gaacttaatg   11340
ggcccgctaa cagcgcgatt tgctggtgac ccaatgcgac cagatgctcc acgcccagtc   11400
gcgtaccgtc ttcatgggag aaaataatac tgttgatggg tgtctggtca gagacatcaa   11460
gaaataacgc cggaacatta gtgcaggcag cttccacagc aatggcatcc tggtcatcca   11520
gcggatagtt aatgatcagc ccactgacgc gttgcgcgag aagattgtgc accgccgctt   11580
tacaggcttc gacgccgctt cgttctacca tcgacaccac cacgctggca cccagttgat   11640
cggcgcgaga tttaatcgcc gcgacaattt gcgacggcgc gtgcagggcc agactggagg   11700
tggcaacgcc aatcagcaac gactgtttgc ccgccagttg ttgtgccacg cggttgggaa   11760
tgtaattcag ctccgccatc gccgcttcca ctttttcccg cgttttcgca gaaacgtggc   11820
tggcctggtt caccacgcgg gaaacggtct gataagagac accggcatac tctgcgacat   11880
cgtataacgt tactggtttc acattcacca ccctgaattg actctcttcc gggcgctatc   11940
atgccatacc gcgaaaggtt ttgcaccatt cgatggtgtc aacgtaaatg catgccgctt   12000
cgccttcgcg cgcgaattgc aagctgatcg gggcttatcg actgcacggt gcaccaatgc   12060
ttctggcgtc aggcagccat cggaagctgt ggtatggctg tgcaggtcgt aaatcactgc   12120
ataattcgtg tcgctcaagg cgcactcccg ttctggataa tgttttttgc gccgacatca   12180
```
taacggttct ggcaaatatt ctgaaatgag ctgttgacaa ttaatcatcg gctcgtataa    12240
tgtgtggaat tgtgagcgga taacaatttc acacaggaaa cagaattaaa agatatgacc    12300
atgattacgc c                                                        12311

<210> SEQ ID NO 58
<211> LENGTH: 9892
<212> TYPE: DNA
<213> ORGANISM: Artificial Sequence
<220> FEATURE:
<223> OTHER INFORMATION: vector

<400> SEQUENCE: 58
ctcgggccgt ctcttgggct tgatcggcct tcttgcgcat ctcacgcgct cctgcggcgg      60
cctgtagggc aggctcatac ccctgccgaa ccgcttttgt cagccggtcg gccacggctt     120
ccggcgtctc aacgcgcttt gagattccca gcttttcggc caatccctgc ggtgcatagg     180
cgcgtggctc gaccgcttgc gggctgatgg tgacgtggcc cactggtggc cgctccaggg     240
cctcgtagaa cgcctgaatg cgcgtgtgac gtgccttgct gccctcgatg cccgttgca     300 gccctagatc ggccacagcg gccgcaaacg tggtctggtc gcgggtcatc tgcgctttgt     360
tgccgatgaa ctccttggcc gacagcctgc cgtcctgcgt cagcggcacc acgaacgcgg     420
tcatgtgcgg gctggtttcg tcacggtgga tgctggccgt cacgatgcga tccgccccgt     480
acttgtccgc cagccacttg tgcgccttct cgaagaacgc cgcctgctgt tcttggctgg     540
ccgacttcca ccattccggg ctggccgtca tgacgtactc gaccgccaac acagcgtcct     600
tgcgccgctt ctctggcagc aactcgcgca gtcggcccat cgcttcatcg gtgctgctgg     660
ccgcccagtg ctcgttctct ggcgtcctgc tggcgtcagc gttgggcgtc tcgcgctcgc     720
ggtaggcgtg cttgagactg gccgccacgt tgcccatttt cgccagcttc ttgcatcgca     780
tgatcgcgta tgccgccatg cctgcccctc ccttttggtg tccaaccggc tcgacggggg     840
cagcgcaagg cggtgcctcc ggcgggccac tcaatgcttg agtatactca ctagactttg     900
cttcgcaaag tcgtgaccgc ctacggcggc tgcggcgccc tacgggcttg ctctccgggc     960
ttcgccctgc gcggtcgctg cgctcccttg ccagcccgtg gatatgtgga cgatggccgc    1020
gagcggccac cggctggctc gcttcgctcg gcccgtggac aaccctgctg gacaagctga    1080
tggacaggct gcgcctgccc acgagcttga ccacaggat tgcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt ggggcagtc gaaggcgaag cccgcccgcc    1380 tgcccccga gcctcacggc ggcgagtgcg ggggttccaa gggggcagcg ccaccttggg    1440
caaggccgaa ggccgcgcag tcgatcaaca gccccggag gggccacttt ttgccggagg    1500
gggagccgcg ccgaaggcgt gggggaaccc cgcagggtg ccctttctttg gcaccaaag    1560 aactagatat agggcgaaat gcgaaagact taaaaatcaa caacttaaaa aagggggta    1620 cgcaacagct cattgcggca cccccccgcaa tagctcattg cgtaggttaa agaaaatctg    1680
taattgactg ccacttttac gcaacgcata attgttgtcg cgctgccgaa aagttgcagc    1740
tgattgcgca tggtgccgca accgtgcggc accctaccgc atggagataa gcatggccac    1800
gcagtccaga gaaatcggca ttcaagccaa gaacaagccc ggtcactggg tgcaaacgga    1860

```
acgcaaagcg catgaggcgt gggccgggct tattgcgagg aaacccacgg cggcaatgct    1920
gctgcatcac ctcgtggcgc agatgggcca ccagaacgcc gtggtggtca gccagaagac    1980
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
tgccgccgtg gtggttgatc acgacgacca ggacgaatcg ctgttggggc atggcgacct    2220
gcgccgcatc ccgaccctgt atccgggcga gcagcaacta ccgaccggcc ccggcgagga    2280
gccgcccagc cagcccggca ttccgggcat ggaaccagac ctgccagcct tgaccgaaac    2340
ggaggaatgg gaacggcgcg ggcagcagcg cctgccgatg cccgatgagc cgtgttttct    2400
ggacgatggc gagccgttgg agccgccgac acgggtcacg ctgccgcgcc ggtagcactt    2460
gggttgcgca gcaacccgta agtgcgctgt tccagactat cggctgtagc cgcctcgccg    2520
ccctatacct tgtctgcctc cccgcgttgc gtcgcggtgc atggagcggg gccacctcga    2580
cctgaatgga agccggcggc acctcgctaa cggattcacc gtttttatca ggctctggga    2640
ggcagaataa atgatcatat cgtcaattat tacctccacg gggagagcct gagcaaactg    2700
gcctcaggca tttgagaagc acacggtcac actgcttccg gtagtcaata aaccggtaaa    2760
ccagcaatag acataagcgg ctatttaacg accctgccct gaaccgacga ccgggtcgaa    2820
tttgctttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagacgccag gattgaacag taccaccagc acgcccatgt ctatccggtc catgatcgtt    3300
cttctcccgt aggtcgaagt tgccaggcca ggaccagccc ggccagaacg agaagggcgc    3360
cggcgaggaa tggcgcgccg ccagggggca gcggcgcgag cggaccgctg ccccagtgga    3420
acaggccgct catcagcggc ggaccgacga tcgcggcgag gctcatcagg ctgctcagca    3480
cgccctgcaa ctcgccctgg cggtcgaccg gcacgcgggc cgagagcagc ccctgcatgg    3540
ccggggtggc gaggctgccg agcgcgaagg gcagcagcgc gcagaccagc cagaatgacg    3600
agtcgaccag ggcgaacagc agcaggccgc agccttgcag ggcgaggccc aggcgcagca    3660
ggcgggcgtc gtccaggcgc cgcttgcaga ggttcacgcc gagggtctgg gcagcaccg    3720
cgagcacgcc gtagagggcc agcgagtagc cgatccaggc gctgctccag tgaaacttct    3780
cgatcacgaa gaacgccag accaccatca ccgcctgcaa gccgaggaat accagggcaa    3840
gcaccgccag caggcgtccg accccggtt gccgagccag gccgctgatc gagcgcaagg    3900
cattcatccg cctcgggtcc aggcggcggc gtcgcgtcgg gggcagggtt cctcgagga    3960
acaggccggc gagcagggcg ttgagcaggc acaggccggc ggccagcaac agcggcagcg    4020
tcgtgccgtg caccgccagc agcccaccga gggcggggcc gaggatcatg cccagggcga    4080
ggccggcgta cagccagccg aagtgccggg tgcgctgccc gtgcgtgccg aggtcagccg    4140
cgcaggccat cgcggtggcc acgctggcgc cggtgagccc ggccagcgcg cgaccgagga    4200
acagcatcca gaggctgtcg gccagcgcca gcagcagata gctgagggcg aagccgagca    4260
```

```
tcgccaggac caggacgggg cggcgtccga agcggtcgct gaggctgccg aggaccggcg   4320
aaaagaacaa ttgcagcagc gcgaaggtca tcaccagggc ggcgccccag gtggccgcgt   4380
cgcggaccgc cagcggcgcc acgctgccga tcagcgtcgg cagcaggggc acgatcaggc   4440
cgacgccagc ggcatccagc aggcaggtga ggaacagcag aggcaggacg cgtttcgcgc   4500
cgggaccgtg ttcccgcgtg gcggaggggc agaggctggt cgtggacacg ccaggatcct   4560
cccgcgaac acaggaaatc ctgatcttgg gacgccagcg agggcaaggg aaactaccgg   4620
aattcacagg ttcgacgaac ggtcgcggca acgccggcgg gcggcgtgat gtcataatga   4680
tgcgacccgt gcgccagtcg ggtatccttg ccggcctctc atctagaggg aatgcgtttc   4740
gccgactagg ccttggcctt gccggaagct acggacgcca cggccgggcc ggcgaggcgc   4800
ttcagcaggc gcgggcggtt ggtctccagc gcgccgccgc gtccccgcag gccgtcccac   4860
aggccccagc ccaggcagcg cagcttgagc agcttgtcgc gttcgagcag gagcaccgcg   4920
aggccctggg tcagggtcgg caggttcgcc agcagggcca gcggcgagga ccgggcgtag   4980
cggcgcagga ccagcaggcc gttgcgcgcc aggtagtagc ggcgcagcgg ggcgtggttc   5040
atcgcgctga ggctgagacc gccgaggcgg cgggtcttgc gcgtgccgat gcggtgctcg   5100
aggaccagcc gcgggtcgac gtacaggggc acgtccagcg cctgggcgcg caggctgtat   5160
tcggtgtcca cgtggtcgat gaacagttcc tcgtcgaagt ggccgaggcg ctggtaggcc   5220
tcgcgggtca gcaggcagcc ggaggagatc aggaacgagg tgcgctgcgg ggtcgtcagg   5280
ccgtccagag acaattgcct gagcgtcagt ccgtcgagat ggatggccgg caggaagcgc   5340
cggtcacccc ggtcgaagat ccgtgggccg agcaggcagg cctgaccgtt gcgcgcctgc   5400
aggttgcgcc actgggcggc gaggaaggcg ccgccgggac gggagtcctg gtcgagcagc   5460
agcacaccct gcacgccacg ccggaatagc gcgtcgagtc cctggttgaa ggcgccggcg   5520
atgccctgcc ggttgccgtg gtgcagcacg gcgatgcctt gcccgcgcag ccgggcattg   5580
cgctgcggat cgctgtgcgg tgagttgtcg acggcaagga agcgcagttg cggaaacgcc   5640
gccgccagtt cgccaaggtg ttccaggtcg tcgtcgccag gattgaacag taccaccagc   5700
acgcccatgt ctatccggtc catgatcgtt cttctcccgt aggtcaggac gcagccttca   5760
gccatcgcgc atccccctcc ctatgacaac gttcgaccac ctgggccgct ttaccgcaag   5820
cgatactgtg cggttgtgac aattccatga aacgccgaca ggccgccgcc atggccgggt   5880
cctcgagcaa gcgccacagc gccccgcgca actcctgctc gcgcaatggc acgcccaggc   5940
gcatcccgca gccgagccgg accagccgtt cggcattgtc gaactggtcg tgggcgcagg   6000
gcagcagcac ctgcggcacc cccgccgcca aggccaggct catggcgccg ataccgcccg   6060
gatgaccag cccggcgcac gatggcagca aggctcccag tggcgcgtag gcgcgctgca   6120
gcacgtggtt cggcaagccg cgcagcggtt cctggccggc gccggtgagg aagatcccac   6180
gcgcgccgag gcgttccagc gcgcgcaggg ccatggcgta gaagtcgccc tgcaggtgtt   6240
cggtcgagcc ctgggtgaac accagcggcc ggctgccctg atcgagaaag cgttgcagtt   6300
cgtcgtcgag cggggtcccc gggatactgc cgtcgaacag cgggaagccg gtcatgtgca   6360
ggggttgcgg ccaatcctgc tggggcggcg cgaaccaggc cgggaacagg cagaccacgc   6420
cctgcggcga atgcatccat gggtgaaga tgcgcttcac cggcgtctcc aggccgacct   6480
tgcgccgcac cgcgttgata tccgcgcgcg aggtgcgatc cagcttgaag cgctcgatgc   6540
agcgccagag cagcttgcgc atcgccacgc gcatctgctc gggcacgttg aacttggggt   6600
```

```
gtaccggcgg caggtgcgcc gacaacaagg tcgatggcga gacctgcgcg gacaggtagg    6660
gaatcccgta cttctcgtga gcgatgcgtg cgcccagcgc ccagagcgag ccgaccacca    6720
cgatgtcgtc atggcgctgc gccgagacgt actcgtagac cggctcgatc atcccggcga    6780
tggtttgcca gagcacgccg aaggacgtct tggggtccca caggcgcgga tcgcccatgg    6840
tccggcggta ggtcagttcg tcgctcagcg ggacgaacgc gatgccgtgc tgctccaccg    6900
cgtcgcgaaa caccgggatg gtgcagaggc tcacgcggtg cccgcgcaat ttcagggtcc    6960
gggccaggcc gatgaaggga aatacgtcgc cggccgagcc gatggcgatg aggatggcgt    7020
gcatggtgct actccgtgcg ttatgcaacc gcaaagcccg gccaggcggg gtcttcgcag    7080
gtcaagggtt caggcgtagc cgatggccat ctcgtggaat cccgccgcgc gttccgcccg    7140
ctgcggctcc ggttgcttca gcaggtgctc gagcagggcg cggtgcacgc gtaccgcggc    7200
cagcttggac tccaggtcga ggaaatgccc ggtgccctcc acccgcgaga aactgcagtg    7260
cggcaggtag tcgcggaact ggcgggcgtc ctcggcggtg gtgtattcgt cccagctgcc    7320
gttgatgaaa tgcacgtggc tctggatccg ctccaggcaa gccaggtagc cccgatcgtt    7380
gagcgccagc acctggtcga tgtgaaagcg cgcctgctcg tattcgccgg tggccagcga    7440
agccatgtgc tgatggttgc tggctttcag gcgcggcggc aggtatttgc cgacggtctc    7500
gttgagcaga tggccgatcg ccgacttgtc gtccagctcg atcagcgcct gcgcccgccc    7560
gacgtagtcg agcatcgcct ggttcagtcc aggggcgaat gccatcacca ccgagctgcg    7620
gatgccgcgc ggattgcgcg acagcgccag cagcgtggag ataccgcccc aggacgcgga    7680
gaccaggtga ttgacctcga agcgctcgat cagcgccagg aggatttcca cctcgtcgtc    7740
cttggtgatc aaccccgct gcgggttgtg ctgacgcgac tgcccggcga agggcaggtc    7800
gaacagcacc acgttgaaat gttcggccag gcacttgcag gtccgggcga acgaggcggt    7860
ggtcgccatc gcgccgttga ccagcatcac cgtgctgcgc ccgggatcct gcccaacgcg    7920
ctcgacatgt acccgcaggc ccttgcaaac cgataccaac agactttcgc gccgcatttc    7980
acacctccca aaaatgccag atcccccggg ctgcaggaat tcgatatcaa gcttatcgat    8040
accgtcgacc tcgagggggg gcccggtacc cagcttttgt tccctttagt gagggttaat    8100
tgcgcgcttg gcgtaatcat ggtcatagct gtttcctgtg tgaaattgtt atccgctcac    8160
aattccacac aacatacgag ccggaagcat aaagtgtaaa gcctggggtg cctaatgagt    8220
gagctaactc acattaattg cgttgcgctc actgcccgct ttccagtcgg gaaacctgtc    8280
gtgccagctg cattaatgaa tcggccaacg cgcggggaga ggcggtttgc gtattgggcg    8340
catgcataaa aactgttgta attcattaag cattctgccg acatggaagc catcacaaac    8400
ggcatgatga acctgaatcg ccagcggcat cagcaccttg tcgccttgcg tataatattt    8460
gcccatgggg gtgggcgaag aactccagca tgagatcccc gcgctggagg atcatccagc    8520
cggcgtcccg gaaaacgatt ccgaagccca acctttcata aaggcgcgcg gtggaatcga    8580
aatctcgtga tggcaggttg ggcgtcgctt ggtcggtcat ttcgaacccc agagtcccgc    8640
tcagaagaac tcgtcaagaa ggcgatagaa ggcgatgcgc tgcgaatcgg gagcggcgat    8700
accgtaaagc acgaggaagc ggtcagccca ttcgccgcca agctcttcag caatatcacg    8760
ggtagccaac gctatgtcct gatagcggtc cgccacaccc agccggccac agtcgatgaa    8820
tccagaaaag cggccatttt ccaccatgat attcggcaag caggcatcgc catgggtcac    8880
gacgagatcc tcgccgtcgg gcatgcgcgc cttgagcctg gcgaacagtt cggctggcgc    8940
gagcccctga tgctcttcgt ccagatcatc ctgatcgaca agaccggctt ccatccgagt    9000
```

| | |
|---|---:|
| acgtgctcgc tcgatgcgat gtttcgcttg gtggtcgaat gggcaggtag ccggatcaag | 9060 |
| cgtatgcagc cgccgcattg catcagccat gatggatact ttctcggcag gagcaaggtg | 9120 |
| agatgacagg agatcctgcc ccggcacttc gcccaatagc agccagtccc ttcccgcttc | 9180 |
| agtgacaacg tcgagcacag ctgcgcaagg aacgcccgtc gtggccagcc acgatagccg | 9240 |
| cgctgcctcg tcctgcagtt cattcagggc accggacagg tcggtcttga caaaaagaac | 9300 |
| cgggcgcccc tgcgctgaca gccggaacac ggcggcatca gagcagccga ttgtctgttg | 9360 |
| tgcccagtca tagccgaata gcctctccac ccaagcggcc ggagaacctg cgtgcaatcc | 9420 |
| atcttgttca atcatgcgaa acgatcctca tcctgtctct tgatcagatc ttgatcccct | 9480 |
| gcgccatcag atccttggcg gcaagaaagc catccagttt actttgcagg gcttcccaac | 9540 |
| cttaccagag ggcgcccag ctggcaattc cggttcgctt gctgtccata aaaccgccca | 9600 |
| gtctagctat cgccatgtaa gcccactgca agctacctgc tttctctttg cgcttgcgtt | 9660 |
| ttcccttgtc cagatagccc agtagctgac attcatccca ggtggcactt ttcggggaaa | 9720 |
| tgtgcgcgcc cgcgttcctg ctggcgctgg gcctgtttct ggcgctggac ttcccgctgt | 9780 |
| tccgtcagca gcttttcgcc cacggccttg atgatcgcgg cggccttggc ctgcatatcc | 9840 |
| cgattcaacg gccccagggc gtccagaacg ggcttcaggc gctcccgaag gt | 9892 |

```
<210> SEQ ID NO 59
<211> LENGTH: 1477
<212> TYPE: DNA
<213> ORGANISM: Pseudomonas aeruginosa

<400> SEQUENCE: 59
```

| | |
|---|---:|
| tgagaggccg gcaaggatac ccgactggcg cacgggtcgc atcattatga catcacgccg | 60 |
| cccgccggcg ttgccgcgac cgttcgtcga acctgtgaat tccggtagtt tcccttgccc | 120 |
| tcgctggcgt cccaagatca ggatttcctg tgttcgccgg gaggatcctg gcgtgtccac | 180 |
| gaccagcctc tgcccctccg ccacgcggga acacggtccc ggcgcgaaac gcgtcctgcc | 240 |
| tctgctgttc ctcacctgcc tgctggatgc cgctggcgtc ggcctgatcg tgcccctgct | 300 |
| gccgacgctg atcggcagcg tggcgccgct ggcggtccgc gacgcggcca ctggggcgc | 360 |
| cgccctggtg atgaccttcg cgctgctgca attgttcttt cgccggtcc tcggcagcct | 420 |
| cagcgaccgc ttcggacgcc gccccgtcct ggtcctggcg atgctcggct cgccctcag | 480 |
| ctatctgctg ctggcgctgg ccgacagcct ctggatgctg ttcctcggtc gcgcgctggc | 540 |
| cgggctcacc ggcgccagcg tggccaccgc gatggcctgc gcggctgacc tcggcacgca | 600 |
| cgggcagcgc acccggcact tcggctggct gtacgccggc ctcgccctgg catgatcct | 660 |
| cggcccccgcc ctcggtgggc tgctggcggt gcacggcacg acgctgccgc tgttgctggc | 720 |
| cgccggcctg tgcctgctca acgccctgct cgccggcctg ttcctcgagg aaaccctgcc | 780 |
| cccgacgcga cgccgccgcc tggacccgag gcggatgaat gccttgcgct cgatcagcgg | 840 |
| cctggctcgg caaccgggg tcggacgcct gctggcggtg cttgccctgg tattcctcgg | 900 |
| cttgcaggcg gtgatggtgg tctggccgtt cttcgtgatc gagaagtttc actggagcag | 960 |
| cgcctggatc ggctactcgc tggccctcta cggcgtgctc gcggtgctcg cccagaccct | 1020 |
| cggcgtgaac ctctgcaagc ggcgcctgga cgacgcccgc ctgctgcgcc tgggcctcgc | 1080 |
| cctgcaaggc tgcggcctgc tgctgttcgc cctggtcgac tcgtcattct ggctggtctg | 1140 |
| cgcgctgctg cccttcgcgc tcggcagcct cgccaccccg gccatgcagg ggctgctctc | 1200 |

```
ggcccgcgtg ccggtcgacc gccagggcga gttgcagggc gtgctgagca gcctgatgag    1260
cctcgccgcg atcgtcggtc cgccgctgat gagcggcctg ttccactggg gcagcggtcc    1320
gctcgcgccg ctgccctgg ccggcgcgcc attcctcgcc ggcgcccttc tcgttctggc    1380
cgggctggtc ctggcctggc aacttcgacc tacgggagaa gaacgatcat ggaccggata    1440
gacatgggcg tgctggtggt actgttcaat cctggcg                            1477

<210> SEQ ID NO 60
<211> LENGTH: 32
<212> TYPE: DNA
<213> ORGANISM: Artificial Sequence
<220> FEATURE:
<223> OTHER INFORMATION: primer

<400> SEQUENCE: 60
aggaaatcta gatgagaggc cggcaaggat ac                                  32

<210> SEQ ID NO 61
<211> LENGTH: 32
<212> TYPE: DNA
<213> ORGANISM: Artificial Sequence
<220> FEATURE:
<223> OTHER INFORMATION: primer

<400> SEQUENCE: 61
ccaggttcta gacgccagga ttgaacagta cc                                  32

<210> SEQ ID NO 62
<211> LENGTH: 7332
<212> TYPE: DNA
<213> ORGANISM: Artificial Sequence
<220> FEATURE:
<223> OTHER INFORMATION: vector

<400> SEQUENCE: 62
cgaaaatttt tgggaggtgt gaaatgcggc gcgaaagtct gttggtatcg gtttgcaagg      60
gcctgcgggt acatgtcgag cgcgttgggc aggatcccgg gcgcagcacg gtgatgctgg    120
tcaacggcgc gatggcgacc accgcctcgt tcgcccggac ctgcaagtgc ctggccgaac    180
atttcaacgt ggtgctgttc gacctgccct tcgccgggca gtcgcgtcag cacaacccgc    240
agcgcgggtt gatcaccaag gacgacgagg tggaaatcct cctggcgctg atcgagcgct    300
tcgaggtcaa tcacctggtc tccgcgtcct ggggcggtat ctccacgctg ctggcgctgt    360
cgcgcaatcc gcgcggcatc cgcagctcgg tggtgatggc attcgcccct ggactgaacc    420
aggcgatgct cgactacgtc gggcgggcgc aggcgctgat cgagctggac gacaagtcgg    480
cgatcggcca tctgctcaac gagaccgtcg gcaaatacct gccgcagcgc ctgaaagcca    540
gcaaccatca gcacatggct tcgctggcca ccggcgaata cgagcaggcg cgctttcaca    600
tcgaccaggt gctggcgctc aacgatcggg gctacttggc ttgcctggag cggatccaga    660
gccacgtgca tttcatcaac ggcagctggg acgaatacac caccgccgag gacgcccgcc    720
agttccgcga ctacctgccg cactgcagtt tctcgcgggt ggagggcacc gggcatttcc    780
tcgacctgga gtccaagctg gcagcggtac gcgtgcaccg cgccctgctc gagcacctgc    840
tgaagcaacc ggagccgcag cgggcggaac gcggcggcgg attccacgag atggccatcg    900
gctacgcctg aacccttgac ctgcgaagac ccggcctggc cgggctttgc ggttgcataa    960
cgcacggagt agcccatgc acgccatcct catcgccatc ggctcggccg gcgacgtatt    1020
tcccttcatc ggcctggccc ggaccctgaa actgcgcggg caccgcgtga gcctctgcac    1080
```

-continued

```
catcccggtg tttcgcgacg cggtggagca gcacggcatc gcgttcgtcc cgctgagcga  1140
cgaactgacc taccgccgga ccatgggcga tccgcgcctg tgggacccca agacgtcctt  1200
cggcgtgctc tggcaagcca tcgccgggat gatcgagccg gtctacgagt acgtctcggc  1260
gcagcgccat gacgacatcg tggtggtcgg ctcgctatgg gcgctgggcg cacgcatcgc  1320
tcacgagaag tacgggattc cctacctgtc cgcgcaggtc tcgccatcga ccctgttgtc  1380
ggcgcacctg ccgccggtac accccaagtt caacgtgccc gagcagatgc cgctggcgat  1440
gcgcaagctg ctctggcgct gcatcgagcg cttcaagctg gatcgcacct gcgcgccgga  1500
gatcaacgcg gtgcgccgca aggtcggcct ggaaacgccg gtgaagcgca tcttcaccca  1560
atggatgcat cgccgcagg gcgtggtctg cctgttcccg gcctggttcg cgccgcccca  1620
gcaggattgg ccgcaacccc tgcacatgac cggcttcccg ctgttcgacg gcagtatccc  1680
ggggaccccg ctcgacgacg aactgcaacg cttttctcgat cagggcagcc ggccgctggt  1740
gttcacccag ggctcgaccg aacacctgca gggcgacttc tacgccatgg ccctgcgcgc  1800
gctggaacgc ctcggcgcgc gtgggatctt cctcaccggc gccggccagg aaccgctgcg  1860
cggcttgccg aaccacgtgc tgcagcgcgc ctacgcgcca ctgggagcct tgctgccatc  1920
gtgcgccggg ctggtccatc cgggcggtat cggcgccatg agcctagcct tggcggcggg  1980
ggtgccgcag gtgctgctgc cctgtgccca cgaccagttc gacaatgccg aacggctggt  2040
ccggctcggc tgcgggatgc gcctgggcgt gccgttgcgc gagcaggagt tgcgcggggc  2100
gctgtgcgcg ttgctcgagg acccggccat ggcggcggcc tgtcggcgtt tcatggaatt  2160
gtcacaaccg cacagtatcg cttgcggtaa agcggcccag gtggtcgaac gttgtcatag  2220
ggaggggat gctcgatggc tgaaggctgc gtcctgaacg gtctagagcg gccgccaccg  2280
cggtggagct ccaattcgcc ctatagtgag tcgtattacg cgcgctcact ggccgtcgtt  2340
ttacaacgtc gtgactggga aaaccctggc gttacccaac ttaatcgcct tgcagcacat  2400
ccccctttcg ccagctggcg taatagcgaa gaggcccgca ccgatcgccc ttcccaacag  2460
ttgcgcagcc tgaatggcga atggaaattg taagcgttaa tattttgtta aaattcgcgt  2520
taaatttttg ttaaatcagc tcattttta accaataggc cgactgcgat gagtggcagg  2580
gcggggcgta attttttaa ggcagttatt ggtgcccta aacgcctggt gctacgcctg  2640
aataagtgat aataagcgga tgaatggcag aaattcgaaa gcaaattcga cccggtcgtc  2700
ggttcagggc agggtcgtta aatagccgct tatgtctatt gctggtttac cggtttattg  2760
actaccggaa gcagtgtgac cgtgtgcttc tcaaatgcct gaggccagtt tgctcaggct  2820
ctccccgtgg aggtaataat tgacgatatg atcatttatt ctgcctccca gagcctgata  2880
aaaacggtga atccgttagc gaggtgccgc cggcttccat tcaggtcgag gtggcccggc  2940
tccatgcacc gcgacgcaac gcggggaggc agacaaggta tagggcggcg aggcggctac  3000
agccgatagt ctggaacagc gcacttacgg gttgctgcgc aacccaagtg ctaccggcgc  3060
ggcagcgtga cccgtgtcgg cggctccaac ggctcgccat cgtccagaaa acacggctca  3120
tcgggcatcg gcaggcgctg ctgcccgcgc cgttcccatt cctccgtttc ggtcaaggct  3180
ggcaggtctg gttccatgcc cggaatgccg ggctggctgg gcggctcctc gccggggccg  3240
gtcggtagtt gctgctcgcc cggatacagg gtcgggatgc ggcgcaggtc gccatgcccc  3300
aacagcgatt cgtcctggtc gtcgtgatca accaccacgg cggcactgaa caccgacagg  3360
cgcaactggt cgcggggctg gccccacgcc acgcggtcat tgaccacgta ggccgacacg  3420
```

```
gtgccggggc cgttgagctt cacgacggag atccagcgct cggccaccaa gtccttgact    3480
gcgtattgga ccgtccgcaa agaacgtccg atgagcttgg aaagtgtctt ctggctgacc    3540
accacggcgt tctggtggcc catctgcgcc acgaggtgat gcagcagcat tgccgccgtg    3600
ggtttcctcg caataagccc ggcccacgcc tcatgcgctt tgcgttccgt ttgcacccag    3660
tgaccgggct tgttcttggc ttgaatgccg atttctctgg actgcgtggc catgcttatc    3720
tccatgcggt agggtgccgc acggttgcgg caccatgcgc aatcagctgc aacttttcgg    3780
cagcgcgaca acaattatgc gttgcgtaaa agtggcagtc aattacagat tttctttaac    3840
ctacgcaatg agctattgcg gggggtgccg caatgagctg ttgcgtaccc cccttttta    3900
agttgttgat ttttaagtct ttcgcatttc gccctatatc tagttctttg gtgcccaaag    3960
aagggcaccc ctgcgggggtt cccccacgcc ttcggcgcgg ctcccctcc ggcaaaaagt    4020
ggcccctccg gggcttgttg atcgactgcg cggccttcgg ccttgcccaa ggtggcgctg    4080
cccccttgga accccgcac tcgccgccgt gaggctcggg gggcaggcgg gcgggcttcg    4140
ccttcgactg cccccactcg cataggcttg gtcgttcca ggcgcgtcaa ggccaagccg    4200
ctgcgcggtc gctgcgcgag ccttgacccg ccttccactt ggtgtccaac cggcaagcga    4260
agcgcgcagg ccgcaggccg gaggcttttc cccagagaaa attaaaaaaa ttgatggggc    4320
aaggccgcag gccgcgcagt tggagccggt gggtatgtgg tcgaaggctg ggtagccggt    4380
gggcaatccc tgtggtcaag ctcgtgggca ggcgcagcct gtccatcagc ttgtccagca    4440
gggttgtcca cgggccgagc gaagcgagcc agccggtggc cgctcgcggc catcgtccac    4500
atatccacgg gctggcaagg gagcgcagcg accgcgcagg gcgaagcccg gagagcaagc    4560
ccgtagggcg ccgcagccgc cgtaggcggt cacgactttg cgaagcaaag tctagtgagt    4620
atactcaagc attgagtggc ccgccggagg caccgccttg cgctgccccc gtcgagccgg    4680
ttggacacca aaagggaggg gcaggcatgg cggcatacgc gatcatgcga tgcaagaagc    4740
tggcgaaaat gggcaacgtg gcggccagtc tcaagcacgc ctaccgcgag cgcgagacgc    4800
ccaacgctga cgccagcagg acgccagaga acgagcactg ggcggccagc agcaccgatg    4860
aagcgatggg ccgactgcgc gagttgctgc agagaagcg gcgcaaggac gctgtgttgg    4920
cggtcgagta cgtcatgacg gccagcccgg aatggtggaa gtcggccagc caagaacagc    4980
aggcggcgtt cttcgagaag gcgcacaagt ggctggcgga caagtacggg gcggatcgca    5040
tcgtgacggc cagcatccac cgtgacgaaa ccagcccgca catgaccgcg ttcgtggtgc    5100
cgctgacgca ggacggcagg ctgtcggcca aggagttcat cggcaacaaa gcgcagatga    5160
cccgcgacca gaccacgttt gcggccgctg tggccgatct agggctgcaa cggggcatcg    5220
agggcagcaa ggcacgtcac acgcgcattc aggcgttcta cgaggccctg agcggccac    5280
cagtgggcca cgtcaccatc agcccgcaag cggtcgagcc acgcgcctat gcaccgcagg    5340
gattggccga aaagctggga atctcaaagc gcgttgagac gccggaagcc gtggccgacc    5400
ggctgacaaa agcggttcgg caggggtatg agcctgccct acaggccgcc gcaggagcgc    5460
gtgagatgcg caagaaggcc gatcaagccc aagagacggc ccgagacctt cgggagcgcc    5520
tgaagcccgt tctggacgcc ctgggccgt tgaatcggga tatgcaggcc aaggccgccg    5580
cgatcatcaa ggccgtgggc gaaaagctgc tgacggaaca gcgggaagtc cagcgccaga    5640
aacaggccca gcgccagcag gaacgcgggc gcgcacattt ccccgaaaag tgccacctgg    5700
gatgaatgtc agctactggg ctatctggac aaggaaaac gcaagcgcaa agagaaagca    5760
ggtagcttgc agtgggctta catggcgata gctagactgg gcggttttat ggacagcaag    5820
```

| | |
|---|---|
| cgaaccggaa ttgccagctg gggcgccctc tggtaaggtt gggaagccct gcaaagtaaa | 5880 |
| ctggatggct ttcttgccgc caaggatctg atggcgcagg ggatcaagat ctgatcaaga | 5940 |
| gacaggatga ggatcgtttc gcatgattga acaagatgga ttgcacgcag gttctccggc | 6000 |
| cgcttgggtg gagaggctat tcggctatga ctgggcacaa cagacaatcg gctgctctga | 6060 |
| tgccgccgtg ttccggctgt cagcgcaggg gcgcccggtt cttttttgtca agaccgacct | 6120 |
| gtccggtgcc ctgaatgaac tgcaggacga ggcagcgcgg ctatcgtggc tggccacgac | 6180 |
| gggcgttcct tgcgcagctg tgctcgacgt tgtcactgaa gcgggaaggg actggctgct | 6240 |
| attgggcgaa gtgccggggc aggatctcct gtcatctcac cttgctcctg ccagaaaagt | 6300 |
| atccatcatg gctgatgcaa tgcggcggct gcatacgctt gatccggcta cctgcccatt | 6360 |
| cgaccaccaa gcgaaacatc gcatcgagcg agcacgtact cggatggaag ccggtcttgt | 6420 |
| cgatcaggat gatctggacg aagagcatca ggggctcgcg ccagccgaac tgttcgccag | 6480 |
| gctcaaggcg cgcatgcccg acggcgagga tctcgtcgtg acccatggcg atgcctgctt | 6540 |
| gccgaatatc atggtggaaa atggccgctt ttctggattc atcgactgtg gccggctggg | 6600 |
| tgtggcggac cgctatcagg acatagcgtt ggctacccgt gatattgctg aagagcttgg | 6660 |
| cggcgaatgg gctgaccgct tcctcgtgct ttacggtatc gccgctcccg attcgcagcg | 6720 |
| catcgccttc tatcgccttc ttgacgagtt cttctgagcg ggactctggg gttcgaaatg | 6780 |
| accgaccaag cgacgcccaa cctgccatca cgagatttcg attccaccgc cgccttctat | 6840 |
| gaaaggttgg gcttcggaat cgttttccgg gacgccggct ggatgatcct ccagcgcggg | 6900 |
| gatctcatgc tggagttctt cgcccacccc catgggcaaa tattatacgc aaggcgacaa | 6960 |
| ggtgctgatg ccgctggcga ttcaggttca tcatgccgtt tgtgatggct tccatgtcgg | 7020 |
| cagaatgctt aatgaattac aacagttttt atgcatgcgc ccaatacgca aaccgcctct | 7080 |
| ccccgcgcgt tggccgattc attaatgcag ctggcacgac aggtttcccg actggaaagc | 7140 |
| gggcagtgag cgcaacgcaa ttaatgtgag ttagctcact cattaggcac cccaggcttt | 7200 |
| acactttatg cttccggctc gtatgttgtg tggaattgtg agcggataac aatttcacac | 7260 |
| aggaaacagc tatgaccatg attacgccaa gcgcgcaatt aaccctcact aaagggaaca | 7320 |
| aaagctgggt ac | 7332 |

<210> SEQ ID NO 63
<211> LENGTH: 7354
<212> TYPE: DNA
<213> ORGANISM: Artificial Sequence
<220> FEATURE:
<223> OTHER INFORMATION: vector

<400> SEQUENCE: 63

| | |
|---|---|
| cgaattcaaa acttttggg aggtgtgaga tgcggcgcga aagtctgttg gtaacggtat | 60 |
| gcaagggcct gcgggtacat gtcgagcgcg tgggcagga tcccgggcgc gacacggtga | 120 |
| tgctggtcaa cggcgcgatg gcgaccaccg cctcgttcgc ccggacctgc aagtgcctgg | 180 |
| ccgaacattt caacgtggtg ctgttcgacc tgcccttcgc cgggcagtcg cggcagcaca | 240 |
| atccgcagcg cgggttgatc accaaggacg acgaggtgga gattcctctg cgctgatcg | 300 |
| agcgcttcgc tgtcaaccac ctggtctcgg cctcctgggg cggcatctcc acgctgctgg | 360 |
| cgctgtcgcg caaccgcgc ggggtccgca gtcggtggt gatggcgttc gcgcggggc | 420 |
| tgaaccaggc gatgctcgat tatgtcgggc gggcccagga actgatcgaa ctggacgaca | 480 |

```
agtcggcgat cggccacctg ctcaacgaga ccgtcggcaa gtacctgccg ccgcggctga    540
aggccagcaa ccatcagcac atggcctccc tggccactgg cgagtacgag caggcgcgtt    600
tccacatcga ccaggtgctg cgctcaatg accgtggcta cctgagctgc ctggggcaga     660
tccagagtca cgtgcatttc atcaacggca gctgggacga gtacaccacc gccgaggacg    720
cccgccagtt ccgcgattac ctgccgcatt gcagtttttc gcgggtggaa ggcaccgggc    780
acttcctcga cctggagtcc aagctggcgg cggcgcgtgt gcaccgggcg ttgctcgagc    840
acctgctggc gcaaccggaa ccgtggcgct ccgagcaggc ggcgggattc cacgagatgg    900
ccatcggcta cgcctgaccc gtcgggatct gcgaaggccc ggcatggccg ggccttgccg    960
ttgcacaacg caaggagtag ccccatgcac gccattctca tcgccatcgg ttcggccggc   1020
gacgtgttcc ccttcatcgg cctggcccgc accctgaagt tgcgcggcca ccgcgtcagc   1080
ctgtgcacca ttccggtgtt tcgcgccgcg gtggagcagc acggcatcga gttcgtcccg   1140
ctcagcgacg aactgaccta ccgccggacc atgggcgacc cgcgcctgtg ggatccgaag   1200
acctcgttcg gagtgctctg gcaggccatc gccgggatga tcgagccggt ctacgagtac   1260
gtctgcgcac agcgccacga cgacatcgtg gtggtcggtt cgctgtgggc cctgggcgcg   1320
cggatcgccc atgagaaata cgggattccc tacctgtcgg tgcaggtctc gccgtcgacc   1380
ctgctgtcgg cgcacctgcc gccggtccac cccaggttca acgtgcccga gcaggtcccg   1440
ctggcgatgc gcaagttgct ctggcgctgc atcgaacgct tcaagctgga ccgcacctgc   1500
gccccggaga tcaacgcggt gcgccgcaag gtcggcctgg tcggcccggc gaagcgcatc   1560
ttcacccagt ggatgcattc gccacaggga gtgctctgcc tgttcccggc ctggttcgca   1620
ccgccccagc aggactggcc gcaaccgctg cacatgaccg gcttcccgct gttcgacggc   1680
agcgtcccgg ggacccgcct cgacgacgag ttgcagcgct tcctcgagca gggcagtcgg   1740
ccgctggtgt tcacccaggg ttcgaccgag cacctgcagg gagacttcta tgccatggcc   1800
ttgcgcgcgc tggagcgtct cggcgcccgc ggcatcttcc tcaccggcgc cggccaggag   1860
ccgctgcgtg gcttgccgag ccacgtgctg caacgctcgt acgtgccgtt gggggccttg   1920
ctgccggcgt gcgccgggct ggtccacccg gccggcatcg gcgccatgag cctggcgctg   1980
gcggcggggg tgccgcaggt gctgctgcct tgcgcccacg accagttcga caacgccgaa   2040
cgcctggtcc gcctcggctg cggtatccgc ctgggcctgc cgctacgcga gcaggcgctg   2100
cgcgagtcgc tctggcggct gctcgaggac ccggcgctgg cggcggcctg tcggcgtttc   2160
atggaattgt cacaaccgca cagtatcgct tgcggtaaag cggcccaagt ggtcgaacgt   2220
tgtcataggg aggggatgt gcgatggctg aaagccgcgt cctgagccgt gctggcagaa    2280
ttctctagag cggccgccac cgcggtggag ctccaattcg ccctatagtg agtcgtatta   2340
cgcgcgctca ctggccgtcg ttttacaacg tcgtgactgg gaaaaccctg gcgttaccca   2400
acttaatcgc cttgcagcac atccccctttt cgccagctgg cgtaatagcg aagaggcccg   2460
caccgatcgc ccttcccaac agttgcgcag cctgaatggc gaatggaaat tgtaagcgtt   2520
aatattttgt taaaattcgc gttaaatttt tgttaaatca gctcattttt taaccaatag   2580
gccgactgcg atgagtggca gggcggggcg taattttttt aaggcagtta ttggtgccct   2640
taaacgcctg gtgctacgcc tgaataagtg ataataagcg gatgaatggc agaaattcga   2700
aagcaaattc gacccggtcg tcggttcagg gcagggtcgt taaatagccg cttatgtcta   2760
ttgctggttt accggtttat tgactaccgg aagcagtgtg accgtgtgct tctcaaatgc   2820
ctgaggccag tttgctcagg ctctccccgt ggaggtaata attgacgata tgatcattta   2880
```

```
ttctgcctcc cagagcctga taaaaacggt gaatccgtta gcgaggtgcc gccggcttcc    2940
attcaggtcg aggtggcccg gctccatgca ccgcgacgca acgcggggag gcagacaagg    3000
tatagggcgg cgaggcggct acagccgata gtctggaaca gcgcacttac gggttgctgc    3060
gcaacccaag tgctaccggc gcggcagcgt gacccgtgtc ggcggctcca acggctcgcc    3120
atcgtccaga aaacacggct catcgggcat cggcaggcgc tgctgcccgc gccgttccca    3180
ttcctccgtt tcggtcaagg ctggcaggtc tggttccatg cccggaatgc cgggctggct    3240
gggcggctcc tcgccggggc cggtcggtag ttgctgctcg cccggataca gggtcgggat    3300
gcggcgcagg tcgccatgcc ccaacagcga ttcgtcctgg tcgtcgtgat caaccaccac    3360
ggcggcactg aacaccgaca ggcgcaactg gtcgcggggc tggccccacg ccacgcggtc    3420
attgaccacg taggccgaca cggtgccggg gccgttgagc ttcacgacgg agatccagcg    3480
ctcggccacc aagtccttga ctgcgtattg gaccgtccgc aaagaacgtc cgatgagctt    3540
ggaaagtgtc ttctggctga ccaccacggc gttctggtgg cccatctgcg ccacgaggtg    3600
atgcagcagc attgccgccg tgggtttcct cgcaataagc ccggcccacg cctcatgcgc    3660
tttgcgttcc gtttgcaccc agtgaccggg cttgttcttg gcttgaatgc cgatttctct    3720
ggactgcgtg ccatgctta tctccatgcg gtagggtgcc gcacggttgc ggcaccatgc    3780
gcaatcagct gcaactttc ggcagcgcga caacaattat gcgttgcgta aaagtggcag    3840
tcaattacag attttcttta acctacgcaa tgagctattg cggggggtgc cgcaatgagc    3900
tgttgcgtac ccccctttt taagttgttg atttttaagt ctttcgcatt tcgccctata    3960
tctagttctt tggtgcccaa agaagggcac ccctgcgggg ttccccacg ccttcggcgc    4020 ggctcccct ccggcaaaaa gtggcccctc cggggcttgt tgatcgactg cgcggccttc    4080
ggccttgccc aaggtggcgc tgccccttg gaaccccgc actcgccgcc gtgaggctcg    4140
gggggcaggc gggcgggctt cgccttcgac tgcccccact cgcataggct tgggtcgttc    4200
caggcgcgtc aaggccaagc cgctgcgcgg tcgctgcgcg agccttgacc cgccttccac    4260
ttggtgtcca accggcaagc gaagcgcgca ggccgcaggc cggaggcttt tccccagaga    4320
aaattaaaaa aattgatggg gcaaggccgc aggccgcgca gttggagccg gtgggtatgt    4380
ggtcgaaggc tgggtagccg gtgggcaatc cctgtggtca agctcgtggg caggcgcagc    4440
ctgtccatca gcttgtccag cagggttgtc cacgggccga gcgaagcgag ccagccggtg    4500
gccgctcgcg gccatcgtcc acatatccac gggctggcaa gggagcgcag cgaccgcgca    4560
gggcgaagcc cggagagcaa gcccgtaggg cgccgcagcc gccgtaggcg gtcacgactt    4620
tgcgaagcaa agtctagtga gtatactcaa gcattgagtg gcccgccgga ggcaccgcct    4680
tgcgctgccc ccgtcgagcc ggttggacac caaaagggag gggcaggcat ggcggcatac    4740
gcgatcatgc gatgcaagaa gctggcgaaa atgggcaacg tggcggccag tctcaagcac    4800
gcctaccgcg agcgcgagac gcccaacgct gacgccagca ggacgccaga gaacgagcac    4860
tgggcggcca gcagcaccga tgaagcgatg gccgactgc gcgagttgct gccagagaag    4920
cggcgcaagg acgctgtgtt ggcggtcgag tacgtcatga cggccagccc ggaatggtgg    4980
aagtcggcca gccaagaaca gcaggcggcg ttcttcgaga aggcgcacaa gtggctggcg    5040
gacaagtacg gggcggatcg catcgtgacg gccagcatcc accgtgacga accagcccg    5100 cacatgaccg cgttcgtggt gccgctgacg caggacggca ggctgtcggc caaggagttc    5160
atcggcaaca aagcgcagat gacccgcgac cagaccacgt ttgcggccgc tgtggccgat    5220
```

```
ctagggctgc aacggggcat cgagggcagc aaggcacgtc acacgcgcat tcaggcgttc      5280
tacgaggccc tggagcggcc accagtgggc cacgtcacca tcagcccgca agcggtcgag      5340
ccacgcgcct atgcaccgca gggattggcc gaaaagctgg gaatctcaaa gcgcgttgag      5400
acgccggaag ccgtggccga ccggctgaca aaagcggttc ggcaggggta tgagcctgcc      5460
ctacaggccg ccgcaggagc gcgtgagatg cgcaagaagg ccgatcaagc ccaagagacg      5520
gcccgagacc ttcgggagcg cctgaagccc gttctggacg ccctgggcc gttgaatcgg       5580 gatatgcagg ccaaggccgc cgcgatcatc aaggccgtgg gcgaaaagct gctgacggaa      5640
cagcgggaag tccagcgcca gaaacaggcc cagcgccagc aggaacgcgg gcgcgcacat      5700
ttccccgaaa agtgccacct gggatgaatg tcagctactg gctatctgg acaagggaaa       5760 acgcaagcgc aaagagaaag caggtagctt gcagtgggct tacatggcga tagctagact      5820
gggcggtttt atggacagca agcgaaccgg aattgccagc tggggcgccc tctggtaagg      5880
ttgggaagcc ctgcaaagta aactggatgg cttctcttgcc gccaaggatc tgatggcgca     5940
ggggatcaag atctgatcaa gagacaggat gaggatcgtt tcgcatgatt gaacaagatg      6000
gattgcacgc aggttctccg gccgcttggg tggagaggct attcggctat gactgggcac      6060
aacagacaat cggctgctct gatgccgccg tgttccggct gtcagcgcag gggcgcccgg      6120 ttcttttttgt caagaccgac ctgtccggtg ccctgaatga actgcaggac gaggcagcgc    6180
ggctatcgtg gctggccacg acgggcgttc cttgcgcagc tgtgctcgac gttgtcactg      6240
aagcgggaag ggactggctg ctattgggcg aagtgccggg gcaggatctc ctgtcatctc      6300
accttgctcc tgccgagaaa gtatccatca tggctgatgc aatgcggcgg ctgcatacgc      6360
ttgatccggc tacctgccca ttcgaccacc aagcgaaaca tcgcatcgag cgagcacgta     6420
ctcggatgga agccggtctt gtcgatcagg atgatctgga cgaagagcat caggggctcg     6480
cgccagccga actgttcgcc aggctcaagg cgcgcatgcc cgacggcgag gatctcgtcg     6540
tgacccatgg cgatgcctgc ttgccgaata tcatggtgga aaatggccgc ttttctggat     6600
tcatcgactg tggccggctg ggtgtggcgg accgctatca ggacatagcg ttggctaccc     6660
gtgatattgc tgaagagctt ggcggcgaat gggctgaccg cttcctcgtg ctttacggta     6720
tcgccgctcc cgattcgcag cgcatcgcct tctatcgcct tcttgacgag ttcttctgag     6780
cgggactctg gggttcgaaa tgaccgacca agcgacgccc aacctgccat cacgagattt     6840
cgattccacc gccgccttct atgaaaggtt gggcttcgga atcgttttcc gggacgccgg     6900
ctggatgatc ctccagcgcg ggatctcat gctggagttc ttcgcccacc cccatgggca      6960
aatattatac gcaaggcgac aaggtgctga tgccgctggc gattcaggtt catcatgccg     7020
tttgtgatgg cttccatgtc ggcagaatgc ttaatgaatt acaacagttt ttatgcatgc     7080
gcccaatacg caaaccgcct ctccccgcgc gttggccgat tcattaatgc agctggcacg     7140
acaggtttcc cgactggaaa gcgggcagtg agcgcaacgc aattaatgtg agttagctca     7200
ctcattaggc accccaggct ttacacttta tgcttccggc tcgtatgttg tgtggaattg     7260
tgagcggata acaatttcac acaggaaaca gctatgacca tgattacgcc aagcgcgcaa     7320
ttaaccctca ctaaagggaa caaaagctgg gtac                                 7354
```

<210> SEQ ID NO 64
<211> LENGTH: 2298
<212> TYPE: DNA
<213> ORGANISM: Artificial Sequence
<220> FEATURE:
<223> OTHER INFORMATION: syn operon

<400> SEQUENCE: 64

```
aagcttgaat tcggtaccga aaattttgg gaggtgtgaa atgcggcgcg aaagtctgtt      60
ggtatcggtt tgcaagggcc tgcgggtaca tgtcgagcgc gttgggcagg atcccgggcg    120
cagcacggtg atgctggtca acggcgcgat ggcgaccacc gcctcgttcg cccggacctg    180
caagtgcctg gccgaacatt tcaacgtggt gctgttcgac ctgcccttcg ccggcagtc    240
gcgtcagcac aacccgcagc gcgggttgat caccaaggac gacgaggtgg aaatcctcct    300
ggcgctgatc gagcgcttcg aggtcaatca cctggtctcc gcgtcctggg gcggtatctc    360
cacgctgctg gcgctgtcgc gcaatccgcg cggcatccgc agctcggtgg tgatggcatt    420
cgcccctgga ctgaaccagg cgatgctcga ctacgtcggg cgggcgcagg cgctgatcga    480
gctggacgac aagtcggcga tcggccatct gctcaacgag accgtcggca aatacctgcc    540
gcagcgcctg aaagccagca accatcagca catggcttcg ctggccaccg gcgaatacga    600
gcaggcgcgc tttcacatcg accaggtgct ggcgctcaac gatcgggct acttggcttg    660
cctggagcgg atccagagcc acgtgcattt catcaacggc agctgggacg aatacaccac    720
cgccgaggac gcccgccagt tccgcgacta cctgccgcac tgcagtttct cgcgggtgga    780
gggcaccggg catttcctcg acctggagtc caagctggca gcggtacgcg tgcaccgcgc    840
cctgctcgag cacctgctga agcaaccgga gccgagcgg gcggaacgcg cggcgggatt    900
ccacgagatg gccatcggct acgcctgaac ccttgacctg cgaagacccg gctggccgg    960
gctttgcggt tgcataacgc acggagtagc cccatgcacg ccatcctcat cgccatcggc   1020
tcggccggcg acgtattcc cttcatcggc ctggcccgga cctgaaaact gcgcgggcac   1080
cgcgtgagcc tctgcaccat cccggtgttt cgcgacgcgg tggagcagca cggcatcgcg   1140
ttcgtcccgc tgagcgacga actgacctac cgccggacca tgggcgatcc gcgcctgtgg   1200
gaccccaaga cgtccttcgg cgtgctctgg caagccatcg ccgggatgat cgagccggtc   1260
tacgagtacg tctcggcgca cgccatgac gacatcgtgg tggtcggctc gctatgggcg   1320
ctgggcgcac gcatcgctca cgagaagtac gggattccct acctgtccgc gcaggtctcg   1380
ccatcgaccc tgttgtcggc gcacctgccg ccggtacacc ccaagttcaa cgtgcccgag   1440
cagatgccgc tggcgatgcg caagctgctc tggcgctgca tcgagcgctt caagctggat   1500
cgcacctgcg cgccggagat caacgcggtg cgccgcaagg tcggcctgga acgccggtg   1560
aagcgcatct tcacccaatg gatgcattcg ccgcagggcg tggtctgcct gttcccggcc   1620
tggttcgcgc cgccccagca ggattggccg caaccctgc acatgaccgg cttcccgctg   1680
ttcgacggca gtatcccggg gaccccgctc gacgacgaac tgcaacgctt tctcgatcag   1740
ggcagccggc cgctggtgtt cacccagggc tcgaccgaac acctgcaggg cgacttctac   1800
gccatggccc tgcgcgcgct ggaacgcctc ggcgcgcgtg ggatcttcct caccggcgcc   1860
ggccaggaac cgctgcgcgg cttgccgaac acgtgctgc agcgcgccta cgcgccactg   1920
ggagccttgc tgccatcgtg cgccgggctg gtccatccgg gcggtatcgg cgccatgagc   1980
ctagccttgg cggcggggt gccgcaggtg ctgctgccct gtgcccacga ccagttcgac   2040
aatgccgaac ggctggtccg gctcggctgc gggatgcgcc tggcgtgcc gttgcgcgag   2100
caggagttgc gcggggcgct gtggcgcttg ctcgaggacc cggccatggc ggcggcctgt   2160
cggcgtttca tggaattgtc acaaccgcac agtatcgctt gcggtaaagc ggcccaggtg   2220
gtcgaacgtt gtcataggga gggggatgct cgatggctga aggctgcgtc ctgaacggtc   2280
```

| | |
|---|---:|
| tagagaattc ggcgcgcc | 2298 |

<210> SEQ ID NO 65
<211> LENGTH: 2302
<212> TYPE: DNA
<213> ORGANISM: Artificial Sequence
<220> FEATURE:
<223> OTHER INFORMATION: syn operon

<400> SEQUENCE: 65

| | |
|---|---:|
| ggtaccgaat tcaaaacttt ttgggaggtg tgagatgcgg cgcgaaagtc tgttggtaac | 60 |
| ggtatgcaag ggcctgcggg tacatgtcga gcgcgtgggg caggatcccg ggcgcgacac | 120 |
| ggtgatgctg gtcaacggcg cgatggcgac caccgcctcg ttcgcccgga cctgcaagtg | 180 |
| cctggccgaa catttcaacg tggtgctgtt cgacctgccc ttcgccgggc agtcgcggca | 240 |
| gcacaatccg cagcgcgggt tgatcaccaa ggacgacgag gtggagattc tcctggcgct | 300 |
| gatcgagcgc ttcgctgtca accacctggt ctcggcctcc tggggcggca tctccacgct | 360 |
| gctggcgctg tcgcgcaacc cgcgcggggt ccgcagctcg gtggtgatgg cgttcgcgcc | 420 |
| ggggctgaac caggcgatgc tcgattatgt cgggcgggcc caggaactga tcgaactgga | 480 |
| cgacaagtcg gcgatcggcc acctgctcaa cgagaccgtc ggcaagtacc tgccgccgcg | 540 |
| gctgaaggcc agcaaccatc agcacatggc ctccctggcc actggcgagt acgagcaggc | 600 |
| gcgtttccac atcgaccagg tgctggcgct caatgaccgt ggctacctga gctgcctggg | 660 |
| gcagatccag agtcacgtgc atttcatcaa cggcagctgg gacgagtaca ccaccgccga | 720 |
| ggacgcccgc cagttccgcg attacctgcc gcattgcagt ttttcgcggg tggaaggcac | 780 |
| cgggcacttc ctcgacctgg agtccaagct ggcggcggcg cgtgtgcacc gggcgttgct | 840 |
| cgagcacctg ctggcgcaac cggaaccgtg gcgctccgag caggcggcgg gattccacga | 900 |
| gatggccatc ggctacgcct gacccgtcgg gatctgcgaa ggcccggcat ggccgggcct | 960 |
| tgccgttgca caacgcaagg agtagcccca tgcacgccat tctcatcgcc atcggttcgg | 1020 |
| ccggcgacgt gttccccttc atcggcctgg cccgcaccct gaagttgcgc ggccaccgcg | 1080 |
| tcagcctgtg caccattccg gtgtttcgcg ccgcggtgga gcagcacggc atcgagttcg | 1140 |
| tcccgctcag cgacgaactg acctaccgcc ggaccatggg cgacccgcgc ctgtgggatc | 1200 |
| cgaagacctc gttcggagtg ctctggcagg ccatcgccgg gatgatcgag ccggtctacg | 1260 |
| agtacgtctg cgcacagcgc cacgacgaca tcgtggtggt cggttcgctg tgggccctgg | 1320 |
| gcgcgcggat cgcccatgag aaatacggga ttccctacct gtcggtgcag gtctcgccgt | 1380 |
| cgaccctgct gtcggcgcac ctgccgccgg tccacccag gttcaacgtg cccgagcagg | 1440 |
| tcccgctggc gatgcgcaag ttgctctggc gctgcatcga acgcttcaag ctggaccgca | 1500 |
| cctgcgcccc ggagatcaac gcggtgcgcc gcaaggtcgg cctggtcggc ccggcgaagc | 1560 |
| gcatcttcac ccagtggatg cattcgccac agggagtgct ctgcctgttc ccggcctggt | 1620 |
| tcgcaccgcc ccagcaggac tggccgcaac cgctgcacat gaccggcttc ccgctgttcg | 1680 |
| acggcagcgt cccggggacc cgcctcgacg acgagttgca gcgcttcctc gagcagggca | 1740 |
| gtcggccgct ggtgttcacc cagggttcga ccgagcacct gcaggagac ttctatgcca | 1800 |
| tggccttgcg cgcgctggag cgtctcggcg cccgcggcat cttcctcacc ggcgccggcc | 1860 |
| aggagccgct gcgtggcttg ccgagccacg tgctgcaacg ctcgtacgtg ccgttggggg | 1920 |
| ccttgctgcc ggcgtgcgcc gggctggtcc accggccgg catcggcgcc atgagcctgg | 1980 |
| cgctggcggc gggggtgccg caggtgctgc tgccttgcgc ccacgaccag ttcgacaacg | 2040 |

-continued

| | |
|---|---|
| ccgaacgcct ggtccgcctc ggctgcggta tccgcctggg cctgccgcta cgcgagcagg | 2100 |
| cgctgcgcga gtcgctctgg cggctgctcg aggacccggc gctggcggcg gcctgtcggc | 2160 |
| gtttcatgga attgtcacaa ccgcacagta tcgcttgcgg taaagcggcc caagtggtcg | 2220 |
| aacgttgtca tagggagggg gatgtgcgat ggctgaaagc cgcgtcctga gccgtgctgg | 2280 |
| cagaattctc tagaggcgcg cc | 2302 |

<210> SEQ ID NO 66
<211> LENGTH: 8325
<212> TYPE: DNA
<213> ORGANISM: Artificial Sequence
<220> FEATURE:
<223> OTHER INFORMATION: vector

<400> SEQUENCE: 66

| | |
|---|---|
| ctagatacgg gagaagaacg atcatggacc ggatagacat gggcgtgctg gtggtgctgt | 60 |
| tcaatcctgg cgacgacgac ctggaacacc ttggcgaact ggcggcggcc tttccgcaac | 120 |
| tgcgcttcct cgccgtcgac aactcgccgc acagcgatcc gcagcgcaac gcccggctgc | 180 |
| gcgggcaagg catcgccgtg ctctaccacg gcaaccggca gggcatcgcc ggcgccttca | 240 |
| accaggggct cgacacgctg ttccggcgcg gcctgcaggg tgtgctgctg ctcgaccagg | 300 |
| actcccgtcc cggcggcgcc ttcctcgccg ccagtggcg caacctgcag gcatgcaacg | 360 |
| gccaggcctg cctgctcggc ccacggatct tcgaccgggg cgaccggcgc ttcctgccgg | 420 |
| ccatccacct cgacgggctg cgctcaggc aactgtccct ggacggcctg acgaccccac | 480 |
| agcgcacctc gttcctgatc tcctccggct gcctgctgac ccgcgaggcc taccagcgcc | 540 |
| tcggccactt cgacgaggaa ctgttcatcg accacgtgga caccgagtac agcctgcgcg | 600 |
| cccaggcgct ggacgtgccc ctgtacgtcg acccgcggct ggtcctcgag caccgcatcg | 660 |
| gcacgcgcaa gacccgccgc ctcggcggtc tcagcctcag cgcgatgaac cacgccccac | 720 |
| tgccgccgcta ctacctggcg cgcaacggcc tgctggtcct gcgccgctac gcccggtcct | 780 |
| cgccgctggc cctgctggcg aacctgccga ccctgaccca gggcctcgcg gtgctcctgc | 840 |
| tcgaacgcga caagctgctc aagctgcgct gcctgggctg gggcctgtgg acggcctgc | 900 |
| gggggcgcgg cggcgcgctg gagcgcaacc gcccgcgcct gctgaagcgc ctcgccggtc | 960 |
| cggcggtggc gcccacagtt cccggcaagg ccaaggccta gtcggcgaaa cgcattgagc | 1020 |
| tccaattcgc cctatagtga gtcgtattac gcgcgctcac tggccgtcgt tttacaacgt | 1080 |
| cgtgactggg aaaaccctgg cgttacccaa cttaatcgcc ttgcagcaca tccccctttc | 1140 |
| gccagctggc gtaatagcga agaggcccgc accgatcgcc cttcccaaca gttgcgcagc | 1200 |
| ctgaatggcg aatggaaatt gtaagcgtta atattttgtt aaaattcgcg ttaaattttt | 1260 |
| gttaaatcag ctcattttt aaccatagg ccgactgcga tgagtggcag ggcggggcgt | 1320 |
| aattttttta aggcagttat tggtgccctt aaacgcctgg tgctacgcct gaataagtga | 1380 |
| taataagcgg atgaatggca gaaattcgaa agcaaattcg acccggtcgt cggttcaggg | 1440 |
| cagggtcgtt aaatagccgc ttatgtctat tgctggttta ccggtttatt gactaccgga | 1500 |
| agcagtgtga ccgtgtgctt ctcaaatgcc tgaggccagt ttgctcaggc tctccccgtg | 1560 |
| gaggtaataa ttgacgatat gatcatttat tctgcctccc agagcctgat aaaaacggtg | 1620 |
| aatccgttag cgaggtgccg ccggcttcca ttcaggtcga ggtggcccgg ctccatgcac | 1680 |
| cgcgacgcaa cgcggggagg cagacaaggt atagggcggc gaggcggcta cagccgatag | 1740 |

```
tctggaacag cgcacttacg ggttgctgcg caacccaagt gctaccggcg cggcagcgtg    1800
acccgtgtcg gcggctccaa cggctcgcca tcgtccagaa acacggctc atcgggcatc    1860 ggcaggcgct gctgcccgcg ccgttcccat tcctccgttt cggtcaaggc tggcaggtct    1920
ggttccatgc ccggaatgcc gggctggctg gcggctcct cgccggggcc ggtcggtagt    1980
tgctgctcgc ccggatacag ggtcgggatg cggcgcaggt cgccatgccc caacagcgat    2040
tcgtcctggt cgtcgtgatc aaccaccacg gcggcactga acaccgacag gcgcaactgg    2100
tcgcggggct ggccccacgc cacgcggtca ttgaccacgt aggccgacac ggtgccgggg    2160
ccgttgagct tcacgacgga gatccagcgc tcggccacca agtccttgac tgcgtattgg    2220
accgtccgca aagaacgtcc gatgagcttg aaaagtgtct tctggctgac caccacggcg    2280
ttctggtggc ccatctgcgc cacgaggtga tgcagcagca ttgccgccgt gggtttcctc    2340
gcaataagcc cggcccacgc ctcatgcgct ttgcgttccg tttgcaccca gtgaccgggc    2400
ttgttcttgg cttgaatgcc gatttctctg gactgcgtgg ccatgcttat ctccatgcgg    2460
tagggtgccg cacggttgcg gcaccatgcg caatcagctg caacttttcg gcagcgcgac    2520
aacaattatg cgttgcgtaa aagtggcagt caattacaga ttttctttaa cctacgcaat    2580
gagctattgc gggggggtgcc gcaatgagct gttgcgtacc cccctttttt aagttgttga    2640
tttttaagtc tttcgcattt cgccctatat ctagttcttt ggtgcccaaa gaagggcacc    2700 cctgcgggt tccccacgc cttcggcgcg gctccccctc cggcaaaaag tggcccctcc    2760
ggggcttgtt gatcgactgc gcggccttcg gccttgccca aggtggcgct gccccccttgg   2820 aaccccgca ctcgccgccg tgaggctcgg ggggcaggcg ggcgggcttc gccttcgact    2880
gcccccactc gcataggctt gggtcgttcc aggcgcgtca aggccaagcc gctgcgcggt    2940
cgctgcgcga gccttgaccc gccttccact tggtgtccaa ccggcaagcg aagcgcgcag    3000
gccgcaggcc ggaggctttt ccccagagaa aattaaaaaa attgatgggg caaggccgca    3060
ggccgcgcag ttggagccgg tgggtatgtg gtcgaaggct gggtagccgg tgggcaatcc    3120
ctgtggtcaa gctcgtgggc aggcgcagcc tgtccatcag cttgtccagc agggttgtcc    3180
acgggccgag cgaagcgagc cagccggtgg ccgctcgcgg ccatcgtcca catatccacg    3240
ggctggcaag ggagcgcagc gaccgcgcag gcgaagccc ggagagcaag cccgtagggc    3300
gccgcagccg ccgtaggcgg tcacgacttt gcgaagcaaa gtctagtgag tatactcaag    3360
cattgagtgg cccgccggag gcaccgcctt cgcgctgcccc cgtcgagccg gttggacacc    3420
aaaagggagg ggcaggcatg gcggcatacg cgatcatgcg atgcaagaag ctggcgaaaa    3480
tgggcaacgt ggcggccagt ctcaagcacg cctaccgcga gcgcgagacg cccaacgctg    3540
acgccagcag gacgccagag aacgagcact gggcggccag cagcaccgat gaagcgatgg    3600
gccgactgcg cgagttgctg ccagagaagc ggcgcaagga cgctgtgttg gcggtcgagt    3660
acgtcatgac ggccagcccg gaatggtgga agtcggccag ccaagaacag caggcggcgt    3720
tcttcgagaa ggcgcacaag tggctggcgg acaagtacgg ggcggatcgc atcgtgacgg    3780
ccagcatcca ccgtgacgaa accagcccgc acatgaccgc gttcgtggtg ccgctgacgc    3840
aggacggcag gctgtcggcc aaggagttca tcggcaacaa agcgcagatg acccgcgacc    3900
agaccacgtt tgcggccgct gtggccgatc tagggctgca acggggcatc gagggcagca    3960
aggcacgtca cacgcgcatt caggcgttct acgaggccct ggagcggcca ccagtgggcc    4020
acgtcaccat cagcccgcaa gcggtcgagc cacgcgccta tgcaccgcag ggattggccg    4080
aaaagctggg aatctcaaag cgcgttgaga cgccggaagc cgtggccgac cggctgacaa    4140
```

```
aagcggttcg gcaggggtat gagcctgccc tacaggccgc cgcaggagcg cgtgagatgc    4200
gcaagaaggc cgatcaagcc caagagacgg cccgagacct tcgggagcgc ctgaagcccg    4260
ttctggacgc cctggggccg ttgaatcggg atatgcaggc caaggccgcc gcgatcatca    4320
aggccgtggg cgaaaagctg ctgacggaac agcgggaagt ccagcgccag aaacaggccc    4380
agcgccagca ggaacgcggg cgcgcacatt tccccgaaaa gtgccacctg ggatgaatgt    4440
cagctactgg gctatctgga caagggaaaa cgcaagcgca aagagaaagc aggtagcttg    4500
cagtgggctt acatggcgat agctagactg ggcggtttta tggacagcaa gcgaaccgga    4560
attgccagct ggggcgccct ctggtaaggt tgggaagccc tgcaaagtaa actggatggc    4620
tttcttgccg ccaaggatct gatggcgcag gggatcaaga tctgatcaag agacaggatg    4680
aggatcgttt cgcatgattg aacaagatgg attgcacgca ggttctccgg ccgcttgggt    4740
ggagaggcta ttcggctatg actgggcaca acagacaatc ggctgctctg atgccgccgt    4800
gttccggctg tcagcgcagg ggcgcccggt tcttttttgtc aagaccgacc tgtccggtgc    4860
cctgaatgaa ctgcaggacg aggcagcgcg gctatcgtgg ctggccacga cgggcgttcc    4920
ttgcgcagct gtgctcgacg ttgtcactga agcgggaagg gactggctgc tattgggcga    4980
agtgccgggg caggatctcc tgtcatctca ccttgctcct gccgagaaag tatccatcat    5040
ggctgatgca atgcggcggc tgcatacgct tgatccggct acctgcccat tcgaccacca    5100
agcgaaacat cgcatcgagc gagcacgtac tcggatggaa gccggtcttg tcgatcagga    5160
tgatctggac gaagagcatc aggggctcgc gccagccgaa ctgttcgcca ggctcaaggc    5220
gcgcatgccc gacggcgagg atctcgtcgt gacccatggc gatgcctgct tgccgaatat    5280
catggtggaa aatggccgct tttctggatt catcgactgt ggccggctgg gtgtggcgga    5340
ccgctatcag gacatagcgt tggctacccg tgatattgct gaagagcttg gcggcgaatg    5400
ggctgaccgc ttcctcgtgc tttacggtat cgccgctccc gattcgcagc gcatcgcctt    5460
ctatcgcctt cttgacgagt tcttctgagc gggactctgg ggttcgaaat gaccgaccaa    5520
gcgacgccca acctgccatc acgagatttc gattccaccg ccgccttcta tgaaaggttg    5580
ggcttcggaa tcgttttccg gacgccggc tggatgatcc tccagcgcgg ggatctcatg    5640
ctggagttct tcgcccaccc ccatgggcaa atattatacg caaggcgaca aggtgctgat    5700
gccgctggcg attcaggttc atcatgccgt ttgtgatggc ttccatgtcg gcagaatgct    5760
taatgaatta caacagtttt tatgcatgcg cccaatacgc aaaccgcctc tccccgcgcg    5820
ttggccgatt cattaatgca gctggcacga caggtttccc gactggaaag cgggcagtga    5880
gcgcaacgca attaatgtga gttagctcac tcattaggca ccccaggctt tacactttat    5940
gcttccggct cgtatgttgt gtggaattgt gagcggataa caatttcaca caggaaacag    6000
ctatgaccat gattacgcca agcgcgcaat taaccctcac taaagggaac aaaagctggg    6060
taccgaaaat ttttgggagg tgtgaaatgc ggcgcgaaag tctgttggta tcggtttgca    6120
agggcctgcg ggtacatgtc gagcgcgttg gcaggatcc cgggcgcagc acggtgatgc    6180
tggtcaacgg cgcgatggcg accaccgcct cgttcgcccg gacctgcaag tgcctggccg    6240
aacatttcaa cgtggtgctg ttcgacctgc ccttcgccgg gcagtcgcgt cagcacaacc    6300
cgcagcgcgg gttgatcacc aaggacgacg aggtggaaat cctcctggcg ctgatcgagc    6360
gcttcgaggt caatcacctg gtctccgcgt cctgggcgg tatctccacg ctgctggcgc    6420
tgtcgcgcaa tccgcgcggc atccgcagct cggtggtgat ggcattcgcc cctggactga    6480
```

| | |
|---|---|
| accaggcgat gctcgactac gtcgggcggg cgcaggcgct gatcgagctg gacgacaagt | 6540 |
| cggcgatcgg ccatctgctc aacgagaccg tcggcaaata cctgccgcag cgcctgaaag | 6600 |
| ccagcaacca tcagcacatg gcttcgctgg ccaccggcga atacgagcag gcgcgctttc | 6660 |
| acatcgacca ggtgctggcg ctcaacgatc ggggctactt ggcttgcctg gagcggatcc | 6720 |
| agagccacgt gcatttcatc aacggcagct gggacgaata caccaccgcc gaggacgccc | 6780 |
| gccagttccg cgactacctg ccgcactgca gtttctcgcg ggtggagggc accgggcatt | 6840 |
| tcctcgacct ggagtccaag ctggcagcgg tacgcgtgca ccgcgccctg ctcgagcacc | 6900 |
| tgctgaagca accggagccg cagcgggcgg aacgcgcggc gggattccac gagatggcca | 6960 |
| tcggctacgc ctgaacccctt gacctgcgaa gacccggcct ggccgggctt gcggttgca | 7020 |
| taacgcacgg agtagcccca tgcacgccat cctcatcgcc atcggctcgg ccggcgacgt | 7080 |
| atttcccttc atcggcctgg cccggaccct gaaactgcgc gggcaccgcg tgagcctctg | 7140 |
| caccatcccg gtgtttcgcg acgcggtgga gcagcacggc atcgcgttcg tcccgctgag | 7200 |
| cgacgaactg acctaccgcc ggaccatggg cgatccgcgc ctgtgggacc caagacgtc | 7260 |
| cttcggcgtg ctctggcaag ccatcgccgg gatgatcgag ccggtctacg agtacgtctc | 7320 |
| ggcgcagcgc catgacgaca tcgtggtggt cggctcgcta tgggcgctgg gcgcacgcat | 7380 |
| cgctcacgag aagtacggga ttccctacct gtccgcgcag gtctcgccat cgaccctgtt | 7440 |
| gtcggcgcac ctgccgccgg tacacccccaa gttcaacgtg cccgagcaga tgccgctggc | 7500 |
| gatgcgcaag ctgctctggc gctgcatcga gcgcttcaag ctggatcgca cctgcgcgcc | 7560 |
| ggagatcaac gcggtgcgcc gcaaggtcgg cctggaaacg ccggtgaagc gcatcttcac | 7620 |
| ccaatggatg cattcgccgc agggcgtggt ctgcctgttc ccggcctggt tcgcgccgcc | 7680 |
| ccagcaggat tggccgcaac ccctgcacat gaccggcttc ccgctgttcg acggcagtat | 7740 |
| cccggggacc ccgctcgacg acgaactgca acgctttctc gatcagggca gccggccgct | 7800 |
| ggtgttcacc cagggctcga ccgaacacct gcagggcgac ttctacgcca tggccctgcg | 7860 |
| cgcgctggaa cgcctcggcg cgcgtgggat cttcctcacc ggcgccggcc aggaaccgct | 7920 |
| gcgcggcttg ccgaaccacg tgctgcagcg cgcctacgcg ccactgggag ccttgctgcc | 7980 |
| atcgtgcgcc gggctggtcc atccgggcgg tatcggcgcc atgagcctag ccttggcggc | 8040 |
| gggggtgccg caggtgctgc tgccctgtgc ccacgaccag ttcgacaatg ccgaacggct | 8100 |
| ggtccggctc ggctgcggga tgcgcctggg cgtgccgttg cgcgagcagg agttgcgcgg | 8160 |
| ggcgctgtgg cgcttgctcg aggacccggc catggcggcg gcctgtcggc gtttcatgga | 8220 |
| attgtcacaa ccgcacagta tcgcttgcgg taaagcggcc caggtggtcg aacgttgtca | 8280 |
| tagggagggg gatgctcgat ggctgaaggc tgcgtcctga acggt | 8325 |

<210> SEQ ID NO 67
<211> LENGTH: 8335
<212> TYPE: DNA
<213> ORGANISM: Artificial Sequence
<220> FEATURE:
<223> OTHER INFORMATION: vector

<400> SEQUENCE: 67

| | |
|---|---|
| ctagatacgg gagaagaacg atcatgacga tcctgggggc gctggtgatt ctgtacgacc | 60 |
| cgacggacga gcagttgtcg gggctggagg cgctcgcgcg cgacagcgac gcgctcgtgg | 120 |
| tcgtggacaa cacgccgcac gagcacgcgg cggcgcgcga gcgggtgcgt gcgctgtcgg | 180 |
| cgcggacgaa cacggtgtgg cgacaccacg gcaaccgggg cggggtcgcg ggcgggtaca | 240 |

```
acgcggggct gtcggtgctg ttcgcgcagg gcgtcgaggc ggtcgcgctg ttcgaccagg    300
actcgacggt gccggccggg tacttcgagc ggatgcgcga ggcgtgcgcg caactgggtg    360
agcaaccggg cgcgcacgcg ggcgcgttca tcgcgggccc gcggatctac gacgcgaacg    420
agcagcgctt cctgccggag ctgatgacga gcggggtgac ggtgcgccgc gtgcgggtgg    480
agggcgagac ggcgccgcag cgctgcgcgt tcctgatctc gtcgggcagc gtgatttcgc    540
gggccgcgta cgcgcggctc ggtcgattcg acgaggcgct gttcatcgat cacgtcgaca    600
ccgagtattg cctgcgcgcg ctcgcgcaca acgtgccgct gtacgtggtg ccgccgctcg    660
tgctgacgca ccggatcggc gcgcggcgcc ggcacaaggt ggggccgttc gagctgacgg    720
cgatgcatca cggtggttg cgccgatact acggcgcgcg caacgcgatg caactggggc    780
tgcagtacgg cttgcggttt ccggtggcgc tggtgccgaa tctgctgacg atatggcagg    840
tgatccaggt ggtgctgtgc gagcgggaga agggcgcgaa gctgcgcggg atcgcgctgg    900
gcgtgctcga cggcctgttc gggcggctgg gatcgttcga cgatgcgcgc gcgggcgcgg    960
cggcgcgcga gccggtgcgg caggaatgat cggcgaaacg cattgagctc caattcgccc   1020
tatagtgagt cgtattacgc gcgctcactg gccgtcgttt tacaacgtcg tgactgggaa   1080
aaccctggcg ttacccaact taatcgcctt gcagcacatc cccctttcgc cagctggcgt   1140
aatagcgaag aggcccgcac cgatcgccct tcccaacagt tgcgcagcct gaatggcgaa   1200
tggaaattgt aagcgttaat attttgttaa aattcgcgtt aaattttgt taaatcagct   1260 catttttta ccataggcc gactgcgatg agtggcaggg cggggcgtaa ttttttaag   1320 gcagttattg gtgcccttaa acgcctggtg ctacgcctga ataagtgata ataagcggat   1380
gaatggcaga aattcgaaag caaattcgac ccggtcgtcg gttcagggca gggtcgttaa   1440
atagccgctt atgtctattg ctggtttacc ggtttattga ctaccggaag cagtgtgacc   1500
gtgtgcttct caaatgcctg aggccagttt gctcaggctc tccccgtgga ggtaataatt   1560
gacgatatga tcatttattc tgcctcccag agcctgataa aaacggtgaa tccgttagcg   1620
aggtgccgcc ggcttccatt caggtcgagg tggcccggct ccatgcaccg cgacgcaacg   1680
cggggaggca gacaaggtat agggcggcga ggcggctaca gccgatagtc tggaacagcg   1740
cacttacggg ttgctgcgca acccaagtgc taccggcgcg gcagcgtgac ccgtgtcggc   1800
ggctccaacg gctcgccatc gtccagaaaa cacggctcat cggcatcgg caggcgctgc   1860 tgcccgcgcc gttcccattc ctccgtttcg gtcaaggctg gcaggtctgg ttccatgccc   1920
ggaatgccgg gctggctggg cggctcctcg ccggggccgg tcgtagttg ctgctcgccc   1980 ggatacaggg tcgggatgcg gcgcaggtcg ccatgcccca acagcgattc gtcctggtcg   2040
tcgtgatcaa ccaccacggc ggcactgaac accgacaggc gcaactggtc gcggggctgg   2100
ccccacgcca cgcggtcatt gaccacgtag gccgacacgg tgccggggcc gttgagcttc   2160
acgacggaga tccagcgctc ggccaccaag tccttgactg cgtattggac cgtccgcaaa   2220
gaacgtccga tgagcttgga aagtgtcttc tggctgacca ccacggcgtt ctggtggccc   2280
atctgcgcca cgaggtgatg cagcagcatt gccgccgtgg gtttcctcgc aataagcccg   2340
gcccacgcct catgcgcttt gcgttccgtt tgcacccagt gaccgggctt gttcttggct   2400
tgaatgccga tttctctgga ctgcgtggcc atgcttatct ccatgcggta gggtgccgca   2460
cggttgcggc accatgcgca atcagctgca acttttcggc agcgcgacaa caattatgcg   2520
ttgcgtaaaa gtggcagtca attacagatt ttctttaacc tacgcaatga gctattgcgg   2580
```

| | |
|---|---|
| ggggtgccgc aatgagctgt tgcgtacccc cctttttttaa gttgttgatt tttaagtctt | 2640 |
| tcgcatttcg ccctatatct agttctttgg tgcccaaaga agggcacccc tgcggggttc | 2700 |
| ccccacgcct tcggcgcggc tcccccctccg gcaaaaagtg gcccctccgg ggcttgttga | 2760 |
| tcgactgcgc ggccttcggc cttgcccaag gtggcgctgc cccccttggaa cccccgcact | 2820 |
| cgccgccgtg aggctcgggg ggcaggcggg cgggcttcgc cttcgactgc ccccactcgc | 2880 |
| ataggcttgg gtcgttccag gcgcgtcaag gccaagccgc tgcgcggtcg ctgcgcgagc | 2940 |
| cttgacccgc cttccacttg gtgtccaacc ggcaagcgaa gcgcgcaggc cgcaggccgg | 3000 |
| aggcttttcc ccagagaaaa ttaaaaaaat tgatggggca aggccgcagg ccgcgcagtt | 3060 |
| ggagccggtg ggtatgtggt cgaaggctgg gtagccggtg ggcaatccct gtggtcaagc | 3120 |
| tcgtgggcag gcgcagcctg tccatcagct tgtccagcag ggttgtccac gggccgagcg | 3180 |
| aagcgagcca gccggtggcc gctcgcggcc atcgtccaca tatccacggg ctggcaaggg | 3240 |
| agcgcagcga ccgcgcaggg cgaagcccgg agagcaagcc cgtagggcgc cgcagccgcc | 3300 |
| gtaggcggtc acgactttgc gaagcaaagt ctagtgagta tactcaagca ttgagtggcc | 3360 |
| cgccggaggc accgccttgc gctgcccccg tcgagccggt tggacaccaa aagggagggg | 3420 |
| caggcatggc ggcatacgcg atcatgcgat gcaagaagct ggcgaaaatg ggcaacgtgg | 3480 |
| cggccagtct caagcacgcc taccgcgagc gcgagacgcc caacgctgac gccagcagga | 3540 |
| cgccagagaa cgagcactgg gcggccagca gcaccgatga agcgatgggc cgactgcgcg | 3600 |
| agttgctgcc agagaagcgg cgcaaggacg ctgtgttggc ggtcgagtac gtcatgacgg | 3660 |
| ccagcccgga atggtggaag tcggccagcc aagaacagca ggcggcgttc ttcgagaagg | 3720 |
| cgcacaagtg gctggcggac aagtacgggg cggatcgcat cgtgacggcc agcatccacc | 3780 |
| gtgacgaaac cagcccgcac atgaccgcgt tcgtggtgcc gctgacgcag acggcaggc | 3840 |
| tgtcggccaa ggagttcatc ggcaacaaag cgcagatgac ccgcgaccag accacgtttg | 3900 |
| cggccgctgt ggccgatcta gggctgcaac ggggcatcga gggcagcaag gcacgtcaca | 3960 |
| cgcgcattca ggcgttctac gaggccctgg agcggccacc agtgggccac gtcaccatca | 4020 |
| gcccgcaagc ggtcgagcca cgcgcctatg caccgcaggg attggccgaa aagctgggaa | 4080 |
| tctcaaagcg cgttgagacg ccggaagccg tggccgaccg gctgacaaaa gcggttcggc | 4140 |
| aggggtatga gcctgcccta caggccgccg caggagcgcg tgagatgcgc aagaaggccg | 4200 |
| atcaagccca agagacggcc cgagaccttc gggagcgcct gaagcccgtt ctggacgccc | 4260 |
| tggggccgtt gaatcgggat atgcaggcca aggccgccgc gatcatcaag gccgtgggcg | 4320 |
| aaaagctgct gacggaacag cgggaagtcc agcgccagaa acaggcccag cgccagcagg | 4380 |
| aacgcgggcg cgcacatttc cccgaaaagt gccacctggg atgaatgtca gctactgggc | 4440 |
| tatctggaca agggaaaacg caagcgcaaa gagaaagcag gtagcttgca gtgggcttac | 4500 |
| atggcgatag ctagactggg cggttttatg gacagcaagc gaaccggaat tgccagctgg | 4560 |
| ggcgccctct ggtaaggttg ggaagccctg caaagtaaac tggatggctt tcttgccgcc | 4620 |
| aaggatctga tggcgcaggg gatcaagatc tgatcaagag acaggatgag gatcgtttcg | 4680 |
| catgattgaa caagatggat tgcacgcagg ttctccggcc gcttgggtgg agaggctatt | 4740 |
| cggctatgac tgggcacaac agacaatcgg ctgctctgat gccgccgtgt tccggctgtc | 4800 |
| agcgcagggg cgcccggttc tttttgtcaa gaccgacctg tccggtgccc tgaatgaact | 4860 |
| gcaggacgag gcagcgcggc tatcgtggct ggccacgacg ggcgttcctt gcgcagctgt | 4920 |
| gctcgacgtt gtcactgaag cgggaaggga ctggctgcta ttgggcgaag tgccggggca | 4980 |

-continued

```
ggatctcctg tcatctcacc ttgctcctgc cgagaaagta tccatcatgg ctgatgcaat    5040
gcggcggctg catacgcttg atccggctac ctgcccattc gaccaccaag cgaaacatcg    5100
catcgagcga gcacgtactc ggatggaagc cggtcttgtc gatcaggatg atctggacga    5160
agagcatcag gggctcgcgc cagccgaact gttcgccagg ctcaaggcgc gcatgcccga    5220
cggcgaggat ctcgtcgtga cccatggcga tgcctgcttg ccgaatatca tggtggaaaa    5280
tggccgcttt tctggattca tcgactgtgg ccggctgggt gtggcggacc gctatcagga    5340
catagcgttg gctacccgtg atattgctga agagcttggc ggcgaatggg ctgaccgctt    5400
cctcgtgctt tacggtatcg ccgctcccga ttcgcagcgc atcgccttct atcgccttct    5460
tgacgagttc ttctgagcgg gactctgggg ttcgaaatga ccgaccaagc gacgcccaac    5520
ctgccatcac gagatttcga ttccaccgcc gccttctatg aaaggttggg cttcggaatc    5580
gttttccggg acgccggctg gatgatcctc cagcgcgggg atctcatgct ggagttcttc    5640
gcccaccccc atgggcaaat attatacgca aggcgacaag gtgctgatgc cgctggcgat    5700
tcaggttcat catgccgttt gtgatggctt ccatgtcggc agaatgctta atgaattaca    5760
acagttttta tgcatgcgcc caatacgcaa accgcctctc cccgcgcgtt ggccgattca    5820
ttaatgcagc tggcacgaca ggtttcccga ctggaaagcg ggcagtgagc gcaacgcaat    5880
taatgtgagt tagctcactc attaggcacc ccaggcttta cactttatgc ttccggctcg    5940
tatgttgtgt ggaattgtga gcggataaca atttcacaca ggaaacagct atgaccatga    6000
ttacgccaag cgcgcaatta accctcacta aagggaacaa aagctgggta ccgaattcaa    6060
aacttttgg gaggtgtgag atgcggcgcg aaagtctgtt ggtaacggta tgcaagggcc    6120
tgcgggtaca tgtcgagcgc gtggggcagg atcccgggcg cgacacgtg atgctggtca    6180
acggcgcgat ggcgaccacc gcctcgttcg cccggacctg caagtgcctg gccgaacatt    6240
tcaacgtggt gctgttcgac ctgcccttcg ccgggcagtc gcggcagcac aatccgcagc    6300
gcgggttgat caccaaggac gacgaggtgg agattctcct ggcgctgatc gagcgcttcg    6360
ctgtcaacca cctggtctcg gcctcctggg gcggcatctc cacgctgctg gcgctgtcgc    6420
gcaacccgcg cggggtccgc agctcggtgg tgatggcgtt cgcgccgggg ctgaaccagg    6480
cgatgctcga ttatgtcggg cgggcccagg aactgatcga actggacgac aagtcggcga    6540
tcggccacct gctcaacgag accgtcggca agtacctgcc gccgcggctg aaggccagca    6600
accatcagca catggcctcc ctggccactg gcgagtacga gcaggcgcgt ttccacatcg    6660
accaggtgct ggcgctcaat gaccgtggct acctgagctg cctggggcag atccagagtc    6720
acgtgcattt catcaacggc agctgggacg agtacaccac cgccgaggac gcccgccagt    6780
tccgcgatta cctgccgcat tgcagttttt cgcgggtgga aggcaccggg cacttcctcg    6840
acctggagtc caagctggcg gcggcgcgtg tgcaccgggc gttgctcgag cacctgctgg    6900
cgcaaccgga accgtggcgc tccgagcagg cggcggatt ccacgagatg gccatcggct    6960
acgcctgacc cgtcgggatc tgcgaaggcc cggcatggcc gggccttgcc gttgcacaac    7020
gcaaggagta gccccatgca cgccattctc atcgccatcg gttcggccgg cgacgtgttc    7080
cccttcatcg gcctggcccg caccctgaag ttgcgcggcc accgcgtcag cctgtgcacc    7140
attccggtgt ttcgcgccgc ggtggagcag cacggcatcg agttcgtccc gctcagcgac    7200
gaactgacct accgccggac catgggcgac ccgcgcctgt gggatccgaa gacctcgttc    7260
ggagtgctct ggcaggccat cgccgggatg atcgagccgg tctacgagta cgtctgcgca    7320
```

-continued

```
cagcgccacg acgacatcgt ggtggtcggt tcgctgtggg ccctgggcgc gcggatcgcc    7380
catgagaaat acgggattcc ctacctgtcg gtgcaggtct cgccgtcgac cctgctgtcg    7440
gcgcacctgc cgccggtcca ccccaggttc aacgtgcccg agcaggtccc gctggcgatg    7500
cgcaagttgc tctggcgctg catcgaacgc ttcaagctgg accgcacctg cgccccggag    7560
atcaacgcgg tgcgccgcaa ggtcggcctg gtcggcccgg cgaagcgcat cttcacccag    7620
tggatgcatt cgccacaggg agtgctctgc ctgttcccgg cctggttcgc accgcccag    7680 caggactggc cgcaaccgct gcacatgacc ggcttccgc tgttcgacgg cagcgtcccg    7740
gggacccgcc tcgacgacga gttgcagcgc ttcctcgagc agggcagtcg gccgctggtg    7800
ttcacccagg gttcgaccga gcacctgcag ggagacttct atgccatggc cttgcgcgcg    7860
ctggagcgtc tcggcgcccg cggcatcttc ctcaccggcg ccggccagga gccgctgcgt    7920
ggcttgccga gccacgtgct gcaacgctcg tacgtgccgt tgggggcctt gctgccggcg    7980
tgcgccgggc tggtccaccc ggccggcatc ggcgccatga gcctggcgct ggcggcgggg    8040
gtgccgcagg tgctgctgcc ttgcgcccac gaccagttca caacgccga acgcctggtc    8100 cgcctcggct gcggtatccg cctgggcctg ccgctacgcg agcaggcgct gcgcgagtcg    8160 ctctggcgg tgctcgagga cccggcgctg gcggcggcct gtcggcgttt catggaattg    8220
tcacaaccgc acagtatcgc ttgcggtaaa gcggcccaag tggtcgaacg ttgtcatagg    8280
gagggggatg tgcgatggct gaaagccgcg tcctgagccg tgctggcaga attct          8335
```

<210> SEQ ID NO 68
<211> LENGTH: 1023
<212> TYPE: DNA
<213> ORGANISM: Pseudomonas aeruginosa

<400> SEQUENCE: 68

```
tctagatacg ggagaagaac gatcatggac cggatagaca tgggcgtgct ggtggtgctg      60
ttcaatcctg cgacgacga cctggaacac cttggcgaac tggcggcggc ctttccgcaa     120
ctgcgcttcc tcgccgtcga caactcgccg cacagcgatc cgcagcgcaa cgcccggctg     180
cgcgggcaag gcatcgccgt gctctaccac ggcaaccggc agggcatcgc cggcgccttc     240 aaccagggc tcgacacgct gttccggcgc ggcctgcagg tgtgctgct gctcgaccag     300 gactcccgtc ccgcggcgc cttcctcgcc gcccagtggc gcaacctgca ggcatgcaac     360
ggccaggcct gcctgctcgg cccacggatc ttcgaccggg gcgaccggcg cttcctgccg     420
gccatccacc tcgacgggct ggcgctcagg caactgtccc tggacggcct gacgacccca     480
cagcgcacct cgttcctgat ctcctccggc tgcctgctga cccgcgaggc ctaccagcgc     540
ctcggccact tcgacgagga actgttcatc gaccacgtgg acaccgagta cagcctgcgc     600
gcccaggcgc tggacgtgcc cctgtacgtc gacccgcggc tggtcctcga gcaccgcatc     660
ggcacgcgca agaccccgcg cctcggcggt tcagcctca gcgcgatgaa ccacgcccca     720
ctgcgccgct actacctggc gcgcaacggc ctgctggtcc tgcgccgcta cgcccggtcc     780
tcgccgctgg ccctgctggc gaacctgccg acctgaccc agggcctcgc ggtgctcctg     840
ctcgaacgcg acaagctgct caagctgcgc tgcctgggct ggggcctgtg gacggcctg     900 cggggcgcg gcggcgcgct ggagcgcaac cgcccgcgcc tgctgaagcg cctcgccggt     960
ccggcggtgg cgcccacagt tcccggcaag gccaaggcct agtcggcgaa acgcattgag    1020
ctc                                                                  1023
```

-continued

<210> SEQ ID NO 69
<211> LENGTH: 13768
<212> TYPE: DNA
<213> ORGANISM: Artificial Sequence
<220> FEATURE:
<223> OTHER INFORMATION: vector

<400> SEQUENCE: 69

| | | | | | |
|---|---|---|---|---|---|
| ctagaggtgg | acggccgcac | gtatgagcac | gcggtgacgc | aggtgctgca | ggccacgggg | 60 |
| gtgcggggga | ttctgctcgc | gccggatgcg | ccggatgcgc | cggcggcatc | ggacggggcg | 120 |
| gcgctgctca | agcgccgcta | cgtgccgctc | gcggcgttgc | tgccgcgctg | ccgggcgctg | 180 |
| gtgcaccacg | ggggatcgg | gacggcgtcg | ctcgcgtacg | cggcggggt | gccgcaggtg | 240 |
| gtgacgccgt | tcgcgcacga | ccagttcgac | aacgcgcagc | gggtggcggc | gagcggctgc | 300 |
| ggggtgcggc | tggacgcgcc | ggtgcgcggc | gagccgctcg | cgcgggcgct | ggcgcaggtg | 360 |
| ctgggcgacg | cggcgatggc | ggcgcgctgc | gcgcaggtgc | gcgcgcggat | ggcggcggag | 420 |
| ccgaacggct | gcgacgcggc | ggcgcgcttc | atcgagcgct | tcgcgcccgg | cgtcgcggcg | 480 |
| cggcgggcgc | agccggcatg | agcgcgcagg | cgatgtcggc | ggatcaggcg | ggcgttgcgc | 540 |
| cgccggcggc | cgccccgctg | cgcggcgcga | agctcgcgct | gctgacgttc | gcgctgtcgc | 600 |
| tcgcgacgtt | catcgaagtg | ctggattcga | cggtggcgaa | cgtggcggtg | ccggcgatct | 660 |
| cgggcagcct | cggggtgtcg | aacagccagg | gcacgtgggt | gatcagctcg | tactcggtgg | 720 |
| ccgcggcgat | cgcggtgccg | ctgacggggt | ggcttgcgcg | gcgcgtgggc | gagctgaggc | 780 |
| tgttcgtggc | gtcggtgatc | ctgttcacgc | tgacgtcgct | gctgtgcggg | ctcgcgcggg | 840 |
| acctggaggt | gctggttgcg | tgccgggcgc | tgcaggggct | gttctcgggg | ccgatggtgc | 900 |
| cgctgtcgca | gacgatcctg | atgcgcgcgt | tcccgccggc | gcggcgcacg | ctggcgctgg | 960 |
| cgctgtgggg | gatgacggtg | ctgctcgcgc | cgatcttcgg | gccggtggtg | ggcggctggc | 1020 |
| tgatcgacaa | cttctcgtgg | ccgtggatct | tcctgatcaa | cctgccgatc | gggctgttct | 1080 |
| cgttcgcggt | gtgcacgctg | atgctgcgcc | gcaggcgca | gcgcggcgag | gcgagcccga | 1140 |
| tcgacgcgcc | ggggatcgtg | ctgctggtga | tcgggtggg | ctcgctgcag | gcgatgctgg | 1200 |
| acctggggca | cgaccggggc | tggttcgatt | cgccgctgat | cacggcgctg | gcgatcgcgg | 1260 |
| cgggggtgtc | gctcgtgtcg | ctgctgatct | gggagctggg | cgaggcgcat | ccggtggtgg | 1320 |
| atctgagcct | gttccgggag | cggaccttca | cgttctgcgt | ggtgatcatc | tcgctgggga | 1380 |
| tgatgagctt | ctcggtggtg | ggggtggtgt | ttccgctgtg | gctgcaggcg | gtgatgggat | 1440 |
| acacggcgta | ccaggcgggg | ctggcgacg | cgtcgatggg | ggtgctggcg | ctggtgttct | 1500 |
| cgatcctggt | ggggctgtac | gcgagccggg | tggacgcgcg | ggtgctggtg | acgttcgggt | 1560 |
| tcggggtgtt | tgcggcggtg | atgtggtgga | gcacgcactt | cacgcgtgtcg | atgacgttcg | 1620 |
| cgcaggtggt | gacgccgcgg | ctgattcagg | ggatggggct | gccgtgcttc | ttcataccgc | 1680 |
| tgacggcggc | gacgctgtcg | cgggtgccgg | acgagaagct | ggcggcggcg | tcgagcctgt | 1740 |
| cgaacttcct | gcgacgctg | tcggcggcgt | tcggcacggc | gctgagcgtg | acgtggtggg | 1800 |
| acaaccgggc | gacgtaccac | tacgcggtgg | tgtcgcaatc | ggtgacgcgc | gcctcggaga | 1860 |
| acacgcagcg | gtacgtggac | gcgctgcacg | cgatgggcct | gcacgcgcg | cgggagctga | 1920 |
| gctcgctgca | ccaggtggtg | cggcagcagg | cgtacatgat | ggcgacgaac | gacatgttct | 1980 |
| acatggcgag | cgcgacgtgc | ctgctgctgg | cggggctgat | gtggctgacg | cggccgaagc | 2040 |
| ggggcgcggc | ggcggcgctc | gggcactgag | gcgaggcatg | tcgcgccccg | catgacgaag | 2100 |

```
gcgaaggaga aggggcgatgc gccgaagtcc tggggacgcg cgcgtcgat gcggcaacga    2160
agcgggcatt tcggcattcc gaaccaccaa agggaagagc gatgacgatc ctggggcgc     2220
tggtgttcgg gcggctggga tcgttcgacg atgcgcgcgc gggcgcggcg gcgcgcgagc    2280
cggtgcggca ggaatgaacg gaacgggccg cagcgggata ccggaaagca agaaggacgc    2340
atcatacgaa tgacgcagac agcaacgcaa gcagccactc gcgcgatgat cgcgacagga    2400
agccgcgcgg cgcggccggct cgcggcagcc gcgctcgcgt gggcgctcgc cggctgcgtg   2460
ccgtcgggct tcgagccggc gctcgcgccg cgcacgccgg gcgacgacgc gctcgcgcac    2520
acggcggggg gcgccgcgca cggcgcatgg ccgagcccg actgggtccg gcagctcggc     2580
gatccgcaac tcgacgcgct cgtcgacgag gcgctgcggc agaacccgac gctgcaggcc    2640
gcgcaggcgc gcatcggcgt cgcgcagtcg cagctcagc agttcgaatc gctgacgggg     2700
ctcaccgcga cggcgggcgc gtcgctctcc aaggcgcacg tgccgcgctc gggcggcacc    2760
atcaatacga cgttcaacgg cttgccggtg tcggtgccgc tcgtcggcga atcggtggtg    2820
tcgtcgtcgt cgctgttcgt cgggctgaac tatcagctgg acctgtgggg caagaacgcg    2880
gcggccacgc gcgggctgct gtcgatgcgc gatgcggccgc gcgtggaggc cgagcaggcg   2940
cggctcgcgc tgtcggtggc gatcgtgacg ctgtacggcg agctggaccg cgcgtatgcg    3000
ctgcgcgagc tgctgcagca gaagcgccgc gcgagcgagc aggtggagac ggtgctgcgc    3060
gagcgcgcg cgcgcgggat cgacaacggc tacgatgcgg acgacgcggc gctcaagcgg     3120
ggcaagctgc tcgagcagct cgcgctgacc gacgagcaga tccagttgca gaagctgcaa    3180
ctgggggtgc tgagcgggcg ggggccggag cgcgggctgt cgctcgcgcg gccgaagctc    3240
gcgccgctcg cggacgcgcc gctgccggcg cggctgccgg ccgggctgct ggggcggcgg    3300
ccggacatcg tcgcggcgcg gctgcgggtg gaggcggcgt acgcggcgat cgacggcacg    3360
cgcgcgtcgt tctacccgga cgtgaacctg gcggcgctgg gcgggctgtt cgcgctcacg    3420
ccggcgtcgc tgttcaagca cgatgcgctg gggggctcga tcggtccggc gctgtcgctg    3480
ccgatcttcg atcgcggccg gctgaaggcg aagctggggg gcgacgtggc gaacgcggac    3540
gtggcgctgc gcctgtacaa ccagacggtg gatgcgcgcg tgggcgaggt ggcgcggcag    3600
ttgacgtcgc tgtcgacggt ggatgcgctg ctcgaggcgc agcagcaggc ggtgcgctcg    3660
gcgcagcgga tggtggcgct ggcgcaggac cggcaccggc gggggatggg gatgcgcaag    3720
gacgtgaacg tggcgaagct gacgctgctg gacgagcgtg cgcacgtgat cgagctgcag    3780
gcgcggcggc ggacgctgcg ggtggggctg atcggggcgc tgggcggcgg cttcgacgcg    3840
cggccggcgg gcggcgcgcc gctcgcgcag ggcaagccgt tcgcggcggc gagcgacagg    3900
ccgcccgatt gagcggcacg cacgcatgcg gcccgaagcc accgacaccc gaagacaccg    3960
acaccaacgc caccttcacc gtgtacacga gcgattcaac cgacaccgcc cccgagcatc    4020
gaagcccgtc gggccgatcc gcgacggctt gcggccggc ccggccgttg ccggccggcg     4080
ccaccgacat cacgcacgcg aagaccttga acgataccgc caccgatacc ccgcgcgcga    4140
aggcgcccac cgatccggcc gcccttcgacg gcgcgcacgc gcagcccgtg ccggcgcacg    4200
agcgcggatc gcctccgccg ccggaagccg cggcgacgct cgccgcgcgc cgcgcgacgc    4260
gccgccggcg cttcgcgctg ttcttcgggc tgctggcgct ggccgcgctg accgcggggc    4320
tctactggtt cgtcgccggg cgcttcagcg aggagacgga cgacgcgtac gtggccggca    4380
acgtggtgca gatcgccgcg cagatccagg ggacggtgac cgacgtgctg gtggcggaca    4440
cgcagcaggt gaaggcgggg caggcgctgg tgaagctcga cgacgcggac gcgtcggcgg    4500
```

-continued

```
cgttcgcgca ggcgcgggcg cagctcgcgc aggcggtgcg gcaggtggcg aacacgcggc    4560
tctcgatggg gatgtacgag gagacggtga aggcgcgcga ggcggacctg aagcttgcgc    4620
agcaggcgta tccggaggaa ctggcgcggc gaaagtcgtc gctggcgaac gcgcaggcgg    4680
cgctggcggg ggcgcaggcg cagctggagg cggcgcgcgc gctgggcagc gagcggccgc    4740
tcgagcagaa cccggcggtg cagcaggcgg ccgcgcagtt caagctggcg taccggaacc    4800
tgaggcgcac gacgatcgtg tcgccggtgg acggcacggt cggtcagcgg tcggtgcaga    4860
tcggtcagca ggtggggccg ggggtgccgc tgatgtcggt ggtgcagttg cggcaggtgt    4920
gggtggaggc gaacttcaag gaagggcaga tccggcacat gcgggtgggc cagccggtgc    4980
ggctcgaatc ggacctgtac ggcgcgcggg tgacgtacca cggccgggtg gaggggggtct    5040 cggcgggcac gggcagcgcg ttctcgatgc tgccgtcgca gaacgcggcg gggaactgga    5100
tcaaggtggt gcagcgcctg ccggtggtga tctcgctgga gccgtcggag ctggcggcgc    5160
acccgctgcg ggtggggctg tcgatgcgcg cgacggtgga gacgaaggtg cgtggcggcc    5220
gcctgctcga cggcgacgcg ccgctgccgg ggctgcgcac gcgggtgcac gaagcgcagg    5280
cgggcgaggc cgaggccgcg gcttcggcag tgattcggga gaatgacggc cgcaggtgac    5340
gggcggttgc gggatcgctc tagagcggcc gccaccgcgg tggagctcca attcgcccta    5400
tagtgagtcg tattacgcgc gctcactggc cgtcgtttta caacgtcgtg actgggaaaa    5460
ccctggcgtt acccaactta atcgccttgc agcacatccc cctttcgcca gctggcgtaa    5520
tagcgaagag gcccgcaccg atcgcccttc ccaacagttg cgcagcctga atggcgaatg    5580
gaaattgtaa gcgttaatat tttgttaaaa ttcgcgttaa attttttgtta aatcagctca    5640 ttttttaacc aataggccga ctgcgatgag tggcagggcg gggcgtaatt ttttaaggc     5700 agttattggt gcccttaaac gcctggtgct acgcctgaat aagtgataat aagcggatga    5760
atggcagaaa ttcgaaagca aattcgaccc ggtcgtcggt tcagggcagg gtcgttaaat    5820
agccgcttat gtctattgct ggtttaccgg tttattgact accggaagca gtgtgaccgt    5880
gtgcttctca aatgcctgag gccagtttgc tcaggctctc cccgtggagg taataattga    5940
cgatatgatc atttattctg cctcccagag cctgataaaa acggtgaatc cgttagcgag    6000
gtgccgccgg cttccattca ggtcgaggtg gcccggctcc atgcaccgcg acgcaacgcg    6060
gggaggcaga caaggtatag ggcggcgagg cggctacagc cgatagtctg aacagcgca    6120 cttacgggtt gctgcgcaac ccaagtgcta ccggcgcggc agcgtgaccc gtgtcggcgg    6180
ctccaacggc tcgccatcgt ccagaaaaca cggctcatcg ggcatcggca ggcgctgctg    6240
cccgcgccgt tcccattcct ccgtttcggt caaggctggc aggtctggtt ccatgcccgg    6300
aatgccgggc tggctgggcg gctcctcgcc ggggccggtc ggtagttgct gctcgcccgg    6360
atacagggtc gggatgcggc gcaggtcgcc atgccccaac agcgattcgt cctggtcgtc    6420
gtgatcaacc accacggcgg cactgaacac cgacaggcgc aactggtcgc ggggctggcc    6480
ccacgccacg cggtcattga ccacgtaggc cgacacggtg ccggggccgt tgagcttcac    6540
gacggagatc cagcgctcgg ccaccaagtc cttgactgcg tattggaccg tccgcaaaga    6600
acgtccgatg agcttggaaa gtgtcttctg gctgaccacc acggcgttct ggtggcccat    6660
ctgcgccacg aggtgatgca gcagcattgc cgccgtgggt ttcctcgcaa taagcccggc    6720
ccacgcctca tgcgctttgc gttccgtttg cacccagtga ccgggcttgt tcttggcttg    6780
aatgccgatt tctctggact gcgtggccat gcttatctcc atgcggtagg gtgccgcacg    6840
```

```
gttgcggcac catgcgcaat cagctgcaac ttttcggcag cgcgacaaca attatgcgtt    6900
gcgtaaaagt ggcagtcaat tacagatttt ctttaaccta cgcaatgagc tattgcgggg    6960
ggtgccgcaa tgagctgttg cgtaccccccc tttttaagt tgttgatttt taagtctttc    7020
gcatttcgcc ctatatctag ttctttggtg cccaaagaag ggcacccctg cggggttccc    7080
ccacgccttc ggcgcggctc cccctccggc aaaaagtggc ccctccgggg cttgttgatc    7140
gactgcgcgg ccttcggcct tgcccaaggt ggcgctgccc ccttggaacc cccgcactcg    7200
ccgccgtgag gctcgggggg caggcgggcg ggcttcgcct tcgactgccc ccactcgcat    7260
aggcttgggt cgttccaggc gcgtcaaggc caagccgctg cgcggtcgct gcgcgagcct    7320
tgacccgcct tccacttggt gtccaaccgg caagcgaagc gcgcaggccg caggccggag    7380
gcttttcccc agagaaaatt aaaaaaattg atggggcaag gccgcaggcc gcgcagttgg    7440
agccggtggg tatgtggtcg aaggctgggt agccggtggg caatcccttgt ggtcaagctc    7500
gtgggcaggc gcagcctgtc catcagcttg tccagcaggg ttgtccacgg gccgagcgaa    7560
gcgagccagc cggtggccgc tcgcggccat cgtccacata tccacgggct ggcaaggggag    7620
cgcagcgacc gcgcagggcg aagcccggag agcaagcccg tagggcgccg cagccgccgt    7680
aggcggtcac gactttgcga agcaaagtct agtgagtata ctcaagcatt gagtggcccg    7740
ccggaggcac cgccttgcgc tgcccccgtc gagccggttg gacaccaaaa gggaggggca    7800
ggcatggcgg catacgcgat catgcgatgc aagaagctgg cgaaaatggg caacgtggcg    7860
gccagtctca gcacgccta ccgcgagcgc gagacgccca acgctgacgc cagcaggacg    7920
ccagagaacg agcactgggc ggccagcagc accgatgaag cgatgggccg actgcgcgag    7980
ttgctgccag agaagcggcg caaggacgct gtgttggcgg tcgagtacgt catgacggcc    8040
agcccggaat ggtggaagtc ggccagccaa gaacagcagg cggcgttctt cgagaaggcg    8100
cacaagtggc tggcggacaa gtacggggcg gatcgcatcg tgacggccag catccaccgt    8160
gacgaaacca gcccgcacat gaccgcgttc gtggtgccgc tgacgcagga cggcaggctg    8220
tcggccaagg agttcatcgg caacaaagcg cagatgaccc gcgaccagac cacgtttgcg    8280
gccgctgtgg ccgatctagg gctgcaacgg ggcatcgagg gcagcaaggc acgtcacacg    8340
cgcattcagg cgttctacga ggccctggag cggccaccag tgggccacgt caccatcagc    8400
ccgcaagcgg tcgagccacg cgcctatgca ccgcagggat tggccgaaaa gctgggaatc    8460
tcaaagcgcg ttgagacgcc ggaagccgtg gccgaccggc tgacaaaagc ggttcggcag    8520
gggtatgagc ctgccctaca ggccgccgca ggagcgcgtg agatgcgcaa gaaggccgat    8580
caagcccaag agacggcccg agaccttcgg gagcgcctga gcccgttcct ggacgccctg    8640
gggccgttga atcgggatat gcaggccaag gccgccgcga tcatcaaggc cgtgggcgaa    8700
aagctgctga cggaacagcg ggaagtccag cgccagaaac aggcccagcg ccagcaggaa    8760
cgcgggcgcg cacatttccc cgaaaagtgc cacctgggat gaatgtcagc tactgggcta    8820
tctggacaag ggaaaacgca agcgcaaaga gaaagcaggt agcttgcagt gggcttacat    8880
ggcgatagct agactgggcg gttttatgga cagcaagcga accggaattg ccagctgggg    8940
cgccctctgg taaggttggg aagccctgca aagtaaactg gatggctttc ttgccgccaa    9000
ggatctgatg gcgcagggga tcaagatctg atcaagagac aggatgagga tcgtttcgca    9060
tgattgaaca agatggattg cacgcaggtt ctccggccgc ttgggtggag aggctattcg    9120
gctatgactg ggcacaacag acaatcggct gctctgatgc cgccgtgttc cggctgtcag    9180
cgcaggggcg cccggttctt tttgtcaaga ccgacctgtc cggtgccctg aatgaactgc    9240
```

-continued

```
aggacgaggc agcgcggcta tcgtggctgg ccacgacggg cgttccttgc gcagctgtgc    9300
tcgacgttgt cactgaagcg ggaagggact ggctgctatt gggcgaagtg ccggggcagg    9360
atctcctgtc atctcacctt gctcctgccg agaaagtatc catcatggct gatgcaatgc    9420
ggcggctgca tacgcttgat ccggctacct gcccattcga ccaccaagcg aaacatcgca    9480
tcgagcgagc acgtactcgg atggaagccg tcttgtcga tcaggatgat ctggacgaag     9540
agcatcaggg gctcgcgcca gccgaactgt tcgccaggct caaggcgcgc atgcccgacg    9600
gcgaggatct cgtcgtgacc catggcgatg cctgcttgcc gaatatcatg gtggaaaatg    9660
gccgcttttc tggattcatc gactgtggcc ggctgggtgt ggcggaccgc tatcaggaca    9720
tagcgttggc tacccgtgat attgctgaag agcttggcgg cgaatgggct gaccgcttcc    9780
tcgtgcttta cggtatcgcc gctcccgatt cgcagcgcat cgccttctat cgccttcttg    9840
acgagttctt ctgagcggga ctctggggtt cgaaatgacc gaccaagcga cgcccaacct    9900
gccatcacga gatttcgatt ccaccgccgc cttctatgaa aggttgggct tcggaatcgt    9960
tttccgggac gccggctgga tgatcctcca gcgcgggat ctcatgctgg agttcttcgc    10020 ccaccccat gggcaaatat tatacgcaag gcgacaaggt gctgatgccg ctggcgattc    10080
aggttcatca tgccgtttgt gatggcttcc atgtcggcag aatgcttaat gaattacaac    10140
agtttttatg catgcgccca atacgcaaac cgctctcccc cgcgcgttgg ccgattcatt    10200
aatgcagctg gcacgacagg tttcccgact ggaaagcggg cagtgagcgc aacgcaatta    10260
atgtgagtta gctcactcat taggcacccc aggctttaca ctttatgctt ccggctcgta    10320
tgttgtgtgg aattgtgagc ggataacaat ttcacacagg aaacagctat gaccatgatt    10380
acgccaagcg cgcaattaac cctcactaaa gggaacaaaa gctgggtacc gggcccccc     10440 tcgaggtcga cggtatcgat aagcttgata tcgaattcct gcagcccggg ggatctggca    10500
tttttgggag gtgtgaaatg cggcgcgaaa gtctgttggt atcggtttgc aagggcctgc    10560
gggtacatgt cgagcgcgtt gggcaggatc ccgggcgcag cacggtgatg ctggtcaacg    10620
gcgcgatggc gaccaccgcc tcgttcgccc ggacctgcaa gtgcctggcc gaacatttca    10680
acgtggtgct gttcgacctg cccttcgccg ggcagtcgcg tcagcacaac ccgcagcggg    10740
ggttgatcac caaggacgac gaggtggaaa tcctcctggc gctgatcgag cgcttcgagg    10800
tcaatcacct ggtctccgcg tcctgggcg gtatctccac gctgctggcg ctgtcgcgca    10860
atccgcgcgg catccgcagc tcggtggtga tggcattcgc ccctggactg aaccaggcga    10920
tgctcgacta cgtcgggcgg gcgcaggcgc tgatcgagct ggacgacaag tcggcgatcg    10980
gccatctgct caacgagacc gtcggcaaat acctgccgcc gcgcctgaaa gccagcaacc    11040
atcagcacat ggcttcgctg gccaccgcg aatacgagca ggcgcgcttt cacatcgacc     11100
aggtgctggc gctcaacgat cggggctacc tggcttgcct ggagcggatc cagagccacg    11160
tgcatttcat caacgcgagc tgggacgaat acaccaccgc cgaggacgcc cgccagttcc    11220
gcgactacct gccgcactgc agtttctcgc gggtggaggg caccgggcat ttcctcgacc    11280
tggagtccaa gctggccgcg gtacgcgtgc accgcgccct gctcgagcac ctgctgaagc    11340
aaccggagcc gcagcgggcg gaacgcgcgg cgggattcca cgagatggcc atcggctacg    11400
cctgaaccct tgacctgcga agacccggcc tggccgggct ttgcggttgc ataacgcacg    11460
gagtagcacc atgcacgcca tcctcatcgc catcggctcg gccggcgacg tatttcccctt    11520 catcggcctg gcccggaccc tgaaattgcg cgggcaccgc gtgagcctct gcaccatccc    11580
```

```
ggtgtttcgc gacgcggtgg agcagcacgg catcgcgttc gtcccgctga gcgacgaact    11640
gacctaccgc cggaccatgg gcgatccgcg cctgtgggac cccaagacgt ccttcggcgt    11700
gctctggcaa accatcgccg ggatgatcga gccggtctac gagtacgtct cggcgcagcg    11760
ccatgacgac atcgtggtgg tcggctcgct ctgggcgctg gcgcacgca tcgctcacga    11820
gaagtacggg attccctacc tgtccgcgca ggtctcgcca tcgaccttgt tgtcggcgca    11880
cctgccgccg gtacacccca agttcaacgt gcccgagcag atgccgctgg cgatgcgcaa    11940
gctgctctgg cgctgcatcg agcgcttcaa gctggatcgc acctgcgcgc cggatatcaa    12000
cgcggtgcgg cgcaaggtcg gcctggagac gccggtgaag cgcatcttca cccaatggat    12060
gcattcgccg cagggcgtgg tctgcctgtt cccggcctgg ttcgcgccgc cccagcagga    12120
ttggccgcaa ccctgcaca tgaccggctt cccgctgttc gacggcagta tcccggggac    12180
cccgctcgac gacgaactgc aacgctttct cgatcagggc agccggccgc tggtgttcac    12240
ccagggctcg accgaacacc tgcagggcga cttctacgcc atgggcctgc gcgcgctgga    12300
acgcctcggc gcgcgtggga tcttcctcac cggcgccggc caggaaccgc tgcgcggctt    12360
gccgaaccac gtgctgcagc gcgcctacgc gccactggga gccttgctgc catcgtgcgc    12420
cgggctggtc catccgggcg gtatcggcgc catgagcctg gccttggcgg cggggggtgcc    12480
gcaggtgctg ctgccctgcg cccacgacca gttcgacaat gccgaacggc tggtccggct    12540
cggctgcggg atgcgcctgg gcgtgccatt gcgcgagcag gagttgcgcg gggcgctgtg    12600
gcgcttgctc gaggacccgg ccatggcggc ggcctgtcgg cgtttcatgg aattgtcaca    12660
accgcacagt atcgcttgcg gtaaagcggc ccaggtggtc gaacgttgtc atagggaggg    12720
ggatgcgcga tggctgaagg ctgcgtcctg acctacggga gaagaacgat catggaccgg    12780
atagacatgg gcgtgctggt ggtactgttc aatcctggcg acgacgacct ggaacacctt    12840
ggcgaactgg cggcggcgtt tccgcaactg cgcttccttg ccgtcgacaa ctcaccgcac    12900
agcgatccgc agcgcaatgc ccggctgcgc gggcaaggca tcgccgtgct gcaccacggc    12960
aaccggcagg gcatcgccgg cgccttcaac cagggactcg acgcgctatt ccggcgtggc    13020
gtgcagggtg tgctgctgct cgaccaggac tcccgtcccg gcggcgcctt cctgccgcc    13080
cagtggcgca acctgcaggc gcgcaacggt caggcctgcc tgctcggccc acggatcttc    13140
gaccggggtg accggcgctt cctgccggcc atccatctcg acggactgac gctcaggcaa    13200
ttgtctctgg acggcctgac gaccccgcag cgcacctcgt tcctgatctc ctccggctgc    13260
ctgctgacc gcgaggccta ccagcgcctc ggccacttcg acgaggaact gttcatcgac    13320
cacgtggaca ccgaatacag cctgcgcgcc caggcgctgg acgtgcccct gtacgtcgac    13380
ccgcggctgg tcctcgagca ccgcatcggc acgcgcaaga cccgccgcct cggcggtctc    13440
agcctcagcg cgatgaacca cgccccgctg cgccgctact acctggcgcg caacggcctg    13500
ctggtcctgc gccgctacgc ccggtcctcg ccgctggccc tgctggcgaa cctgccgacc    13560
ctgacccagg gcctcgcggt gctcctgctc gaacgcgaca agctgctcaa gctgcgctgc    13620
ctgggctggg gcctgtggga cggcctgcgg ggacgcggcg gcgcgctgga gaccaaccgc    13680
ccgcgcctgc tgaagcgcct cgccggcccg gcgtggcgt ccgtagcttc cggcaaggcc    13740
aaggcctagt cggcgaaacg cattccct                                       13768
```

<210> SEQ ID NO 70
<211> LENGTH: 5365
<212> TYPE: DNA
<213> ORGANISM: Artificial Sequence
<220> FEATURE:
<223> OTHER INFORMATION: synth operon

<400> SEQUENCE: 70

```
tctagaggtg gacggccgca cgtatgagca cgcggtgacg caggtgctgc aggccacggg      60
ggtgcggggg attctgctcg cgccggatgc gccggatgcg ccggcggcat cggacggggc     120
ggcgctgctc aagcgccgct acgtgccgct cgcggcgttg ctgccgcgct gccgggcgct     180
ggtgcaccac gggggatcg ggacggcgtc gctcgcgtac gcggcggggg tgccgcaggt     240
ggtgacgccg ttcgcgcacg accagttcga caacgcgcag cgggtggcgg cgagcggctg     300
cggggtgcgg ctggacgcgc cggtgcgcgg cgagccgctc gcgcgggcgc tggcgcaggt     360
gctgggcgac gcggcgatgg cggcgcgctg cgcgcaggtg cgcgcgcgga tggcggcgga     420
gccgaacggg tgcgacgcgg cggcgcgctt catcgagcgc ttcgcgccgg gcgtcgcggc     480
gcggcgggcg cagccggcat gagcgcgcag gcgatgtcgg cggatcaggc gggcgttgcg     540
ccgccggcgg ccgccccgct gcgcggcgcg aagctcgcgc tgctgacgtt cgcgctgtcg     600
ctcgcgacgt tcatcgaagt gctggattcg acggtggcga acgtggcggt gccggcgatc     660
tcgggcagcc tcggggtgtc gaacagccag ggcacgtggg tgatcagctc gtactcggtg     720
gccgcggcga tcgcggtgcc gctgacgggg tggcttgcgc ggcgcgtggg cgagctgagg     780
ctgttcgtgg cgtcggtgat cctgttcacg ctgacgtcgc tgctgtgcgg gctcgcgcgg     840
gacctggagg tgctggttgc gtgccgggcg ctgcaggggc tgttctcggg gccgatggtg     900
ccgctgtcgc agacgatcct gatgcgcgcg ttcccgccgg cgcggcgcac gctggcgctg     960
gcgctgtggg ggatgacggt gctgctcgcg ccgatcttcg ggccggtggt gggcggctgg    1020
ctgatcgaca acttctcgtg gccgtggatc ttcctgatca acctgccgat cgggctgttc    1080
tcgttcgcgg tgtgcacgct gatgctgcgc ccgcaggcgc agcgcggcga ggcgagcccg    1140
atcgacgcgc cggggatcgt gctgctggtg atcggggtgg gctcgctgca ggcgatgctg    1200
gacctggggc acgaccgggg ctggttcgat tcgccgctga tcacggcgct ggcgatcgcg    1260
gcggggtgt cgctcgtgtc gctgctgatc tgggagctgg gcgaggcgca tccggtggtg    1320
gatctgagcc tgttccggga gcggaccttc acgttctgcg tggtgatcat ctcgctgggg    1380
atgatgagct tctcggtggt gggggtggtg tttccgctgt ggctgcaggc ggtgatggga    1440
tacacggcgt accaggcggg gctggcgacg cgtcgatgg gggtgctggc gctggtgttc    1500
tcgatcctgg tggggctgta cgcgagccgg gtggacgcgc gggtgctggt gacgttcggg    1560
ttcggggtgt ttgcggcggt gatgtggtgg agcacgcact tcacgctgtc gatgacgttc    1620
gcgcaggtgg tgacgccgcg gctgattcag gggatggggc tgccgtgctt cttcataccg    1680
ctgacgcgcg cgacgctgtc gcgggtgccg gacgagaagc tggcggcggc gtcgagcctg    1740
tcgaacttcc tgcggacgct gtcggcggcg ttcggcacgg cgctgagcgt gacgtggtgg    1800
gacaaccggg cgacgtacca ctacgcgtg gtgtcgcaat cggtgacgcg cgcctcggag    1860
aacacgcagc ggtacgtgga cgcgctgcac gcgatggggc tgcacggcgc gcgggagctg    1920
agctcgctgc accaggtggt gcggcagcag gcgtacatga tggcgacgaa cgacatgttc    1980
tacatggcga gcgcgacgtg cctgctgctg gcggggctga tgtggctgac gcggccgaag    2040
cggggcgcgg cggcggcgct cgggcactga ggcgaggcat gtcgcgcccc gcatgacgaa    2100
ggcgaaggag aagggcgatg cgccgaagtc ctggggacgc ggcgcgtcga tgcggcaacg    2160
aagcgggcat ttcggcattc cgaaccacca aagggaagag cgatgacgat cctgggggcg    2220
```

```
ctggtgttcg gcggctggg atcgttcgac gatgcgcgcg cgggcgcggc ggcgcgcgag      2280
ccggtgcggc aggaatgaac ggaacgggcc gcagcgggat accggaaagc aagaaggacg      2340
catcatacga atgacgcaga cagcaacgca agcagccact cgcgcgatga tcgcgacagg      2400
aagccgcgcg gcgcgccggc tcgcggcagc cgcgctcgcg tgggcgctcg ccggctgcgt      2460
gccgtcgggc ttcgagccgg cgctcgcgcc gcgcacgccg ggcgacgacg cgctcgcgca      2520
cacggcgggg ggcgccgcgc acggcgcatg gccgagcccc gactgggtcc ggcagctcgg      2580
cgatccgcaa ctcgacgcgc tcgtcgacga ggcgctgcgg cagaacccga cgctgcaggc      2640
cgcgcaggcg cgcatcggcg tcgcgcagtc gcagctgcag cagttcgaat cgctgacggg      2700
gctcaccgcg acggcgggcg cgtcgctctc caaggcgcac gtgccgcgct cgggcggcac      2760
catcaatacg acgttcaacg gcttgccggt gtcggtgccg ctcgtcggcg aatcggtggt      2820
gtcgtcgtcg tcgctgttcg tcgggctgaa ctatcagctg gacctgtggg gcaagaacgc      2880
ggcggccacg cgcgggctgc tgtcgatgcg cgatgcggcg cgcgtggagg ccgagcaggc      2940
gcggctcgcg ctgtcggtgg cgatcgtgac gctgtacggc gagctggacc gcgcgtatgc      3000
gctgcgcgag ctgctgcagc agaagcgccg cgcgagcgag caggtggaga cggtgctgcg      3060
cgagcgcgcg gcgcgcggga tcgacaacgg ctacgatgcg gacgacgcgg cgctcaagcg      3120
gggcaagctg ctcgagcagc tcgcgctgac cgacgagcag atccagttgc agaagctgca      3180
actggggggtg ctgagcgggc gggggccgga gcgcgggctg tcgctcgcgc ggccgaagct      3240
cgcgccgctc gcggacgcgc cgctgccggc gcggctgccg gccgggctgc tggggcggcg      3300
gccggacatc gtcgcggcgc ggctgcgggt ggaggcggcg tacgcggcga tcgacggcac      3360
gcgcgcgtcg ttctacccgg acgtgaacct ggcggcgctg ggcgggctgt tcgcgctcac      3420
gccggcgtcg ctgttcaagc acgatgcgct gggggggctcg atcggtccgg cgctgtcgct      3480
gccgatcttc gatcgcggcc ggctgaaggc gaagctgggg ggcgacgtgg cgaacgcgga      3540
cgtggcgctg cgcgctgtaca accagacggt ggatgcggcg ctgggcgagg tggcgcggca      3600
gttgacgtcg ctgtcgacgg tggatgcgct gctcgaggcg cagcagcagg cggtgcgctc      3660
ggcgcagcgc atggtggcgc tggcgcagga ccggcaccgg cggggatgg ggatgcgcaa      3720
ggacgtgaac gtggcgaagc tgacgctgct ggacgagcgt gcgcacgtga tcgagctgca      3780
ggcgcggcgc cggacgctgc gggtgggggct gatcggggcg ctgggcggcg gcttcgacgc      3840
gcggccggcg ggcggcgcgc cgctcgcgca gggcaagccg ttcgcggcgg cgagcgacag      3900
gccgcccgat tgagcggcac gcacgcatgc ggcccgaagc caccgacacc cgaagacacc      3960
gacaccaacg ccaccttcac cgtgtacacg agcgattcaa ccgacaccgc ccccgagcat      4020
cgaagcccgt cgggccgatc cgcgacggct tgcgggccgg cccggccgtt gccggccggc      4080
gccaccgaca tcacgcacgc gaagaccttg aacgataccg ccaccgatac cccgcgcgcg      4140
aaggcgccca ccgatccggc cgccctcgac ggcgcgcacg cgcagcccgt gccggcgcac      4200
gagcgcggat cgcctccgcc gccggaagcc gcggcgacgc tcgccgcgcg ccgcgcgacg      4260
cgccgccggc gcttcgcgct gttcttcggg ctgctggcgc tggccgcgct gaccgcgggg      4320
ctctactggt tcgtcgccgg gcgcttcagc gaggagacgg acgacgcgta cgtgccggc       4380
aacgtggtgc agatcgccgc gcagatccag gggacggtga ccgacgtgct ggtggcggac      4440
acgcagcagg tgaaggcggg gcaggcgctg tgaagctcg acgacgcgga cgcgtcggcg      4500
gcgttcgcgc aggcgcgggc gcagctcgcg caggcggtgc ggcaggtggc gaacacgcgg      4560
ctctcgatgg ggatgtacga ggagacggtg aaggcgcgcg aggcggacct gaagcttgcg      4620
```

```
cagcaggcgt atccggagga actggcgcgg cgaaagtcgt cgctggcgaa cgcgcaggcg    4680
gcgctggcgg gggcgcaggc gcagctggag gcggcgcgcg cgctgggcag cgagcggccg    4740
gtcgagcaga acccggcggt gcagcaggcg gccgcgcagt tcaagctggc gtaccggaac    4800
ctgaggcgca cgacgatcgt gtcgccggtg gacggcacgg tcggtcagcg gtcggtgcag    4860
atcggtcagc aggtgggggcc gggggtgccg ctgatgtcgg tggtgcagtt gcggcaggtg    4920
tgggtggagg cgaacttcaa ggaagggcag atccggcaca tgcgggtggg ccagccggtg    4980
cggctcgaat cggacctgta cggcgcgcgg gtgacgtacc acggccgggt ggaggggggtc    5040 tcggcgggca cgggcagcgc gttctcgatg ctgccgtcgc agaacgcggc ggggaactgg    5100
atcaaggtgg tgcagcgcct gccggtggtg atctcgctgg agccgtcgga gctggcggcg    5160
cacccgctgc gggtggggct gtcgatgcgc gcgacggtgg agacgaaggt gcgtggcggc    5220
cgcctgctcg acggcgacgc gccgctgccg gggctgcgca cgcgggtgca cgaagcgcag    5280
gcgggcgagg ccgaggccgc ggcttcggca gtgattcggg agaatgacgg ccgcaggtga    5340
cgggcggttg cgggatcgct ctaga                                         5365

<210> SEQ ID NO 71
<211> LENGTH: 34
<212> TYPE: DNA
<213> ORGANISM: Artificial Sequence
<220> FEATURE:
<223> OTHER INFORMATION: primer

<400> SEQUENCE: 71
tatatataac cggtattaat gcagctggca cgac                               34

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
ggccgaccgg tactagtgga                                               20

<210> SEQ ID NO 73
<211> LENGTH: 11960
<212> TYPE: DNA
<213> ORGANISM: Artificial Sequence
<220> FEATURE:
<223> OTHER INFORMATION: vector

<400> SEQUENCE: 73
accttcggga gcgcctgaag cccgttctgg acgccctggg gccgttgaat cgggatatgc    60
aggccaaggc cgccgcgatc atcaaggccg tgggcgaaaa gctgctgacg gaacagcggg    120
aagtccagcg ccagaaacag gcccagcgcc agcaggaacg cgggcgcgca catttccccg    180
aaaagtgcca cctgggatga atgtcagcta ctgggctatc tggacaaggg aaaacgcaag    240
cgcaaagaga aagcaggtag cttgcagtgg gcttacatgg cgatagctag actgggcggt    300
tttatggaca gcaagcgaac cggaattgcc agctggggcg ccctctggta aggttgggaa    360
gccctgcaaa gtaaactgga tggctttctt gccgccaagg atctgatggc gcaggggatc    420
aagatctgat caagagacag gatgaggatc gtttcgcatg attgaacaag atggattgca    480
cgcaggttct ccggccgctt gggtggagag gctattcggc tatgactggg cacaacagac    540
```

```
aatcggctgc tctgatgccg ccgtgttccg gctgtcagcg caggggcgcc cggttctttt    600
tgtcaagacc gacctgtccg gtgccctgaa tgaactgcag gacgaggcag cgcggctatc    660
gtggctggcc acgacgggcg ttccttgcgc agctgtgctc gacgttgtca ctgaagcggg    720
aagggactgg ctgctattgg gcgaagtgcc ggggcaggat ctcctgtcat ctcaccttgc    780
tcctgccgag aaagtatcca tcatggctga tgcaatgcgg cggctgcata cgcttgatcc    840
ggctacctgc ccattcgacc accaagcgaa acatcgcatc gagcgagcac gtactcggat    900
ggaagccggt cttgtcgatc aggatgatct ggacgaagag catcaggggc tcgcgccagc    960
cgaactgttc gccaggctca aggcgcgcat gcccgacggc gaggatctcg tcgtgaccca   1020
tggcgatgcc tgcttgccga atatcatggt ggaaaatggc cgcttttctg gattcatcga   1080
ctgtggccgg ctgggtgtgg cggaccgcta tcaggacata gcgttggcta cccgtgatat   1140
tgctgaagag cttggcggcg aatgggctga ccgcttcctc gtgctttacg gtatcgccgc   1200
tcccgattcg cagcgcatcg ccttctatcg ccttcttgac gagttcttct gagcgggact   1260
ctggggttcg aaatgaccga ccaagcgacg cccaacctgc catcacgaga tttcgattcc   1320
accgccgcct tctatgaaag gttgggcttc ggaatcgttt tccgggacgc cggctggatg   1380
atcctccagc gcggggatct catgctggag ttcttcgccc accccatgg gcaaatatta   1440
tacgcaaggc gacaaggtgc tgatgccgct ggcgattcag gttcatcatg ccgtttgtga   1500
tggcttccat gtcggcagaa tgcttaatga attacaacag ttttatgca tgcgcccaat    1560
acgcaaaccg cctctccccg cgcgttggcc gattcattaa tgcagctggc acgacaggtt   1620
tcccgactgg aaagcgggca gtgagcgcaa cgcaattaat gtgagttagc tcactcatta   1680
ggcaccccag gctttacact ttatgcttcc ggctcgtatg ttgtgtggaa ttgtgagcgg   1740
ataacaattt cacacaggaa acagctatga ccatgattac gccaagcgcg caattaaccc   1800
tcactaaagg gaacaaaagc tgggtaccgg gccccccctc gaggtcgacg gtatcgataa   1860
gctttgggag gtgtgaaatg cggcgcgaaa gtctgttggt atcggtttgc aagggcctgc   1920
gggtacatgt cgagcgcgtt gggcaggatc ccgggcgcag cacggtgatg ctggtcaacg   1980
gcgcgatggc gaccaccgcc tcgttcgccc ggacctgcaa gtgcctggcc gaacatttca   2040
acgtggtgct gttcgacctg cccttcgccg gcagtcgcg tcagcacaac ccgcagcgcg    2100
ggttgatcac caaggacgac gaggtggaaa tcctcctggc gctgatcgag cgcttcgagg   2160
tcaatcacct ggtctccgcg tcctggggcg gtatctccac gctgctggcg ctgtcgcgca   2220
atccgcgcgg catccgcagc tcggtggtga tggcattcgc ccctggactg aaccaggcga   2280
tgctcgacta cgtcgggcgg gcgcaggcgc tgatcgagct ggacgacaag tcggcgatcg   2340
gccatctgct caacgagacc gtcggcaaat acctgccgca gcgcctgaaa gccagcaacc   2400
atcagcacat ggcttcgctg ccaccggcg aatacgagca ggcgcgcttt cacatcgacc    2460
aggtgctggc gctcaacgat cggggctact ggcttgcct ggagcggatc cagagccacg    2520
tgcatttcat caacggcagc tgggacgaat acaccaccgc cgaggacgcc cgccagttcc   2580
gcgactacct gccgcactgc agtttctcgc gggtggaggg caccgggcat ttcctcgacc   2640
tggagtccaa gctggcagcg gtacgcgtgc accgcgccct gctcgagcac ctgctgaagc   2700
aaccggagcc gcagcgggcg gaacgcgcgg cgggattcca cgagatggcc atcggctacg   2760
cctgaaccct tgacctgcga agacccggcc tggccgggct ttgcggttgc ataacgcacg   2820
gagtagcccc atgcacgcca tcctcatcgc catcggctcg gccggcgacg tatttcccctt   2880
catcggcctg gcccggaccc tgaaactgcg cgggcaccgc gtgagcctct gcaccatccc   2940
```

```
ggtgtttcgc gacgcggtgg agcagcacgg catcgcgttc gtcccgctga gcgacgaact   3000
gacctaccgc cggaccatgg gcgatccgcg cctgtgggac cccaagacgt ccttcggcgt   3060
gctctggcaa gccatcgccg ggatgatcga gccggtctac gagtacgtct cggcgcagcg   3120
ccatgacgac atcgtggtgg tcggctcgct atgggcgctg ggcgcacgca tcgctcacga   3180
gaagtacggg attccctacc tgtccgcgca ggtctcgcca tcgaccctgt tgtcggcgca   3240
cctgccgccg gtacacccca agttcaacgt gcccgagcag atgccgctgg cgatgcgcaa   3300
gctgctctgg cgctgcatcg agcgcttcaa gctggatcgc acctgcgcgc cggagatcaa   3360
cgcggtgcgc cgcaaggtcg gcctggaaac gccggtgaag cgcatcttca cccaatggat   3420
gcattcgccg cagggcgtgg tctgcctgtt cccggcctgg ttcgcgccgc cccagcagga   3480
ttggccgcaa cccctgcaca tgaccggctt ccgctgttc gacggcagta tcccggggac   3540
cccgctcgac gacgaactgc aacgctttct cgatcagggc agccggccgc tggtgttcac   3600
ccagggctcg accgaacacc tgcagggcga cttctacgcc atgggcctgc gcgcgctgga   3660
acgcctcggc gcgcgtggga tcttcctcac cggcgccggc caggaaccgc tgcgcggctt   3720
gccgaaccac gtgctgcagc gcgcctacgc gccactggga gccttgctgc atcgtgcgc   3780 cgggctggtc catccgggcg gtatcggcgc catgagccta gccttggcgg cggggtgcc   3840 gcaggtgctg ctgccctgtg cccacgacca gttcgacaat gccgaacggc tggtccggct   3900
cggctgcggg atgcgcctgg gcgtgccgtt gcgcgagcag gagttgcgcg ggcgctgtg   3960 gcgcttgctc gaggacccgg ccatggcggc ggcctgtcgg cgtttcatgg aattgtcaca   4020
accgcacagt atcgcttgcg gtaaagcggc ccaggtggtc gaacgttgtc atagggaggg   4080
ggatgctcga tggctgaagg ctgcgtcctg aacggtgctg gcataacagt ctagagcggc   4140
cgccaccgcg gtggagctcc aattcgccct atagtgagtc gtattacgcg cgctcactgg   4200
ccgtcgtttt acaacgtcgt gactgggaaa accctggcgt tacccaactt aatcgccttg   4260
cagcacatcc cccttcgcc agctggcgta atagcgaaga ggcccgcacc gatcgccctt   4320
cccaacagtt gcgcagcctg aatggcgaat ggaaattgta agcgttaata ttttgttaaa   4380
attcgcgtta aatttttgtt aaatcagctc attttttaac caataggccg actgcgatga   4440
gtggcagggc ggggcgtaat tttttaagg cagttattgg tgcccttaaa cgcctggtgc   4500
tacgcctgaa taagtgataa taagcggatg aatggcagaa attcgaaagc aaattcgacc   4560
cggtcgtcgg ttcagggcag ggtcgttaaa tagccgctta tgtctattgc tggtttaccg   4620
gtaggtcaac tttcgcaaca tccggcttga ccataacggc gctgtcggcc gcattgagaa   4680
ctgcttcagc gataagctcc gcatcaccac tttcgtgcga agccgaggca taacggcctt   4740
cttgatgacc gaacgcatgc caatgctgtt cgagcgcatc gtccgtgagc gaagataggt   4800
ctgggtatcg attccgataa taagccagat ccagcacaaa tcgccttgag ccagtctttt   4860
tctgggggac gggcactgaa tttcccttaa catgcatgct cggctgcaca tctacgctcg   4920
gcaagccttc cttaacagac atttttcact ttcctatgaa tattcaagag cgccagaccg   4980
ctgaaacatg aagaatgacg tctaacctgc cgagccccga ggctattata attttgttg   5040 ggttgttcaa catgaatgca agaactgcca tcactctaat tcctatttca ggaatactga   5100
caaataaaaa tgacactttc caaccccgg aaacgaaccc gacttccaga tgcgcacccc   5160
gcgctgccat gccagcgaa ctagagtccc aggatagcgg tagcttaagg ccctctagac   5220
ttgtcagcac ccagatttgt ctccgtgagt tgcatcgctc aaacaactgt tcttgcatg   5280
```

```
gacacctgac gactccctgt tgtgtctagg caaccatgag gtcaccttcc accgctgcaa    5340
cggctcctcc tcttccagcg tgagcagatc ggcacggtca gtaccggcac ccagcagtgt    5400 attttcgac atcagggtgg tctaattccg gcagcgctag cagctcgcct tgcgttgccg    5460
gggcgaagtt tctcagcgtc atctgtctac gacaacacct tttgtccaat tagagccaaa    5520
ttatgattct agtaacaggc ggagccggct tcatcggctc aaatttcgta ctgcaatggt    5580
gtgcgcacaa tgaggaaccc gtcctcaacc tcgacgccct gacctacgca ggcaacctgg    5640
ccaacctgca gccgctggaa ggcaaccctc agcatcgctt tgtgcaaggc aatatttgcg    5700
atgctgcgct tctgaccaag ctgttcgcag agcaccgccc gcgcgccgtg gttcacttcg    5760
cggcggaatc ccatgtagac cgctcaatca ccggccccga agcgtttgtc gaaaccaacg    5820
tgatgggcac gtttcgcttg cttgaagccg cccgggcgca ttggaatagt ttggaaggtg    5880
cagagaagga ggccttccgt ttcctccatg tctctaccga cgaagtctac ggcacactag    5940
ggccaaacga cccggcgttc accgaaacca cgccgtacgc gccgaacagc ccatactccg    6000
ccagcaaggc agccagcgac catctggtac gctcgtattt ccatacctac ggcatgccgg    6060
tactcactac caactgctcc aacaattacg ggccgctcca cttcccggaa aaactgatcc    6120
cgctgatgat cgtcaacgca ctcgccggta aggcgctgcc tgtctatggc gacggccagc    6180
aaatccgcga ctggctgtat gtcgaagatc actgctcggg catccgtcgc gtactggaag    6240
ccggtgcgtt cggcgagacg tacaatattg gcggctggaa tgaaaaagcc aacattgaca    6300
ttgtgcgtac actctgcagc cttctcgacg agatggcacc tgcggcatcg cgccaggtaa    6360
tcaatcagaa gaccggcgag cctgtcgaac agtatgcaga actcatcgcc tacgtaaccg    6420
accgcccagg ccatgaccgc cgttatgcca tcgatgcacg caagatcgag cgggagctcg    6480
gctggaaacc tgccgaaacc ttcgagacgg gcattcgaaa gacagtcgct tggtacttgg    6540
ccaaccagaa atgggtaaaa ggtgtcatgg acggcagcta ccgtgactgg gtggcacaac    6600
aatacggggc aaataaagcg tgaaaatcct gctgttgggg aaaaacgggc aagtaggctg    6660
ggagctacag cgcgccttgg cgccgctggg tgaggtcatt gcgctggatc gtcaggggc    6720 cgagggctta tgtggcgact tgtccaacct ggacggcttg gccgctacga ttcgtcagct    6780
ggcgccggac gtgatcgtca acgctgctgc ctacactgca gtggataaag ctgagagcga    6840
tcaggcactg gctgcaatga tcaatgccgc ggctcctgct gtattagcac gtgaaacagc    6900
agctttgggc gcctggttga ttcactattc caccgattat gtatttgacg gcagcggcag    6960
tcagcgctgg gaggaaactg cgcctaccgg ccccctttcg gtctacgcc ggaccaagct    7020 ggaaggcgag catgccattc tcgccagcgg cgccaaggcc gtggtactgc gcaccagctg    7080
ggtgtatgct gcgcgcgggc acaattttgc caagaccatg ctgcgcctgg cggcggagcg    7140
tgagacgttg agcgtggtag cagaccaatt tggcgcaccc acgggcgctg acctgatcgc    7200
cgacgttact gcacacatcc tgcggcaaat cttcaatggg caagacaacc gtcacctggc    7260
agggatttac cacttggctg cgtccggtga aacctcttgg catggttttg ctcagttcgt    7320
gctggcgcat gctcaacgca ctggcgtagc gctgaaagtg acagctgata aggttgccgc    7380
aatcagcacc gaagcttatc cagtacctgc accacgtccg cgcaactcgc gcctggcact    7440
gggcaaactg gaaaacacgt tcaatttcaa aatgccgctt gggagcaag gcgtgcaacg    7500 tatgctggac gaaatccagt aatagggact ctcatggctc gtaaaggaat tattctggcc    7560
ggcggttcgg gtacacgcct gcatccgcc acactttcgg tttcgaagca gctgctgccg    7620
gtgtatgaca aaccgatgat ctactacccg ctgagcaccc tgctgctcgc tggtatccgg    7680
```

```
gacatcctga tcatttccac cccgcaggac accccgcgct tcgaacagct gctgggcgat    7740
ggcagccagt ggggcctgaa cctgtcatac gcaatacaac caagcccgga tggcttggcg    7800
caagcgttca ccatcggcgc tgacttcatc ggtaacgacc cttctgcgtt ggttctcggt    7860
gacaatattt tctacggcca tgacttccag gcactgctat tgaacgcaga taaacgtgaa    7920
tccggtgctt cagtattcgc ttatcatgtt catgacccag aacgctatgg cgtagcggag    7980
tttgacgata gcggtcgcgt attgtcgctg aagaaaaac cggcagttcc aaagtctagc     8040
tatgcggtca ccggcctgta tttctatgac aatcaggtag tcaatctggc tcgcgagctg    8100
aagccttccc cacgtggcga gctggaaatc accgacctca acaacctta cttgcagcag     8160 cagcagttgc aggtcgaaat catgggccgt ggctatgcgt ggctcgacac cggcacgcac    8220
gacagtctgc tggaggctag ccagtacatc gcaaccatgg agcgccgtca gggcttgaaa    8280
gtcgcctgcc ctgaggaaat tgctaccgc gctggctgga tcaacgctga gcaactcgag     8340
tgcctggctc aaccactgct gaaaaacggt tatggcaagt atctgcagaa cttgctgaaa    8400
gagaaggtgt tctgatgcaa gccattccgc tggatatccc cgaagtcgtg ctgtttaccc    8460
ccaaggtttt tggcgacgaa cgtggttct tctacgagag cttcaacgcc cgtgttttca     8520
gcgaagtgac cggcctgcag cccgacttcg tacaagacaa ccactcgcgc tcggtaaaag    8580
gcgtgctccg tggcctgcac tatcagctgg cacctcacgc ccagggcaag ctggtgcgtg    8640
tggtgcaagg cgaagtcttc gatgttgcgg tggatatccg tcgctcgtcc acaaccttcg    8700
gtaaatgggt aggtgcggtg ttgtcggccg agaacaagaa ccagctgtgg atcccgccag    8760
ggttcgcaca cgggttcgtc acgttgagtg aaaccgcaga gttcctctac aagaccaccg    8820
acttctactc gccgcagtgc gagcgctgca ttgcctggaa tgatccggca gtgggtatcg    8880
aatggcccat cgactccgta ccaagcttgt ctggcaagga ccagcttggg gtcgcattgg    8940
ctgacgccga actgttcgac taacggtttt agcggagaag ggctgcggta gcgcagcctt    9000
gtctctgaac acatgccata ccgggtcttg ccgatagtgg cgttttcac acgccactaa     9060 gaagcaaccg ctgcatggcc tggcaaataa tcagaatttg ccccttcctt gtaggccatt    9120
tcccaaagat accctgcgc ctgttttcca ttgcacacgt taaacgtgag acttagtctc     9180
gacccgtcgc tgccaaatca gtgaccggtt tattgactac cggaagcagt gtgaccgtgt    9240
gcttctcaaa tgcctgaggc cagtttgctc aggctctccc cgtggaggta ataattgacg    9300
atatgatcat ttattctgcc tcccagagcc tgataaaaac ggtgaatccg ttagcgaggt    9360
gccgccggct tccattcagg tcgaggtggc ccggctccat gcaccgcgac gcaacgcggg    9420
gaggcagaca aggtataggg cggcgaggcg gctacagccg atagtctgga acagcgcact    9480
tacgggttgc tgcgcaaccc aagtgctacc ggcgcggcag cgtgacccgt gtcggcggct    9540
ccaacggctc gccatcgtcc agaaaacacg gctcatcggg catcggcagg cgctgctgcc    9600
cgcgccgttc ccattcctcc gtttcggtca aggctgcag gtctggttcc atgcccggaa     9660
tgccgggctg gctgggcggc tcctcgccgg ggccggtcgg tagttgctgc tcgcccggat    9720
acagggtcgg gatgcggcgc aggtcgccat gccccaacag cgattcgtcc tggtcgtcgt    9780
gatcaaccac cacggcggca ctgaacaccg acaggcgcaa ctggtcgcgg ggctggcccc    9840
acgccacgcg gtcattgacc acgtaggccg acacggtgcc ggggccgttg agcttcacga    9900
cggagatcca gcgctcggcc accaagtcct tgactgcgta ttggaccgtc cgcaaagaac    9960
gtccgatgag cttggaaagt gtcttctggc tgaccaccac ggcgttctgg tggcccatct   10020
```

```
gcgccacgag gtgatgcagc agcattgccg ccgtgggttt cctcgcaata agcccggccc    10080
acgcctcatg cgctttgcgt tccgtttgca cccagtgacc gggcttgttc ttggcttgaa    10140
tgccgatttc tctggactgc gtggccatgc ttatctccat gcggtagggt gccgcacggt    10200
tgcggcacca tgcgcaatca gctgcaactt ttcggcagcg cgacaacaat tatgcgttgc    10260
gtaaaagtgg cagtcaatta cagattttct ttaacctacg caatgagcta ttgcgggggg    10320
tgccgcaatg agctgttgcg taccccccct ttttaagttg ttgattttta agtcttccgc    10380
atttcgccct atatctagtt ctttggtgcc caaagaaggg caccctgcg gggttccccc     10440 acgccttcgg cgcggctccc cctccggcaa aaagtggccc ctccggggct tgttgatcga    10500
ctgcgcggcc ttcggccttg cccaaggtgg cgctgccccc ttggaacccc cgcactcgcc    10560
gccgtgaggc tcgggggca ggcgggcggg cttcgccttc gactgccccc actcgcatag     10620
gcttgggtcg ttccaggcgc gtcaaggcca agccgctgcg cggtcgctgc gcgagccttg    10680
acccgccttc cacttggtgt ccaaccggca agcgaagcgc gcaggccgca ggccggaggc    10740
ttttccccag agaaaattaa aaaaattgat ggggcaaggc cgcaggccgc gcagttggag    10800
ccggtgggta tgtggtcgaa ggctgggtag ccggtgggca atccctgtgg tcaagctcgt    10860
gggcaggcgc agcctgtcca tcagcttgtc cagcagggtt gtccacgggc cgagcgaagc    10920
gagccagccg gtggccgctc gcggccatcg tccacatatc cacgggctgg caaggagcg     10980 cagcgaccgc gcagggcgaa gcccggagag caagcccgta gggcgccgca gccgccgtag    11040
gcggtcacga ctttgcgaag caaagtctag tgagtatact caagcattga gtggcccgcc    11100
ggaggcaccg ccttgcgctg cccccgtcga gccggttgga caccaaaagg gaggggcagg    11160
catggcggca tacgcgatca tgcgatgcaa gaagctggcg aaaatgggca acgtggcggc    11220
cagtctcaag cacgcctacc gcgagcgcga gacgcccaac gctgacgcca gcaggacgcc    11280
agagaacgag cactgggcgg ccagcagcac cgatgaagcg atgggccgac tgcgcgagtt    11340
gctgccagag aagcggcgca aggacgctgt gttggcggtc gagtacgtca tgacggccag    11400
cccggaatgg tggaagtcgg ccagccaaga acagcaggcg gcgttcttcg agaaggcgca    11460
caagtggctg gcgacaagt acggggcgga tcgcatcgtg acggccagca tccaccgtga    11520
cgaaaccagc ccgcacatga ccgcgttcgt ggtgccgctg acgcaggacg gcaggctgtc    11580
ggccaaggag ttcatcggca acaaagcgca gatgacccgc gaccagacca cgtttgcggc    11640
cgctgtggcc gatctagggc tgcaacgggg catcgagggc agcaaggcac gtcacacgcg    11700
cattcaggcg ttctacgagg ccctggagcg gccaccagtg ggccacgtca ccatcagccc    11760
gcaagcggtc gagccacgcg cctatgcacc gcagggattg gccgaaaagc tgggaatctc    11820
aaagcgcgtt gagacgccgg aagccgtggc cgaccggctg acaaaagcgg ttcggcaggg    11880
gtatgagcct gccctacagg ccgccgcagg agcgcgtgag atgcgcaaga aggccgatca    11940
agcccaagag acggcccgag                                                11960
```

<210> SEQ ID NO 74
<211> LENGTH: 13289
<212> TYPE: DNA
<213> ORGANISM: Artificial Sequence
<220> FEATURE:
<223> OTHER INFORMATION: vector

<400> SEQUENCE: 74

```
ccggtcactg atttggcagc gacgggtcga gactaagtct cacgtttaac gtgtgcaatg      60
gaaaacaggc gcaggggtat ctttgggaaa tggcctacaa ggaagggca aattctgatt      120
```

-continued

```
atttgccagg ccatgcagcg gttgcttctt agtggcgtgt gaaaaacgcc actatcggca    180
agacccggta tggcatgtgt tcagagacaa ggctgcgcta ccgcagccct tctccgctaa    240
aaccgttagt cgaacagttc ggcgtcagcc aatgcgaccc caagctggtc cttgccagac    300
aagcttggta cggagtcgat gggccattcg atacccactg ccggatcatt ccaggcaatg    360
cagcgctcgc actgcggcga gtagaagtcg gtggtcttgt agaggaactc tgcggtttca    420
ctcaacgtga cgaacccgtg tgcgaaccct ggcgggatcc acagctggtt cttgttctcg    480
gccgacaaca ccgcacctac ccatttaccg aaggttgtgg acgagcgacg atatccacc     540 gcaacatcga agacttcgcc ttgcaccaca cgcaccagct tgccctgggc gtgaggtgcc    600
agctgatagt gcaggccacg gagcacgcct tttaccgagc gcgagtggtt gtcttgtacg    660
aagtcgggct gcaggccggt cacttcgctg aaaacgggg cgttgaagct ctcgtagaag    720
aaaccacgtt cgtcgccaaa aaccttgggg gtaaacagca cgacttcggg gatatccagc    780
ggaatggctt gcatcagaac accttctctt tcagcaagtt ctgcagatac ttgccataac    840 cgttttttcag cagtggttga gccaggcact cgagttgctc agcgttgatc cagccagcgc    900
ggtagcaaat ttcctcaggg caggcgactt tcaagccctg acggcgctcc atggttgcga    960
tgtactggct agcctccagc agactgtcgt gcgtgccggt gtcgagccac gcatagccac    1020
ggcccatgat ttcgacctgc aactgctgct gctgcaagta aaggttgttg aggtcggtga    1080
tttccagctc gccacgtggg gaaggcttca gctcgcgagc cagattgact acctgattgt    1140
catagaaata caggccggtg accgcatagc tagactttgg aactgccggt ttttcttcca    1200
gcgacaatac gcgaccgcta tcgtcaaact ccgctacgcc atagcgttct gggtcatgaa    1260
catgataagc gaatactgaa gcaccggatt cacgtttatc tgcgttcaat agcagtgcct    1320
ggaagtcatg gccgtagaaa atattgtcac cgagaaccaa cgcagaaggg tcgttaccga    1380
tgaagtcagc gccgatggtg aacgcttgcg ccaagccatc cgggcttggt tgtattgcgt    1440
atgacaggtt caggccccac tggctgccat cgcccagcag ctgttcgaag cgcggggtgt    1500 cctgcgggt ggaaatgatc aggatgtccc ggataccagc gagcagcagg gtgctcagcg     1560
ggtagtagat catcggtttg tcatacaccg gcagcagctg cttcgaaacc gaaagtgtgg    1620
ccggatgcag gcgtgtaccc gaaccgccgg ccagaataat tcctttacga gccatgagag    1680
tccctattac tggatttcgt ccagcatacg ttgcacgcct tgctcccaaa gcggcatttt    1740
gaaattgaac gtgttttcca gtttgcccag tgccaggcgc gagttgcgcg gacgtggtgc    1800
aggtactgga taagcttcgg tgctgattgc ggcaaccta tcagctgtca ctttcagcgc    1860
tacgccagtg cgttgagcat gcgccagcac gaactgagca aaaccatgcc aagaggtttc    1920
accggacgca gccaagtggt aaatccctgc caggtgacgg ttgtcttgcc cattgaagat    1980
ttgccgcagg atgtgtgcag taacgtcggc gatcaggtca gcgcccgtgg gtgcgccaaa    2040
ttggtctgct accacgctca acgtctcacg ctccgccgcc aggcgcagca tggtcttggc    2100
aaaattgtgc ccgcgcgcag catacaccca gctggtgcgc agtaccacgg ccttggcgcc    2160
gctggcgaga atggcatgct cgccttccag cttggtccgg ccgtagaccg aaagggggcc    2220
ggtaggcgca gtttcctccc agcgctgact gccgctgccc tcaaatacat aatcggtgga    2280
atagtgaatc aaccaggcgc ccaaagctgc tgtttcacgt gctaatacag caggagccgc    2340
ggcattgatc attgcagcca gtgcctgatc gctctcagct ttatccactg cagtgtaggc    2400
agcagcgttg acgatcacgt ccggcgccag ctgacgaatc gtagcggcca agccgtccag    2460
```

```
gttggacaag tcgccacata agccctcggc ccctgacga tccagcgcaa tgacctcacc   2520
cagcggcgcc aaggcgcgct gtagctccca gcctacttgc ccgttttcc ccaacagcag    2580 gattttcacg ctttatttgc cccgtattgt tgtgccaccc agtcacggta gctgccgtcc   2640
atgacacctt ttacccattt ctggttggcc aagtaccaag cgactgtctt tcgaatgccc   2700
gtctcgaagg tttcggcagg tttccagccg agctcccgct cgatcttgcg tgcatcgatg   2760
gcataacggc ggtcatggcc tgggcggtcg gttacgtagg cgatgagttc tgcatactgt   2820
tcgacaggct cgccggtctt ctgattgatt acctggcgcg atgccgcagg tgccatctcg   2880
tcgagaaggc tgcagagtgt acgcacaatg tcaatgttgg cttttcatt ccagccgcca    2940 atattgtacg tctcgccgaa cgcaccggct tccagtacgc gacggatgcc cgagcagtga   3000
tcttcgacat acagccagtc gcggatttgc tggccgtcgc catagacagg cagcgcctta   3060
ccggcgagtg cgttgacgat catcagcggg atcagttttt ccgggaagtg gagcggcccg   3120
taattgttgg agcagttggt agtgagtacc ggcatgccgt aggtatggaa atacgagcgt   3180
accagatggt cgctggctgc cttgctggcg gagtatgggc tgttcggcgc gtacggcgtg   3240
gtttcggtga acgccgggtc gtttggccct agtgtgccgt agacttcgtc ggtagagaca   3300
tggaggaaac ggaaggcctc cttctctgca ccttccaaac tattccaatg cgcccgggcg   3360
gcttcaagca agcgaaacgt gcccatcacg ttggtttcga caaacgcttc ggggccggtg   3420
attgagcggt ctacatggga ttccgccgcg aagtgaacca cggcgcgcgg gcggtgctct   3480
gcgaacagct tggtcagaag cgcagcatcg caaatattgc cttgcacaaa gcgatgctga   3540
gggttgcctt ccagcggctg caggttggcc aggttgcctg cgtaggtcag ggcgtcgagg   3600
ttgaggacgg gttcctcatt gtgcgcacac cattgcagta cgaaatttga gccgatgaag   3660
ccggctccgc ctgttactag aatcataatt tggctctaat tggacaaaag gtgttgtcgt   3720
agacagatga cgctgagaaa cttcgccccg gcaacgcaag gcgagctgct agcgctgccg   3780
gaattagacc accctgatgt cgaaaaatac actgctgggt gccggtactg accgtgccga   3840
tctgctcacg ctggaagagg aggagccgtt gcagcggtgg aaggtgacct catggttgcc   3900
tagacacaac agggagtcgt caggtgtcca tgcaagaaac agttgtttga gcgatgcaac   3960
tcacggagac aaatctgggt gctgacaagt ctagagggcc ttaagctacc gctatcctgg   4020
gactctagtt cgctgggcat ggcagcgcgg ggtgcgcatc tggaagtcgg gttcgtttcc   4080
gggggttgga aagtgtcatt tttatttgtc agtattcctg aaataggaat tagagtgatg   4140
gcagttcttg cattcatgtt gaacaaccca acaaaaatta taatagcctc ggggctcggc   4200
aggttagacg tcattcttca tgtttcagcg gtctggcgct cttgaatatt cataggaaag   4260
tgaaaaatgt ctgttaagga aggcttgccg agcgtagatg tgcagccgag catgcatgtt   4320
aagggaaatt cagtgcccgt cccccagaaa aagactggct caaggcgatt tgtgctggat   4380
ctggcttatt atcggaatcg atacccgac ctatcttcgc tcacggacga tgcgctcgaa    4440
cagcattggc atgcgttcgg tcatcaagaa ggccgttatg cctcggcttc gcacgaaagt   4500
ggtgatgcgg agcttatcgc tgaagcagtt ctcaatgcgg ccgacagcgc cgttatggtc   4560
aagccggatt ttgcgaaagt tgacctaccg gtaaaccagc aatagacata agcggctatt   4620
taacgaccct gccctgaacc gacgaccggg tcgaatttgc tttcgaattt ctgccattca   4680
tccgcttatt atcacttatt caggcgtagc accaggcgtt taagggcacc aataactgcc   4740
ttaaaaaaat tacgccccgc cctgccactc atcgcagtcg gcctattggt taaaaatga    4800 gctgatttaa caaaaattta acgcgaattt taacaaaata ttaacgctta caatttccat   4860
```

```
tcgccattca ggctgcgcaa ctgttgggaa gggcgatcgg tgcgggcctc ttcgctatta   4920
cgccagctgg cgaaaggggg atgtgctgca aggcgattaa gttgggtaac gccagggttt   4980
tcccagtcac gacgttgtaa aacgacggcc agtgagcgcg cgtaatacga ctcactatag   5040
ggcgaattgg agctccaccg cggtggcggc cgctctagaa gtaccaccag cacgcccatg   5100
tctatccggt ccatgatcgt tcttctcccg taggtcgaag ttgccaggcc aggaccagcc   5160
cggccagaac gagaagggcg ccggcgagga atggcgcgcc ggccagggc agcggcgcga    5220 gcggaccgct gccccagtgg aacaggccgc tcatcagcgg cggaccgacg atcgcggcga   5280
ggctcatcag gctgctcagc acgccctgca actcgccctg gcggtcgacc ggcacgcggg   5340
ccgagagcag cccctgcatg gccggggtgg cgaggctgcc gagcgcgaag gcagcagcg    5400 cgcagaccag ccagaatgac gagtcgacca gggcgaacag cagcaggccg cagccttgca   5460
gggcgaggcc caggcgcagc aggcgggcgt cgtccaggcg ccgcttgcag aggttcacgc   5520
cgagggtctg ggcgagcacc gcgagcacgc cgtagagggc cagcgagtag ccgatccagg   5580
cgctgctcca gtgaaacttc tcgatcacga agaacggcca gaccaccatc accgcctgca   5640
agccgaggaa taccagggca agcaccgcca gcaggcgtcc gacccccggt tgccgagcca   5700
ggccgctgat cgagcgcaag gcattcatcc gcctcgggtc caggcggcgg cgtcgcgtcg   5760
ggggcagggt ttcctcgagg aacaggccgg cgagcagggc gttgagcagg cacaggccgg   5820
cggccagcaa cagcggcagc gtcgtgccgt gcaccgccag cagcccaccg agggcggggc   5880
cgaggatcat gcccagggcg aggccggcgt acagccagcc gaagtgccgg gtgcgctgcc   5940
cgtgcgtgcc gaggtcagcc gcgcaggcca tcgcggtggc cacgctggcg ccggtgagcc   6000
cggccagcgc gcgaccgagg aacagcatcc agaggctgtc ggccagcgcc agcagcagat   6060
agctgagggc gaagccgagc atcgccagga ccaggacggg gcggcgtccg aagcggtcgc   6120
tgaggctgcc gaggaccggc gaaaagaaca attgcagcag cgcgaaggtc atcaccaggg   6180
cggcgcccca ggtggccgcg tcgcggaccg ccagcggcgc cacgctgccg atcagcgtcg   6240
gcagcagggg cacgatcagg ccgacgccag cggcatccag caggcaggtg aggaacagca   6300
gaggcaggac gcgtttcgcg ccgggaccgt gttcccgcgt ggcggagggg cagaggctgg   6360
tcgtggacac gccaggatcc tcccggcgtc aggacgcagc cttcagccat cgcgcatccc   6420
cctccctatg acaacgttcg accacctggg ccgctttacc gcaagcgata ctgtgcggtt   6480
gtgacaattc catgaaacgc cgacaggccg ccgccatggc cgggtcctcg agcaagcgcc   6540
acagcgcccc gcgcaactcc tgctcgcgca atggcacgcc caggcgcatc ccgcagccga   6600
gccggaccag ccgttcggca ttgtcgaact ggtcgtgggc gcagggcagc agcacctgcg   6660 gcaccccgc cgccaaggcc aggctcatgg cgccgatacc gccggatgg accagcccg     6720 cgcacgatgg cagcaaggct cccagtggcg cgtaggcgcg ctgcagcacg tggttcggca   6780
agccgcgcag cggttcctgg ccggcgccgg tgaggaagat cccacgcgcg ccgaggcgtt   6840
ccagcgcgcg cagggccatg gcgtagaagt cgccctgcag gtgttcggtc gagccctggg   6900
tgaacaccag cggccggctg ccctgatcga gaaagcgttg cagttcgtcg tcgagcgggg   6960
tccccgggat actgccgtcg aacagcggga agccggtcat gtgcagggt tgcggccaat    7020 cctgctgggg cggcgcgaac caggccggga acaggcagac cacgccctgc ggcgaatgca   7080
tccattgggt gaagatgcgc ttcaccggcg tctccaggcc gaccttgcgc cgcaccgcgt   7140
tgatatccgg cgcgcaggtg cgatccagct tgaagcgctc gatgcagcgc cagagcagct   7200
```

```
tgcgcatcgc cagcggcatc tgctcgggca cgttgaactt ggggtgtacc ggcggcaggt   7260
gcgccgacaa caaggtcgat ggcgagacct cgcggacag gtagggaatc ccgtacttct    7320
cgtgagcgat gcgtgcgccc agcgcccaga gcgagccgac caccacgatg tcgtcatggc   7380
gctgcgccga gacgtactcg tagaccggct cgatcatccc ggcgatggtt tgccagagca   7440
cgccgaagga cgtcttgggg tcccacaggc gcggatcgcc catggtccgg cggtaggtca   7500
gttcgtcgct cagcgggacg aacgcgatgc cgtgctgctc caccgcgtcg cgaaacaccg   7560
ggatggtgca gaggctcacg cggtgcccgc gcaatttcag ggtccgggcc aggccgatga   7620
agggaaatac gtcgccggcc gagccgatgg cgatgaggat ggcgtgcatg gtgctactcc   7680
gtgcgttatg caaccgcaaa gcccggccag gccgggtctt cgcaggtcaa gggttcaggc   7740
gtagccgatg gccatctcgt ggaatcccgc cgcgcgttcc gcccgctgcg gctccgttg    7800
cttcagcagg tgctcgagca gggcgcggtg cacgcgtacc gcggccagct tggactccag   7860
gtcgaggaaa tgcccggtgc cctccacccg cgagaaactg cagtgcggca ggtagtcgcg   7920
gaactggcgg gcgtcctcgg cggtggtgta ttcgtcccag ctgccgttga tgaaatgcac   7980
gtggctctgg atccgctcca ggcaagccag gtagccccga tcgttgagcg ccagcacctg   8040
gtcgatgtga aagcgcgcct gctcgtattc gccggtggcc agcgaagcca tgtgctgatg   8100
gttgctggct ttcaggcgcg gcggcaggta tttgccgacg gtctcgttga gcagatggcc   8160
gatcgccgac ttgtcgtcca gctcgatcag cgcctgcgcc cgcccgacgt agtcgagcat   8220
cgcctggttc agtccagggg cgaatgccat caccaccgag ctgcggatgc cgcgcggatt   8280
gcgcgacagc gccagcagcg tggagatacc gccccaggac gcggagacca ggtgattgac   8340
ctcgaagcgc tcgatcagcg ccaggaggat ttccacctcg tcgtccttgg tgatcaaccc   8400
ccgctgcggg ttgtgctgac gcgactgccc ggcgaagggc aggtcgaaca gcaccacgtt   8460
gaaatgttcg gccaggcact gcaggtccg ggcgaacgag gcggtggtcg ccatcgcgcc    8520
gttgaccagc atcaccgtgc tgcgcccggg atcctgccca acgcgctcga catgtacccg   8580
caggcccttg caaaccgata ccaacagact ttcgcgccgc atttcacacc tcccaaaaat   8640
gccagatccc ccgggctgca ggaattcgat atcaagctta tcgataccgt cgacctcgag   8700
ggggggcccg gtacccagct tttgttccct ttagtgaggg ttaattgcgc gcttggcgta   8760
atcatggtca tagctgtttc ctgtgtgaaa ttgttatccg ctcacaattc cacacaacat   8820
acgagccgga agcataaagt gtaaagcctg ggtgcctaa tgagtgagct aactcacatt    8880
aattgcgttg cgctcactgc ccgctttcca gtcgggaaac ctgtcgtgcc agctgcatta   8940
atgaatcggc caacgcgcgg ggagaggcgg tttgcgtatt gggcgcatgc ataaaaactg   9000
ttgtaattca ttaagcattc tgccgacatg gaagccatca caaacggcat gatgaacctg   9060
aatcgccagc ggcatcagca ccttgtcgcc ttgcgtataa tatttgccca tggggtggg    9120
cgaagaactc cagcatgaga tccccgcgct ggaggatcat ccagccggcg tcccggaaaa   9180
cgattccgaa gcccaacctt tcatagaagg cggcggtgga atcgaaatct cgtgatggca   9240
ggttgggcgt cgcttggtcg gtcatttcga accccagagt cccgctcaga agaactcgtc   9300
aagaaggcga tagaaggcga tgcgctgcga atcgggagcg cgataccgt aaagcacgag    9360
gaagcggtca gcccattcgc cgccaagctc ttcagcaata tcacgggtag ccaacgctat   9420
gtcctgatag cggtccgcca cacccagccg gccacagtcg atgaatccag aaaagcggcc   9480
attttccacc atgatattcg gcaagcaggc atcgccatgg gtcacgacga gatcctcgcc   9540
gtcgggcatg cgcgccttga gcctggcgaa cagttcggct ggcgcgagcc cctgatgctc   9600
```

```
ttcgtccaga tcatcctgat cgacaagacc ggcttccatc cgagtacgtg ctcgctcgat    9660
gcgatgtttc gcttggtggt cgaatgggca ggtagccgga tcaagcgtat gcagccgccg    9720
cattgcatca gccatgatgg atactttctc ggcaggagca aggtgagatg acaggagatc    9780
ctgccccggc acttcgccca atagcagcca gtcccttccc gcttcagtga caacgtcgag    9840
cacagctgcg caaggaacgc ccgtcgtggc cagccacgat agccgcgctg cctcgtcctg    9900
cagttcattc agggcaccgg acaggtcggt cttgacaaaa agaaccgggc gccctgcgc     9960 tgacagccgg aacacggcgg catcagagca gccgattgtc tgttgtgccc agtcatagcc   10020
gaatagcctc tccacccaag cggccggaga acctgcgtgc aatccatctt gttcaatcat   10080
gcgaaacgat cctcatcctg tctcttgatc agatcttgat ccctgcgcc atcagatcct    10140 tggcggcaag aaagccatcc agtttacttt gcagggcttc ccaaccttac cagagggcgc   10200
cccagctggc aattccggtt cgcttgctgt ccataaaacc gcccagtcta gctatcgcca   10260
tgtaagccca ctgcaagcta cctgctttct ctttgcgctt gcgttttccc ttgtccagat   10320
agcccagtag ctgacattca tcccaggtgg cacttttcgg ggaaatgtgc gcgcccgcgt   10380
tcctgctggc gctgggcctg tttctggcgc tggacttccc gctgttccgt cagcagcttt   10440
tcgcccacgg ccttgatgat cgcggcggcc ttggcctgca tcccgatt caacggcccc     10500 agggcgtcca gaacgggctt caggcgctcc gaaggtctc gggccgtctc ttgggcttga    10560
tcggccttct tgcgcatctc acgcgctcct gcggcggcct gtagggcagg ctcataccc    10620 tgccgaaccg cttttgtcag ccggtcggcc acggcttccg gcgtctcaac gcgctttgag   10680
attcccagct ttttcggccaa tccctgcggt gcataggcgc gtggctcgac cgcttgcggg   10740
ctgatggtga cgtggcccac tggtggccgc tccaggcct cgtagaacgc ctgaatgcgc    10800
gtgtgacgtg ccttgctgcc ctcgatgccc cgttgcagcc ctagatcggc cacagcggcc   10860
gcaaacgtgg tctggtcgcg ggtcatctgc gctttgttgc cgatgaactc cttggccgac   10920
agcctgccgt cctgcgtcag cggcaccacg aacgcgtca tgtgcgggct ggtttcgtca    10980
cggtggatgc tggccgtcac gatgcgatcc gccccgtact tgtccgccag ccacttgtgc   11040
gccttctcga agaacgccgc ctgctgttct tggctggccg acttccacca ttccgggctg   11100
gccgtcatga cgtactcgac cgccaacaca gcgtccttgc gccgcttctc tggcagcaac   11160
tcgcgcagtc ggcccatcgc ttcatcggtg ctgctggccg cccagtgctc gttctctggc   11220
gtcctgctgg cgtcagcgtt gggcgtctcg cgctcgcggt aggcgtgctt gagactggcc   11280 gccacgtttgc ccatttttcgc cagcttcttg catcgcatga tcgcgtatgc cgccatgcct   11340 gccctccct tttggtgtcc aaccggctcg acggggcag cgcaaggcgg tgcctccggc    11400
gggccactca atgcttgagt atactcacta gactttgctt cgcaaagtcg tgaccgccta   11460
cggcggctgc ggcgccctac gggcttgctc tccgggcttc gccctgcgcg gtcgctgcgc   11520
tcccttgcca gcccgtggat atgtggacga tggccgcgag cggccaccgg ctggctcgct   11580
tcgctcggcc cgtggacaac cctgctggac aagctgatgg acaggctgcg cctgcccacg   11640
agcttgacca cagggattgc ccaccggcta cccagccttc gaccacatac ccaccggctc   11700 caactcgcgcg gcctgcggcc ttgccccatc aattttttta attttctctg gggaaaagcc   11760
tccggcctgc ggcctgcgcg cttcgcttgc cggttggaca ccaagtggaa ggcgggtcaa   11820
ggctcgcgca gcgaccgcgc agcggcttgg ccttgacgcg cctggaacga cccaagccta   11880
tgcgagtggg ggcagtcgaa ggcgaagccc gcccgcctgc ccccgagcc tcacggcggc    11940
```

```
gagtgcgggg gttccaaggg ggcagcgcca ccttgggcaa ggccgaaggc cgcgcagtcg   12000
atcaacaagc cccggagggg ccacttttg  ccggaggggg agccgcgccg aaggcgtggg   12060
ggaaccccgc aggggtgccc ttctttgggc accaaagaac tagatatagg gcgaaatgcg   12120
aaagacttaa aaatcaacaa cttaaaaaag gggggtacgc aacagctcat tgcggcaccc   12180
cccgcaatag ctcattgcgt aggttaaaga aaatctgtaa ttgactgcca cttttacgca   12240
acgcataatt gttgtcgcgc tgccgaaaag ttgcagctga ttgcgcatgg tgccgcaacc   12300
gtgcggcacc ctaccgcatg agataagca  tggccacgca gtccagagaa atcggcattc   12360
aagccaagaa caagcccggt cactgggtgc aaacggaacg caaagcgcat gaggcgtggg   12420
ccgggcttat tgcgaggaaa cccacggcgg caatgctgct gcatcacctc gtggcgcaga   12480
tgggccacca gaacgccgtg gtggtcagcc agaagacact ttccaagctc atcggacgtt   12540
ctttgcggac ggtccaatac gcagtcaagg acttggtggc cgagcgctgg atctccgtcg   12600
tgaagctcaa cggcccccggc accgtgtcgg cctacgtggt caatgaccgc gtggcgtggg   12660
gccagccccg cgaccagttg cgcctgtcgg tgttcagtgc cgccgtggtg gttgatcacg   12720
acgaccagga cgaatcgctg ttggggcatg gcgacctgcg ccgcatcccg accctgtatc   12780
cgggcgagca gcaactaccg accggccccg gcgaggagcc gccagccag  cccggcattc   12840
cgggcatgga accagacctg ccagccttga ccgaaacgga ggaatgggaa cggcgcgggc   12900
agcagcgcct gccgatgccc gatgagccgt gttttctgga cgatggcgag ccgttggagc   12960
cgccgacacg ggtcacgctg ccgcgccggt agcacttggg ttgcgcagca acccgtaagt   13020
gcgctgttcc agactatcgg ctgtagccgc ctcgccgccc tataccttgt ctgcctcccc   13080
gcgttgcgtc gcggtgcatg gagccgggcc acctcgacct gaatggaagc cggcggcacc   13140
tcgctaacgg attcaccgtt tttatcaggc tctgggaggc agaataaatg atcatatcgt   13200
caattattac ctccacgggg agagcctgag caaactggcc tcaggcattt gagaagcaca   13260
cggtcacact gcttccggta gtcaataaa                                   13289
```

<210> SEQ ID NO 75
<211> LENGTH: 14250
<212> TYPE: DNA
<213> ORGANISM: Artificial Sequence
<220> FEATURE:
<223> OTHER INFORMATION: vector

<400> SEQUENCE: 75

```
ctcgggccgt ctcttgggct tgatcggcct tcttgcgcat ctcacgcgct cctgcggcgg     60
cctgtagggc aggctcatac ccctgccgaa ccgcttttgt cagccggtcg gccacggctt    120
ccggcgtctc aacgcgcttt gagattccca gcttttcggc caatccctgc ggtgcatagg    180
cgcgtggctc gaccgcttgc gggctgatgg tgacgtggcc cactggtggc cgctccaggg    240
cctcgtagaa cgcctgaatg cgcgtgtgac gtgccttgct gccctcgatg ccccgttgca    300
gccctagatc ggccacagcg gccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgcccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt ctctgcagc  aactcgcgca gtcggcccat cgcttcatcg gtgctgctgg    660
ccgcccagtg ctcgttctct ggcgtcctgc tggcgtcagc gttgggcgtc tcgcgctcgc    720
```

```
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcggcgccc tacgggcttg ctctccgggc    960
ttcgccctgc gcggtcgctg cgctcccttg ccagcccgtg gatatgtgga cgatggccgc   1020
gagcggccac cggctggctc gcttcgctcg gcccgtggac aaccctgctg acaagctga    1080 tggacaggct gcgcctgccc acgagcttga ccacagggat tgcccaccgg ctacccagcc   1140
ttcgaccaca tacccaccgg ctccaactgc gcggcctgcg gccttgcccc atcaattttt   1200
ttaattttct ctggggaaaa gcctccggcc tgcggcctgc gcgcttcgct tgccggttgg   1260
acaccaagtg gaaggcgggt caaggctcgc gcagcgaccg cgcagcggct tggccttgac   1320
gcgcctggaa cgacccaagc ctatgcgagt gggggcagtc gaaggcgaag cccgcccgcc   1380 tgcccccga gcctcacggc ggcgagtgcg ggggttccaa gggggcagcg ccaccttggg    1440
caaggccgaa ggccgcgcag tcgatcaaca agccccggag gggccacttt tgccggagg    1500 gggagccgcg ccgaaggcgt gggggaaccc cgcaggggtg cccttctttg gcaccaaag    1560 aactagatat agggcgaaat gcgaaagact taaaaatcaa caacttaaaa aaggggggta   1620
cgcaacagct cattgcggca cccccgcaa tagctcattg cgtaggttaa agaaaatctg     1680
taattgactg ccacttttac gcaacgcata attgttgtcg cgctgccgaa agttgcagc    1740 tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggcggggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280 gccgccagc cagcccggca ttccgggcat ggaaccagac ctgccagcct tgaccgaaac    2340
ggaggaatgg gaacggcgcg ggcagcagcg cctgccgatg cccgatgagc cgtgttttct   2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520 ccctataccct tgtctgcctc cccgcgttgc gtcgcggtgc atggagccgg ccacctcga   2580 cctgaatgga agccggcggc acctcgctaa cggattcacc gttttttatca ggctctggga   2640 ggcagaataa atgatcatat cgtcaattat tacctccacg gggagagcct gagcaaactg   2700
gcctcaggca tttgagaagc acacggtcac actgcttccg gtagtcaata aaccggtcac   2760
tgatttggca gcgacgggtc gagactaagt ctcacgttta acgtgtgcaa tggaaaacag   2820
gcgcaggggt atctttggga aatggcctac aaggaagggg caaattctga ttatttgcca   2880
ggccatgcag cggttgcttc ttagtggcgt gtgaaaaacg ccactatcgg caagacccgg   2940
tatggcatgt gttcagagac aaggctgcgc taccgcagcc cttctccgct aaaaccgtta   3000
gtcgaacagt tcggcgtcag ccaatgcgac cccaagctgg tccttgccag acaagcttgg   3060
```

```
tacggagtcg atgggccatt cgatacccac tgccggatca ttccaggcaa tgcagcgctc    3120
gcactgcggc gagtagaagt cggtggtctt gtagaggaac tctgcggttt cactcaacgt    3180
gacgaacccg tgtgcgaacc ctggcgggat ccacagctgg ttcttgttct cggccgacaa    3240
caccgcacct acccatttac cgaaggttgt ggacgagcga cggatatcca ccgcaacatc    3300
gaagacttcg ccttgcacca cacgcaccag cttgccctgg gcgtgaggtg ccagctgata    3360
gtgcaggcca cggagcacgc cttttaccga gcgcgagtgg ttgtcttgta cgaagtcggg    3420
ctgcaggccg gtcacttcgc tgaaaacacg ggcgttgaag ctctcgtaga agaaaccacg    3480
ttcgtcgcca aaaaccttgg gggtaaacag cacgacttcg gggatatcca gcggaatggc    3540
ttgcatcaga acaccttctc tttcagcaag ttctgcagat acttgccata accgtttttc    3600
agcagtggtt gagccaggca ctcgagttgc tcagcgttga tccagccagc gcggtagcaa    3660
atttcctcag ggcaggcgac tttcaagccc tgacggcgct ccatggttgc gatgtactgg    3720
ctagcctcca gcagactgtc gtgcgtgccg gtgtcgagcc acgcatagcc acggcccatg    3780
atttcgacct gcaactgctg ctgctgcaag taaaggttgt tgaggtcggt gatttccagc    3840
tcgccacgtg gggaaggctt cagctcgcga gccagattga ctacctgatt gtcatagaaa    3900
tacaggccgg tgaccgcata gctagacttt ggaactgccg ttttcttc cagcgacaat      3960
acgcgaccgc tatcgtcaaa ctccgctacg ccatagcgtt ctgggtcatg aacatgataa    4020
gcgaatactg aagcaccgga ttcacgttta tctgcgttca atagcagtgc ctggaagtca    4080
tggccgtaga aaatattgtc accgagaacc aacgcagaag ggtcgttacc gatgaagtca    4140
gcgccgatgg tgaacgcttg cgccaagcca tccgggcttg gttgtattgc gtatgacagg    4200
ttcaggcccc actggctgcc atcgcccagc agctgttcga agcgcggggt gtcctgcggg    4260
gtggaaatga tcaggatgtc ccggatacca gcgagcagca gggtgctcag cgggtagtag    4320
atcatcggtt tgtcatacac cggcagcagc tgcttcgaaa ccgaaagtgt ggccggatgc    4380
aggcgtgtac ccgaaccgcc ggccagaata attcctttac gagccatgag agtccctatt    4440
actggatttc gtccagcata cgttgcacgc cttgctccca aagcggcatt tgaaattga    4500
acgtgttttc cagtttgccc agtgccaggc gcgagttgcg cggacgtggt gcaggtactg    4560
gataagcttc ggtgctgatt gcggcaacct tatcagctgt cactttcagc gctacgccag    4620
tgcgttgagc atgcgccagc acgaactgag caaaaccatg ccaagaggtt tcaccggacg    4680
cagccaagtg gtaaatccct gccaggtgac ggttgtcttg cccattgaag atttgccgca    4740
ggatgtgtgc agtaacgtcg gcgatcaggt cagcgcccgt gggtgcgcca aattggtctg    4800
ctaccacgct caacgtctca cgctccgccg ccaggcgcag catggtcttg gcaaaattgt    4860
gcccgcgcgc agcatacacc cagctggtgc gcagtaccac ggccttggcg ccgctggcga    4920
gaatggcatg ctcgccttcc agcttggtcc ggccgtagac cgaaggggg ccggtaggcg     4980
cagtttcctc ccagcgctga ctgccgctgc cgtcaaatac ataatcggtg aatagtgaa     5040
tcaaccaggc gcccaaagct gctgtttcac gtgctaatac agcaggagcc gcggcattga    5100
tcattgcagc cagtgcctga tcgctctcag ctttatccac tgcagtgtag gcagcagcgt    5160
tgacgatcac gtccggcgcc agctgacgaa tcgtagcggc caagccgtcc aggttggaca    5220
agtcgccaca taagccctcg gccccctgac gatccagcgc aatgacctca cccagcggcg    5280
ccaaggcgcg ctgtagctcc cagcctactt gcccgttttt ccccaacagc aggattttca    5340
cgctttattt gccccgtatt gttgtgccac ccagtcacgg tagctgccgt ccatgacacc    5400
ttttacccat ttctggttgg ccaagtacca agcgactgtc tttcgaatgc ccgtctcgaa    5460
```

```
ggtttcggca ggtttccagc cgagctcccg ctcgatcttg cgtgcatcga tggcataacg    5520
gcggtcatgg cctgggcggt cggttacgta ggcgatgagt tctgcatact gttcgacagg    5580
ctcgccggtc ttctgattga ttacctggcg cgatgccgca ggtgccatct cgtcgagaag    5640
gctgcagagt gtacgcacaa tgtcaatgtt ggcttttca ttccagccgc caatattgta     5700
cgtctcgccg aacgcaccgg cttccagtac gcgacggatg cccgagcagt gatcttcgac    5760
atacagccag tcgcggattt gctggccgtc gccatagaca ggcagcgcct taccggcgag    5820
tgcgttgacg atcatcagcg ggatcagttt ttccgggaag tggagcggcc cgtaattgtt    5880
ggagcagttg gtagtgagta ccggcatgcc gtaggtatgg aaatacgagc gtaccagatg    5940
gtcgctggct gccttgctgg cggagtatgg gctgttcggc gcgtacggcg tggtttcggt    6000
gaacgccggg tcgtttggcc ctagtgtgcc gtagacttcg tcggtagaga catggaggaa    6060
acggaaggcc tccttctctg caccttccaa actattccaa tgcgcccggg cggcttcaag    6120
caagcgaaac gtgcccatca cgttggtttc gacaaacgct tcggggccgg tgattgagcg    6180
gtctacatgg gattccgccg cgaagtgaac cacggcgcgc gggcggtgct ctgcgaacag    6240
cttggtcaga agcgcagcat cgcaaatatt gccttgcaca aagcgatgct gagggttgcc    6300
ttccagcggc tgcaggttgg ccaggttgcc tgcgtaggtc agggcgtcga ggttgaggac    6360
gggttcctca ttgtgcgcac accattgcag tacgaaattt gagccgatga agccggctcc    6420
gcctgttact agaatcataa tttggctcta attggacaaa aggtgttgtc gtagacagat    6480
gacgctgaga aacttcgccc cggcaacgca aggcgagctg ctagcgctgc cggaattaga    6540
ccaccctgat gtcgaaaaat acactgctgg gtgccggtac tgaccgtgcc gatctgctca    6600
cgctggaaga ggaggagccg ttgcagcggt ggaaggtgac ctcatggttg cctagacaca    6660
acagggagtc gtcaggtgtc catgcaagaa acagttgttt gagcgatgca actcacggag    6720
acaaatctgg gtgctgacaa gtctagaggg ccttaagcta ccgctatcct gggactctag    6780
ttcgctgggc atggcagcgc ggggtgcgca tctggaagtc gggttcgttt ccggggttg     6840
gaaagtgtca tttttatttg tcagtattcc tgaaatagga attagagtga tggcagttct    6900
tgcattcatg ttgaacaacc caacaaaaat tataatagcc tcggggctcg gcaggttaga    6960
cgtcattctt catgtttcag cggtctggcg ctcttgaata ttcataggaa agtgaaaaat    7020
gtctgttaag gaaggcttgc cgagcgtaga tgtgcagccg agcatgcatg ttaagggaaa    7080
ttcagtgccc gtcccccaga aaaagactgg ctcaaggcga tttgtgctgg atctggctta    7140
ttatcggaat cgatacccag acctatcttc gctcacggac gatgcgctcg aacagcattg    7200
gcatgcgttc ggtcatcaag aaggccgtta tgcctcggct tcgcacgaaa gtggtgatgc    7260
ggagcttatc gctgaagcag ttctcaatgc ggccgacagc gccgttatgg tcaagccgga    7320
tgttgcgaaa gttgacctac cggtaaacca gcaatagaca taagcggcta tttaacgacc    7380
ctgccctgaa ccgacgaccg ggtcgaattt gctttcgaat ttctgccatt catccgctta    7440
ttatcactta ttcaggcgta gcaccaggcg tttaagggca ccaataactg ccttaaaaaa    7500
attacgcccc gccctgccac tcatcgcagt cggcctattg gttaaaaaat gagctgattt    7560
aacaaaaatt taacgcgaat tttaacaaaa tattaacgct tacaatttcc attcgccatt    7620
caggctgcgc aactgttggg aagggcgatc ggtgcgggcc tcttcgctat tacgccagct    7680
ggcgaaaggg ggatgtgctg caaggcgatt aagttgggta acgccagggt tttcccagtc    7740
acgacgttgt aaaacgacgg ccagtgagcg cgcgtaatac gactcactat agggcgaatt    7800
```

```
ggagctccac cgcggtggcg gccgctctag agggaatgcg tttcgccgac taggccttgg    7860
ccttgccgga agctacggac gccacggccg ggccggcgag gcgcttcagc aggcgcgggc    7920
ggttggtctc cagcgcgccg ccgcgtcccc gcaggccgtc ccacaggccc cagcccaggc    7980
agcgcagctt gagcagcttg tcgcgttcga gcaggagcac cgcgaggccc tgggtcaggg    8040
tcggcaggtt cgccagcagg gccagcggcg aggaccgggc gtagcggcgc aggaccagca    8100
ggccgttgcg cgccaggtag tagcggcgca gcggggcgtg gttcatcgcg ctgaggctga    8160
gaccgccgag gcggcgggtc ttgcgcgtgc cgatgcggtg ctcgaggacc agccgcgggt    8220
cgacgtacag gggcacgtcc agcgcctggg cgcgcaggct gtattcggtg tccacgtggt    8280
cgatgaacag ttcctcgtcg aagtggccga ggcgctggta ggcctcgcgg gtcagcaggc    8340
agccggagga gatcaggaac gaggtgcgct gcgggtcgt caggccgtcc agagacaatt    8400
gcctgagcgt cagtccgtcg agatggatgg ccggcaggaa gcgccggtca ccccggtcga    8460
agatccgtgg gccgagcagg caggcctgac cgttgcgcgc ctgcaggttg cgccactggg    8520
cggcgaggaa ggcgccgccg ggacgggagt cctggtcgag cagcagcaca ccctgcacgc    8580
cacgccggaa tagcgcgtcg agtccctggt tgaaggcgcc ggcgatgccc tgccggttgc    8640
cgtggtgcag cacggcgatg ccttgcccgc gcagccgggc attgcgctgc ggatcgctgt    8700
gcggtgagtt gtcgacggca aggaagcgca gttgcggaaa cgccgccgcc agttcgccaa    8760
ggtgttccag gtcgtcgtcg ccaggattga acagtaccac cagcacgccc atgtctatcc    8820
ggtccatgat cgttcttctc ccgtaggtcg aagttgccag gccaggacca gcccggccag    8880
aacgagaagg gcgccggcga ggaatggcgc gccggccagg ggcagcggcg cgagcggacc    8940
gctgccccag tggaacaggc cgctcatcag cggcggaccg acgatcgcgg cgaggctcat    9000
caggctgctc agcacgccct gcaactcgcc ctggcggtcg accggcacgc gggccgagag    9060
cagcccctgc atggccgggg tggcgaggct gccgagcgcg aagggcagca gcgcgcagac    9120
cagccagaat gacgagtcga ccagggcgaa cagcagcagg ccgcagcctt gcagggcgag    9180
gcccaggcgc agcaggcggg cgtcgtccag gcgccgcttg cagaggttca gccgagggt    9240
ctgggcgagc accgcgagca cgccgtagag ggccagcgag tagccgatcc aggcgctgct    9300
ccagtgaaac ttctcgatca cgaagaacgg ccagaccacc atcaccgcct gcaagccgag    9360
gaataccagg gcaagcaccg ccagcaggcg tccgacccc ggttgccgag ccaggccgct    9420
gatcgagcgc aaggcattca tccgcctcgg gtccaggcgg cggcgtcgcg tcggggcag    9480
ggtttcctcg aggaacaggc cggcgagcag ggcgttgagc aggcacaggc cggcggccag    9540
caacagcggc agcgtcgtgc cgtgcaccgc cagcagccca ccgagggcgg ggccgaggat    9600
catgcccagg gcgaggccgg cgtacagcca gccgaagtgc cgggtgcgct gcccgtgcgt    9660
gccgaggtca gccgcgcagg ccatcgcggt ggccacgctg gcgccggtga gcccggccag    9720
cgcgcgaccg aggaacagca tccagaggct gtcggcagc gccagcagca gatagctgag    9780
ggcgaagccg agcatcgcca ggaccaggac ggggcggcgt ccgaagcggt cgctgaggct    9840
gccgaggacc ggcgaaaaga acaattgcag cagcgcgaag gtcatcacca gggcggcgcc    9900
ccaggtggcc gcgtcgcgga ccgccagcgg cgccacgctg ccgatcagcg tcggcagcag    9960
gggcacgatc aggccgacgc cagcggcatc cagcaggcag gtgaggaaca gcagaggcag   10020
gacgcgtttc gcgccgggac cgtgttcccg cgtggcggag gggcagaggc tggtcgtgga   10080
cacgccagga tcctcccggc gtcaggacgc agccttcagc catcgcgcat cccctcccct   10140
atgacaacgt tcgaccacct gggccgcttt accgcaagcg atactgtgcg gttgtgacaa   10200
```

```
ttccatgaaa cgccgacagg ccgccgccat ggccgggtcc tcgagcaagc gccacagcgc   10260
cccgcgcaac tcctgctcgc gcaatggcac gcccaggcgc atcccgcagc cgagccggac   10320
cagccgttcg gcattgtcga actggtcgtg ggcgcagggc agcagcacct gcggcacccc   10380
cgccgccaag gccaggctca tggcgccgat accgcccgga tggaccagcc cggcgcacga   10440
tggcagcaag gctcccagtg gcgcgtaggc gcgctgcagc acgtggttcg gcaagccgcg   10500
cagcggttcc tggccggcgc cggtgaggaa gatcccacgc gcgccgaggc gttccagcgc   10560
gcgcagggcc atggcgtaga agtcgccctg caggtgttcg gtcgagccct gggtgaacac   10620
cagcggccgc ctgccctgat cgagaaagcg ttgcagttcg tcgtcgagcg gggtccccgg   10680
gatactgccg tcgaacagcg ggaagccggt catgtgcagg ggttgcggcc aatcctgctg   10740
gggcggcgcg aaccaggccg ggaacaggca gaccacgccc tgcggcgaat gcatccattg   10800
ggtgaagatg cgcttcaccg gcgtctccag gccgaccttg cgccgcaccg cgttgatatc   10860
cggcgcgcag gtgcgatcca gcttgaagcg ctcgatgcag cgccagagca gcttgcgcat   10920
cgccagcggc atctgctcgg gcacgttgaa cttggggtgt accggcggca ggtgcgccga   10980
caacaaggtc gatggcgaga cctgcgcgga caggtaggga atcccgtact tctcgtgagc   11040
gatgcgtgcg cccagcgccc agagcgagcc gaccaccacg atgtcgtcat ggcgctgcgc   11100
cgagacgtac tcgtagaccg gctcgatcat cccggcgatg gtttgccaga gcacgccgaa   11160
ggacgtcttg gggtcccaca ggcgcggatc gcccatggtc cggcggtagg tcagttcgtc   11220
gctcagcggg acgaacgcga tgccgtgctg ctccaccgcg tcgcgaaaca ccgggatggt   11280
gcagaggctc acgcggtgcc cgcgcaattt cagggtccgg gccaggccga tgaagggaaa   11340
tacgtcgccg gccgagccga tggcgatgag gatggcgtgc atggtgctac tccgtgcgtt   11400
atgcaaccgc aaagcccggc caggccgggt cttcgcaggt caagggttca ggcgtagccg   11460
atggccatct cgtggaatcc cgccgcgcgt tccgcccgct gcggctccgg ttgcttcagc   11520
aggtgctcga gcagggcgcg gtgcacgcgt accgcggcca gcttggactc caggtcgagg   11580
aaatgcccgg tgccctccac ccgcgagaaa ctgcagtgcg gcaggtagtc gcggaactgg   11640
cgggcgtcct cggcggtggt gtattcgtcc cagctgccgt tgatgaaatg cacgtggctc   11700
tggatccgct ccaggcaagc caggtagccc cgatcgttga gcgccagcac ctggtcgatg   11760
tgaaagcgcg cctgctcgta ttcgccggtg gccagcgaag ccatgtgctg atggttgctg   11820
gctttcaggc gcggcggcag gtatttgccg acggtctcgt tgagcagatg gccgatcgcc   11880
gacttgtcgt ccagctcgat cagcgcctgc gcccgcccga cgtagtcgag catcgcctgg   11940
ttcagtccag gggcgaatgc catcaccacc gagctgcgga tgccgcgcgg attgcgcgac   12000
agcgccagca gcgtggagat accgcccag gacgcggaga ccaggtgatt gacctcgaag   12060
cgctcgatca gcgccaggag gatttccacc tcgtcgtcct tggtgatcaa ccccgctgc    12120 gggttgtgct gacgcgactg cccggcgaag ggcaggtcga acagcaccac gttgaaatgt   12180
tcggccaggc acttgcaggt ccgggcgaac gaggcggtgg tcgccatcgc gccgttgacc   12240
agcatcaccg tgctgcgccc gggatcctgc ccaacgcgct cgacatgtac ccgcaggccc   12300
ttgcaaaccg ataccaacag actttcgcgc gcatttcac acctcccaaa aatgccagat    12360 ccccgggct gcaggaattc gatatcaagc ttatcgatac cgtcgacctc gagggggggc    12420
ccggtaccca gcttttgttc cctttagtga gggttaattg cgcgcttggc gtaatcatgg   12480
tcatagctgt ttcctgtgtg aaattgttat ccgctcacaa ttccacacaa catacgagcc   12540
```

```
ggaagcataa agtgtaaagc ctggggtgcc taatgagtga gctaactcac attaattgcg   12600
ttgcgctcac tgcccgcttt ccagtcggga aacctgtcgt gccagctgca ttaatgaatc   12660
ggccaacgcg cggggagagg cggtttgcgt attgggcgca tgcataaaaa ctgttgtaat   12720
tcattaagca ttctgccgac atggaagcca tcacaaacgg catgatgaac ctgaatcgcc   12780
agcggcatca gcaccttgtc gccttgcgta taatatttgc ccatgggggt gggcgaagaa   12840
ctccagcatg agatcccgc gctggaggat catccagccg gcgtcccgga aaacgattcc   12900
gaagcccaac ctttcataga aggcggcggt ggaatcgaaa tctcgtgatg gcaggttggg   12960
cgtcgcttgg tcggtcattt cgaacccag agtcccgctc agaagaactc gtcaagaagg   13020
cgatagaagg cgatgcgctg cgaatcggga gcggcgatac cgtaaagcac gaggaagcgg   13080
tcagcccatt cgccgccaag ctcttcagca atatcacggg tagccaacgc tatgtcctga   13140
tagcggtccg ccacacccag ccggccacag tcgatgaatc cagaaaagcg gccattttcc   13200
accatgatat tcggcaagca ggcatcgcca tgggtcacga cgagatcctc gccgtcgggc   13260
atgcgcgcct tgagcctggc gaacagttcg gctggcgcga gccccctgatg ctcttcgtcc   13320 agatcatcct gatcgacaag accggcttcc atccgagtac gtgctcgctc gatgcgatgt   13380
ttcgcttggt ggtcgaatgg gcaggtagcc ggatcaagcg tatgcagccg ccgcattgca   13440
tcagccatga tggatacttt ctcggcagga gcaaggtgag atgacaggag atcctgcccc   13500
ggcacttcgc ccaatagcag ccagtccctt cccgcttcag tgacaacgtc gagcacagct   13560
gcgcaaggaa cgcccgtcgt ggccagccac gatagccgcg ctgcctcgtc ctgcagttca   13620
ttcagggcac cggacaggtc ggtcttgaca aaaagaaccg ggcgcccctg cgctgacagc   13680
cggaacacgg cggcatcaga gcagccgatt gtctgttgtg cccagtcata gccgaatagc   13740
ctctccaccc aagcggccgg agaacctgcg tgcaatccat cttgttcaat catgcgaaac   13800
gatcctcatc ctgtctcttg atcagatctt gatccctgc gccatcagat ccttggcggc   13860
aagaaagcca tccagtttac tttgcagggc ttcccaacct taccagaggg cgccccagct   13920
ggcaattccg gttcgcttgc tgtccataaa accgcccagt ctagctatcg ccatgtaagc   13980
ccactgcaag ctacctgctt tctctttgcg cttgcgtttt cccttgtcca gatagccag   14040 tagctgacat tcatcccagg tggcactttt cggggaaatg tgcgcgcccg cgttcctgct   14100
ggcgctgggc ctgtttctgg cgctggactt cccgctgttc cgtcagcagc ttttcgccca   14160
cggccttgat gatcgcggcg gccttggcct gcatatcccg attcaacggc ccagggcgt   14220 ccagaacggg cttcaggcgc tcccgaaggt                                    14250
```

<210> SEQ ID NO 76
<211> LENGTH: 1011
<212> TYPE: DNA
<213> ORGANISM: Burkholderia thailandensis

<400> SEQUENCE: 76

```
tctagatacg ggagaagaac gatcatgacg atcctggggg cgctggtgat tctgtacgac     60
ccgacggacg agcagttgtc ggggctggag gcgctcgcgc gcgacagcga cgcgctcgtg    120
gtcgtggaca acacgccgca cgagcacgcg cggcgcgcg agcgggtgcg tgcgctgtcg    180
gcgcggacga acacggtgtg gcgacaccac ggcaaccggg gcggggtcgc gggcgggtac    240
aacgcggggc tgtcggtgct gttgcgcgca ggcgtcgagg cggtcgcgct gttcgaccag    300
gactcgacgt tgcggccgg gtacttcgag cggatcgcg aggcgtgcgc gcaactgggt    360
gagcaaccgg gcgcgcacgc gggcgcgttc atcgcgggcc cgcggatcta cgacgcgaac    420
```

```
gagcagcgct tcctgccgga gctgatgacg agcggggtga cggtgcgccg cgtgcgggtg    480
gagggcgaga cggcgccgca gcgctgcgcg ttcctgatct cgtcgggcag cgtgatttcg    540
cgggccgcgt acgcgcggct cggtcgattc gacgaggcgc tgttcatcga tcacgtcgac    600
accgagtatt gcctgcgcgc gctcgcgcac aacgtgccgc tgtacgtggt gccgccgctc    660
gtgctgacgc accggatcgg cgcgcggcgc cggcacaagg tggggccgtt cgagctgacg    720
gcgatgcatc acgggtggtt cgccgatac tacggcgcgc gcaacgcgat gcaactgggg    780
ctgcagtacg gcttgcggtt tccggtggcg ctggtgccga atctgctgac gatatggcag    840
gtgatccagg tggtgctgtg cgagcgggag aagggcgcga gctgcgcgg gatcgcgctg    900 ggcgtgctcg acggcctgtt cgggcggctg ggatcgttcg acgatgcgcg cgcgggcgcg    960
gcggcgcgcg agccggtgcg gcaggaatga tcggcgaaac gcattgagct c           1011

<210> SEQ ID NO 77
<211> LENGTH: 888
<212> TYPE: DNA
<213> ORGANISM: Pseudomonas aeruginosa
<220> FEATURE:
<221> NAME/KEY: CDS
<222> LOCATION: (1)..(888)

<400> SEQUENCE: 77 atg cgg cgc gaa agt ctg ttg gta tcg gtt tgc aag ggc ctg cgg gta    48
Met Arg Arg Glu Ser Leu Leu Val Ser Val Cys Lys Gly Leu Arg Val
1               5                   10                  15 cat gtc gag cgc gtt ggg cag gat ccc ggg cgc agc acg gtg atg ctg    96
His Val Glu Arg Val Gly Gln Asp Pro Gly Arg Ser Thr Val Met Leu
            20                  25                  30 gtc aac ggc gcg atg gcg acc acc gcc tcg ttc gcc cgg acc tgc aag   144
Val Asn Gly Ala Met Ala Thr Thr Ala Ser Phe Ala Arg Thr Cys Lys
        35                  40                  45 tgc ctg gcc gaa cat ttc aac gtg gtg ctg ttc gac ctg ccc ttc gcc   192
Cys Leu Ala Glu His Phe Asn Val Val Leu Phe Asp Leu Pro Phe Ala
    50                  55                  60 ggg cag tcg cgt cag cac aac ccg cag cgc ggg ttg atc acc aag gac   240
Gly Gln Ser Arg Gln His Asn Pro Gln Arg Gly Leu Ile Thr Lys Asp
65                  70                  75                  80 gac gag gtg gaa atc ctc ctg gcg ctg atc gag cgc ttc gag gtc aat   288
Asp Glu Val Glu Ile Leu Leu Ala Leu Ile Glu Arg Phe Glu Val Asn
                85                  90                  95 cac ctg gtc tcc gcg tcg tgg ggc ggt atc tcc acg ctg ctg gcg ctg   336
His Leu Val Ser Ala Ser Trp Gly Gly Ile Ser Thr Leu Leu Ala Leu
            100                 105                 110 tcg cgc aat ccg cgc ggc atc cgc agc tcg gtg gtg atg gca ttc gcc   384
Ser Arg Asn Pro Arg Gly Ile Arg Ser Ser Val Val Met Ala Phe Ala
        115                 120                 125 cct gga ctg aac cag gcg atg ctc gac tac gtc ggg cgg gcg cag gcg   432
Pro Gly Leu Asn Gln Ala Met Leu Asp Tyr Val Gly Arg Ala Gln Ala
    130                 135                 140 ctg atc gag ctg gac gac aag tcg gcg atc ggc cat ctg ctc aac gag   480
Leu Ile Glu Leu Asp Asp Lys Ser Ala Ile Gly His Leu Leu Asn Glu
145                 150                 155                 160 acc gtc ggc aaa tac ctg ccg ccg cgc ctg aaa gcc agc aac cat cag   528
Thr Val Gly Lys Tyr Leu Pro Pro Arg Leu Lys Ala Ser Asn His Gln
                165                 170                 175 cac atg gct tcg ctg gcc acc ggc gaa tac gag cag gcg cgc ttt cac   576
His Met Ala Ser Leu Ala Thr Gly Glu Tyr Glu Gln Ala Arg Phe His
            180                 185                 190
```

-continued

```
atc gac cag gtg ctg gcg ctc aac gat cgg ggc tac ctg gct tgc ctg      624
Ile Asp Gln Val Leu Ala Leu Asn Asp Arg Gly Tyr Leu Ala Cys Leu
            195                 200                 205 gag cgg atc cag agc cac gtg cat ttc atc aac ggc agc tgg gac gaa      672
Glu Arg Ile Gln Ser His Val His Phe Ile Asn Gly Ser Trp Asp Glu
    210                 215                 220 tac acc acc gcc gag gac gcc cgc cag ttc cgc gac tac ctg ccg cac      720
Tyr Thr Thr Ala Glu Asp Ala Arg Gln Phe Arg Asp Tyr Leu Pro His
225                 230                 235                 240 tgc agt ttc tcg cgg gtg gag ggc acc ggg cat ttc ctc gac ctg gag      768
Cys Ser Phe Ser Arg Val Glu Gly Thr Gly His Phe Leu Asp Leu Glu
                245                 250                 255 tcc aag ctg gcc gcg gta cgc gtg cac cgc gcc ctc ctc gag cac ctg      816
Ser Lys Leu Ala Ala Val Arg Val His Arg Ala Leu Leu Glu His Leu
            260                 265                 270 ctg aag caa ccg gag ccg cag cgg gcg gaa cgc gcg gcg gga ttc cac      864
Leu Lys Gln Pro Glu Pro Gln Arg Ala Glu Arg Ala Ala Gly Phe His
        275                 280                 285 gag atg gcc atc ggc tac gcc tga                                      888
Glu Met Ala Ile Gly Tyr Ala
    290                 295
```

<210> SEQ ID NO 78
<211> LENGTH: 295
<212> TYPE: PRT
<213> ORGANISM: Pseudomonas aeruginosa

<400> SEQUENCE: 78

```
Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220
```

```
Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
            245                 250                 255

Ser Lys Leu Ala Ala Val Arg Val His Arg Ala Leu Leu Glu His Leu
        260                 265                 270

Leu Lys Gln Pro Glu Pro Gln Arg Ala Glu Arg Ala Ala Gly Phe His
    275                 280                 285

Glu Met Ala Ile Gly Tyr Ala
290                 295

<210> SEQ ID NO 79
<211> LENGTH: 888
<212> TYPE: DNA
<213> ORGANISM: Pseudomonas aeruginosa
<220> FEATURE:
<221> NAME/KEY: CDS
<222> LOCATION: (1)..(888)

<400> SEQUENCE: 79 atg cgg cgc gaa agt ctg ttg gta tcg gtt tgc aag ggc ctg cgg gta    48
Met Arg Arg Glu Ser Leu Leu Val Ser Val Cys Lys Gly Leu Arg Val
1               5                   10                  15 cat gtc gag cgc gtt ggg cag gat ccc ggg cgc agc acg gtg atg ctg    96
His Val Glu Arg Val Gly Gln Asp Pro Gly Arg Ser Thr Val Met Leu
                20                  25                  30 gtc aac ggc gcg atg gcg acc acc gcc tcg ttc gcc cgg acc tgc aag   144
Val Asn Gly Ala Met Ala Thr Thr Ala Ser Phe Ala Arg Thr Cys Lys
            35                  40                  45 tgc ctg gcc gaa cat ttc aac gtg gtg ctg ttc gac ctg ccc ttc gcc   192
Cys Leu Ala Glu His Phe Asn Val Val Leu Phe Asp Leu Pro Phe Ala
    50                  55                  60 ggg cag tcg cgt cag cac aac ccg cag cgc ggg ttg atc acc aag gac   240
Gly Gln Ser Arg Gln His Asn Pro Gln Arg Gly Leu Ile Thr Lys Asp
65                  70                  75                  80 gac gag gtg gaa atc ctc ctg gcg ctg atc gag cgc ttc gag gtc aat   288
Asp Glu Val Glu Ile Leu Leu Ala Leu Ile Glu Arg Phe Glu Val Asn
                85                  90                  95 cac ctg gtc tcc gcg tcc tgg ggc ggt atc tcc acg ctg ctg gcg ctg   336
His Leu Val Ser Ala Ser Trp Gly Gly Ile Ser Thr Leu Leu Ala Leu
                100                 105                 110 tcg cgc aat ccg cgc ggc atc cgc agc tcg gtg gtg atg gca ttc gcc   384
Ser Arg Asn Pro Arg Gly Ile Arg Ser Ser Val Val Met Ala Phe Ala
            115                 120                 125 cct gga ctg aac cag gcg atg ctc gac tac gtc ggg cgg gcg cag gcg   432
Pro Gly Leu Asn Gln Ala Met Leu Asp Tyr Val Gly Arg Ala Gln Ala
    130                 135                 140 ctg atc gag ctg gac gac aag tcg gcg atc ggc cat ctg ctc aac gag   480
Leu Ile Glu Leu Asp Asp Lys Ser Ala Ile Gly His Leu Leu Asn Glu
145                 150                 155                 160 acc gtc ggc aaa tac ctg ccg cag cgc ctg aaa gcc agc aac cat cag   528
Thr Val Gly Lys Tyr Leu Pro Gln Arg Leu Lys Ala Ser Asn His Gln
                165                 170                 175 cac atg gct tcg ctg gcc acc ggc gaa tac gag cag gcg cgc ttt cac   576
His Met Ala Ser Leu Ala Thr Gly Glu Tyr Glu Gln Ala Arg Phe His
                180                 185                 190 atc gac cag gtg ctg gcg ctc aac gat cgg ggc tac ttg gct tgc ctg   624
Ile Asp Gln Val Leu Ala Leu Asn Asp Arg Gly Tyr Leu Ala Cys Leu
            195                 200                 205 gag cgg atc cag agc cac gtg cat ttc atc aac ggc agc tgg gac gaa   672
```

| | | | | | | | | | | | | | | | |
|---|---|---|---|---|---|---|---|---|---|---|---|---|---|---|---|
| Glu | Arg | Ile | Gln | Ser | His | Val | His | Phe | Ile | Asn | Gly | Ser | Trp | Asp | Glu |
| | 210 | | | | 215 | | | | | 220 | | | | | |

```
tac acc acc gcc gag gac gcc cgc cag ttc cgc gac tac ctg ccg cac       720
Tyr Thr Thr Ala Glu Asp Ala Arg Gln Phe Arg Asp Tyr Leu Pro His
225             230                 235                 240 tgc agt ttc tcg cgg gtg gag ggc acc ggg cat ttc ctc gac ctg gag       768
Cys Ser Phe Ser Arg Val Glu Gly Thr Gly His Phe Leu Asp Leu Glu
                245                 250                 255 tcc aag ctg gca gcg gta cgc gtg cac cgc gcc ctg ctc gag cac ctg       816
Ser Lys Leu Ala Ala Val Arg Val His Arg Ala Leu Leu Glu His Leu
            260                 265                 270 ctg aag caa ccg gag ccg cag cgg gcg gaa cgc gcg gcg gga ttc cac       864
Leu Lys Gln Pro Glu Pro Gln Arg Ala Glu Arg Ala Ala Gly Phe His
        275                 280                 285 gag atg gcc atc ggc tac gcc tga                                       888
Glu Met Ala Ile Gly Tyr Ala
    290                 295

<210> SEQ ID NO 80
<211> LENGTH: 295
<212> TYPE: PRT
<213> ORGANISM: Pseudomonas aeruginosa

<400> SEQUENCE: 80

Met Arg Arg Glu Ser Leu Leu Val Ser Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Gln Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255
```

```
Ser Lys Leu Ala Ala Val Arg Val His Arg Ala Leu Leu Glu His Leu
         260                 265                 270
Leu Lys Gln Pro Glu Pro Gln Arg Ala Glu Arg Ala Ala Gly Phe His
         275                 280                 285
Glu Met Ala Ile Gly Tyr Ala
         290                 295

<210> SEQ ID NO 81
<211> LENGTH: 888
<212> TYPE: DNA
<213> ORGANISM: Pseudomonas aeruginosa
<220> FEATURE:
<221> NAME/KEY: CDS
<222> LOCATION: (1)..(888)

<400> SEQUENCE: 81 atg cgg cgc gaa agt ctg ttg gta acg gta tgc aag ggc ctg cgg gta      48
Met Arg Arg Glu Ser Leu Leu Val Thr Val Cys Lys Gly Leu Arg Val
1                 5                  10                  15 cat gtc gag cgc gtg ggg cag gat ccc ggg cgc gac acg gtg atg ctg      96
His Val Glu Arg Val Gly Gln Asp Pro Gly Arg Asp Thr Val Met Leu
                 20                  25                  30 gtc aac ggc gcg atg gcg acc acc gcc tcg ttc gcc cgg acc tgc aag     144
Val Asn Gly Ala Met Ala Thr Thr Ala Ser Phe Ala Arg Thr Cys Lys
             35                  40                  45 tgc ctg gcc gaa cat ttc aac gtg gtg ctg ttc gac ctg ccc ttc gcc     192
Cys Leu Ala Glu His Phe Asn Val Val Leu Phe Asp Leu Pro Phe Ala
     50                  55                  60 ggg cag tcg cgg cag cac aat ccg cag cgc ggg ttg atc acc aag gac     240
Gly Gln Ser Arg Gln His Asn Pro Gln Arg Gly Leu Ile Thr Lys Asp
 65                  70                  75                  80 gac gag gtg gag att ctc ctg gcg ctg atc gag cgc ttc gct gtc aac     288
Asp Glu Val Glu Ile Leu Leu Ala Leu Ile Glu Arg Phe Ala Val Asn
                 85                  90                  95 cac ctg gtc tcg gcc tcc tgg ggc ggc atc tcc acg ctg ctg gcg ctg     336
His Leu Val Ser Ala Ser Trp Gly Gly Ile Ser Thr Leu Leu Ala Leu
                100                 105                 110 tcg cgc aac ccg cgc ggg gtc cgc agc tcg gtg gtg atg gcg ttc gcg     384
Ser Arg Asn Pro Arg Gly Val Arg Ser Ser Val Val Met Ala Phe Ala
            115                 120                 125 ccg ggg ctg aac cag gcg atg ctc gat tat gtc ggg cgg gcc cag gaa     432
Pro Gly Leu Asn Gln Ala Met Leu Asp Tyr Val Gly Arg Ala Gln Glu
        130                 135                 140 ctg atc gaa ctg gac gac aag tcg gcg atc ggc cac ctg ctc aac gag     480
Leu Ile Glu Leu Asp Asp Lys Ser Ala Ile Gly His Leu Leu Asn Glu
145                 150                 155                 160 acc gtc ggc aag tac ctg ccg ccg cgg ctg aag gcc agc aac cat cag     528
Thr Val Gly Lys Tyr Leu Pro Pro Arg Leu Lys Ala Ser Asn His Gln
                165                 170                 175 cac atg gcc tcc ctg gcc act ggc gag tac gag cag gcg cgt ttc cac     576
His Met Ala Ser Leu Ala Thr Gly Glu Tyr Glu Gln Ala Arg Phe His
            180                 185                 190 atc gac cag gtg ctg gcg ctc aat gac cgt ggc tac ctg agc tgc ctg     624
Ile Asp Gln Val Leu Ala Leu Asn Asp Arg Gly Tyr Leu Ser Cys Leu
        195                 200                 205 ggg cag atc cag agt cac gtg cat ttc atc aac ggc agc tgg gac gag     672
Gly Gln Ile Gln Ser His Val His Phe Ile Asn Gly Ser Trp Asp Glu
    210                 215                 220 tac acc acc gcc gag gac gcc cgc cag ttc cgc gat tac ctg ccg cat     720
Tyr Thr Thr Ala Glu Asp Ala Arg Gln Phe Arg Asp Tyr Leu Pro His
225                 230                 235                 240
```

```
tgc agt ttt tcg cgg gtg gaa ggc acc ggg cac ttc ctc gac ctg gag      768
Cys Ser Phe Ser Arg Val Glu Gly Thr Gly His Phe Leu Asp Leu Glu
            245                 250                 255 tcc aag ctg gcg gcg gcg cgt gtg cac cgg gcg ttg ctc gag cac ctg      816
Ser Lys Leu Ala Ala Ala Arg Val His Arg Ala Leu Leu Glu His Leu
        260                 265                 270 ctg gcg caa ccg gaa ccg tgg cgc tcc gag cag gcg gcg gga ttc cac      864
Leu Ala Gln Pro Glu Pro Trp Arg Ser Glu Gln Ala Ala Gly Phe His
    275                 280                 285 gag atg gcc atc ggc tac gcc tga                                      888
Glu Met Ala Ile Gly Tyr Ala
        290                 295
```

<210> SEQ ID NO 82
<211> LENGTH: 295
<212> TYPE: PRT
<213> ORGANISM: Pseudomonas aeruginosa

<400> SEQUENCE: 82

```
Met Arg Arg Glu Ser Leu Leu Val Thr Val Cys Lys Gly Leu Arg Val
1               5                   10                  15

His Val Glu Arg Val Gly Gln Asp Pro Gly Arg Asp Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Ala Val Asn
                85                  90                  95

His Leu Val Ser Ala Ser Trp Gly Gly Ile Ser Thr Leu Leu Ala Leu
            100                 105                 110

Ser Arg Asn Pro Arg Gly Val Arg Ser Ser Val Val Met Ala Phe Ala
        115                 120                 125

Pro Gly Leu Asn Gln Ala Met Leu Asp Tyr Val Gly Arg Ala Gln Glu
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ser Cys Leu
        195                 200                 205

Gly Gln Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Ala Arg Val His Arg Ala Leu Leu Glu His Leu
            260                 265                 270

Leu Ala Gln Pro Glu Pro Trp Arg Ser Glu Gln Ala Ala Gly Phe His
        275                 280                 285
```

```
Glu Met Ala Ile Gly Tyr Ala
    290                 295
```

<210> SEQ ID NO 83
<211> LENGTH: 1281
<212> TYPE: DNA
<213> ORGANISM: Pseudomonas aeruginosa
<220> FEATURE:
<221> NAME/KEY: CDS
<222> LOCATION: (1)..(1281)

<400> SEQUENCE: 83

```
atg cac gcc att ctc atc gcc atc ggt tcg gcc ggc gac gtg ttc ccc      48
Met His Ala Ile Leu Ile Ala Ile Gly Ser Ala Gly Asp Val Phe Pro
1               5                   10                  15 ttc atc ggc ctg gcc cgc acc ctg aag ttg cgc ggc cac cgc gtc agc      96
Phe Ile Gly Leu Ala Arg Thr Leu Lys Leu Arg Gly His Arg Val Ser
            20                  25                  30 ctg tgc acc att ccg gtg ttt cgc gcc gcg gtg gag cag cac ggc atc     144
Leu Cys Thr Ile Pro Val Phe Arg Ala Ala Val Glu Gln His Gly Ile
        35                  40                  45 gag ttc gtc ccg ctc agc gac gaa ctg acc tac cgc gga acc atg ggc     192
Glu Phe Val Pro Leu Ser Asp Glu Leu Thr Tyr Arg Arg Thr Met Gly
    50                  55                  60 gac ccg cgc ctg tgg gat ccg aag acc tcg ttc gga gtg ctc tgg cag     240
Asp Pro Arg Leu Trp Asp Pro Lys Thr Ser Phe Gly Val Leu Trp Gln
65                  70                  75                  80 gcc atc gcc ggg atg atc gag ccg gtc tac gag tac gtc tgc gca cag     288
Ala Ile Ala Gly Met Ile Glu Pro Val Tyr Glu Tyr Val Cys Ala Gln
                85                  90                  95 cgc cac gac gac atc gtg gtg gtc ggt tcg ctg tgg gcc ctg ggc gcg     336
Arg His Asp Asp Ile Val Val Val Gly Ser Leu Trp Ala Leu Gly Ala
            100                 105                 110 cgg atc gcc cat gag aaa tac ggg att ccc tac ctg tcg gtg cag gtc     384
Arg Ile Ala His Glu Lys Tyr Gly Ile Pro Tyr Leu Ser Val Gln Val
        115                 120                 125 tcg ccg tcg acc ctg ctg tcg gcg cac ctg ccg ccg gtc cac ccc agg     432
Ser Pro Ser Thr Leu Leu Ser Ala His Leu Pro Pro Val His Pro Arg
    130                 135                 140 ttc aac gtg ccc gag cag gtc ccg ctg gcg atg cgc aag ttg ctc tgg     480
Phe Asn Val Pro Glu Gln Val Pro Leu Ala Met Arg Lys Leu Leu Trp
145                 150                 155                 160 cgc tgc atc gaa cgc ttc aag ctg gac cgc acc tgc gcc ccg gag atc     528
Arg Cys Ile Glu Arg Phe Lys Leu Asp Arg Thr Cys Ala Pro Glu Ile
                165                 170                 175 aac gcg gtg cgc cgc aag gtc ggc ctg gtc ggc ccg gcg aag cgc atc     576
Asn Ala Val Arg Arg Lys Val Gly Leu Val Gly Pro Ala Lys Arg Ile
            180                 185                 190 ttc acc cag tgg atg cat tcg cca cag gga gtg ctc tgc ctg ttc ccg     624
Phe Thr Gln Trp Met His Ser Pro Gln Gly Val Leu Cys Leu Phe Pro
        195                 200                 205 gcc tgg ttc gca ccg ccc cag cag gac tgg ccg caa ccg ctg cac atg     672
Ala Trp Phe Ala Pro Pro Gln Gln Asp Trp Pro Gln Pro Leu His Met
    210                 215                 220 acc ggc ttc ccg ctg ttc gac ggc agc gtc ccg ggg acc cgc ctc gac     720
Thr Gly Phe Pro Leu Phe Asp Gly Ser Val Pro Gly Thr Arg Leu Asp
225                 230                 235                 240 gac gag ttg cag cgc ttc ctc gag cag ggc agt cgg ccg ctg gtg ttc     768
Asp Glu Leu Gln Arg Phe Leu Glu Gln Gly Ser Arg Pro Leu Val Phe
                245                 250                 255 acc cag ggt tcg acc gag cac ctg cag gga gac ttc tat gcc atg gcc     816
Thr Gln Gly Ser Thr Glu His Leu Gln Gly Asp Phe Tyr Ala Met Ala
```

```
Thr Gln Gly Ser Thr Glu His Leu Gln Gly Asp Phe Tyr Ala Met Ala
            260                 265                 270 ttg cgc gcg ctg gag cgt ctc ggc gcc cgc ggc atc ttc ctc acc ggc      864
Leu Arg Ala Leu Glu Arg Leu Gly Ala Arg Gly Ile Phe Leu Thr Gly
            275                 280                 285 gcc ggc cag gag ccg ctg cgt ggc ttg ccg agc cac gtg ctg caa cgc      912
Ala Gly Gln Glu Pro Leu Arg Gly Leu Pro Ser His Val Leu Gln Arg
        290                 295                 300 tcg tac gtg ccg ttg ggg gcc ttg ctg ccg gcg tgc gcc ggg ctg gtc      960
Ser Tyr Val Pro Leu Gly Ala Leu Leu Pro Ala Cys Ala Gly Leu Val
305                 310                 315                 320 cac ccg gcc ggc atc ggc gcc atg agc ctg gcg ctg gcg gcg ggg gtg     1008
His Pro Ala Gly Ile Gly Ala Met Ser Leu Ala Leu Ala Ala Gly Val
                325                 330                 335 ccg cag gtg ctg ctg cct tgc gcc cac gac cag ttc gac aac gcc gaa     1056
Pro Gln Val Leu Leu Pro Cys Ala His Asp Gln Phe Asp Asn Ala Glu
            340                 345                 350 cgc ctg gtc cgc ctc ggc tgc ggt atc cgc ctg ggc ctg ccg cta cgc     1104
Arg Leu Val Arg Leu Gly Cys Gly Ile Arg Leu Gly Leu Pro Leu Arg
        355                 360                 365 gag cag gcg ctg cgc gag tcg ctc tgg cgg ctg ctc gag gac ccg gcg     1152
Glu Gln Ala Leu Arg Glu Ser Leu Trp Arg Leu Leu Glu Asp Pro Ala
370                 375                 380 ctg gcg gcg gcc tgt cgg cgt ttc atg gaa ttg tca caa ccg cac agt     1200
Leu Ala Ala Ala Cys Arg Arg Phe Met Glu Leu Ser Gln Pro His Ser
385                 390                 395                 400 atc gct tgc ggt aaa gcg gcc caa gtg gtc gaa cgt tgt cat agg gag     1248
Ile Ala Cys Gly Lys Ala Ala Gln Val Val Glu Arg Cys His Arg Glu
                405                 410                 415 ggg gat gtg cga tgg ctg aaa gcc gcg tcc tga                         1281
Gly Asp Val Arg Trp Leu Lys Ala Ala Ser
            420                 425

<210> SEQ ID NO 84
<211> LENGTH: 426
<212> TYPE: PRT
<213> ORGANISM: Pseudomonas aeruginosa

<400> SEQUENCE: 84

Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
                20                  25                  30

Leu Cys Thr Ile Pro Val Phe Arg Ala Ala Val Glu Gln His Gly Ile
            35                  40                  45

Glu Phe Val Pro Leu Ser Asp Glu Leu Thr Tyr Arg Arg Thr Met Gly
        50                  55                  60

Asp Pro Arg Leu Trp Asp Pro Lys Thr Ser Phe Gly Val Leu Trp Gln
65                  70                  75                  80

Ala Ile Ala Gly Met Ile Glu Pro Val Tyr Glu Tyr Val Cys Ala Gln
                85                  90                  95

Arg His Asp Asp Ile Val Val Gly Ser Leu Trp Ala Leu Gly Ala
                100                 105                 110

Arg Ile Ala His Glu Lys Tyr Gly Ile Pro Tyr Leu Ser Val Gln Val
            115                 120                 125

Ser Pro Ser Thr Leu Leu Ser Ala His Leu Pro Pro Val His Pro Arg
        130                 135                 140

Phe Asn Val Pro Glu Gln Val Pro Leu Ala Met Arg Lys Leu Leu Trp
```

|     |     |     |     |     |     |     |     |     |     |     |     |     |     |     |     |
| --- | --- | --- | --- | --- | --- | --- | --- | --- | --- | --- | --- | --- | --- | --- | --- |
| 145 |     |     |     |     | 150 |     |     |     |     | 155 |     |     |     |     | 160 |

Arg Cys Ile Glu Arg Phe Lys Leu Asp Arg Thr Cys Ala Pro Glu Ile
                165                 170                 175

Asn Ala Val Arg Arg Lys Val Gly Leu Val Gly Pro Ala Lys Arg Ile
                180                 185                 190

Phe Thr Gln Trp Met His Ser Pro Gln Gly Val Leu Cys Leu Phe Pro
                195                 200                 205

Ala Trp Phe Ala Pro Pro Gln Gln Asp Trp Pro Gln Pro Leu His Met
                210                 215                 220

Thr Gly Phe Pro Leu Phe Asp Gly Ser Val Pro Gly Thr Arg Leu Asp
225                 230                 235                 240

Asp Glu Leu Gln Arg Phe Leu Glu Gln Gly Ser Arg Pro Leu Val Phe
                245                 250                 255

Thr Gln Gly Ser Thr Glu His Leu Gln Gly Asp Phe Tyr Ala Met Ala
                260                 265                 270

Leu Arg Ala Leu Glu Arg Leu Gly Ala Arg Gly Ile Phe Leu Thr Gly
                275                 280                 285

Ala Gly Gln Glu Pro Leu Arg Gly Leu Pro Ser His Val Leu Gln Arg
                290                 295                 300

Ser Tyr Val Pro Leu Gly Ala Leu Leu Pro Ala Cys Ala Gly Leu Val
305                 310                 315                 320

His Pro Ala Gly Ile Gly Ala Met Ser Leu Ala Leu Ala Ala Gly Val
                325                 330                 335

Pro Gln Val Leu Leu Pro Cys Ala His Asp Gln Phe Asp Asn Ala Glu
                340                 345                 350

Arg Leu Val Arg Leu Gly Cys Gly Ile Arg Leu Gly Leu Pro Leu Arg
                355                 360                 365

Glu Gln Ala Leu Arg Glu Ser Leu Trp Arg Leu Leu Glu Asp Pro Ala
                370                 375                 380

Leu Ala Ala Ala Cys Arg Arg Phe Met Glu Leu Ser Gln Pro His Ser
385                 390                 395                 400

Ile Ala Cys Gly Lys Ala Ala Gln Val Val Glu Arg Cys His Arg Glu
                405                 410                 415

Gly Asp Val Arg Trp Leu Lys Ala Ala Ser
                420                 425

```
<210> SEQ ID NO 85
<211> LENGTH: 1281
<212> TYPE: DNA
<213> ORGANISM: Pseudomonas aeruginosa
<220> FEATURE:
<221> NAME/KEY: CDS
<222> LOCATION: (1)..(1281)

<400> SEQUENCE: 85
``` atg cac gcc atc ctc atc gcc atc ggc tcg gcc ggc gac gta ttt ccc      48
Met His Ala Ile Leu Ile Ala Ile Gly Ser Ala Gly Asp Val Phe Pro
1               5                   10                  15 ttc atc ggc ctg gcc cgg acc ctg aaa ctg cgc ggg cac cgc gtg agc      96
Phe Ile Gly Leu Ala Arg Thr Leu Lys Leu Arg Gly His Arg Val Ser
                20                  25                  30 ctc tgc acc atc ccg gtg ttt cgc gac gcg gtg gag cag cac ggc atc     144
Leu Cys Thr Ile Pro Val Phe Arg Asp Ala Val Glu Gln His Gly Ile
            35                  40                  45 gcg ttc gtc ccg ctg agc gac gaa ctg acc tac cgc cgg acc atg ggc     192
Ala Phe Val Pro Leu Ser Asp Glu Leu Thr Tyr Arg Arg Thr Met Gly
        50                  55                  60

```
gat ccg cgc ctg tgg gac ccc aag acg tcc ttc ggc gtg ctc tgg caa      240
Asp Pro Arg Leu Trp Asp Pro Lys Thr Ser Phe Gly Val Leu Trp Gln
65                  70                  75                  80 gcc atc gcc ggg atg atc gag ccg gtc tac gag tac gtc tcg gcg cag      288
Ala Ile Ala Gly Met Ile Glu Pro Val Tyr Glu Tyr Val Ser Ala Gln
                85                  90                  95 cgc cat gac gac atc gtg gtg gtc ggc tcg cta tgg gcg ctg ggc gca      336
Arg His Asp Asp Ile Val Val Val Gly Ser Leu Trp Ala Leu Gly Ala
            100                 105                 110 cgc atc gct cac gag aag tac ggg att ccc tac ctg tcc gcg cag gtc      384
Arg Ile Ala His Glu Lys Tyr Gly Ile Pro Tyr Leu Ser Ala Gln Val
        115                 120                 125 tcg cca tcg acc ctg ttg tcg gcg cac ctg ccg ccg gta cac ccc aag      432
Ser Pro Ser Thr Leu Leu Ser Ala His Leu Pro Pro Val His Pro Lys
    130                 135                 140 ttc aac gtg ccc gag cag atg ccg ctg gcg atg cgc aag ctg ctc tgg      480
Phe Asn Val Pro Glu Gln Met Pro Leu Ala Met Arg Lys Leu Leu Trp
145                 150                 155                 160 cgc tgc atc gag cgc ttc aag ctg gat cgc acc tgc gcg ccg gag atc      528
Arg Cys Ile Glu Arg Phe Lys Leu Asp Arg Thr Cys Ala Pro Glu Ile
                165                 170                 175 aac gcg gtg cgc cgc aag gtc ggc ctg gaa acg ccg gtg aag cgc atc      576
Asn Ala Val Arg Arg Lys Val Gly Leu Glu Thr Pro Val Lys Arg Ile
            180                 185                 190 ttc acc caa tgg atg cat tcg ccg cag ggc gtg gtc tgc ctg ttc ccg      624
Phe Thr Gln Trp Met His Ser Pro Gln Gly Val Val Cys Leu Phe Pro
        195                 200                 205 gcc tgg ttc gcg ccg ccc cag cag gat tgg ccg caa ccc ctg cac atg      672
Ala Trp Phe Ala Pro Pro Gln Gln Asp Trp Pro Gln Pro Leu His Met
    210                 215                 220 acc ggc ttc ccg ctg ttc gac ggc agt atc ccg ggg acc ccg ctc gac      720
Thr Gly Phe Pro Leu Phe Asp Gly Ser Ile Pro Gly Thr Pro Leu Asp
225                 230                 235                 240 gac gaa ctg caa cgc ttt ctc gat cag ggc agc cgg ccg ctg gtg ttc      768
Asp Glu Leu Gln Arg Phe Leu Asp Gln Gly Ser Arg Pro Leu Val Phe
                245                 250                 255 acc cag ggc tcg acc gaa cac ctg cag ggc gac ttc tac gcc atg gcc      816
Thr Gln Gly Ser Thr Glu His Leu Gln Gly Asp Phe Tyr Ala Met Ala
            260                 265                 270 ctg cgc gcg ctg gaa cgc ctc ggc gcg cgt ggg atc ttc ctc acc ggc      864
Leu Arg Ala Leu Glu Arg Leu Gly Ala Arg Gly Ile Phe Leu Thr Gly
        275                 280                 285 gcc ggc cag gaa ccg ctg cgc ggc ttg ccg aac cac gtg ctg cag cgc      912
Ala Gly Gln Glu Pro Leu Arg Gly Leu Pro Asn His Val Leu Gln Arg
    290                 295                 300 gcc tac gcg cca ctg gga gcc ttg ctg cca tcg tgc gcc ggg ctg gtc      960
Ala Tyr Ala Pro Leu Gly Ala Leu Leu Pro Ser Cys Ala Gly Leu Val
305                 310                 315                 320 cat ccg ggc ggt atc ggc gcc atg agc cta gcc ttg gcg gcg ggg gtg     1008
His Pro Gly Gly Ile Gly Ala Met Ser Leu Ala Leu Ala Ala Gly Val
                325                 330                 335 ccg cag gtg ctg ctg ccc tgt gcc cac gac cag ttc gac aat gcc gaa     1056
Pro Gln Val Leu Leu Pro Cys Ala His Asp Gln Phe Asp Asn Ala Glu
            340                 345                 350 cgg ctg gtc cgg ctc ggc tgc ggg atg cgc ctg ggc gtg ccg ttg cgc     1104
Arg Leu Val Arg Leu Gly Cys Gly Met Arg Leu Gly Val Pro Leu Arg
        355                 360                 365 gag cag gag ttg cgc ggg gcg ctg tgg cgc ttg ctc gag gac ccg gcc     1152
Glu Gln Glu Leu Arg Gly Ala Leu Trp Arg Leu Leu Glu Asp Pro Ala
```

```
                    370                 375                 380
atg gcg gcg gcc tgt cgg cgt ttc atg gaa ttg tca caa ccg cac agt      1200
Met Ala Ala Ala Cys Arg Arg Phe Met Glu Leu Ser Gln Pro His Ser
385                 390                 395                 400 atc gct tgc ggt aaa gcg gcc cag gtg gtc gaa cgt tgt cat agg gag      1248
Ile Ala Cys Gly Lys Ala Ala Gln Val Val Glu Arg Cys His Arg Glu
                405                 410                 415 ggg gat gct cga tgg ctg aag gct gcg tcc tga                          1281
Gly Asp Ala Arg Trp Leu Lys Ala Ala Ser
                420                 425

<210> SEQ ID NO 86
<211> LENGTH: 426
<212> TYPE: PRT
<213> ORGANISM: Pseudomonas aeruginosa

<400> SEQUENCE: 86

Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
                20                  25                  30

Leu Cys Thr Ile Pro Val Phe Arg Asp Ala Val Glu Gln His Gly Ile
            35                  40                  45

Ala Phe Val Pro Leu Ser Asp Glu Leu Thr Tyr Arg Arg Thr Met Gly
        50                  55                  60

Asp Pro Arg Leu Trp Asp Pro Lys Thr Ser Phe Gly Val Leu Trp Gln
65                  70                  75                  80

Ala Ile Ala Gly Met Ile Glu Pro Val Tyr Glu Tyr Val Ser Ala Gln
                85                  90                  95

Arg His Asp Asp Ile Val Val Val Gly Ser Leu Trp Ala Leu Gly Ala
            100                 105                 110

Arg Ile Ala His Glu Lys Tyr Gly Ile Pro Tyr Leu Ser Ala Gln Val
        115                 120                 125

Ser Pro Ser Thr Leu Leu Ser Ala His Leu Pro Pro Val His Pro Lys
130                 135                 140

Phe Asn Val Pro Glu Gln Met Pro Leu Ala Met Arg Lys Leu Leu Trp
145                 150                 155                 160

Arg Cys Ile Glu Arg Phe Lys Leu Asp Arg Thr Cys Ala Pro Glu Ile
                165                 170                 175

Asn Ala Val Arg Arg Lys Val Gly Leu Glu Thr Pro Val Lys Arg Ile
            180                 185                 190

Phe Thr Gln Trp Met His Ser Pro Gln Gly Val Val Cys Leu Phe Pro
        195                 200                 205

Ala Trp Phe Ala Pro Pro Gln Gln Asp Trp Pro Gln Pro Leu His Met
    210                 215                 220

Thr Gly Phe Pro Leu Phe Asp Gly Ser Ile Pro Gly Thr Pro Leu Asp
225                 230                 235                 240

Asp Glu Leu Gln Arg Phe Leu Asp Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Gly Ala Arg Gly Ile Phe Leu Thr Gly
        275                 280                 285

Ala Gly Gln Glu Pro Leu Arg Gly Leu Pro Asn His Val Leu Gln Arg
    290                 295                 300
```

```
Ala Tyr Ala Pro Leu Gly Ala Leu Leu Pro Ser Cys Ala Gly Leu Val
305                 310                 315                 320

His Pro Gly Gly Ile Gly Ala Met Ser Leu Ala Leu Ala Ala Gly Val
                325                 330                 335

Pro Gln Val Leu Leu Pro Cys Ala His Asp Gln Phe Asp Asn Ala Glu
            340                 345                 350

Arg Leu Val Arg Leu Gly Cys Gly Met Arg Leu Gly Val Pro Leu Arg
        355                 360                 365

Glu Gln Glu Leu Arg Gly Ala Leu Trp Arg Leu Leu Glu Asp Pro Ala
    370                 375                 380

Met Ala Ala Ala Cys Arg Arg Phe Met Glu Leu Ser Gln Pro His Ser
385                 390                 395                 400

Ile Ala Cys Gly Lys Ala Ala Gln Val Val Glu Arg Cys His Arg Glu
                405                 410                 415

Gly Asp Ala Arg Trp Leu Lys Ala Ala Ser
                420                 425

<210> SEQ ID NO 87
<211> LENGTH: 1281
<212> TYPE: DNA
<213> ORGANISM: Pseudomonas aeruginosa
<220> FEATURE:
<221> NAME/KEY: CDS
<222> LOCATION: (1)..(1281)

<400> SEQUENCE: 87
```

| | | | | | | | | | | | | | | | | |
|---|---|---|---|---|---|---|---|---|---|---|---|---|---|---|---|---|
| atg | cac | gcc | atc | ctc | atc | gcc | atc | ggc | tcg | gcc | ggc | gac | gta | ttt | ccc | 48 |
| Met | His | Ala | Ile | Leu | Ile | Ala | Ile | Gly | Ser | Ala | Gly | Asp | Val | Phe | Pro | |
| 1 | | | 5 | | | | | 10 | | | | | 15 | | | |
| ttc | atc | ggc | ttg | gcc | cgg | acc | ctg | aaa | ttg | cgc | ggg | cac | cgc | gtg | agc | 96 |
| Phe | Ile | Gly | Leu | Ala | Arg | Thr | Leu | Lys | Leu | Arg | Gly | His | Arg | Val | Ser | |
| | | 20 | | | | | 25 | | | | | 30 | | | | |
| ctc | tgc | acc | atc | ccg | gtg | ttt | cgc | gac | gcg | gtg | gag | cag | cac | ggc | atc | 144 |
| Leu | Cys | Thr | Ile | Pro | Val | Phe | Arg | Asp | Ala | Val | Glu | Gln | His | Gly | Ile | |
| | 35 | | | | | 40 | | | | | 45 | | | | | |
| gcg | ttc | gtc | ccg | ctg | agc | gac | gaa | ctg | acc | tac | cgc | cgg | acc | atg | ggc | 192 |
| Ala | Phe | Val | Pro | Leu | Ser | Asp | Glu | Leu | Thr | Tyr | Arg | Arg | Thr | Met | Gly | |
| 50 | | | | | 55 | | | | | 60 | | | | | | |
| gat | ccg | cgc | ctg | tgg | gac | ccc | aag | acg | tcc | ttc | ggc | gtg | ctc | tgg | caa | 240 |
| Asp | Pro | Arg | Leu | Trp | Asp | Pro | Lys | Thr | Ser | Phe | Gly | Val | Leu | Trp | Gln | |
| 65 | | | | 70 | | | | | 75 | | | | | 80 | | |
| gcc | atc | gcc | ggg | atg | atc | gag | ccg | gtc | tac | gag | tac | gtc | tcg | gcg | cag | 288 |
| Ala | Ile | Ala | Gly | Met | Ile | Glu | Pro | Val | Tyr | Glu | Tyr | Val | Ser | Ala | Gln | |
| | | | | 85 | | | | | 90 | | | | | 95 | | |
| cgc | cat | gac | gac | atc | gtg | gtg | gtc | ggc | tcg | ctc | tgg | gcg | ctg | ggc | gca | 336 |
| Arg | His | Asp | Asp | Ile | Val | Val | Val | Gly | Ser | Leu | Trp | Ala | Leu | Gly | Ala | |
| | | | | 100 | | | | | 105 | | | | | 110 | | |
| cgc | atc | gct | cac | gag | aag | tac | ggg | att | ccc | tac | ctg | tcc | gcg | cag | gtc | 384 |
| Arg | Ile | Ala | His | Glu | Lys | Tyr | Gly | Ile | Pro | Tyr | Leu | Ser | Ala | Gln | Val | |
| | | 115 | | | | | 120 | | | | | 125 | | | | |
| tcg | cca | tcg | acc | ttg | ttg | tcg | gcg | cac | ctg | ccg | ccg | gta | cac | ccc | aag | 432 |
| Ser | Pro | Ser | Thr | Leu | Leu | Ser | Ala | His | Leu | Pro | Pro | Val | His | Pro | Lys | |
| | 130 | | | | | 135 | | | | | 140 | | | | | |
| ttc | aac | gtg | ccc | gag | cag | atg | ccg | ctg | gcg | atg | cgc | aag | ctg | ctc | tgg | 480 |
| Phe | Asn | Val | Pro | Glu | Gln | Met | Pro | Leu | Ala | Met | Arg | Lys | Leu | Leu | Trp | |
| 145 | | | | | 150 | | | | | 155 | | | | | 160 | |
| cgc | tgc | atc | gag | cgc | ttc | aag | ctg | gat | cgc | acc | tgc | gcg | ccg | gag | atc | 528 |
| Arg | Cys | Ile | Glu | Arg | Phe | Lys | Leu | Asp | Arg | Thr | Cys | Ala | Pro | Glu | Ile | |
| | | | | 165 | | | | | 170 | | | | | 175 | | |

| | | |
|---|---|---|
| aac gcg gtg cgc cgc aag gtc ggc ctg gag acg ccg gtg aag cgc atc<br>Asn Ala Val Arg Arg Lys Val Gly Leu Glu Thr Pro Val Lys Arg Ile<br>180                        185                      190 | | 576 |
| ttc acc caa tgg atg cat tcg ccg cag ggc gtg gtc tgc ctg ttc ccg<br>Phe Thr Gln Trp Met His Ser Pro Gln Gly Val Val Cys Leu Phe Pro<br>       195                      200                      205 | | 624 |
| gcc tgg ttc gcg ccg ccc cag cag gat tgg ccg caa ccc ctg cac atg<br>Ala Trp Phe Ala Pro Pro Gln Gln Asp Trp Pro Gln Pro Leu His Met<br>210                        215                      220 | | 672 |
| acc ggc ttc ccg ctg ttc gac ggc agt atc ccg ggg acc ccg ctc gac<br>Thr Gly Phe Pro Leu Phe Asp Gly Ser Ile Pro Gly Thr Pro Leu Asp<br>225                        230                      235                      240 | | 720 |
| gac gaa ctg caa cgc ttt ctc gat cag ggc agc cgg ccg ctg gtg ttc<br>Asp Glu Leu Gln Arg Phe Leu Asp Gln Gly Ser Arg Pro Leu Val Phe<br>                      245                      250                      255 | | 768 |
| acc cag ggc tcg acc gaa cac ctg cag ggc gac ttc tac gcc atg gcc<br>Thr Gln Gly Ser Thr Glu His Leu Gln Gly Asp Phe Tyr Ala Met Ala<br>                  260                      265                      270 | | 816 |
| ctg cgc gcg ctg gaa cgc ctc ggc gcg cgt ggg atc ttc ctc acc ggc<br>Leu Arg Ala Leu Glu Arg Leu Gly Ala Arg Gly Ile Phe Leu Thr Gly<br>275                        280                      285 | | 864 |
| gcc ggc cag gaa ccg ctg cgc ggc ttg ccg aat cac gtg ctg cag cgc<br>Ala Gly Gln Glu Pro Leu Arg Gly Leu Pro Asn His Val Leu Gln Arg<br>290                        295                      300 | | 912 |
| gcc tac gcg cca ctg gga gcc ttg ctg cca tcg tgc gcc ggg ctg gtc<br>Ala Tyr Ala Pro Leu Gly Ala Leu Leu Pro Ser Cys Ala Gly Leu Val<br>305                        310                      315                      320 | | 960 |
| cat ccg ggc ggt atc ggc gcc atg agc ctg gcc ttg gcg gcg ggg gtg<br>His Pro Gly Gly Ile Gly Ala Met Ser Leu Ala Leu Ala Ala Gly Val<br>                      325                      330                      335 | | 1008 |
| ccg cag gtg ctg ctg ccc tgc gcc cac gac cag ttc gac aat gcc gaa<br>Pro Gln Val Leu Leu Pro Cys Ala His Asp Gln Phe Asp Asn Ala Glu<br>                  340                      345                      350 | | 1056 |
| cgg ctg gtc cgg ctc ggc tgc ggg atg cgc ctg ggc gtg ccg ttg cgc<br>Arg Leu Val Arg Leu Gly Cys Gly Met Arg Leu Gly Val Pro Leu Arg<br>355                        360                      365 | | 1104 |
| gag cag gag ttg cgc ggg gcg ctg tgg cgc ttg ctc gag gac ccg gcc<br>Glu Gln Glu Leu Arg Gly Ala Leu Trp Arg Leu Leu Glu Asp Pro Ala<br>370                        375                      380 | | 1152 |
| atg gcg gcg gcc tgt cgg cgt ttc atg gaa ttg tca caa ccg cac agt<br>Met Ala Ala Ala Cys Arg Arg Phe Met Glu Leu Ser Gln Pro His Ser<br>385                        390                      395                      400 | | 1200 |
| atc gct tgc ggt aaa gcg gcc cac gtg gtc gaa cgt tgt cat agg gag<br>Ile Ala Cys Gly Lys Ala Ala His Val Val Glu Arg Cys His Arg Glu<br>                  405                      410                      415 | | 1248 |
| ggg gat gcg cga tgg ctg aag gct gcg tcc tga<br>Gly Asp Ala Arg Trp Leu Lys Ala Ala Ser<br>420                        425 | | 1281 |

<210> SEQ ID NO 88
<211> LENGTH: 426
<212> TYPE: PRT
<213> ORGANISM: Pseudomonas aeruginosa

<400> SEQUENCE: 88

Met His Ala Ile Leu Ile Ala Ile Gly Ser Ala Gly Asp Val Phe Pro
1                 5                    10                   15

Phe Ile Gly Leu Ala Arg Thr Leu Lys Leu Arg Gly His Arg Val Ser
                 20                    25                   30

Leu Cys Thr Ile Pro Val Phe Arg Asp Ala Val Glu Gln His Gly Ile

```
              35                  40                  45
Ala Phe Val Pro Leu Ser Asp Glu Leu Thr Tyr Arg Arg Thr Met Gly
 50                  55                  60

Asp Pro Arg Leu Trp Asp Pro Lys Thr Ser Phe Gly Val Leu Trp Gln
 65                  70                  75                  80

Ala Ile Ala Gly Met Ile Glu Pro Val Tyr Glu Tyr Val Ser Ala Gln
                 85                  90                  95

Arg His Asp Asp Ile Val Val Gly Ser Leu Trp Ala Leu Gly Ala
             100                 105                 110

Arg Ile Ala His Glu Lys Tyr Gly Ile Pro Tyr Leu Ser Ala Gln Val
             115                 120                 125

Ser Pro Ser Thr Leu Leu Ser Ala His Leu Pro Val His Pro Lys
130                 135                 140

Phe Asn Val Pro Glu Gln Met Pro Leu Ala Met Arg Lys Leu Leu Trp
145                 150                 155                 160

Arg Cys Ile Glu Arg Phe Lys Leu Asp Arg Thr Cys Ala Pro Glu Ile
                165                 170                 175

Asn Ala Val Arg Arg Lys Val Gly Leu Glu Thr Pro Val Lys Arg Ile
             180                 185                 190

Phe Thr Gln Trp Met His Ser Pro Gln Gly Val Val Cys Leu Phe Pro
             195                 200                 205

Ala Trp Phe Ala Pro Pro Gln Gln Asp Trp Pro Gln Pro Leu His Met
210                 215                 220

Thr Gly Phe Pro Leu Phe Asp Gly Ser Ile Pro Gly Thr Pro Leu Asp
225                 230                 235                 240

Asp Glu Leu Gln Arg Phe Leu Asp Gln Gly Ser Arg Pro Leu Val Phe
                245                 250                 255

Thr Gln Gly Ser Thr Glu His Leu Gln Gly Asp Phe Tyr Ala Met Ala
             260                 265                 270

Leu Arg Ala Leu Glu Arg Leu Gly Ala Arg Gly Ile Phe Leu Thr Gly
             275                 280                 285

Ala Gly Gln Glu Pro Leu Arg Gly Leu Pro Asn His Val Leu Gln Arg
290                 295                 300

Ala Tyr Ala Pro Leu Gly Ala Leu Leu Pro Ser Cys Ala Gly Leu Val
305                 310                 315                 320

His Pro Gly Gly Ile Gly Ala Met Ser Leu Ala Leu Ala Ala Gly Val
                325                 330                 335

Pro Gln Val Leu Leu Pro Cys Ala His Asp Gln Phe Asp Asn Ala Glu
             340                 345                 350

Arg Leu Val Arg Leu Gly Cys Gly Met Arg Leu Gly Val Pro Leu Arg
             355                 360                 365

Glu Gln Glu Leu Arg Gly Ala Leu Trp Arg Leu Leu Glu Asp Pro Ala
370                 375                 380

Met Ala Ala Ala Cys Arg Arg Phe Met Glu Leu Ser Gln Pro His Ser
385                 390                 395                 400

Ile Ala Cys Gly Lys Ala Ala His Val Val Glu Arg Cys His Arg Glu
                405                 410                 415

Gly Asp Ala Arg Trp Leu Lys Ala Ala Ser
             420                 425

<210> SEQ ID NO 89
<211> LENGTH: 978
<212> TYPE: DNA
<213> ORGANISM: Pseudomonas aeruginosa
```

```
<220> FEATURE:
<221> NAME/KEY: CDS
<222> LOCATION: (1)..(978)

<400> SEQUENCE: 89
```

| | | | | | | | | | | | | | | | | |
|---|---|---|---|---|---|---|---|---|---|---|---|---|---|---|---|---|
| atg | gac | cgg | ata | gac | atg | ggc | gtg | ctg | gtg | gtg | ctg | ttc | aat | cct | ggc | 48 |
| Met | Asp | Arg | Ile | Asp | Met | Gly | Val | Leu | Val | Val | Leu | Phe | Asn | Pro | Gly | |
| 1 | | | | 5 | | | | | 10 | | | | | 15 | | |
| gac | gac | gac | ctg | gaa | cac | ctt | ggc | gaa | ctg | gcg | gcg | gcc | ttt | ccg | caa | 96 |
| Asp | Asp | Asp | Leu | Glu | His | Leu | Gly | Glu | Leu | Ala | Ala | Ala | Phe | Pro | Gln | |
| | | | 20 | | | | | 25 | | | | | 30 | | | |
| ctg | cgc | ttc | ctc | gcc | gtc | gac | aac | tcg | ccg | cac | agc | gat | ccg | cag | cgc | 144 |
| Leu | Arg | Phe | Leu | Ala | Val | Asp | Asn | Ser | Pro | His | Ser | Asp | Pro | Gln | Arg | |
| | | 35 | | | | | 40 | | | | | 45 | | | | |
| aac | gcc | cgg | ctg | cgc | ggg | caa | ggc | atc | gcc | gtg | ctc | tac | cac | ggc | aac | 192 |
| Asn | Ala | Arg | Leu | Arg | Gly | Gln | Gly | Ile | Ala | Val | Leu | Tyr | His | Gly | Asn | |
| 50 | | | | | 55 | | | | | 60 | | | | | | |
| cgg | cag | ggc | atc | gcc | ggc | gcc | ttc | aac | cag | ggg | ctc | gac | acg | ctg | ttc | 240 |
| Arg | Gln | Gly | Ile | Ala | Gly | Ala | Phe | Asn | Gln | Gly | Leu | Asp | Thr | Leu | Phe | |
| 65 | | | | 70 | | | | | 75 | | | | | 80 | | |
| cgg | cgc | ggc | ctg | cag | ggt | gtg | ctg | ctc | gac | cag | gac | tcc | cgt | ccc | | 288 |
| Arg | Arg | Gly | Leu | Gln | Gly | Val | Leu | Leu | Asp | Gln | Asp | Ser | Arg | Pro | | |
| | | | | 85 | | | | | 90 | | | | | 95 | | |
| ggc | ggc | gcc | ttc | ctc | gcc | gcc | cag | tgg | cgc | aac | ctg | cag | gca | tgc | aac | 336 |
| Gly | Gly | Ala | Phe | Leu | Ala | Ala | Gln | Trp | Arg | Asn | Leu | Gln | Ala | Cys | Asn | |
| | | | 100 | | | | | 105 | | | | | 110 | | | |
| ggc | cag | gcc | tgc | ctg | ctc | ggc | cca | cgg | atc | ttc | gac | cgg | ggc | gac | cgg | 384 |
| Gly | Gln | Ala | Cys | Leu | Leu | Gly | Pro | Arg | Ile | Phe | Asp | Arg | Gly | Asp | Arg | |
| | | 115 | | | | | 120 | | | | | 125 | | | | |
| cgc | ttc | ctg | ccg | gcc | atc | cac | ctc | gac | ggg | ctg | gcg | ctc | agg | caa | ctg | 432 |
| Arg | Phe | Leu | Pro | Ala | Ile | His | Leu | Asp | Gly | Leu | Ala | Leu | Arg | Gln | Leu | |
| | 130 | | | | | 135 | | | | | 140 | | | | | |
| tcc | ctg | gac | ggc | ctg | acg | acc | cca | cag | cgc | acc | tcg | ttc | ctg | atc | tcc | 480 |
| Ser | Leu | Asp | Gly | Leu | Thr | Thr | Pro | Gln | Arg | Thr | Ser | Phe | Leu | Ile | Ser | |
| 145 | | | | | 150 | | | | | 155 | | | | | 160 | |
| tcc | ggc | tgc | ctg | ctg | acc | cgc | gag | gcc | tac | cag | cgc | ctc | ggc | cac | ttc | 528 |
| Ser | Gly | Cys | Leu | Leu | Thr | Arg | Glu | Ala | Tyr | Gln | Arg | Leu | Gly | His | Phe | |
| | | | | 165 | | | | | 170 | | | | | 175 | | |
| gac | gag | gaa | ctg | ttc | atc | gac | cac | gtg | gac | acc | gag | tac | agc | ctg | cgc | 576 |
| Asp | Glu | Glu | Leu | Phe | Ile | Asp | His | Val | Asp | Thr | Glu | Tyr | Ser | Leu | Arg | |
| | | | 180 | | | | | 185 | | | | | 190 | | | |
| gcc | cag | gcg | ctg | gac | gtg | ccc | ctg | tac | gtc | gac | ccg | cgg | ctg | gtc | ctc | 624 |
| Ala | Gln | Ala | Leu | Asp | Val | Pro | Leu | Tyr | Val | Asp | Pro | Arg | Leu | Val | Leu | |
| | | 195 | | | | | 200 | | | | | 205 | | | | |
| gag | cac | cgc | atc | ggc | acg | cgc | aag | acc | cgc | cgc | ctc | ggc | ggt | ctc | agc | 672 |
| Glu | His | Arg | Ile | Gly | Thr | Arg | Lys | Thr | Arg | Arg | Leu | Gly | Gly | Leu | Ser | |
| | 210 | | | | | 215 | | | | | 220 | | | | | |
| ctc | agc | gcg | atg | aac | cac | gcc | cca | ctg | cgc | cgc | tac | tac | ctg | gcg | cgc | 720 |
| Leu | Ser | Ala | Met | Asn | His | Ala | Pro | Leu | Arg | Arg | Tyr | Tyr | Leu | Ala | Arg | |
| 225 | | | | | 230 | | | | | 235 | | | | | 240 | |
| aac | ggc | ctg | ctg | gtc | ctg | cgc | cgc | tac | gcc | cgg | tcc | tcg | ccg | ctg | gcc | 768 |
| Asn | Gly | Leu | Leu | Val | Leu | Arg | Arg | Tyr | Ala | Arg | Ser | Ser | Pro | Leu | Ala | |
| | | | | 245 | | | | | 250 | | | | | 255 | | |
| ctg | ctg | gcg | aac | ctg | ccg | acc | ctg | acc | cag | ggc | ctc | gcg | gtg | ctc | ctg | 816 |
| Leu | Leu | Ala | Asn | Leu | Pro | Thr | Leu | Thr | Gln | Gly | Leu | Ala | Val | Leu | Leu | |
| | | | 260 | | | | | 265 | | | | | 270 | | | |
| ctc | gaa | cgc | gac | aag | ctg | ctc | aag | ctg | cgc | tgc | ctg | ggc | tgg | ggc | ctg | 864 |
| Leu | Glu | Arg | Asp | Lys | Leu | Leu | Lys | Leu | Arg | Cys | Leu | Gly | Trp | Gly | Leu | |
| | | 275 | | | | | 280 | | | | | 285 | | | | |
| tgg | gac | ggc | ctg | cgg | ggg | cgc | ggc | ggc | gcg | ctg | gag | cgc | aac | cgc | ccg | 912 |

```
Trp Asp Gly Leu Arg Gly Arg Gly Gly Ala Leu Glu Arg Asn Arg Pro
    290                 295                 300 cgc ctg ctg aag cgc ctc gcc ggt ccg gcg gtg gcg ccc aca gtt ccc    960
Arg Leu Leu Lys Arg Leu Ala Gly Pro Ala Val Ala Pro Thr Val Pro
305                 310                 315                 320 ggc aag gcc aag gcc tag                                            978
Gly Lys Ala Lys Ala
                325
```

<210> SEQ ID NO 90
<211> LENGTH: 325
<212> TYPE: PRT
<213> ORGANISM: Pseudomonas aeruginosa

<400> SEQUENCE: 90

```
Met Asp Arg Ile Asp Met Gly Val Leu Val Leu Phe Asn Pro Gly
1               5                   10                  15

Asp Asp Asp Leu Glu His Leu Gly Glu Leu Ala Ala Ala Phe Pro Gln
                20                  25                  30

Leu Arg Phe Leu Ala Val Asp Asn Ser Pro His Ser Asp Pro Gln Arg
            35                  40                  45

Asn Ala Arg Leu Arg Gly Gln Gly Ile Ala Val Leu Tyr His Gly Asn
50                  55                  60

Arg Gln Gly Ile Ala Gly Ala Phe Asn Gln Gly Leu Asp Thr Leu Phe
65                  70                  75                  80

Arg Arg Gly Leu Gln Gly Val Leu Leu Leu Asp Gln Asp Ser Arg Pro
                85                  90                  95

Gly Gly Ala Phe Leu Ala Ala Gln Trp Arg Asn Leu Gln Ala Cys Asn
            100                 105                 110

Gly Gln Ala Cys Leu Leu Gly Pro Arg Ile Phe Asp Arg Gly Asp Arg
        115                 120                 125

Arg Phe Leu Pro Ala Ile His Leu Asp Gly Leu Ala Leu Arg Gln Leu
130                 135                 140

Ser Leu Asp Gly Leu Thr Thr Pro Gln Arg Thr Ser Phe Leu Ile Ser
145                 150                 155                 160

Ser Gly Cys Leu Leu Thr Arg Glu Ala Tyr Gln Arg Leu Gly His Phe
                165                 170                 175

Asp Glu Glu Leu Phe Ile Asp His Val Asp Thr Glu Tyr Ser Leu Arg
            180                 185                 190

Ala Gln Ala Leu Asp Val Pro Leu Tyr Val Asp Pro Arg Leu Val Leu
        195                 200                 205

Glu His Arg Ile Gly Thr Arg Lys Thr Arg Arg Leu Gly Gly Leu Ser
210                 215                 220

Leu Ser Ala Met Asn His Ala Pro Leu Arg Arg Tyr Tyr Leu Ala Arg
225                 230                 235                 240

Asn Gly Leu Leu Val Leu Arg Arg Tyr Ala Arg Ser Ser Pro Leu Ala
                245                 250                 255

Leu Leu Ala Asn Leu Pro Thr Leu Thr Gln Gly Leu Ala Val Leu Leu
            260                 265                 270

Leu Glu Arg Asp Lys Leu Leu Lys Leu Arg Cys Leu Gly Trp Gly Leu
        275                 280                 285

Trp Asp Gly Leu Arg Gly Arg Gly Gly Ala Leu Glu Arg Asn Arg Pro
290                 295                 300

Arg Leu Leu Lys Arg Leu Ala Gly Pro Ala Val Ala Pro Thr Val Pro
305                 310                 315                 320
```

Gly Lys Ala Lys Ala
               325

<210> SEQ ID NO 91
<211> LENGTH: 978
<212> TYPE: DNA
<213> ORGANISM: Pseudomonas aeruginosa
<220> FEATURE:
<221> NAME/KEY: CDS
<222> LOCATION: (1)..(978)

<400> SEQUENCE: 91

| | | | | | | | | | | | | | | | | |
|---|---|---|---|---|---|---|---|---|---|---|---|---|---|---|---|---|
| atg | gac | cgg | ata | gac | atg | ggc | gtg | ctg | gtg | gta | ctg | ttc | aat | cct | ggc | 48 |
| Met | Asp | Arg | Ile | Asp | Met | Gly | Val | Leu | Val | Val | Leu | Phe | Asn | Pro | Gly | |
| 1 | | | | 5 | | | | | 10 | | | | | 15 | | |
| gac | gac | gac | ctg | gaa | cac | ctt | ggc | gaa | ctg | gcg | gcg | gcg | ttt | ccg | caa | 96 |
| Asp | Asp | Asp | Leu | Glu | His | Leu | Gly | Glu | Leu | Ala | Ala | Ala | Phe | Pro | Gln | |
| | | | 20 | | | | | 25 | | | | | 30 | | | |
| ctg | cgc | ttc | ctc | gcc | gtc | gac | aac | tca | ccg | cac | agc | gat | ccg | cag | cgc | 144 |
| Leu | Arg | Phe | Leu | Ala | Val | Asp | Asn | Ser | Pro | His | Ser | Asp | Pro | Gln | Arg | |
| | 35 | | | | | 40 | | | | | 45 | | | | | |
| aat | gcc | cgg | ctg | cgc | ggg | caa | ggc | atc | gcc | gtg | ctg | cac | cac | ggc | aac | 192 |
| Asn | Ala | Arg | Leu | Arg | Gly | Gln | Gly | Ile | Ala | Val | Leu | His | His | Gly | Asn | |
| 50 | | | | | 55 | | | | | 60 | | | | | | |
| cgg | cag | ggc | atc | gcc | ggc | gcc | ttc | aac | cag | ggg | ctc | gac | gcg | ctg | ttc | 240 |
| Arg | Gln | Gly | Ile | Ala | Gly | Ala | Phe | Asn | Gln | Gly | Leu | Asp | Ala | Leu | Phe | |
| 65 | | | | 70 | | | | | 75 | | | | | 80 | | |
| cgg | cgt | ggc | gtg | cag | ggt | gtg | ctg | ctc | gac | cag | gac | tcc | cgt | ccc | | 288 |
| Arg | Arg | Gly | Val | Gln | Gly | Val | Leu | Leu | Asp | Gln | Asp | Ser | Arg | Pro | | |
| | | | | 85 | | | | | 90 | | | | | 95 | | |
| ggc | ggc | gcc | ttc | ctc | gcc | gcc | cag | tgg | cgc | aac | ctg | cag | gcg | cgc | aac | 336 |
| Gly | Gly | Ala | Phe | Leu | Ala | Ala | Gln | Trp | Arg | Asn | Leu | Gln | Ala | Arg | Asn | |
| | | | 100 | | | | | 105 | | | | | 110 | | | |
| ggt | cag | gcc | tgc | ctg | ctc | ggc | cca | cgg | atc | ttc | gac | cgg | ggt | gac | cgg | 384 |
| Gly | Gln | Ala | Cys | Leu | Leu | Gly | Pro | Arg | Ile | Phe | Asp | Arg | Gly | Asp | Arg | |
| | | 115 | | | | | 120 | | | | | 125 | | | | |
| cgc | ttc | ctg | ccg | gcc | atc | cat | ctc | gac | gga | ctg | acg | ctc | agg | caa | ttg | 432 |
| Arg | Phe | Leu | Pro | Ala | Ile | His | Leu | Asp | Gly | Leu | Thr | Leu | Arg | Gln | Leu | |
| | 130 | | | | | 135 | | | | | 140 | | | | | |
| tct | ctg | gac | ggc | ctg | acg | acc | ccg | cag | cgc | acc | tcg | ttc | ctg | atc | tcc | 480 |
| Ser | Leu | Asp | Gly | Leu | Thr | Thr | Pro | Gln | Arg | Thr | Ser | Phe | Leu | Ile | Ser | |
| 145 | | | | | 150 | | | | | 155 | | | | | 160 | |
| tcc | ggc | tgc | ctg | ctg | acc | cgc | gag | gcc | tac | cag | cgc | ctc | ggc | cac | ttc | 528 |
| Ser | Gly | Cys | Leu | Leu | Thr | Arg | Glu | Ala | Tyr | Gln | Arg | Leu | Gly | His | Phe | |
| | | | | 165 | | | | | 170 | | | | | 175 | | |
| gac | gag | gaa | ctg | ttc | atc | gac | cac | gtg | gac | acc | gaa | tac | agc | ctg | cgc | 576 |
| Asp | Glu | Glu | Leu | Phe | Ile | Asp | His | Val | Asp | Thr | Glu | Tyr | Ser | Leu | Arg | |
| | | | 180 | | | | | 185 | | | | | 190 | | | |
| gcc | cag | gcg | ctg | gac | gtg | ccc | ctg | tac | gtc | gac | ccg | cgg | ctg | gtc | ctc | 624 |
| Ala | Gln | Ala | Leu | Asp | Val | Pro | Leu | Tyr | Val | Asp | Pro | Arg | Leu | Val | Leu | |
| | | 195 | | | | | 200 | | | | | 205 | | | | |
| gag | cac | cgc | atc | ggc | acg | cgc | aag | acc | cgc | cgc | ctc | ggc | ggt | ctc | agc | 672 |
| Glu | His | Arg | Ile | Gly | Thr | Arg | Lys | Thr | Arg | Arg | Leu | Gly | Gly | Leu | Ser | |
| | 210 | | | | | 215 | | | | | 220 | | | | | |
| ctc | agc | gcg | atg | aac | cac | gcc | ccg | ctg | cgc | cgc | tac | tac | ctg | gcg | cgc | 720 |
| Leu | Ser | Ala | Met | Asn | His | Ala | Pro | Leu | Arg | Arg | Tyr | Tyr | Leu | Ala | Arg | |
| 225 | | | | | 230 | | | | | 235 | | | | | 240 | |
| aac | ggc | ctg | ctg | gtc | ctg | cgc | cgc | tac | gcc | cgg | tcc | tcg | ccg | ctg | gcc | 768 |
| Asn | Gly | Leu | Leu | Val | Leu | Arg | Arg | Tyr | Ala | Arg | Ser | Ser | Pro | Leu | Ala | |
| | | | | 245 | | | | | 250 | | | | | 255 | | |
| ctg | ctg | gcg | aac | ctg | ccg | acc | ctg | acc | cag | ggc | ctc | gcg | gtg | ctc | ctg | 816 |

```
Leu Leu Ala Asn Leu Pro Thr Leu Thr Gln Gly Leu Ala Val Leu Leu
                260                 265                 270 ctc gaa cgc gac aag ctg ctc aag ctg cgc tgc ctg ggc tgg ggc ctg      864
Leu Glu Arg Asp Lys Leu Leu Lys Leu Arg Cys Leu Gly Trp Gly Leu
                275                 280                 285 tgg gac ggc ctg cgg gga cgc ggc ggc gcg ctg gag cgc aac cgc ccg      912
Trp Asp Gly Leu Arg Gly Arg Gly Gly Ala Leu Glu Arg Asn Arg Pro
        290                 295                 300 cgc ctg ctg aag cgc ctc gcc ggc ccg gcc gtg gcg tcc gta gct tcc      960
Arg Leu Leu Lys Arg Leu Ala Gly Pro Ala Val Ala Ser Val Ala Ser
305                 310                 315                 320 ggc aag gcc aag gcc tag                                              978
Gly Lys Ala Lys Ala
                325

<210> SEQ ID NO 92
<211> LENGTH: 325
<212> TYPE: PRT
<213> ORGANISM: Pseudomonas aeruginosa

<400> SEQUENCE: 92

Met Asp Arg Ile Asp Met Gly Val Leu Val Leu Phe Asn Pro Gly
1               5                   10                  15

Asp Asp Asp Leu Glu His Leu Gly Glu Leu Ala Ala Ala Phe Pro Gln
                20                  25                  30

Leu Arg Phe Leu Ala Val Asp Asn Ser Pro His Ser Asp Pro Gln Arg
            35                  40                  45

Asn Ala Arg Leu Arg Gly Gln Gly Ile Ala Val Leu His His Gly Asn
        50                  55                  60

Arg Gln Gly Ile Ala Gly Ala Phe Asn Gln Gly Leu Asp Ala Leu Phe
65                  70                  75                  80

Arg Arg Gly Val Gln Gly Val Leu Leu Leu Asp Gln Asp Ser Arg Pro
                85                  90                  95

Gly Gly Ala Phe Leu Ala Ala Gln Trp Arg Asn Leu Gln Ala Arg Asn
            100                 105                 110

Gly Gln Ala Cys Leu Leu Gly Pro Arg Ile Phe Asp Arg Gly Asp Arg
        115                 120                 125

Arg Phe Leu Pro Ala Ile His Leu Asp Gly Leu Thr Leu Arg Gln Leu
130                 135                 140

Ser Leu Asp Gly Leu Thr Thr Pro Gln Arg Thr Ser Phe Leu Ile Ser
145                 150                 155                 160

Ser Gly Cys Leu Leu Thr Arg Glu Ala Tyr Gln Arg Leu Gly His Phe
                165                 170                 175

Asp Glu Glu Leu Phe Ile Asp His Val Asp Thr Glu Tyr Ser Leu Arg
            180                 185                 190

Ala Gln Ala Leu Asp Val Pro Leu Tyr Val Asp Pro Arg Leu Val Leu
        195                 200                 205

Glu His Arg Ile Gly Thr Arg Lys Thr Arg Arg Leu Gly Gly Leu Ser
210                 215                 220

Leu Ser Ala Met Asn His Ala Pro Leu Arg Arg Tyr Tyr Leu Ala Arg
225                 230                 235                 240

Asn Gly Leu Leu Val Leu Arg Arg Tyr Ala Arg Ser Ser Pro Leu Ala
                245                 250                 255

Leu Leu Ala Asn Leu Pro Thr Leu Thr Gln Gly Leu Ala Val Leu Leu
            260                 265                 270

Leu Glu Arg Asp Lys Leu Leu Lys Leu Arg Cys Leu Gly Trp Gly Leu
```

```
                275                 280                 285
Trp Asp Gly Leu Arg Gly Arg Gly Gly Ala Leu Glu Arg Asn Arg Pro
    290                 295                 300

Arg Leu Leu Lys Arg Leu Ala Gly Pro Ala Val Ala Ser Val Ala Ser
305                 310                 315                 320

Gly Lys Ala Lys Ala
                325
```